(12) United States Patent
Shiers et al.

(10) Patent No.: US 10,336,702 B2
(45) Date of Patent: Jul. 2, 2019

(54) PHARMACEUTICALLY ACTIVE COMPOUNDS

(71) Applicant: BERGENBIO ASA, Bergen (NO)

(72) Inventors: Jason John Shiers, Nottingham (GB); John Paul Watts, Nottingham (GB); Stuart Thomas Onions, Nottingham (GB); Mohammed Abdul Quddus, Nottingham (GB); Joseph William Wrigglesworth, Nottingham (GB); Colin Peter Sambrook-Smith, Nottingham (GB); Alan Naylor, Herts (GB); Derek Londesbrough, Sunderland (GB)

(73) Assignee: BerGenBio ASA, Bergen (NO)

( * ) Notice: Subject to any disclaimer, the term of this patent is extended or adjusted under 35 U.S.C. 154(b) by 0 days.

(21) Appl. No.: 15/533,048

(22) PCT Filed: Dec. 23, 2015

(86) PCT No.: PCT/EP2015/081168
§ 371 (c)(1),
(2) Date: Jun. 5, 2017

(87) PCT Pub. No.: WO2016/102672
PCT Pub. Date: Jun. 30, 2016

(65) Prior Publication Data
US 2018/0029985 A1    Feb. 1, 2018

(30) Foreign Application Priority Data

May 22, 2015    (GB) .................................... 1508787.7

(51) Int. Cl.
| | | |
|---|---|---|
| *C07C 227/12* | (2006.01) |
| *C07D 213/75* | (2006.01) |
| *C07D 403/12* | (2006.01) |
| *C07D 401/12* | (2006.01) |
| *C07D 237/20* | (2006.01) |
| *C07D 405/10* | (2006.01) |
| *C07D 405/12* | (2006.01) |
| *C07D 409/04* | (2006.01) |
| *C07D 409/14* | (2006.01) |
| *C07D 413/12* | (2006.01) |
| *A61K 31/44* | (2006.01) |
| *A61K 31/4427* | (2006.01) |
| *A61K 31/4433* | (2006.01) |
| *A61K 31/4436* | (2006.01) |
| *A61K 31/4439* | (2006.01) |
| *A61K 31/444* | (2006.01) |
| *A61K 31/4545* | (2006.01) |
| *A61K 31/50* | (2006.01) |
| *A61K 31/501* | (2006.01) |
| *A61K 31/53* | (2006.01) |
| *A61K 31/5377* | (2006.01) |
| *A61K 45/06* | (2006.01) |
| *C07D 405/14* | (2006.01) |
| *C07D 413/14* | (2006.01) |
| *C07C 227/00* | (2006.01) |

(52) U.S. Cl.
CPC ............ *C07D 213/75* (2013.01); *A61K 31/44* (2013.01); *A61K 31/444* (2013.01); *A61K 31/4427* (2013.01); *A61K 31/4433* (2013.01); *A61K 31/4436* (2013.01); *A61K 31/4439* (2013.01); *A61K 31/4545* (2013.01); *A61K 31/50* (2013.01); *A61K 31/501* (2013.01); *A61K 31/53* (2013.01); *A61K 31/5377* (2013.01); *A61K 45/06* (2013.01); *C07C 227/00* (2013.01); *C07C 227/12* (2013.01); *C07D 237/20* (2013.01); *C07D 401/12* (2013.01); *C07D 403/12* (2013.01); *C07D 405/10* (2013.01); *C07D 405/12* (2013.01); *C07D 405/14* (2013.01); *C07D 409/04* (2013.01); *C07D 409/14* (2013.01); *C07D 413/12* (2013.01); *C07D 413/14* (2013.01)

(58) Field of Classification Search
CPC ................................ C07D 213/30; A61P 35/00
See application file for complete search history.

(56) References Cited

U.S. PATENT DOCUMENTS

| | | |
|---|---|---|
| 6,486,199 B1 | 11/2002 | Vennerstrom et al. |
| 8,912,169 B2 | 12/2014 | Burns et al. |

(Continued)

OTHER PUBLICATIONS

Pilli et al. CAS: 98: 198130, 1983.*
Kettle et al., "Diverse Heterocyclic Scaffolds as Allosteric Inhibitors of AKT," J Med Chem. Feb. 9, 2012;55(3):1261-73.

(Continued)

*Primary Examiner* — Rei Tsang Shiao
(74) *Attorney, Agent, or Firm* — McNeill Baur PLLC

(57) ABSTRACT

The invention is directed to compounds of general formula (I), and pharmaceutical compositions containing such compounds. The compounds and compositions have valuable pharmaceutical properties. In particular, they may be used for the treatment of cancer. Novel intermediates and novel methods of preparation are also disclosed.

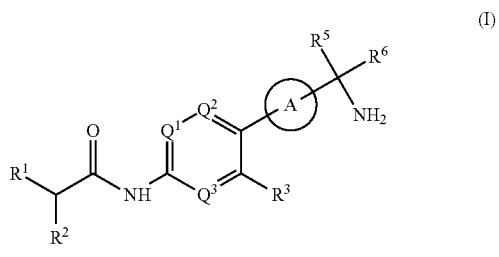

28 Claims, 7 Drawing Sheets

(56) References Cited

U.S. PATENT DOCUMENTS

| | | |
|---|---|---|
| 2007/0185152 A1 | 8/2007 | Yamashita et al. |
| 2009/0042891 A1 | 2/2009 | Vidal et al. |
| 2010/0075970 A1* | 3/2010 | Bilodeau .............. A61K 31/501 |
| | | 514/236.2 |

OTHER PUBLICATIONS

International Search Report and Written Opinion issued in corresponding application PCT/EP2015/081168, dated Jun. 28, 2016, 16 pages.

* cited by examiner

Figure 3
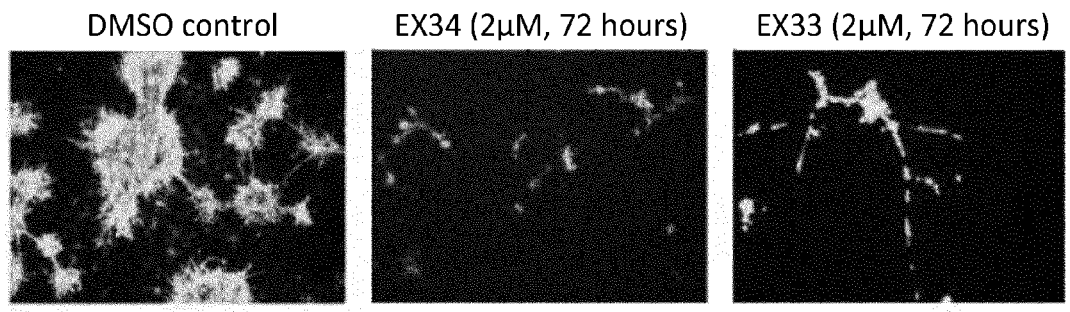
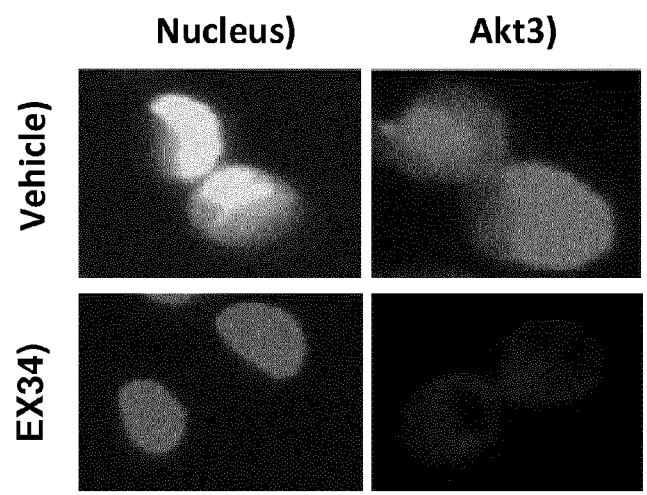
Figure 4
Figure 5
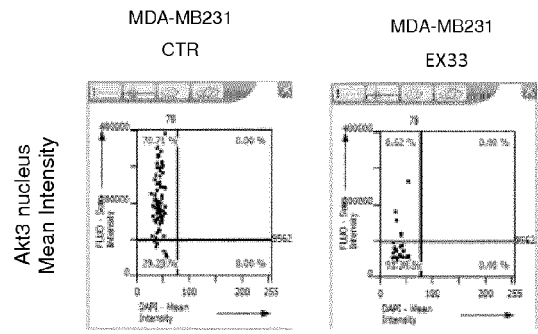

PHARMACEUTICALLY ACTIVE COMPOUNDS

CROSS REFERENCE TO RELATED APPLICATIONS

This application is a national phase entry pursuant to 35 U.S.C. § 371 of International Application No. PCT/EP2015/081168, filed Dec. 23, 2015, which claims the benefit of priority of Application No. GB 1423087.4, filed Dec. 23, 2014, Application No. GB 1508787.7, filed May 22, 2015, and GB 1519919.3, filed Nov. 11, 2015, all of which are incorporated by reference in their entirety.

This invention relates to pyridine, pyridazine and triazine derivatives that are useful in the treatment of cancer and/or other diseases. The compounds are believed to be inhibitors of serine/threonine kinase (Akt), and in particular selective inhibitors of Akt3, and hence are useful in the treatment of conditions associated with Akt3 activity, gene amplification or overexpression.

Akt, also known as "protein kinase B" (PKB), is a family of serine/threonine kinases comprising, in humans, three members: Akt1, Akt2 and Akt3. These three isoforms are transcripted from different genes and have distinct subcellular localisation, expression patterns and knock-out phenotypes.

The Akt family is known to be involved in diverse cellular processes including cell proliferation, motility, growth, glucose homeostasis, cell survival and cell death. Akt regulates cellular survival and metabolism by binding and regulating many downstream effectors, e.g. by activating Nuclear Factor-κB, resulting in the transcription of pro-survival genes, and by phosphorylating and thus deactivating BAD (a pro-apoptotic protein). These effects mean that Akt leads ultimately to cell growth and proliferation.

The effects of Akt on the cell life cycle are not limited to normal, healthy cells. Activated Akt may also enable the proliferation and survival of potentially mutagenic cells, possibly contributing to the development of mutations in other genes. Akt has also been associated with angiogenesis and the development of tumours, particularly with tumour cell survival, proliferation and invasiveness.

The roles for Akt1, Akt2 and Akt3 in normal development have been studied in knock-out mice, revealing that Akt1 is important for overall growth (knock-out mice are generally healthy but have reduced growth), Akt2 is primarily involved in glucose metabolism (knockout mice grow normally but show insulin resistance) and Akt3 is important in brain development (see e.g. Dummler B, Hemmings B A. Physiological roles of PKB/Akt isoforms in development and disease. Biochem Soc Trans 2007; 35:231-5). A more general role for Akt1 and Akt2 is suggested by their widespread expression throughout the body, while Akt3 has more restricted expression in the brain, kidney and heart. Although Akt1, Akt2 and Akt3 have approximately 80% sequence identity, they have been found to have distinct expression patterns, opposing roles in cell migration, invasion and metastasis (see e.g. Virtakoivu R et al, Distinct roles of Akt isoforms in regulating β1-integrin activity, migration, and invasion in prostate cancer. Mol Biol Cell 2012; 23(17): 3357-69) and distinct target specificities. Despite this, the majority of research publications on Akt refer either to Akt1 or to Akt without specifying the family member, a consequence of the widespread use of pan-Akt antibodies which do not distinguish between the family members.

Of the three isoforms, least is known about Akt3. Indeed, in a 2010 review article "Key signalling nodes in mammary gland development and cancer. Signalling downstream of PI3 kinase in mammary epithelium: a play in 3 Akts" (Wickenden J A and Watson C J, Breast Cancer Research 2010, 12, 202), Akt3 is mentioned just three times: once to establish its existence, once to note that it appears to have a minor role in normal mammary gland development and once to note that it does not affect Stat5a phosphorylation during pregnancy and lactation.

Conventional cancer treatments such as chemotherapy act against all actively dividing cells, whether normal or cancerous. However, more recent research into cancer treatment has focused on the development of targeted therapies which interfere with specific molecules involved in cancer cell growth and survival, often seeking to prevent proliferation of cancer cells rather than simply seeking to destroy cancer cells which are already present. Due to this, targeted therapies have improved the treatment of cancer compared to traditional chemotherapeutic and immunosuppressive agents.

Akt is considered an attractive target for cancer therapy, and inhibition of Akt alone or in combination with standard cancer chemotherapeutics has been postulated to reduce the apoptotic threshold and preferentially kill cancer cells (Lindley C W, Curr Top Med Chem, 10, 458, 2010). A recent review of attempts to inhibit Akt members pinpoints Akt2 as the most commonly mutated family member in cancers and suggests that inhibition of Akt1 and Akt2 would be optimal (Mattmann M E et al "Inhibition of Akt with small molecules and biologies: historical perspective and current status of the patent landscape", Expert Opinion on Therapeutic Patents, 21, 1309, 2011). Many of the compounds covered in this review have poor selectivity for Akt compared to other kinases and generally focus on Akt1. Compounds reported in this review with selectivity between the different family members overwhelmingly inhibit Akt1 and/or Akt2, rather than Akt3.

Despite the overwhelming focus on Akt1 in the literature, Akt3 overexpression has been linked to several cancers including melanoma (Cancer Res. 2004 Oct. 1;64(19):7002-10) and ovarian cancer (Cancer Discov. 2012 Jan. 1;2(1): 56-67). WO2013/164788 discusses the use of Akt3 as a biomarker for detecting the occurrence of Epithelial-Mesenchymal Transition (EMT) in a subject and the subsequent use of Akt3 inhibitors to treat cancer, but no examples of Akt3-specific inhibitors are provided.

The Epithelial-Mesenchymal Transition (EMT) is a natural cellular program in which individual epithelial cells lose the gene expression patterns and behaviours characteristic of epithelial cells, and instead begin to look and behave like, and express genes typical of, mesenchymal cells. In so doing, they lose adhesion and apical-basal polarity and gain the ability to migrate and invade the extracellular matrix. EMT is not irreversible. A mirror process called Mesenchymal-Epithelial Transition (MET) results in the loss of mesenchymal characteristics and re-establishment of cell-cell adhesion and apical-basal polarity. EMT is especially important during embryonic development. It plays a fundamental role in gastrulation, where an embryo consisting of a single epithelial cell layer develops into one with the three classical germ layers: ectoderm, mesoderm and endoderm. Slightly later in vertebrate development, EMT gives rise to the neural crest cells. These cells migrate throughout the embryo and give rise to many different structures including ganglia of the peripheral nervous system, bone and cartilage of the face and head, pigment cells and glial cells. Further rounds of MET and EMT are essential for the formation of internal organs from both the mesoderm and endoderm.

Epithelial tissues make up one of the four basic tissue types of the body, along with connective tissue, muscle and nervous tissue. Epithelial cells are characterised by a tendency to form into sheets of polarised cells held together by strong intercellular junctions. As a consequence of this, epithelial cells are not able to move freely and show little migration compared to other cell types. In contrast, mesenchymal-like cells (e.g. fibroblasts) lack strong intercellular junctions and can move as individual cells. They can be highly motile and able to migrate through the extracellular matrix.

In contrast to its importance during embryonic development, the EMT program is seldom activated in healthy adults. It is, however, induced in response to inflammation following injury or disease: EMT plays a role in wound healing and tissue repair, and occurs during organ degenerative disease (e.g. renal fibrosis).

EMT is also increasingly understood to play a key role in cancer metastasis. Carcinomas are epithelial cancers, and, in order for metastasis to occur, individual cells must escape the primary tumour and undergo a series of migrations. These include migration from the primary tumour into the local circulatory or lymphatic system, and extravasation from the vasculature and establishment at the site of metastasis. There is now good and growing evidence that interactions between tumour cells and their microenvironment can lead to induction of EMT in some of the tumour cells. The resulting increased cell migration and invasion potential of these cells then enhances the likelihood of a metastasis becoming established. The receptor tyrosine kinase Axl, which is a chronic myelogenous leukaemia-associated oncogene, has been shown to be an essential EMT-induced effector in the invasion-metastasis cascade (WO2010/103388).

As well as this role in increasing metastatic potential, the EMT program has recently been linked with Cancer Stem Cells (CSCs). These cells have been postulated to represent a subset of tumour cells with stem cell characteristics, i.e. the ability to give rise to all the cell types found in a particular cancer, and thus the ability to form a new tumour. Although they may represent only a tiny fraction of the cells in a tumour, CSCs are thought to be particularly resistant to existing anti-cancer drugs. Even though drug treatment may kill the vast majority of cells in the tumour, a single surviving CSC can therefore lead to a relapse of the disease. Recent evidence suggests an overlap between EMT and CSC phenotypes, suggesting that EMT may also play a role in recurrence of cancer after chemotherapy and the development of drug-resistant tumours.

The role of Akt3 in EMT makes it an attractive target for the development of targeted cancer therapies. While pan-Akt inhibitors are known, they do not show very potent activity against Akt3 and have associated toxicity problems. For example, the inhibition of Akt2 is associated with glucose homeostasis defects. Akt1 is the most widely expressed isoform in the body and, being involved in overall growth, has the most serious knockout phenotype. Furthermore, simultaneous inhibition of Akt1 and Akt2 has been found to lead to feedback amplification of Akt signalling, which may lead to resistance of the cancer against the treatment. There is thus a need to develop inhibitors which have specificity for Akt3, reducing or eliminating the undesirable effects described above that are associated with inhibition of Akt1 and Akt2.

This invention is directed to pyridine, pyridazine and triazine derivatives which are useful in the treatment of cancer.

According to a first aspect of the invention, there is provided a compound of formula (I):

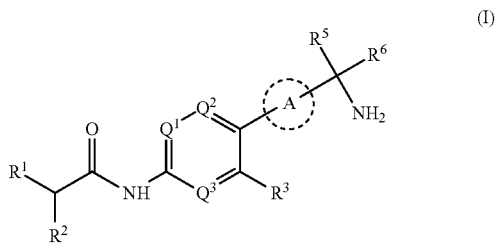

wherein
either
(a) one of $Q^1$ and $Q^2$ represents a nitrogen atom and the other represents CH, or both $Q^1$ and $Q^2$ represent nitrogen atoms, and $Q^3$ represents CH; or
(b) $Q^1$, $Q^2$ and $Q^3$ all represent nitrogen atoms;
A represents an optionally substituted five- or six-membered aromatic ring;
$R^1$ represents an aliphatic carbocyclic or heterocyclic ring, optionally substituted by —(C=O)$_x$NR$^a$R$^b$, —OR$^c$, —SO$_2$R$^g$ or optionally substituted alkyl, in which x is 0 or 1;
$R^a$ and $R^b$ independently represent (a) H, (b) optionally substituted alkyl, (c) optionally substituted cycloalkyl, (d) optionally substituted heterocycloalkyl, (e) —(C=O)R$^d$, or (f) —SO$_2$R$^e$, wherein R$^d$ and R$^e$ independently represent (i) optionally substituted alkyl, (ii) optionally substituted alkoxy, or (iii) optionally substituted cycloalkyl; or R$^a$ and R$^b$ together with the nitrogen atom to which they are attached form an optionally substituted aromatic or aliphatic heterocyclic ring;
$R^c$ represents optionally substituted alkyl;
and
$R^g$ represents optionally substituted cycloalkyl;
$R^2$ represents H, optionally substituted alkyl or halo;
$R^3$ represents an optionally substituted aryl or heteroaryl ring;
$R^5$ and $R^6$ independently represent H or optionally substituted alkyl; or $R^5$ and $R^6$ together with the carbon atom to which they are attached form an optionally substituted cycloalkyl ring, optionally containing a heteroatom;
and the corresponding N-oxides, and their prodrugs; and pharmaceutically acceptable salts and solvates (e.g. hydrates) of such compounds and their N-oxides and prodrugs.

As used in the specification and appended claims, unless specified to the contrary, the following terms have the meaning indicated:

"Oxo" refers to an =O radical.

"Alkyl" refers to a straight or branched saturated hydrocarbon chain radical consisting solely of carbon and hydrogen atoms, having from one to twelve carbon atoms, preferably one to eight carbon atoms or one to six carbon atoms, and which is attached to the rest of the molecule by a single bond, for example, methyl, ethyl, n-propyl, 1-methylethyl, 1,1-dimethylethyl, 2,2-dimethylpropyl, t-butyl and the like. "$C_{1-6}$ alkyl" refers to an alkyl as described above, having from one to six carbon atoms.

"Alkoxy" refers to a radical of the formula —OR$^8$ where R$^8$ is an alkyl radical as defined above containing from one to twelve carbon atoms. $C_{1-6}$ alkoxy refers to an alkoxy as previously defined, wherein $R^8$ is an alkyl radical containing from one to six carbon atoms.

"Aryl" refers to an aromatic hydrocarbon ring system radical comprising hydrogen and from five to ten carbon atoms. An aryl radical is commonly, but not necessarily, attached to the compound via an aromatic ring of the aryl radical. Aryl radicals include, but are not limited to, aryl radicals derived from benzene.

"Cycloalkyl" or "carbocycle" refers to a stable non-aromatic monocyclic hydrocarbon radical consisting solely of carbon and hydrogen atoms, having from three to ten carbon atoms, preferably having from three to six carbon atoms, and which is unsaturated and attached to the rest of the molecule by a single bond. Cycloalkyl radicals include, for example, cyclopropyl, cyclobutyl, cyclopentyl, cyclohexyl, cycloheptyl and cyclooctyl. $C_{3-6}$ cycloalkyl refers to cycloalkyl groups containing from three to six carbon atoms, e.g. cyclopropyl, cyclobutyl, cyclopentyl and cyclohexyl.

"Halo" refers to a halogen radical, i.e. F, Cl, Br or I.

"Heterocycloalkyl" or "heterocycle" refers to a stable 3- to 10-membered aliphatic mono or bicyclic ring radical which comprises one to nine carbon atoms and from one to four heteroatoms selected from the group consisting of nitrogen, oxygen and sulfur. Unless stated otherwise, the nitrogen, carbon or sulfur atoms in the heterocycloalkyl radical may be optionally oxidized; the nitrogen atom may be optionally quaternized; and the heterocycloalkyl radical may be partially or fully saturated. Examples of such heterocycloalkyl radicals include, but are not limited to morpholinyl, oxazolidinyl, oxetanyl, piperidyl, pyrrolidinyl and octahydro-2(1H)-quinolinonyl.

"Heteroaryl" refers to a 5- to 10-membered ring system radical comprising hydrogen atoms, one to nine carbon atoms, one to four heteroatoms selected from the group consisting of nitrogen, oxygen and sulfur, and at least one aromatic ring, the aromatic ring comprising at least one of the heteroatoms. A heteroaryl radical is commonly, but not necessarily, attached to the compound via an aromatic ring of the heteroaryl radical. For purposes of this invention, the heteroaryl radical may be a monocyclic, bicyclic or tricyclic ring system, but is preferably monocyclic. The nitrogen, carbon or sulfur atoms in the heteroaryl radical may be optionally oxidized, and the nitrogen atom may be optionally quaternized. Examples of heteroaryl radicals include, but are not limited to, piperazinyl, pyridyl, thienyl and triazinyl.

Certain chemical groups named herein may be preceded by a shorthand notation indicating the total number of carbon atoms that are to be found in the indicated chemical group. For example, $C_{1-6}$ alkyl describes an alkyl group, as defined above, having a total of from 1 to 6 carbon atoms, and $C_{3-6}$ cycloalkyl describes a cycloalkyl group, as defined above, having a total of from 3 to 6 carbon atoms. The total number of carbons in the shorthand notation does not include carbons that may exist in substituents of the group described.

"Optional" or "optionally" means that the subsequently described condition may or may not occur. For example, "optionally substituted aryl" means that the aryl radical may carry one or more substituents or may be unsubstituted. Unless indicated otherwise, "optionally substituted" means that one or more substituents may be present, and where there is more than one substituent, those substituents may be the same or different.

In general, but without limitation and unless otherwise indicated:

a) an "optionally substituted alkyl" group may carry one or more substituents selected from alkoxy (e.g. $C_{1-6}$ alkoxy), cycloalkyl (e.g. $C_{1-3}$ cycloalkyl) and halo.

b) an "optionally substituted cycloalkyl" group may carry one or more substituents selected from alkyl (e.g. $C_{1-6}$ alkyl), alkoxy (e.g. $C_{1-6}$ alkoxy), OH and halo.

c) an "optionally substituted heterocycloalkyl" group may carry one or more substituents selected from alkyl (e.g. $C_{1-6}$ alkyl), alkoxy (e.g. $C_{1-6}$ alkoxy), OH and halo.

d) an "optionally substituted alkoxy" group may carry one or more substituents selected from alkyl (e.g. $C_{1-6}$ alkyl), cycloalkyl (e.g. $C_{1-3}$ cycloalkyl) and halo.

e) an "optionally substituted aromatic or aliphatic heterocyclic" group may carry one or more substituents selected from alkyl (e.g. $C_{1-6}$ alkyl), alkoxy (e.g. $C_{1-6}$ alkoxy), oxo and halo.

f) an "optionally substituted aryl" group may carry one or more substituents selected from alkyl (e.g. $C_{1-6}$ alkyl), alkoxy (e.g. $C_{1-6}$ alkoxy), OH and halo.

g) an "optionally substituted heteroaryl" group may carry one or more substituents selected from alkyl (e.g. $C_{1-6}$ alkyl), alkoxy (e.g. $C_{1-6}$ alkoxy), OH and halo h) an "optionally substituted five- or six-membered aromatic ring" may carry one or more substituents selected from alkyl (e.g. $C_{1-6}$ alkyl), alkoxy (e.g. $C_{1-6}$ alkoxy), OH and halo.

"Pharmaceutically acceptable excipient" includes without limitation any adjuvant, carrier, excipient, glidant, sweetening agent, diluent, preservative, dye/colourant, flavour enhancer, surfactant, wetting agent, dispersing agent, suspending agent, stabilizer, isotonic agent, solvent, or emulsifier which is suitable for use in humans or domestic animals.

"Pharmaceutically acceptable salt" includes both acid and base addition salts.

"Prodrug" means a compound which is convertible in vivo by metabolic means (e.g. by hydrolysis) to a compound of formula (I), including N-oxides thereof. For example, an ester of a compound of formula (I) containing a hydroxy group may be convertible by hydrolysis in vivo to the compound of formula (I).

"Therapeutically effective amount" refers to that amount of a compound of the invention which, when administered to a subject, preferably a mammal, and more particularly a human, is sufficient to effect treatment, as defined below, of a disease or condition of interest in the subject, preferably a human. The amount of a compound of the invention which constitutes a "therapeutically effective amount" will vary depending on the compound, the disease or condition and its severity, and the age of the subject to be treated, but can be determined routinely by one of ordinary skill in the art having regard to his own knowledge and to this disclosure.

"Treating" or "treatment" as used herein covers the treatment of the disease or condition of interest in a subject, preferably a mammal, and more particularly a human, having the disease or condition of interest, and includes:

(i) preventing the disease or condition from occurring in a subject, in particular, when such subject is predisposed to the condition but has not yet been diagnosed as having it;

(ii) inhibiting the disease or condition, i.e., arresting its development;

(iii) relieving the disease or condition, i.e., causing regression of the disease or condition; or (iv) stabilizing the disease or condition.

The compounds of the invention, or their pharmaceutically acceptable salts, may contain one or more asymmetric centres and may thus give rise to enantiomers, diastereomers, and other stereoisomeric forms that may be defined, in terms of absolute stereochemistry, as (R)- or (S)- or as (D)- or (L)- for amino acids. The present invention includes all such possible isomers, as well as their racemic and optically pure forms. Optically active (+) and (−), (R)- and (S)-, or (D)- and (L)-isomers may be prepared using chiral synthons or chiral reagents, or resolved using conventional techniques, such as HPLC using a chiral column. When the compounds described herein contain olefinic double bonds or other centres of geometric asymmetry, and unless specified otherwise, it is intended that the compounds include both E and Z geometric isomers. Likewise, all tautomeric forms are also intended to be included.

A "stereoisomer" refers to a compound made up of the same atoms bonded by the same bonds but having different three-dimensional structures, which are not interchangeable. The present invention contemplates various stereoisomers and mixtures thereof and includes "enantiomers", which refers to two stereoisomers whose molecules are nonsuperimposeable mirror images of one another.

A "tautomer" refers to a proton shift from one atom of a molecule to another atom of the same molecule. The present invention includes tautomers of any said compounds. "Atropisomers" are stereoisomers resulting from hindered rotation about single bonds where the barrier to rotation is high enough to allow for the isolation of the conformers (Eliel, E. L.; Wilen, S. H. Stereochemistry of Organic Compounds; Wiley & Sons: New York, 1994; Chapter 14). Atropisomerism is significant because it introduces an element of chirality in the absence of stereogenic atoms. The invention is meant to encompass atropisomers, for example in cases of limited rotation around the single bonds emanating from the core triazole structure, atropisomers are also possible and are also specifically included in the compounds of the invention.

Particular embodiments of the compounds of formula (I) described in the first aspect of the invention are set out below. It is to be understood that this invention covers all appropriate combinations of the substituents referred to herein, and that, where alternatives are provided for any one substituent, the invention covers all lists which may be formed by combinations of these alternatives.

In the compounds of formula (I), unless otherwise stated, any or all alkyl groups may independently be $C_{1-6}$ alkyl groups, any or all alkoxy groups may independently be $C_{1-6}$ alkoxy groups, and/or any or all cycloalkyl groups may independently be $C_{3-6}$ cycloalkyl groups.

One of $Q^1$ and $Q^2$ may represent a nitrogen atom while the other represents CH, i.e. $Q^1$ represents a nitrogen atom and $Q^2$ represents CH, or $Q^1$ represents CH and $Q^2$ represents a nitrogen atom. When one of $Q^1$ or $Q^2$ represents CH, $Q^3$ represents CH.

Alternatively, $Q^1$ and $Q^2$ may both represent nitrogen atoms, and $Q^3$ may represent CH.

Alternatively, $Q^1$, $Q^2$ and $Q^3$ may all represent nitrogen atoms.

A may represent an optionally substituted five- or six-membered aromatic ring, and may be carbocyclic or heterocyclic.

A may represent an optionally substituted five- or six-membered heterocyclic ring. The heterocyclic ring may contain one, two or three heteroatoms, which may be the same or different, and may be selected from N, O and/or S. For example, A may represent optionally substituted pyridyl, pyrimidinyl, thienyl, oxadiazolyl or pyridazinyl.

A may represent optionally substituted phenyl.

A may be optionally substituted by halo, e.g. F, or by $C_{1-6}$ alkoxy, e.g. —$OCH_3$.

$R^1$ may represent a six-membered aliphatic carbocyclic or heterocyclic ring, optionally substituted by —$(C=O)_xN$-$R^aR^b$, —$OR^c$, —$SO_2R^g$ or optionally substituted alkyl.

$R^1$ may represent an aliphatic carbocyclic ring optionally substituted by —$(C=O)_xNR^aR^b$, —$OR^c$, —$SO_2R^g$ or optionally substituted alkyl.

$R^1$ may represent a six-membered aliphatic carbocyclic ring, optionally substituted by —$(C=O)_xNR^aR^b$, —$OR^c$, —$SO_2R^g$ or optionally substituted alkyl.

$R^1$ may represent a six-membered aliphatic carbocyclic ring, optionally substituted by —$(C=O)_xNR^aR^b$ or —$OR^c$.

$R^1$ may represent a six-membered aliphatic carbocyclic ring, optionally substituted by —$(C=O)_xNR^aR^b$.

$R^1$ may represent a six-membered aliphatic carbocyclic ring, optionally substituted by —$OR^c$.

$R^1$ may represent a six-membered aliphatic heterocyclic ring, optionally substituted by —$(C=O)_xNR^aR^b$, —$OR^c$, —$SO_2R^g$ or optionally substituted alkyl.

$R^1$ may represent a six-membered aliphatic heterocyclic ring, optionally substituted by —$SO_2R^g$ or optionally substituted alkyl.

$R^1$ may represent a six-membered aliphatic heterocyclic ring, optionally substituted by —$SO_2R^g$.

$R^1$ may represent a six-membered aliphatic heterocyclic ring, optionally substituted by optionally substituted alkyl.

$R^1$ may represent a six-membered aliphatic heterocyclic ring, optionally substituted by alkyl.

x may be 0, or x may be 1.

$R^a$ and/or $R^b$ may represent H.

$R^a$ and/or $R^b$ may represent optionally substituted alkyl, optionally substituted cycloalkyl or optionally substituted heterocycloalkyl.

$R^a$ and/or $R^b$ may represent alkyl optionally substituted by alkoxy, cycloalkyl or a heterocycloalkyl ring, any of which is optionally substituted by alkyl.

$R^a$ and/or $R^b$ may represent alkyl optionally substituted by alkoxy, for example —$OCH_3$.

$R^a$ and/or $R^b$ may represent cycloalkyl optionally substituted by alkyl.

For instance, $R^a$ and/or $R^b$ may represent cyclopropyl or cyclobutyl, any of which is optionally substituted by alkyl.

$R^a$ and/or $R^b$ may represent a heterocycloalkyl ring optionally substituted by alkyl.

For instance, $R^a$ and/or $R^b$ may represent a 3- to 6-membered heterocycloalkyl ring, optionally substituted by alkyl.

$R^a$ and/or $R^b$ may represent a 4-membered heterocycloalkyl ring, optionally substituted by alkyl.

$R^a$ and/or $R^b$ may represent oxetanyl, optionally substituted by alkyl.

$R^a$ and/or $R^b$ may represent —$(C=O)R^d$, or $R^a$ and/or $R^b$ may represent —$SO_2R^e$.

$R^a$ and $R^b$ may, together with the nitrogen atom to which they are attached, form an optionally substituted aromatic or aliphatic heterocyclic ring, for example an optionally substituted 5- or 6-membered aromatic or aliphatic heterocyclic ring. The ring may be optionally substituted by oxo or alkyl.

In particular, $R^a$ and $R^b$ may, together with the nitrogen atom to which they are attached, form a 5- or 6-membered aromatic or aliphatic heterocyclic ring selected from triazinyl, oxazolidinyl, pyrrolidinyl, piperidinyl and morpholinyl, any of which may be optionally substituted by oxo or alkyl.

$R^a$ and $R^b$ may, together with the nitrogen atom to which they are attached, form triazinyl, morpholinonyl, oxazolidinonyl, pyrrolidonyl or piperidonyl, any of which may be optionally substituted by alkyl.

One of $R^a$ and $R^b$ may represent H or optionally substituted alkyl, while the other of $R^a$ and $R^b$ represents (i) optionally substituted alkyl, (ii) optionally substituted cycloalkyl, (iii) optionally substituted heterocycloalkyl, (v) —(C=O)$R^d$, or (vi) —SO$_2$$R^e$.

One of $R^a$ and $R^b$ may represent H or alkyl, while the other of $R^a$ and $R^b$ represents (i) alkyl optionally substituted by alkoxy, (ii) cycloalkyl optionally substituted by alkyl, (iii) a 3- to 6-membered heterocycloalkyl ring optionally substituted by alkyl, (iv) —(C=O)$R^d$, or (v) —SO$_2$$R^e$.

$R^d$ and/or $R^e$ may represent optionally substituted alkyl, for instance alkyl optionally substituted by cycloalkyl, halo, e.g. F, or alkoxy, e.g. —OCH$_3$.

$R^d$ and/or $R^e$ may represent —CH$_3$, —CHF$_2$, —C(CH$_3$)$_2$CF$_3$, —C(CH$_3$)$_3$, —CH$_2$C(CH$_3$)$_3$, —CH(CH$_3$)$_2$, —CH$_2$CH$_3$ or —CH$_2$CH$_2$CH$_3$.

$R^d$ and/or $R^e$ may represent alkyl optionally substituted by cyclopropyl or cyclobutyl, for example —CH$_2$-cyclopropyl.

$R^d$ and/or $R^e$ may represent alkoxy, for example —OCH$_3$ or —OCH$_2$CH$_3$.

$R^d$ and/or $R^e$ may represent optionally substituted cycloalkyl, for example cycloalkyl optionally substituted by alkyl.

In particular, $R^d$ and/or $R^e$ may represent cyclopropyl or cyclobutyl optionally substituted by alkyl, for example methyl.

$R^c$ may represent alkyl, for example methyl.

$R^g$ may represent cycloalkyl, for example cyclopropyl.

$R^2$ may be H.

$R^2$ may be optionally substituted alkyl, or $R^2$ may be alkyl, for example methyl.

$R^2$ may be halo, for example F.

$R^3$ may be an optionally substituted 5- or 6-membered aryl or heteroaryl ring, for example optionally substituted by alkyl or halo, for instance F.

In particular, $R^3$ may be phenyl, optionally substituted by alkyl, e.g. methyl, or halo, e.g. F.

$R^3$ may be phenyl.

$R^3$ may be thienyl optionally substituted by alkyl, e.g. methyl, or halo, e.g. F.

$R^3$ may be thienyl.

$R^3$ may be pyridyl optionally substituted by alkyl, e.g. methyl, or halo, e.g. F.

$R^3$ may be pyridyl.

$R^5$ and/or $R^6$ may represent H.

$R^5$ and/or $R^6$ may represent alkyl, e.g. methyl, optionally substituted by halo, e.g. F.

$R^5$ and/or $R^6$ may represent methyl optionally substituted by F.

$R^5$ and/or $R^6$ may represent —CHF$_2$.

$R^5$ and/or $R^6$ may represent alkyl, for example methyl.

$R^5$ and $R^6$ may represent methyl.

$R^5$ and $R^6$ may, together with the carbon atom to which they are attached, form an optionally substituted cycloalkyl ring, optionally containing a heteroatom. The ring may be an optionally substituted 3- or 4-membered cycloalkyl ring, optionally containing a heteroatom. Optional substituents include OH, alkyl and/or halo.

Thus, $R^5$ and $R^6$ may, together with the carbon atom to which they are attached, form a 3- or 4-membered cycloalkyl ring, optionally containing a heteroatom and optionally substituted by —OH, alkyl and/or F.

In particular, $R^5$ and $R^6$ may, together with the carbon atom to which they are attached, form a cyclopropyl or cyclobutyl ring, optionally substituted by —OH, alkyl and/or F.

$R^5$ and $R^6$ may, together with the carbon atom to which they are attached, form a cyclopropyl ring.

$R^5$ and $R^6$ may, together with the carbon atom to which they are attached, form a cyclobutyl ring, optionally substituted by —OH, alkyl and/or F.

$R^5$ and $R^6$ may, together with the carbon atom to which they are attached, form 2,2-difloro-cyclobutyl or 2-methyl-2-hydroxy-cyclobutyl.

$R^5$ and $R^6$ may, together with the carbon atom to which they are attached, form a 3- or 4-membered cycloalkyl ring, containing a heteroatom selected from N, O and S, and optionally substituted by —OH, alkyl and/or halo.

$R^5$ and $R^6$ may, together with the carbon atom to which they are attached, form a 3- or 4-membered cycloalkyl ring, containing an oxygen heteroatom and optionally substituted by —OH, alkyl and/or halo.

$R^5$ and $R^6$ may, together with the carbon atom to which they are attached, form an oxetanyl ring, optionally substituted by —OH, alkyl and/or halo.

$R^5$ and $R^6$ may, together with the carbon atom to which they are attached, form an oxetanyl ring.

A preferred embodiment of the compound of formula (I), as described above, is where the compound of formula (I) is a compound of formula (Ia):

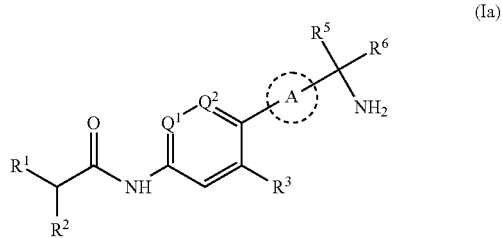

(Ia)

wherein one of $Q^1$ and $Q^2$ represents a nitrogen atom and the other represents CH, or both $Q^1$ and $Q^2$ represent nitrogen atoms;

A represents an optionally substituted five- or six-membered aromatic ring;

$R^1$ represents an aliphatic carbocyclic or heterocyclic ring, optionally substituted by —(C=O)$_x$NR$^a$R$^b$, —OR$^c$, —SO$_2$R$^g$ or optionally substituted alkyl, in which x is 0 or 1;

$R^a$ and $R^b$ independently represent (a) H, (b) optionally substituted alkyl, (c) optionally substituted cycloalkyl, (d) optionally substituted heterocycloalkyl, (e) —(C=O)R$^d$, or (f) —SO$_2$R$^e$, wherein R$^d$ and R$^e$ independently represent (i) optionally substituted alkyl, (ii) optionally substituted alkoxy, or (iii) optionally substituted cycloalkyl; or R$^a$ and R$^b$ together with the nitrogen atom to which they are attached form an optionally substituted aromatic or aliphatic heterocyclic ring;

$R^c$ represents optionally substituted alkyl; and $R^g$ represents optionally substituted cycloalkyl;

$R^2$ represents H, optionally substituted alkyl or halo;

$R^3$ represents an optionally substituted aryl or heteroaryl ring;

$R^5$ and $R^6$ independently represent H or optionally substituted alkyl; or $R^5$ and $R^6$ together with the carbon atom to which they are attached form an optionally substituted cycloalkyl ring, optionally containing a heteroatom;

and the corresponding N-oxides, and their prodrugs; and pharmaceutically acceptable salts and solvates (e.g. hydrates) of such compounds and their N-oxides and prodrugs.

Particular embodiments of the compounds of formula (Ia) described above are set out below. It is to be understood that this invention covers all appropriate combinations of the substituents referred to herein, and that, where alternatives are provided for any one substituent, the invention covers all lists which may be formed by combinations of these alternatives.

In the compounds of formula (Ia), unless otherwise stated, any or all alkyl groups may independently be $C_{1-6}$ alkyl groups, any or all alkoxy groups may independently be $C_{1-6}$ alkoxy groups, and/or any or all cycloalkyl groups may independently be $C_{3-6}$ cycloalkyl groups.

One of $Q^1$ and $Q^2$ may represent a nitrogen atom while the other represents CH, i.e. $Q^1$ represents a nitrogen atom and $Q^2$ represents CH, or $Q^1$ represents CH and $Q^2$ represents a nitrogen atom.

Alternatively, $Q^1$ and $Q^2$ may both represent nitrogen atoms.

A may represent an optionally substituted five- or six-membered aromatic ring, and may be carbocyclic or heterocyclic.

A may represent an optionally substituted five- or six-membered heterocyclic ring. The heterocyclic ring may contain one, two or three heteroatoms, which may be the same or different, and may be selected from N, O and/or S. For example, A may represent optionally substituted pyridyl, pyrimidinyl, thienyl, oxadiazolyl or pyridazinyl.

A may represent optionally substituted phenyl.

A may be optionally substituted by halo, e.g. F, or by $C_{1-6}$ alkoxy, e.g. —OCH$_3$.

$R^1$ may represent a six-membered aliphatic carbocyclic or heterocyclic ring, optionally substituted by —(C=O)$_x$NR$^a$R$^b$, —OR$^c$, —SO$_2$R$^g$ or optionally substituted alkyl.

$R^1$ may represent an aliphatic carbocyclic ring optionally substituted by —(C=O)$_x$NR$^a$R$^b$, —OR$^c$, —SO$_2$R$^g$ or optionally substituted alkyl.

$R^1$ may represent a six-membered aliphatic carbocyclic ring, optionally substituted by —(C=O)$_x$NR$^a$R$^b$, —OR$^c$, —SO$_2$R$^g$ or optionally substituted alkyl.

$R^1$ may represent a six-membered aliphatic carbocyclic ring, optionally substituted by —(C=O)$_x$NR$^a$R$^b$ or —OR$^c$.

$R^1$ may represent a six-membered aliphatic carbocyclic ring, optionally substituted by —(C=O)$_x$NR$^a$R$^b$.

$R^1$ may represent a six-membered aliphatic carbocyclic ring, optionally substituted by —OR$^c$.

$R^1$ may represent a six-membered aliphatic heterocyclic ring, optionally substituted by —(C=O)$_x$NR$^a$R$^b$, —OR$^c$, —SO$_2$R$^g$ or optionally substituted alkyl.

$R^1$ may represent a six-membered aliphatic heterocyclic ring, optionally substituted by —SO$_2$R$^g$ or optionally substituted alkyl.

$R^1$ may represent a six-membered aliphatic heterocyclic ring, optionally substituted by —SO$_2$R$^g$.

$R^1$ may represent a six-membered aliphatic heterocyclic ring, optionally substituted by optionally substituted alkyl.

$R^1$ may represent a six-membered aliphatic heterocyclic ring, optionally substituted by alkyl.

x may be 0, or x may be 1.

$R^a$ and/or $R^b$ may represent H.

$R^a$ and/or $R^b$ may represent optionally substituted alkyl, optionally substituted cycloalkyl or optionally substituted heterocycloalkyl.

$R^a$ and/or $R^b$ may represent alkyl optionally substituted by alkoxy, cycloalkyl or a heterocycloalkyl ring, any of which is optionally substituted by alkyl.

$R^a$ and/or $R^b$ may represent alkyl optionally substituted by alkoxy, for example —OCH$_3$.

$R^a$ and/or $R^b$ may represent cycloalkyl optionally substituted by alkyl.

For instance, $R^a$ and/or $R^b$ may represent cyclopropyl or cyclobutyl, any of which is optionally substituted by alkyl.

$R^a$ and/or $R^b$ may represent a heterocycloalkyl ring optionally substituted by alkyl.

For instance, $R^a$ and/or $R^b$ may represent a 3- to 6-membered heterocycloalkyl ring, optionally substituted by alkyl.

$R^a$ and/or $R^b$ may represent a 4-membered heterocycloalkyl ring, optionally substituted by alkyl.

$R^a$ and/or $R^b$ may represent oxetanyl, optionally substituted by alkyl.

$R^a$ and/or $R^b$ may represent —(C=O)R$^d$, or $R^a$ and/or $R^b$ may represent —SO$_2$R$^e$.

$R^a$ and $R^b$ may, together with the nitrogen atom to which they are attached, form an optionally substituted aromatic or aliphatic heterocyclic ring, for example an optionally substituted 5- or 6-membered aromatic or aliphatic heterocyclic ring. The ring may be optionally substituted by oxo or alkyl.

In particular, $R^a$ and $R^b$ may, together with the nitrogen atom to which they are attached, form a 5- or 6-membered aromatic or aliphatic heterocyclic ring selected from triazinyl, oxazolidinyl, pyrrolidinyl, piperidinyl and morpholinyl, any of which may be optionally substituted by oxo or alkyl.

$R^a$ and $R^b$ may, together with the nitrogen atom to which they are attached, form triazinyl, morpholinonyl, oxazolidinonyl, pyrrolidonyl or piperidonyl, any of which may be optionally substituted by alkyl.

One of $R^a$ and $R^b$ may represent H or optionally substituted alkyl, while the other of $R^a$ and $R^b$ represents (i) optionally substituted alkyl, (ii) optionally substituted cycloalkyl, (iii) optionally substituted heterocycloalkyl, (v) —(C=O)R$^d$, or (vi) —SO$_2$R$^e$.

One of $R^a$ and $R^b$ may represent H or alkyl, while the other of $R^a$ and $R^b$ represents (i) alkyl optionally substituted by alkoxy, (ii) cycloalkyl optionally substituted by alkyl, (iii) 3- to 6-membered heterocycloalkyl ring optionally substituted by alkyl, (iv) —(C=O)R$^d$, or (v) —SO$_2$R$^e$.

$R^d$ and/or $R^e$ may represent optionally substituted alkyl, for instance alkyl optionally substituted by cycloalkyl, halo, e.g. F, or alkoxy, e.g. —OCH$_3$.

$R^d$ and/or $R^e$ may represent —CH$_3$, —CHF$_2$, —C(CH$_3$)$_2$CF$_3$, —C(CH$_3$)$_3$, —CH$_2$C(CH$_3$)$_3$, —CH(CH$_3$)$_2$ or —CH$_2$CH$_2$CH$_3$.

$R^d$ and/or $R^e$ may represent alkyl optionally substituted by cyclopropyl or cyclobutyl, for example —CH$_2$-cyclopropyl.

$R^d$ and/or $R^e$ may represent alkoxy, for example —OCH$_3$ or —OCH$_2$CH$_3$.

$R^d$ and/or $R^e$ may represent optionally substituted cycloalkyl, for example cycloalkyl optionally substituted by alkyl.

In particular, $R^d$ and/or $R^e$ may represent cyclopropyl or cyclobutyl optionally substituted by alkyl, for example methyl.

$R^c$ may represent alkyl, for example methyl.

$R^g$ may represent cycloalkyl, for example cyclopropyl.

$R^2$ may be H.

$R^2$ may be optionally substituted alkyl, or $R^2$ may be alkyl, for example methyl.

$R^2$ may be halo, for example F.

$R^3$ may be an optionally substituted 5- or 6-membered aryl or heteroaryl ring, for example optionally substituted by alkyl or halo, for instance F.

In particular, $R^3$ may be phenyl, optionally substituted by alkyl, e.g. methyl, or halo, e.g. F.

$R^3$ may be phenyl.

$R^3$ may be thienyl optionally substituted by alkyl, e.g. methyl, or halo, e.g. F.

$R^3$ may be thienyl.

$R^3$ may be pyridyl optionally substituted by alkyl, e.g. methyl, or halo, e.g. F.

$R^3$ may be pyridyl.

$R^5$ and/or $R^6$ may represent H.

$R^5$ and/or $R^6$ may represent alkyl, e.g. methyl, optionally substituted by halo, e.g. F.

$R^5$ and/or $R^6$ may represent methyl optionally substituted by F.

$R^5$ and/or $R^6$ may represent —$CHF_2$.

$R^5$ and/or $R^6$ may represent alkyl, for example methyl.

$R^5$ and $R^6$ may represent methyl.

$R^5$ and $R^6$ may, together with the carbon atom to which they are attached, form an optionally substituted cycloalkyl ring, optionally containing a heteroatom. The ring may be an optionally substituted 3- or 4-membered cycloalkyl ring, optionally containing a heteroatom. Optional substituents include OH, alkyl and/or halo.

Thus, $R^5$ and $R^6$ may, together with the carbon atom to which they are attached, form a 3- or 4-membered cycloalkyl ring, optionally containing a heteroatom and optionally substituted by —OH, alkyl and/or F.

In particular, $R^5$ and $R^6$ may, together with the carbon atom to which they are attached, form a cyclopropyl or cyclobutyl ring, optionally substituted by —OH, alkyl and/or F.

$R^5$ and $R^6$ may, together with the carbon atom to which they are attached, form a cyclopropyl ring.

$R^5$ and $R^6$ may, together with the carbon atom to which they are attached, form a cyclobutyl ring, optionally substituted by —OH, alkyl and/or F.

$R^5$ and $R^6$ may, together with the carbon atom to which they are attached, form 2,2-difloro-cyclobutyl or 2-methyl-2-hydroxy-cyclobutyl.

$R^5$ and $R^6$ may, together with the carbon atom to which they are attached, form a 3- or 4-membered cycloalkyl ring, containing a heteroatom selected from N, O and S, and optionally substituted by —OH, alkyl and/or halo.

$R^5$ and $R^6$ may, together with the carbon atom to which they are attached, form a 3- or 4-membered cycloalkyl ring, containing an oxygen heteroatom and optionally substituted by —OH, alkyl and/or halo.

$R^5$ and $R^6$ may, together with the carbon atom to which they are attached, form an oxetanyl ring, optionally substituted by —OH, alkyl and/or halo.

$R^5$ and $R^6$ may, together with the carbon atom to which they are attached, form an oxetanyl ring.

A preferred embodiment of the compound of formula (I), as described above, is where the compound of formula (I) is a compound of formula (Ib):

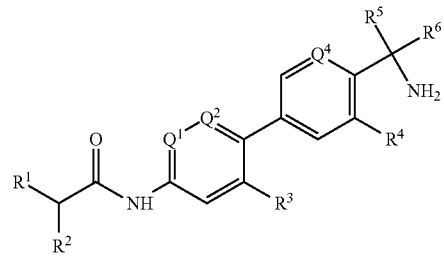

(Ib)

wherein
one of $Q^1$ and $Q^2$ represents a nitrogen atom and the other represents CH, or both $Q^1$ and $Q^2$ represent nitrogen atoms;
$Q^4$ represents CH or a nitrogen atom;
$R^1$ represents an aliphatic carbocyclic or heterocyclic ring, optionally substituted by —(C=O)$_x$NR$^a$R$^b$, —OR$^c$, —SO$_2$R$^g$ or optionally substituted alkyl, in which
  x is 0 or 1;
  $R^a$ and $R^b$ independently represent (a) H, (b) optionally substituted alkyl, (c) optionally substituted cycloalkyl, (d) optionally substituted heterocycloalkyl, (e) —(C=O)R$^d$, or (f) —SO$_2$R$^e$, wherein R$^d$ and R$^e$ independently represent (i) optionally substituted alkyl, (ii) optionally substituted alkoxy, or (iii) optionally substituted cycloalkyl; or R$^a$ and R$^b$ together with the nitrogen atom to which they are attached form an optionally substituted aromatic or aliphatic heterocyclic ring;
  R$^c$ represents optionally substituted alkyl;
  and
  R$^g$ represents optionally substituted cycloalkyl;
$R^2$ represents H, optionally substituted alkyl or halo;
$R^3$ represents an optionally substituted aryl or heteroaryl ring;
$R^4$ represents H, halo or —OR$^f$, where R$^f$ is optionally substituted alkyl;
$R^5$ and $R^6$ independently represent H or optionally substituted alkyl; or $R^5$ and $R^6$ together with the carbon atom to which they are attached form an optionally substituted cycloalkyl ring, optionally containing a heteroatom;
and the corresponding N-oxides, and their prodrugs; and pharmaceutically acceptable salts and solvates (e.g. hydrates) of such compounds and their N-oxides and prodrugs.

Particular embodiments of the compounds of formula (Ib) described above are set out below. It is to be understood that this invention covers all appropriate combinations of the substituents referred to herein, and that, where alternatives are provided for any one substituent, the invention covers all lists which may be formed by combinations of these alternatives.

In the compounds of formula (Ib), unless otherwise stated, any or all alkyl groups may independently be $C_{1-6}$ alkyl groups, any or all alkoxy groups may independently be $C_{1-6}$ alkoxy groups, and/or any or all cycloalkyl groups may independently be $C_{3-6}$ cycloalkyl groups.

One of $Q^1$ and $Q^2$ may represent a nitrogen atom while the other represents CH, i.e. $Q^1$ represents a nitrogen atom and $Q^2$ represents CH, or $Q^1$ represents CH and $Q^2$ represents a nitrogen atom.

Alternatively, $Q^1$ and $Q^2$ may both represent nitrogen atoms.

$Q^4$ may represent CH, or $Q^4$ may represent a nitrogen atom.

$R^1$ may represent a six-membered aliphatic carbocyclic or heterocyclic ring, optionally substituted by —(C=O)$_x$NR$^a$R$^b$, —OR$^c$, —SO$_2$R$^g$ or optionally substituted alkyl.

$R^1$ may represent an aliphatic carbocyclic ring optionally substituted by —(C=O)$_x$NR$^a$R$^b$, —OR$^c$, —SO$_2$R$^g$ or optionally substituted alkyl.

$R^1$ may represent a six-membered aliphatic carbocyclic ring, optionally substituted by —(C=O)$_x$NR$^a$R$^b$, —OR$^c$, —SO$_2$R$^g$ or optionally substituted alkyl.

$R^1$ may represent a six-membered aliphatic carbocyclic ring, optionally substituted by —(C=O)$_x$NR$^a$R$^b$ or —OR$^c$.

$R^1$ may represent a six-membered aliphatic carbocyclic ring, optionally substituted by —(C=O)$_x$NR$^a$R$^b$.

$R^1$ may represent a six-membered aliphatic carbocyclic ring, optionally substituted by —OR$^c$.

$R^1$ may represent a six-membered aliphatic heterocyclic ring, optionally substituted by —(C=O)$_x$NR$^a$R$^b$, —OR$^c$, —SO$_2$R$^g$ or optionally substituted alkyl.

$R^1$ may represent a six-membered aliphatic heterocyclic ring, optionally substituted by —SO$_2$R$^g$ or optionally substituted alkyl.

$R^1$ may represent a six-membered aliphatic heterocyclic ring, optionally substituted by —SO$_2$R$^g$.

$R^1$ may represent a six-membered aliphatic heterocyclic ring, optionally substituted by optionally substituted alkyl.

$R^1$ may represent a six-membered aliphatic heterocyclic ring, optionally substituted by alkyl.

x may be 0, or x may be 1.

$R^a$ and/or $R^b$ may represent H.

$R^a$ and/or $R^b$ may represent optionally substituted alkyl, optionally substituted cycloalkyl or optionally substituted heterocycloalkyl.

$R^a$ and/or $R^b$ may represent alkyl optionally substituted by alkoxy, cycloalkyl or a heterocycloalkyl ring, any of which is optionally substituted by alkyl.

$R^a$ and/or $R^b$ may represent alkyl optionally substituted by alkoxy, for example —OCH$_3$.

$R^a$ and/or $R^b$ may represent cycloalkyl optionally substituted by alkyl.

For instance, $R^a$ and/or $R^b$ may represent cyclopropyl or cyclobutyl, any of which is optionally substituted by alkyl.

$R^a$ and/or $R^b$ may represent a heterocycloalkyl ring optionally substituted by alkyl.

For instance, $R^a$ and/or $R^b$ may represent a 3- to 6-membered heterocycloalkyl ring, optionally substituted by alkyl.

$R^a$ and/or $R^b$ may represent a 4-membered heterocycloalkyl ring, optionally substituted by alkyl.

$R^a$ and/or $R^b$ may represent oxetanyl, optionally substituted by alkyl.

$R^a$ and/or $R^b$ may represent —(C=O)R$^d$, or $R^a$ and/or $R^b$ may represent —SO$_2$R$^e$.

$R^a$ and $R^b$ may, together with the nitrogen atom to which they are attached, form an optionally substituted aromatic or aliphatic heterocyclic ring, for example an optionally substituted 5- or 6-membered aromatic or aliphatic heterocyclic ring. The ring may be optionally substituted by oxo or alkyl.

In particular, $R^a$ and $R^b$ may, together with the nitrogen atom to which they are attached, form a 5- or 6-membered aromatic or aliphatic heterocyclic ring selected from triazinyl, oxazolidinyl, pyrrolidinyl, piperidinyl and morpholinyl, any of which may be optionally substituted by oxo or alkyl.

$R^a$ and $R^b$ may, together with the nitrogen atom to which they are attached, form triazinyl, morpholinonyl, oxazolidinonyl, pyrrolidonyl or piperidonyl, any of which may be optionally substituted by alkyl.

One of $R^a$ and $R^b$ may represent H or optionally substituted alkyl, while the other of $R^a$ and $R^b$ represents (i) optionally substituted alkyl, (ii) optionally substituted cycloalkyl, (iii) optionally substituted heterocycloalkyl, (v) —(C=O)R$^d$, or (vi) —SO$_2$R$^e$.

One of $R^a$ and $R^b$ may represent H or alkyl, while the other of $R^a$ and $R^b$ represents (i) alkyl optionally substituted by alkoxy, (ii) cycloalkyl optionally substituted by alkyl, (iii) a 3- to 6-membered heterocycloalkyl ring optionally substituted by alkyl, (iv) —(C=O)R$^d$, or (v) —SO$_2$R$^e$.

$R^d$ and/or $R^e$ may represent optionally substituted alkyl, for instance alkyl optionally substituted by cycloalkyl, halo, e.g. F, or alkoxy, e.g. —OCH$_3$.

$R^d$ and/or $R^e$ may represent —CH$_3$, —CHF$_2$, —C(CH$_3$)$_2$CF$_3$, —C(CH$_3$)$_3$, —CH$_2$C(CH$_3$)$_3$, —CH(CH$_3$)$_2$, —CH$_2$CH$_3$ or —CH$_2$CH$_2$CH$_3$.

$R^d$ and/or $R^e$ may represent alkyl optionally substituted by cyclopropyl or cyclobutyl, for example —CH$_2$-cyclopropyl.

$R^d$ and/or $R^e$ may represent alkoxy, for example —OCH$_3$ or —OCH$_2$CH$_3$.

$R^d$ and/or $R^e$ may represent optionally substituted cycloalkyl, for example cycloalkyl optionally substituted by alkyl.

In particular, $R^d$ and/or $R^e$ may represent cyclopropyl or cyclobutyl optionally substituted by alkyl, for example methyl.

$R^c$ may represent alkyl, for example methyl.

$R^g$ may represent cycloalkyl, for example cyclopropyl.

$R^2$ may be H.

$R^2$ may be optionally substituted alkyl, or $R^2$ may be alkyl, for example methyl.

$R^2$ may be halo, for example F.

$R^3$ may be an optionally substituted 5- or 6-membered aryl or heteroaryl ring, for example optionally substituted by alkyl or halo, for instance F.

In particular, $R^3$ may be phenyl, optionally substituted by alkyl, e.g. methyl, or halo, e.g. F.

$R^3$ may be phenyl.

$R^3$ may be thienyl optionally substituted by alkyl, e.g. methyl, or halo, e.g. F.

$R^3$ may be thienyl.

$R^3$ may be pyridyl optionally substituted by alkyl, e.g. methyl, or halo, e.g. F.

$R^3$ may be pyridyl.

$R^4$ may represent H.

$R^4$ may represent halo, for example F.

$R^4$ may represent —OR$^f$.

$R^f$ may represent optionally substituted alkyl.

$R^f$ may represent alkyl, for example methyl.

$R^5$ and/or $R^6$ may represent H.

$R^5$ and/or $R^6$ may represent alkyl, e.g. methyl, optionally substituted by halo, e.g. F.

$R^5$ and/or $R^6$ may represent methyl optionally substituted by F.

$R^5$ and/or $R^6$ may represent —CHF$_2$.

$R^5$ and/or $R^6$ may represent alkyl, for example methyl.

$R^5$ and $R^6$ may represent methyl.

$R^5$ and $R^6$ may, together with the carbon atom to which they are attached, form an optionally substituted cycloalkyl ring, optionally containing a heteroatom. The ring may be an optionally substituted 3- or 4-membered cycloalkyl ring, optionally containing a heteroatom. Optional substituents include OH, alkyl and/or halo.

Thus, $R^5$ and $R^6$ may, together with the carbon atom to which they are attached, form a 3- or 4-membered cycloalkyl ring, optionally containing a heteroatom and optionally substituted by —OH, alkyl and/or F.

In particular, $R^5$ and $R^6$ may, together with the carbon atom to which they are attached, form a cyclopropyl or cyclobutyl ring, optionally substituted by —OH, alkyl and/or F.

$R^5$ and $R^6$ may, together with the carbon atom to which they are attached, form a cyclopropyl ring.

$R^5$ and $R^6$ may, together with the carbon atom to which they are attached, form a cyclobutyl ring, optionally substituted by —OH, alkyl and/or F.

$R^5$ and $R^6$ may, together with the carbon atom to which they are attached, form 2,2-difloro-cyclobutyl or 2-methyl-2-hydroxy-cyclobutyl.

$R^5$ and $R^6$ may, together with the carbon atom to which they are attached, form a 3- or 4-membered cycloalkyl ring, containing a heteroatom selected from N, O and S, and optionally substituted by —OH, alkyl and/or halo.

$R^5$ and $R^6$ may, together with the carbon atom to which they are attached, form a 3- or 4-membered cycloalkyl ring, containing an oxygen heteroatom and optionally substituted by —OH, alkyl and/or halo.

$R^5$ and $R^6$ may, together with the carbon atom to which they are attached, form an oxetanyl ring, optionally substituted by —OH, alkyl and/or halo.

$R^5$ and $R^6$ may, together with the carbon atom to which they are attached, form an oxetanyl ring.

A preferred embodiment of the compound of formula (I), as described above, is where the compound of formula (I) is a compound of formula (Ic):

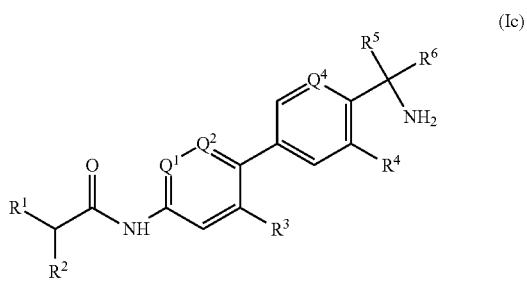

(Ic)

one of $Q^1$ and $Q^2$ represents a nitrogen atom and the other represents CH, or both $Q^1$ and $Q^2$ represent nitrogen atoms;

$Q^4$ represents CH or a nitrogen atom;

$R^1$ represents a six-membered aliphatic carbocyclic or heterocyclic ring, optionally substituted by —(C=O)$_x$N-$R^aR^b$, —OR$^c$, —SO$_2R^g$ or $C_{1-6}$ alkyl, in which
  x is 0 or 1;
  $R^a$ and $R^b$ independently represent (a) H, (b) $C_{1-6}$ alkyl optionally substituted by $C_{1-6}$ alkoxy, (c) $C_{3-6}$ cycloalkyl optionally substituted by $C_{1-6}$ alkyl, (d) a 3- to 6-membered heterocycloalkyl ring optionally substituted by $C_{1-6}$ alkyl, (ie) —(C=O)$R^d$, or (f) —SO$_2R^e$, wherein $R^d$ and $R^e$ independently represent (i) $C_{1-6}$ alkyl optionally substituted by cycloalkyl or halo, (ii) $C_{1-6}$ alkoxy, or (iii) $C_{3-6}$ cycloalkyl optionally substituted by $C_{1-6}$ alkyl; or $R^a$ and $R^b$ together with the nitrogen atom to which they are attached form a 5- or 6-membered aromatic or aliphatic heterocyclic ring optionally substituted by oxo or $C_{1-6}$ alkyl;
  $R^c$ represents $C_{1-6}$ alkyl;
  and
  $R^g$ represents $C_{3-6}$ cycloalkyl;

$R^2$ represents H, $C_{1-6}$ alkyl or halo;

$R^3$ represents a 5- or 6-membered aryl or heteroaryl ring, optionally substituted by $C_{1-6}$ alkyl or halo;

$R^4$ represents H, halo or —OR$^f$, where $R^f$ is $C_{1-6}$ alkyl;

$R^5$ and $R^6$ independently represent H or $C_{1-6}$ alkyl optionally substituted by halo; or $R^5$ and $R^6$ together with the carbon atom to which they are attached form a 3- or 4-membered cycloalkyl ring, optionally containing a heteroatom and optionally substituted by —OH, $C_{1-6}$ alkyl or halo;

and the corresponding N-oxides, and their prodrugs; and pharmaceutically acceptable salts and solvates (e.g. hydrates) of such compounds and their N-oxides and prodrugs.

Particular embodiments of the compounds of formula (Ic) described above are set out below. It is to be understood that this invention covers all appropriate combinations of the substituents referred to herein, and that, where alternatives are provided for any one substituent, the invention covers all lists which may be formed by combinations of these alternatives.

In the compounds of formula (Ic), unless otherwise stated, any or all alkyl groups may independently be $C_{1-6}$ alkyl groups, any or all alkoxy groups may independently be $C_{1-6}$ alkoxy groups, and/or any or all cycloalkyl groups may independently be $C_{3-6}$ cycloalkyl groups.

One of $Q^1$ and $Q^2$ may represent a nitrogen atom while the other represents CH, i.e. $Q^1$ represents a nitrogen atom and $Q^2$ represents CH, or $Q^1$ represents CH and $Q^2$ represents a nitrogen atom.

Alternatively, $Q^1$ and $Q^2$ may both represent nitrogen atoms.

$Q^4$ may represent CH, or $Q^4$ may represent a nitrogen atom.

$R^1$ may represent a six-membered aliphatic carbocyclic or heterocyclic ring, optionally substituted by —(C=O)$_x$N-$R^aR^b$, —OR$^c$, —SO$_2R^g$ or $C_{1-6}$ alkyl.

$R^1$ may represent an aliphatic carbocyclic ring optionally substituted by —(C=O)$_x$NR$^aR^b$, —OR$^c$, —SO$_2R^g$ or $C_{1-6}$ alkyl.

$R^1$ may represent a six-membered aliphatic carbocyclic ring, optionally substituted by —(C=O)$_x$NR$^aR^b$, —OR$^c$, —SO$_2R^g$ or $C_{1-6}$ alkyl.

$R^1$ may represent a six-membered aliphatic carbocyclic ring, optionally substituted by —(C=O)$_x$NR$^aR^b$ or —OR$^c$.

$R^1$ may represent a six-membered aliphatic carbocyclic ring, optionally substituted by —(C=O)$_x$NR$^aR^b$.

$R^1$ may represent a six-membered aliphatic carbocyclic ring, optionally substituted by —OR$^c$.

$R^1$ may represent a six-membered aliphatic heterocyclic ring, optionally substituted by —(C=O)$_x$NR$^aR^b$, —OR$^c$, —SO$_2R^g$ or $C_{1-6}$ alkyl.

$R^1$ may represent a six-membered aliphatic heterocyclic ring, optionally substituted by —SO$_2R^g$ or $C_{1-6}$ alkyl.

$R^1$ may represent a six-membered aliphatic heterocyclic ring, optionally substituted by —SO$_2R^g$.

$R^1$ may represent a six-membered aliphatic heterocyclic ring, optionally substituted by $C_{1-6}$ alkyl.

x may be 0, or x may be 1.

$R^a$ and/or $R^b$ may represent H.

$R^a$ and/or $R^b$ may represent $C_{1-6}$ alkyl optionally substituted by $C_{1-6}$ alkoxy, $C_{3-6}$ cycloalkyl optionally substituted by $C_{1-6}$ alkyl, or a 3- to 6-membered heterocycloalkyl ring optionally substituted by $C_{1-6}$ alkyl.

$R^a$ and/or $R^b$ may represent $C_{1-6}$ alkyl optionally substituted by $C_{1-6}$ alkoxy, for example —OCH$_3$.

$R^a$ and/or $R^b$ may represent $C_{3-6}$ cycloalkyl optionally substituted by $C_{1-6}$ alkyl.

For instance, $R^a$ and/or $R^b$ may represent cyclopropyl or cyclobutyl, any of which is optionally substituted by $C_{1-6}$ alkyl.

$R^a$ and/or $R^b$ may represent a 3- to 6-membered heterocycloalkyl ring optionally substituted by $C_{1-6}$ alkyl.

$R^a$ and/or $R^b$ may represent a 4-membered heterocycloalkyl ring, optionally substituted by $C_{1-6}$ alkyl.

$R^a$ and/or $R^b$ may represent oxetanyl, optionally substituted by $C_{1-6}$ alkyl.

$R^a$ and/or $R^b$ may represent $-(C=O)R^d$, or $R^a$ and/or $R^b$ may represent $-SO_2R^e$.

$R^a$ and $R^b$ may, together with the nitrogen atom to which they are attached, form a 5- or 6-membered aromatic or aliphatic heterocyclic ring, optionally substituted by oxo or $C_{1-6}$ alkyl.

In particular, $R^a$ and $R^b$ may, together with the nitrogen atom to which they are attached, form a 5- or 6-membered aromatic or aliphatic heterocyclic ring selected from triazinyl, oxazolidinyl, pyrrolidinyl, piperidinyl and morpholinyl, any of which may be optionally substituted by oxo or $C_{1-6}$ alkyl.

$R^a$ and $R^b$ may, together with the nitrogen atom to which they are attached, form triazinyl, morpholinonyl, oxazolidinonyl, pyrrolidonyl or piperidonyl, any of which may be optionally substituted by $C_{1-6}$ alkyl.

One of $R^a$ and $R^b$ may represent H or $C_{1-6}$ alkyl optionally substituted by $C_{1-6}$ alkoxy, while the other of $R^a$ and $R^b$ represents (i) $C_{1-6}$ alkyl optionally substituted by $C_{1-6}$ alkoxy, (ii) $C_{3-6}$ cycloalkyl optionally substituted by $C_{1-6}$ alkyl, (iii) a 3- to 6-membered heterocycloalkyl ring optionally substituted by $C_{1-6}$ alkyl, (v) $-(C=O)R^d$, or (vi) $-SO_2R^e$.

$R^d$ and/or $R^e$ may represent $C_{1-6}$ alkyl optionally substituted by cycloalkyl, halo or alkoxy.

$R^d$ and/or $R^e$ may represent $-CH_3$, $-CHF_2$, $-C(CH_3)_2CF_3$, $-C(CH_3)_3$, $-CH_2C(CH_3)_3$, $-CH(CH_3)_2$, $-CH_2CH_3$ or $-CH_2CH_2CH_3$.

$R^d$ and/or $R^e$ may represent $C_{1-6}$ alkyl optionally substituted by cyclopropyl or cyclobutyl, for example $-CH_2$-cyclopropyl.

$R^d$ and/or $R^e$ may represent $C_{1-6}$ alkoxy, for example $-OCH_3$ or $-OCH_2CH_3$.

$R^d$ and/or $R^e$ may represent $C_{3-6}$ cycloalkyl optionally substituted by $C_{1-6}$ alkyl.

In particular, $R^d$ and/or $R^e$ may represent cyclopropyl or cyclobutyl optionally substituted by $C_{1-6}$ alkyl, for example methyl.

$R^c$ may represent $C_{1-6}$ alkyl, for example methyl.

$R^g$ may represent $C_{3-6}$ cycloalkyl, for example cyclopropyl.

$R^2$ may be H.

$R^2$ may $C_{1-6}$ alkyl, for example methyl.

$R^2$ may be halo, for example F.

$R^3$ may be a 5- or 6-membered aryl or heteroaryl ring, optionally substituted by $C_{1-6}$ alkyl or halo, for instance F.

In particular, $R^3$ may be phenyl, optionally substituted by $C_{1-6}$ alkyl, e.g. methyl, or halo, e.g. F.

$R^3$ may be phenyl.

$R^3$ may be thienyl optionally substituted by $C_{1-6}$ alkyl, e.g. methyl, or halo, e.g. F.

$R^3$ may be thienyl.

$R^3$ may be pyridyl optionally substituted by $C_{1-6}$ alkyl, e.g. methyl, or halo, e.g. F.

$R^3$ may be pyridyl.

$R^4$ may represent H.

$R^4$ may represent halo, for example F.

$R^4$ may represent $-OR^f$.

$R^f$ may represent $C_{1-6}$ alkyl.

$R^f$ may represent methyl.

$R^5$ and/or $R^6$ may represent H.

$R^5$ and/or $R^6$ may represent $C_{1-6}$ alkyl, e.g. methyl, optionally substituted by halo, e.g. F.

$R^5$ and/or $R^6$ may represent methyl optionally substituted by F.

$R^5$ and/or $R^6$ may represent $-CHF_2$.

$R^5$ and/or $R^6$ may represent $C_{1-6}$ alkyl, for example methyl.

$R^5$ and $R^6$ may represent methyl.

$R^5$ and $R^6$ may, together with the carbon atom to which they are attached, form a 3- or 4-membered cycloalkyl ring, optionally containing a heteroatom and optionally substituted by $-OH$, $C_{1-6}$ alkyl or halo.

In particular, $R^5$ and $R^6$ may, together with the carbon atom to which they are attached, form a cyclopropyl or cyclobutyl ring, optionally substituted by $-OH$, $C_{1-6}$ alkyl and/or F.

$R^5$ and $R^6$ may, together with the carbon atom to which they are attached, form a cyclopropyl ring.

$R^5$ and $R^6$ may, together with the carbon atom to which they are attached, form a cyclobutyl ring, optionally substituted by $-OH$, $C_{1-6}$ alkyl and/or F.

$R^5$ and $R^6$ may, together with the carbon atom to which they are attached, form 2,2-difloro-cyclobutyl or 2-methyl-2-hydroxy-cyclobutyl.

$R^5$ and $R^6$ may, together with the carbon atom to which they are attached, form a 3- or 4-membered cycloalkyl ring, containing a heteroatom selected from N, O and S, and optionally substituted by $-OH$, $C_{1-6}$ alkyl and/or halo.

$R^5$ and $R^6$ may, together with the carbon atom to which they are attached, form a 3- or 4-membered cycloalkyl ring, containing an oxygen heteroatom and optionally substituted by $-OH$, $C_{1-6}$ alkyl and/or halo.

$R^5$ and $R^6$ may, together with the carbon atom to which they are attached, form an oxetanyl ring, optionally substituted by $-OH$, $C_{1-6}$ alkyl and/or halo.

$R^5$ and $R^6$ may, together with the carbon atom to which they are attached, form an oxetanyl ring.

A preferred embodiment of the compound of formula (I), as described above, is where the compound of formula (I) is a compound of formula (Id):

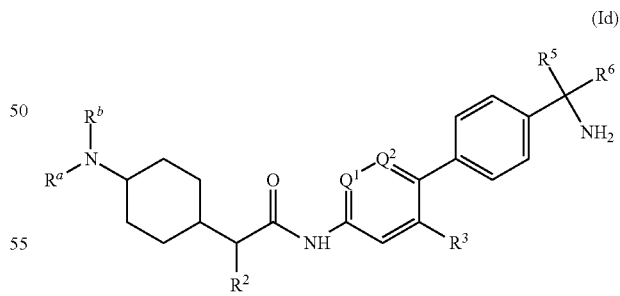

(Id)

wherein
one of $Q^1$ and $Q^2$ represents a nitrogen atom and the other represents CH, or both $Q^1$ and $Q^2$ represent nitrogen atoms;

$R^a$ and $R^b$ independently represent (a) H, (b) optionally substituted alkyl, (c) optionally substituted cycloalkyl, (d) optionally substituted heterocycloalkyl, (e) $-(C=O)R^d$, or (f) $-SO_2R^e$, wherein $R^d$ and $R^e$ independently represent (i) optionally substituted alkyl, (ii) alkoxy, or (iii)

optionally substituted cycloalkyl; or $R^a$ and $R^b$ together with the nitrogen atom to which they are attached form an optionally substituted aromatic or aliphatic heterocyclic ring;

$R^2$ is H, optionally substituted alkyl or halo;

$R^3$ is an optionally substituted aryl or heteroaryl ring;

$R^5$ and $R^6$ independently represent H or optionally substituted alkyl; or $R^5$ and $R^6$ together with the carbon atom to which they are attached form an optionally substituted cycloalkyl ring, optionally containing a heteroatom;

and the corresponding N-oxides, and their prodrugs; and pharmaceutically acceptable salts and solvates (e.g. hydrates) of such compounds and their N-oxides and prodrugs.

Particular embodiments of the compounds of formula (Id) described above are set out below. It is to be understood that this invention covers all appropriate combinations of the substituents referred to herein, and that, where alternatives are provided for any one substituent, the invention covers all lists which may be formed by combinations of these alternatives.

In the compounds of formula (Id), unless otherwise stated, any or all alkyl groups may independently be $C_{1-6}$ alkyl groups, any or all alkoxy groups may independently be $C_{1-6}$ alkoxy groups, and/or any or all cycloalkyl groups may independently be $C_{3-6}$ cycloalkyl groups.

One of $Q^1$ and $Q^2$ may represent a nitrogen atom while the other represents CH, i.e. $Q^1$ represents a nitrogen atom and $Q^2$ represents CH, or $Q^1$ represents CH and $Q^2$ represents a nitrogen atom.

Alternatively, $Q^1$ and $Q^2$ may both represent nitrogen atoms.

$R^a$ and/or $R^b$ may represent H.

$R^a$ and/or $R^b$ may represent optionally substituted alkyl, optionally substituted cycloalkyl or optionally substituted heterocycloalkyl.

$R^a$ and/or $R^b$ may represent alkyl optionally substituted by alkoxy, cycloalkyl or a heterocycloalkyl ring, any of which is optionally substituted by alkyl.

$R^a$ and/or $R^b$ may represent alkyl optionally substituted by alkoxy, for example —$OCH_3$.

$R^a$ and/or $R^b$ may represent cycloalkyl optionally substituted by alkyl.

For instance, $R^a$ and/or $R^b$ may represent cyclopropyl or cyclobutyl, any of which is optionally substituted by alkyl.

$R^a$ and/or $R^b$ may represent a heterocycloalkyl ring optionally substituted by alkyl.

For instance, $R^a$ and/or $R^b$ may represent a 3- to 6-membered heterocycloalkyl ring, optionally substituted by alkyl.

$R^a$ and/or $R^b$ may represent a 4-membered heterocycloalkyl ring, optionally substituted by alkyl.

$R^a$ and/or $R^b$ may represent oxetanyl, optionally substituted by alkyl.

$R^a$ and/or $R^b$ may represent —(C=O)$R^d$, or $R^a$ and/or $R^b$ may represent —$SO_2R^e$.

$R^a$ and $R^b$ may, together with the nitrogen atom to which they are attached, form an optionally substituted aromatic or aliphatic heterocyclic ring, for example an optionally substituted 5- or 6-membered aromatic or aliphatic heterocyclic ring. The ring may be optionally substituted by oxo or alkyl.

In particular, $R^a$ and $R^b$ may, together with the nitrogen atom to which they are attached, form a 5- or 6-membered aromatic or aliphatic heterocyclic ring selected from triazinyl, oxazolidinyl, pyrrolidinyl, piperidinyl and morpholinyl, any of which may be optionally substituted by oxo or alkyl.

$R^a$ and $R^b$ may, together with the nitrogen atom to which they are attached, form triazinyl, morpholinonyl, oxazolidinonyl, pyrrolidonyl or piperidonyl, any of which may be optionally substituted by alkyl.

One of $R^a$ and $R^b$ may represent H or optionally substituted alkyl, while the other of $R^a$ and $R^b$ represents (i) optionally substituted alkyl, (ii) optionally substituted cycloalkyl, (iii) optionally substituted heterocycloalkyl, (v) —(C=O)$R^d$, or (vi) —$SO_2R^e$.

One of $R^a$ and $R^b$ may represent H or alkyl, while the other of $R^a$ and $R^b$ represents (i) alkyl optionally substituted by alkoxy, (ii) cycloalkyl optionally substituted by alkyl, (iii) a 3- to 6-membered heterocycloalkyl ring optionally substituted by alkyl, (iv) —(C=O)$R^d$, or (v) —$SO_2R^e$.

$R^d$ and/or $R^e$ may represent optionally substituted alkyl, for instance alkyl optionally substituted by cycloalkyl, halo, e.g. F, or alkoxy, e.g. —$OCH_3$.

$R^d$ and/or $R^e$ may represent —$CH_3$, —$CHF_2$, —$C(CH_3)_2CF_3$, —$C(CH_3)_3$, —$CH_2C(CH_3)_3$, —$CH(CH_3)_2$, —$CH_2CH_3$ or —$CH_2CH_2CH_3$.

$R^d$ and/or $R^e$ may represent alkyl optionally substituted by cyclopropyl or cyclobutyl, for example —$CH_2$-cyclopropyl.

$R^d$ and/or $R^e$ may represent alkoxy, for example —$OCH_3$ or —$OCH_2CH_3$.

$R^d$ and/or $R^e$ may represent optionally substituted cycloalkyl, for example cycloalkyl optionally substituted by alkyl.

In particular, $R^d$ and/or $R^e$ may represent cyclopropyl or cyclobutyl optionally substituted by alkyl, for example methyl.

$R^2$ may be H.

$R^2$ may be optionally substituted alkyl, or $R^2$ may be alkyl, for example methyl.

$R^2$ may be halo, for example F.

$R^3$ may be an optionally substituted 5- or 6-membered aryl or heteroaryl ring, for example optionally substituted by alkyl or halo, for instance F.

In particular, $R^3$ may be phenyl, optionally substituted by alkyl, e.g. methyl, or halo, e.g. F.

$R^3$ may be phenyl.

$R^3$ may be thienyl optionally substituted by alkyl, e.g. methyl, or halo, e.g. F.

$R^3$ may be thienyl.

$R^3$ may be pyridyl optionally substituted by alkyl, e.g. methyl, or halo, e.g. F.

$R^3$ may be pyridyl.

$R^5$ and/or $R^6$ may represent H.

$R^5$ and/or $R^6$ may represent alkyl, e.g. methyl, optionally substituted by halo, e.g. F.

$R^5$ and/or $R^6$ may represent methyl optionally substituted by F.

$R^5$ and/or $R^6$ may represent —$CHF_2$.

$R^5$ and/or $R^6$ may represent alkyl, for example methyl.

$R^5$ and $R^6$ may represent methyl.

$R^5$ and $R^6$ may, together with the carbon atom to which they are attached, form an optionally substituted cycloalkyl ring, optionally containing a heteroatom. The ring may be an optionally substituted 3- or 4-membered cycloalkyl ring, optionally containing a heteroatom. Optional substituents include OH, alkyl and/or halo.

Thus, $R^5$ and $R^6$ may, together with the carbon atom to which they are attached, form a 3- or 4-membered cycloalkyl ring, optionally containing a heteroatom and optionally substituted by —OH, alkyl and/or F.

In particular, $R^5$ and $R^6$ may, together with the carbon atom to which they are attached, form a cyclopropyl or cyclobutyl ring, optionally substituted by —OH, alkyl and/or F.

$R^5$ and $R^6$ may, together with the carbon atom to which they are attached, form a cyclopropyl ring.

$R^5$ and $R^6$ may, together with the carbon atom to which they are attached, form a cyclobutyl ring, optionally substituted by —OH, alkyl and/or F.

$R^5$ and $R^6$ may, together with the carbon atom to which they are attached, form 2,2-difloro-cyclobutyl or 2-methyl-2-hydroxy-cyclobutyl.

$R^5$ and $R^6$ may, together with the carbon atom to which they are attached, form a 3- or 4-membered cycloalkyl ring, containing a heteroatom selected from N, O and S, and optionally substituted by —OH, alkyl and/or halo.

$R^5$ and $R^6$ may, together with the carbon atom to which they are attached, form a 3- or 4-membered cycloalkyl ring, containing an oxygen heteroatom and optionally substituted by —OH, alkyl and/or halo.

$R^5$ and $R^6$ may, together with the carbon atom to which they are attached, form an oxetanyl ring, optionally substituted by —OH, alkyl and/or halo.

$R^5$ and $R^6$ may, together with the carbon atom to which they are attached, form an oxetanyl ring.

Currently most preferred compounds of formula (I) are those of formula (Ie)

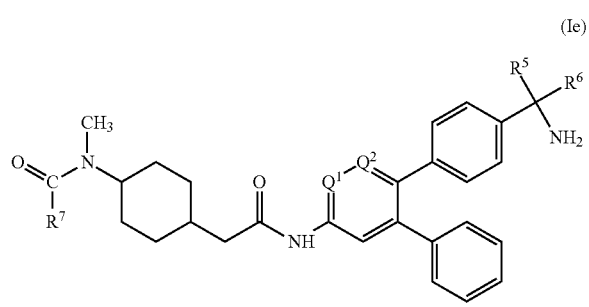

(Ie)

wherein one of $Q^1$ and $Q^2$ represents a nitrogen atom and the other represents CH, or both $Q^1$ and $Q^2$ represent nitrogen atoms;

$R^5$ and $R^6$ independently represent H or optionally substituted alkyl; or $R^5$ and $R^6$ together with the carbon atom to which they are attached form an optionally substituted cycloalkyl ring, optionally containing a heteroatom;

$R^7$ represents alkyl, alkoxy or cycloalkyl;

and the corresponding N-oxides, and their prodrugs; and pharmaceutically acceptable salts and solvates (e.g. hydrates) of such compounds and their N-oxides and prodrugs.

Particular embodiments of the compounds of formula (Ie) described above are set out below. It is to be understood that this invention covers all appropriate combinations of the substituents referred to herein, and that, where alternatives are provided for any one substituent, the invention covers all lists which may be formed by combinations of these alternatives.

In the compounds of formula (Ie), unless otherwise stated, any or all alkyl groups may independently be $C_{1-6}$ alkyl groups, any or all alkoxy groups may independently be $C_{1-6}$ alkoxy groups, and/or any or all cycloalkyl groups may independently be $C_{3-6}$ cycloalkyl groups.

One of $Q^1$ and $Q^2$ may represent a nitrogen atom while the other represents CH, i.e. $Q^1$ represents a nitrogen atom and $Q^2$ represents CH, or $Q^1$ represents CH and $Q^2$ represents a nitrogen atom.

Alternatively, $Q^1$ and $Q^2$ may both represent nitrogen atoms.

$R^5$ and/or $R^6$ may represent H.

$R^5$ and/or $R^6$ may represent alkyl, e.g. methyl, optionally substituted by halo, e.g. F.

$R^5$ and/or $R^6$ may represent methyl optionally substituted by F.

$R^5$ and/or $R^6$ may represent —$CHF_2$.

$R^5$ and/or $R^6$ may represent alkyl, for example methyl.

$R^5$ and $R^6$ may represent methyl.

$R^5$ and $R^6$ may, together with the carbon atom to which they are attached, form an optionally substituted cycloalkyl ring, optionally containing a heteroatom. The ring may be an optionally substituted 3- or 4-membered cycloalkyl ring, optionally containing a heteroatom. Optional substituents include OH, alkyl and/or halo.

Thus, $R^5$ and $R^6$ may, together with the carbon atom to which they are attached, form a 3- or 4-membered cycloalkyl ring, optionally containing a heteroatom and optionally substituted by —OH, alkyl and/or F.

In particular, $R^5$ and $R^6$ may, together with the carbon atom to which they are attached, form a cyclopropyl or cyclobutyl ring, optionally substituted by —OH, alkyl and/or F.

$R^5$ and $R^6$ may, together with the carbon atom to which they are attached, form a cyclopropyl ring.

$R^5$ and $R^6$ may, together with the carbon atom to which they are attached, form a cyclobutyl ring, optionally substituted by —OH, alkyl and/or F.

$R^5$ and $R^6$ may, together with the carbon atom to which they are attached, form 2,2-difloro-cyclobutyl or 2-methyl-2-hydroxy-cyclobutyl.

$R^5$ and $R^6$ may, together with the carbon atom to which they are attached, form a 3- or 4-membered cycloalkyl ring, containing a heteroatom selected from N, O and S, and optionally substituted by —OH, alkyl and/or halo.

$R^5$ and $R^6$ may, together with the carbon atom to which they are attached, form a 3- or 4-membered cycloalkyl ring, containing an oxygen heteroatom and optionally substituted by —OH, alkyl and/or halo.

$R^5$ and $R^6$ may, together with the carbon atom to which they are attached, form an oxetanyl ring, optionally substituted by —OH, alkyl and/or halo.

$R^5$ and $R^6$ may, together with the carbon atom to which they are attached, form an oxetanyl ring.

$R^7$ may represent alkyl, e.g. methyl or ethyl.

$R^7$ may represent alkoxy, e.g. —$OCH_3$.

$R^7$ may represent cycloalkyl, e.g. cyclopropyl.

Particular compounds of the invention are:

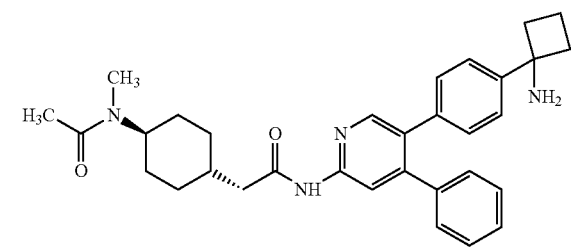

-continued
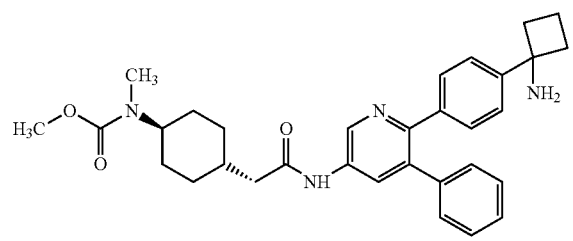
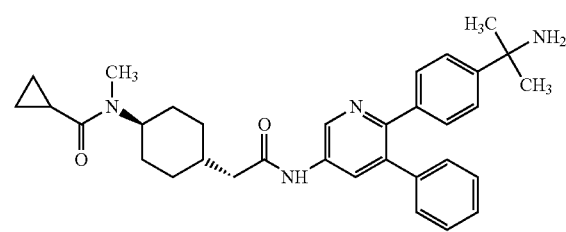
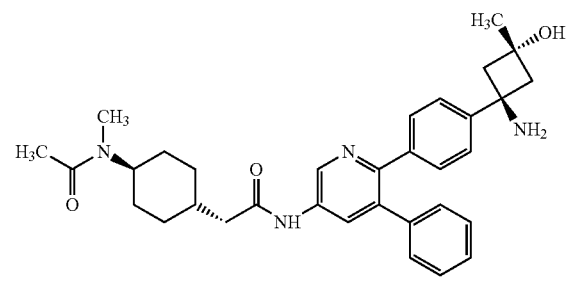
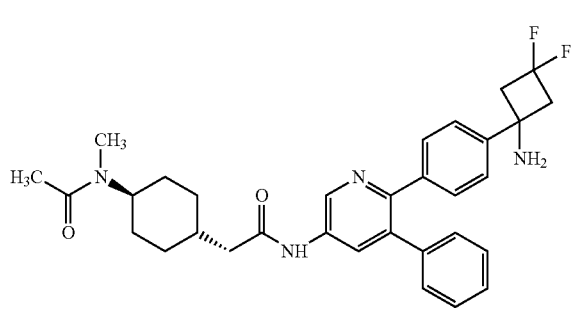
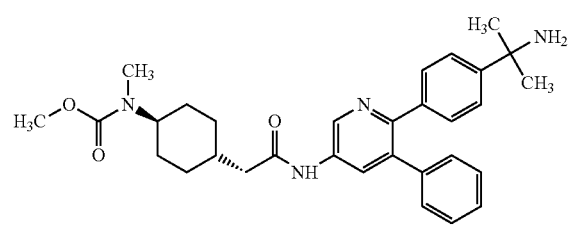
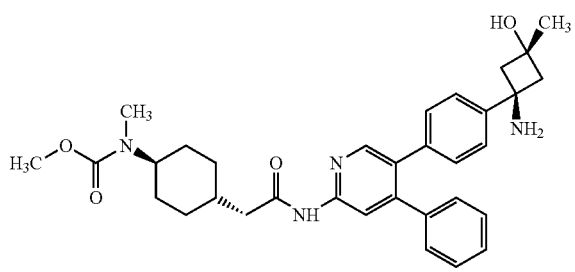
-continued
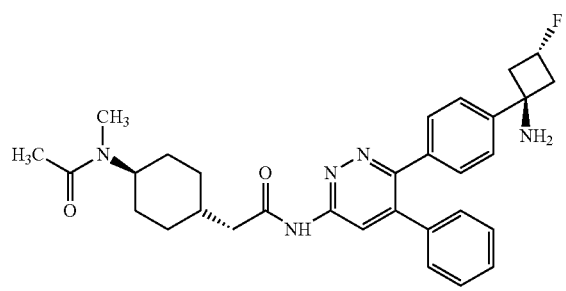
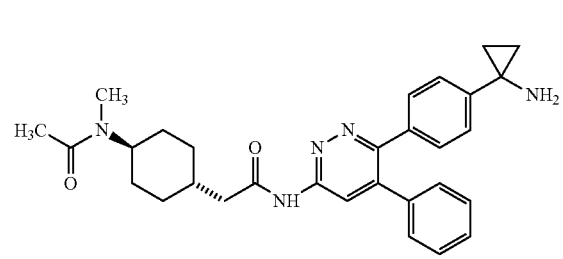
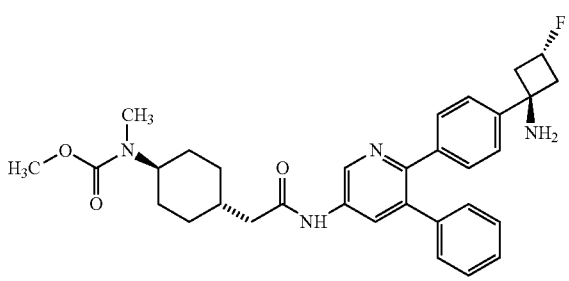
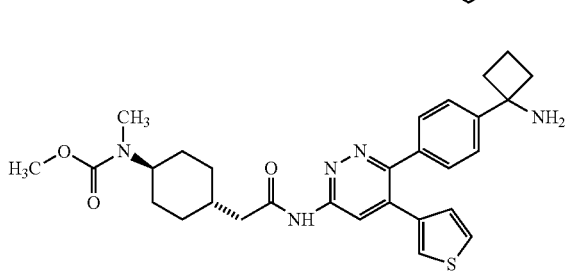
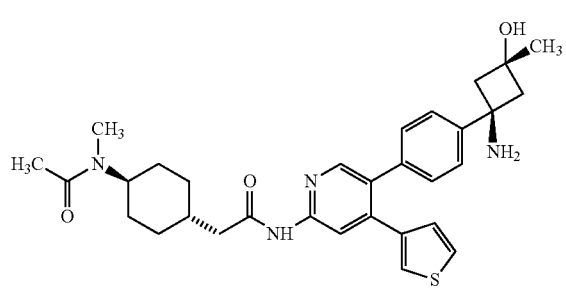
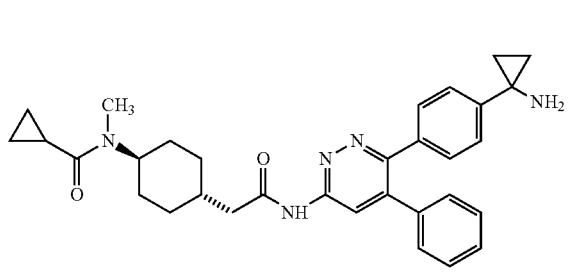

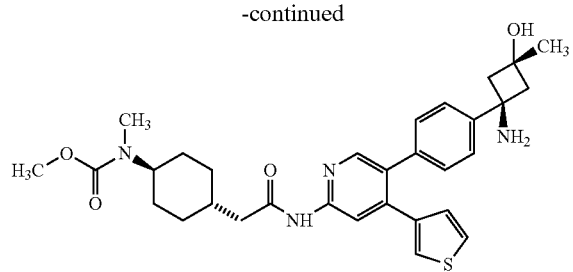
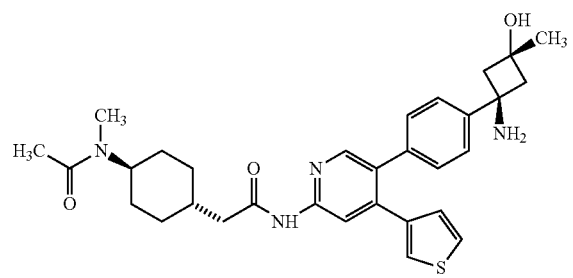
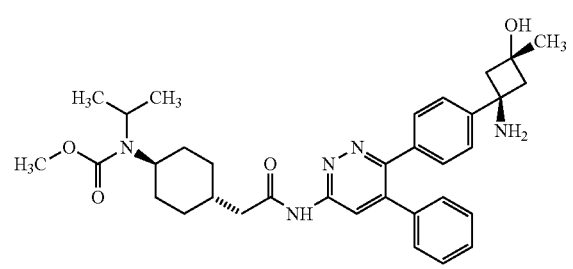
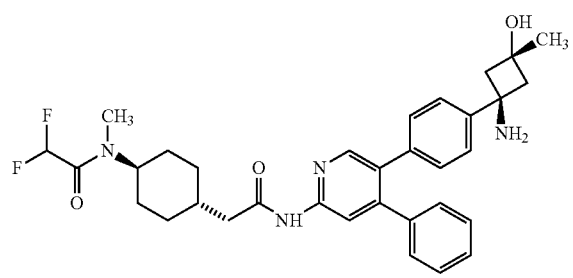
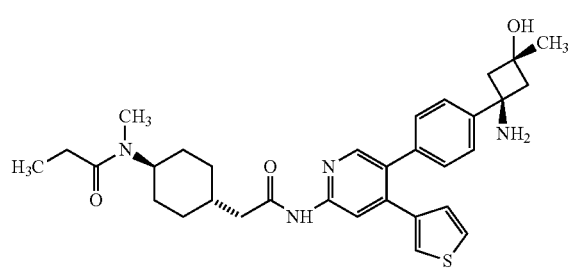
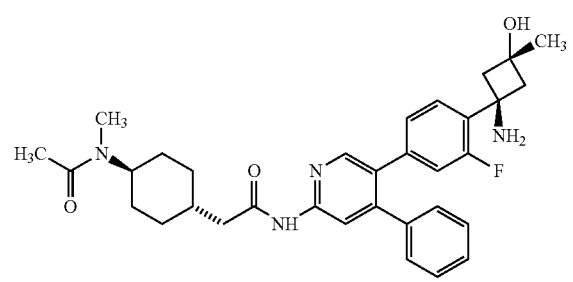
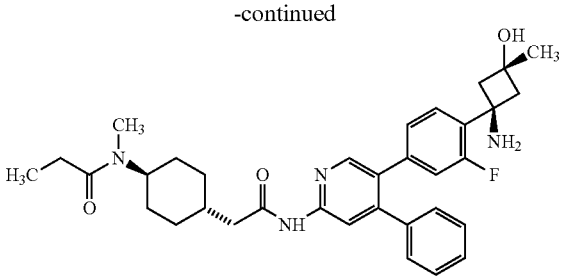
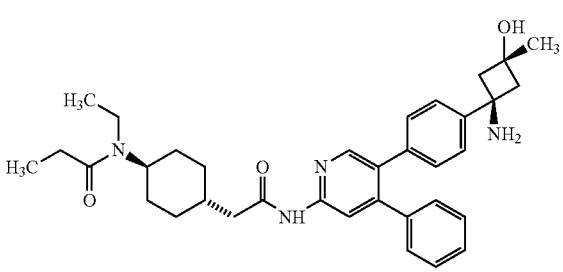
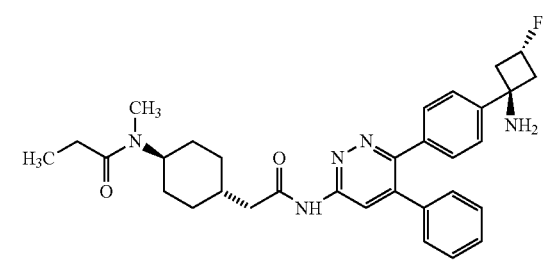
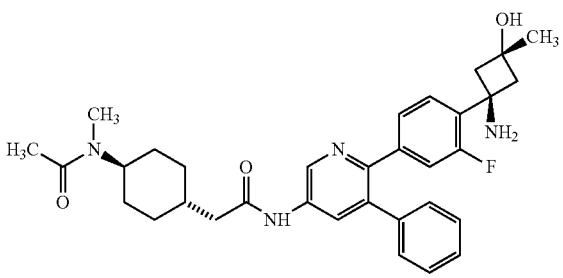
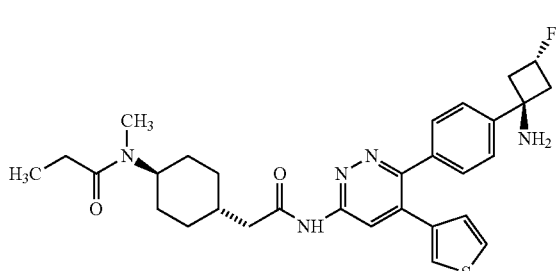
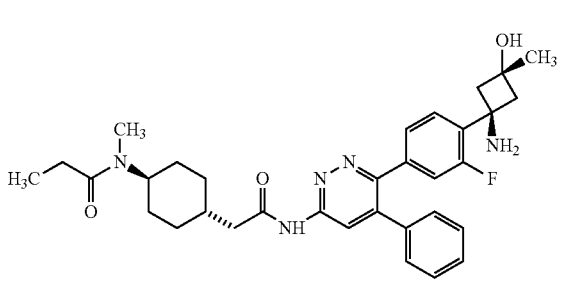

-continued

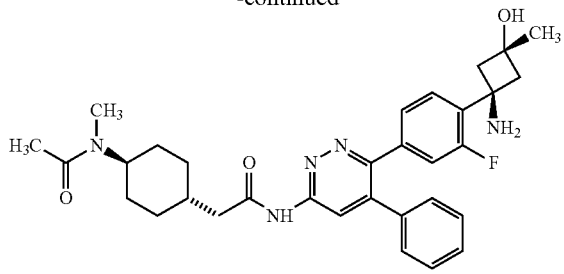

and the corresponding N-oxides, and their prodrugs; and pharmaceutically acceptable salts and solvates (e.g. hydrates) of such compounds and their N-oxides and prodrugs.

The compound of the invention may be selected from the following group:

N-(6-(4-(trans-1-amino-3-hydroxy-3-methylcyclobutyl) phenyl)-5-phenylpyridin-3-yl)-2-(trans-4-(N-methylacetamido)cyclohexyl)acetamide;

2-(trans-4-acetamidocyclohexyl)-N-(6-(4-(trans-1-amino-3-hydroxy-3-methylcyclobutyl)phenyl)-5-phenylpyridin-3-yl)acetamide;

N-(6-(4-(2-aminopropan-2-yl)phenyl)-5-phenylpyridin-3-yl)-2-(trans-4-(N-methylacetamido)cyclohexyl)acetamide;

N-(trans-4-(2-((6-(4-(2-aminopropan-2-yl)phenyl)-5-phenylpyridin-3-yl)amino)-2-oxoethyl)cyclohexyl)-N-methylisobutyramide;

N-(6-(4-(1-amino-3,3-difluorocyclobutyl)phenyl)-5-phenylpyridin-3-yl)-2-(trans-4-(N-methylacetamido)cyclohexyl)acetamide;

N-(6-(4-(2-aminopropan-2-yl)phenyl)-5-(thiophen-3-yl) pyridin-3-yl)-2-(trans-4-(N-methylacetamido)cyclohexyl)acetamide;

N-(6-(4-((S)-1-aminoethyl)phenyl)-5-phenylpyridin-3-yl)-2-(trans-4-(N-methylacetamido)cyclohexyl)acetamide;

N-(6-(4-((R)-1-aminoethyl)phenyl)-5-phenylpyridin-3-yl)-2-(trans-4-(N-methylacetamido)cyclohexyl)acetamide;

N-(6-(4-(2-aminopropan-2-yl)phenyl)-5-(2-fluorophenyl) pyridin-3-yl)-2-(trans-4-(N-methylacetamido)cyclohexyl)acetamide;

N-(6-(4-(1-aminocyclobutyl)phenyl)-5-phenylpyridin-3-yl)-2-(trans-4-(N-methylacetamido)cyclohexyl)acetamide;

N-(6-(4-((S)-1-amino-2,2-difluoroethyl)phenyl)-5-phenylpyridin-3-yl)-2-(trans-4-(N-methylacetamido)cyclohexyl)acetamide;

N-(6-(4-(1-aminocyclopropyl)phenyl)-5-phenylpyridin-3-yl)-2-(trans-4-(N-methylacetamido)cyclohexyl)acetamide;

2-(trans-4-acetamidocyclohexyl)-N-(6-(4-(trans-1-amino-3-hydroxycyclobutyl)phenyl)-5-phenylpyridin-3-yl)acetamide;

2-(trans-4-acetamidocyclohexyl)-N-(6-(4-(3-aminooxetan-3-yl)phenyl)-5-phenylpyridin-3-yl)acetamide;

2-(trans-4-acetamidocyclohexyl)-N-(6-(4-(trans-1-amino-3-fluorocyclobutyl)phenyl)-5-phenylpyridin-3-yl)acetamide;

N-(6-(4-(1-aminocyclobutyl)phenyl)-5-(2-fluorophenyl) pyridin-3-yl)-2-(trans-4-(N-methylacetamido)cyclohexyl)acetamide;

N-(6-(4-(1-aminocyclobutyl)phenyl)-5-(thiophen-3-yl)pyridin-3-yl)-2-(trans-4-(N-methylmethylsulfonamido)cyclohexyl)acetamide;

2-(trans-4-acetamidocyclohexyl)-N-(6-(4-(1-aminocyclobutyl)phenyl)-5-(2-methylthiophen-3-yl)pyridin-3-yl)acetamide;

N-(6-(4-(1-aminocyclobutyl)phenyl)-5-(4-methylthiophen-3-yl)pyridin-3-yl)-2-(trans-4-(N-methylmethylsulfonamido)cyclohexyl)acetamide;

N-(trans-4-(2-((2-(4-(1-aminocyclobutyl)phenyl)-[3,3'-bipyridin]-5-yl)amino)-2-oxoethyl)cyclohexyl)-3,3,3-trifluoro-2,2-dimethylpropanamide;

N-(6-(4-(3-aminooxetan-3-yl)phenyl)-5-phenylpyridin-3-yl)-2-(4-methoxycyclohexyl)acetamide;

N-(6-(4-(3-aminooxetan-3-yl)phenyl)-5-phenylpyridin-3-yl)-2-((2R,6S)-2,6-dimethyltetrahydro-2H-pyran-4-yl)acetamide;

N-(6-(4-(2-aminopropan-2-yl)phenyl)-5-phenylpyridin-3-yl)-2-(trans-4-(3-methyl-4H-1,2,4-triazol-4-yl)cyclohexyl)acetamide;

N-(6-(4-(2-aminopropan-2-yl)phenyl)-5-phenylpyridin-3-yl)-2-(trans-4-(2-oxopyrrolidin-1-yl)cyclohexyl)acetamide;

2-(trans-4-acetamidocyclohexyl)-N-(6-(4-(1-amino-3,3-difluorocyclobutyl)phenyl)-5-phenylpyridin-3-yl)acetamide;

N-(trans-4-(2-((6-(4-(2-aminopropan-2-yl)phenyl)-5-(thiophen-3-yl)pyridin-3-yl)amino)-2-oxoethyl)cyclohexyl) cyclopropanecarboxamide;

N-(trans-4-(2-((6-(4-(2-aminopropan-2-yl)phenyl)-5-(thiophen-3-yl)pyridin-3-yl)amino)-2-oxoethyl)cyclohexyl)-N-methylcyclopropanecarboxamide;

N-(6-(4-(2-aminopropan-2-yl)phenyl)-5-phenylpyridin-3-yl)-2-(trans-4-(2-oxopiperidin-1-yl)cyclohexyl)acetamide;

N-(6-(4-(2-aminopropan-2-yl)phenyl)-5-phenylpyridin-3-yl)-2-(trans-4-(2-cyclopropylacetamido)cyclohexyl)acetamide;

N-(6-(4-(2-aminopropan-2-yl)phenyl)-5-phenylpyridazin-3-yl)-2-(trans-4-(N-methylacetamido)cyclohexyl)acetamide;

N-(6-(4-(2-aminopropan-2-yl)-3-fluorophenyl)-5-phenylpyridin-3-yl)-2-(trans-4-(N-methylacetamido)cyclohexyl)acetamide;

N-(6-(4-(trans-1-amino-3-fluorocyclobutyl)phenyl)-5-phenylpyridin-3-yl)-2-(trans-4-(N-methylacetamido)cyclohexyl)acetamide;

N-(5-(4-(1-aminocyclobutyl)phenyl)-4-phenylpyridin-2-yl)-2-(trans-4-(N-methylacetamido)cyclohexyl)acetamide;

methyl (trans-4-(2-((6-(4-(2-aminopropan-2-yl)phenyl)-5-phenylpyridin-3-yl)amino)-2-oxoethyl)cyclohexyl) (methyl)carbamate;

N-(6-(4-(2-aminopropan-2-yl)phenyl)-5-phenylpyridin-3-yl)-2-(trans-4-(methyl(3-methyloxetan-3-yl)amino)cyclohexyl)acetamide;

N-(6-(4-(3-aminooxetan-3-yl)phenyl)-5-phenylpyridin-3-yl)-2-(4,4-dimethoxycyclohexyl)acetamide;

N-(6-(4-(3-aminooxetan-3-yl)phenyl)-5-phenylpyridin-3-yl)-2-(trans-4-(cyclopropanesulfonamido)cyclohexyl)acetamide;

N-(6-(4-(1-aminocyclobutyl)phenyl)-5-(thiophen-3-yl)pyridin-3-yl)-2-(trans-4-morpholinocyclohexyl)acetamide;

N-(6-(4-(1-aminocyclobutyl)phenyl)-5-(thiophen-3-yl)pyridin-3-yl)-2-(trans-4-((2-methoxyethyl)(methyl)amino) cyclohexyl)acetamide;

N-(6-(4-(1-aminocyclobutyl)phenyl)-5-phenylpyridin-3-yl)-2-(1-(cyclopropylsulfonyl)piperidin-4-yl)-2-fluoroacetamide;

2-(trans-4-acetamidocyclohexyl)-N-(6-(4-(1-aminocyclobutyl)phenyl)-5-phenylpyridin-3-yl)propanamide;
N-(6-(4-(2-aminopropan-2-yl)phenyl)-5-phenylpyridin-3-yl)-2-(trans-4-(2-oxooxazolidin-3-yl)cyclohexyl)acetamide;
N-(6'-(2-aminopropan-2-yl)-3-phenyl-[2,3'-bipyridin]-5-yl)-2-(trans-4-(N-methylacetamido)cyclohexyl)acetamide;
methyl (trans-4-(2-((6-(4-(trans-1-amino-3-hydroxy-3-methylcyclobutyl)phenyl)-5-phenylpyridin-3-yl)amino)-2-oxoethyl)cyclohexyl)(methyl)carbamate;
N-(6-(4-(trans-1-amino-3-fluorocyclobutyl)phenyl)-5-phenylpyridazin-3-yl)-2-(trans-4-(2-oxooxazolidin-3-yl)cyclohexyl)acetamide;
N-(6-(4-(trans-1-amino-3-fluorocyclobutyl)phenyl)-5-phenylpyridazin-3-yl)-2-(trans-4-(N-methylacetamido)cyclohexyl)acetamide;
N-(trans-4-(2-((6-(4-(2-aminopropan-2-yl)phenyl)-5-phenylpyridin-3-yl)amino)-2-oxoethyl)cyclohexyl)-N-methylcyclobutanecarboxamide;
N-(6-(4-(1-aminocyclobutyl)phenyl)-5-(thiophen-3-yl)pyridin-3-yl)-2-(trans-4-(2-oxopyrrolidin-1-yl)cyclohexyl)acetamide;
N-(6-(4-(1-aminocyclobutyl)phenyl)-5-phenylpyridin-3-yl)-2-(trans-4-(N-isopropylacetamido)cyclohexyl)acetamide;
(S)-N-(6-(4-(1-aminocyclobutyl)phenyl)-5-phenylpyridin-3-yl)-2-(1-(cyclopropylsulfonyl)piperidin-4-yl)-2-fluoroacetamide;
methyl (trans-4-(2-((6-(4-(1-aminocyclobutyl)phenyl)-5-phenylpyridin-3-yl)amino)-2-oxoethyl)cyclohexyl) (isopropyl)carbamate;
methyl (trans-4-(2-((6-(4-(1-aminocyclobutyl)phenyl)-5-phenylpyridin-3-yl)amino)-1-fluoro-2-oxoethyl)cyclohexyl)(methyl)carbamate;
N-(trans-4-(2-((6-(4-(2-aminopropan-2-yl)-3-fluorophenyl)-5-phenylpyridin-3-yl)amino)-2-oxoethyl)cyclohexyl)-N-methylcyclopropanecarboxamide;
methyl (trans-4-(1-((6-(4-(1-aminocyclobutyl)phenyl)-5-phenylpyridin-3-yl)amino)-1-oxopropan-2-yl)cyclohexyl)(methyl)carbamate;
trans-4-(2-((6-(4-(2-aminopropan-2-yl)phenyl)-5-phenylpyridin-3-yl)amino)-2-oxoethyl)-N,N-dimethylcyclohexane-1-carboxamide;
methyl (trans-4-(2-((6-(4-(2-aminopropan-2-yl)phenyl)-5-phenylpyridazin-3-yl)amino)-2-oxoethyl)cyclohexyl)(methyl)carbamate;
N-(6-(4-(trans-1-amino-3-hydroxy-3-methylcyclobutyl)phenyl)-5-phenylpyridazin-3-yl)-2-(trans-4-(N-methylacetamido)cyclohexyl)acetamide;
N-(6-(4-(trans-1-amino-3-hydroxy-3-methylcyclobutyl)phenyl)-5-phenylpyridazin-3-yl)-2-(trans-4-(2-oxooxazolidin-3-yl)cyclohexyl)acetamide;
methyl (trans-4-(2-((6-(4-(trans-1-amino-3-hydroxy-3-methylcyclobutyl)phenyl)-5-phenylpyridazin-3-yl)amino)-2-oxoethyl)cyclohexyl)(methyl)carbamate;
methyl (trans-4-(2-((6-(4-(1-amino-3,3-difluorocyclobutyl)phenyl)-5-phenylpyridazin-3-yl)amino)-2-oxoethyl)cyclohexyl)(methyl)carbamate;
N-(6-(4-(1-amino-3,3-difluorocyclobutyl)phenyl)-5-phenylpyridazin-3-yl)-2-(trans-4-(2-oxooxazolidin-3-yl)cyclohexyl)acetamide;
methyl (trans-4-(2-((6-(4-(1-aminocyclopropyl)-3-fluorophenyl)-5-phenylpyridin-3-yl)amino)-2-oxoethyl)cyclohexyl(methyl)carbamate;
N-(5-(4-(2-aminopropan-2-yl)phenyl)-4-phenylpyridin-2-yl)-2-(trans-4-(N-methylacetamido)cyclohexyl)acetamide;
N-(5-(4-(2-aminopropan-2-yl)phenyl)-4-phenylpyridin-2-yl)-2-(trans-4-(2-oxooxazolidin-3-yl)cyclohexyl)acetamide;
N-(6-(4-(2-aminopropan-2-yl)phenyl)-5-phenylpyridazin-3-yl)-2-(trans-4-(2-oxooxazolidin-3-yl)cyclohexyl)acetamide;
N-(6-(4-(1-aminocyclobutyl)phenyl)-5-phenylpyridazin-3-yl)-2-(trans-4-(2-oxooxazolidin-3-yl)cyclohexyl)acetamide;
methyl (trans-4-(2-((5-(4-(trans-1-amino-3-hydroxy-3-methylcyclobutyl)phenyl)-4-phenylpyridin-2-yl)amino)-2-oxoethyl)cyclohexyl)(methyl)carbamate;
N-(6-(4-(trans-1-amino-3-hydroxy-3-methylcyclobutyl)phenyl)-5-(2-fluorophenyl)-1,2,4-triazin-3-yl)-2-(trans-4-(2-oxooxazolidin-3-yl)cyclohexyl)acetamide;
N-(6-(4-(2-aminopropan-2-yl)phenyl)-5-phenyl-1,2,4-triazin-3-yl)-2-(4-(2-oxooxazolidin-3-yl)cyclohexyl)acetamide;
N-(5-(4-(1-aminocyclobutyl)phenyl)-4-(thiophen-3-yl)pyridin-2-yl)-2-(trans-4-(2-oxooxazolidin-3-yl)cyclohexyl) acetamide;
N-(trans-4-(2-((6-(4-(trans-1-amino-3-fluorocyclobutyl)phenyl)-5-phenylpyridazin-3-yl)amino)-2-oxoethyl)cyclohexyl)-N-methylcyclopropanecarboxamide;
N-(6-(4-(1-aminocyclopropyl)phenyl)-5-phenylpyridazin-3-yl)-2-(trans-4-(N-methylacetamido)cyclohexyl)acetamide;
N-(6-(4-(1-amino-3,3-difluorocyclobutyl)phenyl)-5-phenylpyridazin-3-yl)-2-(trans-4-(N-methylacetamido)cyclohexyl)acetamide;
N-(6-(4-(trans-1-amino-3-fluorocyclobutyl)phenyl)-5-phenylpyridazin-3-yl)-2-(trans-4-(2-oxopyrrolidin-1-yl)cyclohexyl)acetamide;
N-(6-(4-(trans-1-amino-3-fluorocyclobutyl)phenyl)-5-(thiophen-3-yl)pyridazin-3-yl)-2-(trans-4-(N-methylacetamido)cyclohexyl)acetamide;
N-(5'-(4-(1-aminocyclobutyl)phenyl)-[2,4'-bipyridin]-2'-yl)-2-(trans-4-(N-methylacetamido)cyclohexyl)acetamide;
Methyl (trans-4-(2-((6-(4-(trans-1-amino-3-fluorocyclobutyl)phenyl)-5-phenylpyridin-3-yl)amino)-2-oxoethyl)cyclohexyl)(methyl)carbamate;
N-(6-(4-(trans-1-amino-3-fluorocyclobutyl)phenyl)-5-phenylpyridin-3-yl)-2-(trans-4-(2-oxooxazolidin-3-yl)cyclohexyl)acetamide;
N-(6-(4-(trans-1-amino-3-fluorocyclobutyl)phenyl)-5-(thiophen-3-yl)pyridazin-3-yl)-2-(trans-4-(2-oxooxazolidin-3-yl)cyclohexyl)acetamide;
N-(6-(4-(2-aminopropan-2-yl)phenyl)-5-(thiophen-3-yl)pyridazin-3-yl)-2-(trans-4-(2-oxooxazolidin-3-yl)cyclohexyl)acetamide;
methyl (trans-4-(2-((6-(4-(1-aminocyclobutyl)phenyl)-5-(thiophen-3-yl)pyridazin-3-yl)amino)-2-oxoethyl)cyclohexyl)(methyl)carbamate;
N-(trans-4-(2-((5-(4-(trans-1-amino-3-hydroxy-3-methylcyclobutyl)phenyl)-4-phenylpyridin-2-yl)amino)-2-oxoethyl)cyclohexyl)-N-methylpropionamide;
N-(trans-4-(2-((6-(4-(trans-1-amino-3-hydroxy-3-methylcyclobutyl)phenyl)-5-phenylpyridazin-3-yl)amino)-2-oxoethyl)cyclohexyl)-N-methylpropionamide;
methyl (trans-4-(2-((6-(4-(trans-1-amino-3-hydroxy-3-methylcyclobutyl)phenyl)-5-(thiophen-3-yl)pyridazin-3-yl)amino)-2-oxoethyl)cyclohexyl)(methyl)carbamate;

N-(trans-4-(2-((5-(4-(trans-1-amino-3-hydroxy-3-methylcyclobutyl)phenyl)-4-phenylpyridin-2-yl)amino)-2-oxoethyl)cyclohexyl)-N-methylisobutyramide;

methyl (trans-4-(2-((5'-(4-(1-aminocyclobutyl)phenyl)-[2,4'-bipyridin]-2'-yl)amino)-2-oxoethyl)cyclohexyl)(methyl)carbamate;

N-(trans-4-(2-((6-(4-(1-aminocyclopropyl)phenyl)-5-phenylpyridazin-3-yl)amino)-2-oxoethyl)cyclohexyl)-N-methylcyclopropanecarboxamide;

N-(trans-4-(2-((6-(4-(2-aminopropan-2-yl)phenyl)-5-(thiophen-3-yl)pyridazin-3-yl)amino)-2-oxoethyl)cyclohexyl)-N-methylpropionamide;

methyl (trans-4-(2-((5-(4-(trans-1-amino-3-hydroxy-3-methylcyclobutyl)phenyl)-4-(thiophen-3-yl)pyridin-2-yl)amino)-2-oxoethyl)cyclohexyl)(methyl)carbamate;

N-(trans-4-(2-((6-(4-(1-aminocyclopropyl)-3-fluorophenyl)-5-phenylpyridin-3-yl)amino)-2-oxoethyl)cyclohexyl)-N-methylpropionamide;

N-(trans-4-(2-((6-(4-(trans-1-amino-3-hydroxy-3-methylcyclobutyl)phenyl)-5-(thiophen-3-yl)pyridazin-3-yl)amino)-2-oxoethyl)cyclohexyl)-N-methylpropionamide;

N-(6-(4-(1-aminocyclopropyl)-3-fluorophenyl)-5-(thiophen-3-yl)pyridazin-3-yl)-2-(trans-4-(N-methylacetamido)cyclohexyl)acetamide;

N-(5-(4-(trans-1-amino-3-hydroxy-3-methylcyclobutyl)phenyl)-4-(thiophen-3-yl)pyridin-2-yl)-2-(trans-4-(N-methylacetamido)cyclohexyl)acetamide;

N-(5-(4-(trans-1-amino-3-hydroxy-3-methylcyclobutyl)phenyl)-4-(2-fluorophenyl)pyridin-2-yl)-2-(trans-4-(N-methylacetamido)cyclohexyl)acetamide;

N-(trans-4-(2-((5-(4-(trans-1-amino-3-hydroxy-3-methylcyclobutyl)phenyl)-4-(2-fluorophenyl)pyridin-2-yl)amino)-2-oxoethyl)cyclohexyl)-N-methylpropionamide;

methyl (trans-4-(2-((5-(4-(trans-1-amino-3-hydroxy-3-methylcyclobutyl)phenyl)-4-(2-fluorophenyl)pyridin-2-yl)amino)-2-oxoethyl)cyclohexyl)(methyl)carbamate;

ethyl (trans-4-(2-((6-(4-(trans-1-amino-3-hydroxy-3-methylcyclobutyl)phenyl)-5-phenylpyridin-3-yl)amino)-2-oxoethyl)cyclohexyl)(methyl)carbamate;

N-(trans-4-(2-((6-(4-(trans-1-amino-3-hydroxy-3-methylcyclobutyl)phenyl)-5-phenylpyridin-3-yl)amino)-2-oxoethyl)cyclohexyl)-N-methylpropionamide;

N-(trans-4-(2-((6-(4-(trans-1-amino-3-hydroxy-3-methylcyclobutyl)phenyl)-5-phenylpyridazin-3-yl)amino)-2-oxoethyl)cyclohexyl)-N-methylisobutyramide;

N-(6-(4-(trans-1-amino-3-hydroxy-3-methylcyclobutyl)phenyl)-5-phenylpyridazin-3-yl)-2-(trans-4-(N-isopropylacetamido)cyclohexyl)acetamide;

methyl (trans-4-(2-((6-(4-(trans-1-amino-3-hydroxy-3-methylcyclobutyl)phenyl)-5-phenylpyridazin-3-yl)amino)-2-oxoethyl)cyclohexyl) (isopropyl)carbamate;

N-(5-(4-(trans-1-amino-3-hydroxy-3-methylcyclobutyl)phenyl)-4-phenylpyridin-2-yl)-2-(trans-4-(N-isopropylacetamido)cyclohexyl)acetamide;

methyl (trans-4-(2-((5-(4-(trans-1-amino-3-hydroxy-3-methylcyclobutyl)phenyl)-4-phenylpyridin-2-yl)amino)-2-oxoethyl)cyclohexyl)carbamate;

N-(trans-4-(2-((6-(4-(trans-1-amino-3-hydroxy-3-methylcyclobutyl)phenyl)-5-phenylpyridazin-3-yl)amino)-2-oxoethyl)cyclohexyl)-N-isopropylpropionamide;

N-(trans-4-(2-((6-(4-(trans-1-amino-3-hydroxy-3-methylcyclobutyl)phenyl)-5-phenylpyridazin-3-yl)amino)-2-oxoethyl)cyclohexyl)-N-isopropylcyclopropanecarboxamide;

N-(6-(4-(trans-1-amino-3-hydroxy-3-methylcyclobutyl)phenyl)-5-phenylpyridazin-3-yl)-2-(trans-4-(N-ethylacetamido)cyclohexyl)acetamide;

N-(trans-4-(2-((5-(4-(trans-1-amino-3-hydroxy-3-methylcyclobutyl)phenyl)-4-phenylpyridin-2-yl)amino)-2-oxoethyl)cyclohexyl)-2-methoxy-N-methylacetamide;

N-(5-(4-(trans-1-amino-3-hydroxy-3-methylcyclobutyl)phenyl)-4-phenylpyridin-2-yl)-2-(trans-4-(N-ethylacetamido)cyclohexyl)acetamide;

N-(trans-4-(2-((5-(4-(trans-1-amino-3-hydroxy-3-methylcyclobutyl)phenyl)-4-phenylpyridin-2-yl)amino-2-yl)-2-oxoethyl)cyclohexyl)-2,2-difluoro-N-methylacetamide;

N-(trans-4-(2-((5-(4-(trans-1-amino-3-hydroxy-3-methylcyclobutyl)phenyl)-4-(thiophen-3-yl)pyridin-2-yl)amino)-2-oxoethyl)cyclohexyl)-N-methylpropionamide;

N-(5-(4-(trans-1-amino-3-hydroxy-3-methylcyclobutyl)-3-fluorophenyl)-4-phenylpyridin-2-yl)-2-(trans-4-(N-methylacetamido)cyclohexyl)acetamide;

N-(trans-4-(2-((5-(4-(trans-1-amino-3-hydroxy-3-methylcyclobutyl)-3-fluorophenyl)-4-phenylpyridin-2-yl)amino)-2-oxoethyl)cyclohexyl)-N-methylpropionamide;

N-(trans-4-(2-((6-(4-(trans-1-amino-3-hydroxy-3-methylcyclobutyl)phenyl)-5-phenylpyridazin-3-yl)amino)-2-oxoethyl)cyclohexyl)-N-ethylpropionamide;

N-(trans-4-(2-((6-(4-(trans-1-amino-3-hydroxy-3-methylcyclobutyl)phenyl)-5-phenylpyridazin-3-yl)amino)-2-oxoethyl)cyclohexyl)-N-ethylcyclopropanecarboxamide;

N-(trans-4-(2-((5-(4-(trans-1-amino-3-hydroxy-3-methylcyclobutyl)phenyl)-4-phenylpyridin-2-yl)amino)-2-oxoethyl)cyclohexyl)-N-ethylpropionamide;

methyl (trans-4-(2-((5-(4-(trans-1-amino-3-hydroxy-3-methylcyclobutyl)phenyl)-4-phenylpyridin-2-yl)amino)-2-oxoethyl)cyclohexyl)(ethyl)carbamate;

N-(5-(4-(trans-1-amino-3-hydroxy-3-methylcyclobutyl)phenyl)-4-phenylpyridin-2-yl)-2-(trans-4-(N-(2,2,2-trifluoroethyl)acetamido)cyclohexyl)acetamide;

methyl (trans-4-(2-((6-(4-(trans-1-amino-3-hydroxy-3-methylcyclobutyl)phenyl)-5-phenylpyridin-3-yl)amino)-2-oxoethyl)cyclohexyl)(ethyl)carbamate;

N-(trans-4-(2-((6-(4-(trans-1-amino-3-hydroxy-3-methylcyclobutyl)phenyl)-5-phenylpyridin-3-yl)amino)-2-oxoethyl)cyclohexyl)-N-ethylpropionamide;

N-(6-(4-(trans-1-amino-3-hydroxy-3-methylcyclobutyl)phenyl)-5-phenylpyridin-3-yl)-2-(trans-4-(N-isopropylacetamido)cyclohexyl)acetamide;

methyl (trans-4-(2-((6-(4-(trans-1-amino-3-hydroxy-3-methylcyclobutyl)phenyl)-5-phenylpyridin-3-yl)amino)-2-oxoethyl)cyclohexyl) (isopropyl)carbamate;

N-(trans-4-(2-((6-(4-(trans-1-amino-3-hydroxy-3-methylcyclobutyl)phenyl)-5-phenylpyridin-3-yl)amino)-2-oxoethyl)cyclohexyl)-N-isopropylpropionamide;

N-(trans-4-(2-((6-(4-(trans-1-amino-3-fluorocyclobutyl)phenyl)-5-phenylpyridazin-3-yl)amino)-2-oxoethyl)cyclohexyl)-N-methylpropionamide;

N-(6-(4-(trans-1-amino-3-hydroxy-3-methylcyclobutyl)-3-fluorophenyl)-5-phenylpyridin-3-yl)-2-(trans-4-(N-methylacetamido)cyclohexyl)acetamide;

N-(trans-4-(2-((6-(4-(trans-1-amino-3-fluorocyclobutyl)phenyl)-5-(thiophen-3-yl)pyridazin-3-yl)amino)-2-oxoethyl)cyclohexyl)-N-methylpropionamide;

N-(trans-4-(2-((6-(4-(trans-1-amino-3-hydroxy-3-methylcyclobutyl)-3-fluorophenyl)-5-phenylpyridazin-3-yl)amino)-2-oxoethyl)cyclohexyl)-N-methylpropionamide;

N-(6-(4-(trans-1-amino-3-hydroxy-3-methylcyclobutyl)-3-fluorophenyl)-5-phenylpyridazin-3-yl)-2-(trans-4-(N-methylacetamido)cyclohexyl)acetamide;

N-(5-(4-(trans-1-amino-3-hydroxy-3-methylcyclobutyl)phenyl)-4-phenylpyridin-2-yl)-2-(trans-4-((2-methoxyethyl)(methyl)amino)cyclohexyl)acetamide;

methyl (trans-4-(2-((6-(4-(trans-1-amino-3-hydroxy-3-methylcyclobutyl)phenyl)-5-phenylpyridazin-3-yl)amino)-2-oxoethyl)cyclohexyl)(ethyl)carbamate.

Other compounds of the invention are those of the following group:

methyl (trans-4-(2-((6-(4-(1-aminocyclobutyl)phenyl)-5-phenylpyridin-3-yl)amino)-2-oxoethyl)cyclohexyl)(methyl)carbamate;
N-(6-(4-(1-amino-3,3-difluorocyclobutyl)phenyl)-5-phenylpyridin-3-yl)-2-(trans-4-morpholinocyclohexyl)acetamide;
N-(6-(4-(1-amino-3,3-difluorocyclobutyl)phenyl)-5-phenylpyridin-3-yl)-2-(trans-4-(2-oxooxazolidin-3-yl)cyclohexyl)acetamide;
methyl (trans-4-(2-((6-(4-(1-amino-3,3-difluorocyclobutyl)phenyl)-5-phenylpyridin-3-yl)amino)-2-oxoethyl)cyclohexyl)(methyl)carbamate;
N-(trans-4-(2-((6-(4-(1-amino-3-hydroxy-3-methylcyclobutyl)phenyl)-5-phenylpyridin-3-yl)amino)-2-oxoethyl)cyclohexyl)-2,2-difluoroacetamide;
N-(trans-4-(2-((6-(4-(3-aminooxetan-3-yl)phenyl)-5-phenylpyridin-3-yl)amino)-2-oxoethyl)cyclohexyl)-3,3,3-trifluoro-2,2-dimethylpropanamide;
N-(trans-4-(2-((6-(4-(2-aminopropan-2-yl)phenyl)-5-phenylpyridin-3-yl)amino)-2-oxoethyl)cyclohexyl)-2,2-difluoro-N-methylacetamide;
2-(trans-4-acetamidocyclohexyl)-N-(6-(4-((S)-1-aminoethyl)phenyl)-5-phenylpyridin-3-yl)acetamide;
2-(trans-4-acetamidocyclohexyl)-N-(6-(4-((R)-1-aminoethyl)phenyl)-5-phenylpyridin-3-yl)acetamide;
N-(trans-4-(2-((6-(4-((S)-1-aminoethyl)phenyl)-5-phenylpyridin-3-yl)amino)-2-oxoethyl)cyclohexyl)-3,3,3-trifluoro-2,2-dimethylpropanamide;
N-(trans-4-(2-((6-(4-((R)-1-aminoethyl)phenyl)-5-phenylpyridin-3-yl)amino)-2-oxoethyl)cyclohexyl)-3,3,3-trifluoro-2,2-dimethylpropanamide;
2-(trans-4-acetamidocyclohexyl)-N-(6-(4-((S)-1-amino-2,2-difluoroethyl)phenyl)-5-phenylpyridin-3-yl)acetamide;
N-(6-(4-((S)-1-aminoethyl)phenyl)-5-phenylpyridin-3-yl)-2-(trans-4-(N-methylmethylsulfonamido)cyclohexyl)acetamide;
N-(6-(4-(1-aminocyclobutyl)phenyl)-5-(thiophen-3-yl)pyridin-3-yl)-2-(trans-4-(2-oxopiperidin-1-yl)cyclohexyl)acetamide;
N-(6-(4-(trans-1-amino-3-hydroxy-3-methylcyclobutyl)phenyl)-5-phenylpyridin-3-yl)-2-(trans-4-morpholinocyclohexyl)acetamide;
N-(6-(4-(1-aminocyclobutyl)phenyl)-5-(2-fluorophenyl)pyridin-3-yl)-2-(trans-4-(N-methylmethylsulfonamido)cyclohexyl)acetamide;
N-(6-(4-(1-aminocyclobutyl)phenyl)-5-phenylpyridin-3-yl)-2-(trans-4-(3-methyl-4H-1,2,4-triazol-4-yl)cyclohexyl)acetamide;
N-(6-(4-(2-aminopropan-2-yl)phenyl)-5-phenylpyridin-3-yl)-2-(trans-4-morpholinocyclohexyl)acetamide;
2-(trans-4-acetamidocyclohexyl)-N-(6-(4-(2-aminopropan-2-yl)phenyl)-5-phenylpyridin-3-yl)acetamide;
N-(trans-4-(2-((6-(4-(2-aminopropan-2-yl)phenyl)-5-phenylpyridin-3-yl)amino)-2-oxoethyl)cyclohexyl)cyclopropanecarboxamide;
N-(trans-4-(2-((6-(4-(2-aminopropan-2-yl)phenyl)-5-phenylpyridin-3-yl)amino)-2-oxoethyl)cyclohexyl)-1-methylcyclopropane-1-carboxamide;
N-(trans-4-(2-((6-(4-(2-aminopropan-2-yl)phenyl)-5-phenylpyridin-3-yl)amino)-2-oxoethyl)cyclohexyl)isobutyramide;
2-(trans-4-acetamidocyclohexyl)-N-(6-(4-(2-aminopropan-2-yl)phenyl)-5-(thiophen-3-yl)pyridin-3-yl)acetamide;
N-(6-(4-(2-aminopropan-2-yl)phenyl)-5-(thiophen-3-yl)pyridin-3-yl)-2-(trans-4-(N-methylmethylsulfonamido)cyclohexyl)acetamide;
N-(6-(4-(2-aminopropan-2-yl)phenyl)-5-phenylpyridin-3-yl)-2-(trans-4-(N-methylmethylsulfonamido)cyclohexyl)acetamide;
N-(6-(4-(2-aminopropan-2-yl)phenyl)-5-(2-fluorophenyl)pyridin-3-yl)-2-(trans-4-(N-methylmethylsulfonamido)cyclohexyl)acetamide;
N-(6-(4-(1-aminocyclobutyl)phenyl)-5-phenylpyridin-3-yl)-2-(trans-4-(2-oxooxazolidin-3-yl)cyclohexyl)acetamide;
methyl (trans-4-(2-((6-(4-(2-aminopropan-2-yl)-3-fluorophenyl)-5-phenylpyridin-3-yl)amino)-2-oxoethyl)cyclohexyl)(methyl)carbamate;
N-(trans-4-(2-((6-(4-(2-aminopropan-2-yl)phenyl)-5-phenylpyridin-3-yl)amino)-2-oxoethyl)cyclohexyl)-N-methylcyclopropanecarboxamide;
N-(trans-4-(2-((6-(4-(2-aminopropan-2-yl)phenyl)-5-phenylpyridin-3-yl)amino)-2-oxoethyl)cyclohexyl)-N,3,3-trimethylbutanamide;
N-(trans-4-(2-((6-(4-(2-aminopropan-2-yl)phenyl)-5-phenylpyridin-3-yl)amino)-2-oxoethyl)cyclohexyl)-N,1-dimethylcyclopropane-1-carboxamide;
N-(trans-4-(2-((6-(4-(2-aminopropan-2-yl)phenyl)-5-phenylpyridin-3-yl)amino)-2-oxoethyl)cyclohexyl)-2-cyclopropyl-N-methylacetamide;
N-(trans-4-(2-((6-(4-(1-aminocyclopropyl)phenyl)-5-phenylpyridin-3-yl)amino)-2-oxoethyl)cyclohexyl)-N-methylbutyramide;
N-(trans-4-(2-((6-(4-(2-aminopropan-2-yl)phenyl)-5-phenylpyridin-3-yl)amino)-2-oxoethyl)cyclohexyl)pivalamide;
N-(trans-4-(2-((6-(4-(1-aminocyclobutyl)phenyl)-5-phenylpyridin-3-yl)amino)-2-oxoethyl)cyclohexyl)-2,2-difluoroacetamide;
N-(trans-4-(2-((6-(4-(2-aminopropan-2-yl)phenyl)-5-phenylpyridin-3-yl)amino)-2-oxoethyl)cyclohexyl)cyclobutanecarboxamide;
N-(trans-4-(2-((6-(4-(2-aminopropan-2-yl)phenyl)-5-phenylpyridin-3-yl)amino)-2-oxoethyl)cyclohexyl)-3,3-dimethylbutanamide;
2-(trans-4-acetamidocyclohexyl)-N-(6-(4-(1-aminocyclobutyl)phenyl)-5-phenylpyridin-3-yl)acetamide;
N-(trans-4-(2-((6-(4-(1-aminocyclobutyl)phenyl)-5-phenylpyridin-3-yl)amino)-2-oxoethyl)cyclohexyl)cyclopropanecarboxamide;
N-(trans-4-(2-((6-(4-(1-aminocyclobutyl)phenyl)-5-(thiophen-3-yl)pyridin-3-yl)amino)-2-oxoethyl)cyclohexyl)pivalamide;
N-(trans-4-(2-((6-(4-(1-aminocyclopropyl)phenyl)-5-phenylpyridin-3-yl)amino)-2-oxoethyl)cyclohexyl)butyramide;
N-(trans-4-(2-((6-(4-(1-aminocyclopropyl)phenyl)-5-phenylpyridin-3-yl)amino)-2-oxoethyl)cyclohexyl)-2,2-difluoroacetamide;
N-(trans-4-(2-((6-(4-(1-aminocyclopropyl)phenyl)-5-phenylpyridin-3-yl)amino)-2-oxoethyl)cyclohexyl)pivalamide;
N-(6-(4-(2-aminopropan-2-yl)phenyl)-5-phenylpyridin-3-yl)-2-(trans-4-(N-isopropylacetamido)cyclohexyl)acetamide;
methyl (trans-4-(1-((6-(4-(2-aminopropan-2-yl)phenyl)-5-phenylpyridin-3-yl)amino)-1-oxopropan-2-yl)cyclohexyl)(methyl)carbamate;

N-(6-(4-(2-aminopropan-2-yl)phenyl)-5-phenylpyridin-3-yl)-2-(trans-4-(morpholine-4-carbonyl)cyclohexyl)acetamide;

N-(6-(4-(2-aminopropan-2-yl)phenyl)-5-phenylpyridin-3-yl)-2-(trans-4-(pyrrolidine-1-carbonyl)cyclohexyl)acetamide;

methyl (trans-4-(2-((5-(4-(2-aminopropan-2-yl)phenyl)-4-phenylpyridin-2-yl)amino)-2-oxoethyl)cyclohexyl)(methyl)carbamate;

N-(5-(4-(2-aminopropan-2-yl)phenyl)-4-phenylpyridin-2-yl)-2-(trans-4-(2-oxopyrrolidin-1-yl)cyclohexyl)acetamide;

N-(6-(4-(1-aminocyclopropyl)-3-fluorophenyl)-5-phenylpyridazin-3-yl)-2-(trans-4-(2-oxooxazolidin-3-yl)cyclohexyl)acetamide;

N-(5-(4-(1-aminocyclopropyl)phenyl)-4-phenylpyridin-2-yl)-2-(trans-4-(2-oxooxazolidin-3-yl)cyclohexyl)acetamide;

N-(5-(4-(2-aminopropan-2-yl)phenyl)-4-(thiophen-3-yl)pyridine-2-yl)-2-(trans-4-(2-oxooxazolidin-3-yl)cyclohexyl)acetamide;

N-(5-(4-(trans-1-amino-3-fluorocyclobutyl)phenyl)-4-phenylpyridin-2-yl)-2-(trans-4-(2-oxooxazolidin-3-yl)cyclohexyl)acetamide;

N-(6-(4-(1-aminocyclopropyl)-3-fluorophenyl)-5-phenylpyridazin-3-yl)-2-(trans-4-(N-methylacetamido)cyclohexyl)acetamide;

methyl (trans-4-(2-((6-(4-(1-aminocyclobutyl)phenyl)-5-phenylpyridazin-3-yl)amino)-2-oxoethyl)cyclohexyl)(methyl)carbamate;

N-(6-(4-(1-aminocyclobutyl)phenyl)-5-phenylpyridazin-3-yl)-2-(trans-4-(N-methylacetamido)cyclohexyl)acetamide;

N-(5-(4-(trans-1-amino-3-hydroxy-3-methylcyclobutyl)phenyl)-4-phenylpyridin-2-yl)-2-(trans-4-(2-oxooxazolidin-3-yl)cyclohexyl)acetamide;

N-(5-(4-(trans-1-amino-3-hydroxy-3-methylcyclobutyl)phenyl)-4-phenylpyridin-2-yl)-2-(trans-4-(N-methylacetamido)cyclohexyl)acetamide;

N-(5-(4-((1r,3r)-1-amino-3-fluorocyclobutyl)phenyl)-4-phenylpyridin-2-yl)-2-(trans-4-(N-methylacetamido)cyclohexyl)acetamide;

methyl (trans-4-(2-((6-(4-(trans-1-amino-3-fluorocyclobutylphenyl)-5-phenylpyridazin-3-yl)amino)-2-oxoethyl)cyclohexyl)(methyl)carbamate;

methyl (trans-4-(2-((5-(4-(1-aminocyclobutyl)phenyl)-4-phenylpyridin-2-yl)amino)-2-oxoethyl)cyclohexyl)(methyl)carbamate;

N-(5-(4-(1-aminocyclobutyl)phenyl)-4-(2-fluorophenyl)pyridin-2-yl)-2-(trans-4-(N-methylacetamido)cyclohexyl)acetamide;

methyl (trans-4-(2-((5-(4-(1-aminocyclobutyl)phenyl)-4-(2-fluorophenyl)pyridin-2-yl)amino)-2-oxoethyl)cyclohexyl)(methyl)carbamate;

N-(5-(4-(1-aminocyclobutyl)phenyl)-4-(thiophen-3-yl)pyridin-2-yl)-2-(trans-4-(N-methylacetamido)cyclohexyl)acetamide;

N-(5-(4-(1-aminocyclobutyl)phenyl)-4-(2-fluorophenyl)pyridin-2-yl)-2-(trans-4-(2-oxooxazolidin-3-yl)cyclohexyl)acetamide;

methyl (trans-4-(2-((6-(4-(trans-1-amino-3-fluorocyclobutyl)phenyl)-5-(thiophen-3-yl)pyridin-3-yl)amino)-2-oxoethyl)cyclohexyl)(methyl)carbamate;

methyl (trans-4-(2-((6-(4-(2-aminopropan-2-yl)phenyl)-5-(thiophen-3-yl)pyridin-3-yl)amino)-2-oxoethyl)cyclohexyl)(methyl)carbamate;

methyl (trans-4-(2-((6-(4-(1-aminocyclobutyl)phenyl)-5-(thiophen-3-yl)pyridin-3-yl)amino)-2-oxoethyl)cyclohexyl)(methyl)carbamate;

methyl (trans-4-(2-((6-(4-(2-aminopropan-2-yl)phenyl)-5-(thiophen-3-yl)pyridazin-3-yl)amino)-2-oxoethyl)cyclohexyl)(methyl)carbamate;

methyl (trans-4-(2-((6-(4-(trans-1-amino-3-fluorocyclobutyl)phenyl)-5-(thiophen-3-yl)pyridazin-3-yl)amino)-2-oxoethyl)cyclohexyl)(methyl)carbamate;

N-(5-(4-(1-aminocyclobutyl)phenyl)-4-phenylpyridin-2-yl)-2-(trans-4-(2-oxopyrrolidin-1-yl)cyclohexyl)acetamide;

N-(trans-4-(2-((5-(4-(1-aminocyclobutyl)phenyl)-4-phenylpyridin-2-yl)amino)-2-oxoethyl)cyclohexyl)-N-methylcyclopropanecarboxamide;

ethyl (trans-4-(2-((5-(4-(trans-1-amino-3-hydroxy-3-methylcyclobutyl)phenyl)-4-phenylpyridin-2-yl)amino)-2-oxoethyl)cyclohexyl)(methyl)carbamate;

isopropyl (trans-4-(2-((5-(4-(trans-1-amino-3-hydroxy-3-methylcyclobutyl)phenyl)-4-phenylpyridin-2-yl)amino)-2-oxoethyl)cyclohexyl)(methyl)carbamate;

N-(trans-4-(2-((5-(4-(trans-1-amino-3-hydroxy-3-methylcyclobutyl)phenyl)-4-phenylpyridin-2-yl)amino)-2-oxoethyl)cyclohexyl)-N-methylcyclopropanecarboxamide;

N-(trans-4-(2-((5-(4-(trans-1-amino-3-hydroxy-3-methylcyclobutyl)phenyl)-4-phenylpyridin-2-yl)amino)-2-oxoethyl)cyclohexyl)-N-methylcyclobutanecarboxamide;

methyl (trans-4-(2-((6-(4-(1-aminocyclopropyl)phenyl)-5-phenylpyridazin-3-yl)amino)-2-oxoethyl)cyclohexyl)(methyl)carbamate;

N-(trans-4-(2-((6-(4-(trans-1-amino-3-hydroxy-3-methylcyclobutyl)phenyl)-5-phenylpyridazin-3-yl)amino)-2-oxoethyl)cyclohexyl)-N-methylcyclopropanecarboxamide;

N-(trans-4-(2-((6-(4-(trans-1-amino-3-hydroxy-3-methylcyclobutyl)phenyl)-5-phenylpyridazin-3-yl)amino)-2-oxoethyl)cyclohexyl)-N-methylisobutyramide;

ethyl (trans-4-(2-((6-(4-(trans-1-amino-3-hydroxy-3-methylcyclobutyl)phenyl)-5-phenylpyridazin-3-yl)amino)-2-oxoethyl)cyclohexyl)(methyl)carbamate;

N-(trans-4-(2-((5-(4-(1-aminocyclopropyl)phenyl)-4-phenylpyridin-2-yl)amino)-2-oxoethyl)cyclohexyl)-N-methylpropionamide;

N-(5-(4-(trans-1-amino-3-hydroxy-3-methylcyclobutyl)phenyl)-4-phenylpyridin-2-yl)-2-(trans-4-(2-oxopyrrolidin-1-yl)cyclohexyl)acetamide;

N-(5-(4-(1-aminocyclopropyl)phenyl)-4-phenylpyridin-2-yl)-2-(trans-4-(2-oxopyrrolidin-1-yl)cyclohexyl)acetamide;

N-(trans-4-(2-((6-(4-(2-aminopropan-2-yl)phenyl)-5-phenylpyridazin-3-yl)amino)-2-oxoethyl)cyclohexyl)-N-methylpropionamide;

N-(trans-4-(2-((6-(4-(2-aminopropan-2-yl)phenyl)-5-phenylpyridazin-3-yl)amino)-2-oxoethyl)cyclohexyl)-N-methylisobutyramide;

N-(trans-4-(2-((6-(4-(2-aminopropan-2-yl)phenyl)-5-phenylpyridazin-3-yl)amino)-2-oxoethyl)cyclohexyl)-N-methylcyclopropanecarboxamide;

N-(trans-4-(2-((6-(4-(2-aminopropan-2-yl)phenyl)-5-phenylpyridazin-3-yl)amino)-2-oxoethyl)cyclohexyl)-N-methylcyclobutanecarboxamide;

methyl (trans-4-(2-((5'-(4-(1-aminocyclopropyl)phenyl)-[2,4'-bipyridin]-2'-yl)amino)-2-oxoethyl)cyclohexyl)(methyl)carbamate;

N-(6-(4-(1-aminocyclopropyl)-3-fluorophenyl)-5-phenylpyridin-3-yl)-2-(trans-4-(N-methylacetamido)cyclohexyl)acetamide;

ethyl (trans-4-(2-((5-(4-(trans-1-amino-3-hydroxy-3-methylcyclobutyl)phenyl)-4-(thiophen-3-yl)pyridin-2-yl)amino)-2-oxoethyl)cyclohexyl)(methyl)carbamate;
N-(trans-4-(2-((6-(4-(1-aminocyclopropyl)phenyl)-5-phenylpyridazin-3-yl)amino)-2-oxoethyl)cyclohexyl)-N-methylpropionamide;
N-(trans-4-(2-((6-(4-(1-aminocyclopropyl)phenyl)-5-phenylpyridazin-3-yl)amino)-2-oxoethyl)cyclohexyl)-N-methylisobutyramide;
N-(trans-4-(2-((6-(4-(1-aminocyclopropyl)phenyl)-5-phenylpyridazin-3-yl)amino)-2-oxoethyl)cyclohexyl)-N-methylcyclobutanecarboxamide;
ethyl (trans-4-(2-((6-(4-(1-aminocyclopropyl)phenyl)-5-phenylpyridazin-3-yl)amino)-2-oxoethyl)cyclohexyl)(methyl)carbamate;
N-(trans-4-(2-((6-(4-(2-aminopropan-2-yl)phenyl)-5-phenylpyridin-3-yl)amino)-2-oxoethyl)cyclohexyl)-N-methylpropionamide;
N-(6-(4-(2-aminopropan-2-yl)phenyl)-5-(thiophen-3-yl)pyridazin-3-yl)-2-(trans-4-(N-methylacetamido)cyclohexyl)acetamide;
N-(6-(4-(1-aminocyclobutyl)phenyl)-5-(thiophen-3-yl)pyridazin-3-yl)-2-(trans-4-(N-methylacetamido)cyclohexyl)acetamide;
N-(6-(4-(trans-1-amino-3-hydroxy-3-methylcyclobutyl)phenyl)-5-phenylpyridazin-3-yl)-2-(trans-4-(2-oxopiperidin-1-yl)cyclohexyl)acetamide;
ethyl (trans-4-(2-((6-(4-(2-aminopropan-2-yl)phenyl)-5-phenylpyridin-3-yl)amino)-2-oxoethyl)cyclohexyl)(methyl)carbamate;
methyl (trans-4-(2-((6-(4-(1-aminocyclopropyl)-3-fluorophenyl)-5-(thiophen-3-yl)pyridazin-3-yl)amino)-2-oxoethyl)cyclohexyl)(methyl)carbamate;
N-(trans-4-(2-((6-(4-(1-aminocyclopropyl)-3-fluorophenyl)-5-(thiophen-3-yl)pyridazin-3-yl)amino)-2-oxoethyl)cyclohexyl)-N-methylpropionamide;
N-(trans-4-(2-((5-(4-(1-aminocyclobutyl)phenyl)-4-(2-fluorophenyl)pyridin-2-yl)amino)-2-oxoethyl)cyclohexyl)-N-methylpropionamide;
N-(trans-4-(2-((6-(4-(1-aminocyclopropyl)-3-fluorophenyl)-5-phenylpyridazin-3-yl)amino)-2-oxoethyl)cyclohexyl)-N-methylpropionamide;
methyl (trans-4-(2-((6-(4-(1-aminocyclopropyl)-3-fluorophenyl)-5-phenylpyridazin-3-yl)amino)-2-oxoethyl)cyclohexyl)(methyl)carbamate;
methyl (trans-4-(2-((5-(4-(trans-1-amino-3-hydroxy-3-methylcyclobutyl)phenyl)-4-phenylpyridin-2-yl)amino)-2-oxoethyl)cyclohexyl) (isopropyl)carbamate;
methyl (trans-4-(2-((5-(4-(1-aminocyclopropyl)-3-fluorophenyl)-4-phenylpyridin-2-yl)amino)-2-oxoethyl)cyclohexyl)carbamate;
N-(trans-4-(2-((5-(4-(trans-1-amino-3-hydroxy-3-methylcyclobutyl)phenyl)-4-phenylpyridin-2-yl)amino)-2-oxoethyl)cyclohexyl)-N-isopropylpropionamide;
N-(trans-4-(2-((5-(4-(trans-1-amino-3-hydroxy-3-methylcyclobutyl)phenyl)-4-phenylpyridin-2-yl)amino)-2-oxoethyl)cyclohexyl)-N-isopropylcyclopropanecarboxamide.

Akt3 exists in both active and inactive forms, and it is in its active form that it is implicated in EMT, and hence in cancer metastasis. It is believed that the compounds of the invention are potent and specific inhibitors of Akt3, and the compounds are referred to herein as Akt3 inhibitors. It should be understood, however, that whilst this represents the applicant's current belief, the possibility cannot be precluded that the compounds exert a beneficial effect for some other reason. Without wishing to be bound by theory, it is believed that the compounds of the invention inhibit Akt3 by stabilising the inactive form of Akt3, rather than by directly blocking its mechanism of action. By binding to an allosteric binding site in the inactive form of the Akt3 protein, the PH-in conformation of the protein is stabilised, in turn blocking access to the ATP binding site and thus inhibiting the function of the Akt3 protein. This helps to reduce or prevent Akt3-mediated EMT.

The use of Akt3-specific inhibitors has a number of advantages over the known pan-Akt inhibitors. Existing pan-Akt inhibitors have relatively low potency against Akt3, and therefore do little to inhibit this isoform. The disclosed Akt3 inhibitors are also believed to have lower toxicity than known pan-Akt inhibitors; Akt1 is the most widely expressed isoform and, being related to perinatal mortality and general growth, has the most serious knockout phenotype, and inhibition of Akt2 has been linked to glucose homeostasis defects. The specificity of the compounds described herein for Akt3 reduces or eliminates these undesirable effects, and may also avoid triggering the feedback amplification of Akt signalling seen when both Akt1 and Akt2 are inhibited.

The compounds of the invention may be used in the treatment of cancer. The compounds are believed to inhibit Akt3, the expression of which is frequently associated with resistance to therapy, and the compounds of the invention may therefore be used in the treatment of cancers which are resistant to conventional cancer therapies.

Thus, there is provided a compound of formula (I) as described above for use in the treatment of cancer. Likewise, there is provided a compound of formula (I) as described above for use in the manufacture of a medicament for the treatment of cancer.

The cancer to be treated by a compound of the invention may be one or more of leukaemias such as, but not limited to, acute leukaemia, acute lymphocytic leukaemia, acute lymphoblastic leukaemia, acute myelocytic leukaemias such as myeloblastic, promyelocytic, myelomonocytic, monocytic, erythroleukaemia leukaemias and myelodysplasia syndrome, chronic leukaemias such as, but not limited to, chronic myelocytic (granulocytic) leukaemia, chronic lymphocytic leukaemia, hairy cell leukaemia; polycythemia vera; lymphomas such as, but not limited to, Hodgkin's disease, non-Hodgkin's disease; multiple myelomas such as, but not limited to, smouldering multiple myeloma, nonsecretory myeloma, osteosclerotic myeloma, plasma cell leukaemia, solitary plasmacytoma and extramedullary plasmacytoma; Waldenstrom's macroglobulinemia; monoclonal gammopathy of undetermined significance; benign monoclonal gammopathy; heavy chain disease; bone and connective tissue sarcomas such as, but not limited to, bone sarcoma, osteosarcoma, chondrosarcoma, Ewing's sarcoma, malignant giant cell tumour, fibrosarcoma of bone, chordoma, periosteal sarcoma, soft-tissue sarcomas, angiosarcoma (hemangiosarcoma), fibrosarcoma, Kaposi's sarcoma, leiomyosarcoma, liposarcoma, lymphangiosarcoma, metastatic cancers, neurilemmoma, rhabdomyosarcoma, synovial sarcoma; brain tumours such as, but not limited to, glioma, astrocytoma, brain stem glioma, ependymoma, oligodendroglioma, nonglial tumour, acoustic neurinoma, craniopharyngioma, medulloblastoma, meningioma, pineocytoma, pineoblastoma, primary brain lymphoma; breast cancer, including, but not limited to, adenocarcinoma, lobular (small cell) carcinoma, intraductal carcinoma, medullary breast cancer, mucinous breast cancer, tubular breast cancer, papillary breast cancer, primary cancers, Paget's disease, and inflammatory breast cancer; adrenal cancer such as, but not limited to, pheochromocytom and adrenocortical carcinoma; thyroid cancer such as, but not limited to, papillary or follicular thyroid cancer, medullary thyroid cancer and anaplastic thyroid cancer; pancreatic cancer such as, but not limited to, insulinoma, gastrinoma, glucagonoma, vipoma, somatostatin-secreting tumour, and carcinoid or islet cell tumour; pituitary cancers such as, but not limited to, Cushing's disease, prolactin-secreting tumour, acromegaly, and diabetes insipius; eye cancers such as, but not limited to, ocular melanoma such as iris melanoma, choroidal melanoma, and cilliary body melanoma, and retinoblastoma; vaginal cancers such as squamous cell carcinoma, adenocarcinoma, and melanoma; vulvar cancer such as squamous cell carcinoma, melanoma, adenocarcinoma, basal cell carcinoma, sarcoma, and Paget's disease; cervical cancers such as, but not limited to, squamous cell carcinoma, and adenocarcinoma; uterine cancers such as, but not limited to, endometrial carcinoma and uterine sarcoma; ovarian cancers such as, but not limited to, ovarian epithelial carcinoma, borderline tumour, germ cell tumour, and stromal tumour; oesophageal cancers such as, but not limited to, squamous cancer, adenocarcinoma, adenoid cyctic carcinoma, mucoepidermoid carcinoma, adenosquamous carcinoma, sarcoma, melanoma, plasmacytoma, verrucous carcinoma, and oat cell (small cell) carcinoma; stomach cancers such as, but not limited to, adenocarcinoma, fungating (polypoid), ulcerating, superficial spreading, diffusely spreading, malignant lymphoma, liposarcoma, fibrosarcoma, and carcinosarcoma; colon cancers; rectal cancers; liver cancers such as, but not limited to, hepatocellular carcinoma and hepatoblastoma, gallbladder cancers such as adenocarcinoma; cholangiocarcinomas such as, but not limited to, papillary, nodular, and diffuse; lung cancers such as non-small cell lung cancer, squamous cell carcinoma (epidermoid carcinoma), adenocarcinoma, large-cell carcinoma and small-cell lung cancer; testicular cancers such as, but not limited to, germinal tumour, seminoma, anaplastic, classic (typical), spermatocytic, nonseminoma, embryonal carcinoma, teratoma carcinoma, choriocarcinoma (yolk-sac tumour), prostate cancers such as, but not limited to, adenocarcinoma, leiomyosarcoma, and rhabdomyosarcoma; genital cancers such as penile cancer; oral cancers such as, but not limited to, squamous cell carcinoma; basal cancers; salivary gland cancers such as, but not limited to, adenocarcinoma, mucoepidermoid carcinoma, and adenoidcystic carcinoma; pharynx cancers such as, but not limited to, squamous cell cancer, and verrucous; skin cancers such as, but not limited to, basal cell carcinoma, squamous cell carcinoma and melanoma, superficial spreading melanoma, nodular melanoma, lentigo malignant melanoma, acral lentiginous melanoma; kidney cancers such as, but not limited to, renal cell cancer, clear cell renal cell carcinoma, adenocarcinoma, hypernephroma, fibrosarcoma, transitional cell cancer (renal pelvis and/or ureter); Wilms' tumour; bladder cancers such as, but not limited to, transitional cell carcinoma, squamous cell cancer, adenocarcinoma, carcinosarcoma. In addition, cancers include myxosarcoma, osteogenic sarcoma, endotheliosarcoma, lymphangioendotheliosarcoma, mesothelioma, synovioma, hemangioblastoma, epithelial carcinoma, cystadenocarcinoma, bronchogenic carcinoma, sweat gland carcinoma, sebaceous gland carcinoma, papillary carcinoma, papillary adenocarcinomas, gastrointestinal stromal tumour, head and neck cancer, colorectal cancer and myelodysplastic syndromes.

Particular cancers in the treatment of which the compounds of the invention may be effective include lung cancer, melanoma, breast cancer, ovarian cancer and carcinoma. More particularly, the cancer is selected from squamous cell lung cancer, resistant melanoma, endocrine therapy-resistant Her2$^+$ breast cancer, cisplatin-resistant ovarian cancer or heptacellular carcinoma.

Thus, in another aspect of the invention, there is provided a compound of formula (I) for use in the treatment of cancer, wherein the cancer is selected from lung cancer, melanoma, breast cancer, ovarian cancer or carcinoma. Likewise, there is provided a compound of formula (I) as described above for use in the manufacture of a medicament for the treatment of cancer, wherein the cancer is selected from lung cancer, melanoma, breast cancer, ovarian cancer or carcinoma.

There is also provided a compound of formula (I) for use in the treatment of cancer, wherein the cancer is selected from squamous cell lung cancer, resistant melanoma, endocrine therapy-resistant Her2$^+$ breast cancer, cisplatin resistant ovarian cancer or heptacellular carcinoma. Likewise, there is provided a compound of formula (I) as described above for use in the manufacture of a medicament for the treatment of cancer, wherein the cancer is selected from squamous cell lung cancer, resistant melanoma, endocrine therapy-resistant Her2$^+$ breast cancer, cisplatin resistant ovarian cancer or heptacellular carcinoma.

The cancer may be metastatic. The treatment of metastatic cancer depends on where the primary tumour is located. When breast cancer spreads to the lungs, for example, it remains a breast cancer and the treatment is determined by the metastatic cancer origin within the breast, not by the fact that it is now in the lung. About 5 percent of the time, metastatic cancer is discovered but the primary tumour cannot be identified. The treatment of these metastatic cancers is dictated by their location rather than their origin. Metastatic cancers are named by the tissue of the original tumour (if known). For example, a breast cancer that has spread to the brain is called metastatic breast cancer to the brain. Akt3 activity may be used to help guide treatment options, for example, if Akt3 expression is shown to be upregulated in a primary tumour, this can be used to infer an increased probability of metastasis. This information can be used as a guide to treatment options, i.e. more aggressive anti-cancer surgical, chemotherapeutic or radiotherapeutic treatment such as radical mastectomy.

Compounds of the invention may be used in the treatment of cancer alone, but more usually will be used in combination with known cancer treatments. For example, compounds of the invention may be used in combination with one or more chemotherapeutic agents, or in combination with one or more immune checkpoint modulating antibodies.

The chemotherapeutic agent or agents used in combination with a compound of the invention may be any suitable chemotherapeutic agent known in the art. In particular, suitable chemotherapeutic agents include, but are not limited to, those selected from the following classes:

Alkylating Agents

Alkylating agents act to prevent the cancer cell from reproducing by causing damage to DNA, and work in all phases of the cell cycle. Alkylating agents include:

Nitrogen mustards, including mechlorethamine, chlorambucil, cyclophosphamide, ifosfamide, melphalan, estramustine and uramustine.

Nitrosoureas, including streptozocin, carmustine and lomustine.

Alkyl sulfonates, including busulfan.

Triazines, including dacarbazine, temozolamide and procarbazine.

Ethylenimines, including thiotepa and altretamine.

Platinum compounds, including cisplatin, carboplatin, oxaliplatin, satraplatin, and picoplatin onnaplatin, tetraplatin, sprioplatin, iproplatin, chloro(diethylenediamino)-platinum (II) chloride, dichloro(ethylenediamino)-platinum (II), diamino(2-ethylmalonato) platinum (II), (1,2-diaminocyclohexane)malonatoplatinum (II), (4-carboxyphthalo)-(1,2-diaminocyclohexane)platinum (II), (1,2-diaminocyclohexane)-(isocitrato)platinum (II), and (1,2-diaminocyclohexane)-cis-(pyruvato)platinum (II).

Antimetabolites

Antimetabolites interfere with DNA and RNA growth, damaging cells during the S phase.

Antimetabolites include 5-fluorouracil, 6-mercaptopurine, capecitabine, cladribine, clofarabine, cytarabine, floxuridine, fludarabine, gemcitabine, hydroxyurea, methotrexate, pemetrexed, pentostatin, thioguanine, raltitrexed, trimetrexate, azacitidine, capecitabine, edatrexate, troxacitabine and chlorodeoxyadenosine.

Anti-tumour Antibiotics

Anti-tumour antibiotics include anthracyclines, which interfere with enzymes involved in DNA replication. Anthracyclines include daunorubicin, doxorubicin, epirubicin, idarubicin and valrubicin.

Other anti-tumour antibiotics include actinomycin-D, bleomycin, mitomycin-C, dactinomycin, mithramycin, mitoxantrane and parfiromycin.

Topoisomerase Inhibitors

Topoisomerase inhibitors interfere with the topoisomerase enzymes, which are involved in DNA replication. Topoisomerase inhibitors include:
Topoisomerase I inhibitors, including topotecan and irinotecan.
Topoisomerase II inhibitors, including etoposide, teniposide, mitoxantrone, actinomycin, podophyllotoxin, amsacrine and losoxantrone.

Mitotic Inhibitors

Mitotic inhibitors prevent mitosis or inhibit enzymes from making proteins required for cell reproduction. Mitotic inhibitors include:
Taxanes, including paclitazel and docetaxel.
Epothilones, including ixabepilone.
Vinca alkaloids, including vinblastine, vincristine, vinorelbine, vinvesir and vindesine.
Estramustine.

Corticosteroids

Corticosteroids include prednisone, methylprednisolone and dexamethasone.

Targeted Therapies

Targeted therapies are designed to attack cancer cells more specifically. They include:
Gene therapy agents
Antisense therapy agents
Tyrosine kinase inhibitors, including erlotinib hydrochloride, gefitinib, imatinib, lapatinib, mesylate and semaxinib.
Raf inhibitors, including sorafenib.
Gene expression modulators, including adapalene, bexarotene, trans-retinoic acid, 9-cis-retinoic acid and N-(4-hydroxypheny)retinamide.
Axl inhibitors, including 1-(6,7-dihydro-5H-benzo[6,7]cyclohepta[1,2-c]pyridazin-3-yl)-N3-((7-(S)-pyrrolidin-1-yl)-6,7,8,9-tetrahydro-5H-benzo[7]annulene-2-yl)-1H-1,2,4-triazole-3,5-diamine (BGB324/R428), CH5451098 (Roche) and Axl inhibitors described in PCT/US07/089177, PCT/US2010/021275 and PCT/EP2011/004451, particularly the AXL inhibitor BGB324/R[428].

PKB pathway inhibitors, including perifosine, enzastaurin hydrochloride, and triciribine.
P13K inhibitors such as semaphore and SF1126.
MTOR inhibitors such as rapamycin and analogues.
CDK inhibitors, including seliciclib, alvocidib, and 7-hydroxystaurosporine.
COX-2 inhibitors, including celecoxib.
HDAC inhibitiors, including trichostatin A, suberoylanilide hydroxamic acid, and chlamydocin.
DNA methylase inhibitors, including temozolomide.

Differentiating Agents

Differentiating agents act on cancer cells to make them mature into normal cells. Differentiating agents include retinoids, tretinoin, bexarotene and arsenic trioxide.

Hormone Therapy

Hormone therapy is used to change the action or production of female or male hormones, preventing a cancer from using a hormone it needs to grow or preventing the body from making that hormone. Hormone therapy includes:
Anti-oestrogens, including fulvestrant, tamoxifen, toremifene and raloxifene.
Aromatase inhibitors, including anastrozole, exemestane, letrozole, aminoglutethimide and formestane.
Progestins, including megestrol acetate and medroxyprogesterone acetate.
Oestrogens, including diethylstilbestrol.
Anti-androgens, including bicalutamide, flutamide, nilutamide and cyproterone.
Luteinizing hormone-releasing hormone agonists or analogs, including leuprolide, goserelin, abarelix, buserelin, nafarelin acetate, histrelin, descrelin and triptorelin.
Thyroid hormones, including levothyroxine and liothyronine.
Androgens, including fluoxymesterone and testolactone.

Immunotherapy

Immunotherapy drugs stimulate the body's natural immune system to recognise and attack cancer cells. Immunotherapy drugs include:
Monoclonal antibody therapy, including rituximab, alemtuzumab, bevacizumab, cetuximab, ibritumomab, tiuxetan and trastuxumab.
Non-specific immunotherapies and adjuvants, including BCG, interleukin-2 and interferon-α2a, interferon-α2b, aldesleuikin, denileukin difititox and oprelvekin.
Immunomodulating drugs, including thalidomide and lenalidomide.
Cancer vaccines, including Provenge®.
Immunotoxins, including gemtuzumab ozogamicin.
Radioimmunoconjugates, including I-tositumobab.

Other

Other chemotherapeutic agents which do not fall into the above classes include L-asparaginase, PEG L-asparaginase, altretamine, gallium nitrate, levamisole, mitotane, hydroxyurea, octreotide, procarbazine and surabin.

Other anticancer therapies which may be used in combination with compounds of formula (I) include protective or adjunctive agents, including:
Cytoprotective agents, including amifostine and dexrazoxane.
Phosphonates, including pamidronate and zoledronic acid.
Stimulating factors, including epoetin, darbeopetin, filgrastim, PEG-filgrastim and sargramostim.

Many combination chemotherapeutic regimens are known to the art, and may be used in combination with compounds of the present invention. These include, but are not limited to, combinations of carboplatin/paclitaxel, capecitabine/docetaxel, fluorauracil/levamisole, fluorauracil/leucovorin, methotrexate/leucovorin and trastuzumab/paclitaxel, alone or in further combination with carboplatin, and the like.

There is thus provided a compound of formula (I) for use in the treatment of cancer, wherein the treatment further comprises one or more chemotherapeutic agents. Likewise, there is provided the use of a compound of formula (I) in the manufacture of a medicament for the treatment of cancer, wherein the treatment further comprises one or more chemotherapeutic agents.

There is also provided a compound of formula (I) for use in the treatment of cancer, or the use of such a compound in the manufacture of a medicament for the treatment of cancer, wherein the treatment further comprises one or more chemotherapeutic agents selected from alkylating agents, antimetabolites, anti-tumour antibiotics, topoisomerase inhibitors, mitotic inhibitors, corticosteroids, targeted therapies, differentiating agents, hormone therapy, immunotherapy drugs, other chemotherapeutic agents not falling into the preceding classes and/or protective or adjunctive agents.

There is also provided a compound of formula (I) for use in the treatment of cancer, or the use of such a compound in the manufacture of a medicament for the treatment of cancer, wherein the treatment further comprises one or more chemotherapeutic agents selected from nitrogen mustards, nitrosoureas, alkyl sulfonates, triazines, ethylenimines, platinum compounds, antimetabolites, anthracyclines, anti-tumour antibiotics, topoisomerase I inhibitors, topoisomerase II inhibitors, taxanes, epothilones, vinca alkaloids, estramustine, corticosteroids, gene therapy agents, antisense therapy agents, tyrosine kinase inhibitors, Raf inhibitors, gene expression modulators, Axl inhibitors, PKB pathway inhibitors, P13K inhibitors, MTOR inhibitors, CDK inhibitors, COX-2 inhibitors, HDAC inhibitiors, DNA methylase inhibitors, differentiating agents, anti-oestrogens, aromatase inhibitors, progestins, oestrogens, anti-androgens, luteinizing hormone-releasing hormone agonists or analogs, thyroid hormones, androgens, monoclonal antibody therapy, non-specific immunotherapies and adjuvants, immunomodulating drugs, cancer vaccines, immunotoxins, radioimmunoconjugates, L-asparaginase, PEG L-asparaginase, altretamine, gallium nitrate, levamisole, mitotane, hydroxyurea, octreotide, procarbazine, surabin, cytoprotective agents, phosphonates and/or stimulating factors.

There is also provided a compound of formula (I) for use in the treatment of cancer, or the use of such a compound in the manufacture of a medicament for the treatment of cancer, wherein the treatment further comprises one or more chemotherapeutic agents, and wherein the cancer is selected from lung cancer, melanoma, breast cancer, ovarian cancer or carcinoma.

There is also provided a compound of formula (I) for use in the treatment of cancer, or the use of such a compound in the manufacture of a medicament for the treatment of cancer, wherein the treatment further comprises one or more chemotherapeutic agents, and wherein the cancer is selected from squamous cell lung cancer, resistant melanoma, endocrine therapy-resistant Her2$^+$ breast cancer, cisplatin-resistant ovarian cancer or heptacellular carcinoma.

The compound of the invention may be administered before the one or more chemotherapeutic agents, simultaneously with the one or more chemotherapeutic agents, or after the one or more chemotherapeutic agents.

The immune checkpoint modulating antibodies used in combination with a compound of the invention may be any suitable immune checkpoint modulating antibody known in the art. In particular, suitable immune checkpoint modulating antibodies include:

CTLA-4 targeting antibodies, including Ipilimumab and Tremelimumab.

PD-1 targeting antibodies, including Pembrolizumab, Mivolumab and AMP-514/MEDI0680.

BD-L1 targeting antibodies, including MPDL3280A, MEDI4736, MSB0010718C and BMS-936559.

4-1BB targeting antibodies, including Urelumab and PF-05082566.

OX-40 targeting antibodies, including MEDI6469, MEDI6383 (rOX40L) and MOXR0916.

GITR targeting antibodies, including TRX518.

CD27 targeting antibodies, including CDX-1127.

CD40 targeting antibodies, including CP-870,893.

LAG3 targeting antibodies, including BMS-986016.

Immune checkpoints, which are inhibitory pathways in the immune system, may be co-opted by tumours to induce immune resistance. The use of antibodies to block or modulate immune checkpoints, including T-cell stimulatory and inhibitory receptors and dendritic cell stimulatory receptors, and thus to reduce or reverse the immune resistance of the cancer, is thus an important avenue in cancer research.

T-cell stimulatory receptors which may be modulated through the use of immune checkpoint modulating antibodies include CD28, ICOS, 4-1BB, OX40, GITR, CD27, TWEAKR, HVEM and TIM-1. T-cell inhibitory receptors which maybe modulated through the use of immune checkpoint modulating antibodies include PD-L1, CTLA-4, PD-1, BTLA, TIM-3, VISTA, LAG-3 and TIGIT. Dendritic cell stimulatory receptors which may be modulated through the use of immune checkpoint modulating antibodies include CD40 and 4-1BB.

Where a combination of immune checkpoint modulating antibodies are used in conjunction with a compound of the invention, all of the antibodies used may target inhibitory receptors, all of the antibodies used may target stimulatory receptors, or a combination of inhibitory receptor and stimulatory receptor targeting antibodies may be used.

Thus, there is thus provided a compound of formula (I) for use in the treatment of cancer, wherein the treatment further comprises one or more immune checkpoint modulating antibodies. Likewise, there is provided the use of a compound of formula (I) in the manufacture of a medicament for the treatment of cancer, wherein the treatment further comprises one or more immune checkpoint modulating antibodies.

There is also provided a compound of formula (I) for use in the treatment of cancer, or the use of such a compound in the manufacture of a medicament for the treatment of cancer, wherein the treatment further comprises one or more immune checkpoint modulating antibodies selected from Ipilimumab, Tremelimumab, Pembrolizumab, Mivolumab, AMP-514/MEDI0680, MPDL3280A, MEDI4736, MSB0010718C, BMS-936559, Urelumab, PF-05082566, MEDI6469, MEDI6383 (rOX40L), MOXR0916, TRX518, CDX-1127, CP-870,893 and BMS-986016.

The compound of the invention may be administered before the one or more immune checkpoint modulating antibodies, simultaneously with the one or more immune checkpoint modulating antibodies, or after the one or more immune checkpoint modulating antibodies.

There is also provided a compound of formula (I) for use in the treatment of cancer, or the use of such a compound in the manufacture of a medicament for the treatment of cancer, wherein the treatment further comprises one or more immune checkpoint modulating antibodies, and wherein the cancer is selected from lung cancer, melanoma, breast cancer, ovarian cancer or carcinoma.

There is also provided a method of treating a subject having cancer, which method comprises administration to the subject of a therapeutically or prophylactically effective amount of a compound of formula (I).

There is also provided a method of treating a subject having lung cancer, melanoma, breast cancer, ovarian cancer or carcinoma, which method comprises administration to the subject of a therapeutically or prophylactically effective amount of a compound of formula (I).

There is also provided a method of treating a subject having squamous cell lung cancer, resistant melanoma, endocrine therapy-resistant Her2$^+$ breast cancer, cisplatin resistant ovarian cancer or heptacellular carcinoma, which method comprises administration to the subject of a therapeutically or prophylactically effective amount of a compound of formula (I).

There is also provided a method of treating a subject having cancer, which method comprises administration to the subject of a therapeutically or prophylactically effective amount of a compound of formula (I), in combination with one or more chemotherapeutic agents.

There is also provided a method of treating a subject having cancer, which method comprises administration to the subject of a therapeutically or prophylactically effective amount of a compound of formula (I), in combination with one or more chemotherapeutic agents selected from alkylating agents, antimetabolites, anti-tumour antibiotics, topoisomerase inhibitors, mitotic inhibitors, corticosteroids, targeted therapies, differentiating agents, hormone therapy, immunotherapy drugs, other chemotherapeutic agents not falling into the preceding classes and/or protective or adjunctive agents.

There is also provided a method of treating a subject having cancer, which method comprises administration to the subject of a therapeutically or prophylactically effective amount of a compound of formula (I), in combination with one or more chemotherapeutic agents selected from nitrogen mustards, nitrosoureas, alkyl sulfonates, triazines, ethylenimines, platinum compounds, antimetabolites, anthracyclines, anti-tumour antibiotics, topoisomerase I inhibitors, topoisomerase II inhibitors, taxanes, epothilones, vinca alkaloids, estramustine, corticosteroids, gene therapy agents, antisense therapy agents, tyrosine kinase inhibitors, Raf inhibitors, gene expression modulators, Axl inhibitors, PKB pathway inhibitors, P13K inhibitors, MTOR inhibitors, CDK inhibitors, COX-2 inhibitors, HDAC inhibitiors, DNA methylase inhibitors, differentiating agents, anti-oestrogens, aromatase inhibitors, progestins, oestrogens, anti-androgens, luteinizing hormone-releasing hormone agonists or analogs, thyroid hormones, androgens, monoclonal antibody therapy, non-specific immunotherapies and adjuvants, immunomodulating drugs, cancer vaccines, immunotoxins, radioimmunoconjugates, L-asparaginase, PEG L-asparaginase, altretamine, gallium nitrate, levamisole, mitotane, hydroxyurea, octreotide, procarbazine, surabin, cytoprotective agents, phosphonates and/or stimulating factors.

There is also provided a method of treating a subject having lung cancer, melanoma, breast cancer, ovarian cancer or carcinoma, which method comprise administration to the subject of a therapeutically or prophylactically effective amount of a compound of formula (I) in combination with one or more chemotherapeutic agents.

There is also provided a method of treating a subject having squamous cell lung cancer, resistant melanoma, endocrine therapy-resistant Her2$^+$ breast cancer, cisplatin-resistant ovarian cancer or heptacellular carcinoma, which method comprises administration to the subject of a therapeutically or prophylactically effective amount of a compound of formula (I) in combination with one or more chemotherapeutic agents.

There is also provided a method of treating a subject having cancer, which method comprises administration to the subject of a therapeutically or prophylactically effective amount of a compound of formula (I), in combination with one or more immune checkpoint modulating antibodies.

There is also provided a method of treating a subject having cancer, which method comprises administration to the subject of a therapeutically or prophylactically effective amount of a compound of formula (I), in combination with one or more immune checkpoint modulating antibodies selected from Ipilimumab, Tremelimumab, Pembrolizumab, Mivolumab, AMP-514/MEDI0680, MPDL3280A, MEDI4736, MSB0010718C, BMS-936559, Urelumab, PF-05082566, MEDI6469, MEDI6383 (rOX40L), MOXR0916, TRX518, CDX-1127, CP-870,893 and BMS-986016.

More generally, the compounds of the invention may be useful in treating a disease or condition associated with Akt3 activity, gene amplification or overexpression in a mammal. Thus, the invention also provides a method of treating a subject suffering from, or susceptible too, a disease or condition associated with Akt3 activity, gene amplification or overexpression, which method comprises administering to the subject a therapeutically or prophylactically effective amount of a compound of formula (I). Further, there are provided a compound of formula (I), for use in the treatment of a disease or condition associated with Akt3 activity, gene amplification or overexpression, and the use of a compound of formula (I) in the manufacture of a medicament for the treatment of a disease or condition associated with Akt3 activity, gene amplification or overexpression.

Other diseases which may be treated by compounds of the invention include pheochromocytoma; inflammatory conditions e.g. rheumatoid arthritis; endometriosis; vascular disease/injury, e.g. restenosis, atherosclerosis and thrombosis; psoriasis; visual impairment due to macular degeneration; diabetic retinopathy; retinopathy of prematurity; kidney disease, e.g. glomerulonephritis, diabetic nephropathy and renal transplant rejection; pulmonary disorders, e.g. COPD; osteoporosis; osteoarthritis; viral infections; fibrotic disease; cataracts; infant tauopathies, e.g. hemimegalencephaly; tuberous sclerosis complex; focal cortical dysplasia 2; ganglioglioma. Fibrotic disorders of interest include strabmisus, scleroderma, keloid, Nephrogenic systemic fibrosis, pulmonary fibrosis, idiopathic pulmonary fibrosis (IPF), cystic fibrosis (CF), systemic sclerosis, cardiac fibrosis, non-alcoholic steatohepatitis (NASH), other types of liver fibrosis, primary biliary cirrhosis, renal fibrosis, cancer, and atherosclerosis. In these diseases, the chronic development of fibrosis in tissue leads to marked alterations in the architecture of the affected organs and subsequently cause defective organ function. As a result of this process of sustained attrition to organs, many diseases that involve fibrosis are often progressive conditions and have a poor long-term prognosis (see Rockey, D. C., Bell, P. D. and Hill, J. A. (2015), N. Engl. Med., Vol. 372, pp. 1138-1149).

A further aspect of the invention is directed to a pharmaceutical composition comprising a compound of formula (I) as defined above and one or more pharmaceutically acceptable excipients.

Also provided are pharmaceutical compositions comprising a compound of formula (Ia), a compound of formula (Ib), a compound of formula (Ic), a compound of formula (Id) or a compound of formula (Ie) as described above and one or more pharmaceutically acceptable excipients.

Also provided are pharmaceutical compositions comprising any of the particular compounds of the invention and one or more pharmaceutically acceptable excipients.

The choice of pharmaceutical carrier, excipient or diluent can be selected with regard to the intended route of administration and standard pharmaceutical practice. The pharmaceutical compositions may comprise as, or in addition to, the carrier, excipient or diluent any suitable binder(s), lubricant(s), suspending agent(s), coating agent(s), solubilising agent(s), buffer(s), flavouring agent(s), surface active agent(s), thickener(s), preservative(s) (including anti-oxidants) and the like, and substances included for the purpose of rendering the formulation isotonic with the blood of the intended recipient. Examples of suitable binders include starch, gelatin, natural sugars such as glucose, anhydrous lactose, free-flow lactose, beta-lactose, corn sweeteners, natural and synthetic gums, such as acacia, tragacanth or sodium alginate, carboxymethyl cellulose and polyethylene glycol.

Examples of suitable lubricants include sodium oleate, sodium stearate, magnesium stearate, sodium benzoate, sodium acetate, sodium chloride and the like.

Preservatives, stabilizers, dyes and even flavouring agents may be provided in the pharmaceutical composition. Examples of preservatives include sodium benzoate, sorbic acid and esters of p-hydroxybenzoic acid. Antioxidants and suspending agents may be also used.

Pharmaceutical formulations include those suitable for oral, topical (including dermal, buccal and sublingual), rectal or parenteral (including subcutaneous, intradermal, intramuscular and intravenous), nasal and pulmonary administration, e.g. by inhalation. The formulation may, where appropriate, be conveniently presented in discrete dosage units and may be prepared by any of the methods well known in the art.

Pharmaceutical formulations suitable for oral administration wherein the carrier is a solid are most preferably presented as unit dose formulations such as boluses, capsules or tablets each containing a predetermined amount of active agent. A tablet may be made by compression or moulding, optionally with one or more accessory ingredients. Compressed tablets may be prepared by compressing in a suitable machine an active agent in a free-flowing form such as a powder or granules optionally mixed with a binder, lubricant, inert diluent, lubricating agent, surface-active agent or dispersing agent. Moulded tablets may be made by moulding an active agent with an inert liquid diluent. Tablets may be optionally coated and, if uncoated, may optionally be scored. Capsules may be prepared by filling an active agent, either alone or in admixture with one or more accessory ingredients, into the capsule shells and then sealing them in the usual manner. Cachets are analogous to capsules wherein an active agent together with any accessory ingredient(s) is sealed in a rice paper envelope. An active agent may also be formulated as dispersible granules, which may for example be suspended in water before administration, or sprinkled on food. The granules may be packaged, e.g., in a sachet. Formulations suitable for oral administration wherein the carrier is a liquid may be presented as a solution or a suspension in an aqueous or non-aqueous liquid, or as an oil-in-water liquid emulsion. Formulations for oral administration include controlled release dosage forms, e.g., tablets wherein an active agent is formulated in an appropriate release-controlling matrix, or is coated with a suitable release-controlling film. Such formulations may be particularly convenient for prophylactic use.

Pharmaceutical formulations suitable for parenteral administration include sterile solutions or suspensions of an active agent in aqueous or oleaginous vehicles.

Injectable preparations may be adapted for bolus injection or continuous infusion. Such preparations are conveniently presented in unit dose or multi-dose containers which are sealed after introduction of the formulation until required for use. Alternatively, an active agent may be in powder form which is constituted with a suitable vehicle, such as sterile, pyrogen-free water, before use.

An active compound may also be formulated as long-acting depot preparations, which may be administered by intramuscular injection or by implantation, e.g., subcutaneously or intramuscularly. Depot preparations may include, for example, suitable polymeric or hydrophobic materials, or ion-exchange resins. Such long-acting formulations are particularly convenient for prophylactic use.

Formulations suitable for pulmonary administration via the buccal cavity are presented such that particles containing an active compound and desirably having a diameter in the range of 0.5 to 7 microns are delivered in the bronchial tree of the recipient. As one possibility such formulations are in the form of finely comminuted powders which may conveniently be presented either in a pierceable capsule, suitably of, for example, gelatin, for use in an inhalation device, or alternatively as a self-propelling formulation comprising an active agent, a suitable liquid or gaseous propellant and optionally other ingredients such as a surfactant and/or a solid diluent. Suitable liquid propellants include hydrocarbons such as propane and butane, and the hydrofluorocarbons, and suitable gaseous propellants include carbon dioxide. Self-propelling formulations may also be employed wherein an active agent is dispensed in the form of droplets of solution or suspension.

Pharmaceutically acceptable carriers are well known to those skilled in the art and include aqueous and non-aqueous solutions, suspensions, buffers and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's or fixed oils. Preservatives and other additives may also be present, such as, for example, antimicrobials, antioxidants, chelating agents, inert gases and the like.

Compounds of formula (I) may be prepared by various methods that will be familiar or readily apparent to those skilled in the art. One such method, that represents a further aspect of the invention, comprises the steps of (i) reacting a compound of formula (II)

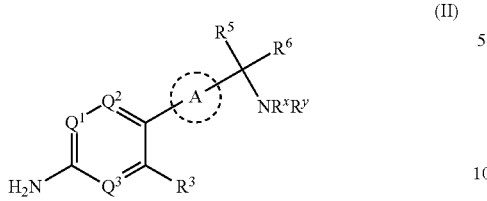

in which $Q^1$, $Q^2$, $Q^3$, A, $R^3$, $R^5$ and $R^6$ are as defined in connection with formula (I), and $R^x$ and $R^y$ independently represent H or a protecting group,
with a compound of formula (III)

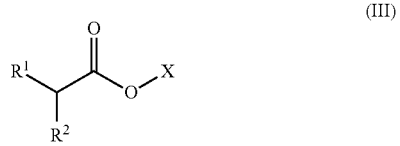

in which $R^1$ and $R^2$ are as defined in connection with formula (I), and X represents H or a halogen atom; and
(ii) removing any protecting groups.

In step (i):
One or both of $R^x$ and $R^y$ will generally represent a protecting group.
The reaction is preferably carried out in the presence of a suitable coupling agent.

Suitable amino protecting groups are known in the art, and include 9-fluorenylmethyl carbamate (Fmoc-NR$_2$), t-butyl carbamate (Boc-NR$_2$), benzyl carbamate (Cbz-NR$_2$/Z—NR$_2$), acetamide (Ac—NR$_2$), trifluoroacetamide, phthalimide, benzylamine (Bn-NR$_2$), triphenylmethylamine (Tr-NR$_2$), benzylideneamine and p-toluenesulfonamide (Ts-NR$_2$).

Suitable coupling agents are known in the art, and include:
- carbodiimides, e.g. dicyclohexylcarbodiimide (DCC), diisopropylcarbodiimide (DIC) and 1-ethyl-3-(3-dimethylaminopropyl)carbodiimide (EDC);
- phosphonium-based reagents, e.g. (benzotriazol-1-yloxy)tris(dimethylamino)phosphonium hexafluorophosphate (BOP), (benzotriazol-1-yloxy)tripyrrolidinophosphonium hexafluorophosphate (PyBOP), (7-Azabenzotriazol-1-yloxy)tripyrrolidinophosphonium hexafluorophosphate (PyAOP), Bromo-tris-pyrrolidino phosphoniumhexafluorophosphate (PyBrOP) and bis (2-oxo-3-oxazolidinyl)phosphonic chloride (BOP-Cl);
- aminium-based reagents, e.g. O-(benzotriazol-1-yl)-N,N,N',N'-tetramethyluronium tetrafluorophosphate (HBTU), O-(benzotriazol-1-yl)-N,N,N',N'-tetramethyluronium tetrafluoroborate (TBTU), O-(7-Azabenzotriazol-1-yl)-N,N,N',N'-tetramethyluronium hexafluorophosphate (HATU), O-(6-Chlorobenzotriazol-1-yl)-N,N,N',N'-tetramethyluronium hexafluorophosphate (HCTU), O-(7-Azabenzotriazole-1-yl)-N,N,N',N'-tetramethyluronium tetrafluoroborate (TATU) and 2-(6-Chloro-1H-benzotriazole-1-yl)-1,1,3,3-tetramethylaminium hexafluorophosphate (HCTU);
- uronium-based reagents, e.g. O-(3,4-Dihydro-4-oxo-1,2,3-benzotriazine-3-yl)-N,N,N',N'-tetramethyluronium tetrafluoroborate (TDBTU), O—(N-Succinimidyl)-1,1,3,3-tetramethyl uranium tetrafluoroborate (TSTU), 2-(5-Norborene-2,3-dicarboximido)-1,1,3,3-tetramethyluronium tetrafluoroborate (TNTU), O-[(Ethoxycarbonyl)cyanomethylenamino]-N,N,N',N'-tetramethyluronium tetrafluoroborate (TOTU) and 2-(2-Pyridon-1-yl)-1,1,3,3-tetramethyluronium tetrafluoroborate (TPTU);
- other coupling agents, including 3-(Diethylphosphoryloxy)-1,2,3-benzotriazin-4(3H)-one (DEPBT), Carbonyldilmidazole (CDI) and N,N,N',N'-tetramethylchloroformamidinium hexafluorophosphate (TCFH).

Compounds of formula (II) may be prepared by reduction of compounds of formula (IV):

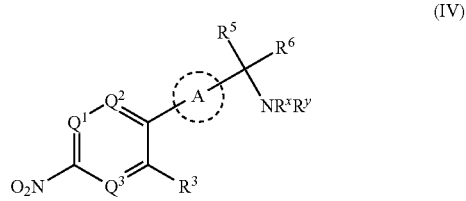

in which $Q^1$, $Q^2$, $Q^3$, A, $R^3$, $R^5$ and $R^6$ are as defined in connection with compounds of formula (I) and $R^x$ and $R^y$ independently represent H or a protecting group.

Methods of reducing aryl-nitro groups are known, and reduction of the compound of formula (IV) may be carried out by any suitable method known in the art. For example, reduction of the nitro group to an amine group may be carried out: in the presence of a reducing metal (e.g. Fe, Sn or Zn) in acidic conditions (e.g. in the presence of HCl, ethanoic acid or NH$_4$Cl); by hydrazine in the presence of a base; through catalytic hydrogenation over palladium-on-carbon, platinum (IV) oxide, or platinum-on-carbon; or by sodium sulphide in ammonium hydroxide solution.

Compounds of formula (II) and formula (IV) are believed to be novel and represent further aspects of the invention, which thus provides compounds useful as intermediates in the synthesis of compounds of formula (I), which intermediate compounds are of formula (II):

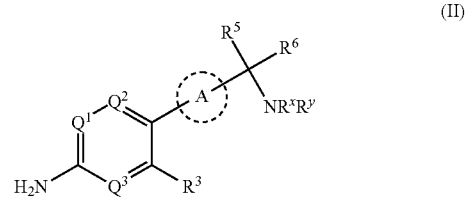

or formula (IV):

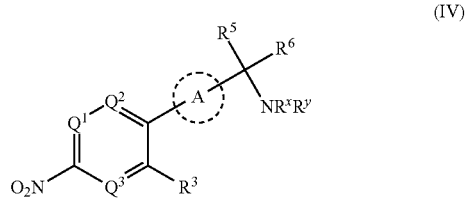

in which $Q^1$, $Q^2$, $Q^3$, A, $R^3$, $R^5$ and $R^6$ are as defined in connection with compounds of formula (I) and $R^x$ and $R^y$ independently represent H or a protecting group.

In particular embodiments of compounds of formula (II) and formula (IV), $Q^1$, $Q^2$, $Q^3$, A, $R^3$, $R^5$ and $R^6$ may have any of the meanings described in relation to compounds of formulae (I), (Ia), (Ib), (Ic), (Id) or (Ie).

More specifically, the compounds of Formula (I) may be prepared by methods analogous to Schemes 1-4 below. All of the starting materials are commercially available, readily made from commercially available starting materials by those of skill in the art or prepared according to literature reports unless otherwise noted in the experimental section.

General Schemes

Abbreviations aq: aqueous; Boc: tert-butoxycarbonyl; Boc$_2$O: di-tert-butyl dicarbonate; br: broad; ca.: circa; Bn: benzyl; Cbz: carboxybenzyl; CbzCl: benzyl chloroformate; conc.: concentrated; DCM: dichloromethane; DIPEA: diisopropylethylamine; dioxane: 1-4-dioxane; DIPPF: 1,1'-Bis(di-isopropylphosphino)ferrocene; d: doublet; Et$_2$O: diethyl ether; Et$_3$N: triethylamine; EtOAc: ethyl acetate; DMF: dimethylformamide; EtOH: ethanol; HATU: 1-(Bis-(dimethylamino) methylene)-1,2,3-triazolo[4,5-b]pyridinium 3-oxide hexafluorophosphate; h: hours; HPLC: high performance liquid chromatography; IPA: isopropanol; LCMS: liquid chromatography—mass spectrometry; LiHMDS: lithium hexamethyldisilazide; LiOH: lithium hydroxide; m: multiplet; M: molar, molecular ion; MeCN: acetonitrile; MeOH: methanol; min: minutes; MS: mass spectrometry; NBS: N-bromosuccinimide; NMR: nuclear magnetic resonance; Pd(dppf)Cl$_2$: [1,1'-bis-(diphenylphosphino)ferrocene]dichloropalladium(II); q: quartet; RT: room temperature (ca. 20° C.); R$_T$: retention time; s: singlet; SCX: strong cation exchange; t: triplet; SPhos Precatalyst 3G: (2-Dicyclohexylphosphino-2',6'-dimethoxy-1,1'-biphenyl) [2-(2'-amino-1,1'-biphenyl)]palladium(II) methanesulfonate; T3P: propylphosphonic anhydride; TEMPO: 2,2,6,6-Tetramethyl-1-piperidinyloxy, free radical; TFA: trifluoroacetic acid; THF: tetrahydrofuran; UV: ultra-violet; XPhos: 2-dicyclohexylphosphino-2',4',6'-triisopropylbiphenyl; XPhos Precatalyst 2G: Chloro(2-dicyclohexylphosphino-2',4',6'-triisopropyl-1,1'-biphenyl)[2-(2'-amino-1,1'-biphenyl)]palladium(II).

Other abbreviations are intended to convey their generally accepted meaning.

Scheme 1

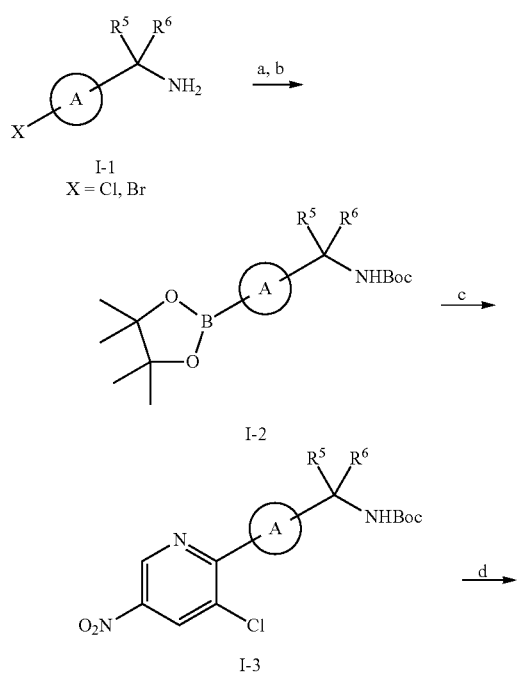

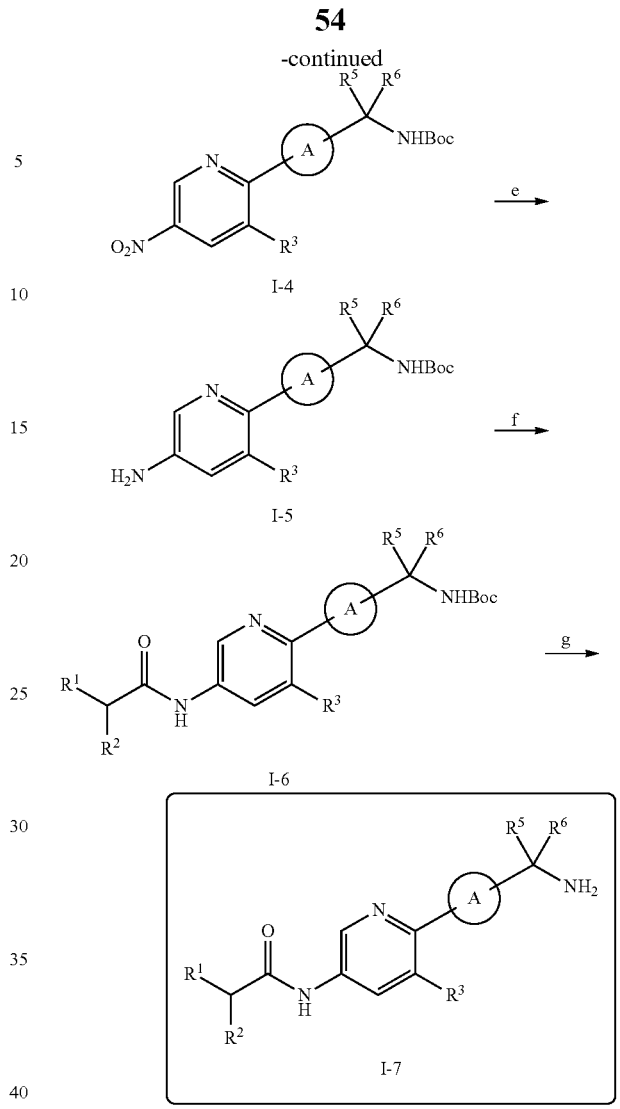

Reagents: (a) Boc$_2$O, Et$_3$N, DCM; (b) bis-(pinacolato)diboron, Pd(OAc)$_2$, XPhos, MeCN, 75° C.; (c) 2,3-dichloro-5-nitropyridine, Pd(PPh$_3$)$_4$, Na$_2$CO$_3$(aq), dioxane, 90° C.; (d) Pd(PPh$_3$)$_4$, Na$_2$CO$_3$(aq), dioxane, 90° C.; (e) Iron, NH$_4$Cl, IPA(aq), reflux; (f) HATU, DIPEA, THF, 50° C.; (g) TFA(aq).

Protection of amine (I-1), for example with a Boc group, followed by Miyaura borylation provided the boronic ester (I-2), which underwent regiospecific Suzuki arylation with 2,3-dichloro-5-nitropyridine (I-3). Subsequent Suzuki arylation with the appropriate boronic acid or ester provided the nitropyridine intermediate (I-4), which was reduced to the corresponding aminopyridine (I-5). Amide formation using the appropriate carboxylic acid and a coupling agent, such as HATU, followed by removal of the protecting group from the amino group of intermediate (I-6) afforded the amide (I-7).

Scheme 2

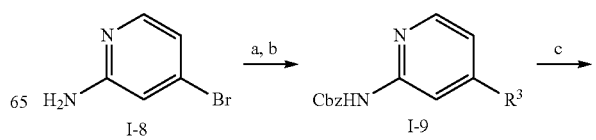

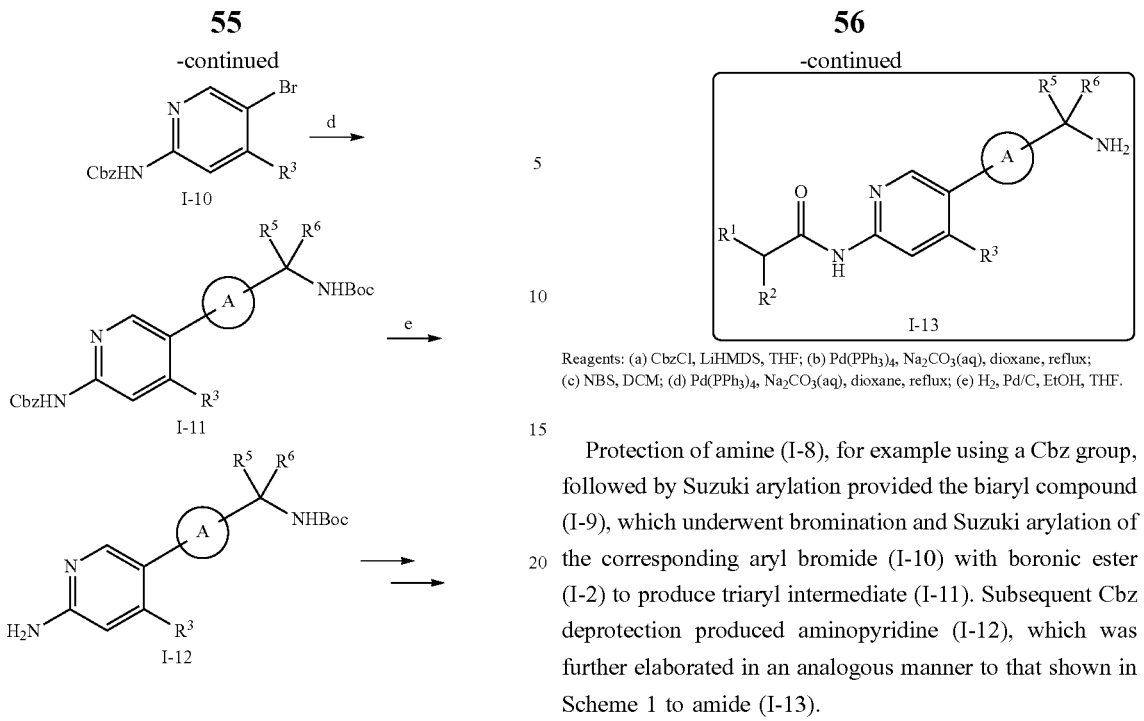

Reagents: (a) CbzCl, LiHMDS, THF; (b) Pd(PPh$_3$)$_4$, Na$_2$CO$_3$(aq), dioxane, reflux; (c) NBS, DCM; (d) Pd(PPh$_3$)$_4$, Na$_2$CO$_3$(aq), dioxane, reflux; (e) H$_2$, Pd/C, EtOH, THF.

Protection of amine (I-8), for example using a Cbz group, followed by Suzuki arylation provided the biaryl compound (I-9), which underwent bromination and Suzuki arylation of the corresponding aryl bromide (I-10) with boronic ester (I-2) to produce triaryl intermediate (I-11). Subsequent Cbz deprotection produced aminopyridine (I-12), which was further elaborated in an analogous manner to that shown in Scheme 1 to amide (I-13).

Scheme 3

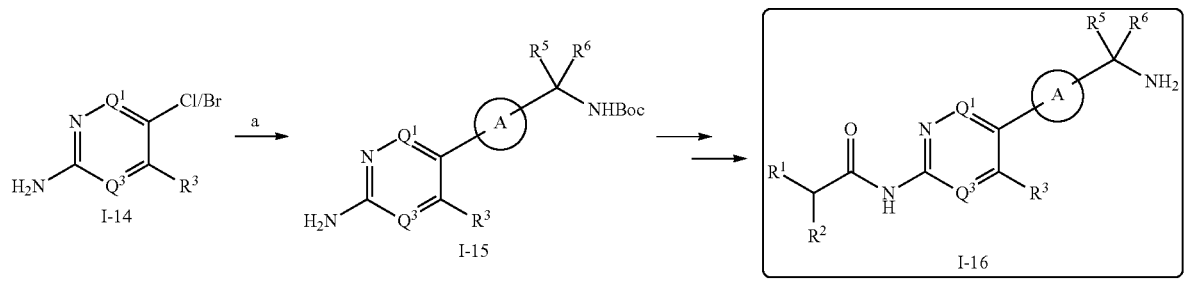

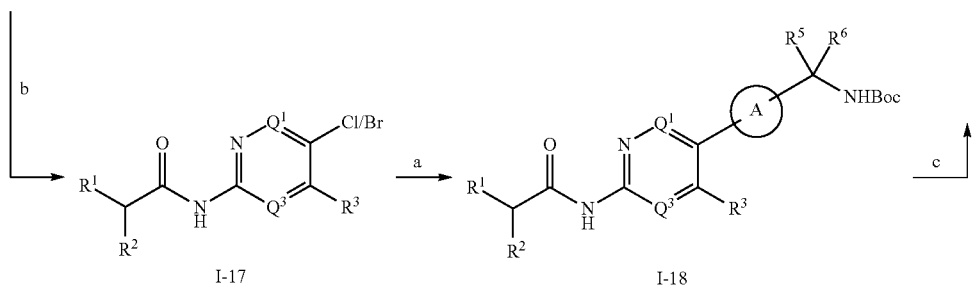

Reagents: (a) Pd(PPh$_3$)$_4$, Na$_2$CO$_3$(aq), dioxane, 90° C.; (b) 1-chloro-N,N,2-trimethylprop-1-en-1-amine, pyridine, DCM; (c) TFA, DCM.

Suzuki arylation of I-14 provided the triaryl compound (I-15), which was further elaborated in an analogous manner to that shown in Scheme 1 to the amide (I-16). Alternatively, I-14 could be coupled with the required carboxylic acid prior to Suzuki arylation to the triaryl compound (I-18) and deprotection to I-16.

Additionally, intermediates from Schemes 1-3 above can be further elaborated prior to removal of the amino protecting group.

Carboxylic acids of structure I-26 can be prepared by reaction of amine I-21 with a chloroformate (for example, $R^c$=Bn or Me), followed by deprotonation at the nitrogen centre and subsequent alkylation to provide I-23. This intermediate may be directly hydrolysed to the corresponding carboxylic acid (I-26), or in the case R=Bn, hydrogenolysis provided the secondary amine (I-24), which was subsequently acylated prior to hydrolysis.

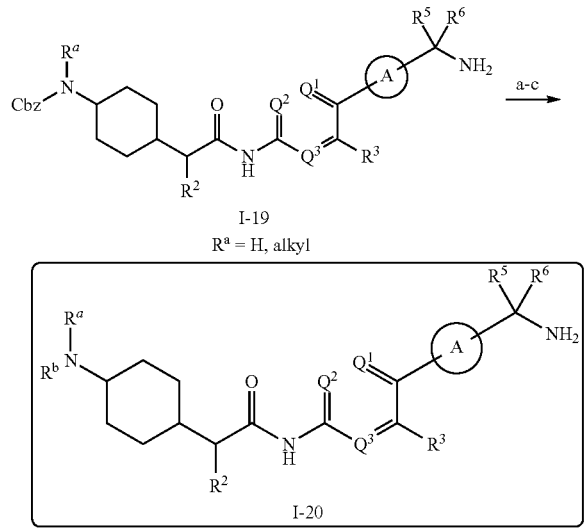

Scheme 4

Reagents: (a) H$_2$, Pd/C, EtOH; (b) alkyl halide, aldehyde, ketone or activated carboxylic acid; (c) TFA(aq).

Cbz cleavage from intermediate (I-19), followed by acylation and Boc cleavage afforded the amide (I-20). When $R^7$=H and $R^8$ possesses suitable functionality, $R^7$ and $R^8$ may be readily converted into a heterocyclic ring system.

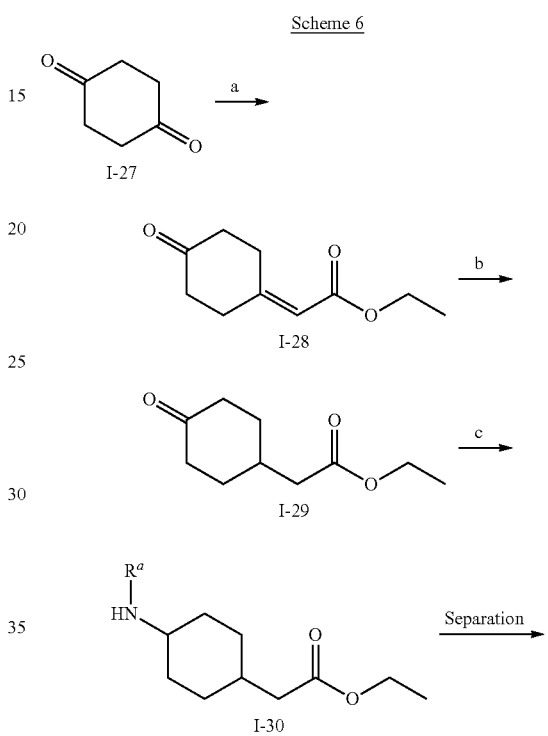

Scheme 6

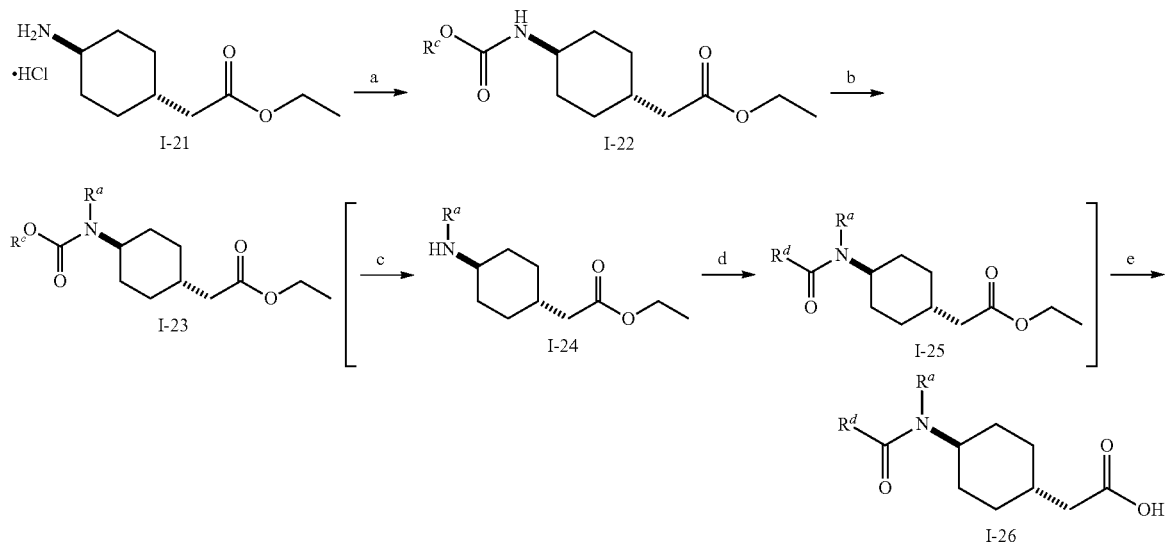

Scheme 5

Reagents: (a) chloroformate, NaHCO$_3$(aq), THF; (b) alkyl halide, NaH, THF, 0° C. to RT; (c) H$_2$, 10% Pd/C, MeOH, 50° C.; (d) acid chloride, acid anhydride, alkyl chloroformate or activated carboxylic acid; (e) LiOH(aq), THF, MeOH.

-continued

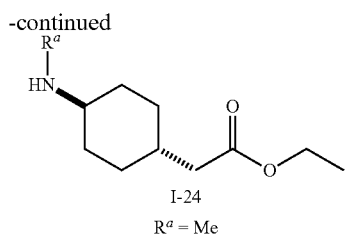

I-24
$R^a$ = Me

Reagents: (a) ethyl triethylphosphonoacetate, NaH, THF, 0° C. to RT; (b) H$_2$, 5% Pd/C, EtOAc; (c) R$^3$NH$_2$, MeOH, NaBH(OAc)$_3$ Alternatively, diketone (I-27) may be elaborated by way of a Horner-Wadsworth-Emmons reaction to unsaturated ester I-28. Palladium catalysed hydrogenation to I-29, followed by reductive amination, provided the secondary amine (I-30) as a mixture of diastereomers, which could be separated to provide the trans isomer I-24.

Step a: Ethyl 2-(4-oxocyclohexylidene)acetate: Triethyl phosphonoacetate (48.9 ml, 0.25 mol) was added drop-wise to sodium hydride (8.0 g, 0.20 mol, 60% w/w in mineral oil) in THF (300 ml) at 0-5° C. After stirring at 18-25° C. for 1 h, the resultant solution was added dropwise to a suspension of 1,4-cyclohexanedione (125 g, 1.11 mol) in THF (500 ml) at 0-5° C. The reaction was stirred at 18-25° C. for 18 h, then quenched with saturated NH$_4$Cl(aq) (300 ml). Water (200 ml) was added and the phases separated. The aqueous phase was extracted with EtOAc (200 ml). The combined organic phases were then washed with brine (200 ml), dried over MgSO$_4$, filtered and concentrated to dryness. Purification by column chromatography on silica gel (400 g, 30% EtOAc/heptane) yielded the title compound as a white solid (36.8 g, 0.25 mol); $^1$H NMR (400 MHz, CDCl$_3$) δ: 1.27 (3H, t), 2.49 (4H, observed q), 2.64 (2H, observed t), 3.18 (2H, observed td), 4.17 (2H, q), 5.83 (1H, s).

Step b: Ethyl 2-(4-oxocyclohexyl)acetate: A suspension of palladium (1.1 g, 5% w/w on carbon, 50% wet) in MeOH (50 ml) was sparged with H$_2$ for 10 min. A solution of the product from Step a above (10.8 g, 0.06 mol) in MeOH (60 ml) was added and the reaction sparged with hydrogen at 18-25° C. for 1 h. The mixture was filtered through Celite® (30 g) washing with methanol (3×50 ml). The filtrate was concentrated to afford a clear colourless oil. Purification by column chromatography on silica gel (400 g, 30% EtOAc/heptane) yielded the title compound as a clear colourless oil (8.6 g, 47 mmol); $^1$H NMR (400 MHz, CDCl$_3$) δ:1.25 (3H, t), 1.39-1.51 (2H, m), 2.09-2.21 (2H, m), 2.13-2.29 (3H, m), 2.35-2.42 (4H, m), 4.13 (2H, q).

Step c: Ethyl 2-(4-(methylamino)cyclohexyl)acetate: A solution of the product from Step b above (1.0 g, 5.43 mmol) in MeOH (1 ml) was added dropwise to a solution of methylamine (2 M in MeOH, 11.8 ml, 23.6 mmol) at 0-5° C. Sodium triacetoxyborohydride (2.6 g, 12.3 mmol) was then added portionwise at 0-5° C. The resultant reaction was allowed to warm to 18-25° C. and was stirred for 18 h. The reaction was quenched by the addition of a 20% w/w K$_2$CO$_3$(aq) (20 mL) and the MeOH removed in vacuo. The remaining aqueous phase was extracted with EtOAc (3×20 ml). The combined organic phases were washed with brine (20 ml), dried over MgSO$_4$, filtered and the solvent removed in vacuo to afford the title compound as clear yellow oil (895 mg, 4.48 mmol) as a mixture of the cis and trans isomers in a ~40:60 ratio by $^1$H NMR. $^1$H NMR (400 MHz, DMSO-d$_6$) (selected peaks for the trans-isomer) δ 0.88-1.01 (4H, m), 1.16 (3H, t), 1.49-1.76 (3H, m), 1.83-1.87 (2H, m), 2.14-2.18 (2H, d overlapping 1H, m), 2.24 (3H, s), 4.02 (2H, q).

BRIEF DESCRIPTION OF THE DRAWINGS

FIG. 1 shows representative pictures from each of the indicated treatment conditions. MDA-MD-231 cells were treated with increasing concentrations of EX34 or EX33 for 9 days. Treatment was initiated one day after tumour cell seeding. DMSO was used as control. The graphs in FIG. 2 show average tumour size±SEM following treatment with each of EX34 and EX33. Images of the 3D cultures were batch analysed with AMIDA software.

FIG. 3 shows immunofluorescence microscopy (GFP) images of invasive 3D tumour cell colonies obtained by seeding MDA-MB-231-D3H2LN/GPF-Luc cells in matrigel, following treatment of the cell colonies with EX34 or EX33 for 72 hours.

FIGS. 4 and 5 refer to the cellular localization of Akt3 in MDA-MB-231 cells that were treated for 36 hours with EX33 or EX34. In FIG. 4, cells were stained to visualize the nucleus (top left panel) and Akt3 (top right panel) and analyzed using immune fluorescence microscopy. After treatment with EX33, Akt3 stains cytoplasmic (see bottom right panel). FIG. 5 shows the mean intensity of Akt3 in the nucleus after treatment with DMSO (control) or EX33. The results were obtained using TissueQuest Software.

FIG. 10 shows the effect of different dosages of EX33 on α-sma mRNA levels. LX2 cells were treated for 24 hours with the indicated dosages of EX33 (μM). mRNA was isolated and analyzed by RT-PCR for α-SMA expression. Expression level in Vehicle treated cells (0 EX33) was set to 1, and α-sma expression levels following treatment with indicated dosages of EX33 calculated relative to that.

EXAMPLES

General Experimental Conditions

Figure 1:
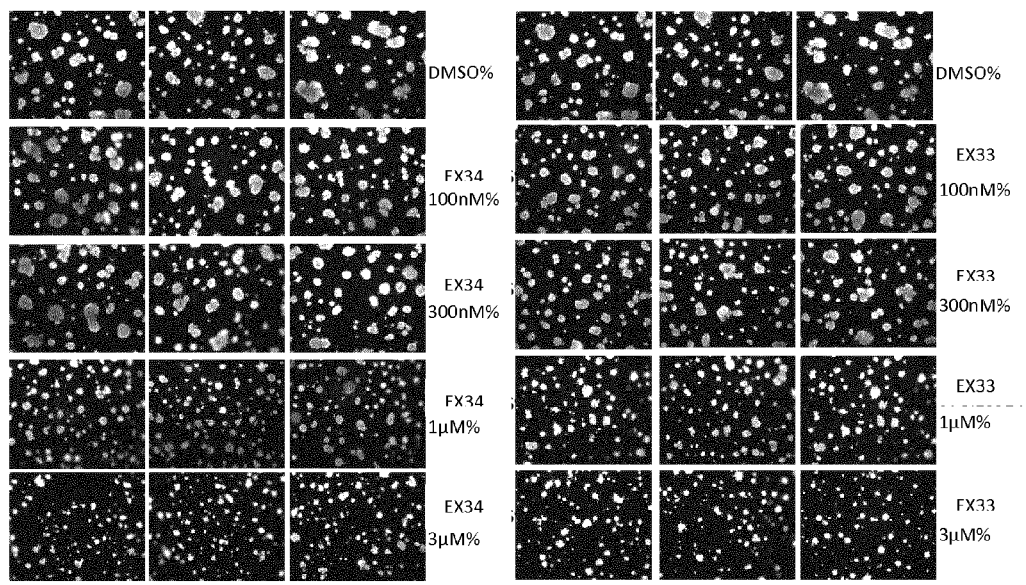
FIGS. 1 and 2 demonstrate the inhibition of tumour growth by two compounds of the invention: the compound of Example 34 (denoted hereafter as EX34) and the compound of Example 33 (denoted hereafter as EX33).

All starting materials and solvents were obtained either from commercial sources or prepared according to the literature citation. Reaction mixtures were magnetically stirred unless otherwise indicated.

Column chromatography was performed on an automated flash chromatography system, such as CombiFlash Companion or CombiFlash Rf system, using RediSep® Rf prepacked silica (230-400 mesh, 40-63 μm) cartridges, unless otherwise indicated. $^1$H NMR spectra were recorded using a Bruker Avance III spectrometer (400 MHz). Chemical shifts are expressed in parts per million using either the central peaks of the residual protic solvent or an internal standard of tetramethylsilane as references. The spectra were recorded at ambient temperature unless otherwise stated.

Analytical LCMS experiments to determine retention times and associated mass ions were performed using an Agilent 1200 series HPLC system coupled to an Agilent 6110 or 6120 series single quadrupole mass spectrometer running one of the analytical methods described below.

Preparative HPLC purifications were performed using a Waters X-Select CSH C18, 5 μm, 19×50 mm or Waters X-Bridge BEH C18, 5 μm, 19×50 mm column using either a gradient of 0.1% formic acid in MeCN and 0.1% aqueous formic acid, or a gradient of MeCN and 10 mM ammonium bicarbonate(aq). Fractions were collected following detection by either UV at a single wavelength measured by a variable wavelength detector on a Gilson 215 or a Varian PrepStar preparative HPLC, or by mass ion and UV detection at a single wavelength measured by a ZQ single quadropole mass spectrometer, with positive and negative ion electrospray, and dual wavelength detection on a Waters FractionLynx LCMS.

SCX resin was purchased from Sigma Aldrich or Silicycle and washed with MeOH prior to use.

Nomenclature of structures was generated using 'Structure to Name' conversion from ChemDraw® Professional 15 (PerkinElmer).

Analytical Methods

Method 1—Acidic 4 min method

Column: Waters X-Select CSH C18, 2.5 μm, 4.6×30 mm

Detection: UV at 254 nm (or 215 nm) or total ion current

MS ionisation: Electrospray

Solvent A: Water/0.1% Formic acid

Solvent B: MeCN/0.1% Formic acid

Gradient:

| Time | % A | % B | Flow rate (ml/min) |
|---|---|---|---|
| 0.0 | 95.0 | 5.0 | 2.5 |
| 3.0 | 5.0 | 95.0 | 2.5 |
| 3.01 | 5.0 | 95.0 | 4.5 |
| 3.6 | 5.0 | 95.0 | 4.5 |
| 3.7 | 95.0 | 5.0 | 2.5 |
| 4.0 | 95.0 | 5.0 | 2.5 |

Method 2—Basic 4 min method

Column: Waters X-Bridge BEH C18, 2.5 μm, 4.6×30 mm

Solvent A: Water/10 mM ammonium bicarbonate

Solvent B: MeCN (other parameters the same as Method 1)

Method 3—Basic 15 min method

Column: Waters X-Bridge BEH C18, 2.5 μm, 4.6×30 mm

Detection: UV at 254 nm (or 215 nm) or total ion current

MS ionisation: Electrospray

Solvent A: Water/10 mM ammonium bicarbonate

Solvent B: MeCN

Gradient:

| Time | % A | % B | Flow rate (ml/min) |
|---|---|---|---|
| 0.0 | 95 | 5 | 2.5 |
| 14.0 | 5 | 95 | 2.5 |
| 14.01 | 5 | 95 | 4.5 |
| 14.5 | 5 | 95 | 4.5 |
| 14.6 | 95 | 5 | 3.5 |
| 14.9 | 95 | 5 | 3.5 |
| 15.0 | 95 | 5 | 2.5 |

Intermediate 1 tert-butyl (trans-1-(4-(5-amino-3-phenylpyridin-2-yl)phenyl)-3-hydroxy-3-methylcyclobutyl)carbamate

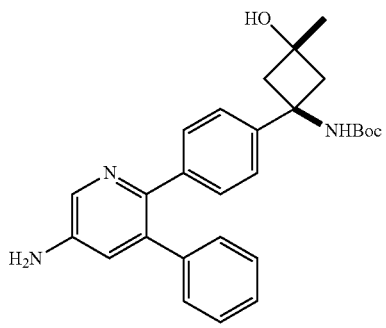 [SMILES: CC(C)(C)OC(=O)N[C@]1(c2ccc(-c3ncc(N)cc3-c3ccccc3)cc2)C[C@@](C)(O)C1]

Step 1: tert-butyl (trans-1-(4-(3-chloro-5-nitropyridin-2-yl)phenyl)-3-hydroxy-3-methylcyclobutyl)carbamate: A mixture of 2,3-dichloro-5-nitropyridine (383 mg, 1.98 mmol), tert-butyl (trans-3-hydroxy-3-methyl-1-(4-(4,4,5,5-tetramethyl-1,3,2-dioxaborolan-2-yl)phenyl)cyclobutyl)carbamate (800 mg, 1.98 mmol, prepared according to Org. Process Res. Dev., 2012, 16, 1069) and tetrakis-(triphenylphosphine)palladium(0) (229 mg, 0.198 mmol) in dioxane (10 ml) was treated with 2 M $Na_2CO_3$(aq) (2.2 ml, 4.46 mmol). The vessel was purged with $N_2$ and then heated at 75° C. for 2 days. The reaction mixture was cooled and filtered through a glass microfibre filter, washing with MeCN, and concentrated in vacuo to afford a brown oil. The oil was partitioned between DCM (50 ml) and water (50 ml), filtered through a phase separation cartridge and the organic phase concentrated in vacuo. The residue was purified by column chromatography (40 g cartridge, 0-50% EtOAc/isohexane) to afford the title compound (501 mg, 1.05 mmol, 94% purity) as a yellow solid. LCMS (Method 1): m/z 378 $(M+H-C_4H_8)^+$ at 2.25 min. $^1$H NMR (400 MHz, Chloroform-d) δ 9.40 (d, J=2.3 Hz, 1H), 8.62 (d, J=2.3 Hz, 1H), 7.86-7.78 (m, 2H), 7.61-7.54 (m, 2H), 5.11 (s, 1H), 2.82-2.52 (m, 4H), 1.63 (s, 3H), 1.43 (br s, 9H).

Step 2: tert-butyl (trans-3-hydroxy-3-methyl-1-(4-(5-nitro-3-phenylpyridin-2-yl)phenyl)cyclobutyl)carbamate: The product from Step 1 above (501 mg, 1.05 mmol, 94% purity), phenylboronic acid (215 mg, 1.760 mmol), 2 M $Na_2CO_3$(aq) (1320 μl, 2.64 mmol) and tetrakis-(triphenylphosphine)palladium(0) (136 mg, 0.117 mmol) were combined in dioxane (20 ml). The vessel was purged with $N_2$ and heated at 90° C. overnight. The resultant mixture was cooled and filtered through a glass microfibre filter and the filtrate concentrated in vacuo. The resultant oil was partitioned between DCM (50 ml) and water (50 ml), filtered through a phase separation cartridge and the organic phase concentrated in vacuo. The residue was purified on a by column chromatography (40 g cartridge, 0 to 50% EtOAc/isohexane) to afford the title compound (438 mg, 0.847 mmol, 92% purity) as a yellow oil. LCMS (Method 1): m/z 420 $(M+H-C_4H_8)^+$, 476 $(M+H)^+$ at 2.43 min. $^1$H NMR (400 MHz, Chloroform-d) δ 9.49 (d, J=2.5 Hz, 1H), 8.51 (d, J=2.5 Hz, 1H), 7.45-7.30 (m, 7H), 7.29-7.21 (m, 2H), 4.94 (s, 1H), 2.75-2.50 (m, 4H), 1.60 (s, 3H), 1.40 (s, 9H).

Step 3: tert-butyl (trans-1-(4-(5-amino-3-phenylpyridin-2-yl)phenyl)-3-hydroxy-3-methylcyclobutyl)carbamate: A stirred suspension of the product from Step 2 above (437 mg, 0.845 mmol), iron powder (513 mg, 9.18 mmol) and $NH_4Cl$ (58.9 mg, 1.10 mmol) in IPA (20 ml) and water (2 ml) was heated under reflux for 3 h. The reaction mixture was cooled and filtered through a glass microfibre filter, washing with MeOH. The filtrate was concentrated in vacuo and the residue partitioned between DCM (50 ml) and water (50 ml), filtered through an phase separation cartridge and the organic phase concentrated in vacuo to afford the title compound (390 mg, 0.832 mmol, 95% purity) as a yellow solid. LCMS (Method 1): m/z 446 $(M+H)^+$ at 1.50 min. $^1$H NMR (400 MHz, DMSO-$d_6$) δ 8.02 (d, J=2.6 Hz, 1H), 7.42 (s, 1H), 7.28 (s, 3H), 7.12 (m, 6H), 6.90 (d, J=2.6 Hz, 1H), 5.49 (br s, 2H), 4.94 (s, 1H), 2.57 (m, 2H), 2.30 (m, 2H), 1.35 (br s, 9H), 1.13 (s, 3H).

Intermediate 2 tert-butyl (2-(4-(5-amino-3-phenylpyridin-2-yl)phenyl)propan-2-yl)carbamate

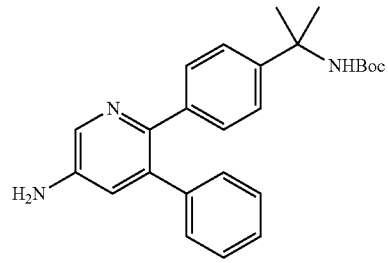

Step 1: tert-butyl (2-(4-bromophenyl)propan-2-yl)carbamate: A solution of 2-(4-bromophenyl)propan-2-amine hydrochloride (10 g, 39.9 mmol) and $Et_3N$ (5.84 ml, 41.9 mmol) in DCM (100 ml) was treated with $Boc_2O$ (9.15 g, 41.9 mmol) and stirred at RT for 18 h. The reaction mixture was washed with a saturated $NH_4Cl$(aq) (100 ml) and the organic phase was concentrated in vacuo. The residue was purified by column chromatography (220 g cartridge, 0-30% EtOAc/isohexane) to afford the title compound (11.4 g, 35.0 mmol, 97% purity) as a flocculent white solid. LCMS (Method 1): m/z 258 $(M+H-C_4H_8)^+$ at 2.64 min.

Step 2: tert-butyl (2-(4-(4,4,5,5-tetramethyl-1,3,2-dioxaborolan-2-yl)phenyl)propan-2-yl)carbamate: The product from Step 1 above (6 g, 18.52 mmol, 97% purity), bis-(pinacolato)diboron (5.82 g, 22.91 mmol), palladium(II) acetate (0.107 g, 0.477 mmol), potassium acetate (5.62 g, 57.3 mmol) and XPhos (0.457 g, 0.955 mmol) were combined in MeCN (50 ml). The vessel was purged with $N_2$ then heated at 75° C. for 18 h. The reaction mixture was cooled, filtered through Celite®, washing with MeCN (2×50 ml), and concentrated in vacuo to afford a brown oil. The residue was partitioned between DCM (50 ml) and water (50 ml). The phases were separated and the organic phase was concentrated in vacuo to afford a brown solid. The crude product was purified by column chromatography (220 g cartridge, 0-20% EtOAc/isohexane) to afford the title compound (5.67 g, 15.1 mmol, 96% purity) as an off-white solid. LCMS (Method 1): m/z 306 $(M+H-C_4H_8)^+$ at 2.83 min.

Step 3: tert-butyl (2-(4-(3-chloro-5-nitropyridin-2-yl)phenyl)propan-2-yl)carbamate: The title compound (3.27 g, 8.09 mmol, 97% purity) was isolated as an off-white solid from the reaction of the product from Step 2 above (3.93 g, 10.4 mmol, 96% purity), 2,3-dichloro-5-nitropyridine (2 g, 10.36 mmol), tetrakis(triphenylphosphine)palladium(0)

(1.20 g, 1.04 mmol) and 2 M Na$_2$CO$_3$(aq) (11.7 ml, 23.3 mmol) in dioxane (100 ml) using essentially the same procedure as in Intermediate 1 Step 1, except the reaction mixture was heated under reflux for 18 h. LCMS (Method 1): m/z 336 (M+H—C$_4$H$_8$)$^+$ at 2.71 min.

Step 4: tert-butyl (2-(4-(5-nitro-3-phenylpyridin-2-yl)phenyl)propan-2-yl)carbamate: The title compound (1.80 g, 4.07 mmol, 98% purity) was isolated as a pale yellow solid from the reaction of the product from Step 3 above (2 g, 4.95 mmol, 97% purity), 4,4,5,5-tetramethyl-2-phenyl-1,3,2-dioxaborolane (1.30 g, 6.38 mmol), tetrakis-(triphenylphosphine)palladium(0) (0.590 g, 0.510 mmol) and 2 M Na$_2$CO$_3$ (aq) (5.74 ml, 11.5 mmol) in dioxane (50 ml) using essentially the same procedure as in Intermediate 1 Step 2, except the reaction mixture was heated under reflux. LCMS (Method 1): 378 (M+H—C$_4$H$_8$)$^+$ at 2.85 min.

Step 5: tert-butyl (2-(4-(5-amino-3-phenylpyridin-2-yl)phenyl)propan-2-yl)carbamate: The title compound (1.49 g, 3.66 mmol, 99% purity) was isolated as a pale yellow solid from the reaction of the product of Step 4 above (1.80 g, 4.07 mmol, 98% purity), iron powder (2.32 g, 41.5 mmol) and NH$_4$Cl (0.289 g, 5.40 mmol) in IPA (90 ml) and water (10 ml) using essentially the same procedure as in Intermediate 1 Step 3, except the reaction mixture was heated for 18 h. LCMS (Method 1): m/z 404 (M+H)$^+$ at 1.72 min.

Intermediate 3 tert-butyl (1-(4-(5-amino-3-phenylpyridin-2-yl)phenyl)-3,3-difluorocyclobutyl)carbamate

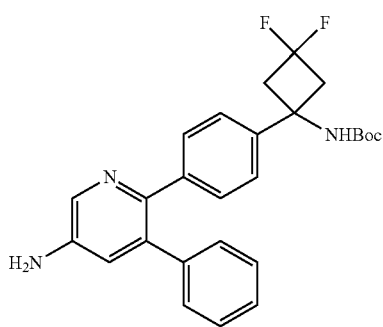 [SMILES: CC(C)(C)OC(=O)NC1(c2ccc(-c3ncc(N)cc3-c3ccccc3)cc2)CC(F)(F)C1]

Step 1: tert-butyl (1-(4-(3-chloro-5-nitropyridin-2-yl)phenyl)-3,3-difluorocyclobutyl)carbamate: A mixture of 2,3-dichloro-5-nitropyridine (244 mg, 1.27 mmol), tert-butyl (3,3-difluoro-1-(4-(4,4,5,5-tetramethyl-1,3,2-dioxaborolan-2-yl)phenyl)cyclobutyl)carbamate (170 mg, 0.415 mmol, prepared according to WO2009148916) and tetrakis-(triphenylphosphine)palladium(0) (133 mg, 0.115 mmol) in dioxane (30 ml) was treated with 2 M Na$_2$CO$_3$(aq) (1.29 ml, 2.59 mmol). The vessel was purged with N$_2$ and then heated at 80° C. overnight. The reaction mixture was cooled and filtered through Celite®, washing with DCM, and concentrated in vacuo to afford a brown oil. The residue was purified by column chromatography (40 g cartridge, 0-50% EtOAc/isohexane) to afford the title compound (146 mg, 0.299 mmol, 90% purity) as a pale yellow solid. $^1$H NMR (400 MHz, DMSO-d$_6$) (two rotamers in a 3:1 ratio) δ 9.41 (d, J=2.3 Hz, 1H), 8.88 (d, J=2.3 Hz, 1H), 8.09 (br s, 1H), 7.79 (d, J=8.4 Hz, 2H), 7.56 (d, J=8.3 Hz, 2H), 3.15 (br t, J=12.2 Hz, 4H), 1.37 (br s, 9H, major), 1.18 (br s, 9H, minor).

Step 2: tert-Butyl (3,3-difluoro-1-(4-(5-nitro-3-phenylpyridin-2-yl)phenyl)cyclobutyl)carbamate: The product from Step 1 above (140 mg, 0.286 mmol, 90% purity), phenylboronic acid (48.5 mg, 0.398 mmol), tetrakis-(triphenylphosphine)palladium(0) (36.8 mg, 0.032 mmol), and 2 M Na$_2$CO$_3$(aq) (358 µl, 0.716 mmol) were combined in dioxane (10 ml). The vessel was purged with N$_2$ for 5 min and then heated at 90° C. overnight. The reaction mixture allowed to cool, diluted with DCM (20 ml), filtered through a pad of Celite®, washing with DCM and concentrated in vacuo to afford a brown oil. The crude product was purified by column chromatography (12 g cartridge, 0-50% EtOAc/isohexane) to afford the title compound (141 mg, 0.264 mmol, 90% purity) as a pale yellow foamy solid. $^1$H NMR (400 MHz, DMSO-d$_6$) (two rotamers in a 3:1 ratio) δ 9.45 (d, J=2.5 Hz, 1H), 8.51 (d, J=2.5 Hz, 1H), 7.96 (br s, 1H), 7.44-7.24 (m, 9H), 3.16-2.93 (m, 4H), 1.34 (br s, 9H, major), 1.15 (br s, 9H, minor).

Step 3: tert-butyl (1-(4-(5-amino-3-phenylpyridin-2-yl)phenyl)-3,3-difluorocyclobutyl)carbamate: A stirred suspension of the product from Step 2 above (140 mg, 0.262 mmol, 90% purity), iron powder (162 mg, 2.91 mmol) and NH$_4$Cl (16.74 mg, 0.313 mmol) in IPA (30 ml) and water (5 ml) was heated under reflux for 90 min. The reaction mixture was allowed to cool and was then filtered through Celite®, washing with MeOH. The filtrate was concentrated in vacuo, the resultant residue dissolved in DCM (100 ml), washed sequentially with water (100 ml) and brine (100 ml), dried over MgSO$_4$, filtered and concentrated in vacuo to afford the title compound (110 mg, 0.244 mmol, 90% purity) as a white solid. $^1$H NMR (400 MHz, DMSO-d$_6$) (two rotamers in a 2:1 ratio) δ 8.03 (d, J=2.6 Hz, 1H), 7.87 (br s, 1H), 7.34-7.21 (m, 3H), 7.21-7.09 (m, 6H), 6.91 (d, J=2.6 Hz, 1H), 5.53 (br s, 2H), 3.18-2.89 (m, 4H), 1.34 (s, 9H, major), 1.15 (s, 9H, minor).

Intermediate 4 tert-butyl (2-(4-(5-amino-3-(thiophen-3-yl)pyridin-2-yl)phenyl)propan-2-yl)carbamate

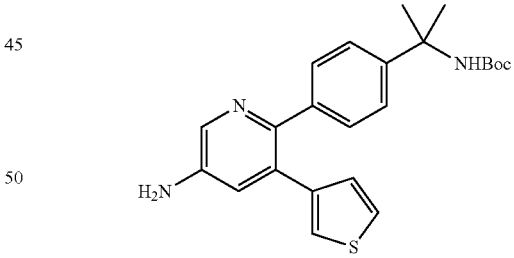

Step 1: tert-butyl (2-(4-(5-nitro-3-(thiophen-3-yl)pyridin-2-yl)phenyl)propan-2-yl)carbamate: The title compound (850 mg, 1.45 mmol, 75% purity) was isolated as a pale yellow solid from the reaction of the product of Intermediate 2 Step 3 (829 mg, 2.12 mmol), 4,4,5,5-tetramethyl-2-(thiophen-3-yl)-1,3,2-dioxaborolane (556 mg, 2.64 mmol), tetrakis-(triphenylphosphine)palladium(0) (244 mg, 0.212 mmol) and 2 M Na$_2$CO$_3$(aq) (2.4 ml, 4.76 mmol) were reacted together in dioxane (10 ml) using essentially the same procedure as in Intermediate 1 Step 2, except Celite® was used in place of a glass microfibre filter in the filtration. $^1$H NMR (400 MHz, DMSO-d$_6$) (two rotamers in a 3:1 ratio) δ 9.40 (d, J=2.5 Hz, 1H), 8.56 (d, J=2.5 Hz, 1H), 7.69

(br s, 1H), 7.51 (dd, J=5.0, 2.9 Hz, 1H), 7.36 (d, J=8.3 Hz, 2H), 7.31 (d, J=8.5 Hz, 2H), 7.30-7.17 (br m, 1H), 6.82 (dd, J=5.0, 1.3 Hz, 1H), 1.49 (s, 6H), 1.34 (s, 9H, major), 1.10 (s, 9H, minor). The compound contained 20% w/w residual EtOAc. This material was used in subsequent reactions without further drying.

Step 2: tert-butyl (2-(4-(5-amino-3-(thiophen-3-yl)pyridin-2-yl)phenyl)propan-2-yl)carbamate: The title compound (688 mg, 1.42 mmol, 89% purity) was isolated as a white solid from the reaction of the product of Step 1 above (830 mg, 1.42 mmol, 75% purity), iron powder (1.06 g, 18.9 mmol) and NH₄Cl (505 mg, 9.44 mmol) in IPA (18 ml) and water (2 ml) using essentially the same method as Intermediate 3 Step 3. ¹H NMR (400 MHz, DMSO-d₆) (two rotamers in a 3:1 ratio) δ 7.98 (d, J=2.6 Hz, 1H), 7.40 (dd, J=4.9, 3.0 Hz, 1H), 7.31 (dd, J=3.0, 1.3 Hz, 1H), 7.16 (d, J=8.6 Hz, 2H), 7.13 (d, J=8.6 Hz, 3H), 6.95 (d, J=2.6 Hz, 1H), 6.71 (dd, J=4.9, 1.3 Hz, 1H), 5.46 (s, 2H), 1.46 (s, 6H), 1.33 (br s, 9H, major), 1.09 (br s, 9H, minor). This material was used in subsequent reactions without further purification.

Intermediate 5 tert-butyl (S)-(1-(4-(5-amino-3-phenylpyridin-2-yl)phenyl)ethyl)carbamate

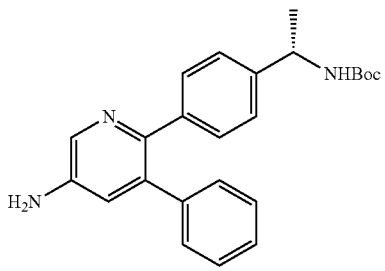 [SMILES: C[C@H](NC(=O)OC(C)(C)C)c1ccc(-c2ncc(N)cc2-c2ccccc2)cc1]

Step 1: (S)-tert-butyl (1-(4-chlorophenyl)ethyl)carbamate: (S)-1-(4-chlorophenyl)ethanamine (2.25 ml, 16.1 mmol) was dissolved in THF (25 ml) and treated with Boc₂O (4.21 g, 19.3 mmol). The resultant solution was allowed to stand at RT for 3 days. The solvent was evaporated in vacuo and the residue triturated with isohexane (20 ml), filtered and washed with isohexane (2×5 ml) and then dried in vacuo at 40° C. to afford the title compound (3.42 g, 12.7 mmol, 95% purity) as a white crystalline solid. ¹H NMR (400 MHz, DMSO-d₆) δ 7.42 (d, J=8.1 Hz, 1H), 7.37 (d, J=8.6 Hz, 2H), 7.31 (d, J=8.5 Hz, 2H), 4.66-4.53 (m, 1H), 1.36 (s, 9H), 1.28 (d, J=7.1 Hz, 3H).

Step 2: (S)-tert-butyl (1-(4-(4,4,5,5-tetramethyl-1,3,2-dioxaborolan-2-yl)phenyl)ethyl)carbamate: The title compound (868 mg, 2.43 mmol, 97% purity) was isolated as a white solid from the reaction of the product from Step 1 above (714 mg, 2.65 mmol, 95% purity), bis-(pinacolato)diboron (851 mg, 3.35 mmol), palladium(II) acetate (31.4 mg, 0.140 mmol), XPhos (134 mg, 0.279 mmol) and potassium acetate (822 mg, 8.38 mmol) in MeCN (12 ml) using essentially the same procedure as in Intermediate 2 Step 2, except the mixture was filtered through a glass microfibre filter, washing with MeCN, and then concentrated and purified by column chromatography (40 g cartridge, 0-20% EtOAc/isohexane). LCMS (Method 1): m/z 292 (M+H—C₄H₈)⁺, 370 (M+Na)⁺ at 2.70 min. ¹H NMR (400 MHz, Chloroform-d) (two rotamers) δ 7.84-7.76 (m, 2H), 7.32 (d, J=7.8 Hz, 2H), 4.93-4.70 (m, 1H), 1.61-1.32 (m, 24H).

Step 3: (S)-tert-butyl (1-(4-(3-chloro-5-nitropyridin-2-yl)phenyl)ethyl)carbamate: The title compound (922 mg, 2.32 mmol, 95% purity) was isolated as a yellow solid from the reaction of 2,3-dichloro-5-nitropyridine (866 mg, 4.49 mmol), the product from Step 2 above (1.56 g, 4.49 mmol), tetrakis-(triphenylphosphine)palladium(0) (519 mg, 0.449 mmol) and 2 M Na₂CO₃(aq) (5.05 ml, 10.1 mmol) in dioxane (10 ml) using essentially the same procedure as in Intermediate 1 Step 1, except the reaction mixture was heated at 50° C. overnight and then at 75° C. for 3 days. LCMS (Method 1): m/z 322 (M+H—C₄H₈)⁺, 400 (M+Na)⁺ at 2.50 min. ¹H NMR (400 MHz, Chloroform-d) (two rotamers) δ 9.40 (d, J=2.3 Hz, 1H), 8.62 (d, J=2.3 Hz, 1H), 7.82 (d, J=8.3 Hz, 2H), 7.47 (d, J=8.3 Hz, 2H), 4.89 (br s, 1H), 1.67-1.32 (m, 12H).

Step 4: (S)-tert-butyl (1-(4-(5-nitro-3-phenylpyridin-2-yl)phenyl)ethyl)carbamate: The title compound (813 mg, 1.82 mmol, 94% purity) was obtained as a yellow oil from the reaction of the product from Step 3 above (921 mg, 2.44 mmol), phenylboronic acid (297 mg, 2.44 mmol), 2 M Na₂CO₃(aq) (2.74 ml, 5.48 mmol) and tetrakis-(triphenylphosphine)palladium(0) (282 mg, 0.244 mmol) in dioxane (20 ml) using essentially the same procedure as in Intermediate 1 Step 2. ¹H NMR (400 MHz, Chloroform-d) δ 9.46 (d, J=2.5 Hz, 1H), 8.49 (d, J=2.5 Hz, 1H), 7.43-7.29 (m, 4H), 7.29-7.15 (m, 5H), 4.76 (br s, 1H), 1.41 (br s, 12H).

Step 5: (S)-tert-butyl (1-(4-(5-amino-3-phenylpyridin-2-yl)phenyl)ethyl)carbamate: The title compound (746 mg, 1.79 mmol, 93% purity) was isolated as a yellow solid from the reaction of the product of Step 4 above (800 mg, 1.79 mmol, 94% purity), iron powder (1.07 g, 19.1 mmol) and NH₄Cl (122 mg, 2.29 mmol) in IPA (50 ml) and water (5 ml) using essentially the same procedure as in Intermediate 1 Step 3, except the reaction mixture was heated overnight. LCMS (Method 1): m/z 390 (M+H)⁺ at 1.60 min.

Intermediate 6 tert-butyl (R)-(1-(4-(5-amino-3-phenylpyridin-2-yl)phenyl)ethyl)carbamate

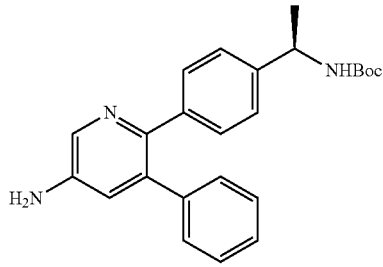 [SMILES: C[C@@H](NC(=O)OC(C)(C)C)c1ccc(-c2ncc(N)cc2-c2ccccc2)cc1]

Step 1: (R)-tert-butyl (1-(4-chlorophenyl)ethyl)carbamate: The title compound (3.47 g, 12.9 mmol, 95% purity) was isolated as a white crystalline solid from the reaction of (R)-1-(4-chlorophenyl)ethanamine (2.25 ml, 16.1 mmol) and Boc₂O (4.21 g, 19.3 mmol) in THF (25 ml) using essentially the same procedure as in Intermediate 5 Step 1. ¹H NMR (400 MHz, DMSO-d₆) δ 7.42 (d, J=8.1 Hz, 1H), 7.37 (d, J=8.6 Hz, 2H), 7.31 (d, J=8.5 Hz, 2H), 4.66-4.53 (m, 1H), 1.36 (s, 9H), 1.28 (d, J=7.1 Hz, 3H).

Step 2: (R)-tert-butyl (1-(4-(4,4,5,5-tetramethyl-1,3,2-dioxaborolan-2-yl)phenyl)ethyl)carbamate: The title compound (1.8 g) was isolated as a yellow oil from the reaction of the product from Step 1 above (1.5 g, 2.65 mmol, 95% purity), bis-(pinacolato)diboron (1.79 g, 7.04 mmol), palladium(II) acetate (66 mg, 0.293 mmol), XPhos (246 mg, 0.514 mmol) and potassium acetate (1.73 g, 17.6 mmol) in MeCN (20 ml) using essentially the same procedure as in Intermediate 2 Step 2, except the mixture was filtered through a glass microfibre filter, washing with MeCN, and then concentrated and purified by column chromatography (40 g cartridge, 0-20% EtOAc/hexane). This material was used in subsequent reactions without analysis.

Step 3: (R)-tert-butyl (1-(4-(3-chloro-5-nitropyridin-2-yl)phenyl)ethyl)carbamate: The title compound (1.12 g, 2.65 mmol, 90% purity) was isolated as a yellow solid from the reaction of 2,3-dichloro-5-nitropyridine (1 g, 5.18 mmol), the product from Step 2 above (1.8 g), tetrakis-(triphenylphosphine)palladium(0) (599 mg, 0.518 mmol) and 2 M Na$_2$CO$_3$(aq) (5.83 ml, 11.7 mmol) in dioxane (20 ml) using essentially the same procedure as in Intermediate 1 Step 1, except the reaction mixture was heated overnight. LCMS (Method 1): m/z 322 (M+H—C$_4$H$_8$)$^+$ at 2.55 min.

Step 4: (R)-tert-butyl (1-(4-(5-nitro-3-phenylpyridin-2-yl)phenyl)ethyl)carbamate: The title compound (632 mg, 1.42 mmol, 94% purity) was obtained as a yellow foam from the reaction of the product from Step 3 above (600 mg, 1.43 mmol, 90% purity), phenylboronic acid (194 mg, 1.59 mmol), 2 M Na$_2$CO$_3$(aq) (1.79 ml, 3.57 mmol) and tetrakis-(triphenylphosphine)palladium(0) (184 mg, 0.159 mmol) in dioxane (10 ml) using essentially the same procedure as in Intermediate 1 Step 2, except after heating at 90° C. overnight the mixture was heated at 105° C. for a further 24 h. LCMS (Method 1): m/z 364 (M+H—C$_4$H$_8$)$^+$, 420 (M+H)$^+$, 442 (M+Na)$^+$, at 2.64 min. $^1$H NMR (400 MHz, DMSO-d$_6$) δ 9.43 (d, J=2.6 Hz, 1H), 8.48 (d, J=2.6 Hz, 1H), 7.42-7.27 (m, 7H), 7.23 (d, J=8.2 Hz, 2H), 7.10 (br s, 2H), 4.59 (br s, 1H), 1.35 (br s, 9H), 1.30 (d, J=7.0 Hz, 3H). The compound contained 6% w/w residual EtOAc. This material was used in subsequent reactions without further drying.

Step 5: (S)-tert-butyl (1-(4-(5-amino-3-phenylpyridin-2-yl)phenyl)ethyl)carbamate: The title compound (566 mg, 1.34 mmol, 92% purity) was isolated as a yellow foam from the reaction of the product of Step 4 above (626 mg, 1.40 mmol, 94% purity), iron powder (834 mg, 14.9 mmol) and NH$_4$Cl (96 mg, 1.79 mmol) in IPA (30 ml) and water (3 ml) using essentially the same procedure as in Intermediate 1 Step 3, except the reaction mixture was heated for 2 h. LCMS (Method 1): m/z 390 (M+H)$^+$ at 1.64 min. This material was used in subsequent reactions without further purification.

Intermediate 7 tert-butyl (2-(4-(5-amino-3-(2-fluorophenyl)pyridin-2-yl)phenyl)propan-2-yl)carbamate

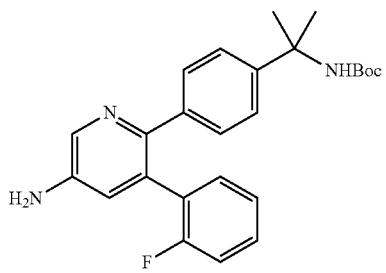 [SMILES: CC(C)(C)OC(=O)NC(C)(C)c1ccc(-c2ncc(N)cc2-c2ccccc2F)cc1]

Step 1: tert-butyl (2-(4-(3-(2-fluorophenyl)-5-nitropyridin-2-yl)phenyl)propan-2-yl)carbamate: The title compound (141 mg, 0.281 mmol, 90% purity) was isolated as a colourless gum from the reaction of the product from the reaction of Intermediate 2 Step 3 (155 mg, 0.396 mmol), 2-fluorophenylboronic acid (69.2 mg, 0.494 mmol), 2 M Na$_2$CO$_3$(aq) (445 µl, 0.890 mmol) and tetrakis-(triphenylphosphine)palladium(0) (45.7 mg, 0.040 mmol) in dioxane (15 ml) using essentially the same procedure as in Intermediate 1 Step 2, except the reaction mixture was heated for 4 h. LCMS (Method 1): m/z 452 (M+H)$^+$ at 2.76 min. $^1$H NMR (400 MHz, DMSO-d$_6$) (two rotamers in a 3:1 ratio) δ 9.49 (d, J=2.6 Hz, 1H), 8.57 (d, J=2.6 Hz, 1H), 7.50-7.41 (m, 1H), 7.40-7.06 (m, 8H), 1.45 (s, 6H), 1.32 (br s, 9H, major), 1.02 (s, 9H, minor).

Step 2: tert-butyl (2-(4-(5-amino-3-(2-fluorophenyl)pyridin-2-yl)phenyl)propan-2-yl)carbamate: The title compound (98 mg, 0.209 mmol, 90% purity) was isolated as a pale yellow foam from the reaction of the product from Step 1 above (141 mg, 0.281 mmol, 90% purity), iron powder (179 mg, 3.21 mmol) and NH$_4$Cl (22.3 mg, 0.418 mmol) in IPA (50 ml) water (5 ml) using essentially the same procedure as in Intermediate 1 Step 3, except the reaction mixture was heated at 90° C. for 1 h. LCMS (Method 1): m/z 422 (M+H)$^+$ at 1.69 min. $^1$H NMR (400 MHz, DMSO-d$_6$) δ 8.06 (d, J=2.6 Hz, 1H), 7.42-7.30 (m, 1H), 7.31-7.22 (m, 1H), 7.21-7.02 (m, 6H), 6.87 (d, J=2.7 Hz, 1H), 5.52 (br s, 2H), 1.43 (s, 6H), 1.32 (br s, 9H, major), 1.01 (br s, 9H, minor).

Intermediate 8 tert-Butyl (1-(4-(5-amino-3-phenylpyridin-2-yl)phenyl)cyclobutyl)carbamate

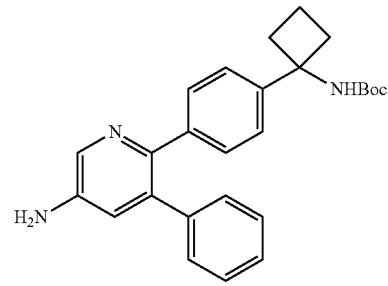 [SMILES: CC(C)(C)OC(=O)NC1(c2ccc(-c3ncc(N)cc3-c3ccccc3)cc2)CCC1]

Step 1: tert-butyl (1-(4-(4,4,5,5-tetramethyl-1,3,2-dioxaborolan-2-yl)phenyl)cyclobutyl)carbamate: tert-butyl (1-(4-bromophenyl)cyclobutyl)carbamate (10.0 g, 30.7 mmol), bis-(pinacolato)diboron (9.34 g, 36.8 mmol), palladium(II) acetate (0.344 g, 1.53 mmol), X-Phos (1.47 g, 3.07 mmol) and potassium acetate (9.03 g, 92 mmol) were combined in MeCN (120 ml). The vessel was purged with N$_2$ for 10 mins and then heated at 75° C. overnight. The mixture was allowed to cool to RT and was filtered through Celite®, washing with MeCN. The filtrate was concentrated in vacuo to afford a pale yellow solid. Purification by column chromatography (220 g cartridge, 0-20% EtOAc/isohexane) afforded the title compound (8.91 g, 23.9 mmol) as a white solid, which was used directly in the next step without analysis.

Step 2: tert-butyl (1-(4-(3-chloro-5-nitropyridin-2-yl)phenyl)cyclobutyl)carbamate: The title compound (5.92 g, 13.2 mmol, 90% purity) was isolated as a yellow oil, which crystallised upon standing, from the reaction of 2,3-dichloro-5-nitropyridine (4.35 g, 22.5 mmol), the product from Step 1 above (8.41 g, 22.5 mmol), tetrakis-(triphenylphosphine)palladium(0) (2.60 g, 2.25 mmol) and 2 M Na$_2$CO$_3$(aq) (25.3 ml, 50.7 mmol) in dioxane (100 ml) using essentially the same procedure as in Intermediate 1 Step 1, except the reaction mixture was heated under reflux overnight. HPLC (Method 1): R$_T$2.75 min. The material contained a small quantity of triphenylphosphine oxide. This material was used in subsequent reactions without further purification.

Step 3: tert-butyl (1-(4-(5-nitro-3-phenylpyridin-2-yl)phenyl)cyclobutyl)carbamate: The title compound (4.82 g, 10.6 mmol, 98% purity) was isolated as a pale yellow solid from the reaction of the product from Step 2 above (5.41 g, 12.0 mmol, 90% purity), phenylboronic acid (2.04 g, 16.7 mmol), tetrakis-(triphenylphosphine)palladium(0) (773 mg, 0.669 mmol) and 2 M Na$_2$CO$_3$(aq) (15.1 ml, 30.1 mmol) in dioxane (100 ml) using essentially the same procedure as in Intermediate 1 Step 2, except the reaction mixture was heated under reflux overnight. LCMS (Method 1): m/z 446 (M+H)$^+$ at 2.93 min.

Step 4: tert-butyl (1-(4-(5-amino-3-phenylpyridin-2-yl)phenyl)cyclobutyl)carbamate: The title compound (4.37 g, 10.3 mmol, 98% purity) was isolated as a cream solid from the reaction of the product of Step 3 above (4.82 g, 10.6 mmol, 98% purity), iron powder (6.04 g, 108 mmol) and NH$_4$Cl (694 mg, 13.0 mmol) in IPA (150 ml) and water (15 ml) using essentially the same procedure as in Intermediate 1 Step 3, except the reaction mixture was heated for 1 h. LCMS (Method 1): m/z 416 (M+H)$^+$ at 1.77 min. $^1$H NMR (400 MHz, DMSO-d$_6$) (two rotamers in a 2:1 ratio) δ 8.03 (d, J=2.6 Hz, 1H), 7.50 (br s, 1H, major), 7.36 (br s, 1H, minor), 7.32-7.22 (m, 3H), 7.22-7.06 (m, 6H), 6.95 (d, J=2.6 Hz, 1H), 5.59 (br s, 2H), 2.42-2.21 (m, 4H), 2.03-1.87 (m, 1H), 1.83-1.64 (m, 1H), 1.33 (br s, 9H, major), 1.11 (br s, 9H, minor).

Intermediate 9

(S)-tert-butyl (1-(4-(5-amino-3-phenylpyridin-2-yl)phenyl)-2,2-difluoroethyl)carbamate

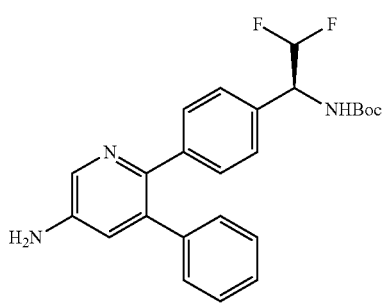 [SMILES: CC(C)(C)OC(=O)N[C@@H](c1ccc(-c2ncc(N)cc2-c2ccccc2)cc1)C(F)F]

Step 1: (S)-tert-butyl (1-(4-chlorophenyl)-2, 2-difluoroethyl)carbamate: A solution of (S)-1-(4-chlorophenyl)-2,2-difluoroethanamine hydrochloride (385 mg, 1.69 mmol, prepared according to *Angew. Chem., Int. Ed.,* 2005, 44, 5882) in THF (5 ml) was treated with Et$_3$N (247 µl, 1.77 mmol), followed by Boc$_2$O (387 mg, 1.77 mmol) and the resultant mixture stirred at RT overnight. The reaction mixture was diluted with water (20 ml) and the phases separated. The aqueous phase was extracted sequentially with EtOAc (2×20 ml) and DCM (20 ml). The combined organic phases were dried over MgSO$_4$, filtered and concentrated in vacuo to afford the title compound (463 mg) as a pale pink solid. The product was used directly in the next step without purification.

Step 2: (S)-tert-butyl (2,2-difluoro-1-(4-(4,4,5,5-tetramethyl-1,3,2-dioxaborolan-2-yl)phenyl)ethyl)carbamate: The title compound (421 mg, 1.04 mmol, 95% purity) was isolated as a colourless oil from the reaction of the product from Step 1 above (459 mg), bis-(pinacolato)diboron (479 mg, 1.89 mmol), palladium(II) acetate (17.7 mg, 0.079 mmol), XPhos (75 mg, 0.157 mmol) and potassium acetate (463 mg, 4.72 mmol) in MeCN (12 ml) using essentially the same procedure as in Intermediate 2 Step 2, except the mixture was filtered through a glass microfibre filter, washing with MeCN, and then concentrated and purified by column chromatography (40 g cartridge, 0-20% EtOAc/isohexane). LCMS (Method 1): m/z 328 (M+H—C$_4$H$_8$)$^+$ at 2.71 min. $^1$H NMR (400 MHz, Chloroform-d) δ 7.85 (d, J=8.1 Hz, 2H), 7.36 (d, J=8.0 Hz, 2H), 6.00 (t, J=55.4 Hz, 1H), 5.22 (br s, 1H), 5.14-4.92 (m, 1H), 1.46 (s, 9H), 1.36 (s, 12H).

Step 3: (S)-tert-butyl (1-(4-(3-chloro-5-nitropyridin-2-yl)phenyl)-2,2-difluoroethyl)carbamate: The title compound (347 mg, 0.813 mmol, 97% purity) was isolated as a yellow oil from the reaction of 2,3-dichloro-5-nitropyridine (210 mg, 1.09 mmol), the product from Step 2 above (417 mg, 1.09 mmol), tetrakis-(triphenylphosphine)palladium(0) (126 mg, 0.109 mmol) and 2 M Na$_2$CO$_3$(aq) (1.23 ml, 2.46 mmol) in dioxane (7 ml) using essentially the same procedure as in Intermediate 1 Step 1, except the reaction mixture was heated overnight. LCMS (Method 1): m/z 358 (M+H—C$_4$H$_8$)$^+$ at 2.55 min. $^1$H NMR (400 MHz, Chloroform-d) δ 9.42 (d, J=2.3 Hz, 1H), 8.64 (d, J=2.4 Hz, 1H), 7.88 (d, J=8.4 Hz, 2H), 7.52 (d, J=8.3 Hz, 2H), 6.06 (td, J=55.2, 1.8 Hz, 1H), 5.39-5.06 (m, 2H), 1.49 (s, 9H).

Step 4: (S)-tert-butyl (2,2-difluoro-1-(4-(5-nitro-3-phenylpyridin-2-yl)phenyl)ethyl)carbamate: The product from Step 3 above (345 mg, 0.808 mmol, 97% purity), phenylboronic acid (122 mg, 1.00 mmol), 2 M Na$_2$CO$_3$(aq) (938 µl, 1.88 mmol) and tetrakis-(triphenylphosphine)palladium(0) (96 mg, 0.083 mmol) were combined in dioxane (5 ml). The vessel was purged with N$_2$ and then heated at 75° C. for 3 days, then at 90° C. for 2 h. Additional phenylboronic acid (50 mg, 0.410 mmol) and tetrakis-(triphenylphosphine)palladium(0) (50 mg, 0.043 mmol) were added and the resultant mixture was heated at 90° C. for 4 h. Additional phenylboronic acid (50 mg, 0.410 mmol), tetrakis-(triphenylphosphine)palladium(0) (50 mg, 0.043 mmol) and 1 M Na$_2$CO$_3$ (aq) (938 µL, 0.938 mmol) were added and the reaction was heated at 90° C. overnight. The mixture was filtered through a glass microfibre filter and the filtrate concentrated in vacuo. The residue was partitioned between DCM (50 ml) and water (50 ml), filtered through a phase separation cartridge and concentrated in vacuo. The residue was purified by column chromatography (12 g cartridge, 10-40% EtOAc/isohexane) to afford the title compound (307 mg, 0.627 mmol, 93% purity) as a yellow solid. LCMS (Method 1): m/z 400 (M+H—C$_4$H$_8$)$^+$, 456 (M+H)$^+$ at 2.75 min.

Step 5: (S)-tert-butyl (1-(4-(5-amino-3-phenylpyridin-2-yl)phenyl)-2,2-difluoroethyl)carbamate: The title compound (289 mg, 0.618 mmol, 91% purity) was isolated as a yellow solid from the reaction of the product from Step 4 above (306 mg, 0.624 mmol, 93% purity), iron powder (375 mg, 6.71 mmol) and NH$_4$Cl (43.1 mg, 0.805 mmol) in IPA (20 ml) and water (2 ml) using essentially the same procedure as in Intermediate 1 Step 3, except the reaction mixture was heated for 2 h. LCMS (Method 1): m/z 426 (M+H)⁺ at 1.70 min.

Intermediate 10 tert-butyl (1-(4-(5-amino-3-phenylpyridin-2-yl)phenyl)cyclopropyl)carbamate

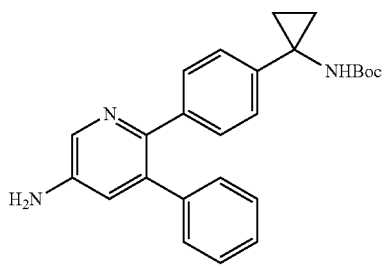 [SMILES: CC(C)(C)OC(=O)NC1(c2ccc(-c3ncc(N)cc3-c3ccccc3)cc2)CC1]

Step 1: tert-butyl (1-(4-bromophenyl)cyclopropyl)carbamate: A stirred solution of 1-(4-bromophenyl)cyclopropanamine (1.00 g, 4.72 mmol) in DCM (10 ml) was treated with Boc$_2$O (1.08 g, 4.95 mmol) and the resultant mixture stirred overnight. The solution was diluted with DCM (20 ml), was washed with brine (20 ml) and filtered through a phase separation cartridge. The filtrate was concentrated in vacuo to afford the title compound (1.43 g, 4.50 mmol, 98% purity) as a white solid. ¹H NMR (400 MHz, Chloroform-d) (two rotamers in a 3:1 ratio) δ 7.44-7.36 (m, 2H), 7.10 (d, J=8.3 Hz, 2H), 5.22 (br s, 1H, major), 5.01 (br s, 1H, minor), 1.43 (br s, 9H), 1.32-1.11 (m, 4H).

Step 2: tert-butyl (1-(4-(4,4,5,5-tetramethyl-1,3,2-dioxaborolan-2-yl)phenyl)cyclopropyl)carbamate: The product from Step 1 above (1.43 g, 4.50 mmol, 98% purity), bis-(pinacolato)diboron (1.39 g, 5.48 mmol), palladium(II) acetate (0.051 g, 0.229 mmol), X-Phos (0.219 g, 0.457 mmol) and potassium acetate (1.35 g, 13.7 mmol) were combined in a vessel, which was evacuated and purged with N$_2$ three times. MeCN (25 ml) was added and the vessel was purged with N$_2$ and then heated at 80° C. overnight. The mixture was diluted with DCM (20 ml) and filtered through Celite®, washing with DCM (3×20 ml). The filtrate was concentrated in vacuo and the residue was purified by column chromatography (80 g cartridge, 0-25% EtOAc/isohexane) to afford the title compound (1.46 g, 3.91 mmol, 96% purity) as a cream powder. ¹H NMR (400 MHz, DMSO-d$_6$) δ 7.74 (s, 1H), 7.62-7.50 (m, 2H), 7.15-7.10 (m, 2H), 1.41-1.22 (m, 21H), 1.17-1.10 (m, 4H).

Step 3: tert-butyl (1-(4-(3-chloro-5-nitropyridin-2-yl)phenyl)cyclopropyl)carbamate: 2,3-dichloro-5-nitropyridine (505 mg, 2.62 mmol), the product from Step 2 above (941 mg, 2.52 mmol, 96% purity), tetrakis-(triphenylphosphine) palladium(0) (303 mg, 0.262 mmol) and Na$_2$CO$_3$ (694 mg, 6.55 mmol) were combined in dioxane (20 ml) and water (5 ml).

The vessel was purged with N$_2$ and heated at 50° C. overnight. The mixture was diluted with water (5 ml) and heated at 60° C. for 4 h. The mixture was concentrated in vacuo to remove most of the dioxane and the residue was partitioned between EtOAc (100 ml) and brine (50 ml). The phases were separated and the organic phase dried over Na$_2$SO$_4$, filtered and concentrated in vacuo. The residue was purified by column chromatography (40 g cartridge, 0-25% EtOAc/isohexane) to afford the title compound (585 mg, 1.43 mmol, 95% purity). ¹H NMR (400 MHz, DMSO-d$_6$) δ 9.40 (d, J=2.3 Hz, 1H), 8.86 (d, J=2.3 Hz, 1H), 7.80 (br s, 1H, major), 7.72 (d, J=8.4 Hz, 2H), 7.52 (br s, 1H, minor), 7.27 (d, J=8.4 Hz, 2H), 1.41 (br s, 9H, major), 1.28 (br s, 9H, minor), 1.24-1.18 (m, 4H).

Step 4: tert-butyl (1-(4-(5-nitro-3-phenylpyridin-2-yl)phenyl)cyclopropyl)carbamate: The product from Step 3 above (585 mg, 1.43 mmol, 95% purity), phenylboronic acid (229 mg, 1.88 mmol), Na$_2$CO$_3$ (358 mg, 3.38 mmol) and tetrakis-(triphenylphosphine)palladium(0) (173 mg, 0.150 mmol) were combined in dioxane (8 ml) and water (1.5 ml). The vessel was purged with N$_2$ and heated at 90° C. overnight. The mixture was allowed to cool and was then partitioned between EtOAc (50 ml) and brine (50 ml). The phases were separated and the organic phase dried over Na$_2$SO$_4$, filtered and concentrated in vacuo. The residue was purified by column chromatography (40 g cartridge, 0-50% EtOAc/isohexane) to afford the title compound (411 mg, 0.933 mmol, 98% purity) as a yellow foam. LCMS (Method 1): m/z 432 (M+H)⁺ at 2.81 min.

Step 5: tert-butyl (1-(4-(5-amino-3-phenylpyridin-2-yl)phenyl)cyclopropyl)carbamate: A stirred suspension of the product from Step 4 above (411 mg, 0.933 mmol, 98% purity), iron powder (532 mg, 9.53 mmol) and NH$_4$Cl (56.0 mg, 1.048 mmol) in IPA (20 ml) and water (2 ml) was heated under reflux for 90 mins. The mixture was allowed to cool and was filtered through Celite®, washing with IPA. The filtrate was concentrated and the residue purified by column chromatography (40 g cartridge, 0-10% (0.7 M NH$_3$/MeOH solution)/DCM) to afford the title compound (355 mg, 0.866 mmol, 98% purity) as a yellow solid. LCMS (Method 1): m/z 402 (M+H)⁺ at 1.71 min.

Intermediate 11 tert-butyl (trans-1-(4-(5-amino-3-phenylpyridin-2-yl)phenyl)-3-hydroxycyclobutyl)carbamate

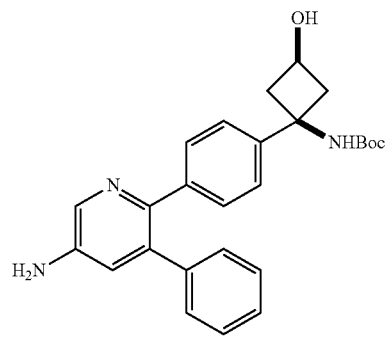 [SMILES: CC(C)(C)OC(=O)N[C@]1(c2ccc(-c3ncc(N)cc3-c3ccccc3)cc2)C[C@H](O)C1]

Step 1: tert-butyl (trans-3-hydroxy-1-(4-(4,4,5,5-tetramethyl-1,3,2-dioxaborolan-2-yl)phenyl)cyclobutyl)carbamate: The title compound (1.16 g) was isolated as a white solid from the reaction of tert-butyl (trans-1-(4-bromophenyl)-3-hydroxycyclobutyl)carbamate (1.7 g, 4.97 mmol, prepared according to WO2009148916), bis-(pinacolato)diboron (1.51 g, 5.96 mmol), palladium(II) acetate (56 mg, 0.248 mmol), XPhos (238 mg, 0.497 mmol) and potassium acetate (1.46 g, 14.9 mmol) in MeCN (50 ml) using essentially the same procedure as in Intermediate 2 Step 2, except the mixture was filtered through Celite®, washing with MeCN, and then concentrated and partially purified by column chromatography (80 g cartridge, 20-100% EtOAc/isohexane). This material was used in subsequent reactions without further purification.

Step 2: tert-butyl (trans-1-(4-(3-chloro-5-nitropyridin-2-yl)phenyl)-3-hydroxycyclobutyl)carbamate: The title compound (597 mg, 1.28 mmol, 90% purity) was isolated as a beige foam from the reaction of 2,3-dichloro-5-nitropyridine (575 mg, 2.98 mmol), the product from Step 1 above (417 mg), tetrakis-(triphenylphosphine)palladium(0) (344 mg, 0.298 mmol) and 2 M Na$_2$CO$_3$(aq) (3.35 ml, 6.70 mmol) in dioxane (40 ml) using essentially the same procedure as in Intermediate 1 Step 1, except the mixture was heated under reflux overnight. LCMS (Method 1): m/z 364 (M+H—C$_4$H$_8$)$^+$ at 2.19 min.

Step 3: tert-butyl (trans-3-hydroxy-1-(4-(5-nitro-3-phenylpyridin-2-yl)phenyl)cyclobutyl)carbamate: The title compound (252 mg, 0.535 mmol, 98% purity) was isolated as a pale yellow foam from the reaction of the product from Step 2 above (310 mg, 0.664 mmol, 90% purity), phenylboronic acid (113 mg, 0.923 mmol), tetrakis-(triphenylphosphine)palladium(0) (43 mg, 0.037 mmol) and 2 M Na$_2$CO$_3$ (aq) (0.831 ml, 1.66 mmol) in dioxane (10 ml) using essentially the same procedure as in Intermediate 1 Step 2, except the reaction mixture was heated under reflux overnight. LCMS (Method 1): m/z 406 (M+H—C$_4$H$_8$)$^+$ at 2.40 min. $^1$H NMR (400 MHz, DMSO-d$_6$) (two rotamers in a 2:1 ratio) δ 9.45 (d, J=2.5 Hz, 1H), 8.50 (d, J=2.5 Hz, 1H), 7.74 (s, 1H, major), 7.55 (s, 1H, minor), 7.43-7.24 (m, 9H), 5.12 (d, J=6.4 Hz, 1H), 4.02-3.84 (m, 1H), 2.77-2.64 (m, 2H), 2.31-2.13 (m, 2H), 1.32 (br s, 9H, major), 1.11 (br s, 9H, minor).

Step 4: tert-butyl (trans-1-(4-(5-amino-3-phenylpyridin-2-yl)phenyl)-3-hydroxycyclobutyl)carbamate: The title compound (206 mg, 0.468 mmol, 98% purity) was isolated as a pale yellow solid from the reaction of the product from Step 3 above (250 mg, 0.531 mmol, 98% purity), iron powder (303 mg, 5.42 mmol) and NH$_4$Cl (35 mg, 0.650 mmol) in IPA (10 ml) and water (1 ml) using essentially the same procedure as in Intermediate 1 Step 3, except the mixture was heated under reflux for 1 h. LCMS (Method 1): m/z 432 (M+H)$^+$ at 1.43 min. $^1$H NMR (400 MHz, DMSO-d$_6$) (two rotamers in a 2:1 ratio) δ 8.02 (d, J=2.6 Hz, 1H), 7.63 (br s, 1H, major), 7.46 (br s, 1H, minor), 7.32-7.22 (m, 3H), 7.20-7.06 (m, 6H), 6.91 (d, J=2.6 Hz, 1H), 5.49 (br s, 2H), 5.07 (d, J=6.4 Hz, 1H), 4.02-3.78 (m, 1H), 2.75-2.62 (m, 2H), 2.29-2.11 (m, 2H), 1.31 (s, 9H, major), 1.12 (s, 9H, minor).

Intermediate 12 benzyl (3-(4-(5-amino-3-phenylpyridin-2-yl)phenyl)oxetan-3-yl)carbamate

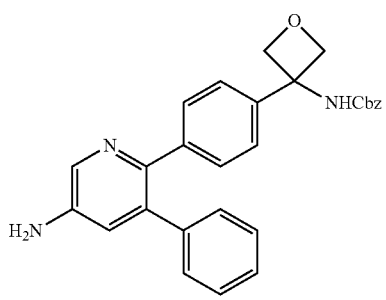 [SMILES: Nc1cnc(-c2ccc(C3(NC(=O)OCc4ccccc4)COC3)cc2)c(-c2ccccc2)c1]

Step 1: benzyl (3-(4-bromophenyl)oxetan-3-yl)carbamate: A stirred suspension of 3-(4-bromophenyl)oxetan-3-amine hydrochloride (1.05 g, 3.97 mmol) in DCM (10 ml) was treated with DIPEA (1.46 ml, 8.34 mmol). The resultant solution was stirred for 10 min and then CbzCl (0.595 ml, 4.17 mmol) was added dropwise. The mixture was stirred for a further 3 h and then diluted with DCM (20 ml), washed sequentially with 0.5 M HCl(aq) (20 ml), saturated NaHCO$_3$ (aq) (20 ml) and brine (20 ml). The organic phase was passed through a phase separation cartridge and concentrated in vacuo to afford a brown oil. The crude product was purified by column chromatography (40 g cartridge, 0-35% EtOAc/isohexane) to afford the title compound (1.5 g, 3.93 mmol, 95% purity) as an off-white solid. LCMS (Method 1): m/z 363 (M+H)$^+$, 361 (M–H)$^-$ at 2.25 min. $^1$H NMR (400 MHz, DMSO-d$_6$) δ 8.58 (br s, 1H), 7.60 (d, J=8.5 Hz, 2H), 7.43 (d, J=8.6 Hz, 2H), 7.43-7.23 (m, 5H), 5.02 (s, 2H), 4.83 (d, J=6.7 Hz, 2H), 4.69 (d, J=6.6 Hz, 2H).

Step 2: benzyl (3-(4-(4,4,5,5-tetramethyl-1,3,2-dioxaborolan-2-yl)phenyl)oxetan-3-yl)carbamate: The title compound (1.55 g) was isolated as a pale yellow oil from the reaction of the product from Step 1 above (1.39 g, 3.64 mmol, 95% purity), bis-(pinacolato)diboron (1.17 g, 4.60 mmol), palladium(II) acetate (43 mg, 0.192 mmol), XPhos (184 mg, 0.384 mmol) and potassium acetate (1.13 g, 11.5 mmol) in MeCN (20 ml) using essentially the same procedure as in Intermediate 2 Step 2, except the mixture was filtered through Celite®, washing with DCM, and then concentrated in vacuo. The residue was redissolved in DCM (30 ml), filtered through a phase separation cartridge and concentrated in vacuo to a final volume of (ca. 5 ml) and partially purified by column chromatography (40 g cartridge, 0-75% EtOAc/isohexane). This material was used in subsequent reactions without further purification.

Step 3: benzyl (3-(4-(3-chloro-5-nitropyridin-2-yl)phenyl)oxetan-3-yl)carbamate: The title compound (1.12 g, 1.12 mmol, 44% purity) was isolated as a yellow oil from the reaction of 2,3-dichloro-5-nitropyridine (731 mg, 3.79 mmol), the product from Step 2 above (1.55 g), tetrakis-(triphenylphosphine)palladium(0) (438 mg, 0.379 mmol) and 2 M Na$_2$CO$_3$(aq) (4.26 ml, 8.52 mmol) in dioxane (30 ml) using essentially the same procedure as in Intermediate 3 Step 1, except the reaction mixture was heated at 90° C. overnight, worked-up and then partially purified twice by column chromatography (40 g cartridge, 0-50% EtOAc/isohexane). LCMS (Method 1): m/z 440 (M+H)$^+$, 438 (M–H)$^-$ at 2.39 min. $^1$H NMR (400 MHz, DMSO-d$_6$) δ 9.43 (d, J=2.3 Hz, 1H), 8.90 (d, J=2.3 Hz, 1H), 8.66 (s, 1H), 7.83 (d, J=8.5 Hz, 2H), 7.67 (d, J=8.5 Hz, 2H), 7.54-7.27 (m, 5H), 5.05 (s, 2H), 4.89 (d, J=6.7 Hz, 2H), 4.78 (d, J=6.6 Hz, 2H). The compound contained 34% w/w pinacol, 15% w/w EtOAc and 7% w/w triphenylphosphine oxide. This material was used in subsequent reactions without further purification.

Step 4: benzyl (3-(4-(5-nitro-3-phenylpyridin-2-yl)phenyl)oxetan-3-yl)carbamate: The title compound (702 mg, 1.09 mmol, 75% purity) was isolated as a pale yellow foam from the reaction of the product from Step 3 above (1.12 g, 1.12 mmol, 44% purity), phenylboronic acid (388 mg, 3.18 mmol), tetrakis-(triphenylphosphine)palladium(0) (294 mg, 0.255 mmol) and 2 M Na$_2$CO$_3$(aq) (2.86 ml, 5.73 mmol) in dioxane (20 ml) using essentially the same procedure as in Intermediate 3 Step 2. LCMS (Method 1): m/z 482 (M+H)$^+$, 480 (M–H)$^-$ at 2.59 min. $^1$H NMR (400 MHz, DMSO-d$_6$) δ 9.47 (d, J=2.5 Hz, 1H), 8.52 (br s, 1H), 8.52 (d, J=2.6 Hz, 1H), 7.51-7.20 (m, 14H), 5.02 (s, 2H), 4.82 (d, J=6.7 Hz, 2H), 4.67 (d, J=6.7 Hz, 2H). The compound contained 14% w/w pinacol. This material was used in subsequent reactions without further purification.

Step 5: benzyl (3-(4-(5-amino-3-phenylpyridin-2-yl)phenyl)oxetan-3-yl)carbamate: The title compound (536 mg, 1.06 mmol, 89% purity) was isolated as a yellow solid from the reaction of the product from Step 4 above (702 mg, 1.09 mmol, 75% purity), iron powder (814 mg, 14.6 mmol) and NH$_4$Cl (84 mg, 1.56 mmol) in IPA (50 ml) and water (5 ml) using essentially the same procedure as in Intermediate 1 Step 3. LCMS (Method 1): m/z 452 (M+H)$^+$ at 1.55 min. $^1$H NMR (400 MHz, DMSO-d$_6$) δ 8.43 (s, 1H), 8.04 (d, J=2.6 Hz, 1H), 7.45-7.10 (m, 14H), 6.91 (d, J=2.6 Hz, 1H), 5.52 (s, 2H), 5.01 (s, 2H), 4.81 (d, J=6.6 Hz, 2H), 4.65 (d, J=6.5 Hz, 2H). This material was used in subsequent reactions without further purification.

Intermediate 13 tert-butyl (trans-1-(4-(5-amino-3-phenylpyridin-2-yl)phenyl)-3-fluorocyclobutyl)carbamate

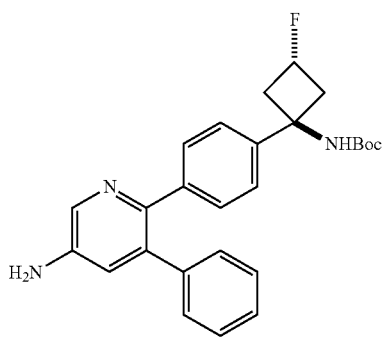 [SMILES: CC(C)(C)OC(=O)N[C@]1(c2ccc(-c3ncc(N)cc3-c3ccccc3)cc2)C[C@@H](F)C1]

Step 1: trans-5-(4-chlorophenyl)-2-oxa-4-azabicyclo[3.1.1]heptan-3-one: A stirred solution of trans-1-(4-chlorophenyl)-3-hydroxycyclobutanecarboxylic acid (6.57 g, 29.0 mmol, prepared according to *Org. Process Res. Dev.,* 2012, 16, 1069) and Et$_3$N (4.04 ml, 29.0 mmol) in tert-butanol (120 ml) and dioxane (120 ml) was treated dropwise with diphenylphosphoryl azide (6.25 ml, 29.0 mmol) over 5 min. The reaction mixture was then heated at 80° C. for 2.5 h and then allowed to cool to RT and concentrated in vacuo. The residue was diluted with EtOAc (200 ml) and washed with saturated NaHCO$_3$(aq) (100 ml). The phases were separated and the organic phase concentrated in vacuo. The residue was diluted with DCM (400 ml), washed with brine (100 ml) and the organic phase filtered through a phase separation cartridge and concentrated in vacuo to afford a white solid. This solid was triturated with EtOAc (40 ml) and filtered, washing with EtOAc (2×5 ml), and then dried in vacuo at 40° C. to afford the title compound (4.62 g, 19.6 mmol, 95% purity) as a white solid. $^1$H NMR (400 MHz, DMSO-d$_6$) δ 8.18 (s, 1H), 7.51-7.44 (m, 2H), 7.43-7.33 (m, 2H), 4.94 (t, J=3.5 Hz, 1H), 2.56-2.45 (m, 2H, obscured by DMSO-d$_5$), 2.01 (dd, J=7.3, 2.4 Hz, 2H).

Step 2: trans-3-amino-3-(4-chlorophenyl)cyclobutanol: A stirred solution of the product from Step 1 above (4.62 g, 19.6 mmol, 95% purity) in IPA (260 ml) containing 4 M KOH(aq) (258 ml, 1.03 mol) was heated at 100° C. overnight. The solvent was removed in vacuo and the residue partitioned between CHCl$_3$ (150 ml) and brine (100 ml). The phases were separated and the organic phase was washed with brine (100 ml) and then filtered through a phase separation cartridge. The filtrate was concentrated in vacuo to afford the title compound (3.81 g, 17.4 mmol, 90% purity) as a sticky pale brown solid. $^1$H NMR (400 MHz, DMSO-d$_6$) δ 7.48 (d, J=8.6 Hz, 2H), 7.35 (d, J=8.6 Hz, 2H), 5.01 (br d, J=5.5 Hz, 1H), 3.85-3.71 (m, 1H), 2.79-2.64 (m, 2H), 2.15-2.00 (m, 4H).

Step 3: tert-butyl (trans-1-(4-chlorophenyl)-3-hydroxycyclobutyl)carbamate: A mixture of the product from Step 2 above (3.81 g, 17.4 mmol, 90% purity) and Et$_3$N (10.8 ml, 77 mmol) was dissolved in THF (60 ml) and treated portionwise with Boc$_2$O (6.71 ml, 28.9 mmol). The resultant solution was stirred at RT for 2 h and then concentrated in vacuo. The residue was partitioned between DCM (80 ml) and saturated NaHCO$_3$(aq) (50 ml) and filtered through a phase separation cartridge. The organic phase was concentrated in vacuo to afford a yellow oil which partially crystallised upon standing. The residue was triturated with DCM and filtered to afford the title compound (2.39 g, 7.23 mmol, 90% purity) as a cream solid. The filtrate was purified by column chromatography (120 g cartridge, 0-100% EtOAc/isohexane) to afford an additional batch of the title compound (1.70 g, 5.42 mmol, 95% purity) as a cream solid. $^1$H NMR (400 MHz, DMSO-d$_6$) (two rotamers in a 2:1 ratio) δ 7.39 (d, J=8.8 Hz, 2H), 7.36 (d, J=8.8 Hz, 2H), 5.13 (d, J=6.5 Hz, 1H), 3.94 (br s, 1H), 2.83-2.63 (m, 2H), 2.33-2.15 (m, 3H), 1.32 (br s, 9H, major), 1.15 (br s, 9H, minor).

Step 4: tert-butyl (trans-1-(4-chlorophenyl)-3-fluorocyclobutyl)carbamate: A solution of the product from Step 3 above (500 mg, 1.60 mmol, 95% purity) in anhydrous DCE (5 ml) was added to XtalFluor E® (769 mg, 3.36 mmol). The resultant mixture was treated with triethylamine trihydrofluoride (547 μl, 3.36 mmol) and the vessel was purged with N$_2$ and stirred at RT overnight. The reaction mixture was poured into saturated NaHCO$_3$(aq) (100 ml) and extracted with DCM (3×50 ml). The combined organic phases were washed with brine (1×50 ml), dried over MgSO$_4$, filtered and concentrated in vacuo. The residue was purified by column chromatography (40 g cartridge, 0-100% EtOAc/isohexane) to afford the title compound (175 mg, 0.526 mmol, 90% purity). $^1$H NMR (400 MHz, DMSO-d$_6$) δ 7.70 (br s, 1H), 7.39 (d, J=8.9 Hz, 2H), 7.33 (d, J=8.8 Hz, 2H), 5.21 (dp, J=56.5, 6.5 Hz, 1H), 3.04-2.89 (m, 2H), 2.49-2.38 (m, 2H), 1.33 (br s, 9H, major), 1.15 (br s, 9H, minor). An additional reaction was carried out on the same scale to afford the title compound (230 mg, 0.690 mmol, 90% purity). The material was combined for use in subsequent reactions.

Step 5: tert-butyl (trans-3-fluoro-1-(4-(4,4,5,5-tetramethyl-1,3,2-dioxaborolan-2-yl)phenyl)cyclobutyl)carbamate: The title compound (457 mg) was isolated as a white solid from the reaction of the product from Step 4 above (400 mg), bis-(pinacolato)diboron (508 mg, 2.00 mmol), palladium(II) acetate (18.7 mg, 0.083 mmol), XPhos (80 mg, 0.167 mmol) and potassium acetate (491 mg, 5.00 mmol) in MeCN (10 ml) using essentially the same procedure as in Intermediate 2 Step 2, except the mixture was heated at 80° C. overnight and then filtered through Celite®, washing with DCM, and then concentrated and partially purified by column chromatography (40 g cartridge, 0-100% EtOAc/isohexane). This material was used in subsequent reactions without further purification.

Step 6: tert-butyl (trans-1-(4-(3-chloro-5-nitropyridin-2-yl)phenyl)-3-fluorocyclobutyl)carbamate: The title compound (195 mg) was isolated as a yellow solid from the reaction of 2,3-dichloro-5-nitropyridine (222 mg, 1.15 mmol), the product from Step 5 above (450 mg), tetrakis- (triphenylphosphine)palladium(0) (133 mg, 0.115 mmol) and 2 M Na$_2$CO$_3$(aq) (1.29 ml, 2.59 mmol) in dioxane (30 ml) using essentially the same procedure as in Intermediate 3 Step 1, except the reaction mixture was heated at 90° C. overnight, worked-up and then partially purified by column chromatography (40 g cartridge, 0-50% EtOAc/isohexane). This material was used in subsequent reactions without further purification.

Step 7: tert-butyl (trans-3-fluoro-1-(4-(5-nitro-3-phenylpyridin-2-yl)phenyl)cyclobutyl)carbamate: The title compound (130 mg, 0.252 mmol, 90% purity) was isolated as a pale yellow foam from the reaction of the product from Step 6 above (190 mg), phenylboronic acid (68.6 mg, 0.563 mmol), tetrakis-(triphenylphosphine)palladium(0) (52.0 mg, 0.045 mmol) and 2 M Na$_2$CO$_3$(aq) (507 µl, 1.01 mmol) in dioxane (10 ml) using essentially the same procedure as in Intermediate 3 Step 2. $^1$H NMR (400 MHz, DMSO-d$_6$) (two rotamers in a 2:1 ratio) δ 9.45 (d, J=2.5 Hz, 1H), 8.51 (d, J=2.6 Hz, 1H), 7.68 (br s, 1H, major), 7.47 (br s, 1H, minor), 7.42-7.14 (m, 9H), 5.20 (dp, J=56.6, 6.5 Hz, 1H), 3.04-2.79 (m, 2H), 2.53-2.35 (m, 2H, obscured by DMSO-d$_5$), 1.33 (br s, 9H, major), 1.12 (br s, 9H, minor).

Step 8: tert-butyl (trans-1-(4-(5-amino-3-phenylpyridin-2-yl)phenyl)-3-fluorocyclobutyl)carbamate: The title compound (100 mg, 0.208 mmol, 90% purity) was isolated as a white solid from the reaction of the product from Step 7 above (130 mg, 0.252 mmol, 90% purity), iron powder (157 mg, 2.80 mmol) and NH$_4$Cl (16.1 mg, 1.08 mmol) in IPA (30 ml) and water (5 ml) using essentially the same procedure as in Intermediate 1 Step 3, except the reaction mixture was heated for 3 h. $^1$H NMR (400 MHz, DMSO-d$_6$) (two rotamers in a 2:1 ratio) δ 8.03 (d, J=2.6 Hz, 1H), 7.56 (br s, 1H), 7.32-7.23 (m, 3H), 7.20-7.05 (m, 6H), 6.90 (d, J=2.6 Hz, 1H), 5.50 (s, 2H), 5.18 (dp, J=56.3, 6.6 Hz, 1H), 3.06-2.75 (m, 2H), 2.48-2.30 (m, 2H), 1.33 (br s, 9H, major), 1.12 (br s, 9H, minor).

Intermediate 14 tert-butyl (1-(4-(5-amino-3-(2-fluorophenyl)pyridin-2-yl)phenyl)cyclobutyl)carbamate

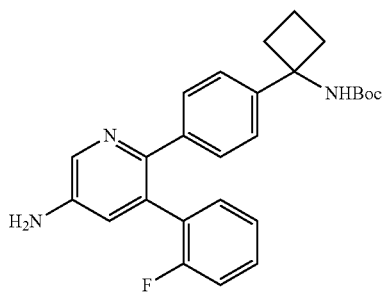 [SMILES: CC(C)(C)OC(=O)NC1(c2ccc(-c3ncc(N)cc3-c3ccccc3F)cc2)CCC1]

Step 1: tert-butyl (1-(4-(3-(2-fluorophenyl)-5-nitropyridin-2-yl)phenyl)cyclobutyl)carbamate: The title compound (245 mg, 0.386 mmol, 73% purity) was isolated as a yellow foam from the reaction of the product of Intermediate 8 Step 2 (300 mg, 0.743 mmol), (2-fluorophenyl)boronic acid (130 mg, 0.929 mmol), tetrakis-(triphenylphosphine)palladium (0) (86 mg, 0.074 mmol) and 2 M Na$_2$CO$_3$(aq) (836 µl, 1.67 mmol) were reacted together in dioxane (15 ml) using essentially the same procedure as in Intermediate 1 Step 2, except the reaction mixture was heated for 4 h and after purification, appropriate fractions were combined in MeOH and concentrated in vacuo. LCMS (Method 1): m/z 464 (M+H)$^+$ at 2.81 min. $^1$H NMR (400 MHz, DMSO-d$_6$) (two rotamers in a 2:1 ratio) δ 8.44 (d, J=8.8 Hz, 1H), 8.31 (d, J=0.9 Hz, 1H), 8.11 (d, J=8.8 Hz, 1H), 7.38-7.27 (m, 5H), 7.07 (dd, J=17.7, 10.9 Hz, 1H), 6.50 (dd, J=17.6, 1.1 Hz, 1H), 5.85-5.72 (m, 1H), 2.34 (d, J=8.6 Hz, 4H), 2.07-1.87 (m, 1H), 1.87-1.65 (m, 1H), 1.34 (s, 9H, major), 1.13 (s, 9H, minor). The compound contained 14% w/w triphenylphosphine oxide and 13% w/w MeOH. This material was used in subsequent reactions without further purification.

Step 2: tert-butyl (1-(4-(5-amino-3-(2-fluorophenyl)pyridin-2-yl)phenyl)cyclobutyl)carbamate: The title compound (179 mg, 0.372 mmol, 90% purity) was isolated as a pale yellow foam from the reaction of the product from Step 1 above (245 mg, 0.386 mmol, 73% purity), iron powder (295 mg, 5.29 mmol) and NH$_4$Cl (30.4 mg, 0.569 mmol) in IPA (50 ml) and water (5 ml) using essentially the same procedure as in Intermediate 1 Step 3, except the reaction mixture was heated at 90° C. for 1 h. LCMS (Method 1): m/z 434 (M+H)$^+$ at 1.75 min. $^1$H NMR (400 MHz, DMSO-d$_6$) (two rotamers in a 2:1 ratio) δ 8.06 (d, J=2.6 Hz, 1H), 7.56-7.03 (m, 9H), 6.88 (d, J=2.6 Hz, 1H), 5.54 (s, 2H), 2.43-2.18 (m, 4H), 2.04-1.85 (m, 1H), 1.84-1.64 (m, 1H), 1.32 (br s, 9H, major), 1.07 (br s, 9H, minor).

Intermediate 15 tert-butyl (1-(4-(5-amino-3-(thiophen-3-yl)pyridin-2-yl)phenyl)cyclobutyl)carbamate

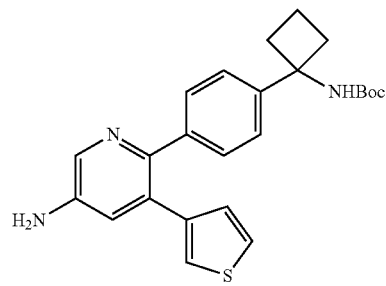 [SMILES: CC(C)(C)OC(=O)NC1(c2ccc(-c3ncc(N)cc3-c3ccsc3)cc2)CCC1]

Step 1: tert-butyl (1-(4-(5-nitro-3-(thiophen-3-yl)pyridin-2-yl)phenyl)cyclobutyl)carbamate: The title compound (250 mg, 0.526 mmol, 95% purity) was isolated as a yellow foam from the reaction of the product of Intermediate 8 Step 2 (250 mg, 0.619 mmol), 4,4,5,5-tetramethyl-2-(thiophen-3-yl)-1,3,2-dioxaborolane (163 mg, 0.774 mmol), tetrakis-(triphenylphosphine)palladium(0) (36 mg, 0.031 mmol) and 2 M Na$_2$CO$_3$(aq) (696 µl, 1.39 mmol) were reacted together in dioxane (6 ml) using essentially the same procedure as in Intermediate 1 Step 2, except the reaction mixture was heated under reflux overnight. LCMS (Method 1): m/z 452 (M+H)$^+$ at 2.88 min. $^1$H NMR (400 MHz, DMSO-d$_6$) (two rotamers in a 2:1 ratio) δ 9.40 (d, J=2.6 Hz, 1H), 8.58 (d, J=2.5 Hz, 1H), 7.71-7.67 (m, 1H), 7.63 (br s, 1H, major), 7.56-7.45 (m, 1H and 1H minor), 7.38 (d, J=8.7 Hz, 2H), 7.36 (d, J=8.7 Hz, 2H), 6.81 (d, J=5.0 Hz, 1H), 2.46-2.29 (m, 4H), 2.08-1.92 (m, 1H), 1.86-1.68 (m, 1H), 1.34 (br s, 9H, major), 1.15 (br s, 9H, minor).

Step 2: tert-butyl (1-(4-(5-amino-3-(thiophen-3-yl)pyridin-2-yl)phenyl)cyclobutyl)carbamate: The title compound (215 mg, 0.485 mmol, 95% purity) was isolated as a pale yellow foam from the reaction of the product from Step 1 above (248 mg, 0.522 mmol, 95% purity), iron powder (307 mg, 5.49 mmol) and NH$_4$Cl (35 mg, 0.659 mmol) in IPA (10 ml) and water (1 ml) using essentially the same procedure as in Intermediate 1 Step 3, except the reaction mixture was heated for 1 h. LCMS (Method 1): m/z 422 (M+H)$^+$ at 1.78 min. $^1$H NMR (400 MHz, DMSO-d$_6$) (two rotamers in a 2:1 ratio) δ 7.99 (d, J=2.6 Hz, 1H), 7.50 (br s, 1H, major), 7.43-7.37 (m, 1H and 1H minor), 7.31 (dd, J=2.9, 1.3 Hz, 1H), 7.23 (d, J=8.5 Hz, 2H), 7.17 (d, J=8.4 Hz, 2H), 7.01 (d, J=2.6 Hz, 1H), 6.77-6.71 (d, J=4.7 Hz, 1H), 5.50 (s, 2H), 2.45-2.27 (m, 4H), 2.05-1.88 (m, 1H), 1.88-1.66 (m, 1H), 1.34 (br s, 9H, major), 1.16 (br s, 9H, minor).

Intermediate 16 tert-butyl (1-(4-(5-amino-3-(2-methylthiophen-3-yl)pyridin-2-yl)phenyl)cyclobutyl)carbamate

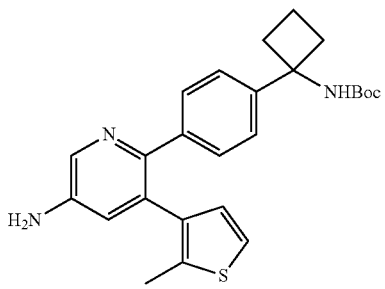 [SMILES: Cc1sccc1-c1cc(N)cnc1-c1ccc(C2(NC(=O)OC(C)(C)C)CCC2)cc1]

Step 1: tert-butyl (1-(4-(3-(2-methylthiophen-3-yl)-5-nitropyridin-2-yl)phenyl)cyclobutyl)carbamate: The title compound (290 mg, 0.623 mmol) was isolated as a yellow solid from the reaction of the product of Intermediate 8 Step 2 (300 mg, 0.743 mmol), (2-methylthiophen-3-yl)boronic acid (127 mg, 0.891 mmol), tetrakis-(triphenylphosphine)palladium(0) (86 mg, 0.074 mmol) and 2 M Na$_2$CO$_3$(aq) (836 μl, 1.67 mmol) were reacted together in dioxane (5 ml) using essentially the same procedure as in Intermediate 1 Step 2, except Celite® was used in place of a glass microfibre filter in the filtration. $^1$H NMR (400 MHz, DMSO-d$_6$) (two rotamers in a 2:1 ratio) δ 9.44 (d, J=2.6 Hz, 1H), 8.44 (d, J=2.5 Hz, 1H), 7.61 (br s, 1H, major), 7.45 (br s, 1H, minor), 7.40-7.30 (m, 5H), 6.96 (d, J=5.3 Hz, 1H), 2.44-2.26 (m, 4H), 2.05-1.86 (m, 4H), 1.83-1.69 (m, 1H), 1.33 (br s, 9H, major), 1.14 (br s, 9H, minor).

Step 2: tert-butyl (1-(4-(5-amino-3-(2-methylthiophen-3-yl)pyridin-2-yl)phenyl)cyclobutyl)carbamate: The title compound (215 mg, 0.445 mmol, 90% purity) was isolated as a white solid from the reaction of the product from Step 1 above (290 mg, 0.623 mmol), iron powder (348 mg, 6.23 mmol) and NH$_4$Cl (35.9 mg, 0.670 mmol) in IPA (30 ml) and water (5 ml) using essentially the same procedure as in Intermediate 3 Step 3. LCMS (Method 1): m/z 436 (M+H)$^+$ at 1.76 min. $^1$H NMR (400 MHz, DMSO-d$_6$) (two rotamers in a 2:1 ratio) δ 8.03 (d, J=2.7 Hz, 1H), 7.49 (br s, 1H, major), 7.36 (br s, 1H, minor), 7.26 (d, J=5.2 Hz, 1H), 7.18 (d, J=8.6 Hz, 2H), 7.13 (d, J=8.6 Hz, 2H), 6.83 (d, J=2.6 Hz, 1H), 6.81 (d, J=5.1 Hz, 1H), 5.45 (s, 2H), 2.43-2.25 (m, 4H), 2.04-1.90 (m, 1H), 1.88 (s, 3H), 1.82-1.67 (m, 1H), 1.32 (s, 9H, major), 1.14 (s, 9H, minor).

Intermediate 17 tert-butyl (1-(4-(5-amino-3-(4-methylthiophen-3-yl)pyridin-2-yl)phenyl)cyclobutyl)carbamate

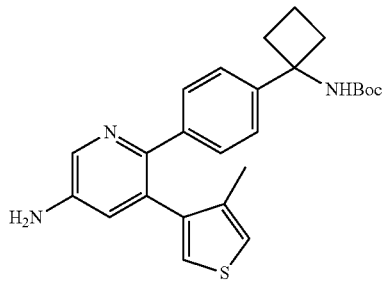 [SMILES: Cc1cscc1-c1cc(N)cnc1-c1ccc(C2(NC(=O)OC(C)(C)C)CCC2)cc1]

Step 1: tert-butyl (1-(4-(3-(4-methylthiophen-3-yl)-5-nitropyridin-2-yl)phenyl)cyclobutyl)carbamate: The title compound (187 mg) was isolated as a yellow solid from the reaction of the product of Intermediate 8 Step 2 (250 mg, 0.619 mmol), (4-methylthiophen-3-yl)boronic acid (105 mg, 0.743 mmol), tetrakis-(triphenylphosphine)palladium(0) (71.5 mg, 0.062 mmol) and 2 M Na$_2$CO$_3$(aq) (696 μl, 1.39 mmol) were reacted together in dioxane (5 ml) using essentially the same procedure as in Intermediate 1 Step 2, except Celite® was used in place of a glass microfibre filter in the filtration. This material was used in subsequent reactions without analysis.

Step 2: tert-butyl (1-(4-(5-amino-3-(4-methylthiophen-3-yl)pyridin-2-yl)phenyl)cyclobutyl)carbamate: The title compound (133 mg, 0.275 mmol, 90% purity) was isolated as a white solid from the reaction of the product from Step 1 above (185 mg), iron powder (222 mg, 3.97 mmol) and NH$_4$Cl (22.9 mg, 0.428 mmol) in IPA (30 ml) and water (5 ml) using essentially the same procedure as in Intermediate 3 Step 3. $^1$H NMR (400 MHz, DMSO-d$_6$) (two rotamers in a 2:1 ratio) δ 8.04 (d, J=2.7 Hz, 1H), 7.48 (br s, 1H), 7.33 (d, J=3.2 Hz, 1H), 7.16 (s, 4H), 7.07 (s, 1H), 6.82 (d, J=2.7 Hz, 1H), 5.46 (s, 2H), 2.42-2.22 (m, 4H), 2.05-1.86 (m, 1H), 1.83-1.67 (m, 1H), 1.60 (s, 3H), 1.32 (br s, 9H, major), 1.12 (br s, 9H, minor).

Intermediate 18 tert-butyl (1-(4-(5-amino-[3,3'-bipyridin]-2-yl)phenyl)cyclobutyl)carbamate

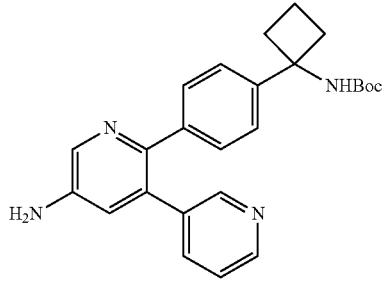 [SMILES: CC(C)(C)OC(=O)NC1(c2ccc(-c3ncc(N)cc3-c3cccnc3)cc2)CCC1]

Step 1: tert-butyl (1-(4-(5-nitro-[3,3'-bipyridin]-2-yl)phenyl)cyclobutyl)carbamate: The title compound (225 mg, 0.494 mmol, 98% purity) was isolated as a yellow solid from the reaction of the product of Intermediate 8 Step 2 (250 mg, 0.619 mmol), pyridin-3-ylboronic acid (76 mg, 0.619 mmol), tetrakis-(triphenylphosphine)palladium(0) (36 mg, 0.031 mmol) and 2 M $Na_2CO_3$(aq) (696 µl, 1.39 mmol) were reacted together in dioxane (4 ml) using essentially the same procedure as in Intermediate 1 Step 2, except the reaction mixture was heated at 110° C. and Celite® was used in place of a glass microfibre filter in the filtration. LCMS (Method 1): m/z 447.1 (M+H)$^+$, at 2.36 min. $^1$H NMR (400 MHz, DMSO-$d_6$) (two rotamers in a 2:1 ratio) δ 9.49 (d, J=2.5 Hz, 1H), 8.65 (d, J=2.5 Hz, 1H), 8.55 (dd, J=4.8, 1.3 Hz, 1H), 8.48 (d, J=1.9 Hz, 1H), 7.74 (dt, J=7.8, 1.9 Hz, 1H), 7.60 (br s, 1H, major), 7.42 (br s, 1H, minor), 7.39 (dd, J=7.8, 4.8 Hz, 1H), 7.32 (s, 4H), 2.44-2.26 (m, 4H), 2.07-1.90 (m, 1H), 1.89-1.65 (m, 1H), 1.33 (br s, 9H, major), 1.11 (br s, 9H, minor).

Step 2: tert-butyl (1-(4-(5-amino-[3,3'-bipyridin]-2-yl)phenyl)cyclobutyl)carbamate: The title compound (195 mg, 0.495 mmol, 98% purity) was isolated as a pale yellow solid from the reaction of the product from Step 1 above (223 mg, 0.489 mmol, 98% purity), iron powder (279 mg, 4.39 mmol) and $NH_4Cl$ (32 mg, 0.599 mmol) in IPA (5 ml) and water (0.5 ml) using essentially the same procedure as in Intermediate 3 Step 3, except the reaction mixture was heated for 1 h. LCMS (Method 1): m/z 417 (M+H)$^+$, at 1.45 min. $^1$H NMR (400 MHz, DMSO-$d_6$) (two rotamers in a 2:1 ratio) δ 8.46 (dd, J=4.8, 1.5 Hz, 1H), 8.34 (d, J=1.8 Hz, 1H), 8.07 (d, J=2.6 Hz, 1H), 7.64-7.24 (m, 3H), 7.19 (d, J=8.4 Hz, 2H), 7.10 (d, J=8.1 Hz, 2H), 6.94 (d, J=2.6 Hz, 1H), 5.57 (s, 2H), 2.43-2.21 (m, 4H), 2.04-1.87 (m, 1H), 1.85-1.63 (m, 1H), 1.33 (br s, 9H, major), 1.11 (br s, 9H, minor).

Intermediate 19 tert-butyl (2-(4-(5-amino-3-phenylpyridin-2-yl)-2-fluorophenyl)propan-2-yl)carbamate

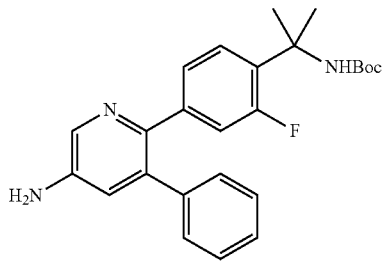 [SMILES: CC(C)(C)OC(=O)NC(C)(C)c1ccc(-c2ncc(N)cc2-c2ccccc2)cc1F]

Step 1: 2-(4-bromo-2-fluorophenyl)propan-2-amine: A solution of 4-bromo-2-fluorobenzonitrile (6.00 g, 30.0 mmol) in $Et_2O$ (100 ml) was treated with methylmagnesium bromide (30.0 ml, 90.0 mmol, 3 M solution in $Et_2O$). The resultant mixture was stirred for 30 min and then titanium (IV) isopropoxide (8.79 ml, 30.0 mmol) was added. The mixture was heated under reflux for 18 h, then cooled to 0° C. and slowly quenched with 10% NaOH(aq) (50 ml). The resultant mixture was stirred at RT for 30 min and then diluted with 5% $Na_2CO_3$(aq) (200 ml) and extracted with $Et_2O$ (3×200 ml). The combined extracts were concentrated in vacuo and the residue partitioned between 1 M HCl(aq) and $Et_2O$. The phases were separated and the aqueous phase washed with $Et_2O$ (100 ml). The aqueous phase was then cooled to 0° C., basified by addition of 20% NaOH(aq) and then extracted with $Et_2O$ (3×200 ml). The combined extracts were dried over $MgSO_4$, filtered and concentrated in vacuo to afford the title compound (4.43 g, 18.1 mmol, 95% purity) as a yellow oil. $^1$H NMR (400 MHz, DMSO-$d_6$) δ 7.57 (dd, J=9.2, 8.4 Hz, 1H), 7.41 (dd, J=11.8, 2.0 Hz, 1H), 7.35 (ddd, J=8.4, 2.0, 0.5 Hz, 1H), 2.01 (s, 2H), 1.39 (d, J=1.3 Hz, 6H).

Step 2: tert-butyl (2-(4-bromo-2-fluorophenyl)propan-2-yl)carbamate: The title compound (3.30 g, 9.64 mmol, 97% purity) was isolated as a white solid from the reaction of the product from Step 1 above (4.43 g, 18.1 mmol, 95% purity) with $Et_3N$ (2.79 ml, 20.0 mmol) and $Boc_2O$ (4.37 g, 20.0 mmol) in DCM (100 ml) using essentially the same procedure as in Intermediate 2 Step 1. LCMS (Method 1): m/z 276 (M+H—$C_4H_8$)$^+$ at 2.63 min. $^1$H NMR (400 MHz, DMSO-$d_6$) (two rotamers in a 4:1 ratio) δ 7.41 (dd, J=11.9, 2.0 Hz, 1H), 7.35 (dd, J=8.5, 2.1 Hz, 1H), 7.32-7.18 (m, 2H), 1.53 (d, J=1.2 Hz, 6H), 1.34 (s, 9H, major), 1.10 (s, 9H, minor).

Step 3: tert-butyl (2-(2-fluoro-4-(4,4,5,5-tetramethyl-1,3,2-dioxaborolan-2-yl)phenyl)propan-2-yl)carbamate: The title compound (1.46 g, 3.66 mmol, 95% purity) was isolated as a sticky yellow solid from the reaction of the product from Step 2 above (2.30 g, 6.71 mmol), bis-(pinacolato)diboron (2.11 g, 8.31 mmol), palladium(II) acetate (78 mg, 0.346 mmol), XPhos (331 mg, 0.692 mmol) and potassium acetate (2.04 g, 20.8 mmol) in MeCN (40 ml) using essentially the same procedure as in Intermediate 2 Step 2. $^1$H NMR (400 MHz, DMSO-$d_6$) δ 7.41 (dd, J=7.7, 1.2 Hz, 1H), 7.32 (t, J=8.0 Hz, 1H), 7.25 (dd, J=12.8, 1.2 Hz, 2H), 1.55 (s, 6H), 1.45-0.88 (m, 21H).

Step 4: tert-butyl (2-(4-(3-chloro-5-nitropyridin-2-yl)-2-fluorophenyl)propan-2-yl)carbamate: The title compound (477 mg, 1.14 mmol, 98% purity) was isolated as an off-white solid, from the reaction of 2,3-dichloro-5-nitropyridine (344 mg, 1.78 mmol), the product from Step 3 above (710 mg, 1.78 mmol, 95% purity), tetrakis-(triphenylphosphine)palladium(0) (0.206 mg, 0.178 mmol) and 2 M $Na_2CO_3$(aq) (2.01 ml, 4.01 mmol) in dioxane (20 ml) using essentially the same procedure as in Intermediate 1 Step 1, except the reaction mixture was heated at 80° C. for 18 h. LCMS (Method 1): m/z 354 (M+H—$C_4H_8$)$^+$ at 2.68 min.

Step 5: tert-butyl (2-(2-fluoro-4-(5-nitro-3-phenylpyridin-2-yl)phenyl)propan-2-yl)carbamate: The title compound (355 mg, 0.747 mmol, 95% purity) was isolated as a pale yellow oil from the reaction of the product from Step 4 above (380 mg, 0.908 mmol, 98% purity), 4,4,5,5-tetramethyl-2-phenyl-1,3,2-dioxaborolane (237 mg, 1.16 mmol), tetrakis-(triphenylphosphine)palladium(0) (107 mg, 0.093 mmol) and 2 M $Na_2CO_3$(aq) (1.04 ml, 2.09 mmol) were reacted together in dioxane (15 ml) using essentially the same procedure as in Intermediate 1 Step 2. LCMS (Method 1): m/z 396 (M+H—$C_4H_8$)$^+$ (ES$^+$) at 2.86 min. $^1$H NMR (400 MHz, DMSO-$d_6$) (two rotamers in a 3:1 ratio) δ 9.46 (d, J=2.5 Hz, 1H), 8.52 (d, J=2.5 Hz, 1H), 7.45-7.29 (m, 5H), 7.29-6.93 (m, 4H), 1.53 (s, 6H), 1.33 (s, 9H, major), 1.09 (s, 9H, minor).

Step 6: tert-butyl (2-(4-(5-amino-3-phenylpyridin-2-yl)-2-fluorophenyl)propan-2-yl)carbamate: The title compound (265 mg, 0.604 mmol, 96% purity) was isolated as a white solid from the reaction of the product from Step 5 above (350 mg, 0.744 mmol, 95% purity), iron powder (433 mg, 7.75 mmol) and $NH_4Cl$ (53.9 mg, 1.01 mmol) in IPA (23 ml) and water (2 ml) using essentially the same procedure as in Intermediate 1 Step 3. LCMS (Method 1): m/z 422 (M+H)$^+$ at 1.81 min.

Intermediate 20 tert-butyl (1-(4-(6-amino-4-phenylpyridin-3-yl)phenyl)cyclobutyl)carbamate

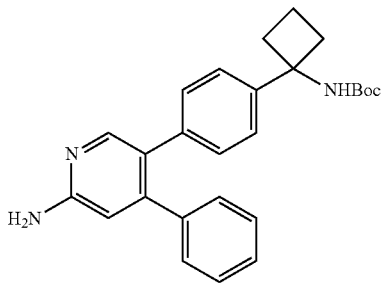 [SMILES: CC(C)(C)OC(=O)NC1(c2ccc(-c3cnc(N)cc3-c3ccccc3)cc2)CCC1]

Step 1: benzyl (4-bromopyridin-2-yl)carbamate: A stirred solution of 4-bromopyridin-2-amine (4 g, 23.1 mmol) in THF (40 ml) was treated with LiHMDS (48.6 ml, 48.6 mmol, 1 M in THF). After 15 min the mixture was cooled to 0° C. and treated with a solution of CbzCl (3.80 ml, 26.6 mmol) in THF (40 ml) and the resultant mixture was allowed to warm to RT and stir overnight. The reaction mixture was concentrated in vacuo and the residue partitioned between EtOAc (100 ml) and 0.1 M HCl (100 ml). The resultant precipitate was collected by filtration, rinsing with EtOAc, and dried in vacuo to afford the title compound (3.43 g, 10.9 mmol, 98% purity) as a tan solid. LCMS (Method 1): m/z 308 (M+H)$^+$ at 2.37 min.

Step 2: benzyl (4-phenylpyridin-2-yl)carbamate: The title compound (3.02 g, 9.82 mmol, 99% purity) was isolated as a pale brown solid from the reaction of the product from Step 1 above (3.43 g, 10.9 mmol, 98% purity), phenylboronic acid (1.50 g, 12.3 mmol), tetrakis-(triphenylphosphine)palladium(0) (1.29 g, 1.12 mmol) and 2 M Na$_2$CO$_3$ (aq) (11.2 ml, 22.3 mmol) in dioxane (100 ml) using essentially the same procedure as in Intermediate 1 Step 2, except the reaction mixture was heated under reflux overnight. LCMS (Method 1): m/z 305 (M+H)$^+$ at 2.37 min.

Step 3: benzyl (5-bromo-4-phenylpyridin-2-yl)carbamate: A stirred solution of the product from Step 2 above (3.02 g, 9.82 mmol, 99% purity) in DCM (100 ml) was treated with NBS (1.94 g, 10.9 mmol) in the dark overnight. Additional NBS (0.5 g, 2.81 mmol) was added and the resultant mixture and stirred at RT in the dark for a further 3 days. The mixture was washed with water (100 ml), filtered through a phase separation cartridge and the organic phase concentrated in vacuo. The residue was triturated with MeOH (3×100 ml) and the resultant solid filtered, rinsing with MeOH, and dried in vacuo to afford the title compound (3.50 g, 9.04 mmol, 99% purity) as a pale yellow solid. LCMS (Method 1): m/z 384 (M+H)$^+$ at 2.78 min.

Step 4: benzyl (5-(4-(1-((tert-butoxycarbonyl)amino)cyclobutyl)phenyl)-4-phenylpyridin-2-yl)carbamate: The title compound (2.26 g, 4.07 mmol, 99% purity) was isolated as a pale yellow solid, from the reaction of the product of Intermediate 8 Step 1 (3.17 g, 8.49 mmol), the product from Step 3 above (3.1 g, 8.09 mmol, 99% purity), tetrakis-(triphenylphosphine)palladium(0) (0.935 g, 0.809 mmol) and 2 M Na$_2$CO$_3$(aq) (9.10 ml, 18.20 mmol) in dioxane (200 ml) using essentially the same procedure as in Intermediate 1 Step 1, except the reaction mixture was heated under reflux overnight and then treated with additional tetrakis-(triphenylphosphine)palladium(0) (0.935 g, 0.809 mmol) and 2 M Na$_2$CO$_3$(aq) (9.10 ml, 18.20 mmol) prior to heating under reflux for a further 24 h. LCMS (Method 1): m/z 550 (M+H)$^+$ at 3.05 min.

Step 5: tert-butyl (1-(4-(6-amino-4-phenylpyridin-3-yl)phenyl)cyclobutyl)carbamate: The product from Step 4 above (2.26 g, 4.07 mmol, 99% purity) was dissolved in a mixture of EtOH (50 ml) and THF (50 ml) and the vessel purged with N$_2$. Palladium (1.75 g, 5% w/w on carbon, Type 87L paste) was added and the vessel further purged with N$_2$. The vessel was then purged with H$_2$ and then stirred at RT under an atmosphere of H$_2$ for a total of 6 days. Twice during this time the vessel was purged with N$_2$ and additional palladium (1.75 g, 5% w/w on carbon, Type 87L paste) was added prior to replacing the H$_2$ atmosphere. At the end of the reaction, the vessel was purged with N$_2$, the reaction mixture was filtered through Celite®, washing with MeOH (50 ml), and concentrated in vacuo to afford the title compound (1.61 g, 3.80 mmol, 98% purity) as a dark brown solid. LCMS (Method 1): m/z 416 (M+H)$^+$ at 1.73 min.

Intermediate 21 tert-Butyl (2-(5-amino-3-phenyl-[2,3'-bipyridin]-6'-yl)propan-2-yl)carbamate

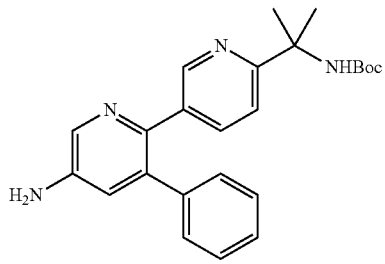

Step 1: 2-(5-bromopyridin-2-yl)propan-2-amine: Methylmagnesium bromide (5.46 ml, 16.4 mmol, 3 M in Et$_2$O) was added slowly into a stirred solution of 5-bromopicolinonitrile (1 g, 5.46 mmol) in toluene (50 ml) at 0° C. The resultant mixture was stirred at RT for 15 min and then heated at 100° C. for 3 days. The mixture was quenched with 2 M HCl(aq) (20 ml). The aqueous phase was basified with 4 M NaOH(aq) (ca. 25 ml) and then extracted with EtOAc (3×100 ml). The combined organic extracts were washed with brine (100 ml), dried over MgSO$_4$, filtered and concentrated in vacuo to afford the title compound (530 mg, 2.22 mmol, 90% purity) as an orange oil. $^1$H NMR (400 MHz, DMSO-d$^6$) δ 8.60 (dd, J=2.4, 0.8 Hz, 1H), 8.03-7.92 (m, 1H), 7.72-7.60 (m, 1H), 2.28-2.03 (br m, 2H), 1.36 (s, 6H).

Step 2: tert-butyl (2-(5-bromopyridin-2-yl)propan-2-yl)carbamate: A mixture of the product from Step 1 above (530 mg, 2.46 mmol) and Et$_3$N (1.37 ml, 9.86 mmol) in THF (60 ml) was treated portionwise with Boc$_2$O (858 μl, 3.70 mmol). The resultant solution was stirred at RT for 2 h. The solvent was removed in vacuo and the residue partitioned between DCM (200 ml) and saturated NaHCO$_3$(aq) (200 ml). The phases were separated and the organic phase dried over MgSO$_4$, filtered and concentrated in vacuo to afford a yellow oil. This material was purified by column chromatography (12 g cartridge, 0-50% EtOAc/isohexane) to afford the title compound (507 mg) as a yellow solid. This material was used in subsequent reactions without analysis.

Step 3: tert-butyl (2-(5-(4,4,5,5-tetramethyl-1,3,2-dioxaborolan-2-yl)pyridin-2-yl)propan-2-yl)carbamate: The title compound (250 mg) was isolated as a pale yellow solid from the reaction of the product from Step 2 above (500 mg), bis-(pinacolato)diboron (483 mg, 1.90 mmol), palladium(II) acetate (17.8 mg, 0.079 mmol), XPhos (76 mg, 0.159 mmol) and potassium acetate (467 mg, 4.76 mmol) in MeCN (10 ml) using essentially the same procedure as in Intermediate 10 Step 2. This material was used directly in subsequent reactions without analysis.

Step 4: tert-butyl (2-(3-chloro-5-nitro-[2,3'-bipyridin]-6'-yl)propan-2-yl)carbamate: The title compound (115 mg, 0.263 mmol, 90% purity) was isolated as a pale yellow solid from the reaction of 2,3-dichloro-5-nitropyridine (189 mg, 0.982 mmol), the product from Step 3 above (250 mg), tetrakis-(triphenylphosphine)palladium(0) (103 mg, 0.089 mmol) and 2 M Na$_2$CO$_3$(aq) (1.00 ml, 2.01 mmol) in dioxane (30 ml) using essentially the same procedure as in Intermediate 3 Step 1. $^1$H NMR (400 MHz, DMSO-d$_6$) (two rotamers in a 4:1 ratio) δ 9.45 (d, J=2.3 Hz, 1H), 8.94 (d, J=2.3 Hz, 1H), 8.88 (s, 1H), 8.17 (dd, J=8.4, 2.4 Hz, 1H), 7.68-7.52 (m, 1H), 7.50-7.31 (m, 1H), 1.56 (s, 6H), 1.37 (s, 9H, major), 1.07 (s, 9H, minor).

Step 5: tert-butyl (2-(5-nitro-3-phenyl-[2,3'-bipyridin]-6'-yl)propan-2-yl)carbamate: The title compound (95 mg) was isolated as a pale yellow foam from the reaction of the product from Step 5 above (111 mg, 255 mmol, 90% purity), phenylboronic acid (43.1 mg, 0.353 mmol), tetrakis-(triphenylphosphine)palladium(0) (32.7 mg, 0.028 mmol) and 2 M Na$_2$CO$_3$(aq) (318 µl, 0.636 mmol) in dioxane (10 ml) using essentially the same procedure as in Intermediate 3 Step 2. This material was used directly in subsequent reactions without analysis.

Step 6: tert-butyl (2-(5-amino-3-phenyl-[2,3'-bipyridin]-6'-yl)propan-2-yl)carbamate: The title compound (60 mg) was isolated as a white solid from the reaction of the product of Step 5 above (95 mg), iron powder (129 mg, 2.30 mmol) and NH$_4$Cl (61.6 mg, 1.15 mmol) in IPA (30 ml) and water (5 ml) using essentially the same method as Intermediate 3 Step 3. This material was used directly in subsequent reactions without analysis.

Example 1

N-(6-(4-(trans-1-amino-3-hydroxy-3-methylcyclobutyl)phenyl)-5-phenylpyridin-3-yl)-2-(trans-4-(N-methylacetamido)cyclohexyl)acetamide

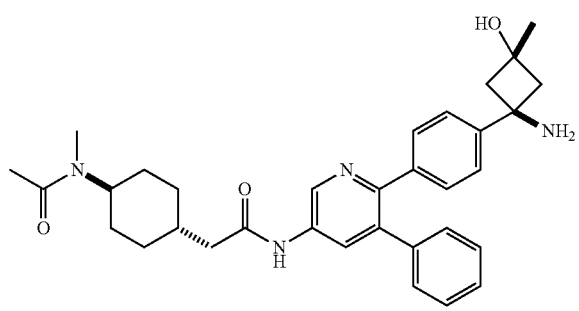

Step 1: Ethyl 2-(trans-4-(((benzyloxy)carbonyl)amino)cyclohexyl)acetate: Et$_3$N (18.9 ml, 135 mmol) was added to a suspension of ethyl 2-(trans-4-aminocyclohexyl)acetate hydrochloride (10 g, 45.1 mmol) in DCM (100 ml). The resultant mixture was stirred at RT for 5 min, then cooled to 0° C. and treated with CbzCl (9.66 ml, 67.7 mmol). The reaction mixture was stirred at RT overnight. The mixture was partitioned between 1 M HCl(aq) (100 ml) and DCM (100 ml) and the phases were separated. The aqueous phase was extracted with DCM (2×100 ml) and the combined organic phases dried over MgSO$_4$, filtered and concentrated in vacuo. The residue was triturated with cyclohexane to afford a white solid (11.5 g). Purification by column chromatography (120 g cartridge, 0-100% EtOAc/isohexane), followed by further trituration with cyclohexane afforded the title compound (7.4 g, 22.9 mmol, 99% purity) as a white solid. $^1$H NMR (400 MHz, Chloroform-d) δ 7.41-7.30 (m, 5H), 5.10 (s, 2H), 4.61 (s, 1H), 4.14 (q, J=7.1 Hz, 2H), 3.46 (s, 1H), 2.21 (d, J=6.8 Hz, 2H), 2.09-1.99 (m, 2H), 1.86-1.70 (m, 2H), 1.27 (t, J=7.1 Hz, 3H), 1.23-1.04 (m, 4H).

Step 2: Ethyl 2-(trans-4-(((benzyloxy)carbonyl)(methyl)amino)cyclohexyl)acetate: Sodium hydride (614 mg, 15.3 mmol, 60% w/w in mineral oil) was added to stirred solution of the product from Step 1 above (3.5 g, 10.9 mmol, 99% purity) in THF (50 ml) at 0° C. The resultant mixture was stirred at 0° C. for 10 min and then iodomethane (1.37 ml, 21.9 mmol) was added and the mixture stirred at RT overnight. The reaction mixture was quenched with EtOH (2 ml) and then diluted with EtOAc (100 ml) and washed sequentially with saturated NH$_4$Cl(aq) (70 ml) and 1 M HCl(aq) (30 ml). The organic phase was dried over MgSO$_4$, filtered and concentrated in vacuo. The residue was purified by column chromatography (80 g cartridge, 0-50% EtOAc/isohexane) to afford the title compound (2.85 g, 8.46 mmol, 99% purity). $^1$H NMR (400 MHz, Chloroform-d) δ 7.41-7.28 (m, 5H), 5.16 (s, 2H), 4.15 (q, J=7.1 Hz, 2H), 4.03 (br s, 1H), 2.82 (s, 3H), 2.21 (d, J=7.1 Hz, 2H), 1.90-1.82 (m, 2H), 1.78-1.69 (m, 3H), 1.56-1.44 (m, 2H), 1.28 (t, J=7.2 Hz, 3H), 1.23-1.06 (m, 2H).

Step 3: Ethyl 2-(trans-4-(methylamino)cyclohexyl)acetate: A solution of the product from Step 2 above (6.47 g, 19.4 mmol) in EtOH was treated with palladium (1.3 g, 1.22 mmol, 10% w/w on carbon). The vessel was purged with N$_2$, followed by H$_2$. The reaction mixture was stirred at RT under H$_2$ (5 bar pressure) for 4 h. The reaction mixture was filtered through a glass microfibre filter, washing with MeOH. The filtrate was concentrated in vacuo to afford the title compound (3.86 g, 19.0 mmol, 98% purity). $^1$H NMR (400 MHz, Chloroform-d) δ 4.15 (q, J=7.1 Hz, 2H), 2.48 (s, 3H), 2.47-2.37 (m, 1H), 2.21 (d, J=6.8 Hz, 2H), 2.08-1.98 (m, 2H), 1.89-1.74 (m, 3H), 1.28 (t, J=7.1 Hz, 3H), 1.25-1.16 (m, 2H), 1.15-0.99 (m, 2H).

Step 4: ethyl 2-(trans-4-(N-methylacetamido)cyclohexyl)acetate: A mixture of the product from Step 3 above (3.86 g, 19.0 mmol 98% purity) and DIPEA (7.44 ml, 42.6 mmol) in THF (50 ml) was treated with acetic anhydride (2.01 ml, 21.3 mmol) and the resultant mixture stirred at RT overnight. The reaction mixture was concentrated in vacuo and the residue dissolved in DCM (50 ml) and washed with saturated NaHCO$_3$(aq) (50 ml), filtered through a phase separation cartridge. The aqueous phase was extracted with DCM (50 ml) and the combined organic phases were concentrated in vacuo to afford the title compound (4.52 g) as a colourless oil. This material was used in subsequent reactions without purification.

Step 5: 2-(trans-4-(N-methylacetamido)cyclohexyl)acetic acid: LiOH (1.35 g, 56.2 mmol) was added to a stirred solution of the product from Step 4 above (4.52 g) in THF (30 ml) and water (10 ml). The resultant mixture was stirred at RT overnight. The solution was acidified with 1 M HCl(aq) and extracted with EtOAc (3×60 ml). The combined organic phases were dried over MgSO$_4$, filtered and concentrated in vacuo to afford the title compound (3.34 g) as a white solid, which was used directly in subsequent reactions without analysis.

Step 6: tert-butyl (trans-3-hydroxy-3-methyl-1-(4-(5-(2-(trans-4-(N-methylacetamido)cyclohexyl)acetamido)-3-phenylpyridin-2-yl)phenyl)cyclobutyl)carbamate: A mixture of Intermediate 1 (50 mg, 0.112 mmol), the product from Step 5 above (47.9 mg), DIPEA (58.8 µl, 0.337 mmol) and HATU (85 mg, 0.224 mmol) in THF (2 ml) was stirred at RT overnight. The reaction heated at 40° C. for 6 h and then cooled and stirred at RT overnight. The reaction was partitioned between saturated NaHCO$_3$(aq) (10 ml) and EtOAc (15 ml). The phases were separated and the aqueous phase extracted with EtOAc (15 ml). The combined organic phases were dried over MgSO$_4$, filtered and concentrated in vacuo. Residue was purified by column chromatography (4 g cartridge, 0-10% MeOH/DCM) to afford the title compound (64 mg, 0.097 mmol, 97% purity) as a white solid. LCMS (Method 1): 293 (M+2H—C$_4$H$_8$)$^{2+}$, 321 (M+2H)$^{2+}$ at 1.99 min.

Step 7: N-(6-(4-(trans-1-amino-3-hydroxy-3-methylcyclobutyl)phenyl)-5-phenylpyridin-3-yl)-2-(trans-4-(N-methylacetamido)cyclohexyl)acetamide: The product from Step 6 above (64 mg, 0.097 mmol, 97% purity) was treated with 90% (v/v) TFA in water (2 ml) was stirred at RT for 1.5 h. The reaction mixture was diluted with MeOH and loaded onto a column of SCX. The column was washed with MeOH and the product was eluted with a 0.7 M solution of ammonia in MeOH. The solvent was removed in vacuo to afford the title compound (29 mg, 0.053 mmol, 98% purity) as a white solid. LCMS (Method 2): m/z 541 (M+H)$^+$ at 1.65 min. $^1$H NMR (400 MHz, 363 K, DMSO-d$_6$) δ 9.93 (s, 1H), 8.81 (d, J=2.4 Hz, 1H), 8.05 (d, J=2.4 Hz, 1H), 7.39-7.17 (m, 9H), 4.42 (s, 1H), 2.85-2.67 (m, 4H), 2.49-2.41 (m, 2H), 2.33-2.26 (m, 2H), 2.26-2.17 (m, 2H), 2.00 (s, 3H), 1.91-1.74 (m, 3H), 1.72-1.48 (s, 4H), 1.51 (s, 3H), 1.28-1.11 (m, 2H).

Example 2

2-(trans-4-acetamidocyclohexyl)-N-(6-(4-(trans-1-amino-3-hydroxy-3-methylcyclobutyl)phenyl)-5-phenylpyridin-3-yl)acetamide

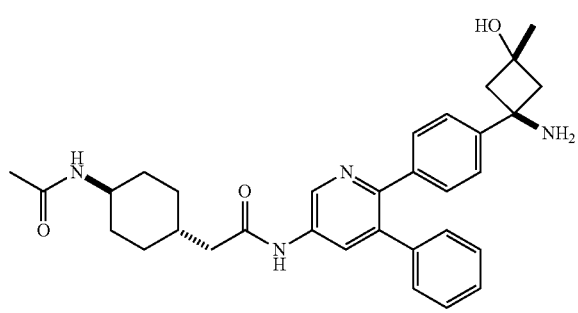

Step 1: ethyl 2-(trans-4-acetamidocyclohexyl)acetate: The title compound (1.18 g) was isolated as a flocculent white solid from the reaction of ethyl 2-(trans-4-aminocyclohexyl)acetate hydrochloride (1 g, 4.51 mmol), acetic anhydride (0.469 ml, 4.96 mmol) and DIPEA (1.73 ml, 9.92 mmol) in THF (10 ml) using essentially the same procedure as in Example 1 Step 4, except the reaction mixture was stirred at RT for 18 h. This material was used in subsequent reactions without purification.

Step 2: 2-(trans-4-acetamidocyclohexyl)acetic acid: The product from Step 1 above (1.18 g) was dissolved in THF (10 ml) and MeOH (1 ml) and treated with 2 M LiOH(aq) (3.11 ml, 6.23 mmol). The resultant mixture was stirred at RT for 18 h. The reaction mixture was concentrated in vacuo and the residue diluted with water (2 ml) and acidified with 1 M HCl(aq). The resultant white precipitate was collected by filtration, washing with water. The aqueous phase was extracted with EtOAc (2×20 ml) and the combined extracts dried over MgSO$_4$, filtered, combined with the previously isolated solid and concentrated in vacuo to afford the title compound (767 mg, 3.48 mmol, 95% purity) as a flocculent white solid. $^1$H NMR (400 MHz, DMSO-d$_6$) δ 7.69 (d, J=7.8 Hz, 1H), 3.54-3.32 (m, 1H, obscured by H$_2$O), 2.09 (d, J=7.0 Hz, 2H), 1.80-1.66 (m, 4H), 1.76 (s, 3H), 1.58 (ttt, J=10.4, 6.8, 3.4 Hz, 1H), 1.22-1.06 (m, 2H), 1.06-0.92 (m, 2H).

Step 3: tert-butyl (trans-1-(4-(5-(2-(trans-4-acetamidocyclohexyl)acetamido)-3-phenylpyridin-2-yl)phenyl)-3-hydroxy-3-methylcyclobutyl)carbamate: A stirred solution of the product from Step 2 above (47 mg, 0.224 mmol, 95% purity), Intermediate 1 (70 mg, 0.157 mmol) and HATU (119 mg, 0.314 mmol) in DMF was treated with DIPEA (138 µl, 0.786 mmol) and the resultant mixture was heated at 50° C. overnight. Additional HATU (59.7 mg, 0.157 mmol) and DIPEA (54.9 µl, 0.314 mmol) were added and heating was continued for a further 24 h. The reaction mixture was poured into EtOAc (100 ml) and washed sequentially with saturated NaHCO$_3$(aq) (50 ml), water (3×50 ml) and brine (50 ml). The organic phase was dried over MgSO$_4$, filtered and concentrated in vacuo. The residue was purified by column chromatography (12 g cartridge, 0-15% MeOH/DCM) to afford the title compound (43 mg, 0.065 mmol, 95% purity) as a brown solid. LCMS (Method 1): m/z 627 (M+H)$^+$ at 1.82 min. $^1$H NMR (400 MHz, DMSO-d$_6$) δ 10.25 (s, 1H), 8.79 (d, J=2.4 Hz, 1H), 8.12 (d, J=2.4 Hz, 1H), 7.69 (d, J=7.9 Hz, 1H), 7.46 (s, 1H), 7.43-7.15 (m, 9H), 4.96 (s, 1H), 3.53-3.41 (m, 1H), 2.39-2.22 (m, 6H), 1.84-1.67 (m, 8H), 1.39-1.27 (m, 12H), 1.24-0.99 (m, 4H).

Step 4: 2-(trans-4-acetamidocyclohexyl)-N-(6-(4-(trans-1-amino-3-hydroxy-3-methylcyclobutyl)phenyl)-5-phenylpyridin-3-yl)acetamide: TFA (1 ml) was added to a stirred solution of the product from Step 3 above (43 mg, 0.065 mmol, 95% purity) in DCM (2 ml). The resultant mixture was stirred at RT for 2 h. The mixture was diluted with toluene (10 ml) and then concentrated in vacuo. The residue was purified by preparative HPLC (Varian PrepStar, Waters X-Bridge BEH C18, 10-40% MeCN in 10 mM ammonium bicarbonate(aq)) to afford the title compound (6 mg, 0.011 mmol, 99% purity) as a white solid. LCMS (Method 1): m/z 527 (M+H)$^+$; 526 (M–H)$^-$ at 1.12 min. $^1$H NMR (400 MHz, DMSO-d$_6$) δ 10.25 (s, 1H), 8.79 (d, J=2.4 Hz, 1H), 8.11 (d, J=2.4 Hz, 1H), 7.69 (d, J=7.8 Hz, 1H), 7.43-7.14 (m, 9H), 4.76 (s, 1H), 3.55-3.41 (m, 1H), 2.34-2.30 (m, 2H), 2.26 (d, J=6.7 Hz, 2H), 2.17-2.10 (m, 2H), 1.83-1.67 (m, 8H), 1.50 (s, 3H), 1.22-0.99 (m, 4H).

Example 3

N-(6-(4-(2-aminopropan-2-yl)phenyl)-5-phenylpyridin-3-yl)-2-(trans-4-(N-methylacetamido)cyclohexyl)acetamide

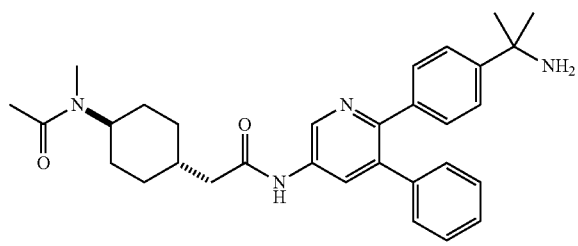

Step 1: tert-butyl (2-(4-(5-(2-(trans-4-(N-methylacetamido)cyclohexyl)acetamido)-3-phenylpyridin-2-yl)phenyl)propan-2-yl)carbamate: The title compound (37.7 mg, 0.059 mmol, 94% purity) was isolated as a beige solid from the reaction of Intermediate 2 (40 mg, 0.099 mmol), the product from Example 1 Step 5 (42.3 mg), DIPEA (51.9 μl, 0.297 mmol) and HATU (83 mg, 0.218 mmol) in a mixture of THF (2 ml) and DMF (500 μL) using essentially the same procedure as in Example 1 Step 6, except the reaction mixture was heated at 50° C. overnight and then worked up. LCMS (Method 1): m/z 272 (M+2H—$C_4H_8$)$^{2+}$, 300 (M+2H)$^{2+}$ at 2.29 min.

Step 2: N-(6-(4-(2-aminopropan-2-yl)phenyl)-5-phenylpyridin-3-yl)-2-(trans-4-(N-methylacetamido)cyclohexyl)acetamide: The title compound (21.8 mg, 0.042 mmol, 97% purity) was isolated as a yellow solid from the reaction of the product from Step 1 above (37.7 mg, 0.059 mmol, 94% purity) with 90% (v/v) TFA in water (2 ml) using essentially the same procedure as in Example 1 Step 7. LCMS (Method 2): m/z 242 (M+2H—$NH_3$)$^{2+}$, 250 (M+2H)$^{2+}$, 499 (M+H)$^+$ at 1.80 min. $^1$H NMR (400 MHz, 363 K, DMSO-$d_6$) δ 9.92 (s, 1H), 8.81 (d, J=2.4 Hz, 1H), 8.05 (d, J=2.4 Hz, 1H), 7.47-7.10 (m, 9H), 2.77 (s, 3H), 2.30 (d, J=6.8 Hz, 2H), 2.07-1.72 (m, 7H), 1.58 (s, 4H), 1.37 (s, 6H), 1.29-1.09 (m, 2H).

Example 4

N-(trans-4-(2-(((6-(4-(2-aminopropan-2-yl)phenyl)-5-phenylpyridin-3-yl)amino)-2-oxoethyl)cyclohexyl)-N-methylisobutyramide

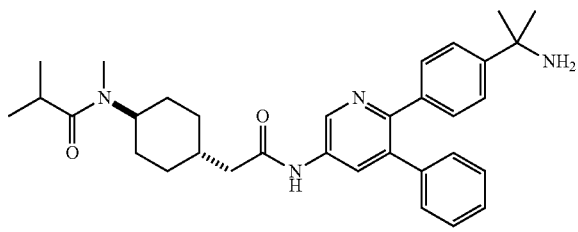

Step 1: 2-(trans-4-(((benzyloxy)carbonyl)(methyl)amino)cyclohexyl)acetic acid: LiOH (77 mg, 3.22 mmol) was added to a stirred solution of the product from Example 1 Step 2 (536 mg, 1.61 mmol) in THF (6 ml), MeOH (0.5 ml, 12.4 mmol) and water (1 ml). The resultant mixture was stirred at RT overnight. The solution was acidified with 1 M HCl(aq) and extracted with EtOAc (3×10 ml). The combined organic extracts were dried over MgSO$_4$, filtered and concentrated in vacuo to afford the title compound (504 mg, 1.568 mmol, 98% purity) as a white solid. $^1$H NMR (400 MHz, Chloroform-d) δ 7.39-7.28 (m, 5H), 5.14 (s, 2H), 3.99 (br s, 1H), 2.80 (s, 3H), 2.25 (d, J=7.0 Hz, 2H), 1.92-1.83 (m, 2H), 1.77-1.66 (m, 3H), 1.57-1.42 (m, 2H), 1.24-1.06 (m, 2H).

Step 2: Benzyl (trans-4-(2-((6-(4-(2-((tert-butoxycarbonyl)amino)propan-2-yl)phenyl)-5-phenylpyridin-3-yl)amino)-2-oxoethyl)cyclohexyl)(methyl)carbamate: A solution of Intermediate 2 (291 mg, 0.720 mmol), the product from Step 1 above (200 mg, 0.622 mmol, 98% purity) and Et$_3$N (548 μl, 3.93 mmol) in EtOAc (3 ml) and THF (0.5 ml) was treated with T3P (1.16 ml, 1.97 mmol, 50% w/w in EtOAc) and the resultant mixture heated at 50° C. overnight. The reaction mixture was quenched with saturated NaHCO$_3$ (aq) (10 ml) and extracted with EtOAc (2×15 ml). The combined organic extracts were dried over MgSO$_4$, filtered and concentrated in vacuo. The residue was purified by column chromatography (12 g cartridge, 0-5% MeOH/DCM) to afford the title compound (226 mg, 0.311 mmol, 95% purity) as a beige solid. LCMS (Method 1): m/z 691 (M+H)$^+$ at 2.80 min.

Step 3: tert-butyl (2-(4-(5-(2-(trans-4-(methylamino)cyclohexyl)acetamido)-3-phenylpyridin-2-yl)phenyl)propan-2-yl)carbamate: A solution of the product from Step 2 above (225 mg, 0.310 mmol 95% purity) in MeOH was hydrogenated in a ThalesNano H-Cube® flow reactor (10% Pd/C, 30×4 mm cartridge, full hydrogen mode, 50° C., 1 ml/min flow rate). The solvent was removed in vacuo to afford the title compound (162 mg, 0.289 mmol, 99% purity) as a white solid. LCMS (Method 1): m/z 279 (M+2H)$^{2+}$, 557 (M+H)$^+$, at 1.69 min.

Step 4: tert-butyl (2-(4-(5-(2-(trans-4-(N-methylisobutyramido)cyclohexyl)acetamido)-3-phenylpyridin-2-yl)phenyl)propan-2-yl)carbamate: Isobutyric anhydride (16.7 μl, 0.101 mmol) was added to a stirred solution of the product from Step 3 above (28 mg, 0.050 mmol) and DIPEA (26.4 μl, 0.151 mmol) in THF (2 ml). The resultant mixture was heated at 50° C. for 3 days. The mixture was partitioned between saturated NaHCO$_3$(aq) (10 ml) and EtOAc (15 ml). The phases were separated and the aqueous phase extracted with EtOAc (15 ml). The combined organic phases were dried over MgSO$_4$, filtered and concentrated in vacuo. The residue was purified by column chromatography (4 g cartridge, 0-10% MeOH) to afford the title compound (17.1 mg, 0.026 mmol, 97% purity) as a white solid. LCMS (Method 1): m/z 314 (M+2H)$^{2+}$, 627 (M+H)$^+$ at 2.40 min.

Step 5: N-(trans-4-(2-(((6-(4-(2-aminopropan-2-yl)phenyl)-5-phenylpyridin-3-yl)amino)-2-oxoethyl)cyclohexyl)-N-methylisobutyramide: The title compound (12 mg, 0.021 mmol, 96% purity) was isolated as a white solid from the reaction of the product from Step 4 above (15 mg, 0.023 mmol, 97% purity) and 90% (v/v) TFA in water (2 ml) using essentially the same procedure as in Example 1 Step 7, except the reaction mixture was stirred overnight. LCMS (Method 1): m/z 255.5 (M+2H—$NH_3$)$^{2+}$, 264 (M+2H)$^{2+}$, 510 (M+2H—$NH_3$)$^{2+}$, 527 (M+H)$^+$ at 1.50 min. $^1$H NMR (400 MHz, DMSO-$d_6$) δ 9.92 (s, 1H), 8.81 (d, J=2.4 Hz, 1H), 8.05 (d, J=2.4 Hz, 1H), 7.41-7.28 (m, 5H), 7.28-7.16 (m, 4H), 2.90-2.75 (m, 4H), 2.46-2.26 (m, 5H), 1.94-1.72 (m, 3H), 1.71-1.49 (m, 4H), 1.38 (s, 6H), 1.30-1.11 (m, 2H), 1.02 (d, J=6.7 Hz, 6H).

Example 5

2-(trans-4-acetamidocyclohexyl)-N-(6-(4-(1-amino-3,3-difluorocyclobutyl)phenyl)-5-phenylpyridin-3-yl)acetamide

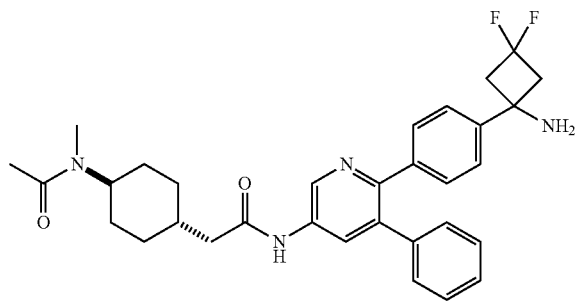

Step 1: tert-butyl (1-(4-(5-(2-(trans-4-acetamidocyclohexyl)acetamido)-3-phenylpyridin-2-yl)phenyl)-3,3-difluorocyclobutyl)carbamate: A stirred solution of the product from Example 1 Step 5 (26.5 mg) and HATU (101 mg, 0.266 mmol) in DMF (5 ml) was treated with DIPEA (0.077 µl, 0.465 mmol). The resultant mixture was stirred at RT for 30 min and then Intermediate 3 (30 mg, 0.066 mmol) was added. The resultant mixture was heated at 50° C. overnight. The reaction mixture was diluted with saturated NaHCO₃ (aq) (100 ml), and extracted with EtOAc (3×50 ml). The combined organic extracts were washed sequentially with water (3×50 ml) and brine (50 ml), dried over MgSO₄, filtered and concentrated in vacuo. The residue was purified by column chromatography (40 g cartridge, 0-15% MeOH/DCM) to afford the title compound (32 mg, 0.046 mmol, 90% purity) as a brown solid. $^1$H NMR (400 MHz, DMSO-$d_6$) (two rotamers in a 5:4 ratio) δ 10.27 (s, 1H), 8.80 (d, J=2.4 Hz, 1H), 8.12 (dd, J=2.3, 0.9 Hz, 1H), 7.91 (s, 1H), 7.41-7.13 (m, 9H), 4.31-4.16 (m, 1H, major), 3.60-3.50 (m, 1H, minor), 3.15-2.90 (m, 4H), 2.79 (s, 3H, major), 2.67 (s, 3H, minor), 2.31-2.25 (m, 2H), 2.02 (s, 3H, minor), 1.97 (s, 3H, major), 1.66-1.73 (m, 3H), 1.72-0.97 (m, 15H).

Step 2: 2-(trans-4-acetamidocyclohexyl)-N-(6-(4-(1-amino-3,3-difluorocyclobutyl)phenyl)-5-phenylpyridin-3-yl)acetamide: The title compound (7 mg, 0.013 mmol, 99% purity) was isolated as a white solid from the reaction of the product from Step 1 above (32 mg, 0.046 mmol, 90% purity) with TFA (0.5 ml) in DCM (2 ml) using essentially the same procedure as in Example 2 Step 4. LCMS (Method 1): m/z 533 (M+H)⁺ at 1.35 min. $^1$H NMR (400 MHz, DMSO-$d_6$, 363 K) δ 9.94 (s, 1H), 8.83 (s, 1H), 8.07 (d, J=2.4 Hz, 1H), 7.40-7.17 (m, 9H), 3.01 (m, 1H) (under water peak), 2.87-2.62 (m, 5H), 2.34-2.44 (m, 1H), 2.30 (d, J=6.7 Hz, 3H), 2.10 (s, 3H), 2.00 (s, 3H), 1.93-1.75 (m, 3H), 1.70-1.49 (m, 3H), 1.30-1.07 (m, 2H).

Example 6

N-(6-(4-(2-aminopropan-2-yl)phenyl)-5-(thiophen-3-yl)pyridin-3-yl)-2-(trans-4-(N-methylacetamido)cyclohexyl)acetamide

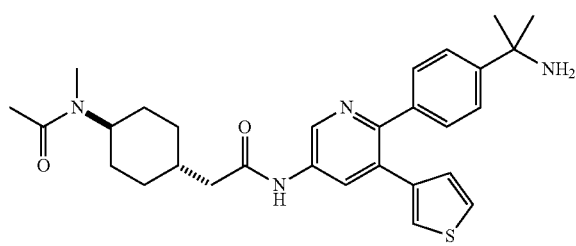

A mixture of Intermediate 4 (50 mg, 91.5 µmol, 75% purity), the product from Example 1 Step 5 (31.2 mg) and Et₃N (0.102 ml, 0.733 mmol) in EtOAc (1.5 ml) was treated with T3P (0.216 ml, 0.366 mmol, 50% w/w in EtOAc) and the resultant mixture stirred at RT overnight. The reaction mixture was quenched with saturated NaHCO₃(aq) (50 ml) and extracted with EtOAc (2×50 ml). The combined organic extracts were dried over MgSO₄, filtered and concentrated in vacuo. The residue was suspended in DCM (2 ml) and then TFA (1 ml, 12.98 mmol) was added and the resultant mixture was stirred at RT for 1 h, then concentrated in vacuo. To remove residual TFA, the residue was thrice resuspended in toluene (20 ml) and concentrated in vacuo. The residue was then purified by preparative HPLC (Gilson 215, Waters X-Bridge Prep-C18, 5 µm, 19×50 mm column, 20-80% MeCN in 10 mM ammonium bicarbonate(aq)) to afford the title compound (25 mg, 0.050 mmol, 99% purity) as a white solid. LCMS (Method 1): m/z 505 (M+H)⁺, 503 (M-H)⁻ at 1.32 min. $^1$H NMR (400 MHz, DMSO-$d_6$) (two rotamers in a 4:3 ratio) δ 10.24 (s, 1H), 8.76 (d, J=2.4 Hz, 1H), 8.13 (dd, J=2.5, 1.0 Hz, 1H), 7.57-7.36 (m, 4H), 7.31-7.14 (m, 2H), 6.74 (dd, J=5.0, 1.3 Hz, 1H), 4.30-4.17 (m, 1H, major), 3.60-3.48 (m, 1H, minor), 2.79 (s, 3H, major), 2.66 (s, 3H, minor), 2.30-2.21 (m, 2H), 2.01 (s, 3H, minor), 1.96 (s, 3H, major), 1.90-1.70 (m, 5H), 1.69-1.40 (m, 4H), 1.34 (s, 6H), 1.27-1.02 (m, 2H).

Example 7

N-(6-(4-((S)-1-aminoethyl)phenyl)-5-phenylpyridin-3-yl)-2-(trans-4-(N-methylacetamido)cyclohexyl)acetamide

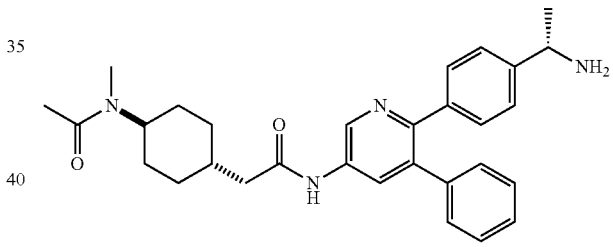

Step 1: tert-butyl ((S)-1-(4-(5-(2-(trans-4-(N-methylacetamido)cyclohexyl)acetamido)-3-phenylpyridin-2-yl)phenyl)ethyl)carbamate: The title compound (69 mg, 0.114 mmol, 97% purity) was isolated as a white solid from the reaction of Intermediate 5 (50 mg, 0.119 mmol, 93% purity), the product from Example 1 Step 5 (55 mg), DIPEA (67.3 µl, 0.385 mmol) and HATU (98 mg, 0.257 mmol) in THF (2 ml) using essentially the same procedure as in Example 1 Step 6, except the reaction mixture was heated at 50° C. overnight and then worked up. LCMS (Method 1): m/z 293 (M+2H)²⁺ at 2.20 min.

Step 2: N-(6-(4-((S)-1-aminoethyl)phenyl)-5-phenylpyridin-3-yl)-2-(trans-4-(N-methylacetamido)cyclohexyl)acetamide: The title compound (12 mg, 0.024 mmol, 98% purity) was isolated as a white solid from the reaction of the product from Step 1 above (68 mg, 0.114 mmol, 97% purity) and 90% (v/v) TFA in water (2 ml) using essentially the same procedure as in Example 1 Step 7, except the reaction mixture was allowed to stand at RT for 3 h. After work-up, the product was purified by preparative HPLC (Waters FractionLynx, Waters X-Bridge Prep-C18, 5 µm, 19×50 mm column, 20-50% MeCN in 10 mM ammonium bicarbonate (aq)). LCMS (Method 2): m/z 234.5 (M+2H—NH₃)²⁺, 243 (M+2H)²⁺, 485 (M+H)⁺; 483 (M-H)⁻ at 1.67 min. $^1$H NMR (400 MHz, DMSO-$d_6$, 363 K) δ 9.93 (s, 1H), 8.81 (d, J=2.4 Hz, 1H), 8.05 (d, J=2.4 Hz, 1H), 7.40-7.27 (m, 4H), 7.27-

7.13 (m, 8H), 3.97 (q, J=6.6 Hz, 1H), 2.77 (br s, 3H), 2.30 (d, J=6.8 Hz, 2H), 2.00 (br s, 3H), 1.94-1.46 (m, 6H), 1.27-1.17 (m, 4H).

Example 8

N-(6-(4-((R)-1-aminoethyl)phenyl)-5-phenylpyridin-3-yl)-2-(trans-4-(N-methylacetamido)cyclohexyl)acetamide

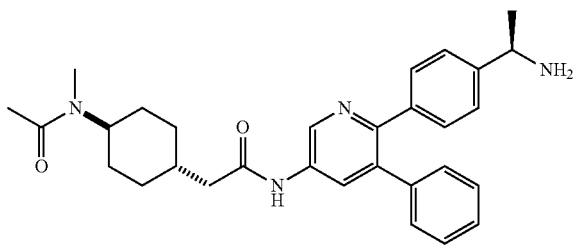

Step 1: tert-butyl ((R)-1-(4-(5-(2-(trans-4-(N-methylacetamido)cyclohexyl)acetamido)-3-phenylpyridin-2-yl)phenyl)ethyl)carbamate: The title compound (66 mg, 0.111 mmol, 98% purity) was isolated as a white solid from the reaction of Intermediate 6 (50 mg, 0.115 mmol, 92% purity), the product from Example 1 Step 5 (55 mg), DIPEA (67.3 µl, 0.385 mmol) and HATU (98 mg, 0.257 mmol) in THF (2 ml) using essentially the same procedure as in Example 1 Step 6, except the reaction mixture was stirred at RT overnight and then heated at 40° C. for a further 24 h. LCMS (Method 1): m/z 293 (M+2H)$^{2+}$ at 2.24 min.

Step 2: N-(6-(4-((R)-1-aminoethyl)phenyl)-5-phenylpyridin-3-yl)-2-(trans-4-(N-methylacetamido)cyclohexyl)acetamide: The title compound (47 mg, 0.095 mmol, 98% purity) was isolated as a white solid from the reaction of the product from Step 1 above (58 mg, 0.098 mmol, 98% purity) and 90% (v/v) TFA in water (2 ml) using essentially the same procedure as in Example 1 Step 7, except the reaction mixture was allowed to stand for 2 h. LCMS (Method 2): m/z 234 (M+2H—NH$_2$)$^{2+}$, 243 (M+2H)$^{2+}$, 485 (M+H)$^+$ at 1.70 min. $^1$H NMR (400 MHz, DMSO-d$_6$) δ 9.92 (s, 1H), 8.81 (d, J=2.5 Hz, 1H), 8.05 (d, J=2.4 Hz, 1H), 7.39-7.27 (m, 3H), 7.27-7.13 (m, 6H), 3.98 (q, J=6.6 Hz, 1H), 2.77 (br s, 3H), 2.30 (d, J=6.8 Hz, 2H), 2.00 (s, 3H), 1.92-1.72 (m, 4H), 1.72-1.43 (m, 4H), 1.26 (d, J=6.6 Hz, 3H), 1.23-1.10 (m, 2H).

Example 9

N-(6-(4-(2-aminopropan-2-yl)phenyl)-5-(2-fluorophenyl)pyridin-3-yl)-2-(trans-4-(N-methylacetamido)cyclohexyl)acetamide

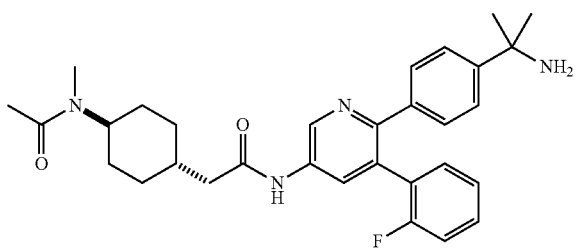

Step 1: tert-butyl (2-(4-(3-(2-fluorophenyl)-5-(2-(trans-4-(N-methylacetamido)cyclohexyl)acetamido)pyridin-2-yl)phenyl)propan-2-yl)carbamate: A solution of Intermediate 7 (27.8 mg, 0.130 mmol) and HATU (58.6 mg, 0.154 mmol) in DMF (1 ml) was treated with DIPEA (41.4 µl, 0.237 mmol) and the resultant mixture stirred for 30 mins whereupon the product from Example 1 Step 5 (50 mg) was added and the reaction mixture was stirred at RT for 16 h. The mixture was diluted with EtOAc (20 ml) and washed sequentially with saturated NaHCO$_3$(aq) (15 ml), water (15 ml) and brine (15 ml). The organic phase was dried over MgSO$_4$, filtered and concentrated in vacuo. The residue was purified by preparative HPLC (Gilson 215, Waters X-Bridge Prep-C18, 5 µm, 19×50 mm column, 40-70% MeCN in 10 mM ammonium bicarbonate(aq)) to afford the title compound (54 mg) as a white solid. This material was used in subsequent reactions without analysis.

Step 2: N-(6-(4-(2-aminopropan-2-yl)phenyl)-5-(2-fluorophenyl)pyridin-3-yl)-2-(trans-4-(N-methylacetamido)cyclohexyl)acetamide: The product from Step 1 above (54 mg) was dissolved in DCM (1 ml) and treated with TFA (0.5 ml). The resultant mixture was stirred at RT overnight. The reaction mixture was loaded onto a column of SCX. The column was washed with MeOH and the product was eluted with a 0.7 M solution of ammonia in MeOH. The solvent was removed in vacuo to afford the title compound (44 mg, 0.081 mmol, 95% purity) as a white solid. LCMS (Method 1): m/z 517 (M+H)$^+$, 515 (M−H)$^−$, at 1.34 min. $^1$H NMR (400 MHz, DMSO-d$_6$) (two rotamers in a 5:4 ratio) δ 10.32 (s, 1H), 8.83 (d, J=2.4 Hz, 1H), 8.11 (d, J=2.4 Hz, 1H), 7.47-7.12 (m, 9H), 4.28-4.20 (m, 1H, major), 3.65-3.49 (m, 1H, minor), 2.79 (s, 3H, minor), 2.67 (s, 3H, major), 2.37-2.24 (m, 2H), 2.02 (s, 3H, minor), 1.96 (s, 3H, major), 1.91-1.69 (m, 3H), 1.69-1.42 (m, 4H), 1.34 (s, 6H), 1.28-1.02 (m, 2H).

Example 10

N-(6-(4-(1-aminocyclobutyl)phenyl)-5-phenylpyridin-3-yl)-2-(trans-4-(N-methylacetamido)cyclohexyl)acetamide

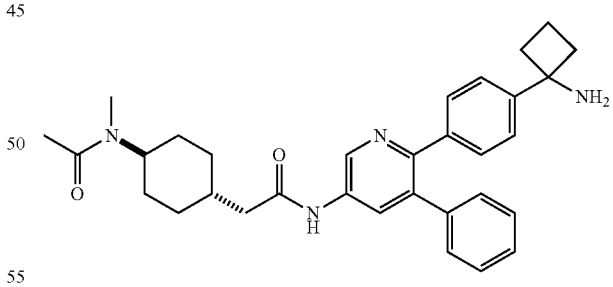

Step 1: Benzyl (trans-4-(2-((6-(4-(1-((tert-butoxycarbonyl)amino)cyclobutyl)phenyl)-5-phenylpyridin-3-yl)amino)-2-oxoethyl)cyclohexyl)(methyl)carbamate: The title compound (355 mg, 0.495 mmol, 98% purity) was isolated as a beige solid from the reaction of Intermediate 8 (277 mg, 0.668 mmol), the product from Example 4 Step 1 (203.9 mg, 0.668 mmol), Et$_3$N (558 µl, 4.01 mmol) and T3P (1.18 ml, 2.00 mmol, 50% w/w in EtOAc) in EtOAc (3 ml) and THF (0.5 ml) using essentially the same procedure as in Example 4 Step 2, except the reaction mixture was stirred at RT. HPLC (Method 1): R$_T$ 3.72 min.

Step 2: tert-Butyl (1-(4-(5-(2-(trans-4-(methylamino)cyclohexyl)acetamido)-3-phenylpyridin-2-yl)phenyl)cyclobutyl)carbamate: The title compound (228 mg, 0.389 mmol, 97% purity) was isolated from the hydrogenation of the product of Step 1 above (353 mg, 0.492 mmol, 98% purity) using essentially the same procedure as in Example 4 Step 3. LCMS (Method 1): m/z 285 (M+2H)$^{2+}$, 569 (M+H)$^{+}$, at 1.75 min.

Step 3: tert-Butyl (1-(4-(5-(2-(trans-4-(N-methylacetamido)cyclohexyl)acetamido)-3-phenylpyridin-2-yl)phenyl)cyclobutyl)carbamate: The title compound (5 mg, 8.19 μmol) was isolated as a white solid from the reaction of acetic anhydride (13.3 μl, 0.141 mmol), the product from Step 2 above (40 mg, 0.068 mmol, 97% purity) and DIPEA (36.8 μl, 0.211 mmol) in THF (2 ml) using essentially the same procedure as in Example 4 Step 4. LCMS (Method 1): m/z 306 (M+2H)$^{2+}$, 611 (M+H)$^{+}$ at 2.26 min.

Step 4: N-(6-(4-(1-aminocyclobutyl)phenyl)-5-phenylpyridin-3-yl)-2-(trans-4-(N-methylacetamido)cyclohexyl)acetamide: The title compound (4 mg, 7.22 μmol, 97% purity) was isolated as a white solid from the reaction of the product from Step 3 above (5 mg, 8.19 μmol) and 90% (v/v) TFA in water (2 ml) using essentially the same procedure as in Example 1 Step 7, except the reaction mixture was stirred for 3 h. LCMS (Method 1): m/z 511 (M+H)$^{+}$, at 1.39 min. $^1$H NMR (400 MHz, 363 K, DMSO-d$_6$) (two rotamers in a 5:4 ratio) δ 9.94 (s, 1H), 8.82 (d, J=2.4 Hz, 1H), 8.06 (d, J=2.4 Hz, 1H), 7.39-7.23 (m, 7H), 7.23-7.17 (m, 2H), 4.20 (br s, 1H, minor), 3.60 (br s, 1H, major), 2.77 (br s, 3H), 2.47-2.38 (m, 2H), 2.30 (d, J=6.8 Hz, 2H), 2.19-2.09 (m, 2H), 2.08-1.94 (m, 4H), 1.92-1.74 (m, 3H), 1.74-1.44 (m, 5H), 1.33-1.08 (m, 2H).

Example 11

N-(6-(4-((S)-1-amino-2,2-difluoroethyl)phenyl)-5-phenylpyridin-3-yl)-2-(trans-4-(N-methylacetamido)cyclohexyl)acetamide

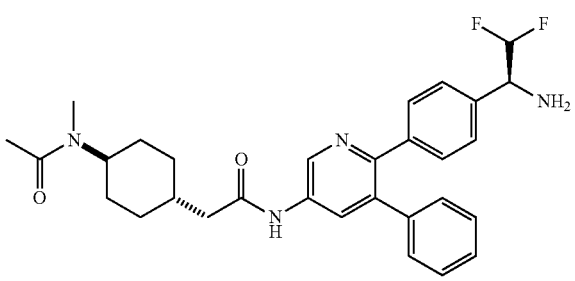 [SMILES: CC(=O)N(C)[C@H]1CC[C@H](CC(=O)Nc2cnc(-c3ccc([C@H](N)C(F)F)cc3)c(-c3ccccc3)c2)CC1]

Step 1: tert-butyl ((S)-2,2-difluoro-1-(4-(5-(2-(trans-4-(N-methylacetamido)cyclohexyl)acetamido)-3-phenylpyridin-2-yl)phenyl)ethyl)carbamate: The title compound (69 mg, 0.109 mmol, 98% purity) was isolated as a white solid from the reaction of Intermediate 9 (51 mg, 0.120 mmol), the product from Example 1 Step 5 (40.9 mg), DIPEA (62.8 μl, 0.360 mmol) and HATU (91 mg, 0.240 mmol) in THF (2 ml) using essentially the same procedure as in Example 1 Step 6, except the reaction mixture was stirred at RT overnight and then worked up. LCMS (Method 1): m/z 311 (M+2H)$^{2+}$ at 2.32 min.

Step 2: N-(6-(4-((S)-1-amino-2, 2-difluoroethyl)phenyl)-5-phenylpyridin-3-yl)-2-(trans-4-(N-methylacetamido)cyclohexyl)acetamide: The product from Step 1 above (69 mg, 0.109 mmol, 98% purity) was treated with 90% (v/v) TFA in water (2 ml) and the resultant mixture allowed to stand at RT for 3 h. The solvent was concentrated in vacuo and the residue purified by preparative HPLC (Waters FractionLynx, Waters X-Bridge Prep-C18, 5 μm, 19×50 mm column, 30-60% MeCN in 10 mM ammonium bicarbonate) to afford the title compound (30 mg, 0.057 mmol, 99% purity) as a white solid. LCMS (Method 2): m/z 261 (M+2H)$^{2+}$, 521 (M+H)$^{+}$ at 2.01 min. $^1$H NMR (400 MHz, DMSO-d$_6$, 363 K) δ 9.94 (br s, 1H), 8.81 (d, J=2.4 Hz, 1H), 8.06 (d, J=2.4 Hz, 1H), 7.47-7.06 (m, 9H), 5.91 (td, J=56.6, 4.2 Hz, 1H), 4.12-4.01 (m, 1H), 2.89-2.62 (m, 2H), 2.29 (d, J=6.8 Hz, 2H), 2.09-1.72 (m, 8H), 1.70-1.46 (m, 4H), 1.26-1.12 (m, 2H).

Example 12

N-(6-(4-(1-aminocyclopropyl)phenyl)-5-phenylpyridin-3-yl)-2-(trans-4-(N-methylacetamido)cyclohexyl)acetamide

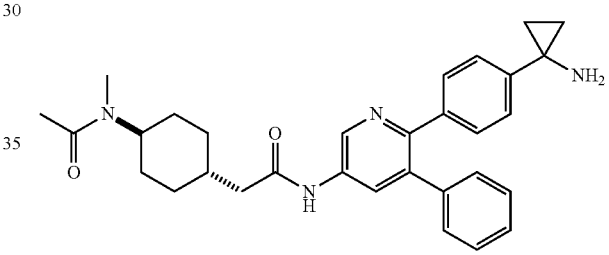

Step 1: tert-butyl (1-(4-(5-(2-(trans-4-(N-methylacetamido)cyclohexyl)acetamido)-3-phenylpyridin-2-yl)phenyl)cyclopropyl)carbamate: The title compound (72 mg, 0.113 mmol, 94% purity) was isolated as a white solid from the reaction of Intermediate 10 (50 mg, 0.125 mmol), the product from Example 1 Step 5 (53.1 mg), DIPEA (65.3 μl, 0.374 mmol) and HATU (95 mg, 0.249 mmol) in THF (2 ml) using essentially the same procedure as in Example 1 Step 6, except the reaction mixture was stirred at RT for 24 h and then heated at 40° C. overnight. LCMS (Method 1): m/z 299 (M+2H)$^{2+}$ at 2.19 min.

Step 2: N-(6-(4-(1-aminocyclopropyl)phenyl)-5-phenylpyridin-3-yl)-2-(trans-4-(N-methylacetamido)cyclohexyl)acetamide: The title compound (51 mg, 0.098 mmol, 95% purity) was isolated from the reaction of the product from Step 1 above (72 mg, 0.113 mmol, 94% purity) with 90% (v/v) TFA in water (2 ml) using essentially the same procedure as in Example 1 Step 7. LCMS (Method 2): m/z 249 (M+2H)$^{2+}$, 497 (M+H)$^{+}$ at 1.87 min. $^1$H NMR (400 MHz, DMSO-d$_6$, 363 K) δ 9.92 (s, 1H), 8.80 (d, J=2.4 Hz, 1H), 8.05 (d, J=2.4 Hz, 1H), 7.36-7.29 (m, 3H), 7.25-7.14 (m, 6H), 2.85-2.65 (m, 4H), 2.30 (d, J=6.8 Hz, 2H), 2.06-1.94 (m, 3H), 1.94-1.73 (m, 3H), 1.73-1.37 (m, 4H), 1.31-1.02 (m, 2H), 1.02-0.82 (m, 4H).

Example 13

2-(trans-4-acetamidocyclohexyl)-N-(6-(4-(trans-1-amino-3-hydroxycyclobutyl)phenyl)-5-phenylpyridin-3-yl)acetamide

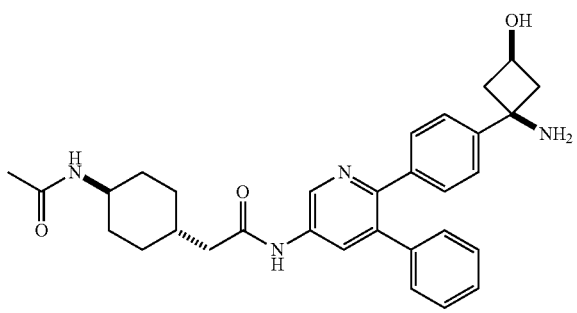 [SMILES: CC(=O)N[C@H]1CC[C@H](CC(=O)Nc2cnc(-c3ccc([C@]4(N)C[C@@H](O)C4)cc3)c(-c3ccccc3)c2)CC1]

A mixture of the product from Example 2 Step 2 (34.6 mg, 0.174 mmol), DIPEA (60.7 μl, 0.348 mmol) and HATU (66.1 mg, 0.174 mmol) in DMF (2 ml) was stirred at RT. After 30 mins the mixture treated with a solution of Intermediate 11 (50 mg, 0.116 mmol) in DMF (1 ml) and heated at 50° C. overnight. The mixture was cooled, diluted with water (5 ml) and the resultant solid filtered, washing with water (3×5 ml). The solid was dissolved in DCM (10 ml), filtered through a phase-sep cartridge and concentrated in vacuo. The residue was purified by column chromatography (4 g cartridge, 0-10% MeOH/(1% Et$_3$N in DCM)) and then dissolved in DCM (3 ml) and treated with TFA (0.5 ml). After 2.5 h the reaction mixture was loaded on to a column of SCX. The column was washed with MeOH and the product was eluted with a 0.7 M solution of ammonia in MeOH. The solvent was removed in vacuo to afford a yellow oil. The residue was purified by preparative HPLC (Waters FractionLynx, Waters X-Bridge Prep-C18, 5 μm, 19×50 mm column, 20-50% MeCN in 10 mM ammonium bicarbonate (aq)) to afford the title compound (4.2 mg, 8.03 μmol, 98% purity) as a white solid. LCMS (Method 1): m/z 513 (M+H)$^+$ at 1.16 min. $^1$H NMR (400 MHz, Methanol-d$_4$) δ 8.83 (d, J=2.4 Hz, 1H), 8.16 (d, J=2.4 Hz, 1H), 7.43-7.37 (m, 2H), 7.34-7.26 (m, 5H), 7.24-7.17 (m, 2H), 3.92 (p, J=7.1 Hz, 1H), 3.70-3.58 (m, 1H), 2.98-2.92 (m, 2H), 2.36 (d, J=6.7 Hz, 2H), 2.23-2.17 (m, 2H), 1.97-1.86 (m, 8H), 1.43-1.10 (m, 5H).

Example 14

2-(trans-4-acetamidocyclohexyl)-N-(6-(4-(3-aminooxetan-3-yl)phenyl)-5-phenylpyridin-3-yl)acetamide

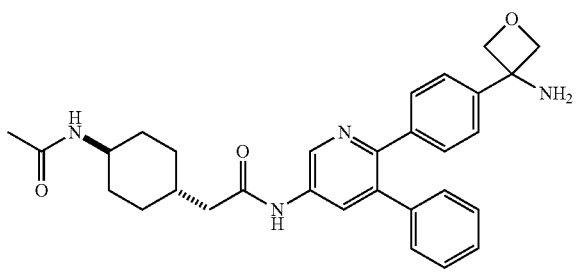 [SMILES: CC(=O)N[C@H]1CC[C@H](CC(=O)Nc2cnc(-c3ccc(C4(N)COC4)cc3)c(-c3ccccc3)c2)CC1]

Step 1: benzyl (3-(4-(5-(2-(trans-4-acetamidocyclohexyl)acetamido)-3-phenylpyridin-2-yl)phenyl)oxetan-3-yl)carbamate: The title compound (34 mg) was isolated as a brown solid from the reaction of Intermediate 12 (50 mg, 0.125 mmol, 89% purity), the product from Example 2 Step 2 (44.1 mg, 0.221 mmol), DIPEA (71.6 mg, 0.554 mmol) and HATU (84 mg, 0.221 mmol) in DMF (5 ml) using essentially the same procedure as in Example 5 Step 1. This material was used in subsequent reactions without analysis.

Step 2: 2-(trans-4-acetamidocyclohexyl)-N-(6-(4-(3-aminooxetan-3-yl)phenyl)-5-phenylpyridin-3-yl)acetamide: A solution of the product from Step 1 above (27 mg) in MeOH (5 ml) was hydrogenated in a ThalesNano H-Cube® flow reactor (10% Pd/C, 30×4 mm cartridge, full hydrogen mode, 50° C., 1 ml/min flow rate). The reaction mixture was concentrated in vacuo and the residue was purified by preparative HPLC (Gilson 215, Waters X-Bridge Prep-C18, 5 μm, 19×50 mm column, 30-70% MeCN in 10 mM aqueous ammonium formate) to afford the title compound (4 mg, 8.02 μmol) as a white solid. LCMS (Method 1): m/z 499 (M+H)+, 497 (M−H)$^−$, at 1.19 min. $^1$H NMR (400 MHz, DMSO-d$_6$) δ 10.27 (s, 1H), 8.81 (s, 1H), 8.13 (s, 1H), 7.68 (d, J=7.8 Hz, 1H), 7.49-7.14 (m, 9H), 4.69 (q, J=6.3 Hz, 4H), 3.53-3.41 (m, 1H), 2.27 (d, J=6.6 Hz, 2H), 1.84-1.65 (m, 8H), 1.30-0.93 (m, 4H).

Example 15

2-(trans-4-acetamidocyclohexyl)-N-(6-(4-(trans-1-amino-3-fluorocyclobutyl)phenyl)-5-phenylpyridin-3-yl)acetamide

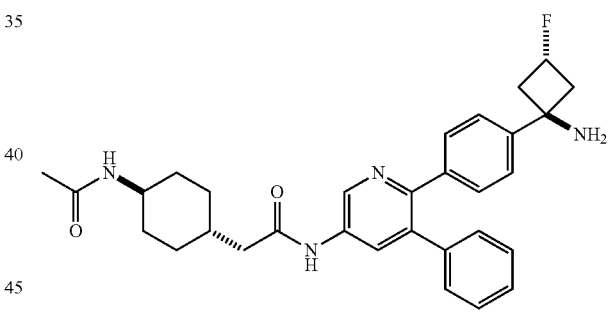

Step 1: tert-butyl (trans-1-(4-(5-(2-(trans-4-acetamidocyclohexyl)acetamido)-3-phenylpyridin-2-yl)phenyl)-3-fluorocyclobutyl)carbamate: The title compound (32 mg) was isolated as a white solid from the reaction of Intermediate 13 (30 mg, 0.062 mmol, 90% purity), the product from Example 2 Step 2 (27.6 mg, 0.138 mmol), DIPEA (80 μl, 0.484 mmol) and HATU (105 mg, 0.277 mmol) in DMF (5 ml) using essentially the same procedure as in Example 5 Step 1. This material was used in subsequent reactions without analysis.

Step 2: 2-(trans-4-acetamidocyclohexyl)-N-(6-(4-(trans-1-amino-3-fluorocyclobutyl)phenyl)-5-phenylpyridin-3-yl)acetamide: The title compound (6 mg, 0.012 mmol, 99% purity) was isolated as a white solid from the reaction of the product from Step 1 above (32 mg) with TFA (0.5 ml) in DCM (2 ml) using essentially the same procedure as in Example 2 Step 4. LCMS (Method 1): m/z 515 (M+H)$^+$ at 1.33 min. $^1$H NMR (400 MHz, DMSO-d$_6$) δ 10.25 (s, 1H), 8.79 (d, J=2.4 Hz, 1H), 8.11 (d, J=2.4 Hz, 1H), 7.69 (d, J=7.8 Hz, 1H), 7.37-7.28 (m, 3H), 7.26-7.17 (m, 6H), 5.33 (dp, J=56.8, 6.6 Hz, 1H), 3.50-3.40 (m, 1H), 2.42-2.29 (m, 2H), 2.25 (d, J=6.6 Hz, 2H), 2.11 (br s, 2H), 1.84-1.66 (m, 8H), 1.22-0.98 (m, 4H).

Example 16

N-(6-(4-(1-aminocyclobutyl)phenyl)-5-(2-fluorophenyl)pyridin-3-yl)-2-(trans-4-(N-methylacetamido)cyclohexyl)acetamide

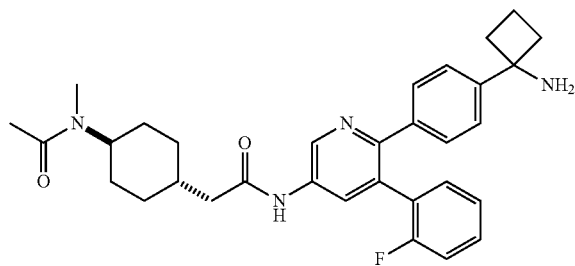 [SMILES: CC(=O)N(C)[C@H]1CC[C@H](CC(=O)Nc2cnc(-c3ccc(C4(N)CCC4)cc3)c(-c3ccccc3F)c2)CC1]

Step 1: tert-butyl (1-(4-(3-(2-fluorophenyl)-5-(2-(trans-4-(N-methylacetamido)cyclohexyl)acetamido)pyridin-2-yl)phenyl)cyclobutyl)carbamate: The title compound (25 mg) was isolated as a white solid from the reaction of Intermediate 14 (50 mg, 0.104 mmol, 90% purity), the product from Example 1 Step 5 (27.1 mg), HATU (57 mg, 0.150 mmol) and DIPEA (40.3 µl, 0.231 mmol) in DMF (1 ml) using essentially the same procedure as in Example 9 Step 1. LCMS (Method 1): m/z 629 (M+H)$^+$, 627 (M−H)$^−$ at 2.33 min.

Step 2: N-(6-(4-(1-aminocyclobutyl)phenyl)-5-(2-fluorophenyl)pyridin-3-yl)-2-(trans-4-(N-methylacetamido)cyclohexyl)acetamide: The title compound (20 mg, 0.036 mmol, 95% purity) was isolated as a white solid from the reaction of the product from Step 1 above (25 mg) with TFA (0.5 ml) in DCM (1 ml) using essentially the same procedure as in Example 9 Step 2. LCMS (Method 1): m/z 529 (M+H)$^+$, 527 (M−H)$^−$, at 1.41 min. $^1$H NMR (400 MHz, DMSO-d$_6$) (two rotamers in a 7:3 ratio) δ 10.32 (s, 1H), 8.84 (d, J=2.4 Hz, 1H), 8.12 (d, J=2.3 Hz, 1H), 7.46-7.28 (m, 4H), 7.28-7.12 (m, 4H), 4.33-4.11 (m, 1H, major), 3.65-3.47 (m, 1H, minor), 2.79 (s, 3H, major), 2.67 (s, 3H, minor), 2.44-2.21 (m, 4H), 2.16-1.91 (m, 5H), 1.85-1.71 (m, 4H), 1.70-1.41 (m, 5H), 1.28-1.04 (m, 2H).

Example 17

N-(6-(4-(1-aminocyclobutyl)phenyl)-5-(thiophen-3-yl)pyridin-3-yl)-2-(trans-4-(N-methylmethylsulfonamido)cyclohexyl)acetamide

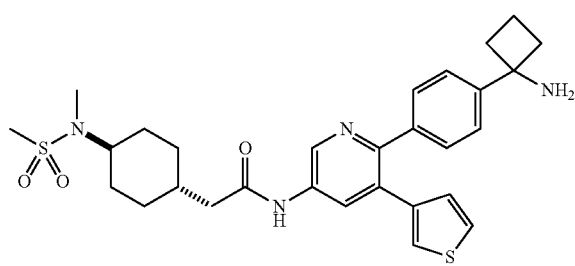 [SMILES: CN([C@H]1CC[C@H](CC(=O)Nc2cnc(-c3ccc(C4(N)CCC4)cc3)c(-c3ccsc3)c2)CC1)S(C)(=O)=O]

Step 1: ethyl 2-(trans-4-(methylsulfonamido)cyclohexyl)acetate: A solution of ethyl 2-(trans-4-aminocyclohexyl)acetate hydrochloride (2 g, 9.02 mmol) and DIPEA (6.30 ml, 36.1 mmol) in THF (30 ml) was cooled in an ice bath, treated with methanesulfonyl chloride (0.843 ml, 10.8 mmol) and the resultant mixture stirred at RT for 18 h. The reaction mixture was quenched with water (10 ml), acidified with 1 M HCl(aq) and extracted with DCM (50 ml), then filtered through a phase separation cartridge. The organic phase was stirred with 50% saturated NaHCO$_3$(aq) for 10 min, filtered through a phase separation cartridge and the organic phase was concentrated in vacuo to afford the title compound (2.5 g, 9.02 mmol, 95% purity) as a yellow oil. $^1$H NMR (400 MHz, Chloroform-d) δ 4.12 (q, J=7.1 Hz, 2H), 3.30-3.20 (m, 1H), 2.97 (s, 3H), 2.19 (d, J=6.9 Hz, 2H), 2.12-2.02 (m, 2H), 1.93-1.81 (m, 2H), 1.81-1.70 (m, 1H), 1.30 (qd, J=13.0, 3.5 Hz, 2H), 1.28 (t, J=7.1 Hz, 3H), 1.12 (qd, J=13.2, 3.3 Hz, 2H).

Step 2: ethyl 2-(trans-4-(N-methylmethylsulfonamido)cyclohexyl)acetate: A solution of the product from Step 1 above (2.5 g, 9.02 mmol, 95% purity) in THF (30 ml) was treated with sodium hydride (0.418 g, 10.4 mmol, 60% w/w in mineral oil) and stirred at RT for 15 min. The resultant mixture was treated with iodomethane (0.653 ml, 10.4 mmol) and stirred at RT for 18 h. The reaction mixture was quenched with water (10 ml) and acidified with 1 M HCl (aq), then extracted with DCM (50 ml) and filtered through a phase separation cartridge. The organic phase was concentrated in vacuo to afford the title compound (3.1 g) as an orange oil. This material was used in subsequent reactions without purification.

Step 3: 2-(trans-4-(N-methylmethylsulfonamido)cyclohexyl)acetic acid: A mixture of the product from Step 2 above (3.1 g) in THF (50 ml) and MeOH (10 ml) was treated with 2 M LiOH(aq) (6.71 ml, 13.4 mmol) and stirred at RT for 18 h. The resultant mixture was diluted with Et$_2$O (100 ml) and stirred for 30 min. The phases were separated and the aqueous phase was acidified with 1 M HCl(aq). The resultant precipitate was collected by filtration, washing with water to afford the title compound (2.1 g, 8.00 mmol, 95% purity) as a tan solid. $^1$H NMR (400 MHz, DMSO-d$_6$) δ 11.99 (s, 1H), 3.54-3.47 (m, 1H), 2.87 (s, 3H), 2.67 (s, 3H), 2.09 (d, J=6.9 Hz, 2H), 1.77-1.74 (m, 2H), 1.70-1.50 (m, 3H), 1.52 (qd, J=12.6, 3.6 Hz, 2H), 1.07 (qd, J=12.6, 3.6 Hz, 2H).

Step 4: tert-butyl (1-(4-(5-(2-(trans-4-(N-methylmethylsulfonamido)cyclohexyl)acetamido)-3-(thiophen-3-yl)pyridin-2-yl)phenyl)cyclobutyl)carbamate: A mixture of the product from Step 3 above (44.4 mg, 0.169 mmol, 95% purity), DIPEA (62.1 µl, 0.356 mmol) and HATU (67.6 mg, 0.178 mmol) in DMF (2 ml) was stirred at RT for 30 min and then treated with a solution of Intermediate 15 (50 mg, 0.119 mmol) in DMF (1 ml). The resultant mixture was heated at 50° C. for 18 h. The reaction mixture was cooled to RT, diluted with water (5 ml) and the resultant solid filtered, washing with water (50 ml). The solid was dissolved in DCM (20 ml), dried over MgSO$_4$, filtered and concentrated in vacuo. The residue was purified by column chromatography (12 g cartridge, 0-5% (0.7 M NH$_3$ in MeOH)/DCM)) to afford the title compound (28 mg, 0.043 mmol) as a colourless glass. HPLC (Method 1): R$_T$ 2.41 min. $^1$H NMR (400 MHz, Methanol-d$_4$) δ 8.74 (d, J=2.4 Hz, 1H), 8.22 (d, J=2.5 Hz, 1H), 7.38 (d, J=8.5 Hz, 1H), 7.32-7.21 (m, 5H), 6.77 (dd, J=5.0, 1.3 Hz, 1H), 3.69 (tt, J=11.9, 3.9 Hz, 1H), 2.87 (s, 3H), 2.79 (s, 3H), 2.53-2.38 (m, 4H), 2.34 (d, J=7.1

Hz, 2H), 2.15-2.02 (m, 1H), 1.99-1.74 (m, 6H), 1.66 (qd, J=12.6, 3.5 Hz, 2H), 1.38 (br s, 9H), 1.24 (qd, J=12.8, 3.5 Hz, 2H).

Step 5: N-(6-(4-(1-aminocyclobutyl)phenyl)-5-(thiophen-3-yl)pyridin-3-yl)-2-(trans-4-(N-methylmethylsulfonamido) cyclohexyl)acetamide: The title compound (23.4 mg, 0.041 mmol, 98% purity) was isolated from the reaction of the product from Step 4 above (28 mg, 0.043 mmol) with 90% (v/v) TFA in water (0.5 ml) using essentially the same procedure as in Example 1 Step 7. LCMS (Method 2): m/z 553 (M+H)$^+$ at 1.99 min. $^1$H NMR (400 MHz, DMSO-d$_6$) δ 10.23 (s, 1H), 8.76 (d, J=2.5 Hz, 1H), 8.14 (d, J=2.5 Hz, 1H), 7.48 (dd, J=5.0, 2.9 Hz, 1H), 7.43 (dd, J=2.9, 1.4 Hz, 1H), 7.35 (d, J=8.6 Hz, 2H), 7.35 (d, J=8.6 Hz, 2H), 6.75 (dd, J=5.0, 1.3 Hz, 1H), 3.55 (tt, J=11.9, 3.9 Hz, 1H), 2.88 (s, 3H), 2.68 (s, 3H), 2.38-2.32 (m, 3H), 2.26 (d, J=6.8 Hz, 2H), 2.11-1.93 (m, 3H), 1.85-1.46 (m, 7H), 1.14 (qd, J=12.6, 3.5 Hz, 2H).

Example 18

2-(trans-4-acetamidocyclohexyl)-N-(6-(4-(1-aminocyclobutyl)phenyl)-5-(2-methylthiophen-3-yl)pyridin-3-yl)acetamide

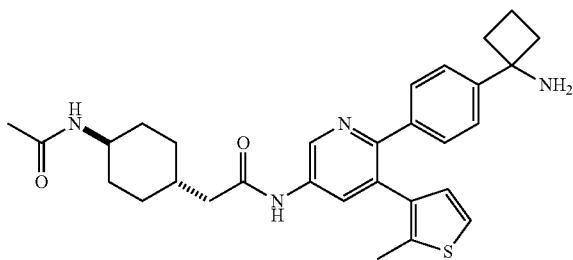 [SMILES: CC(=O)N[C@H]1CC[C@H](CC(=O)Nc2cnc(-c3ccc(C4(N)CCC4)cc3)c(-c3ccsc3C)c2)CC1]

The title compound (17 mg, 0.031 mmol, 95% purity) was isolated as a white solid from the reaction of Intermediate 16 (50 mg, 0.104 mmol, 90% purity), the product from Example 2 Step 2 (34.3 mg, 0.172 mmol), Et$_3$N (0.096 ml, 0.689 mmol) and T3P (0.203 ml, 0.344 mmol, 50% w/w in EtOAc) in EtOAc (1.5 ml) using essentially the same procedure as in Example 6. LCMS (Method 1): m/z 517 (M+H)+; 515 (M−H)$^-$, at 1.34 min. $^1$H NMR (400 MHz, DMSO-d$_6$) δ 10.25 (s, 1H), 8.80 (d, J=2.4 Hz, 1H), 8.04 (d, J=2.5 Hz, 1H), 7.70 (d, J=7.8 Hz, 1H), 7.42-7.24 (m, 5H), 6.82 (d, J=5.2 Hz, 1H), 3.56-3.39 (m, 1H), 2.42-2.33 (m, 2H), 2.26 (d, J=6.6 Hz, 2H), 2.17-2.07 (m, 2H), 2.05-1.94 (m, 4H), 1.83-1.59 (m, 9H), 1.23-0.99 (m, 4H).

Example 19

N-(6-(4-(1-aminocyclobutyl)phen)-5-(4-methylthiophen-3-yl)pyridin-3-yl)-2-(trans-4-(N-methylmethylsulfonamido)cyclohexyl)acetamide

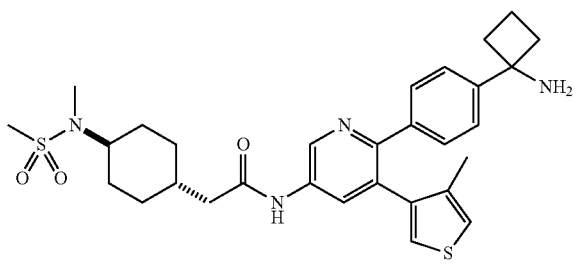 [SMILES: Cc1cscc1-c1cc(NC(=O)C[C@H]2CC[C@H](N(C)S(C)(=O)=O)CC2)cnc1-c1ccc(C2(N)CCC2)cc1]

Step 1: tert-butyl (1-(4-(5-(2-(trans-4-(N-methylmethylsulfonamido)cyclohexyl)acetamido)-3-(4-methylthiophen-3-yl)pyridin-2-yl)phenyl)cyclobutyl)carbamate: The title compound (42 mg, 0.060 mmol, 95% purity) was isolated as a white solid from the reaction of Intermediate 17 (40 mg, 0.083 mmol, 90% purity), the product from Example 17 Step 3 (34.3 mg, 0.138 mmol), Et$_3$N (77 µl, 0.551 mmol) and T3P (162 µl, 0.275 mmol, 50% w/w in EtOAc) in EtOAc (1.5 ml) using essentially the same procedure as in Example 4 Step 2, except the crude product was purified by column chromatography (12 g cartridge, 0-100% EtOAc/isohexane). $^1$H NMR (400 MHz, DMSO-d$_6$) (two rotamers in a 2:1 ratio) δ 10.24 (s, 1H), 8.81 (d, J=2.5 Hz, 1H), 8.03 (d, J=2.4 Hz, 1H), 7.53 (br s, 1H, major), 7.48-7.36 (m, 1H and 1H minor), 7.26 (d, J=8.4 Hz, 2H), 7.22 (d, J=8.5 Hz, 2H), 7.12 (s, 1H), 3.63-3.49 (m, 1H), 2.89 (s, 3H), 2.69 (s, 3H), 2.44-2.21 (m, 6H), 2.07-1.89 (m, 1H), 1.89-1.48 (m, 11H), 1.42-1.02 (m, 11H).

Step 2: N-(6-(4-(1-aminocyclobutyl)phenyl)-5-(4-methylthiophen-3-yl)pyridin-3-yl)-2-(trans-4-(N-methylmethylsulfonamido)cyclohexyl)acetamide: The title compound (22 mg, 0.039 mmol) was isolated as a white solid from the reaction of the product from Step 1 above (42 mg, 0.060 mmol, 95% purity) with TFA (0.5 ml) in DCM (2 ml) using essentially the same procedure as in Example 2 Step 4. LCMS (Method 1): m/z 567 (M+H)$^+$ at 1.50 min. $^1$H NMR (400 MHz, DMSO-d$_6$) δ 10.24 (s, 1H), 8.81 (d, J=2.4 Hz, 1H), 8.02 (d, J=2.5 Hz, 1H), 7.42 (d, J=3.2 Hz, 1H), 7.32 (d, J=8.8 Hz, 2H), 7.28 (d, J=8.8 Hz, 2H), 7.18 (dd, J=3.2, 1.1 Hz, 1H), 3.56 (tt, J=11.8, 3.9 Hz, 1H), 2.89 (s, 3H), 2.69 (s, 3H), 2.39-2.23 (m, 4H), 2.15-1.92 (m, 4H), 1.81 (d, J=13.4 Hz, 2H), 1.71-1.49 (m, 8H), 1.23-1.08 (m, 2H).

Example 20

N-(trans-4-(2-((2-(4-(1-aminocyclobutyl)phenyl)-[3,3'-bipyridin]-5-yl)amino)-2-oxoethyl)cyclohexyl)-3,3,3-trifluoro-2,2-dimethylpropanamide

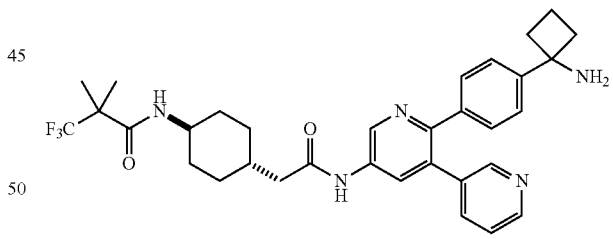

Step 1: ethyl 2-(trans-4-(3,3,3-trifluoro-2,2-dimethylpropanamido)cyclohexyl)acetate: Ethyl 2-(trans-4-aminocyclohexyl)acetate hydrochloride (0.5 g, 2.26 mmol) was suspended in EtOAc (10 ml) and treated with Et$_3$N (1.58 ml, 11.3 mmol), 3,3,3-trifluoro-2,2-dimethylpropanoic acid (0.528 g, 3.38 mmol) and T3P (3.39 ml, 5.75 mmol, 50% w/w in EtOAc). The resultant mixture was heated at 40° C. overnight. The mixture was quenched with water (5 ml) and stirred for 2 min. Saturated NaHCO$_3$(aq) (5 ml) was added and the mixture stirred for a further 1 min. The phases were separated and the aqueous phase washed with EtOAc (2×5 ml). The aqueous phase was then extracted with DCM (10 ml), filtered through a phase separation cartridge and the DCM extract concentrated in vacuo to afford the title compound (710 mg) as a sticky brown solid. This material was used in subsequent reactions without purification.

Step 2: 2-(trans-4-(3,3,3-trifluoro-2,2-dimethylpropanamido)cyclohexyl)acetic acid: A stirred solution of the product from Step 1 above (710 mg) in THF (20 ml) and MeOH (1 ml) was treated with a solution of LiOH (63 mg, 2.63 mmol) in water (2 ml) and stirred at RT for 3 days. The mixture was concentrated in vacuo and the residue diluted with water (2 ml) and acidified (pH 2) with 1 M HCl(aq). The resultant precipitate was collected by filtration, washing with water (2×1 ml), and dried in vacuo to afford a beige solid (383 mg). The solid was dissolved in THF (10 ml) and MeOH (0.5 ml) and treated with LiOH (63 mg, 2.63 mmol) in water (1 ml), then stirred at RT overnight. The mixture was concentrated in vacuo and the residue diluted with water (2 ml) and acidified (pH 2) with 1 M HCl(aq). The precipitate was collected by filtration, washing with water (2×1 ml), and dried in vacuo to afford the title compound (314 mg, 1.04 mmol, 98% purity) as a beige solid. $^1$H NMR (400 MHz, DMSO-$d_6$) δ 12.01 (s, 1H), 7.55 (d, J=8.1 Hz, 1H), 3.62-3.48 (m, 1H), 2.10 (d, J=7.0 Hz, 2H), 1.78-1.65 (m, 4H), 1.65-1.51 (m, 1H), 1.36-1.22 (m, 8H), 1.09-0.93 (m, 2H).

Step 3: tert-butyl (1-(4-(5-(2-(trans-4-(3, 3,3-trifluoro-2, 2-dimethylpropanamido)cyclohexyl)acetamido)-[3,3'-bipyridin]-2-yl)phenyl)cyclobutyl)carbamate: Intermediate 18 (30 mg, 0.072 mmol) was suspended in a mixture of EtOAc (1 ml) and DCM (0.5 ml) and treated with Et$_3$N (50.2 µl, 0.360 mmol), the product from Step 2 above (25.5 mg, 0.084 mmol, 98% purity) and T3P (108 µl, 0.184 mmol, 50% w/w in EtOAc). The resultant solution was stirred at RT overnight. The mixture was treated with further product from Step 2 above (10 mg, 0.033 mmol, 98% purity), Et$_3$N (50.2 µl, 0.360 mmol) and T3P (108 µl, 0.184 mmol, 50% w/w in EtOAc) and stirring continued for 24 h. The mixture was quenched with water (1 ml) and stirred for 2 min. Saturated NaHCO$_3$(aq) (1 ml) was added and the mixture stirred for a further 1 min. The resultant precipitate was collected by filtration to afford the title compound (39 mg, 0.055 mmol, 98% purity) as an off-white solid. LCMS (Method 1): m/z 347 (M+2H)$^{2+}$ at 2.26 min. $^1$H NMR (400 MHz, DMSO-$d_6$) δ 10.34 (s, 1H), 8.83 (d, J=2.4 Hz, 1H), 8.49 (dd, J=4.8, 1.6 Hz, 1H), 8.36 (d, J=1.5 Hz, 1H), 8.16 (d, J=2.4 Hz, 1H), 7.66-7.46 (m, 3H), 7.40-7.11 (m, 5H), 3.65-3.49 (m, 1H), 2.42-2.22 (m, 6H), 2.03-1.88 (m, 1H), 1.82-1.65 (m, 6H), 1.42-0.98 (m, 19H).

Step 4: N-(trans-4-(2-((2-(4-(1-aminocyclobutyl)phenyl)-[3,3'-bipyridin]-5-yl)amino)-2-oxoethyl)cyclohexyl)-3,3,3-trifluoro-2,2-dimethylpropanamide: Formic acid (0.5 ml, 13.0 mmol) was added to the product from Step 3 above (38 mg, 0.054 mmol, 98% purity) and the resultant solution stirred at RT overnight. The solution was loaded onto a column of SCX (0.5 g) in MeOH. The column was washed with MeOH and then the product was eluted with a 7 M solution of ammonia in MeOH. The resultant mixture was concentrated to dryness, azeotroping with DCM, and dried in vacuo to afford the title compound (24 mg, 0.039 mmol, 97% purity) as a tan solid. LCMS (Method 1): m/z 289 (M+2H—NH$_3$)$^+$ at 1.45 min. $^1$H NMR (400 MHz, DMSO-$d_6$) δ 10.33 (s, 1H), 8.84 (d, J=2.4 Hz, 1H), 8.52 (dd, J=4.8, 1.6 Hz, 1H), 8.36 (dd, J=2.3, 0.9 Hz, 1H), 8.17 (d, J=2.4 Hz, 1H), 7.67 (dt, J=7.8, 1.9 Hz, 1H), 7.57 (d, J=8.1 Hz, 1H), 7.40 (ddd, J=7.9, 4.8, 0.9 Hz, 1H), 7.37-7.31 (m, 2H), 7.26-7.18 (m, 2H), 3.66-3.52 (m, 1H), 2.41-2.22 (m, 4H), 2.17-1.90 (m, 3H), 1.84-1.59 (m, 6H), 1.38-1.24 (m, 8H), 1.08 (q, J=12.6 Hz, 2H).

Example 21

N-(6-(4-(3-aminooxetan-3-yl)phenyl)-5-phenylpyridin-3-yl)-2-(4-methoxycyclohexyl)acetamide

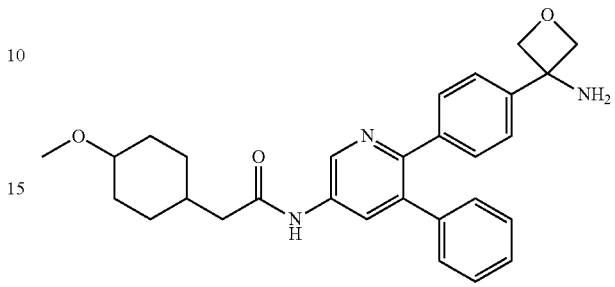

Step 1: Benzyl (3-(4-(5-(2-(4-methoxycyclohexyl)acetamido)-3-phenylpyridin-2-yl)phenyl)oxetan-3-yl)carbamate: A mixture of Intermediate 12 (40 mg, 0.089 mmol), 2-(4-methoxycyclohexyl)acetic acid (22.9 mg, 0.133 mmol) and Et$_3$N (61.7 µl, 0.443 mmol) was suspended in EtOAc (2 ml) and the resultant mixture was heated to 40° C. T3P (133 µl, 0.226 mmol, 50% w/w in EtOAc) was added and the mixture was heated at 40° C. overnight. The mixture was quenched with water (10 ml) and then saturated NaHCO$_3$ (aq) (10 ml) was added. The phases were separated, the aqueous phase was extracted with EtOAc (2×20 ml) and the combined organic phases were concentrated in vacuo. The residue was purified by column chromatography (12 g cartridge, 0-100% EtOAc/isohexane) to afford the title compound (50 mg, 0.083 mmol) as a white solid. LCMS (Method 1): m/z 606 (M+H)$^+$, at 2.25 and 2.32 min (mixture of cis and trans isomers). $^1$H NMR (400 MHz, DMSO-$d_6$) (cis and trans isomers in a 1:2 ratio) δ 10.26 (s, 1H), 8.80 (d, J=2.4 Hz, 1H), 8.46 (s, 1H), 8.12 (d, J=2.5 Hz, 1H), 7.46-7.11 (m, 14H), 5.00 (s, 2H), 4.81 (d, J=6.6 Hz, 2H), 4.65 (d, J=6.6 Hz, 2H), 3.22 (s, 3H, major), 3.20 (s, 3H, minor), 3.11-3.01 (m, 1H), 2.31-2.23 (m, 2H), 2.04-1.93 (m, 1H), 1.81-1.69 (m, 3H), 1.51-1.21 (m, 2H), 1.13-0.96 (m, 3H).

Step 2: N-(6-(4-(3-aminooxetan-3-yl)phenyl)-5-phenylpyridin-3-yl)-2-(4-methoxycyclohexyl)acetamide: A solution of the product from Step 1 above (50 mg, 0.083 mmol) in MeOH (5 ml) was hydrogenated in a ThalesNano H-Cube® flow reactor (10% Pd/C, 30×4 mm, full hydrogen mode, 50° C., 1 ml/min flow rate). The mixture was concentrated in vacuo and the residue purified by column chromatography on the Companion (12 g cartridge, 0-20% (0.7 M ammonia in MeOH)/DCM) to afford the title compound (15 mg, 0.032 mmol) as a white solid. LCMS (Method 1): m/z 472 (M+H)+; 470 (M−H)$^-$, at 1.36 and 1.42 min (mixture of cis and trans isomers). $^1$H NMR (400 MHz, DMSO-$d_6$) (cis and trans isomers in a 1:3 ratio) δ 10.26 (s, 1H), 8.85-8.76 (m, 1H), 8.19-8.07 (m, 1H), 7.44 (d, J=8.5 Hz, 2H), 7.40-7.31 (m, 3H), 7.28 (d, J=8.5 Hz, 2H), 7.25-7.14 (m, 2H), 4.65 (d, J=6.0 Hz, 2H), 4.61 (d, J=6.0 Hz, 2H), 3.23 (s, 3H, major), 3.21 (s, 3H, minor), 3.13-3.01 (m, 1H), 2.67-2.51 (br s, 2H), 2.31-2.22 (m, 2H), 2.05-1.94 (m, 1H), 1.83-1.70 (m, 2H), 1.52-1.22 (m, 3H), 1.19-0.96 (m, 3H).

Example 22

N-(6-(4-(3-aminooxetan-3-yl)phenyl)-5-phenylpyridin-3-yl)-2-((2r,6s)-2,6-dimethyltetrahydro-2H-pyran-4-yl)acetamide

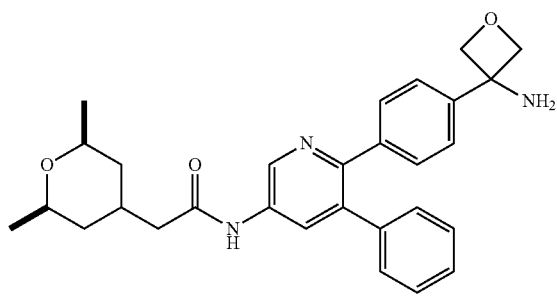

Step 1: tert-butyl 2-(2,6-dimethyldihydro-2H-pyran-4(3H)-ylidene)acetate: A stirred suspension of sodium hydride (0.240 g, 6.01 mmol, 60% w/w in mineral oil) in THF (5 ml) was cooled in an ice bath and treated dropwise with a solution of tert-butyl 2-(dimethoxyphosphoryl)acetate (1.35 g, 6.01 mmol) in THF (5 ml) over 15 min. After stirring for a further 20 min, a solution of 2,6-dimethyldihydro-2H-pyran-4(3H)-one (0.7 g, 5.46 mmol) in toluene (5 ml) was added dropwise over 5 min. The resultant cloudy solution was allowed to warm to RT and was stirred overnight. The mixture was quenched with saturated $NH_4Cl(aq)$ (50 ml) and then extracted with EtOAc (2×75 ml). The combined organic phases were washed with brine (50 ml) and then dried over $MgSO_4$, filtered and concentrated in vacuo to afford a pale yellow oil. The crude product was purified by column chromatography (12 g cartridge, 0-15% EtOAc/isohexane) to afford the title compound (530 mg, 2.23 mmol, 95% purity) as a pale yellow oil. LCMS (Method 1): m/z 171 $(M+H-C_4H_8)^+$, at 2.46 min. $^1$H NMR (400 MHz, DMSO-$d_6$) δ 5.58 (t, J=1.6 Hz, 1H), 3.66 (dt, J=13.6, 1.7 Hz, 1H), 3.47-3.34 (m, 2H), 2.21 (dt, J=13.3, 1.8 Hz, 1H), 1.97-1.87 (m, 1H), 1.72-1.61 (m, 1H), 1.41 (s, 9H), 1.16 (d, J=6.1 Hz, 3H), 1.13 (d, J=6.1 Hz, 3H).

Step 2: tert-butyl 2-(2,6-dimethyltetrahydro-2H-pyran-4-yl)acetate: A solution of the product from Step 1 above (520 mg, 2.18 mmol, 95% purity) in EtOAc (15 ml) was hydrogenated in a ThalesNano H-Cube® flow reactor (10% Pd/C, 70×4 mm, full hydrogen mode, 30° C., 1 ml/min flow rate, 2 passes) and then concentrated in vacuo to afford the title compound (510 mg, 2.14 mmol, 96% purity) as a colourless oil. $^1$H NMR (two diastereomers in a 6:1 ratio) (400 MHz, DMSO-$d_6$) δ 3.43-3.34 (m, 2H), 2.08 (d, J=7.1 Hz, 2H), 1.95-1.81 (m, 1H), 1.61-1.53 (m, 2H), 1.39 (s, 9H), 1.06 (d, J=6.2 Hz, 6H, major), 1.01 (d, J=6.1 Hz, 6H, minor), 0.82-0.69 (m, 2H).

Step 3: 2-((2r,6s)-2,6-dimethyltetrahydro-2H-pyran-4-yl)acetic acid: The product from Step 2 above (365 mg, 1.53 mmol, 96% purity) was dissolved in dioxane (5 ml, 58.5 mmol) and treated with HCl (15 ml, 60.0 mmol, 4 M in dioxane). The resultant mixture was stirred for 20 h. The resultant mixture was concentrated in vacuo and the residue azeotroped with toluene (2×3 ml) to afford the title compound (365 mg) as a pale brown oil. LCMS (Method 1): m/z 173 $(M+H)^+$, 171 $(M-H)^-$, at 1.27 min. $^1$H NMR (400 MHz, DMSO-$d_6$) (two diastereomers in a 6:1 ratio) δ 12.08 (s, 1H), 3.61-3.52 (m, 2H, minor), 3.44-3.34 (m, 2H, major), 2.41 (d, J=7.7 Hz, 2H, minor), 2.11 (d, J=7.0 Hz, 2H, major), 2.31-2.23 (m, 1H, minor), 1.97-1.83 (m, 1H, major), 1.65-1.52 (m, 2H), 1.06 (d, J=6.2 Hz, 6H, major), 1.02 (d, J=6.1 Hz, 6H, minor), 0.82-0.69 (m, 2H). $^1$H NMR data was consistent with that previously reported (U.S. Pat. No. 7,964,624). The compound contained 12 wt % unreacted starting material. This material was used in subsequent reactions without further purification.

Step 4: benzyl (3-(4-(5-(2-((2r,6s)-2,6-dimethyltetrahydro-2H-pyran-4-yl)acetamido)-3-phenylpyridin-2-yl)phenyl)oxetan-3-yl)carbamate: The title compound (41 mg, 0.064 mmol, 95% purity) was isolated as a yellow solid from the reaction of Intermediate 12 (40 mg, 0.089 mmol), the product from Step 3 above (22.9 mg), $Et_3N$ (61.7 μl, 0.443 mmol) and T3P (133 μl, 0.226 mmol, 50% w/w in EtOAc) in EtOAc (2 ml) using essentially the same procedure as in Example 21 Step 1, except the reaction mixture was heated at 50° C. $^1$H NMR (400 MHz, DMSO-$d_6$) (two diastereomers in a 10:1 ratio) δ 10.30 (s, 1H), 8.82 (d, J=2.4 Hz, 1H), 8.46 (s, 1H), 8.14 (d, J=2.5 Hz, 1H), 7.49-7.15 (m, 14H), 5.01 (s, 2H), 4.82 (d, J=6.7 Hz, 2H), 4.66 (d, J=6.6 Hz, 2H), 3.76-3.60 (m, 2H, minor), 3.48-3.37 (m, 2H, major), 2.60 (d, J=7.9 Hz, 2H, minor), 2.29 (d, J=7.1 Hz, 2H, major), 2.15-1.98 (m, 1H), 1.71-1.60 (m, 2H, major), 1.52-1.41 (m, 2H, minor), 1.09 (d, J=6.1 Hz, 6H, major), 1.06 (d, J=6.2 Hz, 6H, minor), 0.97-0.72 (m, 2H).

Step 5: N-(6-(4-(3-aminooxetan-3-yl)phenyl)-5-phenylpyridin-3-yl)-2-((2r,6s)-2,6-dimethyltetrahydro-2H-pyran-4-yl)acetamide: A solution of the product from Step 4 above (41 mg, 0.064 mmol, 95% purity) in MeOH (5 ml) was hydrogenated in a ThalesNano H-Cube® flow reactor (10% Pd/C, 30×4 mm, full hydrogen mode, 50° C., 1 ml/min flow rate). The mixture was concentrated in vacuo and the residue purified by column chromatography on the Companion (12 g cartridge, 0-20% (0.7 M ammonia in MeOH)/DCM) to afford the title compound (12 mg, 0.025 mmol) as a white solid. LCMS (Method 1): m/z 472 $(M+H)^+$, 470 $(M-H)^-$, at 1.34 min. $^1$H NMR (400 MHz, DMSO-$d_6$) (two diastereomers in a 10:1 ratio) δ 10.29 (s, 1H), 8.81 (d, J=2.4 Hz, 1H), 8.13 (d, J=2.4 Hz, 1H), 7.47-7.42 (m, 2H), 7.39-7.31 (m, 3H), 7.31-7.26 (m, 2H), 7.24-7.19 (m, 2H), 4.89 (d, J=6.1 Hz, 2H, minor), 4.78 (d, J=6.2 Hz, 2H, minor), 4.65 (d, J=6.1 Hz, 2H, major), 4.61 (d, J=6.0 Hz, 2H, major), 3.74-3.61 (m, 2H, minor), 3.51-3.35 (m, 2H, major), 2.59 (d, J=7.8 Hz, 2H, minor), 2.29 (d, J=7.1 Hz, 2H, major), 2.14-1.98 (m, 1H), 1.72-1.59 (m, 2H, major), 1.52-1.40 (m, 2H, minor), 1.09 (d, J=6.1 Hz, 6H, major), 1.06 (d, J=6.1 Hz, 6H, minor), 0.91-0.77 (m, 2H).

Example 23

N-(6-(4-(2-aminopropan-2-yl)phenyl)-5-phenylpyridin-3-yl)-2-(trans-4-(3-methyl-4H-1,2,4-triazol-4-yl)cyclohexyl)acetamide

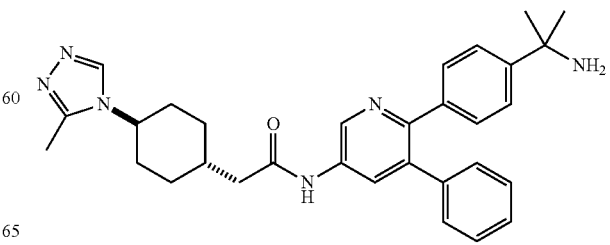

Step 1: ethyl 2-(trans-4-(3-methyl-4H-1,2,4-triazol-4-yl)cyclohexyl)acetate: A mixture of N,N-dimethylformamide dimethyl acetal (0.266 ml, 1.94 mmol) and acethydrazide (132 mg, 1.78 mmol) in MeCN (5 ml, 0.270 mmol) was heated at 50° C. for 30 min. Ethyl 2-(trans-4-aminocyclohexyl)acetate hydrochloride (300 mg, 1.35 mmol) was added and the mixture was heated under reflux overnight. The mixture was cooled and partitioned between EtOAc (50 ml) and water (50 ml). The phases were separated and the aqueous phase extracted with EtOAc (2×50 ml). The combined organic phases were dried over MgSO₄, filtered and concentrated in vacuo to afford the title compound (222 mg) as a colourless gum. This material was used directly in subsequent reactions without purification.

Step 2: 2-(trans-4-(3-methyl-4H-1,2,4-triazol-4-yl)cyclohexyl)acetic acid: The product from Step 1 above (220 mg) was stirred in a mixture of MeOH (0.5 ml), THF (0.5 ml) and water (1 ml). A solution of LiOH (31.4 mg, 1.31 mmol) in water (5 ml) was added and the resultant mixture stirred at RT overnight. The mixture was concentrated in vacuo and the residue suspended in THF (1 ml) and acidified with HCl (4 M in dioxane) and then concentrated in vacuo. The residue was dissolved in MeOH and loaded onto a column of SCX (0.5 g). The column was washed with MeOH and then the product was eluted with a 0.7 M solution of ammonia in MeOH. The resultant mixture was concentrated in vacuo to afford the title compound (120 mg, 0.511 mmol, 95% purity) as a white solid. ¹H NMR (400 MHz, DMSO-d₆) δ 8.51 (s, 1H), 3.90 (tt, J=11.9, 3.8 Hz, 1H), 2.35 (s, 3H), 2.01 (d, J=6.9 Hz, 2H), 1.97-1.51 (m, 7H), 1.25-0.96 (m, 2H).

Step 3: tert-butyl (2-(4-(5-(2-(trans-4-(3-methyl-4H-1,2,4-triazol-4-yl)cyclohexyl)acetamido)-3-phenylpyridin-2-yl)phenyl)propan-2-yl)carbamate: The title compound (30 mg, 0.047 mmol, 95% purity) was isolated as a white solid from the reaction of Intermediate 2 (30 mg, 0.074 mmol), the product from Step 2 above (16.6 mg, 0.070 mmol, 95% purity), Et₃N (51.9 µl, 0.372 mmol) and T3P (111 µl, 0.186 mmol, 50% w/w in EtOAc) in EtOAc (5 ml) using essentially the same procedure as in Example 4 Step 2. ¹H NMR (400 MHz, DMSO-d₆) δ 10.30 (s, 1H), 8.80 (d, J=2.4 Hz, 1H), 8.53 (s, 1H), 8.12 (d, J=2.4 Hz, 1H), 7.39-7.27 (m, 3H), 7.27-7.03 (m, 7H), 3.95 (tt, J=12.1, 3.9 Hz, 1H), 2.36 (s, 3H), 2.35-2.29 (m, 2H), 2.02-1.84 (m, 5H), 1.84-1.63 (m, 2H), 1.45 (s, 6H), 1.32 (br s, 9H, major), 1.32-1.14 (m, 2H), 1.08 (br s, 9H, minor).

Step 4: N-(6-(4-(2-aminopropan-2-yl)phenyl)-5-phenylpyridin-3-yl)-2-(trans-4-(3-methyl-4H-1,2,4-triazol-4-yl)cyclohexyl)acetamide: The title compound (9 mg, 0.018 mmol) was isolated as a white solid from the reaction of the product from Step 3 above (28 mg, 0.044 mmol, 95% purity) with TFA (1 ml) in DCM (2 ml) using essentially the same procedure as in Example 2 Step 4. LCMS (Method 1): m/z 509 (M+H)+; 507 (M−H)⁻, at 1.16 min. ¹H NMR (400 MHz, DMSO-d₆) δ 10.29 (s, 1H), 8.79 (d, J=2.4 Hz, 1H), 8.51 (s, 1H), 8.10 (d, J=2.4 Hz, 1H), 7.44-7.29 (m, 5H), 7.29-7.11 (m, 4H), 4.04-3.85 (m, 1H), 2.35 (s, 3H), 2.32 (d, J=6.6 Hz, 2H), 2.02-1.81 (m, 5H), 1.79-1.64 (m, 2H), 1.33 (s, 6H), 1.31-1.17 (m, 2H).

Example 24

N-(6-(4-(2-aminopropan-2-yl)phenyl)-5-phenylpyridin-3-yl)-2-(trans-4-(2-oxopyrrolidin-1-yl)cyclohexyl)acetamide

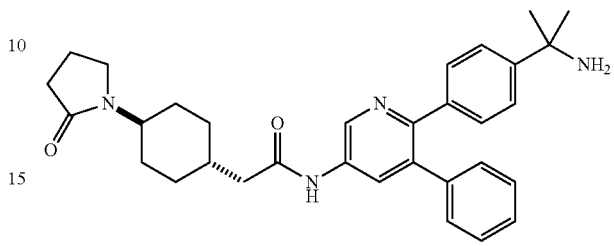

Step 1: tert-butyl (2-(5-(5-(2-(trans-4-(((benzyloxy)carbonyl)amino)cyclohexyl)acetamido)-[1,1'-biphenyl]-2-yl)pyridin-2-yl)propan-2-yl)carbamate: A mixture of 2-(trans-4-(((benzyloxy)carbonyl)amino)cyclohexyl)acetic acid (590 mg, 2.026 mmol), DIPEA (708 µl, 4.05 mmol) and HATU (770 mg, 2.03 mmol) in DMF (20 ml) was stirred at RT for 30 min and then treated with a solution of Intermediate 2 (545 mg, 1.35 mmol) in DMF (10 ml). The resultant mixture was heated at 50° C. for 18 h. The reaction mixture was cooled to RT, diluted with water until a precipitate formed and the resultant solid filtered, washing with water (50 ml). The solid was dissolved in DCM (200 ml), dried over MgSO₄, filtered and concentrated in vacuo to afford the title compound (896 mg) as a dark brown solid. This material was used in subsequent reactions without purification.

Step 2: tert-butyl (2-(4-(5-(2-(trans-4-aminocyclohexyl)acetamido)-3-phenylpyridin-2-yl)phenyl)propan-2-yl)carbamate: The product from Step 1 above (896 mg) was dissolved in a mixture of EtOH (50 ml) and THF (50 ml) and the vessel purged with N₂. Palladium (1.41 g, 10% w/w on carbon, Type 39 paste) was added and the vessel further purged with N₂. The vessel was then purged with H₂ and the reaction mixture stirred at RT under an atmosphere of H₂ for 18 h. The vessel was purged with N₂, palladium (1.41 g, 10% w/w on carbon, Type 39 paste) was added and the vessel further purged with N₂. The vessel was then purged with H₂ and the reaction mixture stirred at RT under an atmosphere of H₂ for 2 days. The vessel was purged with N₂, the reaction mixture filtered through Celite®, washing with MeOH (50 ml), and the filtrate concentrated in vacuo. The residue was purified by column chromatography (12 g cartridge, 0-50% MeOH (0.7 M NH₃)/DCM) to afford the title compound (459 mg, 0.837 mmol) as a tan solid. LCMS (Method 1): m/z 543 (M+H)⁺ at 1.61 min.

Step 3: tert-butyl (2-(4-(5-(2-(trans-4-(4-chlorobutanamido)cyclohexyl)acetamido)-3-phenylpyridin-2-yl)phenyl)propan-2-yl)carbamate: A stirred solution of the product from Step 2 above (50 mg, 0.092 mmol) and Et₃N (64.2 µl, 0.461 mmol) in THF (7.55 µl, 0.092 mmol) was treated dropwise with 4-chlorobutanoyl chloride (20.6 µl, 0.184 mmol). The resultant reaction mixture was stirred at RT overnight. The reaction mixture was poured into water (50 ml) and extracted with EtOAc (3×50 ml). The combined extracts were dried over MgSO₄, filtered and concentrated in vacuo to afford the title compound (55 mg) as a white solid. This material was used in subsequent reactions without purification.

Step 4: tert-butyl (2-(4-(5-(2-(trans-4-(2-oxopyrrolidin-1-yl)cyclohexyl)acetamido)-3-phenylpyridin-2-yl)phenyl)propan-2-yl)carbamate: A stirred solution of the product from Step 3 above (55 mg) in THF (5 ml) was treated with sodium hydride (22.60 mg, 0.565 mmol, 60% w/w in mineral oil) and the resultant mixture was heated at 50° C. for 2 h. The reaction mixture was poured into water (50 ml) and extracted with DCM (3×50 ml). The combined extracts were washed with brine (50 ml), dried over MgSO$_4$, filtered and concentrated in vacuo. The residue was purified by column chromatography (12 g cartridge, 0-15% MeOH/DCM) to afford the title compound (22 mg, 0.032 mmol, 90% purity) as a white solid. LCMS (Method 1): m/z 611 (M+H)$^+$, at 2.29 min.

Step 5: N-(6-(4-(2-aminopropan-2-yl)phenyl)-5-phenylpyridin-3-yl)-2-(trans-4-(2-oxopyrrolidin-1-yl)cyclohexyl)acetamide: The title compound (6 mg, 0.012 mmol) was isolated as a white solid from the reaction of the product from Step 4 above (22 mg, 0.032 mmol, 90% purity) with TFA (1 ml) in DCM (2 ml) using essentially the same procedure as in Example 2 Step 4. LCMS (Method 1): m/z 511 (M+H)$^+$, at 1.47 min. $^1$H NMR (400 MHz, DMSO-d$_6$) δ 10.26 (s, 1H), 8.79 (d, J=2.4 Hz, 1H), 8.09 (d, J=2.4 Hz, 1H), 7.43-7.28 (m, 5H), 7.27-7.11 (m, 4H), 3.78-3.63 (m, 1H), 2.27 (d, J=6.8 Hz, 2H), 2.23-2.16 (m, 2H), 1.94-1.69 (m, 5H), 1.60-1.40 (m, 4H), 1.34 (s, 6H), 1.32-0.98 (m, 4H).

Example 25

2-(trans-4-acetamidocyclohexyl)-N-(6-(4-(1-amino-3,3-difluorocyclobutyl)phenyl)-5-phenylpyridin-3-yl)acetamide

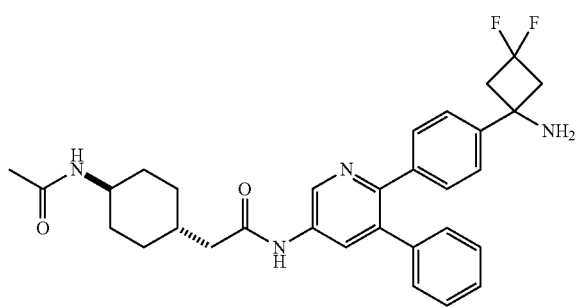 [SMILES: CC(=O)N[C@H]1CC[C@H](CC(=O)Nc2cnc(-c3ccc(C4(N)CC(F)(F)C4)cc3)c(-c3ccccc3)c2)CC1]

Step 1: tert-butyl (1-(4-(5-(2-(trans-4-acetamidocyclohexyl)acetamido)-3-phenylpyridin-2-yl)phenyl)-3,3-difluorocyclobutyl)carbamate: The title compound (32 mg) was isolated as a brown solid from the reaction of Intermediate 3 (30 mg, 0.059 mmol, 90% purity), the product from Example 2 Step 2 (26.5 mg, 0.126 mmol, 95% purity), DIPEA (77 µl, 0.465 mmol) and HATU (101 mg, 0.266 mmol) in DMF (5 ml) using essentially the same procedure as in Example 5 Step 1. This material was used in subsequent reactions without analysis.

Step 2: 2-(trans-4-acetamidocyclohexyl)-N-(6-(4-(1-amino-3,3-difluorocyclobutyl)phenyl)-5-phenylpyridin-3-yl)acetamide: The title compound (7 mg, 0.013 mmol, 99% purity) was isolated as a white solid from the reaction of the product from Step 1 above (32 mg) with TFA (0.5 ml) in DCM (2 ml) using essentially the same procedure as in Example 2 Step 4. LCMS (Method 1): m/z 533 (M+H)$^+$, 531 (M−H)$^−$, at 1.35 min. $^1$H NMR (400 MHz, DMSO-d$_6$) δ 10.27 (s, 1H), 8.80 (d, J=2.4 Hz, 1H), 8.12 (d, J=2.4 Hz, 1H), 7.70 (d, J=7.8 Hz, 1H), 7.37-7.29 (m, 5H), 7.27-7.17 (m, 4H), 3.53-3.39 (m, 1H), 3.03-2.89 (m, 2H), 2.79-2.64 (m, 2H), 2.39-2.19 (m, 4H), 1.84-1.66 (m, 8H), 1.22-0.98 (m, 4H).

Example 26

N-(trans-4-(2-((6-(4-(2-aminopropan-2-yl)phenyl)-5-(thiophen-3-yl)pyridin-3-yl)amino)-2-oxoethyl)cyclohexyl)cyclopropanecarboxamide

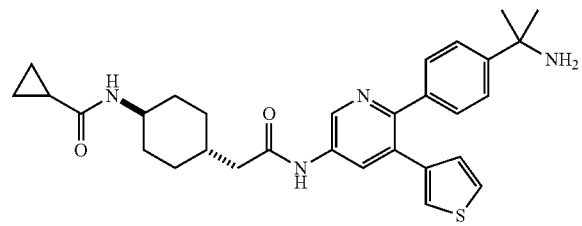 [SMILES: CC(C)(N)c1ccc(-c2ncc(NC(=O)C[C@H]3CC[C@H](NC(=O)C4CC4)CC3)cc2-c2ccsc2)cc1]

Step 1: ethyl 2-(trans-4-(cyclopropanecarboxamido)cyclohexyl)acetate: A suspension of ethyl 2-(trans-4-aminocyclohexyl)acetate hydrochloride (550 mg, 2.48 mmol), cyclopropanecarboxylic acid (260 µl, 3.27 mmol) and Et$_3$N (2.07 ml, 14.8 mmol) in EtOAc (2 ml, 20.4 mmol). The resultant mixture was treated with T3P (660 µl, 8.91 mmol, 50% w/w in EtOAc) and stirred at RT overnight. The mixture was diluted with EtOAc (200 ml) and washed sequentially with saturated NaHCO$_3$(aq) (2×100 ml), water (100 ml) and brine (100 ml). The organic phase was dried over MgSO$_4$, filtered and concentrated in vacuo to afford the title compound (501 mg, 1.78 mmol, 90% purity) as a white solid. $^1$H NMR (400 MHz, DMSO-d$_6$) δ 7.91 (d, J=7.9 Hz, 1H), 4.05 (q, J=7.1 Hz, 2H), 3.54-3.40 (m, 1H), 2.18 (d, J=6.9 Hz, 2H), 1.82-1.72 (m, 2H), 1.72-1.54 (m, 3H), 1.54-1.43 (m, 1H), 1.23-1.09 (m, 5H), 1.01 (qd, J=12.7, 3.1 Hz, 2H), 0.67-0.55 (m, 4H).

Step 2: Lithium 2-(trans-4-(cyclopropanecarboxamido)cyclohexyl)acetate: A stirred solution of the product from Step 1 above (300 mg, 1.07 mmol, 90% purity) in THF (1 ml) was treated with LiOH (53.9 mg, 2.25 mmol). MeOH (1 ml) and water (2 ml) were added and the resultant mixture was stirred at RT overnight. The reaction mixture was concentrated in vacuo to afford the title compound (250 mg) as a white solid. This material was used in subsequent reactions without purification.

Step 3: N-(trans-4-(2-((6-(4-(2-aminopropan-2-yl)phenyl)-5-(thiophen-3-yl)pyridin-3-yl)amino)-2-oxoethyl)cyclohexyl)cyclopropanecarboxamide: The title compound (7 mg, 0.014 mmol) was isolated as a white solid from the reaction of Intermediate 4 (64 mg, 0.139 mmol, 89% purity), the product from Step 2 above (52.8 mg), Et$_3$N (0.131 ml, 0.938 mmol) and T3P (0.276 ml, 0.469 mmol, 50% w/w in EtOAc) in EtOAc (1.5 ml) using essentially the same procedure as in Example 6. LCMS (Method 1): m/z 517 (M+H)$^+$, 515 (M−H)$^−$ at 1.36 min. $^1$H NMR (400 MHz, DMSO-d$_6$) δ 10.27 (s, 1H), 8.78 (d, J=2.4 Hz, 1H), 8.16 (d, J=2.4 Hz, 1H), 7.92 (d, J=7.9 Hz, 1H), 7.50 (dd, J=4.9, 2.9 Hz, 1H), 7.47-7.45 (m, 1H), 7.44 (d, J=8.5 Hz, 2H), 7.31 (d, J=8.5 Hz, 2H), 6.76 (dd, J=4.9, 1.4 Hz, 1H), 3.59-3.44 (m, 1H), 2.27 (d, J=6.6 Hz, 2H), 1.89-1.69 (m, 5H), 1.56-1.44 (m, 7H), 1.32-0.99 (m, 4H), 0.74-0.53 (m, 4H).

Example 27

N-(trans-4-(2-((6-(4-(2-aminopropan-2-yl)phenyl)-5-(thiophen-3-yl)pyridin-3-yl)amino)-2-oxoethyl)cyclohexyl)-N-methylcyclopropanecarboxamide

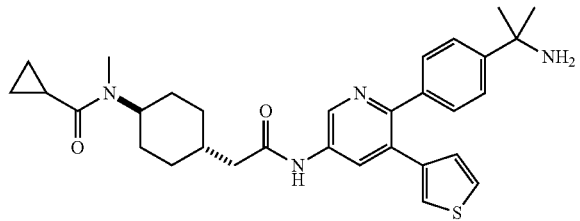 [SMILES: CN(C(=O)C1CC1)[C@H]1CC[C@H](CC(=O)Nc2cnc(-c3ccc(C(C)(C)N)cc3)c(-c3ccsc3)c2)CC1]

Step 1: Ethyl 2-(trans-4-(N-methylcyclopropanecarboxamido)cyclohexyl)acetate: A mixture of the product from Example 1 Step 3 (300 mg, 1.35 mmol), cyclopropanecarboxylic acid (144 µl, 1.81 mmol) and Et$_3$N (1.26 ml, 9.03 mmol) in EtOAc (1.5 ml) was treated with T3P (2.66 ml, 4.52 mmol, 50% w/w in EtOAc) and the resultant mixture stirred at RT overnight. The reaction mixture was quenched with saturated NaHCO$_3$(aq) (50 ml) and extracted with EtOAc (2×50 ml). The combined extracts were dried over MgSO$_4$, filtered and concentrated in vacuo. The crude product was dissolved in MeOH and loaded onto a column of SCX. The column was eluted with MeOH and the eluent was concentrated in vacuo to afford the title compound (274 mg, 0.973 mmol, 95% purity) as a colourless oil. $^1$H NMR (400 MHz, DMSO-d$_6$) (two rotamers in a 3:2 ratio) δ 4.25-4.15 (m, 1H, major), 4.12-4.01 (m, 2H), 4.01-3.90 (m, 1H, minor), 2.96 (s, 3H, major), 2.70 (s, 3H, minor), 2.23-2.14 (m, 2H), 1.96-1.40 (m, 8H), 1.22-1.12 (m, 4H), 1.11-0.97 (m, 1H), 0.77-0.59 (m, 4H).

Step 2: Lithium 2-(trans-4-(N-methylcyclopropanecarboxamido)cyclohexyl)acetate: A stirred solution of the product from Step 1 above (274 mg, 0.973 mmol, 95% purity) in a mixture of THF (1 ml), MeOH (1 ml) and water (2 ml) was treated with LiOH (53.9 mg, 2.25 mmol). The resultant mixture was stirred at RT overnight. The reaction mixture was concentrated in vacuo to afford the title compound (217 mg) as a white solid. This material was used in subsequent reactions without purification.

Step 3: N-(trans-4-(2-((6-(4-(2-aminopropan-2-yl)phenyl)-5-(thiophen-3-yl)pyridin-3-yl)amino)-2-oxoethyl)cyclohexyl)-N-methylcyclopropanecarboxamide: The title compound (22 mg, 0.041 mmol) was isolated as a white solid from the reaction of Intermediate 4 (50 mg, 0.109 mmol, 89% purity), the product from Step 2 above (217 mg), Et$_3$N (102 µl, 0.733 mmol) and T3P (0.216 ml, 0.366 mmol, 50% w/w in EtOAc) in EtOAc (1.5 ml) using essentially the same procedure as in Example 6, except, prior to treatment with TFA in DCM, the material was purified by column chromatography (12 g cartridge, 0-100% EtOAc/isohexane). LCMS (Method 1): m/z 531 (M+H)$^+$, 529 (M−H)$^-$, at 1.44 min. $^1$H NMR (400 MHz, DMSO-d$_6$) (two rotamers in a 3:2 ratio) δ 10.23 (s, 1H), 8.76 (d, J=2.1 Hz, 1H), 8.22-8.09 (m, 1H), 7.55-7.35 (m, 4H), 7.23 (d, J=8.3 Hz, 2H), 6.82-6.69 (m, 1H), 4.31-4.17 (m, 1H, major), 4.04-3.93 (m, 1H, minor), 2.96 (s, 3H, major), 2.70 (s, 3H, minor), 2.34-2.20 (m, 2H), 2.16-1.40 (m, 8H), 1.35 (s, 6H), 1.31-1.03 (m, 2H), 0.76-0.60 (m, 4H).

Example 28

N-(6-(4-(2-aminopropan-2-yl)phenyl)-5-phenylpyridin-3-yl)-2-(trans-4-(2-oxopiperidin-1-yl)cyclohexyl)acetamide

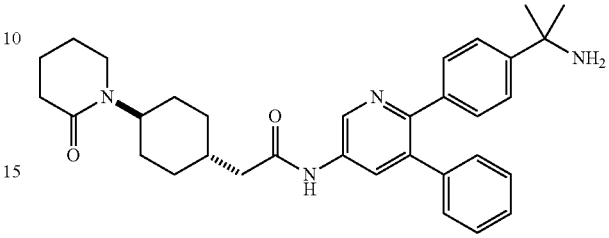

Step 1: Ethyl 2-(trans-4-(5-chloropentanamido)cyclohexyl)acetate: A solution of ethyl 2-(trans-4-aminocyclohexyl)acetate hydrochloride (0.5 g, 2.26 mmol) in THF (5 ml) was treated with Et$_3$N (1.57 ml, 11.3 mmol), followed by 5-chloropentanoyl chloride (0.583 ml, 4.51 mmol). The resultant mixture was stirred at RT for 18 h. The reaction mixture was quenched with 1 M HCl(aq) (10 ml) and partitioned with DCM (10 ml), then filtered through a phase separation cartridge and the organic phase concentrated in vacuo to afford the title compound (913 mg) as a sticky orange solid. This material was used directly in subsequent reactions without purification.

Step 2: 2-(trans-4-(2-oxopiperidin-1-yl)cyclohexyl)acetic acid: A solution of the product from Step 1 above (913 mg) in THF (5 ml) was treated with sodium hydride (841 mg, 21.04 mmol, 60% w/w in mineral oil) and the resultant mixture stirred at RT for 18 h. The reaction mixture was quenched with 1 M HCl(aq) and partitioned with DCM (10 ml), then filtered through a phase separation cartridge. The aqueous phase was concentrated in vacuo to afford the title compound (560 mg) as an orange solid. This material was used directly in subsequent reactions without purification.

Step 3: N-(6-(4-(2-aminopropan-2-yl)phenyl)-5-phenylpyridin-3-yl)-2-(trans-4-(2-oxopiperidin-1-yl)cyclohexyl)acetamide: A stirred mixture of the product from Step 2 above (80 mg) and HATU (141 mg, 0.372 mmol) in THF (3 ml) was treated with DIPEA (0.130 ml, 0.743 mmol) and the resultant mixture was stirred at RT for 40 min. A solution of Intermediate 2 (50 mg, 0.124 mmol) in THF (1 ml) was added and the mixture heated at 50° C. overnight. The mixture was diluted with saturated NaHCO$_3$(aq) (10 ml) and then extracted with EtOAc (2×15 ml). The combined extracts were dried over MgSO$_4$, filtered and concentrated in vacuo. The residue was dissolved in DCM (2 ml) and treated with TFA (1 ml). The resultant mixture was stirred at RT for 1 h, then concentrated in vacuo. To remove residual TFA, the residue was thrice resuspended in toluene (20 ml) and concentrated in vacuo. The residue was purified by preparative HPLC (Gilson, Basic (0.1% Ammonium Bicarbonate), Basic, Waters X-Bridge Prep-C18, 5 µm, 19×50 mm column, 20-50% MeCN in Water) to afford the title compound (27 mg, 0.051 mmol) as a white solid. LCMS (Method 1): m/z 525 (M+H)$^+$; 523 (M−H)$^-$, at 1.45 min. $^1$H NMR (400 MHz, DMSO-d$_6$) δ 10.28 (s, 1H), 8.80 (d, J=2.4 Hz, 1H), 8.10 (d, J=2.4 Hz, 1H), 7.45-7.28 (m, 5H), 7.28-7.13 (m, 4H), 4.38-4.20 (m, 1H), 3.19-3.11 (m, 2H), 2.27 (d, J=6.8 Hz, 2H), 2.25-2.16 (m, 2H), 1.91-1.43 (m, 10H), 1.34 (s, 6H), 1.23-1.04 (m, 3H).

Example 29

N-(6-(4-(2-aminopropan-2-yl)phenyl)-5-phenylpyridin-3-yl)-2-(trans-4-(2-cyclopropylacetamido)cyclohexyl)acetamide

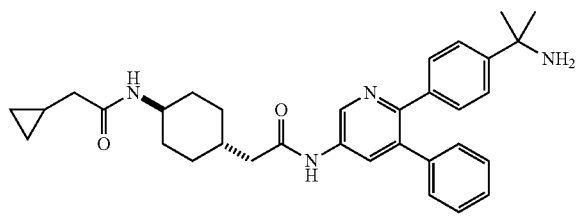 [SMILES: CC(C)(N)c1ccc(-c2ncc(NC(=O)C[C@H]3CC[C@H](NC(=O)CC4CC4)CC3)cc2-c2ccccc2)cc1]

Step 1: tert-butyl (2-(4-(5-(2-(trans-4-(2-cyclopropylacetamido)cyclohexyl)acetamido)-3-phenylpyridin-2-yl)phenyl)propan-2-yl)carbamate: A mixture of 2-cyclopropylacetic acid (7.71 µl, 0.083 mmol), DIPEA (29.0 µl, 0.166 mmol) and HATU (31.5 mg, 0.083 mmol) in DMF (2 ml) was stirred at RT for 30 min. The mixture treated with a solution of the product from Example 24 Step 2 (30 mg, 0.055 mmol) in DMF (1 ml) and stirred at RT for 18 h, then heated at 50° C. for 4 days. The reaction mixture was cooled to RT, treated with a pre-mixed solution of 2-cyclopropylacetic acid (7.71 µl, 0.083 mmol), HATU (31.5 mg, 0.083 mmol) and DIPEA (29.0 µl, 0.166 mmol) in DMF (1 ml), and then heated at 50° C. for 5 days. The reaction mixture was cooled to RT, diluted with water (15 ml) and the resultant precipitate filtered, washing with water (50 ml). The solid was dissolved in DCM (20 ml), dried over MgSO$_4$, filtered and concentrated in vacuo. The crude product was purified by column chromatography (4 g cartridge, 0-5% (0.7 M NH$_3$ in MeOH)/DCM) to afford the title compound (9 mg, 0.013 mmol, 93% purity) as a clear colourless glass. LCMS (Method 1): m/z 625 (M+H)$^+$ at 2.34 min. $^1$H NMR (400 MHz, Chloroform-d) δ 9.13 (br s, 1H), 8.73 (br s, 1H), 8.36 (br s, 1H), 7.30-7.15 (m, 9H), 5.87 (d, J=8.3 Hz, 1H), 4.89 (br s, 1H), 3.86-3.73 (m, 1H), 2.36-2.35 (m, 2H), 2.14-2.13 (m, 2H), 2.04-1.87 (m, 5H), 1.56 (s, 6H), 1.49-1.04 (m, 13H), 0.96-0.89 (m, 1H), 0.61-0.55 (m, 2H), 0.19-0.15 (m, 2H). The compound contained 7% w/w residual DCM. This material was used in subsequent reactions without further drying.

Step 2: N-(6-(4-(2-aminopropan-2-yl)phenyl)-5-phenylpyridin-3-yl)-2-(trans-4-(2-cyclopropylacetamido)cyclohexyl)acetamide: The title compound (7.4 mg, 0.013 mmol, 93% purity) was isolated as a white solid from the reaction of the product from Step 1 above (9 mg, 0.013 mmol, 93% purity) and 90% (v/v) TFA in water (0.5 ml) using essentially the same procedure as in Example 1 Step 7, except the reaction mixture was stirred for 3 h. LCMS (Method 1): m/z 525 (M+H)$^+$ at 1.57 min. $^1$H NMR (400 MHz, Methanol-d$_4$) δ 8.82 (d, J=2.5 Hz, 1H), 8.14 (d, J=2.5 Hz, 1H), 7.43-7.37 (m, 2H), 7.34-7.25 (m, 5H), 7.22-7.16 (m, 2H), 3.69-3.58 (m, 1H), 2.35 (d, J=6.7 Hz, 2H), 2.05 (d, J=7.1 Hz, 2H), 1.98-1.82 (m, 5H), 1.54 (s, 6H), 1.35-1.15 (m, 4H), 1.07-0.96 (m, 1H), 0.55-0.47 (m, 2H), 0.19-0.15 (m, 2H).

Example 30

N-(6-(4-(2-aminopropan-2-yl)phenyl)-5-phenylpyridazin-3-yl)-2-(trans-4-(N-methylacetamido)cyclohexyl)acetamide

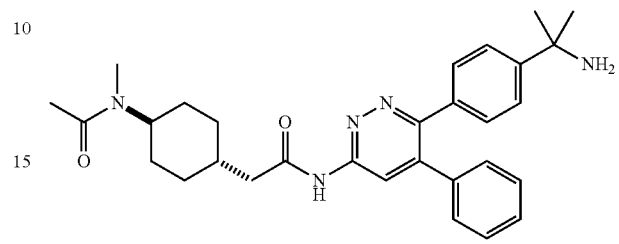

Step 1: tert-butyl (2-(4-(6-amino-4-phenylpyridazin-3-yl)phenyl)propan-2-yl)carbamate: The title compound (105 mg) was isolated as an offwhite solid from the reaction of 6-chloro-5-phenylpyridazin-3-amine (111 mg, 0.540 mmol, prepared according to US2008/0045536), the product of Intermediate 2 Step 2 (215 mg, 0.594 mmol), tetrakis(triphenylphosphine)palladium(0) (62.4 mg, 0.054 mmol) and 2 M Na$_2$CO$_3$(aq) (607 µl, 1.21 mmol) in dioxane (15 ml) using essentially the same procedure as in Intermediate 3 Step 2, except, after work-up, the product was partially purified by column chromatography (12 g cartridge, 0-100% EtOAc/isohexane) and used in subsequent reactions without further purification.

Step 2: N-(6-(4-(2-aminopropan-2-yl)phenyl)-5-phenylpyridazin-3-yl)-2-(trans-4-(N-methylacetamido)cyclohexyl)acetamide: A stirred solution of the product from Example 1 Step 5 (39.5 mg) and HATU (141 mg, 0.371 mmol) in DMF (5 ml) was treated with DIPEA (107 µl, 0.649 mmol) and the resultant mixture stirred at RT for 30 min. The product from Step 1 above (50 mg) was added and the resultant mixture was heated at 50° C. overnight. The mixture was diluted with saturated NaHCO$_3$(aq) (100 ml) and extracted with EtOAc (3×50 ml). The combined extracts were washed sequentially with water (3×50 ml) and brine (50 ml), dried over MgSO$_4$, filtered and concentrated in vacuo. The residue was dissolved in DCM (2 ml) and treated with TFA (1 ml) and stirred at RT for 1 h. The resultant mixture was concentrated in vacuo and, to remove residual TFA, the residue was twice resuspended in toluene (5 ml) and concentrated in vacuo. The residue was purified by preparative HPLC (Gilson 215, Waters X-Bridge Prep-C18, 20-40% MeCN in 10 mM ammonium bicarbonate(aq)), followed by column chromatography (12 g cartridge, 0-10% (7 M NH$_3$ in MeOH) in DCM) to afford the title compound (8 mg, 0.016 mmol, 99% purity) as a white solid. $^1$H NMR (400 MHz, DMSO-d$_6$) (two rotamers in a 3:2 ratio) δ 11.25 (d, J=6.4 Hz, 1H), 8.35 (d, J=1.9 Hz, 1H), 7.47 (d, J=8.5 Hz, 2H), 7.42-7.35 (m, 3H), 7.30-7.24 (m, 4H), 4.30-4.17 (m, 1H, major), 3.62-3.49 (m, 1H, minor), 2.79 (s, 3H, major), 2.67 (s, 3H, minor), 2.46-2.37 (m, 2H), 2.02 (s, 3H, minor), 1.96 (s, 3H, major), 1.88-1.72 (m, 3H), 1.69-1.43 (m, 4H), 1.35 (s, 6H), 1.28-1.6 (m, 2H).

Example 31

N-(6-(4-(2-aminopropan-2-yl)-3-fluorophenyl)-5-phenylpyridin-3-yl)-2-(trans-4-(N-methylacetamido)cyclohexyl)acetamide

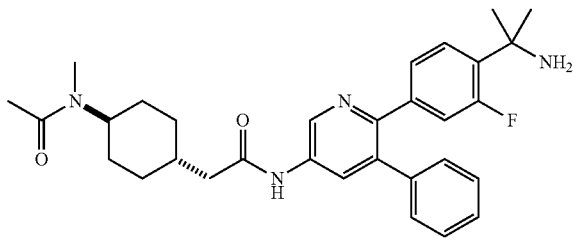 [SMILES: CC(=O)N(C)[C@H]1CC[C@H](CC(=O)Nc2cnc(-c3ccc(C(C)(C)N)c(F)c3)c(-c3ccccc3)c2)CC1]

Step 1: tert-butyl (2-(2-fluoro-4-(5-(2-(trans-4-(N-methylacetamido)cyclohexyl)acetamido)-3-phenylpyridin-2-yl)phenyl)propan-2-yl)carbamate: The title compound (59 mg) was isolated as a white solid from the reaction of Intermediate 19 (50 mg, 0.191 mmol, 96% purity), the product from Example 1 Step 5 (37.9 mg), DIPEA (62.2 μl, 0.356 mmol) and HATU (90 mg, 0.237 mmol) in a mixture of THF (2 ml) using essentially the same procedure as in Example 1 Step 6, except the reaction mixture was heated at 50° C. for 18 h and then worked up. This material was used directly in subsequent reactions without analysis.

Step 2: N-(6-(4-(2-aminopropan-2-yl)-3-fluorophenyl)-5-phenylpyridin-3-yl)-2-(trans-4-(N-methylacetamido)cyclohexyl)acetamide: The product from Step 1 above (59 mg) was dissolved in DCM (5 ml) and treated with TFA (0.5 ml, 6.49 mmol). The resultant mixture was stirred at RT for 2.5 h. The reaction mixture was concentrated in vacuo. To remove residual TFA, the residue was thrice resuspended in toluene (20 ml) and concentrated in vacuo. The residue was loaded onto a column of SCX in MeOH. The column was washed with MeOH and the product was eluted with a 0.7 M solution of ammonia in MeOH. The solvent was removed in vacuo to afford the title compound (38 mg, 0.073 mmol, 99% purity) a white solid. LCMS (Method 1): m/z 517 (M+H)$^+$ at 1.39 min. $^1$H NMR (400 MHz, DMSO-d$_6$) δ 10.29 (s, 1H), 8.81 (s, 1H), 8.11 (s, 1H), 7.47-7.29 (m, 4H), 7.29-7.15 (m, 2H), 7.08-6.90 (m, 2H), 4.33-4.14 (m, 1H, major), 3.65-3.46 (m, 1H, minor), 2.79 (s, 3H, major), 2.66 (s, 3H, minor), 2.27 (dd, J=6.8, 3.6 Hz, 2H), 2.01 (s, 3H, minor), 1.96 (s, 3H, major), 1.86-1.67 (m, 3H), 1.67-1.43 (m, 4H), 1.40 (s, 6H), 1.33-1.03 (m, 2H).

Example 32

N-(6-(4-(trans-1-amino-3-fluorocyclobutyl)phenyl)-5-phenylpyridin-3-yl)-2-(trans-4-(N-methylacetamido)cyclohexyl)acetamide

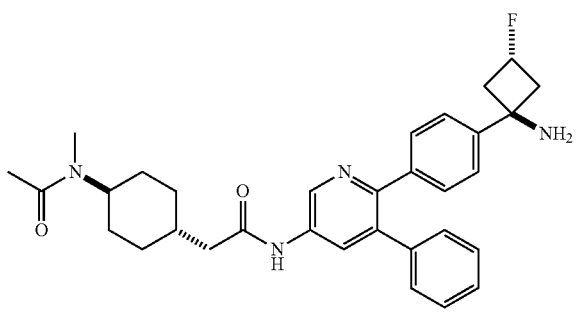 [SMILES: CC(=O)N(C)[C@H]1CC[C@H](CC(=O)Nc2cnc(-c3ccc([C@]4(N)C[C@H](F)C4)cc3)c(-c3ccccc3)c2)CC1]

Step 1: tert-butyl (trans-3-fluoro-1-(4-(5-(2-(trans-4-(N-methylacetamido)cyclohexyl)acetamido)-3-phenylpyridin-2-yl)phenyl)cyclobutyl)carbamate: The title compound (40 mg) was isolated as a white solid from the reaction of Intermediate 13 (30 mg), the product from Example 1 Step 5 (29.5 mg), DIPEA (80 μl, 0.484 mmol) and HATU (105 mg, 0.277 mmol) in DMF (5 ml) using essentially the same procedure as in Example 5 Step 1. This material was used in subsequent reactions without analysis.

Step 2: N-(6-(4-(trans-1-amino-3-fluorocyclobutyl)phenyl)-5-phenylpyridin-3-yl)-2-(trans-4-(N-methylacetamido)cyclohexyl)acetamide: The title compound (6 mg, 0.011 mmol, 95% purity) was isolated as a white solid from the reaction of the product from Step 1 above (40 mg) with TFA (0.5 ml) in DCM (2 ml) using essentially the same procedure as in Example 2 Step 4. LCMS (Method 1): m/z 529 (M+H)+, 527 (M−H)$^-$ at 1.42 min. $^1$H NMR (400 MHz, DMSO-d$_6$) δ 10.26 (br s, 1H), 8.80 (br s, 1H), 8.11 (br s, 1H), 7.40-7.28 (m, 3H), 7.28-7.15 (m, 6H), 5.33 (dp, J=56.7, 6.6 Hz, 1H), 4.33-4.16 (m, 1H, major), 3.64-3.46 (m, 1H, minor), 2.80 (s, 3H, major), 2.67 (s, 3H, minor), 2.45-2.23 (m, 4H), 2.23-2.07 (m, 2H), 2.02 (s, 3H, minor), 1.96 (s, 3H, major), 1.90-1.69 (m, 3H), 1.69-1.39 (m, 4H), 1.29-0.91 (m, 2H).

Example 33

N-(5-(4-(1-aminocyclobutyl)phenyl)-4-phenylpyridin-2-yl)-2-(trans-4-(N-methylacetamido)cyclohexyl)acetamide

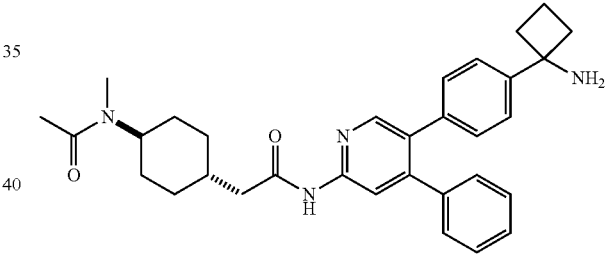

Step 1: tert-butyl (1-(4-(6-(2-(trans-4-(N-methylacetamido)cyclohexyl)acetamido)-4-phenylpyridin-3-yl)phenyl)cyclobutyl)carbamate: A suspension of the product from Example 1 Step 5 (154 mg) in DCM (2 ml) was treated with 1-chloro-N,N,2-trimethyl-1-propenylamine (96 μl, 0.722 mmol) and the resultant mixture stirred at RT for 2 h. The mixture was treated with a solution of Intermediate 20 (100 mg, 0.236 mmol, 98% purity) and DIPEA (126 μl, 0.722 mmol) in DCM (1 ml) and the resultant mixture stirred at RT for 3 days. The mixture was concentrated in vacuo and the residue was triturated with water (5 ml) and the resultant solid filtered, washing with water (50 ml). The solid was dissolved in DCM (20 ml), dried over MgSO$_4$, filtered and concentrated in vacuo. The residue was pre-absorbed onto SiO$_2$ and purified by column chromatography (12 g cartridge, 0-8% (0.7 M NH$_3$ in MeOH)/DCM) to afford the title compound (125 mg, 0.203 mmol, 99% purity) as a clear colourless glass. HPLC (Method 1): R$_T$ 2.62 min.

Step 2: N-(5-(4-(1-aminocyclobutyl)phenyl)-4-phenylpyridin-2-yl)-2-(trans-4-(N-methylacetamido)cyclohexyl)acetamide: The title compound (25 mg, 0.048 mmol, 99% purity) was isolated as a white crystalline solid from the reaction of the product from Step 1 above (125 mg, 0.203 mmol, 99% purity) with formic acid (0.5 ml, 13 mmol) using essentially the same procedure as in Example 20 Step 4, except the product was purified by preparative HPLC (Waters FractionLynx, Waters X-Bridge Prep-C18, 5 μm, 19×50 mm column, 35-65% MeCN in 10 mM ammonium bicarbonate(aq)). LCMS (Method 2): m/z 511 (M+H)⁺ at 2.07 min. ¹H NMR (400 MHz, DMSO-d₆) δ 10.61 (d, J=6.9 Hz, 1H), 8.32 (br s, 1H), 8.17 (d, J=1.8 Hz, 1H), 7.41-7.27 (m, 5H), 7.23-7.14 (m, 2H), 7.14-7.05 (m, 2H), 4.22 (p, J=8.6 Hz, 1H, major), 3.62-3.48 (m, 1H, minor), 2.79 (s, 3H, major), 2.67 (s, 3H, minor), 2.40-2.26 (m, 4H), 2.13-1.89 (m, 6H), 1.85-1.39 (m, 8H), 1.25-1.00 (m, 2H).

Example 34 methyl (trans-4-(2-((6-(4-(2-aminopropan-2-yl)phenyl)-5-phenylpyridin-3-yl)amino)-2-oxoethyl)cyclohexyl)(methyl)carbamate

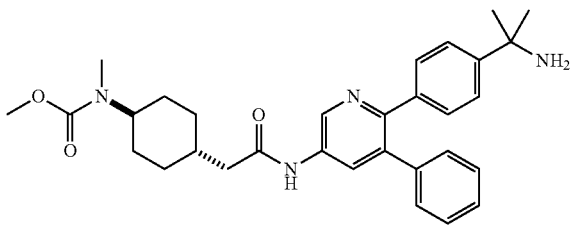

A stirred solution of the product from Example 4 Step 3 (50 mg, 0.090 mmol) and Et₃N (63 μl, 0.449 mmol) in DCM (5 ml) was treated dropwise with methyl chloroformate (8.33 μl, 0.108 mmol) and the resultant mixture stirred at RT for 3 h. The mixture was diluted with DCM (50 ml) and washed sequentially with water (50 ml) and brine (50 ml). The organic phase was dried over MgSO₄, filtered and concentrated in vacuo. The residue was dissolved in DCM (5 ml) and treated with TFA (1 ml). The resultant mixture was stirred at RT for 1 h and then concentrated in vacuo. To remove residual TFA, the residue was thrice resuspended in toluene (50 ml) and concentrated in vacuo. The residue was purified by preparative HPLC (Waters FractionLynx, Waters X-Bridge Prep-C18, 5 μm, 19×50 mm column, 35-65% MeCN in 10 mM ammonium bicarbonate(aq)) to afford the title compound (16 mg, 0.031 mmol) as a white solid. LCMS (Method 1): m/z 515 (M+H)⁺, 513 (M−H)⁻, at 1.51 min. ¹H NMR (400 MHz, DMSO-d₆) δ 10.26 (s, 1H), 8.80 (d, J=2.4 Hz, 1H), 8.10 (d, J=2.4 Hz, 1H), 7.43-7.29 (m, 5H), 7.23-7.17 (m, 4H), 3.93-3.68 (br, 1H), 3.58 (s, 3H), 2.71 (s, 3H), 2.27 (d, J=6.8 Hz, 2H), 1.92-1.70 (m, 3H), 1.67-1.45 (m, 4H), 1.33 (s, 6H), 1.23-1.04 (m, 2H).

Example 35

N-(6-(4-(2-aminopropan-2-yl)phenyl)-5-phenylpyridin-3-yl)-2-(4-(methyl(3-methyloxetan-3-yl)amino)cyclohexyl)acetamide

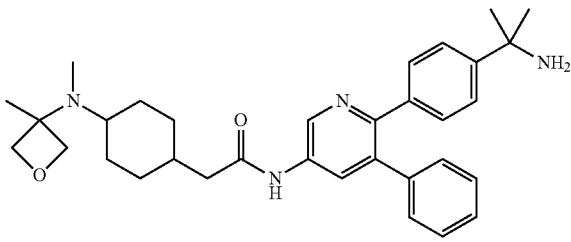 [SMILES: CN(C1CCC(CC(=O)Nc2cnc(-c3ccc(C(C)(C)N)cc3)c(-c3ccccc3)c2)CC1)C1(C)COC1]

Step 1: methyl 2-(4-((3-methyloxetan-3-yl)amino)cyclohexyl)acetate: A mixture of 3-methyloxetan-3-amine (104 mg, 1.20 mmol) and methyl 2-(4-oxocyclohexyl)acetate (170 mg, 1.00 mmol) in THF (20 ml) was treated with titanium(IV) isopropoxide (0.585 ml, 2.00 mmol) and stirred at RT under an atmosphere of N₂ for 20 h. MeOH (2 ml) was added and stirring was continued for 30 min, then sodium borohydride (98 mg, 2.59 mmol) was added. The resultant mixture was stirred at RT for 1 h. The mixture was partitioned between DCM (100 ml) and saturated NaHCO₃(aq) (100 ml). The phases were separated and the organic phase was washed with brine (50 ml), dried over MgSO₄ and concentrated in vacuo. The residue was purified by column chromatography (12 g cartridge, 0-10% (0.7 M NH₃/MeOH solution)/DCM) to afford the title compound (213 mg) as a colourless oil. This material was used in subsequent reactions without analysis.

Step 2: methyl 2-(4-(methyl(3-methyloxetan-3-yl)amino)cyclohexyl)acetate: A solution of the product from Step 1 above (211 mg) and formaldehyde(aq) (0.073 ml, 0.979 mmol, 37% w/w) in methanol (4 ml) was stirred under an atmosphere of N₂ and treated with acetic acid (2 drops). The resultant mixture was stirred for 30 min, then sodium cyanoborohydride (77 mg, 1.224 mmol) was added and the mixture was stirred at RT overnight. The mixture was concentrated in vacuo and the residue partitioned between saturated NaHCO₃(aq) (100 ml) and EtOAc (50 ml). The phases were separated and the aqueous phase extracted with EtOAc (50 ml). The combined organic phases were washed with brine (50 ml), dried over MgSO₄, filtered, and concentrated in vacuo. The residue was purified by column chromatography (12 g cartridge, 0-10% (0.7 M NH₃/MeOH solution)/DCM) to afford the title compound (192 mg) as a colorless oil. This material was used in subsequent reactions without analysis.

Step 3: lithium 2-(4-(methyl(3-methyloxetan-3-yl)amino)cyclohexyl)acetate: The title compound (175 mg) was isolated as a white solid from the reaction of the product of Step 2 above (190 mg) with LiOH (35.6 mg, 1.49 mmol) using essentially the same procedure as in Example 26 Step 2. This material was used in subsequent reactions without purification.

Step 4: N-(6-(4-(2-aminopropan-2-yl)phenyl)-5-phenylpyridin-3-yl)-2-(4-(methyl(3-methyloxetan-3-yl)amino)cyclohexyl)acetamide: The title compound (18 mg, 0.034 mmol) was isolated as a white solid from the reaction of the product of Step 3 above (85 mg), Intermediate 2 (50 mg, 0.124 mmol), HATU (141 mg, 0.372 mmol) and DIPEA (130 μl, 0.743 mmol) in THF (4 ml) using essentially the same procedure as in Example 28 Step 3. LCMS (Method 1): m/z 527 (M+H)⁺, 525 (M−H)⁻, at 1.00 min. ¹H NMR (400 MHz, DMSO-d₆) δ 10.26 (s, 1H), 8.80 (d, J=2.4 Hz, 1H), 8.10 (d, J=2.4 Hz, 1H), 7.48-7.16 (m, 9H), 4.41 (d, J=5.3 Hz, 2H), 4.04 (d, J=5.4 Hz, 2H), 2.23 (d, J=6.7 Hz, 2H), 2.18-2.06 (m, 1H), 1.98 (s, 3H), 1.80-1.55 (m, 5H), 1.43 (s, 6H), 1.34 (s, 3H), 1.30-1.16 (m, 2H), 1.13-0.94 (m, 2H).

Example 36

N-(6-(4-(3-aminooxetan-3-yl)phenyl)-5-phenylpyridin-3-yl)-2-(4,4-dimethoxycyclohexyl)acetamide

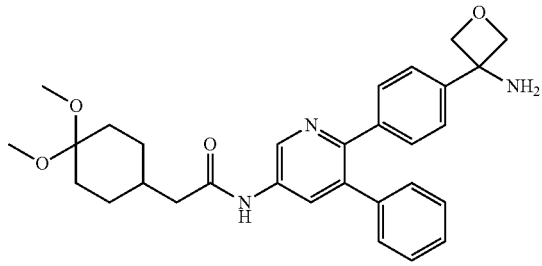 [SMILES: COC1(OC)CCC(CC(=O)Nc2cnc(-c3ccc(C4(N)COC4)cc3)c(-c3ccccc3)c2)CC1]

Step 1: benzyl (3-(4-(5-(2-(1,4-dioxaspiro[4.5]decan-8-yl)acetamido)-3-phenylpyridin-2-yl)phenyl)oxetan-3-yl)carbamate: The title compound (29 mg, 0.044 mmol, 96% purity) was isolated as a yellow solid from the reaction of Intermediate 12 (40 mg, 0.079 mmol, 89% purity), 2-(1,4-dioxaspiro[4.5]decan-8-yl)acetic acid (21.3 mg, 0.106 mmol, prepared according to WO2002008244), T3P (157 µl, 0.266 mmol, 50% w/w in EtOAc), Et₃N (74.1 µl, 0.532 mmol) in EtOAc (1.5 ml) using essentially the same procedure as in Example 4 Step 2. LCMS (Method 1): m/z 634 (M+H)⁺ at 2.30 min. ¹H NMR (400 MHz, DMSO-d₆) δ 10.27 (s, 1H), 8.81 (d, J=2.4 Hz, 1H), 8.46 (s, 1H), 8.13 (d, J=2.4 Hz, 1H), 7.47-7.14 (m, 14H), 5.01 (s, 2H), 4.82 (d, J=6.6 Hz, 2H), 4.66 (d, J=6.6 Hz, 2H), 3.85 (s, 4H), 2.30 (d, J=7.1 Hz, 2H), 1.91-1.80 (m, 1H), 1.76-1.62 (m, 4H), 1.52-1.45 (m, 2H), 1.35-1.21 (m, 2H).

Step 2: N-(6-(4-(3-aminooxetan-3-yl)phenyl)-5-phenylpyridin-3-yl)-2-(4,4-dimethoxycyclohexyl)acetamide:
The product from Step 1 above (28.4 mg, 0.043 mmol, 96% purity) was dissolved in EtOH (1 ml) and treated with palladium (2.39 mg, 5% w/w on carbon, Type 87L paste). The vessel was purged with N₂ and then further purged with H₂. The mixture was stirred at RT under an atmosphere of H₂ (5 bar pressure) for 3 h. The reaction mixture was filtered through a glass microfibre filter, washing with MeOH. The mixture was loaded onto a column of SCX. The column was washed with MeOH and the product was eluted with a 0.7 M solution of ammonia in MeOH. The solvent was removed in vacuo and the residue dissolved in MeCN and passed through a 45 µM filter and then concentrated in vacuo to afford a white solid (16.8 mg). The solid was redissolved in MeOH and loaded onto a column of SCX. The column was washed with MeOH and the product was eluted with a 0.7 M solution of ammonia in MeOH. The solvent was removed in vacuo and the residue treated with TFA/water and stirred for 30 min. The mixture was loaded onto a column of SCX. The column was washed with MeOH and the product was eluted with a 0.7 M solution of ammonia in MeOH. The solvent was removed in vacuo to afford the title compound (9.5 mg, 0.017 mmol, 90% purity) as a white solid. LCMS (Method 1): m/z 502 (M+H)⁺, at 1.36 min. ¹H NMR (400 MHz, DMSO-d₆) δ 10.26 (s, 1H), 8.80 (d, J=2.4 Hz, 1H), 8.11 (d, J=2.4 Hz, 1H), 7.46-7.42 (m, 2H), 7.37-7.27 (m, 5H), 7.24-7.18 (m, 2H), 4.68 (d, J=6.1 Hz, 2H), 4.64 (d, J=6.1 Hz, 2H), 3.07 (s, 3H), 3.05 (s, 3H), 2.29 (d, J=7.2 Hz, 2H), 1.98-1.88 (m, 2H), 1.87-1.75 (m, 1H), 1.65-1.57 (m, 2H), 1.35-1.25 (m, 2H), 1.20-1.10 (m, 2H).

Example 37

N-(6-(4-(3-aminooxetan-3-yl)phenyl)-5-phenylpyridin-3-yl)-2-(trans-4-(cyclopropanesulfonamido)cyclohexyl)acetamide

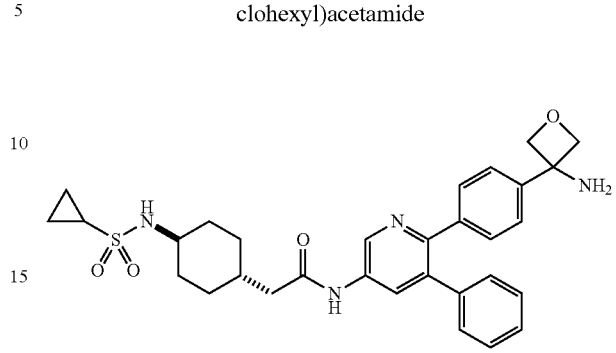

Step 1: Ethyl 2-(trans-4-(cyclopropanesulfonamido)cyclohexyl)acetate: A stirred solution of ethyl 2-(trans-4-aminocyclohexyl)acetate hydrochloride (250 mg, 1.13 mmol) in THF (5 ml) was treated with DIPEA (433 µl, 2.48 mmol), followed by cyclopropanesulfonyl chloride (137 µl, 1.35 mmol). The resultant mixture was stirred at RT overnight. Additional cyclopropanesulfonyl chloride (137 µl, 1.35 mmol) and DIPEA (433 µl, 2.48 mmol) were added and the mixture was treated with NMP (500 µL) to form a solution, which was heated at 50° C. overnight. The reaction mixture was concentrated in vacuo and then partitioned between EtOAc (10 ml) and saturated NaHCO₃(aq) (5 ml). The phases were separated and the aqueous phase was extracted with EtOAc (2×15 ml) and DCM (15 ml). The combined organic phases were dried over MgSO4, filtered and concentrated in vacuo. The residue was purified by column chromatography (12 g cartridge, 0-60% EtOAc/isohexane) to afford the title compound (437 mg, 0.921 mmol, 61% purity) as an orange oil. ¹H NMR (400 MHz, DMSO-d₆) δ 7.03 (d, J=8.0 Hz, 1H), 4.05 (q, J=7.1 Hz, 2H), 3.05-3.03 (m, 1H), 2.68-2.72 (m, 4H), 2.56-2.50 (m, 1H, obscured by solvent), 1.68 (d, J=13.1 Hz, 2H), 1.64-1.51 (m, 1H), 1.31-1.15 (m, 2H), 1.18 (t, J=7.1 Hz, 3H), 1.10-0.96 (m, 2H), 0.95-0.84 (m, 4H). The compound contained 39% w/w residual NMP. This material was used in subsequent reactions without further drying.

Step 2: 2-(trans-4-(cyclopropanesulfonamido)cyclohexyl)acetic acid: A stirred mixture of the product from Step 1 above (326 mg, 0.687 mmol, 61% purity) in THF (2 ml), water (500 µl) and MeOH (500 µl) was treated with LiOH (32.4 mg, 1.35 mmol). The resultant mixture was stirred overnight. The mixture was treated with HCl (680 µL, 2.7 mmol, 4 M in dioxane) and then concentrated in vacuo. To remove residual water, the residue was azeotroped twice with toluene. The residue was dissolved in THF (5 ml) and passed through a column of SCX, eluting with THF. The eluant was concentrated in vacuo to afford the title compound (348 mg) as an orange solid. This material was used in subsequent reactions without purification.

Step 3: benzyl (3-(4-(5-(2-(trans-4-(cyclopropanesulfonamido)cyclohexyl)acetamido)-3-phenylpyridin-2-yl)phenyl)oxetan-3-yl)carbamate: The title compound (33.6 mg, 0.042 mmol, 87% purity) was isolated as a yellow solid from the reaction of Intermediate 12 (45 mg, 0.089 mmol, 89% purity), the product from Step 2 above (39.1 mg), T3P (176 µl, 0.299 mmol, 50% w/w in EtOAc), Et₃N (83 µl, 0.598 mmol) in EtOAc (5 ml) using essentially the same procedure as in Example 4 Step 2. LCMS (Method 1): m/z 695 (M+H)⁺ at 2.19 min. ¹H NMR (400 MHz, DMSO-d₆) δ 10.26 (s, 1H), 8.81 (d, J=2.4 Hz, 1H), 8.46 (s, 1H), 8.13 (d, J=2.4 Hz, 1H), 7.40-7.19 (m, 14H), 7.01 (d, J=7.9 Hz, 1H), 5.01 (s, 2H), 4.82 (d, J=6.7 Hz, 2H), 4.66 (d, J=6.6 Hz, 2H), 3.15-3.02 (m, 1H), 2.57-2.50 (m, 1H, obscured by solvent), 2.26 (d, J=6.7 Hz, 2H), 1.98-1.90 (m, 2H), 1.82-1.63 (m, 3H), 1.32-1.25 (m, 2H), 1.15-1.05 (m, 2H), 0.99-0.85 (m, 4H). The compound contained 11% w/w residual DCM and 2% w/w residual MeOH. This material was used in subsequent reactions without further drying.

Step 4: N-(6-(4-(3-aminooxetan-3-yl)phenyl)-5-phenylpyridin-3-yl)-2-(trans-4-(cyclopropanesulfonamido)cyclohexyl)acetamide: The product from Step 3 above (33.1 mg, 0.042 mmol, 87% purity) was dissolved in EtOH (1 ml) and MeOH (1 ml) and treated with palladium (2.5 mg, 5% w/w on carbon, Type 87L paste). The vessel was purged with N₂ and then further purged with H₂. The mixture was stirred at RT under an atmosphere of H₂ (5 bar pressure) for 3 h. Additional palladium (5% w/w on carbon, Type 87L paste) was added and mixture resubjected to the same conditions for 1 h. The reaction mixture was filtered through a glass microfibre filter, washing with MeOH. The mixture was loaded onto a column of SCX. The column was washed with MeOH and the product was eluted with a 0.7 M solution of ammonia in MeOH. The solvent was removed in vacuo and the residue dissolved in MeCN and passed through a 45 μM filter and then concentrated in vacuo to afford a white solid (19.5 mg). The crude product was purified by preparative HPLC (Varian PrepStar, Waters X-Bridge Prep-C18, 5 μm, 19×50 mm column, 20-50% MeCN in 10 mM ammonium bicarbonate(aq)) to afford the title compound (4 mg, 6.92 μmol, 97% purity) as a white solid. LCMS (Method 1): m/z 561 (M+H)⁺, at 1.31 min. ¹H NMR (400 MHz, DMSO-d₆) δ 10.26 (s, 1H), 8.80 (d, J=2.4 Hz, 1H), 8.12 (d, J=2.4 Hz, 1H), 7.47-7.42 (m, 2H), 7.40-7.32 (m, 3H), 7.32-7.27 (m, 2H), 7.24-7.18 (m, 2H), 7.01 (d, J=7.1 Hz, 1H), 4.65 (d, J=6.0 Hz, 2H), 4.61 (d, J=5.9 Hz, 2H), 3.13-3.03 (m, 1H), 2.56-2.50 (m, 1H, obscured by solvent), 2.26 (d, J=6.7 Hz, 2H), 1.97-1.87 (m, 2H), 1.86-1.66 (m, 3H), 1.32-1.22 (m, 2H), 1.14-1.03 (m, 2H), 0.99-0.84 (m, 4H).

Example 38

N-(6-(4-(1-aminocyclobutyl)phenyl)-5-(thiophen-3-yl)pyridin-3-yl)-2-(trans-4-morpholinocyclohexyl)acetamide

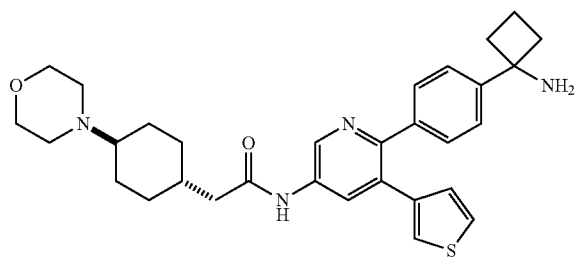 [SMILES: NC1(c2ccc(-c3ncc(NC(=O)C[C@H]4CC[C@H](N5CCOCC5)CC4)cc3-c3ccsc3)cc2)CCC1]

Step 1: Ethyl 2-(trans-4-morpholinocyclohexyl)acetate: A solution of ethyl 2-(trans-4-aminocyclohexyl)acetate hydrochloride (0.5 g, 2.26 mmol) in MeCN (20 ml) was treated with K₂CO₃ (0.779 g, 5.64 mmol) and 1-bromo-2-(2-bromoethoxy)ethane (0.340 ml, 2.71 mmol) and then heated at reflux for 18 h. The reaction mixture was cooled to RT and concentrated in vacuo. The residue was partitioned between water (10 ml) and DCM (10 ml) and passed through a phase separation cartridge. The organic phase was concentrated in vacuo to afford the title compound (656 mg, 2.18 mmol, 85% purity) as an orange oil. ¹H NMR (400 MHz, Methanol-d₄) δ 4.13 (q, J=7.1 Hz, 2H), 3.73-3.71 (m, 4H), 2.63-2.61 (m, 4H), 2.27-2.19 (m, 3H), 2.04-1.97 (m, 2H), 1.88-1.85 (m, 2H), 1.78-1.67 (m, 1H), 1.33-1.25 (m, 5H), 1.11-1.03 (m, 2H).

Step 2: 2-(trans-4-morpholinocyclohexyl)acetic acid: A mixture of the product from Step 1 above (656 mg, 2.18 mmol) in THF (15 ml) and MeOH (1 ml) was treated with 2 M LiOH(aq) (1.54 ml, 3.08 mmol) and the resultant mixture stirred at RT for 18 h. The mixture was acidified with 1M HCl(aq) and concentrated in vacuo. The crude product was loaded onto a column of SCX (5 g) in MeOH. The column was washed with MeOH and then the product was eluted with 0.7 M ammonia in MeOH. The solvent was removed in vacuo to afford the title compound (486 mg, 2.031 mmol, 95% purity) as a pale pink solid. ¹H NMR (400 MHz, Methanol-d₄) δ 3.93-3.79 (m, 4H), 3.06-2.96 (m, 4H), 2.83-2.64 (m, 1H), 2.19-2.06 (m, 4H), 2.01-1.92 (m, 2H), 1.81-1.69 (m, 1H), 1.44 (qd, J=12.5, 3.5 Hz, 2H), 1.11 (qd, J=13.1, 3.3 Hz, 2H).

Step 3: tert-butyl (1-(4-(5-(2-(trans-4-morpholinocyclohexyl)acetamido)-3-(thiophen-3-yl)pyridin-2-yl)phenyl)cyclobutyl)carbamate: The title compound (41 mg, 0.064 mmol, 99% purity) was isolated as an orange oil from the reaction of Intermediate 15 (50 mg, 0.113 mmol, 95% purity), the product from Step 2 above (81 mg, 0.338 mmol, 95% purity), DIPEA (124 μl, 0.712 mmol) and HATU (135 mg, 0.356 mmol) in THF (3 ml) using essentially the same procedure as in Example 1 Step 6, except the reaction mixture was heated at 50° C. overnight and then worked up. LCMS (Method 1): m/z 288 (M+2H—C₄H₈)⁺, 316 (M+2H)²⁺, 631 (M+H)⁺ at 2.44 min.

Step 4: N-(6-(4-(1-aminocyclobutyl)phenyl)-5-(thiophen-3-yl)pyridin-3-yl)-2-(trans-4-morpholinocyclohexyl)acetamide: The title compound (20 mg, 0.036 mmol, 96% purity) was isolated as a yellow solid from the reaction of the product from Step 3 above (41 mg, 0.064 mmol, 99% purity) and 90% (v/v) TFA in water (2 ml) using essentially the same procedure as in Example 1 Step 7. LCMS (Method 2): m/z 257.5 (M+2H—NH₃)²⁺, 266 (M+2H)²⁺, 531 (M+H)⁺ at 1.86 min. ¹H NMR (400 MHz, DMSO-d₆) δ 10.21 (s, 1H), 8.76 (d, J=2.4 Hz, 1H), 8.14 (d, J=2.4 Hz, 1H), 7.48 (dd, J=4.9, 2.9 Hz, 1H), 7.43 (dd, J=3.0, 1.3 Hz, 1H), 7.37-7.33 (m, 2H), 7.27-7.24 (m, 2H), 6.75 (dd, J=4.9, 1.3 Hz, 1H), 3.56-3.52 (m, 4H), 2.47-2.42 (m, 4H), 2.40-2.32 (m, 2H), 2.24 (d, J=7.0 Hz, 2H), 2.17-1.92 (m, 4H), 1.87-1.57 (m, 6H), 1.27-0.90 (m, 4H).

Example 39

N-(6-(4-(1-aminocyclobutyl)phenyl)-5-(thiophen-3-yl)pyridin-3-yl)-2-(trans-4-((2-methoxyethyl)(methyl)amino)cyclohexyl)acetamide

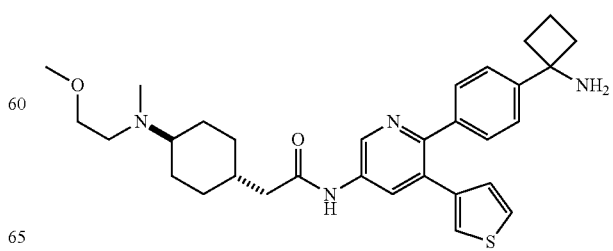

125

Step 1: Ethyl 2-(trans-4-((2-methoxyethyl)(methyl) amino)cyclohexyl)acetate: A solution of the product from Example 1 Step 3 (330 mg, 1.66 mmol) in DMF (2 ml) was treated with DIPEA (723 µl, 4.14 mmol) and 1-bromo-2-methoxyethane (171 µl, 1.82 mmol) and the resultant mixture heated at 50° C. for 18 h. The mixture was cooled to RT, diluted with water (10 ml) and extracted with EtOAc (3×10 ml). The combined extracts were washed with brine, passed through a phase separation cartridge and concentrated in vacuo. The residue was loaded onto a column of SCX (5 g) in EtOH. The column was washed with EtOH and then the product was eluted with 1 M ammonia in EtOH. The solvent was removed in vacuo to afford the title compound (334 mg, 1.17 mmol, 90% purity) as a pale yellow oil. $^1$H NMR (400 MHz, Methanol-$d_4$) δ 4.13 (q, J=7.1 Hz, 2H), 3.50 (t, J=5.8 Hz, 2H), 3.35 (s, 3H), 2.68 (t, J=5.8 Hz, 2H), 2.43 (tt, J=12.0, 3.4 Hz, 1H), 2.31 (s, 3H), 2.21 (d, J=7.0 Hz, 2H), 1.94-1.78 (m, 4H), 1.78-1.65 (m, 1H), 1.39-1.26 (m, 2H), 1.25 (t, J=7.1 Hz, 3H), 1.17-0.98 (m, 2H).

Step 2: Lithium 2-(trans-4-((2-methoxyethyl)(methyl) amino)cyclohexyl)acetate: The title compound (415 mg) was isolated from the reaction of the product of Step 1 above (334 mg, 1.17 mmol, 90% purity) with LiOH (62.2 mg, 2.60 mmol) using essentially the same procedure as in Example 26 Step 2. This material was used in subsequent reactions without purification.

Step 3: tert-butyl (1-(4-(5-(2-(trans-4-((2-methoxyethyl) (methyl)amino)cyclohexyl)acetamido)-3-(thiophen-3-yl) pyridin-2-yl)phenyl)cyclobutyl)carbamate: The title compound (38 mg, 0.060 mmol) was isolated as a colourless oil from the reaction of Intermediate 15 (50 mg, 0.113 mmol, 95% purity), the product from Step 2 above (80 mg), DIPEA (124 µl, 0.712 mmol) and HATU (135 mg, 0.356 mmol) in THF (3 ml) using essentially the same procedure as in Example 1 Step 6, except the reaction mixture was heated at 50° C. overnight and then worked up. LCMS (Method 1): m/z 289 (M+2H—$C_4H_8$)$^{2+}$, 317 (M+2H)$^{2+}$ at 1.78 min.

Step 4: N-(6-(4-(1-aminocyclobutyl)phenyl)-5-(thiophen-3-yl)-2-(trans-4-((2-methoxyethyl)(methyl)amino)cyclo-hexyl)acetamide: The title compound (14 mg, 0.025 mmol, 94% purity) was isolated as a white solid from the reaction of the product from Step 3 above (38 mg, 0.060 mmol) and 90% (v/v) TFA in water (2 ml) using essentially the same procedure as in Example 1 Step 7. LCMS (Method 2): m/z 258.5 (M+2H—NH$_3$)$^{2+}$, 533 (M+H)$^+$ at 1.75 min. $^1$H NMR (400 MHz, DMSO-$d_6$) δ 10.25 (s, 1H), 8.79 (d, J=2.4 Hz, 1H), 8.16 (d, J=2.5 Hz, 1H), 7.51 (dd, J=4.9, 2.9 Hz, 1H), 7.46 (dd, J=2.9, 1.3 Hz, 1H), 7.44-7.33 (m, 4H), 6.78 (dd, J=5.0, 1.3 Hz, 1H), 3.40 (t, J=6.1 Hz, 2H, obscured by H$_2$O), 3.24 (s, 3H), 2.70-2.62 (m, 2H), 2.58-2.49 (m, 2H, obscured by solvent), 2.47-2.32 (m, 2H), 2.29-2.23 (m, 5H), 2.14-2.05 (m, 1H), 1.89-1.66 (m, 7H), 1.35-1.19 (m, 2H), 1.12-0.97 (m, 2H).

126

Example 40

N-(6-(4-(1-aminocyclobutyl)phenyl)-5-phenylpyridin-3-yl)-2-(1-(cyclopropylsulfonyl)piperidin-4-yl)-2-fluoroacetamide

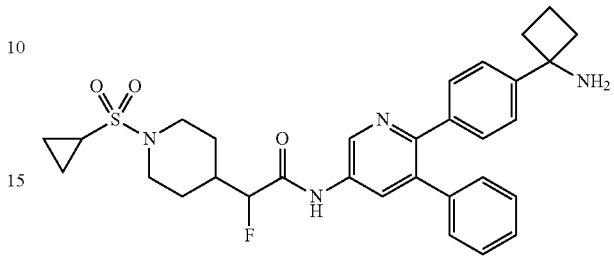

Step 1: benzyl 4-(2-ethoxy-1-fluoro-2-oxoethylidene)piperidine-1-carboxylate: A suspension of ethyl 2-(diethoxyphosphoryl)-2-fluoroacetate (419 µl, 2.07 mmol) in Et$_2$O (5 ml) was cooled to 0° C. whereupon sodium hydride (90 mg, 2.25 mmol, 60% w/w in mineral oil) was added portionwise. The resultant yellow mixture was allowed to warm to RT and after a further 10 min benzyl 4-oxopiperidine-1-carboxylate (438 mg, 1.877 mmol) was added. The mixture was then stirred at RT for 3 days. The reaction mixture was partitioned between water (30 ml) and Et$_2$O (30 ml), the phases separated and the aqueous was extracted with Et$_2$O (3×30 ml). The combined organic phases were washed with brine (20 ml), dried over MgSO$_4$, filtered and concentrated in vacuo. The residue was purified by column chromatography (40 g cartridge, 0-20% EtOAc/isohexane) to afford the title compound (422 mg, 1.25 mmol, 95% purity) as a colourless oil. LCMS (Method 1): m/z 322 (M+H)$^+$, at 2.45 min. $^1$H NMR (400 MHz, DMSO-$d_6$) δ 7.45-7.26 (m, 5H), 5.10 (s, 2H), 4.23 (q, J=7.1 Hz, 2H), 3.56-3.45 (m, 4H), 2.85-2.78 (m, 2H), 2.47-2.41 (m, 2H), 1.26 (t, J=7.1 Hz, 3H).

Step 2: ethyl 2-fluoro-2-(piperidin-4-yl)acetate: A solution of the product from Step 1 above (422 mg, 1.25 mmol, 95% purity) in EtOH (50 ml) was hydrogenated in a ThalesNano H-Cube® flow reactor (10% Pd/C, 30×4 mm, full hydrogen mode, 40° C., 1 ml/min flow rate, 2 passes). The mixture was concentrated in vacuo to afford the title compound (212 mg, 1.06 mmol, 95% purity). $^1$H NMR (400 MHz, DMSO-$d_6$) δ 4.91 (dd, J=48.6, 4.2 Hz, 1H), 4.19 (q, J=7.1 Hz, 1H), 2.95 (d, J=12.2 Hz, 2H), 2.49-2.36 (m, 2H), 1.95-1.82 (m, 1H), 1.58-1.53 (m, 1H), 1.45-1.36 (m, 1H), 1.34-1.13 (m, 2H), 1.23 (t, J=7.1 Hz, 3H).

Step 3: 2-(1-(cyclopropylsulfonyl)piperidin-4-yl)-2-fluoroacetic acid: A solution of cyclopropanesulfonyl chloride (123 µl, 1.22 mmol) and the product from Step 2 above (210 mg, 1.05 mmol, 95% purity) in DCM (5 ml) was treated with DIPEA (233 µl, 1.33 mmol). The resultant solution was stirred at RT for 18 h. The mixture was passed through a column of SCX, eluting with MeOH and then concentrated in vacuo. The residue was dissolved in a mixture of THF (3 ml), MeOH (1 ml) and water (2 ml) and then LiOH (26.6 mg, 1.11 mmol) was added. The resultant solution was stirred at RT for 18 h. The reaction mixture was acidified with 1 M citric acid(aq) (2 ml), diluted with water (5 ml) and extracted with DCM (3×5 ml). The combined organic phases were dried over MgSO$_4$, filtered and concentrated in vacuo to afford the title compound (92 mg, 0.312 mmol, 90% purity) as a pale yellow gum. $^1$H NMR (400 MHz, DMSO-d$_6$) δ 5.00 (ddd, J=62.7, 48.3, 4.1 Hz, 1H), 3.68-3.62 (m, 2H), 2.96-2.74 (m, 2H), 2.60-2.53 (m, 1H), 2.14-1.88 (m, 1H), 1.82-1.75 (m, 1H), 1.65-1.58 (m, 1H), 1.55-1.32 (m, 1H), 1.18-0.85 (m, 5H).

Step 4: tert-butyl (1-(4-(5-(2-(1-(cyclopropylsulfonyl)piperidin-4-yl)-2-fluoroacetamido)-3-phenylpyridin-2-yl)phenyl)cyclobutyl)carbamate: A solution of the product from Step 3 above (92 mg, 0.312 mmol, 90% purity) and HATU (145 mg, 0.381 mmol) in DMF (2 ml) was treated with DIPEA (72.7 μl, 0.416 mmol) and the resultant red solution was stirred for 30 min at RT whereupon Intermediate 8 (144 mg, 0.347 mmol) was added and the mixture was stirred at RT for 18 h. Additional HATU (145 mg, 0.381 mmol) and DIPEA (72.7 μl, 0.416 mmol) were added and the reaction mixture heated at 50° C. for 2 h. The mixture was cooled to RT, diluted with EtOAc (20 ml) and then washed sequentially with saturated NaHCO$_3$(aq) (10 ml), water (10 ml) and brine (10 ml). The organic phase was then dried over MgSO$_4$, filtered and concentrated in vacuo. The residue was purified by preparative HPLC (Gilson 215, Waters X-Bridge Prep-C18, 5 μm, 19×50 mm column, 40-70% MeCN in 10 mM ammonium bicarbonate(aq)) to afford the title compound (29 mg, 0.042 mmol, 95% purity). LCMS (Method 1): m/z 663 (M+H)$^+$, at 2.56 min.

Step 5: N-(6-(4-(1-aminocyclobutyl)phenyl)-5-phenylpyridin-3-yl)-2-(1-(cyclopropylsulfonyl)piperidin-4-yl)-2-fluoroacetamide: The title compound (22 mg, 0.037 mmol, 95% purity) was isolated from the reaction of the product from Step 4 above (29 mg, 0.042 mmol, 95% purity) with TFA (0.5 ml) in DCM (2 ml) using essentially the same procedure as in Example 9 Step 2. LCMS (Method 1): m/z 563 (M+H)$^+$, 561 (M−H)$^-$, at 1.55 min. $^1$H NMR (400 MHz, DMSO-d$_6$) δ 10.53 (s, 1H), 8.94 (d, J=2.4 Hz, 1H), 8.17 (d, J=2.4 Hz, 1H), 7.40-7.17 (m, 9H), 5.08 (dd, J=48.5, 4.4 Hz, 1H), 3.71-3.63 (m, 2H), 2.93-2.77 (m, 2H), 2.64-2.53 (m, 1H), 2.41-2.33 (m, 2H), 2.20-1.92 (m, 4H), 1.87-1.80 (m, 1H), 1.77-1.71 (m, 1H), 1.68-1.47 (m, 3H), 1.00-0.89 (m, 4H).

Example 41

2-(trans-4-acetamidocyclohexyl)-N-(6-(4-(1-aminocyclobutyl)phenyl)-5-phenylpyridin-3-yl)propanamide

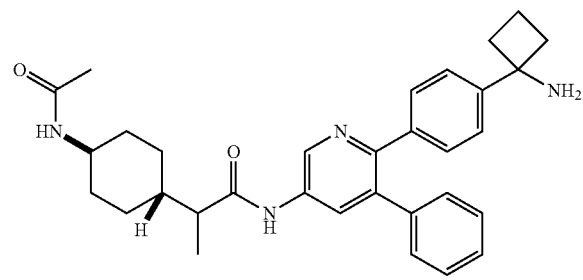

Step 1: ethyl 2-(trans-4-aminocyclohexyl)propanoate: A stirred suspension of sodium sulfate (3 g, 21.1 mmol) in DCM (5 ml) was treated with benzaldehyde (0.229 ml, 2.26 mmol) and ethyl 2-(trans-4-aminocyclohexyl)acetate hydrochloride (500 mg, 2.26 mmol). The resultant cloudy mixture was treated with Et$_3$N (0.314 ml, 2.26 mmol) and stirred at RT for 6 h. Et$_2$O (20 ml) was added and the resultant mixture was filtered and concentrated in vacuo. The residue was dissolved in THF (20 ml) and cooled to −78° C. whereupon LiHMDS (2.26 ml, 2.26 mmol, 1 M in THF) was added dropwise. The mixture was stirred at −78° C. for 1 h, then iodomethane (0.141 ml, 2.26 mmol) was added. The mixture was allowed to warm to RT and stir for 16 h. The reaction mixture was concentrated in vacuo and then partitioned between water (30 ml) and EtOAc (30 ml). The phases were separated and the aqueous layer was extracted with EtOAc (30 ml). The combined organic phases were washed with brine (30 ml), dried over MgSO$_4$, filtered and concentrated to afford yellow oil (508 mg). This material was dissolved in THF (10 ml), cooled to −78° C. and treated dropwise with LiHMDS (2.26 ml, 2.26 mmol, 1 M in THF). The mixture was stirred at −78° C. for 30 min, then iodomethane (0.141 ml, 2.26 mmol) was added. The resultant mixture was allowed to warm to RT and stir for 16 h. The mixture was concentrated in vacuo and then partitioned between water (30 ml) and EtOAc (30 ml). The phases were separated and the aqueous layer was extracted with EtOAc (30 ml). The combined organic phases were washed with brine (30 ml), dried over MgSO$_4$, filtered and concentrated to afford a brown oil. This material was treated with TFA (2 ml) in DCM (10 ml) and the resultant mixture stirred for 3 days. The mixture was concentrated in vacuo to afford a brown oil, which was loaded onto a column of SCX in MeOH. The column was washed with MeOH and the product was eluted with a 0.7 M solution of ammonia in MeOH. The solvent was removed in vacuo to afford the title compound (240 mg) as a brown oil. This material was used in subsequent reactions without purification.

Step 2: 2-(trans-4-acetamidocyclohexyl)propanoic acid: A solution of the product from Step 1 above (120 mg) in DCM (2.5 ml) was treated with DIPEA (231 μl, 1.33 mmol) and acetic anhydride (62.5 μl, 0.662 mmol). The resultant mixture was allowed to stir at RT for 18 h. The reaction mixture was passed through a column of SCX in MeOH. The solvent was removed in vacuo to afford a pale yellow oil, which solidified on standing. This material was dissolved in a mixture of THF (3 ml) and MeOH (1 ml) and was then treated with 2 M LiOH(aq) (331 μl, 0.662 mmol). The resultant mixture was stirred for 2 h, then treated with additional 2 M LiOH(aq) (331 μl, 0.662 mmol). The mixture was then stirred at RT overnight. The mixture was heated at 60° C. for 1 h and then cooled and treated with 1 M HCl(aq) (1.5 ml). The mixture was concentrated in vacuo and then passed through a column of SCX in MeOH. The solvent was removed in vacuo to afford the title compound (44 mg). This material was used in subsequent reactions without purification.

Step 3: 2-(trans-4-acetamidocyclohexyl)-N-(6-(4-(1-aminocyclobutyl)phenyl)-5-phenylpyridin-3-yl)propanamide: A solution of the product from Step 2 above (42 mg) and HATU (82 mg, 0.217 mmol) in DMF (2 ml) was treated with DIPEA (41.3 μl, 0.236 mmol) and the resultant red solution was stirred at RT for 30 min whereupon Intermediate 8 (82 mg, 0.197 mmol) was added and the mixture stirred at RT for 3 days. Additional HATU (82 mg, 0.217 mmol) and DIPEA (41.3 μl, 0.236 mmol) were added and the reaction mixture heated at 50° C. for 1 h. The mixture was allowed to cool to RT and was then diluted with EtOAc (20 ml) and washed sequentially with saturated NaHCO$_3$ (aq) (10 ml), water (10 ml) and brine (10 ml). The organic phase was dried over MgSO$_4$, filtered and concentrated in vacuo. The residue was treated with TFA (0.5 ml) in DCM (5 ml) and stirred at RT for 16 h. The mixture was concentrated in vacuo and then loaded on to a column of SCX in MeOH. The column was washed with MeOH and the product was eluted with a 0.7 M solution of ammonia in MeOH. The solvent was removed in vacuo and the residue purified by preparative HPLC (Gilson 215, Waters X-Bridge Prep-C18, 5 μm, 19×50 mm column, 35-60% MeCN in 10 mM ammonium bicarbonate(aq)) to afford the title compound (19 mg, 0.035 mmol, 95% purity). LCMS (Method 1): m/z 511 (M+H)$^+$, 509 (M−H)$^−$, at 2.56 min. $^1$H NMR (400 MHz, DMSO-d$_6$) δ 10.24 (s, 1H), 8.82 (d, J=2.4 Hz, 1H), 8.14 (d, J=2.4 Hz, 1H), 7.71 (d, J=7.8 Hz, 1H), 7.40-7.26 (m, 5H), 7.26-7.17 (m, 4H), 3.50-3.39 (m, 1H), 2.40-2.17 (m, 4H), 2.10-1.90 (m, 3H), 1.89-1.72 (m, 6H), 1.71-1.53 (m, 2H), 1.49-1.39 (m, 1H), 1.21-0.87 (m, 6H).

Example 42

N-(6-(4-(2-aminopropan-2-yl)phenyl)-5-phenylpyridin-3-yl)-2-(trans-4-(2-oxooxazolidin-3-yl)cyclohexyl)acetamide

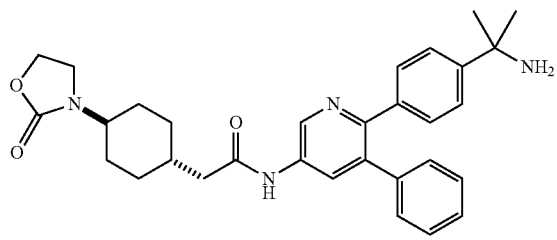

Step 1: Ethyl 2-(trans-4-(((2-chloroethoxy)carbonyl)amino)cyclohexyl)acetate: A solution of ethyl 2-(trans-4-aminocyclohexyl)acetate hydrochloride (0.5 g, 2.25 mmol) in THF (5 ml) was treated with Et$_3$N (1.57 ml, 11.3 mmol), followed by 2-chloroethyl chloroformate (0.467 ml, 4.51 mmol) and the resultant mixture stirred at RT overnight. Additional 2-chloroethyl chloroformate (0.234 ml, 2.26 mmol) was added and the mixture was stirred at RT for a further 24 h. The reaction mixture was quenched with saturated NH$_4$Cl(aq) (10 ml) and extracted with DCM (10 ml), then filtered through a phase separation cartridge. The organic phase was concentrated in vacuo to afford the title compound (609 mg) as a white solid. This material was used directly in subsequent reactions without purification.

Step 2: Ethyl 2-(trans-4-(2-oxooxazolidin-3-yl)cyclohexyl)acetate: A solution of the product of Step 1 above (609 mg) in THF (5 ml) was treated with sodium hydride (417 mg, 10.4 mmol, 60% w/w in mineral oil) and stirred at RT overnight. Additional (417 mg, 10.4 mmol, 60% w/w in mineral oil) was added and the resultant mixture was stirred at RT for a further 24 h. The reaction mixture was quenched with saturated NH$_4$Cl(aq) (10 ml) and acidified with 1 M HCl(aq). The mixture was extracted sequentially with EtOAc (2×50 ml) and DCM (50 ml). The organic phase was concentrated in vacuo. The residue was purified by column chromatography (12 g cartridge, 0-100% EtOAc/isohexane) to afford the title compound (254 mg, 0.975 mmol, 98% purity) as a colourless oil. $^1$H NMR (400 MHz, Methanol-d$_4$) δ 4.39-4.30 (m, 2H), 4.14 (q, J=7.1 Hz, 2H), 3.66-3.53 (m, 3H), 2.24 (d, J=7.0 Hz, 2H), 1.94-1.69 (m, 5H), 1.57 (qd, J=12.7, 3.5 Hz, 2H), 1.26 (t, J=7.1 Hz, 3H), 1.18 (qd, J=13.0, 3.4 Hz, 2H).

Step 3: 2-(trans-4-(2-oxooxazolidin-3-yl)cyclohexyl)acetic acid: A mixture of the product from Step 2 above (253 mg, 0.971 mmol) in THF (5 ml) and MeOH (1 ml) was treated with 2 M LiOH(aq) (991 μl, 1.98 mmol) and the resultant mixture heated at 50° C. for 18 h. The reaction mixture was cooled to RT, concentrated in vacuo and the residue acidified with 1 M HCl(aq). The mixture was extracted with EtOAc (20 ml) and the organic phase passed through a phase separation cartridge and concentrated in vacuo to afford the title compound (162 mg) as a pale yellow solid. This material was used directly in subsequent reactions without purification.

Step 4: tert-butyl (2-(4-(5-(2-(trans-4-(2-oxooxazolidin-3-yl)cyclohexyl)acetamido)-3-phenylpyridin-2-yl)phenyl)propan-2-yl)carbamate: The title compound (32 mg, 0.051 mmol, 98% purity) was isolated as a pale pink glass from the reaction of the product from Step 3 above (50.7 mg), DIPEA (78 μl, 0.446 mmol), HATU (85 mg, 0.223 mmol) and Intermediate 2 (30 mg, 0.074 mmol) in DMF (3 ml) using essentially the same procedure as in Example 17 Step 4, except the reaction mixture was heated for 5 days. LCMS (Method 1): m/z 613 (M+H)$^+$, at 2.31 min.

Step 5: N-(6-(4-(2-aminopropan-2-yl)phenyl)-5-phenylpyridin-3-yl)-2-(trans-4-(2-oxooxazolidin-3-yl)cyclohexyl)acetamide: The title compound (15 mg, 0.029 mmol, 99% purity) was isolated as a colourless glass from the reaction of the product from Step 4 above (32 mg, 0.051 mmol, 98% purity) and 90% (v/v) TFA in water (0.5 ml) using essentially the same procedure as in Example 1 Step 7, except the reaction mixture was stirred for 2 h. After work-up, the product was purified by preparative HPLC (Waters FractionLynx, Waters X-Bridge Prep-C18, 5 μm, 19×50 mm column, 20-50% MeCN in 10 mM ammonium bicarbonate(aq)). LCMS (Method 2): m/z 513 (M+H)$^+$, at 1.81 min. $^1$H NMR (400 MHz, DMSO-d$^6$) δ 10.27 (s, 1H), 8.78 (d, J=2.4 Hz, 1H), 8.09 (d, J=2.4 Hz, 1H), 7.39-7.29 (m, 5H), 7.22-7.16 (m, 4H), 4.27-4.19 (m, 2H), 3.51-3.40 (m, 3H), 2.27 (d, J=6.8 Hz, 2H), 2.09-1.57 (m, 7H), 1.54-1.40 (m, 2H), 1.31 (s, 6H), 1.17-1.08 (m, 2H).

Example 43

N-(6'-(2-aminopropan-2-yl)-3-phenyl-[2,3'-bipyridin]-5-yl)-2-(trans-4-(N-methylacetamido)cyclohexyl)acetamide

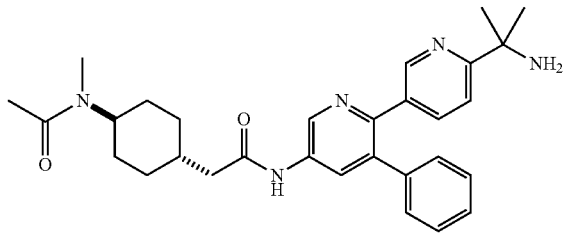

The title compound (22 mg, 0.044 mmol) was isolated as a white solid from the reaction of the product from Example 1 Step 5 (47.5 mg, 0.222 mmol), Intermediate 21 (60 mg), HATU (282 mg, 0.742 mmol) and DIPEA (196 μl, 1.19 mmol) in THF (4 ml) using essentially the same procedure as in Example 17 Step 4. LCMS (Method 1): m/z 500 (M+H)$^+$, 498 (M−H)$^−$, at 1.32 min. $^1$H NMR (400 MHz, DMSO-d$^6$) (two rotomers in a 5:4 ratio) δ 10.36 (s, 1H), 8.85 (d, J=2.4 Hz, 1H), 8.36 (d, J=2.2 Hz, 1H), 8.15 (d, J=2.4 Hz, 1H), 7.59 (dd, J=8.3, 2.3 Hz, 1H), 7.50 (d, J=8.2 Hz, 1H), 7.41-7.32 (m, 3H), 7.26-7.20 (m, 2H), 4.31-4.18 (m, 1H, major), 3.64-3.45 (m, 1H, minor), 2.79 (s, 3H, major), 2.67

(s, 3H, minor), 2.33-2.25 (m, 2H), 2.02 (s, 3H, minor), 1.96 (s, 3H, major), 1.86-1.70 (m, 3H), 1.69-1.42 (m, 4H), 1.35 (s, 6H), 1.27-1.03 (m, 2H).

Example 44

Methyl (trans-4-(2-((6-(4-(trans-1-amino-3-hydroxy-3-methylcyclobutyl)phenyl)-5-phenylpyridin-3-yl)amino)-2-oxoethyl)cyclohexyl)(methyl)carbamate

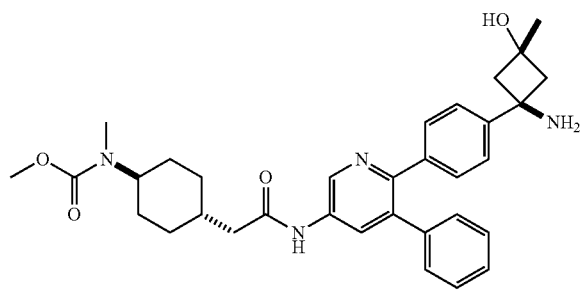

Step 1: benzyl (trans-4-(2-((6-(4-(trans-1-((tert-butoxycarbonyl)amino)-3-hydroxy-3-methylcyclobutyl)phenyl)-5-phenylpyridin-3-yl)amino)-2-oxoethyl)cyclohexyl)(methyl)carbamate: A mixture of Intermediate 1 (40 mg, 0.090 mmol), the product from Example 4 Step 1 (41.1 mg, 0.135 mmol) and Et$_3$N (62.6 µl, 0.449 mmol) was dissolved in EtOAc (0.5 ml) and treated with T3P (132 µl, 0.224 mmol, 50% w/w in EtOAc). The resultant mixture was allowed to stand at RT for 48 h. The mixture was diluted with water (1 ml) and basified with saturated NaHCO$_3$(aq) (1 ml). After 5 min, the mixture was extracted with DCM (4 ml) and filtered through a phase separation cartridge, washing with DCM (1 ml). The combined organic phases were concentrated in vacuo to afford a yellow gum. This material was purified by column chromatography (4 g cartridge, 0-10% (0.7 M NH$_3$/MeOH)/DCM) to afford the title compound (54 mg, 0.072 mmol, 98% purity) as an orange solid. LCMS (Method 1): m/z 733 (M+H)$^+$, at 2.51 min.

Step 2: tert-butyl (trans-3-hydroxy-3-methyl-1-(4-(5-(2-(trans-4-(methylamino)cyclohexyl)acetamido)-3-phenylpyridin-2-yl)phenyl)cyclobutyl)carbamate: The product from Step 1 above (54 mg, 0.072 mmol, 98% purity) was dissolved in EtOH (3.68 ml) and hydrogenated in a ThalesNano H-Cube® flow reactor (10% Pd/C, 30×4 mm cartridge, full hydrogen mode, 50° C., 1 ml/min flow rate). The resultant solution was concentrated in vacuo to afford the title compound (20 mg, 0.032 mmol, 95% purity) as a pale yellow glass. LCMS (Method 1): m/z 599 (M+H)$^+$, 300 (M+2H)$^{2+}$, at 1.45 min.

Step 3: methyl (trans-4-(2-((6-(4-(trans-1-amino-3-hydroxy-3-methylcyclobutyl)phenyl)-5-phenylpyridin-3-yl)amino)-2-oxoethyl)cyclohexyl)(methyl)carbamate: The title compound (4 mg, 6.97 µmol, 97% purity) was isolated as a white solid from the reaction of the product from Step 2 above (20 mg, 0.032 mmol, 95% purity), methyl chloroformate (3.10 µl, 0.040 mmol) and Et$_3$N (23 µl, 0.167 mmol) in DCM (5 ml) using essentially the same procedure as in Example 34. LCMS (Method 1): m/z 557 (M+H)$^+$, at 1.42 min. $^1$H NMR (400 MHz, Methanol-d$^4$) δ 8.73 (d, J=2.4 Hz, 1H), 8.04 (d, J=2.4 Hz, 1H), 7.62 (br s, 1H), 7.30 (d, J=8.2 Hz, 2H), 7.25 (d, J=8.2 Hz, 2H), 7.21-7.14 (m, 3H), 7.14-7.03 (m, 2H), 3.90-3.72 (m, 1H), 3.58 (s, 3H), 2.69 (s, 3H), 2.67 (d, J=13.6 Hz, 2H), 2.47 (d, J=13.5 Hz, 2H), 2.24 (d, J=7.0 Hz, 2H), 1.89-1.69 (m, 3H), 1.66-1.45 (m, 4H), 1.40 (s, 3H), 1.26-1.06 (m, 2H).

Example 45

N-(6-(4-(trans-1-amino-3-fluorocyclobutyl)phenyl)-5-phenylpyridazin-3-yl)-2-(trans-4-(2-oxooxazolidin-3-yl)cyclohexyl)acetamide

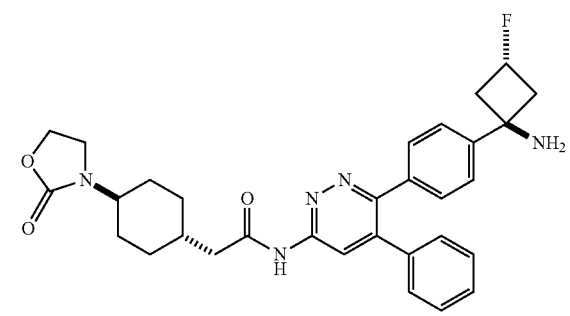

Step 1: tert-butyl (trans-1-(4-(6-amino-4-phenylpyridazin-3-yl)phenyl)-3-fluorocyclobutyl)carbamate: The title compound (103 mg, 0.213 mmol, 90% purity) was isolated as a pale yellow solid from the reaction of 6-chloro-5-phenylpyridazin-3-amine (158 mg, 0.767 mmol, prepared according to US2008/0045536), the product of Intermediate 13 Step 5 (300 mg), tetrakis-(triphenylphosphine)palladium (0) (89 mg, 0.077 mmol) and 2 M Na$_2$CO$_3$(aq) (863 µl, 1.73 mmol) in dioxane (5 ml) using essentially the same procedure as in Intermediate 3 Step 2. $^1$H NMR (400 MHz, DMSO-d$_6$) (two rotamers in a 2:1 ratio) δ 7.61 (s, 1H), 7.41-7.27 (m, 3H), 7.25-7.10 (m, 6H), 6.74 (s, 1H), 6.53 (s, 2H), 5.32-5.06 (m, 1H), 3.04-2.80 (m, 2H), 2.49-2.36 (m, 2H) 1.33 (s, 9H, major), 1.13 (s, 9H, minor). The compound contained 6% w/w residual EtOAc and 3% w/w residual DCM. This material was used in subsequent reactions without further drying.

Step 2: N-(6-(4-(trans-1-amino-3-fluorocyclobutyl)phenyl)-5-phenylpyridazin-3-yl)-2-(trans-4-(2-oxooxazolidin-3-yl)cyclohexyl)acetamide: The title compound (5.5 mg, 10.2 µmol) was isolated as a white solid from the reaction of the product from Example 42 Step 3 (41.8 mg), the product from Step 1 above (40 mg, 0.083 mmol, 90% purity), HATU (105 mg, 0.276 mmol) and DIPEA (107 µl, 0.644 mmol) in DMF (5 ml) using essentially the same procedure as in Example 34 Step 4. LCMS (Method 1): m/z 544 (M+H)$^+$, 542 (M–H)$^-$, at 1.42 min. $^1$H NMR (400 MHz, DMSO-d$_6$) δ 11.29 (s, 1H), 8.35 (s, 1H), 7.45-7.20 (m, 9H), 5.34 (dq, J=56.9, 6.7 Hz, 1H), 4.24 (t, J=7.9 Hz, 2H), 3.58-3.41 (m, 3H), 2.60-2.48 (m, 2H, obscured by solvent), 2.47-2.33 (m, 3H), 2.21 (br s, 2H), 1.88-1.62 (m, 5H), 1.56-1.40 (m, 2H), 1.27-0.96 (m, 3H).

Example 46

N-(6-(4-(trans-1-amino-3-fluorocyclobutyl)phenyl)-5-phenylpyridazin-3-yl)-2-(trans-4-(N-methylacetamido)cyclohexyl)acetamide

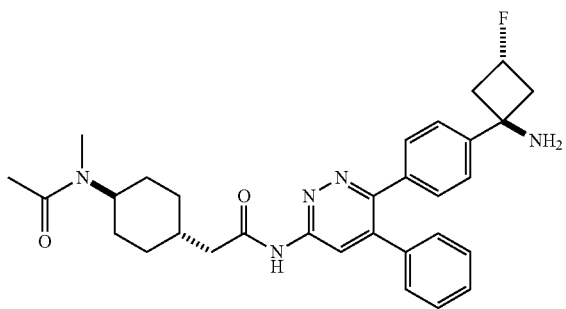

The title compound (7 mg, 0.013 mmol) was isolated as a white solid from the reaction of the product from Example 1 Step 5 (39.3 mg), the product from Example 45 Step 1 (40 mg, 0.083 mmol, 90% purity), HATU (105 mg, 0.276 mmol) and DIPEA (107 µl, 0.644 mmol) in DMF (5 ml) using essentially the same procedure as in Example 34 Step 4. LCMS (Method 1): m/z 530 (M+H)$^+$ at 1.43 min. $^1$H NMR (400 MHz, DMSO-d$_6$) (two rotamers in a 3:2 ratio) δ 11.30 (s, 1H, minor), 11.28 (s, 1H, major), 8.36 (s, 1H, minor), 8.35 (s, 1H, major), 7.48-7.20 (m, 9H), 5.35 (dp, J=56.7, 6.6 Hz, 1H), 4.28-4.16 (m, 1H, major), 3.63-3.50 (m, 1H, minor), 2.79 (s, 3H, major), 2.66 (s, 3H, minor), 2.60-2.47 (m, 2H, obscured by solvent), 2.46-2.32 (m, 4H), 2.20 (br s, 2H), 2.02 (s, 3H, minor), 1.96 (s, 3H, major), 1.86-1.70 (m, 3H), 1.69-1.40 (m, 4H), 1.28-1.04 (m, 2H).

Example 47

N-(trans-4-(2-((6-(4-(2-aminopropan-2-yl)phenyl)-5-phenylpyridin-2-yl)amino)-2-oxoethyl)cyclohexyl)-N-methylcyclobutanecarboxamide

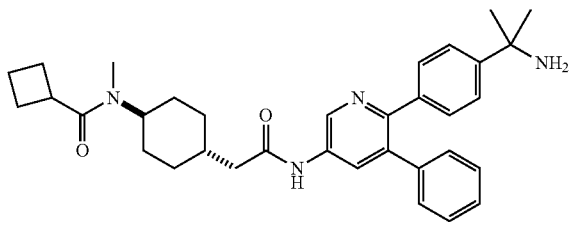

Step 1: tert-butyl (2-(4-(5-(2-(trans-4-(N-methylcyclobutanecarboxamido)cyclohexyl)acetamido)-3-phenylpyridin-2-yl)phenyl)propan-2-yl)carbamate: The title compound (28.5 mg, 0.044 mmol, 98% purity) was isolated as a white solid from the reaction of the product from Example 4 Step 3 (30 mg, 0.054 mmol), the product from cyclobutanecarboxylic acid (17.9 µl, 0.189 mmol), DIPEA (28.2 µl, 0.162 mmol) and HATU (41 mg, 0.108 mmol) in THF (2 ml) using essentially the same procedure as in Example 24 Step 1, except the product was purified by column chromatography (4 g cartridge, 0-5% MeOH/DCM). LCMS (Method 1): m/z 320 (M+2H)$^{2+}$, 639 (M+H)+, at 2.54 min.

Step 2: N-(trans-4-(2-((6-(4-(2-aminopropan-2-yl)phenyl)-5-phenylpyridin-3-yl)amino)-2-oxoethyl)cyclohexyl)-N-methylcyclobutanecarboxamide: The title compound (16.7 mg, 0.030 mmol, 98% purity) was isolated as a white solid from the reaction of the product from Step 1 above (25.6 mg, 0.039 mmol, 98% purity) and 90% (v/v) TFA in water (2 ml) using essentially the same procedure as in Example 1 Step 7, except the reaction mixture was stirred for 3 h. LCMS (Method 1): m/z 261 (M+2H—NH$_3$)$^{2+}$, 270 (M+2H)$^{2+}$, 522 (M+H—NH$_3$)+, 539 (M+H)$^+$, at 1.61 min. $^1$H NMR (400 MHz, DMSO-d$_6$) δ 9.95 (s, 1H), 8.83 (d, J=2.4 Hz, 1H), 8.06 (d, J=2.4 Hz, 1H), 7.42-7.26 (m, 7H), 7.21 (dd, J=6.6, 3.0 Hz, 2H), 6.87 (br s, 2H), 3.36-3.28 (m, 1H), 2.70 (s, 3H), 2.30 (d, J=6.8 Hz, 2H), 2.22-2.06 (m, 4H), 1.98-1.70 (m, 5H), 1.62-1.50 (m, 9H), 1.21-1.17 (m, 2H).

Example 48

N-(6-(4-(1-aminocyclobutyl)phenyl)-5-(thiophen-3-yl)pyridin-3-yl)-2-(trans-4-(2-oxopyrrolidin-1-yl)cyclohexyl)acetamide

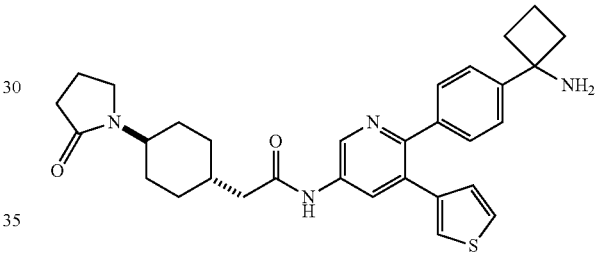

Step 1: ethyl 2-(trans-4-(4-chlorobutanamido)cyclohexyl)acetate: A solution of ethyl 2-(trans-4-aminocyclohexyl)acetate hydrochloride (0.5 g, 2.26 mmol) in THF (5 ml) was treated with Et$_3$N (1.57 ml, 11.3 mmol) followed by 4-chlorobutanoyl chloride (0.505 ml, 4.51 mmol) and stirred at RT for 18 h. The reaction mixture was then treated with additional Et$_3$N (1.57 ml, 11.3 mmol) and 4-chlorobutanoyl chloride (0.505 ml, 4.51 mmol) and stirred at RT for 2 days. The reaction mixture was quenched with water (20 ml) and extracted with EtOAc (2×20 ml). The combined extracts were washed with brine (20 ml), dried over MgSO$_4$, filtered and concentrated in vacuo to afford a pale yellow oil. This material was purified by column chromatography (4 g cartridge, 0-5% (0.7 M NH$_3$/MeOH solution)/DCM) to afford the title compound (453 mg) as a pale yellow oil. This material was used in subsequent reactions without analysis.

Step 2: ethyl 2-(trans-4-(2-oxopyrrolidin-1-yl)cyclohexyl)acetate: A solution of the product from Step 1 above (453 mg) in THF (5 ml) was treated with sodium hydride (438 mg, 10.9 mmol, 60% w/w in mineral oil) and stirred at RT for 18 h. The reaction mixture was quenched with saturated NH$_4$Cl(aq) (10 ml) and concentrated in vacuo. The residue partitioned between DCM (10 ml) and water (10 ml) and filtered through a phase separation cartridge. The organic phase was concentrated in vacuo to afford an orange oil. This material was purified by column chromatography (4 g cartridge, 0-5% (0.7 M NH$_3$/MeOH solution)/DCM) to afford the title compound (169 mg, 0.601 mmol, 90% purity) as a pale yellow solid. $^1$H NMR (400 MHz, Chloroform-d) δ 4.12 (q, J=7.1 Hz, 2H), 3.94 (tt, J=12.1, 3.9 Hz, 1H), 3.33 (t, J=7.0 Hz, 2H), 2.44-2.33 (m, 2H), 2.19 (d, J=7.0 Hz, 2H), 2.02-1.96 (m, 2H), 1.88-1.67 (m, 5H), 1.45 (qd, J=12.7, 3.5 Hz, 2H), 1.25 (t, J=7.1 Hz, 3H), 1.16 (qd, J=12.9, 3.5 Hz, 2H).

Step 3: 2-(trans-4-(2-oxopyrrolidin-1-yl)cyclohexyl)acetic acid: A mixture of the product from Step 2 above (169 mg, 0.601 mmol) in THF (5 ml) and MeOH (1 ml) was treated with 2 M LiOH(aq) (400 µl, 0.801 mmol) and heated at 50° C. for 18 h. The reaction mixture was treated with additional 2 M LiOH(aq) (400 µl, 0.801 mmol) and heating was continued for 2 days. The mixture was cooled to RT and acidified with 1 M HCl(aq). The resultant white precipitate was collected by filtration, washing with Et$_2$O, and dried in vacuo to afford the title compound (152 mg, 0.641 mmol, 95% purity) as an off-white solid. $^1$H NMR (400 MHz, Methanol-d$_4$) δ 3.83 (tt, J=11.9, 3.9 Hz, 1H), 3.47-3.40 (m, 2H), 2.40-2.32 (m, 2H), 2.19 (d, J=7.0 Hz, 2H), 2.06-1.96 (m, 2H), 1.90-1.87 (m, 2H), 1.79-1.65 (m, 3H), 1.56 (qd, J=12.6, 3.5 Hz, 2H), 1.16 (qd, J=12.9, 3.5 Hz, 2H).

Step 4: tert-butyl (1-(4-(5-(2-(trans-4-(2-oxopyrrolidin-1-yl)cyclohexyl)acetamido)-3-(thiophen-3-yl)pyridin-2-yl)phenyl)cyclobutyl)carbamate: A mixture of the product from Step 3 above (53.4 mg, 0.225 mmol, 95% purity), DIPEA (124 µl, 0.712 mmol) and HATU (90 mg, 0.237 mmol) in DMF (2 ml) was stirred at RT for 30 min. A solution of Intermediate 15 (50 mg, 0.113 mmol, 95% purity) in DMF (1 ml) was added and the resultant mixture heated at 50° C. for a total of 3 days. Additional product from Step 3 above (53.4 mg, 0.225 mmol, 95% purity), HATU (90 mg, 0.237 mmol) and DIPEA (124 µl, 0.712 mmol) in DMF (1 ml) was added to the reaction mixture after 18 h and after 2 days. After the third day the reaction mixture was cooled to RT, diluted with water (5 ml) and the resultant precipitate collected by filtration, washing with water (50 ml). This material was dissolved in DCM (20 ml), dried over MgSO4, filtered and concentrated in vacuo. The residue purified by column chromatography (12 g cartridge, 0-5% (0.7 M NH$_3$/MeOH solution)/DCM) to afford the title compound (51 mg, 0.080 mmol, 99% purity) as a clear colourless glass. LCMS (Method 1): m/z 629 (M+H)$^+$, at 2.34 min.

Step 5: N-(6-(4-(1-aminocyclobutyl)phenyl)-5-(thiophen-3-yl)pyridin-3-yl)-2-(trans-4-(2-oxopyrrolidin-1-yl)cyclohexyl)acetamide: The title compound (25 mg, 0.045 mmol, 96% purity) was isolated as an off-white solid from the reaction of the product from Step 4 above (36 mg, 0.056 mmol, 99% purity) with 90% (v/v) TFA in water (0.5 ml) using essentially the same procedure as in Example 1 Step 7, except the reaction mixture was stirred for 18 h. LCMS (Method 2): m/z 529 (M+H)$^+$, at 1.98 min. 1H NMR (400 MHz, DMSO-d$_6$) δ 10.23 (s, 1H), 8.76 (d, J=2.4 Hz, 1H), 8.14 (d, J=2.4 Hz, 1H), 7.48 (dd, J=5.0, 2.9 Hz, 1H), 7.43 (dd, J=3.0, 1.3 Hz, 1H), 7.35 (d, J=8.5 Hz, 2H), 7.26 (d, J=8.4 Hz, 2H), 6.75 (dd, J=4.9, 1.3 Hz, 1H), 3.72 (tt, J=12.0, 4.1 Hz, 1H), 3.28-3.27 (m, 2H), 2.38-2.32 (m, 2H), 2.27 (d, J=6.8 Hz, 2H), 2.21-2.17 (m, 2H), 2.11-1.40 (m, 13H), 1.17-1.08 (m, 2H).

Example 49

N-(6-(4-(1-aminocyclobutyl)phenyl)-5-phenylpyridin-3-yl)-2-(trans-4-(N-isopropylacetamido)cyclohexyl)acetamide

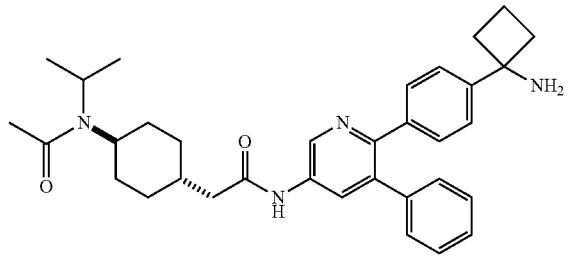

Step 1: ethyl 2-(trans-4-(isopropylamino)cyclohexyl)acetate: A mixture of ethyl 2-(trans-4-aminocyclohexyl)acetate hydrochloride (500 mg, 2.26 mmol), acetic acid (387 µl, 6.77 mmol), acetone (1.66 ml, 22.6 mmol) and activated molecular sieves in 1,2-dichloroethane (5 ml) was stirred at RT for 1 h. The resultant mixture was treated with sodium triacetoxyborohydride (1.43 g, 6.77 mmol) and stirred at RT for 18 h. The mixture was treated with water (10 ml) and K$_2$CO$_3$ (2 g) and stirred at rt for 1 h. The mixture was filtered through a phase separation cartridge and the organic phase was concentrated in vacuo to afford a pale yellow oil. This material was loaded onto a column of SCX in EtOH. The column was washed with EtOH and then the product was eluted with a 2 M solution of ammonia in EtOH. The solvent was removed in vacuo to afford the title compound (526 mg, 2.20 mmol, 95% purity) as a clear colourless oil. $^1$H NMR (400 MHz, Chloroform-d) δ 4.12 (q, J=7.1 Hz, 2H), 2.96 (hept, J=6.3 Hz, 1H), 2.52-2.41 (m, 1H), 2.17 (d, J=6.6 Hz, 2H), 1.97-1.88 (m, 2H), 1.82-1.70 (m, 3H), 1.25 (t, J=7.1 Hz, 3H), 1.12-0.96 (m, 10H).

Step 2: ethyl 2-(trans-4-(N-isopropylacetamido)cyclohexyl)acetate: The title compound (310 mg) was isolated as a clear colourless oil from the reaction of the product from Step 1 above (238 mg, 0.998 mmol, 95% purity), acetic anhydride (109 µl, 1.15 mmol) and DIPEA (402 µl, 2.30 mmol) in THF (3 ml) using essentially the same procedure as in Example 1 Step 4, except after 18 h additional acetic anhydride (109 µl, 1.15 mmol) and DIPEA (402 µl, 2.30 mmol) were added and stirring was continued for 24 h prior to work up.

Step 3: 2-(trans-4-(N-isopropylacetamido)cyclohexyl)acetic acid: The title compound (286 mg) was isolated as a sticky white solid from the reaction of the product from Step 2 above (310 mg) with 2 M LiOH(aq) (400 µl, 0.801 mmol) in THF (5 ml) and MeOH (1 ml) using essentially the same procedure as in Example 48 Step 3, except after 18 h the reaction was worked up. This material was used directly in subsequent reactions without analysis.

Step 4: tert-butyl (1-(4-(5-(2-(trans-4-(N-isopropylacetamido)cyclohexyl)acetamido)-3-phenylpyridin-2-yl)phenyl)cyclobutyl)carbamate: The title compound (50 mg) was isolated as a pale pink glass from the reaction of the product from Step 3 above (58.1 mg), DIPEA (84 µl, 0.481 mmol), HATU (92 mg, 0.241 mmol) and Intermediate 8 (50 mg, 0.120 mmol) in DMF (3 ml) using essentially the same procedure as in Example 17 Step 4, except the reaction mixture was heated for 4 days. LCMS (Method 1): m/z 639 (M+H)$^+$, at 2.53 min.

Step 5: N-(6-(4-(1-aminocyclobutyl)phenyl)-5-phenylpyridin-3-yl)-2-(trans-4-(N-isopropylacetamido)cyclohexyl)acetamide: The title compound (22 mg, 0.040 mmol, 99% purity) was isolated as a clear colourless glass from the reaction of the product from Step 4 above (50 mg) and 90% (v/v) TFA in water (0.5 ml) using essentially the same procedure as in Example 1 Step 7, except the reaction mixture was stirred at RT for 2 h. After work-up, the product was purified by preparative HPLC (Waters FractionLynx, Waters X-Bridge Prep-C18, 5 μm, 19×50 mm column, 20-50% MeCN in 10 mM ammonium bicarbonate(aq)). LCMS (Method 2): m/z 539.0 (M+H)$^+$ at 2.15 min. $^1$H NMR (400 MHz, DMSO-$d_6$) (two rotamers in a 5:4 ratio) δ 10.26 (s, 1H, major), 10.23 (s, 1H, minor), 8.79 (d, J=2.4 Hz, 1H), 8.11-8.09 (m, 1H), 7.38-7.25 (m, 5H), 7.25-7.15 (m, 4H), 3.99-3.86 (m, 1H, minor), 3.53-3.38 (m, 1H, major), 3.02 (br s, 2H, major), 2.42-2.20 (m, 4H and 2H minor), 2.18-1.88 (m, 8H), 1.85-1.50 (m, 6H), 1.41-1.38 (m, 1H), 1.26 (d, J=6.7 Hz, 3H), 1.17-1.07 (m, 5H).

Example 50

(S)—N-(6-(4-(1-aminocyclobutyl)phenyl)-5-phenylpyridin-3-yl)-2-(1-(cyclopropylsulfonyl)piperidin-4-yl)-2-fluoroacetamide

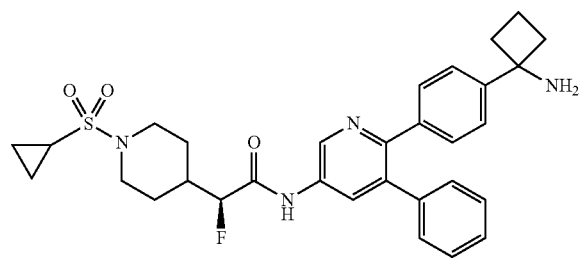 [SMILES: NC1(c2ccc(-c3ncc(NC(=O)[C@@H](F)C4CCN(S(=O)(=O)C5CC5)CC4)cc3-c3ccccc3)cc2)CCC1]

Step 1: (S)-benzyl 4-(2-(4-isopropyl-5,5-dimethyl-2-oxooxazolidin-3-yl)-2-oxoethyl)piperidine-1-carboxylate: A stirred solution of 2-(1-((benzyloxy)carbonyl)piperidin-4-yl)acetic acid (2.01 g, 7.25 mmol) in DCM (50 ml) was treated with oxalyl chloride (0.698 ml, 7.98 mmol). The resultant mixture was heated at reflux for 1 h, then concentrated in vacuo. The crude acid chloride was dissolved in DCM (20 ml). In a separate vessel, a stirred solution of (S)-4-isopropyl-5,5-dimethyloxazolidin-2-one (1.14 g, 7.25 mmol) in DCM (20 ml) was cooled to −78° C. and treated dropwise with n-butyllithium (2.95 ml, 7.98 mmol, 2.7 M in hexanes). The resultant solution was warmed to 0-5° C. and held at this temperature for 30 min. The reaction mixture was cooled to −78° C. and treated dropwise with the acid chloride solution. The resultant mixture was stirred at −78° C. for 1 h, then warmed to RT and stirred for 16 h. The mixture was then quenched with saturated NH$_4$Cl(aq) (50 ml) and the phases were partitioned and separated. The aqueous phase was extracted with EtOAc (2×10 ml) and the combined organic phases were dried over Na$_2$SO$_4$, filtered and concentrated in vacuo. The residue was purified by column chromatography (80 g cartridge, 0-40% EtOAc/isohexane), appropriate fractions were combined in MeOH and concentrated in vacuo to afford the title compound (2.23 g, 4.55 mmol, 85% purity) as a clear mobile oil. $^1$H NMR (400 MHz, DMSO-$d_6$) δ 7.42-7.26 (m, 5H), 5.07 (s, 2H), 4.14 (d, J=2.9 Hz, 1H), 4.04-3.94 (m, 2H), 2.91 (dd, J=16.1, 6.7 Hz, 1H), 2.82 (br s, 2H), 2.74 (dd, J=16.1, 6.8 Hz, 1H), 2.12 (pd, J=6.9, 3.0 Hz, 1H), 2.03-1.90 (m, 1H), 1.76-1.61 (m, 2H), 1.45 (s, 3H), 1.34 (s, 3H), 1.18-1.04 (m, 2H), 0.93 (d, J=7.0 Hz, 3H), 0.84 (d, J=6.8 Hz, 3H). The compound contained 7% w/w residual EtOAc, 4% w/w residual DCM, and 2% w/w residual MeOH. This material was used in subsequent reactions without further drying.

Step 2: benzyl 4-((S)-1-fluoro-2-((S)-4-isopropyl-5,5-dimethyl-2-oxooxazolidin-3-yl)-2-oxoethyl)piperidine-1-carboxylate: A solution of the product from Step 1 above (2.23 g, 5.35 mmol) in DCM (60 ml) was cooled to 0-5° C. and was treated dropwise with titanium(IV) chloride (0.886 ml, 8.03 mmol). The resultant mixture was stirred for 5 min and then treated with Et$_3$N (1.49 ml, 10.7 mmol). The resultant mixture was stirred for a further 30 min, maintaining the temperature at 0-5° C., then N-fluoro-N-(phenylsulfonyl)benzenesulfonamide (3.38 g, 10.7 mmol) was added in one portion. The mixture was stirred for 3 h at RT and was then passed through a pad of silica gel, rinsing with DCM (30 ml) and EtOAc (60 ml). The combined filtrates were concentrated in vacuo and the residue diluted in EtOAc (40 ml) and washed with a saturated NaHCO$_3$(aq) (40 ml). The aqueous phase was extracted with EtOAc (2×20 ml) and the combined organic layers were dried over Na$_2$SO$_4$, filtered and concentrated in vacuo. The residue was partially purified by column chromatography (24 g cartridge, 0-35% EtOAc/isohexane) to afford the title compound (3.00 g). This material was used directly in subsequent reactions without further purification.

Step 3: (S)-2-(1-(cyclopropylsulfonyl)piperidin-4-yl)-2-fluoroacetic acid: The product from Step 2 above (3.00 g) was added to a suspension of palladium (1.47 g, 5% w/w on carbon, Type 87L paste) in EtOH under an atmosphere of N$_2$. The vessel was purged with H$_2$ and the reaction mixture stirred under an atmosphere of H$_2$ for 16 h. The reaction was filtered through a pad of Celite®, rinsing with a 50% v/v solution of MeOH in DCM (20 ml) and then MeOH (20 ml). The combined filtrates were concentrated in vacuo and the residue loaded onto a column of SCX in MeOH. The column was washed with MeOH and then the product was eluted with a 0.7 M solution of ammonia in MeOH. The solvent was removed in vacuo to afford a yellow oil (1.14 g). A portion of this material (300 mg) was combined with dimethylaminopyridine (12 mg, 0.100 mmol) and DIPEA (349 μl, 2.00 mmol) in DCM (10 ml) and was treated dropwise with cyclopropanesulfonyl chloride (131 μl, 1.30 mmol). The resultant mixture was stirred at RT for 16 h. The mixture was diluted with DCM (10 ml) and washed sequentially with saturated NaHCO$_3$(aq) (20 ml) and brine (20 ml). The organic phase was dried over MgSO$_4$, filtered and concentrated in vacuo. The residue was partially purified by column chromatography (12 g cartridge, 0-50% EtOAc/isohexane) to afford a pale yellow oil (130 mg). This material was combined with 30% w/w H$_2$O$_2$(aq) (0.6 ml, 5.87 mmol) in THF (3 ml) and water (1 ml), cooled to 0-5° C. and treated with LiOH (12 mg, 0.482 mmol). The resultant mixture was stirred for 5 min at this temperature and then allowed to warm to RT and stir for 90 min. The reaction was partitioned between with 2 M NaOH(aq) (5 ml) and EtOAc (10 ml). The organic phase was extracted with 2 M NaOH(aq) (5 ml) and the combined aqueous phases were acidified with 1 M HCl(aq) and then extracted with EtOAc (3×10 ml). The combined extracts were dried over Na$_2$SO$_4$, filtered and concentrated in vacuo to afford the title compound (93 mg, 0.333 mmol, 95% purity). LCMS (Method 1): m/z 266 (M+H)$^+$, 264 (M−H)$^−$, at 1.63 min. $^1$H NMR (400 MHz, DMSO-$d_6$) δ 13.30 (s, 1H), 4.93 (dd, J=48.7, 4.0 Hz, 1H), 3.72-3.60 (m, 2H), 2.93-2.75 (m, 2H), 2.61-2.52 (m, 1H), 2.11-1.89 (m, 1H), 1.84-1.71 (m, 1H), 1.69-1.55 (m, 1H), 1.42 (qd, J=12.3, 4.1 Hz, 2H), 1.02-0.83 (m, 4H).

Step 4: (S)-tert-butyl (1-(4-(5-(2-(1-(cyclopropylsulfonyl)piperidin-4-yl)-2-fluoroacetamido)-3-phenylpyridin-2-yl)phenyl)cyclobutyl)carbamate: The product from Step 3 above (46 mg, 0.164 mmol, 95% purity) was combined with Intermediate 8 (60 mg, 0.144 mmol) and Et₃N (0.110 ml, 0.788 mmol) in THF (4 ml) and was treated with HATU (0.180 g, 0.473 mmol). The resultant mixture was heated at 50° C. for 16 h. The mixture was directly concentrated in vacuo onto silica and purified by column chromatography (4 g cartridge, 0-75% EtOAc/isohexane) to afford the title compound (90 mg, 0.129 mmol, 95% purity) as a pale yellow solid. LCMS (Method 1): m/z 663 (M+H)$^+$, at 2.92 min.

Step 5: (S)—N-(6-(4-(1-aminocyclobutyl)phenyl)-5-phenylpyridin-3-yl)-2-(1-(cyclopropylsulfonyl)piperidin-4-yl)-2-fluoroacetamide: A solution of the product from Step 4 above (90 mg, 0.129 mmol, 95% purity) in DCM (5 ml) was treated with TFA (0.418 ml) and the resultant mixture stirred at RT for 16 h. The reaction mixture was concentrated in vacuo and loaded onto a column of SCX in MeOH. The column was washed with MeOH and then the product was eluted with a 0.7 M solution of ammonia in MeOH. The solvent was removed in vacuo and the residue dissolved in DCM (2 ml) and diluted with Et₂O (10 ml). The resultant suspension was filtered and the filtrate diluted with DCM (5 ml) and stirred with saturated NaHCO₃(aq) (10 ml) for 1 h. The resultant mixture was filtered through a phase separation cartridge and the organic phase was concentrated in vacuo to afford the title compound (22 mg, 0.034 mmol, 87% purity) as a white solid. LCMS (Method 1): m/z 563 (M+H)$^+$, at 1.52 min. $^1$H NMR (400 MHz, DMSO-d₆) δ 10.57 (s, 1H), 8.99 (d, J=2.4 Hz, 1H), 8.22 (d, J=2.4 Hz, 1H), 7.47-7.20 (m, 9H), 5.13 (dd, J=48.5, 4.4 Hz, 1H), 3.82-3.66 (m, 2H), 3.01-2.81 (m, 2H), 2.69-2.59 (m, 1H), 2.45-2.32 (m, 2H), 2.30-1.95 (m, 6H), 1.95-1.76 (m, 2H), 1.76-1.44 (m, 3H), 1.10-0.92 (m, 4H). The compound contained 6% w/w tetramethylurea and 7% w/w residual DCM.

Example 51

Methyl (trans-4-(2-((6-(4-(1-aminocyclobutyl)phenyl)-5-phenylpyridin-3-yl)amino)-2-oxoethyl)cyclohexyl)(isopropyl)carbamate

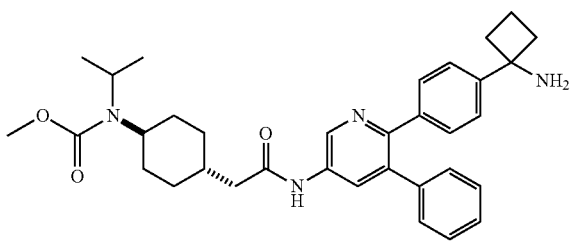

Step 1: tert-butyl (1-(4-(5-(2-(trans-4-(((benzyloxy)carbonyl)amino)cyclohexyl)acetamido)-3-phenylpyridin-2-yl)phenyl)cyclobutyl)carbamate: The title compound (429 mg) was isolated as a pale yellow glass from the reaction of 2-(trans-4-(((benzyloxy)carbonyl)amino)cyclohexyl)acetic acid (358 mg, 1.23 mmol), DIPEA (429 μl, 2.46 mmol), HATU (467 mg, 1.23 mmol) and Intermediate 8 (340 mg, 0.818 mmol) in DMF (5 ml) using essentially the same procedure as in Example 17 Step 4, except the reaction mixture was stirred at RT for 18 h, then heated at 50° C. for 2 days. This material was used directly in subsequent reactions without analysis.

Step 2: tert-butyl (1-(4-(5-(2-(trans-4-aminocyclohexyl)acetamido)-3-phenylpyridin-2-yl)phenyl)cyclobutyl)carbamate: A solution of the product from Step 1 above (429 mg) in EtOH (50 ml) and THF (50 ml) under an atmosphere of N₂ was treated with palladium (663 mg, 10% w/w on carbon, Type 39 paste). The vessel was then purged with H₂ and the reaction mixture stirred at RT under an atmosphere of H₂ for 18 h. The vessel was purged with N₂ and the reaction mixture filtered through Celite®, washing with MeOH (50 ml), and concentrated in vacuo to afford the title compound (208 mg, 0.349 mmol, 93% purity) as a pale yellow glass. LCMS (Method 1): m/z 555 (M+H)$^+$, at 1.74 min.

Step 3: tert-butyl (1-(4-(5-(2-(trans-4-(isopropylamino)cyclohexyl)acetamido)-3-phenylpyridin-2-yl)phenyl)cyclobutyl)carbamate: The title compound (82 mg, 0.136 mmol, 99% purity) was isolated as a clear colourless glass from the reaction of the product from Step 2 above (208 mg, 0.349 mmol, 93% purity), sodium triacetoxyborohydride (238 mg, 1.125 mmol), acetone (275 μl, 3.75 mmol) and acetic acid (64.4 μl, 1.13 mmol) in dichloroethane (5 ml) using essentially the same procedure as in Example 49 Step 1, except molecular sieves were omitted from the reaction mixture and after work up, the material was not loaded onto SCX, but instead purified by column chromatography (24 g cartridge, 0-10% (0.7 M NH₃/MeOH solution)/DCM). LCMS (Method 1): m/z 597 (M+H)$^+$, at 1.78 min.

Step 4: methyl (trans-4-(2-((6-(4-(1-((tert-butoxycarbonyl)amino)cyclobutyl)phenyl)-5-phenylpyridin-3-yl)amino)-2-oxoethyl)cyclohexyl)(isopropyl)carbamate: A mixture of the product from Step 3 above (40 mg, 0.066 mmol, 99% purity) in THF (1 ml) was treated with DIPEA (70.2 μl, 0.402 mmol) and methyl chloroformate (15.6 μl, 0.201 mmol) and the resultant mixture stirred at RT for 18 h. Additional DIPEA (70.2 μl, 0.402 mmol) and methyl chloroformate (15.6 μl, 0.201 mmol) were added and the mixture heated at 50° C. for 24 h. The reaction mixture was cooled to RT, diluted with EtOAc (10 ml) and washed with saturated NaHCO₃(aq) (5 ml). The phases were separated and the organic phase was filtered through a phase separation cartridge to afford a pale orange oil. This material was purified by column chromatography (12 g cartridge, 0-5% (0.7 M NH₃/MeOH solution)/DCM) to afford the title compound (27 mg, 0.041 mmol) as a clear colourless glass. HPLC (Method 1): R$_T$ 2.84 min.

Step 5: methyl (trans-4-(2-((6-(4-(1-aminocyclobutyl)phenyl)-5-phenylpyridin-3-yl)amino)-2-oxoethyl)cyclohexyl)(isopropyl)carbamate: The title compound (17 mg, 0.030 mmol, 99% purity) was isolated as a clear colourless glass from the reaction of the product from Step 4 above (27 mg, 0.041 mmol) and 90% (v/v) TFA in water (0.5 ml) using essentially the same procedure as in Example 1 Step 7, except the reaction mixture was stirred for 2 h. LCMS (Method 2): m/z 555 (M+H)$^+$, at 2.42 min. $^1$H NMR (400 MHz, DMSO-d₆) δ 10.23 (s, 1H), 8.79 (d, J=2.4 Hz, 1H), 8.09 (d, J=2.4 Hz, 1H), 7.37-7.26 (m, 5H), 7.25-7.16 (m, 4H), 3.86-3.81 (m, 1H), 3.56 (s, 3H), 3.53-3.38 (m, 1H), 2.39-2.20 (m, 4H), 2.16-1.91 (m, 5H), 1.89-1.68 (m, 5H), 1.65-1.58 (m, 1H), 1.56-1.51 (m, 2H), 1.15-1.07 (m, 8H).

Example 52

Methyl (trans-4-(2-((6-(4-(1-aminocyclobutyl)phenyl)-5-phenylpyridin-3-yl)amino)-1-fluoro-2-oxoethyl)cyclohexyl)(methyl)carbamate

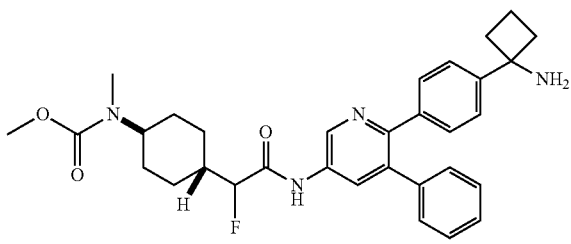

Step 1: benzyl methyl(trans-4-(2-oxo-2-(2-oxooxazolidin-3-yl)ethyl)cyclohexyl)carbamate: The title compound (50 mg, 0.131 mmol, 98% purity) was isolated as a clear gum from the reaction of the product from Example 4 Step 1 (193 mg, 0.619 mmol, 98% purity), oxalyl chloride (66 µl, 0.758 mmol), n-butyllithium (234 µl, 0.633 mmol, 2.7 M in hexanes) and oxazolidin-2-one (46 mg, 0.528 mmol) using essentially the same procedure as in Example 50 Step 1. $^1$H NMR (400 MHz, DMSO-$d_6$) δ 7.43-7.26 (m, 5H), 5.07 (s, 2H), 4.43-4.27 (m, 2H), 3.93-3.73 (m, 3H), 2.73 (s, 3H), 2.72 (d, J=6.6 Hz, 2H), 1.84-1.65 (m, 2H), 1.65-1.42 (m, 5H), 1.14-0.98 (m, 2H). The reaction was repeated on a larger scale to afford additional title compound (64 mg). The material was combined and used directly in subsequent reactions.

Step 2: benzyl (trans-4-(1-fluoro-2-oxo-2-(2-oxooxazolidin-3-yl)ethyl)cyclohexyl)(methyl)carbamate: The title compound (50 mg) was isolated as a clear oil from the reaction of the product from Step 1 above (114 mg, 0.304 mmol), titanium(IV) chloride (50 µl, 0.457 mmol), Et$_3$N (85 µl, 0.609 mmol) and N-fluoro-N-(phenylsulfonyl)benzenesulfonamide (192 mg, 0.609 mmol) in DCM (10 ml) using essentially the same procedure as in Example 50 Step 2. This material was used directly in the next step without analysis.

Step 3: 2-(trans-4-(((benzyloxy)carbonyl)(methyl)amino)cyclohexyl)-2-fluoroacetic acid: A solution of the product from Step 2 above (50 mg) and hydrogen peroxide (0.195 ml, 1.91 mmol) in THF (3 ml) and water (1 ml) was cooled to 0-5° C. and treated with LiOH (4.58 mg, 0.191 mmol). The resultant mixture was stirred for 5 min at this temperature and then allowed to warm to RT and stir for 90 min. The reaction was partitioned between 2 M NaOH(aq) (5 ml) and EtOAc (10 ml). The organic phase was extracted with 2 M NaOH(aq) (5 ml) and the combined aqueous phases were acidified with 1 M HCl(aq) and then extracted with EtOAc (3×10 ml). The combined organic phases were dried over Na$_2$SO$_4$, filtered and concentrated in vacuo to afford the title compound (33 mg) as a colourless oil. This material was used directly in subsequent reactions without analysis.

Step 4: benzyl (trans-4-(2-((6-(4-(1-((tert-butoxycarbonyl)amino)cyclobutyl)phenyl)-5-phenylpyridin-3-yl)amino)-1-fluoro-2-oxoethyl)cyclohexyl)(methyl)carbamate: A solution of the product from Step 3 above (33 mg), Et$_3$N (65 µl, 0.464 mmol) and Intermediate 8 (39 mg, 0.093 mmol) in THF (8 ml) was treated with HATU (106 mg, 0.278 mmol) and the resultant mixture heated at 50° C. for 16 h. The mixture was cooled to RT, diluted with saturated NaHCO$_3$(aq) (10 ml) and extracted with EtOAc (2×20 ml). The combined extracts were dried over Na$_2$SO$_4$, filtered and concentrated in vacuo. The residue was purified by column chromatography (4 g cartridge, 0-50% EtOAc/isohexane) to afford the title compound (46 mg, 0.061 mmol, 95% purity) as a white solid. LCMS (Method 1): m/z 721 (M+H)$^+$, at 2.99 min.

Step 5: tert-butyl (1-(4-(5-(2-fluoro-2-(trans-4-(methylamino)cyclohexyl)acetamido)-3-phenylpyridin-2-yl)phenyl)cyclobutyl)carbamate: The product from Step 4 above (46 mg, 0.061 mmol, 95% purity) was added to a suspension of palladium (6.8 mg, 10% w/w on carbon, Type 39 paste) in EtOH (10 ml) and acetic acid (2 drops) under an atmosphere of N$_2$. The vessel was purged with H$_2$ and the reaction mixture stirred under an atmosphere of H$_2$ for 16 h. The reaction was filtered through a pad of Celite®, rinsing with MeOH (10 ml). The filtrate was concentrated in vacuo and the residue loaded onto a column of SCX in MeOH. The column was washed with MeOH and then the product was eluted with a 0.7 M solution of ammonia in MeOH. The solvent was removed in vacuo to afford the title compound (30 mg). This material was used directly in subsequent reactions without analysis.

Step 6: methyl (trans-4-(2-((6-(4-(1-aminocyclobutyl)phenyl)-5-phenylpyridin-3-yl)amino)-1-fluoro-2-oxoethyl)cyclohexyl)(methyl)carbamate: A mixture of the product from Step 5 above (30 mg) in THF (5 ml) was treated with DIPEA (53.6 µl, 0.307 mmol) and methyl chloroformate (11.9 µl, 0.153 mmol) and the resultant mixture stirred at RT for 32 h. The mixture was concentrated in vacuo and the residue was partitioned between DCM (5 ml) and saturated NaHCO$_3$(aq) (5 ml). The phases were filtered through a phase separation cartridge and the organic phase was concentrated in vacuo. The residue was dissolved in DCM (3 ml) and treated with TFA (153 µl, 1.99 mmol). The resultant mixture was stirred at RT for 4 h. The reaction mixture was concentrated in vacuo and the residue purified by preparative HPLC (Waters FractionLynx, Waters X-Bridge Prep-C18, 5 µm, 19×50 mm column, 35-65% MeCN in 10 mM ammonium bicarbonate) to afford the title compound (3 mg, 5.45 µmol, 99% purity) as a white solid. LCMS (Method 1): m/z 545 (M+H)$^+$, at 1.64 min. 1H NMR (400 MHz, DMSO-$d_6$) δ 10.45 (s, 1H), 8.93 (d, J=2.4 Hz, 1H), 8.16 (d, J=2.4 Hz, 1H), 7.41-7.27 (m, 5H), 7.27-7.15 (m, 4H), 4.98 (dd, J=48.7, 4.3 Hz, 1H), 3.91-3.67 (m, 1H), 3.58 (s, 3H), 2.71 (s, 3H), 2.39-2.26 (m, 2H), 2.13-1.72 (m, 8H), 1.69-1.22 (m, 7H).

Example 53

N-(trans-4-(2-((6-(4-(2-aminopropan-2-yl)-3-fluorophenyl)-5-phenylpyridin-3-yl)amino)-2-oxoethyl)cyclohexyl)-N-methylcyclopropanecarboxamide

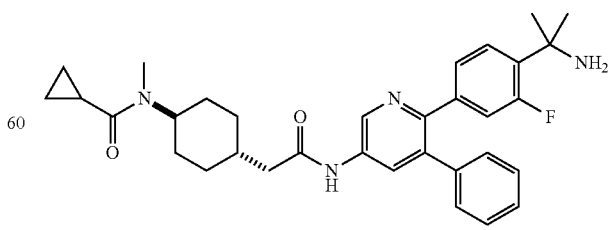

Step 1: benzyl (trans-4-(2-((6-(4-(2-((tert-butoxycarbonyl)amino)propan-2-yl)-3-fluorophenyl)-5-phenylpyridin- 3-yl)amino)-2-oxoethyl)cyclohexyl)(methyl)carbamate: The title compound (101 mg, 0.134 mmol, 94% purity) was isolated as a white solid from the reaction of Intermediate 19 (140 mg, 0.332 mmol), the product from Example 4 Step 1 (152 mg, 0.498 mmol), Et₃N (278 µl, 1.99 mmol) and T3P (0.587 ml, 0.996 mmol, 50% w/w in EtOAc) in EtOAc (3 ml) using essentially the same procedure as in Example 4 Step 2, except the reaction mixture was stirred at RT. LCMS (Method 1): m/z 709 (M+H)⁺, at 2.96 min.

Step 2: tert-butyl (2-(2-fluoro-4-(5-(2-(trans-4-(methylamino)cyclohexyl)acetamido)-3-phenylpyridin-2-yl)phenyl)propan-2-yl)carbamate: A solution of the product from Step 1 above (100 mg, 0.133 mmol, 94% purity) in MeOH (10 ml) was hydrogenated in a ThalesNano H-Cube® flow reactor (10% Pd/C, 30×4 mm cartridge, full hydrogen mode, 50° C., 1 ml/min flow rate). The solvent was removed in vacuo to afford the title compound (77 mg) as a white solid. This material was used directly in subsequent reactions without analysis.

Step 3: tert-butyl (2-(2-fluoro-4-(5-(2-(trans-4-(N-methylcyclopropanecarboxamido)cyclohexyl)acetamido)-3-phenylpyridin-2-yl)phenyl)propan-2-yl)carbamate: The title compound (11 mg, 0.017 mmol, 97% purity) was isolated as a white solid from the reaction of the product from Step 2 above (36 mg), the product from cyclopropanecarboxylic acid (4.8 µl, 0.060 mmol), Et₃N (45.6 µl, 0.327 mmol) and T3P (96 µl, 0.163 mmol, 50% w/w in EtOAc) in EtOAc (1.5 ml) using essentially the same procedure as in Example 4 Step 2, except the reaction mixture was stirred at RT. LCMS (Method 1): m/z 643 (M+H)⁺ at 2.57 min.

Step 4: N-(trans-4-(2-((6-(4-(2-aminopropan-2-yl)-3-fluorophenyl)-5-phenylpyridin-3-yl)amino)-2-oxoethyl)cyclohexyl)-N-methylcyclopropanecarboxamide: The title compound (8.5 mg, 0.015 mmol, 98% purity) was isolated as a white solid from the reaction of the product from Step 3 above (11 mg, 0.017 mmol, 97% purity) with TFA (0.5 ml) in DCM (3 ml) using essentially the same procedure as in Example 31 Step 2. LCMS (Method 1): m/z 543 (M+H)⁺ at 1.55 min. ¹H NMR (two rotamers in a 2:1 ratio) (400 MHz, DMSO-d₆) δ 10.30 (s, 1H), 8.81 (d, J=2.4 Hz, 1H), 8.11 (d, J=2.4 Hz, 1H), 7.46-7.30 (m, 4H), 7.29-7.15 (m, 2H), 7.09-6.92 (m, 2H), 4.34-4.15 (m, 1H, major), 4.11-3.90 (m, 1H, minor), 2.96 (s, 3H, major), 2.70 (s, 3H, minor), 2.37-2.20 (m, 2H), 2.06-1.58 (m, 4H), 1.56-1.32 (m, 8H), 1.34-1.00 (m, 4H), 0.78-0.60 (m, 4H).

Example 54

Methyl (trans-4-(1-((6-(4-(1-aminocyclobutyl)phenyl)-5-phenylpyridin-3-yl)amino)-1-oxopropan-2-yl)cyclohexyl)(methyl)carbamate

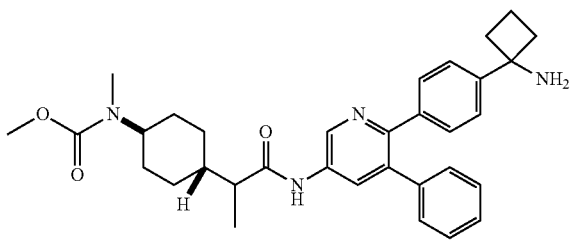

Step 1: ethyl 2-(trans-4-(((benzyloxy)carbonyl)(methyl)amino)cyclohexyl)propanoate: A solution of the product from Example 1 Step 2 (337 mg, 1.01 mmol) in THF (10 ml) was cooled to −78° C. and treated with LiHMDS (1.11 ml, 1.11 mmol, 1 M in THF) and stirred at this temperature for 15 min. The mixture was treated with iodomethane (139 µl, 2.22 mmol) and allowed to warm and stir at RT for 18 h. The reaction mixture was quenched with saturated NH₄Cl(aq) (10 ml) and extracted with EtOAc (10 ml). The extract was concentrated in vacuo to afford pale yellow oil. This material was purified by column chromatography (40 g cartridge, 0-40% EtOAc/isohexane) to afford the title compound (172 mg, 0.436 mmol, 88% purity) as a clear colourless oil. LCMS (Method 1): m/z 348 (M+H)⁺, at 2.70 min.

Step 2: 2-(trans-4-(((benzyloxy)carbonyl)(methyl)amino)cyclohexyl)propanoic acid: A mixture of the product from Step 1 above (172 mg, 0.436 mmol, 88% purity) in THF (5 ml) and MeOH (1 ml) was treated with 2 M LiOH(aq) (495 µl, 0.990 mmol) and the resultant mixture heated at 50° C. for 6 days, during which time the reaction mixture had concentrated to dryness. The residue was acidified with 1 M HCl(aq) and the resultant white precipitate was collected by filtration, washing with Et₂O, and dried in vacuo to afford the title compound (121 mg, 0.352 mmol, 93% purity) as a sticky white solid. LCMS (Method 1): m/z 320 (M+H)⁺, at 2.21 min.

Step 3: benzyl (trans-4-(1-((6-(4-(1-((tert-butoxycarbonyl)amino)cyclobutyl)phenyl)-5-phenylpyridin-3-yl)amino)-1-oxopropan-2-yl)cyclohexyl)(methyl)carbamate: The title compound (33 mg, 0.041 mmol, 90% purity) was isolated as a clear colourless glass from the reaction of the product from Step 2 above (57.6 mg, 0.167 mmol, 93% purity), DIPEA (63 µl, 0.361 mmol), HATU (68.6 mg, 0.180 mmol) and Intermediate 8 (50 mg, 0.120 mmol) in DMF (5 ml) using essentially the same procedure as in Example 17 Step 4. HPLC (Method 1): R_T 2.94 min.

Step 4: tert-butyl (1-(4-(5-(2-(trans-4-(methylamino)cyclohexyl)propanamido)-3-phenylpyridin-2-yl)phenyl)cyclobutyl)carbamate: The title compound (24 mg, 0.037 mmol, 89% purity) was isolated as a dark brown glass from the hydrogenation of the product from Step 3 above (33 mg, 0.041 mmol, 90% purity) using palladium (44.1 mg, 10% w/w on carbon, Type 39 paste) in EtOH (50 ml) and THF (50 ml) using essentially the same procedure as in Example 51 Step 2. LCMS (Method 1): m/z 583 (M+H)⁺, at 1.80 min.

Step 5: methyl (trans-4-(1-((6-(4-(1-((tert-butoxycarbonyl)amino)cyclobutyl)phenyl)-5-phenylpyridin-3-yl)amino)-1-oxopropan-2-yl)cyclohexyl)(methyl)carbamate: A mixture of the product from Step 4 above (24 mg, 0.037 mmol, 89% purity) in THF (2 ml) was treated with DIPEA (43.2 µl, 0.247 mmol) and methyl chloroformate (9.57 µl, 0.124 mmol) and the resultant mixture stirred at RT for 18 h. The reaction mixture was quenched with saturated NH₄Cl (aq) (5 ml) and extracted with EtOAc (3×10 ml). The combined extracts were washed with brine (20 ml), dried over MgSO₄, filtered and concentrated in vacuo to afford the title compound (22 mg, 0.029 mmol, 84% purity) as a pale brown glass. HPLC (Method 1): R_T 2.67 min.

Step 6: methyl (trans-4-(1-((6-(4-(1-aminocyclobutyl)phenyl)-5-phenylpyridin-3-yl)amino)-1-oxopropan-2-yl)cyclohexyl)(methyl)carbamate: The title compound (8 mg, 0.015 mmol, 99% purity) was isolated as a clear colourless glass from the reaction of the product from Step 5 above (22 mg, 0.029 mmol, 84% purity) and 90% (v/v) TFA in water (0.5 ml) using essentially the same procedure as in Example 1 Step 7, except the reaction mixture was stirred for 2 h. After work-up, the product was purified by preparative HPLC (Waters FractionLynx, Waters X-Bridge Prep-C18, 5 µm, 19×50 mm column, 35-65% MeCN in 10 mM ammo-

145 nium bicarbonate(aq)). LCMS (Method 2): m/z 541 (M+H)$^+$, at 2.27 min. $^1$H NMR (400 MHz, DMSO-d$_6$) δ 10.20 (s, 1H), 8.81 (d, J=2.4 Hz, 1H), 8.12 (d, J=2.4 Hz, 1H), 7.38-7.27 (m, 5H), 7.25-7.18 (m, 4H), 3.89-3.63 (m, 1H), 3.57 (s, 3H), 2.69 (s, 3H), 2.37-2.25 (m, 3H), 2.11-1.86 (m, 6H), 1.73-1.69 (m, 1H), 1.67-1.41 (m, 6H), 1.22-1.15 (m, 1H), 1.10 (d, J=6.8 Hz, 3H), 1.05-1.01 (m, 1H).

Example 55 trans-4-(2-((6-(4-(2-aminopropan-2-yl)phenyl)-5-phenylpyridin-3-yl)amino)-2-oxoethyl)-N,N-dimethylcyclohexanecarboxamide

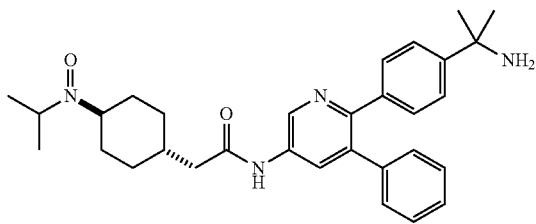

Step 1: 2-(trans-4-(methoxycarbonyl)cyclohexyl)acetic acid A solution of trans-4-(methoxycarbonyl)cyclohexanecarboxylic acid (5.12 g, 27.5 mmol) and oxalyl chloride (2.89 ml, 33.0 mmol) in DCM (20 ml) was treated with DMF (2 drops) and the resultant mixture heated at reflux for 2 h. The reaction mixture was concentrated in vacuo, diluted with THF (20 ml), and treated dropwise with (trimethylsilyl)diazomethane (41.2 ml, 82 mmol, 2 M in hexanes). The resultant mixture was stirred in the dark for 3 h and then quenched with AcOH until effervescence ceased. The mixture was diluted with water (30 ml) and extracted with DCM (2×20 ml). The extracts were dried over Na2SO4, filtered and concentrated in vacuo. The residue was dissolved in a mixture of THF and water (9:1), cooled to 0-5° C. and treated with silver trifluoroacetate (0.778 g, 3.30 mmol) and Et$_3$N (11.5 ml, 82 mmol). The resultant mixture was stirred at RT for 32 h. The mixture was diluted with 1 M NaOH(aq) (60 ml) and washed with EtOAc (2×50 ml). The aqueous phase was acidified with HCl(aq) and extracted with EtOAc (2×50 ml). The combined extracts were dried over Na$_2$SO$_4$, filtered and concentrated in vacuo to afford the title compound (3.87 g) as a mobile brown oil, which solidified upon standing. This material was used directly in subsequent reactions without analysis.

Step 2: trans-methyl 4-(2-((6-(4-(2-((tert-butoxycarbonyl)amino)propan-2-yl)phenyl)-5-phenylpyridin-3-yl)amino)-2-oxoethyl)cyclohexanecarboxylate The title compound (316 mg, 0.469 mmol, 87% purity) was isolated as a viscous orange oil from the reaction of Intermediate 2 (350 mg, 0.867 mmol), the product from Step 1 above (261 mg), Et$_3$N (604 µl, 4.34 mmol) and HATU (989 mg, 2.60 mmol) in THF (20 ml) using essentially the same procedure as in Example 1 Step 6, except the reaction mixture was stirred at RT for 16 h and then worked up. LCMS (Method 1): m/z 586 (M+H)$^+$, at 2.55 min. The compound contained 13% (by UV) residual Intermediate 2. This material was used directly in subsequent reactions without further purification.

Step 3: trans-4-(2-((6-(4-(2-((tert-butoxycarbonyl)amino)propan-2-yl)phenyl)-5-phenylpyridin-3-yl)amino)-2-oxoethyl)cyclohexanecarboxylic acid: A solution of the product from Step 1 above (316 mg, 0.469 mmol, 87% purity) in

146

THF (8 ml), water (4 ml) and MeOH (4 ml) was treated with LiOH (19 mg, 0.809 mmol) and the resultant mixture was stirred at RT for 16 h. The mixture was diluted with 2 M NaOH(aq) (5 ml) and extracted with EtOAC (2×10 ml). The combined extracts were concentrated in vacuo and the residue purified by column chromatography (12 g cartridge, 0-10% MeOH/DCM) to afford the title compound (120 mg, 0.204 mmol, 97% purity) as a tan solid. LCMS (Method 1): m/z 572 (M+H)$^+$, at 2.24 min.

Step 4: tert-butyl (2-(4-(5-(2-(trans-4-(dimethylcarbamoyl)cyclohexyl)acetamido)-3-phenylpyridin-2-yl)phenyl)propan-2-yl)carbamate: A solution of the product from Step 3 above (50 mg, 0.084 mmol, 97% purity), Et$_3$N (0.110 ml, 0.787 mmol) and dimethylamine hydrochloride (21 mg, 0.262 mmol) in THF (6 ml) was treated with HATU (0.100 g, 0.262 mmol) and the resultant mixture stirred for 16 h. The mixture was concentrated in vacuo, the residue partitioned between DCM (5 ml) and saturated NaHCO$_3$(aq) (5 ml) and filtered through a phase separation cartridge. The organic phase was concentrated in vacuo to afford the title compound (70 mg). This material was used directly in subsequent reactions without analysis.

Step 5: trans-4-(2-((6-(4-(2-aminopropan-2-yl)phenyl)-5-phenylpyridin-3-yl)amino)-2-oxoethyl)-N,N-dimethylcyclohexanecarboxamide: A solution of the product from Step 4 above (70 mg) in DCM (3 ml) was treated with TFA (0.180 ml, 2.34 mmol) the resultant mixture stirred at RT for 2 h. The mixture was concentrated in vacuo and the residue purified by preparative HPLC (Waters FractionLynx, Waters X-Bridge Prep-C18, 5 µm, 19×50 mm column, 5-50% MeCN in 10 mM ammonium bicarbonate) to afford the title compound (4 mg, 7.94 µmol, 99% purity) as a tan solid. LCMS (Method 1): m/z 499 (M+H)$^+$, at 1.33 min. $^1$H NMR (400 MHz, DMSO-d$_6$) δ 10.23 (s, 1H), 8.79 (d, J=2.4 Hz, 1H), 8.11 (d, J=2.4 Hz, 1H), 7.42-7.26 (m, 5H), 7.26-7.13 (m, 4H), 3.00 (s, 3H), 2.79 (s, 3H), 2.60-2.52 (m, 1H), 2.27 (d, J=6.5 Hz, 2H), 2.00 (br s, 2H), 1.84-1.61 (m, 5H), 1.45-1.22 (m, 8H), 1.18-1.00 (m, 2H).

Example 56

Methyl (trans-4-(2-((6-(4-(2-aminopropan-2-yl)phenyl)-5-phenylpyridazin-3-yl)amino)-2-oxoethyl)cyclohexyl)(methyl)carbamate

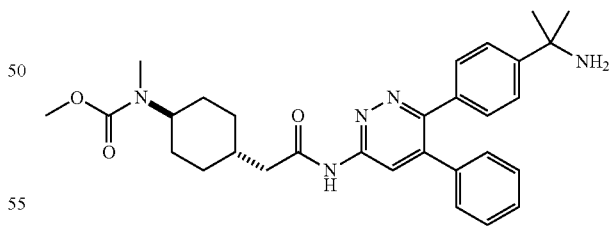

Step 1: Ethyl 2-(trans-4-((methoxycarbonyl)amino)cyclohexyl)acetate: A mixture of ethyl 2-(trans-4-aminocyclohexyl)acetate hydrochloride (2.00 g, 9.02 mmol) and DIPEA (9.45 ml, 54.1 mmol) in DCM (25 ml) was treated with methyl chloroformate (2.10 ml, 27.1 mmol) and the resultant solution was stirred at RT overnight. The reaction mixture was quenched with saturated NH$_4$Cl(aq) (100 ml), the phases were separated and the aqueous phase extracted with DCM (2×50 ml). The combined organic phases were washed with brine (100 ml), dried over MgSO$_4$, filtered and concentrated in vacuo. The residue was purified by column chromatography (40 g cartridge, 0-20% MeOH/DCM) to afford the title compound (1.97 g, 7.85 mmol, 97% purity) as an off-white solid. $^1$H NMR (400 MHz, DMSO-d$_6$) δ 7.00 (d, J=8.0 Hz, 1H), 4.05 (q, J=7.1 Hz, 2H), 3.51 (s, 3H), 3.25-3.13 (m, 1H), 2.17 (d, J=7.0 Hz, 2H), 1.86-1.48 (m, 5H), 1.23-0.91 (m, 7H).

Step 2: Ethyl 2-(trans-4-((methoxycarbonyl)(methyl)amino)cyclohexyl)acetate: A solution of the product from Step 1 above (1.97 g, 7.85 mmol, 97% purity) in THF (20 ml) was cooled to 0° C. and treated with sodium hydride (453 mg, 11.3 mmol, 60% w/w in mineral oil), then stirred for 15 min. The mixture was then treated with iodomethane (1.01 ml, 16.2 mmol) and stirred at RT overnight. The reaction mixture was quenched with saturated NH$_4$Cl(aq) (100 ml) and extracted with EtOAc (3×100 ml). The combined extracts were washed with brine (100 ml), dried over MgSO$_4$, filtered and concentrated in vacuo to afford the title compound (1.99 g, 7.50 mmol, 97% purity) as a pale orange oil. $^1$H NMR (400 MHz, DMSO-d$_6$) δ 4.05 (q, J=7.1 Hz, 2H), 3.85-3.67 (m, 1H), 3.58 (s, 3H), 2.70 (s, 3H), 2.18 (d, J=7.0 Hz, 2H), 1.79-1.43 (m, 7H), 1.18 (t, J=7.1 Hz, 3H), 1.14-0.99 (m, 2H).

Step 3: 2-(trans-4-((methoxycarbonyl)(methyl)amino)cyclohexyl)acetic acid: The title compound (1.7 g, 6.67 mmol, 90% purity) was isolated from the reaction of the product of Step 2 above (1.99 g, 7.50 mmol, 97% purity) with LiOH (372 mg, 15.5 mmol) in THF (10 ml), water (10 ml) and MeOH (5 ml) using essentially the same procedure as in Example 26 Step 2. $^1$H NMR (400 MHz, DMSO-d$_6$) δ 3.76 (br s, 1H), 3.58 (s, 3H), 2.70 (s, 3H), 2.10 (d, J=7.0 Hz, 2H), 1.84-1.69 (m, 2H), 1.67-1.39 (m, 4H), 1.30-1.12 (m, 2H), 1.11-0.97 (m, 2H). The compound contained 5% w/w residual EtOAc. This material was used in subsequent reactions without further drying.

Step 4: Methyl (trans-4-(2-((6-(4-(2-aminopropan-2-yl)phenyl)-5-phenylpyridazin-3-yl)amino)-2-oxoethyl)cyclohexyl)(methyl)carbamate: A stirred solution of the product from Step 3 above (42.5 mg, 0.167 mmol, 90% purity) and HATU (106 mg, 0.278 mmol) in DMF (5 ml) was treated with DIPEA (0.113 ml, 0.649 mmol) and the resultant mixture stirred at RT for 30 min. The product from Example 30 Step 1 (50 mg) was added and the resultant mixture heated at 50° C. overnight. The mixture was diluted with saturated NaHCO$_3$(aq) (100 ml) and extracted with EtOAc (3×50 ml). The combined extracts were washed sequentially with water (3×50 ml) and brine (50 ml) and then dried over MgSO$_4$, filtered and concentrated in vacuo. The residue was dissolved in DCM (2 ml) and treated with TFA (1 ml). The resultant mixture was stirred at RT for 1 h and then concentrated in vacuo. To remove residual TFA, the residue was thrice resuspended in toluene (20 ml) and concentrated in vacuo. The residue was purified by preparative HPLC (Varian PrepStar, Waters X-Bridge Prep-C18, 5 µm, 19×50 mm column, 20-40% MeCN in 10 mM ammonium bicarbonate (aq)), followed by column chromatography (12 g cartridge, 0-10% MeOH/DCM) to afford the title compound (11 mg, 0.021 mmol, 99% purity) as a white solid. LCMS (Method 1): m/z 516 (M+H)$^+$, 514 (M−H)$^−$ at 1.57 min. $^1$H NMR (400 MHz, Methanol-d$_4$) δ 8.51 (s, 1H), 7.54-7.22 (m, 9H), 4.01-3.84 (m, 1H), 3.70 (s, 3H), 2.81 (s, 3H), 2.46 (d, J=7.0 Hz, 2H), 2.02-1.81 (m, 3H), 1.80-1.57 (m, 4H), 1.51 (s, 6H), 1.39-1.16 (m, 2H).

Example 57

N-(6-(4-(trans-1-amino-3-hydroxy-3-methylcyclobutyl)phenyl)-5-phenylpyridazin-3-yl)-2-(trans-4-(N-methylacetamido)cyclohexyl)acetamide

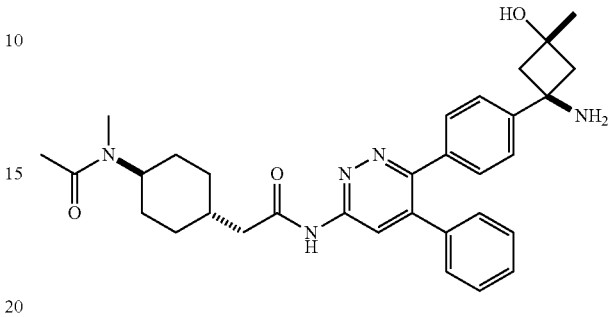

Step 1: tert-butyl (trans-1-(4-(6-amino-4-phenylpyridazin-3-yl)phenyl)-3-hydroxy-3-methylcyclobutyl)carbamate: The title compound (272 mg, 0.579 mmol, 95% purity) was isolated as an offwhite solid from the reaction of 6-chloro-5-phenylpyridazin-3-amine (217 mg, 1.05 mmol, prepared according to US2008/0045536), tert-butyl (trans-3-hydroxy-3-methyl-1-(4-(4,4,5,5-tetramethyl-1,3,2-dioxaborolan-2-yl)phenyl)cyclobutyl)carbamate (500 mg, 1.05 mmol, prepared according to Org. Process Res. Dev., 2012, 16, 1069), tetrakis-(triphenylphosphine)palladium(0) (122 mg, 0.105 mmol) and 2 M Na$_2$CO$_3$(aq) (1.19 ml, 2.37 mmol) in dioxane (5 ml) using essentially the same procedure as in Intermediate 3 Step 2, except, after work-up, the product was purified by column chromatography (12 g cartridge, 0-20% MeOH/DCM). LCMS (Method 1): m/z 447 (M+H)$^+$ at 1.40 min. $^1$H NMR (400 MHz, DMSO-d$_6$) δ 7.49 (s, 1H), 7.40-7.11 (m, 9H), 6.73 (s, 1H), 6.51 (s, 2H), 4.98 (s, 1H), 2.63-2.53 (m, 2H), 2.42-2.26 (m, 2H), 1.36 (s, 9H), 1.13 (s, 3H).

Step 2: N-(6-(4-(trans-1-amino-3-hydroxy-3-methylcyclobutyl)phenyl)-5-phenylpyridazin-3-yl)-2-(trans-4-(N-methylacetamido)cyclohexyl)acetamide: A stirred solution of the product from Example 1 Step 5 (47.8 mg) and the product from Step 1 above (50 mg, 0.106 mmol, 95% purity) in EtOAc (3 ml) was treated with Et$_3$N (78 µl, 0.560 mmol) and stirred at RT for 5 min. T3P (0.198 ml, 0.336 mmol, 50% w/w in EtOAc) was added and the resultant mixture stirred at 40° C. for 45 h. The reaction mixture was diluted with saturated NaHCO$_3$(aq) (100 ml) and extracted with EtOAc (3×50 ml). The combined extracts were washed sequentially with water (3×50 ml) and brine (50 ml), dried over MgSO$_4$, filtered and concentrated in vacuo. The residue was dissolved in DCM (2 ml) and then treated with TFA (1 ml). The resultant mixture was stirred at RT for 1 h and then concentrated in vacuo. To remove residual TFA, the residue was thrice resuspended in toluene (20 ml) and concentrated in vacuo. The crude product was purified by preparative HPLC (Gilson 215, Waters X-Bridge Prep-C18, 5 µm, 19×50 mm column, 20-40% MeCN in 10 mM ammonium bicarbonate (aq)) to afford title compound (19 mg, 0.035 mmol, 99% purity) as a white solid. LCMS (Method 1): m/z 542 (M+H)$^+$ at 1.26 min. $^1$H NMR (400 MHz, DMSO-d$_6$) (two rotamers in a 5:4 ratio) δ 11.28 (s, 1H, minor), 11.27 (s, 1H, major), 8.36 (s, 1H, minor), 8.35 (s, 1H, major), 7.49-7.23 (m, 9H), 4.82 (s, 1H), 4.31-4.18 (m, 1H, major), 3.61-3.50 (m, 1H, minor), 2.79 (s, 3H, major), 2.67 (s, 3H, minor), 2.47-2.35

(m, 4H), 2.31-2.15 (m, 2H), 2.02 (s, 3H, minor), 1.96 (s, 3H, major), 1.89-1.71 (m, 3H), 1.69-1.40 (m, 7H), 1.28-1.04 (m, 2H).

Example 58

N-(6-(4-(trans-1-amino-3-hydroxy-3-methylcyclobutyl)phenyl)-5-phenylpyridazin-3-yl)-2-(trans-4-(2-oxooxazolidin-3-yl)cyclohexyl)acetamide

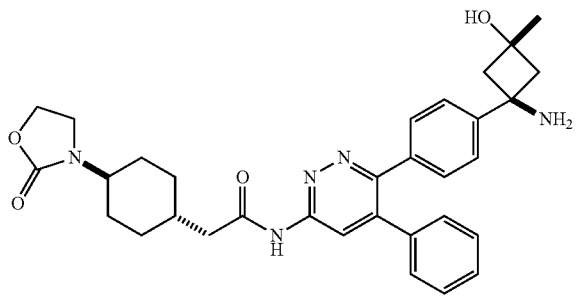 [SMILES: C[C@]1(O)C[C@@](N)(c2ccc(-c3nnc(NC(=O)C[C@H]4CC[C@H](N5CCOC5=O)CC4)cc3-c3ccccc3)cc2)C1]

The title compound (21 mg, 0.038 mmol) was isolated as a white solid from the reaction of the product from Example 42 Step 3 (50.9 mg), the product from Example 2 Step 1 (50 mg, 0.106 mmol, 95% purity), Et₃N (78 µl, 0.560 mmol) and T3P (0.198 ml, 0.336 mmol, 50% w/w in EtOAc) in EtOAc (3 ml) using essentially the same procedure as in Example 2 Step 2, except, instead of purification by preparative HPLC, the residue was loaded onto a column of SCX. The column was washed with MeOH and the product was eluted with a 0.7 M solution of ammonia in MeOH and concentrated in vacuo. LCMS (Method 1): m/z 556 (M+H)⁺, 554 (M−H)⁻ at 1.25 min. ¹H NMR (400 MHz, DMSO-d₆) δ 11.27 (s, 1H), 8.34 (s, 1H), 7.46-7.22 (m, 9H), 4.80 (s, 1H), 4.23 (t, J=9.0 Hz, 2H), 3.54-3.42 (m, 3H), 2.46-2.31 (m, 4H), 2.24-2.10 (m, 2H), 1.94 (s, 1H), 1.89-1.61 (m, 4H), 1.59-1.37 (m, 5H), 1.14 (m, 2H).

Example 59

Methyl (trans-4-(2-((6-(4-(trans-1-amino-3-hydroxy-3-methylcyclobutyl)phenyl)-5-phenylpyridazin-3-yl)amino)-2-oxoethyl)cyclohexyl)(methyl)carbamate

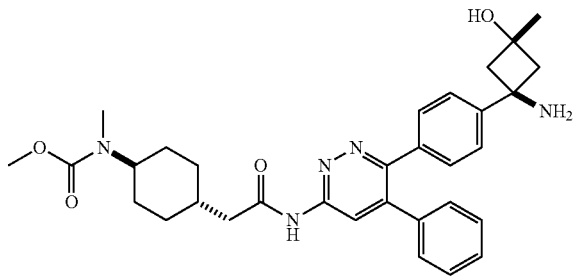 [SMILES: COC(=O)N(C)[C@H]1CC[C@H](CC(=O)Nc2cc(-c3ccccc3)c(-c3ccc([C@]4(N)C[C@](C)(O)C4)cc3)nn2)CC1]

The title compound (29 mg, 0.052 mmol) was isolated as a white solid from the reaction of the product from Example 56 Step 3 (51.3 mg), the product from Example 2 Step 1 (50 mg, 0.106 mmol, 95% purity), HATU (63.9 mg, 0.168 mmol) and DIPEA (130 µl, 0.784 mmol) in DMF (5 ml) using essentially the same procedure as in Example 56 Step 4, except column chromatography was not performed. LCMS (Method 1): m/z 558 (M+H)⁺, 556 (M−H)⁻ at 1.42 min. ¹H NMR (400 MHz, DMSO-d₆) δ 11.24 (s, 1H), 8.34 (s, 1H), 7.52-7.20 (m, 9H), 4.78 (s, 1H), 3.80 (br, 1H), 3.58 (s, 3H), 2.71 (s, 3H), 2.44-2.31 (m, 4H), 2.21-2.11 (m, 2H), 1.99 (s, 2H), 1.88-1.68 (m, 3H), 1.64-1.43 (m, 7H), 1.20-1.06 (m, 2H).

Example 60

Methyl (trans-4-(2-((6-(4-(1-amino-3,3-difluorocyclobutyl)phenyl)-5-phenylpyridazin-3-yl)amino)-2-oxoethyl)cyclohexyl)(methyl)carbamate

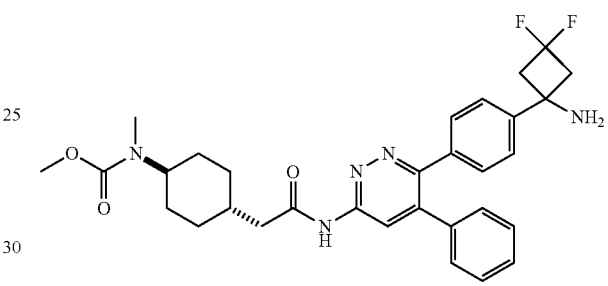

Step 1: tert-butyl (1-(4-(6-amino-4-phenylpyridazin-3-yl)phenyl)-3,3-difluorocyclobutyl)carbamate: The title compound (103 mg, 0.091 mmol, 40% purity) was isolated as a yellow solid from the reaction of 6-chloro-5-phenylpyridazin-3-amine (200 mg, 0.973 mmol, prepared according to US2008/0045536), tert-butyl (3,3-difluoro-1-(4-(4,4,5,5-tetramethyl-1,3,2-dioxaborolan-2-yl)phenyl)cyclobutyl)carbamate (500 mg, 1.22 mmol, prepared according to WO2009148916), tetrakis-(triphenylphosphine)palladium(0) (112 mg, 0.097 mmol) and 2 M Na₂CO₃(aq) (1.09 ml, 2.19 mmol) in dioxane (5 ml) using essentially the same procedure as in Intermediate 3 Step 2. LCMS (Method 1): m/z 453 (M+H)⁺, 451 (M−H)⁻ at 1.68 min. This material contained 55% w/w triphenylphosphine oxide and 5% w/w residual EtOAc, but was used in subsequent reactions without further purification.

Step 2: Methyl (trans-4-(2-((6-(4-(1-amino-3,3-difluorocyclobutyl)phenyl)-5-phenylpyridazin-3-yl)amino)-2-oxoethyl)cyclohexyl)(methyl)carbamate: The title compound (11 mg, 0.019 mmol, 99% purity) was isolated as a white solid from the reaction of the product from Example 56 Step 3 (50.2 mg), the product from Step 1 above (33 mg, 0.029 mmol, 40% purity), HATU (83 mg, 0.219 mmol) and DIPEA (84 µl, 0.511 mmol) in DMF (5 ml) using essentially the same procedure as in Example 56 Step 4, except column chromatography was not performed. LCMS (Method 1): m/z 564 (M+H)⁺, 562 (M−H)⁻ at 1.62 min. ¹H NMR (400 MHz, DMSO-d₆) δ 11.27 (s, 1H), 8.36 (s, 1H), 7.48-7.22 (m, 9H), 3.76 (br, 1H), 3.58 (s, 3H), 3.08-2.92 (m, 2H), 2.86-2.60 (m, 6H), 2.40 (d, J=6.7 Hz, 2H), 1.87-1.70 (m, 2H), 1.65-1.44 (m, 4H), 1.19-1.04 (m, 2H).

Example 61

N-(6-(4-(1-amino-3,3-difluorocyclobutyl)phenyl)-5-phenylpyridazin-3-yl)-2-(trans-4-(2-oxooxazolidin-3-yl)cyclohexyl)acetamide

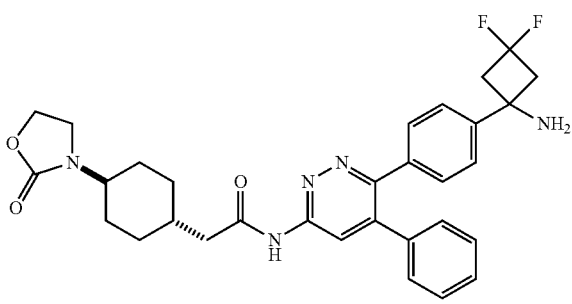 [SMILES: NC1(c2ccc(-c3nnc(NC(=O)C[C@H]4CC[C@H](N5CCOC5=O)CC4)cc3-c3ccccc3)cc2)CC(F)(F)C1]

The title compound (4 mg, 7.12 μmol, 99% purity) was isolated as a white solid from the reaction of the product from Example 42 Step 3 (19.9 mg), the product from Example 60 Step 1 (33 mg, 0.029 mmol, 40% purity), HATU (33 mg, 0.088 mmol) and DIPEA (36 μl, 0.204 mmol) in DMF (5 ml) using essentially the same procedure as in Example 56 Step 4, except column chromatography was not performed. LCMS (Method 1): m/z 562 (M+H)$^+$, 560 (M−H)$^−$ at 1.45 min. $^1$H NMR (400 MHz, DMSO-d$_6$) δ 11.27 (s, 1H), 8.36 (s, 1H), 7.48-7.21 (m, 9H), 4.24 (dd, J=9.0, 7.0 Hz, 2H), 3.59-3.40 (m, 3H), 3.07-2.93 (m, 2H), 2.82-2.67 (m, 2H), 2.41 (d, J=6.8 Hz, 2H), 1.92-1.65 (m, 5H), 1.59-1.39 (m, 2H), 1.32-1.06 (m, 2H).

Example 62

Methyl (trans-4-(2-((6-(4-(1-aminocyclopropyl)-3-fluorophenyl)-5-phenylpyridin-3-yl)amino)-2-oxoethyl)cyclohexyl)(methyl)carbamate

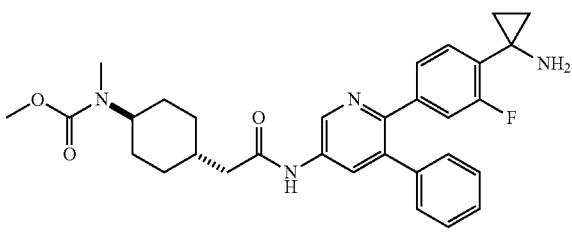 [SMILES: COC(=O)N(C)[C@H]1CC[C@H](CC(=O)Nc2cnc(-c3ccc(C4(N)CC4)c(F)c3)c(-c3ccccc3)c2)CC1]

Step 1: 1-(4-bromo-2-fluorophenyl)cyclopropanamine: 4-bromo-2-fluorobenzonitrile (2 g, 10.0 mmol) was suspended in Et$_2$O (60 ml) and the resultant mixture cooled to −78° C. Titanium(IV) isopropoxide (3.22 ml, 11.0 mmol) was added dropwise and the reaction mixture was stirred for 5 min. Ethylmagnesium bromide (7.33 ml, 22.0 mmol) was added dropwise and the resultant reaction mixture stirred for 30 min at −78° C. The mixture was allowed to warm to RT over 1 h, then boron trifluoride diethyl etherate (4.44 ml, 35.0 mmol) was added dropwise. Stirring was continued for 2 h, then the reaction mixture was cooled to 0° C. and quenched with 1 M HCl(aq) (30 ml). The mixture was partitioned between Et$_2$O (50 ml) and 10% NaOH(aq) (30 ml) and the phases separated. The aqueous phase was extracted with Et$_2$O and the combined organic phases were dried over MgSO$_4$, filtered, and concentrated in vacuo. The residue loaded onto a column of SCX (25 g) in MeOH. The column was washed with MeOH and the product was eluted with a 0.7 M solution of ammonia in MeOH. The solvent was removed in vacuo to afford the title compound (1.76 g, 7.27 mmol) as a yellow oil. $^1$H NMR (400 MHz, DMSO-d$_6$) δ 7.44 (dd, J=10.4, 1.8 Hz, 1H), 7.39-7.29 (m, 2H), 2.30 (br s, 2H), 0.89-0.76 (m, 4H).

Step 2: tert-butyl (1-(4-bromo-2-fluorophenyl)cyclopropyl)carbamate: The title compound (1.56 g, 4.58 mmol, 97% purity) was isolated as an off-white solid from the reaction of the product from Step 1 above (1.76 g, 7.27 mmol), Et$_3$N (1.28 ml, 9.18 mmol) and Boc$_2$O (1.75 g, 8.03 mmol) in DCM (50 ml) using essentially the same procedure as in Intermediate 2 Step 1. LCMS (Method 1): m/z 274 (M+H—C$_4$H$_8$)$^+$ at 2.54 min. $^1$H NMR (400 MHz, DMSO-d$_6$) δ 7.69 (br s, 1H), 7.51-7.27 (m, 3H), 1.32 (s, 9H), 1.09-0.95 (m, 4H).

Step 3: tert-butyl (1-(2-fluoro-4-(4,4,5,5-tetramethyl-1,3,2-dioxaborolan-2-yl)phenyl)cyclopropyl)carbamate: The title compound (1.20 g, 2.86 mmol, 90% purity) was isolated as a sticky yellow solid from the reaction of the product from Step 1 above (1.56 g, 4.58 mmol, 97% purity), bis-(pinacolato)diboron (1.66 g, 6.54 mmol), palladium(II) acetate (61 mg, 0.273 mmol), XPhos (261 mg, 0.545 mmol) and potassium acetate (1.61 g, 16.4 mmol) in MeCN (30 ml) using essentially the same procedure as in Intermediate 2 Step 2. $^1$H NMR (400 MHz, DMSO-d$_6$) δ 7.68 (s, 1H), 7.53-7.35 (m, 2H), 7.26 (d, J=11.2 Hz, 1H), 1.38-1.23 (m, 21H), 1.15-0.99 (m, 4H).

Step 4: tert-butyl (1-(4-(3-chloro-5-nitropyridin-2-yl)-2-fluorophenyl)cyclopropyl)carbamate: The title compound (820 mg, 1.97 mmol, 98% purity) was isolated as an off-white solid from the reaction of 2,3-dichloro-5-nitropyridine (585 mg, 3.03 mmol), the product from Step 3 above (1.20 g, 2.86 mmol, 90% purity), tetrakis-(triphenylphosphine)palladium(0) (350 mg, 0.303 mmol) and 2 M Na$_2$CO$_3$ (aq) (3.41 ml, 6.82 mmol) in dioxane (40 ml) using essentially the same procedure as in Intermediate 1 Step 1, except the reaction mixture was heated at 80° C. for 18 h. LCMS (Method 1): m/z 352 (M+H—C$_4$H$_8$)$^+$ at 2.60 min. $^1$H NMR (400 MHz, DMSO-d$_6$) δ 9.41 (d, J=2.3 Hz, 1H), 8.90 (d, J=2.4 Hz, 1H), 7.77 (s, 1H), 7.68-7.46 (m, 4H), 1.34 (s, 9H), 1.24-1.14 (m, 2H), 1.14-1.02 (m, 2H).

Step 5: tert-butyl (1-(2-fluoro-4-(5-nitro-3-phenylpyridin-2-yl)phenyl)cyclopropyl)carbamate: The title compound (703 mg, 1.55 mmol) was isolated as an off-white solid from the reaction of the product from Step 4 above (820 mg, 1.97 mmol, 98% purity), 4,4,5,5-tetramethyl-2-phenyl-1,3,2-dioxaborolane (513 mg, 2.51 mmol), tetrakis-(triphenylphosphine)palladium(0) (232 mg, 0.201 mmol) and 2 M Na$_2$CO$_3$ (aq) (2.26 ml, 4.52 mmol) were reacted together in dioxane (25 ml) using essentially the same procedure as in Intermediate 1 Step 2. LCMS (Method 1): m/z 394 (M+H—C$_4$H$_8$)$^+$ at 2.77 min. $^1$H NMR (400 MHz, DMSO-d$_6$) (two rotamers in a 2:1 ratio) δ 9.45 (d, J=2.5 Hz, 1H), 8.53 (d, J=2.5 Hz, 1H), 7.70 (s, 1H), 7.55-7.22 (m, 6H), 7.22-6.92 (m, 2H), 1.32 (br s, 9H, major), 1.25 (br s, 9H, minor), 1.10 (br, 4H, minor), 1.03 (br, 4H, major).

Step 6: tert-butyl (1-(4-(5-amino-3-phenylpyridin-2-yl)-2-fluorophenyl)cyclopropyl)carbamate: The title compound (568 mg, 1.34 mmol, 99% purity) was isolated as a white solid from the reaction of the product of Step 5 above (695 mg, 1.55 mmol), iron powder (864 mg, 15.5 mmol) and NH$_4$Cl (108 mg, 2.01 mmol) in IPA (27 ml) and water (3 ml) using essentially the same procedure as in Intermediate 1 Step 3, except the reaction mixture was heated for 18 h.

LCMS (Method 1): m/z 420 (M+H)⁺ at 1.77 min. ¹H NMR (400 MHz, DMSO-d₆) δ 8.03 (d, J=2.6 Hz, 1H), 7.57 (s, 1H), 7.37-7.25 (m, 3H), 7.23-7.09 (m, 3H), 6.99-6.73 (m, 3H), 5.58 (s, 2H), 1.31 (s, 9H), 1.08-0.95 (m, 4H).

Step 7: Methyl (trans-4-(2-((6-(4-(1-(((tert-butoxycarbonyl)amino)cyclopropyl)-3-fluorophenyl)-5-phenylpyridin-3-yl)amino)-2-oxoethyl)cyclohexyl)(methyl)carbamate: A mixture of the product from Step 6 above (50 mg, 0.118 mmol, 99% purity), the product from Example 56 Step 3 (41.0 mg), DIPEA (62.5 μl, 0.358 mmol) and HATU (91 mg, 0.238 mmol) in THF (3 ml) was heated at 50° C. for 18 h. Additional HATU (46 mg, 0.119 mmol) and DIPEA (41.7 μl, 0.239 mmol) were added and heating continued for 30 h. The reaction mixture was partitioned between saturated NaHCO₃(aq) (10 ml) and EtOAc (15 ml) and the phases separated. The aqueous phase was extracted with EtOAc (15 ml) and the combined organic phases were dried over MgSO₄, filtered and concentrated in vacuo. The residue was purified by column chromatography (4 g cartridge, 50-90% EtOAc/isohexane) to afford the title compound (28 mg, 0.043 mmol, 97% purity) as a brown solid. LCMS (Method 1): m/z 631 (M+H)⁺ at 2.60 min.

Step 7: methyl (trans-4-(2-((6-(4-(1-aminocyclopropyl)-3-fluorophenyl)-5-phenylpyridin-3-yl)amino)-2-oxoethyl)cyclohexyl)(methyl)carbamate: A stirred solution of the product from Step 6 above (28 mg, 0.043 mmol, 97% purity) in DCM (2 ml) was treated with TFA (1 ml, 13.0 mmol) and the resultant reaction mixture was stirred at RT for 1 h. The mixture was concentrated in vacuo. To remove residual TFA, the residue was thrice resuspended in toluene (20 ml) and concentrated in vacuo. The residue was purified by preparative HPLC (Gilson 215, Waters X-Bridge Prep-C18, 5 μm, 19×50 mm column, 25-65% MeCN in 10 mM ammonium bicarbonate(aq)) to afford the title compound (15 mg, 0.028 mmol, 99% purity) as a white solid. LCMS (Method 1): m/z 531 (M+H)⁺, 529 (M−H)⁻, at 1.55 min. ¹H NMR (400 MHz, DMSO-d₆) δ 10.3 (s, 1H), 8.81 (d, J=2.4 Hz, 1H), 8.11 (d, J=2.4 Hz, 1H), 7.41-7.32 (m, 3H), 7.31-7.16 (m, 3H), 7.06-6.92 (m, 2H), 3.92-3.68 (m, 1H), 3.58 (s, 3H), 2.71 (s, 3H), 2.43 (br, 2H), 2.27 (d, J=6.8 Hz, 2H), 1.90-1.69 (m, 3H), 1.64-1.42 (m, 4H), 1.23-1.02 (m, 2H), 0.85-0.77 (m, 4H).

Example 63

N-(5-(4-(2-aminopropan-2-yl)phenyl)-4-phenylpyridin-2-yl)-2-(trans-4-(N-methylacetamido)cyclohexyl)acetamide

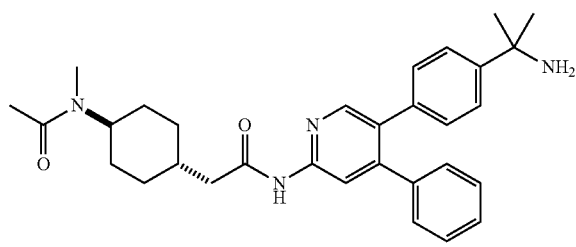 [SMILES: CC(=O)N(C)[C@H]1CC[C@H](CC(=O)Nc2cc(-c3ccccc3)c(-c3ccc(C(C)(C)N)cc3)cn2)CC1]

Step 1: benzyl (5-(4-(2-((tert-butoxycarbonyl)amino)propan-2-yl)phenyl)-4-phenylpyridin-2-yl)carbamate: The title compound (2.62 g, 4.82 mmol, 99% purity) was isolated as a pale yellow solid, from the reaction of the product of Intermediate 2 Step 2 (2.29 g, 6.33 mmol), the product from Intermediate 20 Step 3 (2.31 g, 5.97 mmol, 99% purity), tetrakis-(triphenylphosphine)palladium(0) (0.697 g, 0.603 mmol) and 2 M Na₂CO₃(aq) (6.78 ml, 13.6 mmol) in dioxane (200 ml) using essentially the same procedure as in Intermediate 1 Step 1, except the reaction mixture was heated under reflux for 18 h. LCMS (Method 1): m/z 538 (M+H)⁺ at 3.03 min.

Step 2: tert-butyl (2-(4-(6-amino-4-phenylpyridin-3-yl)phenyl)propan-2-yl)carbamate: The product from Step 1 above (2.62 g, 4.82 mmol, 99% purity) was dissolved in a mixture of EtOH (50 ml) and THF (50 ml) and the vessel purged with N₂. Palladium (5.19 g, 10% w/w on carbon, Type 39 paste) was added and the vessel further purged with N₂. The vessel was then purged with H₂ and then stirred at RT under an atmosphere of H₂ for 3 days. The vessel was purged with N₂, the reaction mixture was filtered through Celite®, washing with MeOH (50 ml), then DCM (5 ml), and concentrated in vacuo. The residue was purified by column chromatography (12 g cartridge, 0-5% (0.7 M NH₃/MeOH solution)/DCM) to afford the title compound (653 mg, 1.62 mmol) as a flocculent white solid. LCMS (Method 1): m/z 404 (M+H)⁺ at 1.71 min.

Step 3: tert-butyl (2-(4-(6-(2-(trans-4-(N-methylacetamido)cyclohexyl)acetamido)-4-phenylpyridin-3-yl)phenyl)propan-2-yl)carbamate: A suspension of Example 1 Step 5 (52.9 mg) in DCE (2 ml) was treated with 1-chloro-N,N,2-trimethylprop-1-en-1-amine (34.4 μl, 0.260 mmol) and stirred at RT for 2 h. The mixture was treated with a solution of the product from Step 2 above (50 mg, 0.124 mmol) in pyridine (500 μl, 6.18 mmol) and the resultant mixture stirred at RT for 3 h. The mixture was quenched with water, the phases separated and the organic phase concentrated in vacuo. The residue was purified by column chromatography (4 g cartridge, 0-5% (0.7 M NH₃/MeOH solution)/DCM) to afford the title compound (45 mg, 0.071 mmol, 95% purity) as a white glass. LCMS (Method 1): m/z 599 (M+H)⁺ at 2.55 min.

Step 4: N-(5-(4-(2-aminopropan-2-yl)phenyl)-4-phenylpyridin-2-yl)-2-(trans-4-(N-methylacetamido)cyclohexyl)acetamide: A solution of the product from Step 3 above (45 mg, 0.071 mmol, 95% purity) in DCM (2 ml) was treated with TFA (29.0 μl, 0.376 mmol) and stirred at RT for 3 h. Additional TFA (100 μl) was added and stirring continued for 18 h. The mixture was loaded onto a column of SCX (100 mg) in MeOH. The column was washed with MeOH and then the product was eluted with 0.7 M ammonia in MeOH. The solvent removed in vacuo and the residue purified by preparative HPLC (Waters FractionLynx, Waters X-Bridge Prep-C18, 5 μm, 19×50 mm column, 35-65% MeCN in 10 mM ammonium bicarbonate(aq)) to afford the title compound (19 mg, 0.038 mmol, 99% purity) as a clear colourless glass. LCMS (Method 1): m/z 499 (M+H)⁺ at 1.44 min. ¹H NMR (400 MHz, DMSO-d₆) δ 10.60 (d, J=7.0 Hz, 1H), 8.30 (s, 1H), 8.15 (s, 1H), 7.42 (d, J=8.4 Hz, 2H), 7.35-7.29 (m, 3H), 7.20-7.14 (m, 2H), 7.06 (d, J=8.3 Hz, 2H), 4.27-4.16 (m, 1H), 3.56-3.50 (m, 1H), 2.78 (s, 2H), 2.66 (s, 2H), 2.34-2.31 (m, 2H), 2.01 (s, 1H), 1.95 (s, 2H), 1.85-1.65 (m, 3H), 1.68-1.52 (m, 2H), 1.48-1.44 (m, 2H), 1.33 (s, 6H), 1.24-1.03 (m, 2H).

Example 64

N-(5-(4-(2-aminopropan-2-yl)phenyl)-4-phenylpyridin-2-yl)-2-(trans-4-(2-oxooxazolidin-3-yl)cyclohexyl)acetamide

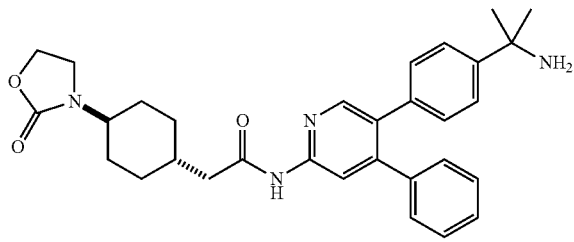 [SMILES: CC(C)(N)c1ccc(-c2cnc(NC(=O)C[C@H]3CC[C@H](N4CCOC4=O)CC3)cc2-c2ccccc2)cc1]

Step 1: tert-butyl (2-(4-(6-(2-(trans-4-(2-oxooxazolidin-3-yl)cyclohexyl)acetamido)-4-phenylpyridin-3-yl)phenyl)propan-2-yl)carbamate: A suspension of Example 42 Step 3 (50.7 mg) in DCM (2 ml) was treated with 1-chloro-N,N,2-trimethylprop-1-en-1-amine (31 µl, 0.234 mmol) and stirred at RT for 2 h. The mixture was treated with a solution of the product from Example 63 Step 2 (45 mg, 0.112 mmol) in pyridine (500 µl, 6.18 mmol) and the resultant mixture stirred at RT for 3 h. The mixture was quenched with water, the phases separated and the organic phase concentrated in vacuo. The residue was redissolved in DCM (10 ml) and treated with 10% CuSO$_4$(aq) (10 ml) and stirred at RT for 30 min. The phases separated and the organic phase concentrated in vacuo to afford the title compound (84 mg, 0.111 mmol, 81% purity) as a pale yellow oil. HPLC (Method 1): R$_T$2.59 min. The compound contained residual product from Example 63 Step 2. This material was used directly in subsequent reactions without further purification Step 2: N-(5-(4-(2-aminopropan-2-yl)phenyl)-4-phenylpyridin-2-yl)-2-(trans-4-(2-oxooxazolidin-3-yl)cyclohexyl)acetamide: A solution of the product from Step 1 above (84 mg, 0.111 mmol, 81% purity) in DCM (0.5 ml) was treated with TFA (500 µl, 6.49 mmol) and the resultant mixture stirred at RT for 2 h. The mixture was concentrated in vacuo and the residue purified by preparative HPLC (Waters FractionLynx, Waters X-Bridge Prep-C18, 5 µm, 19×50 mm column, 35-65% MeCN in 10 mM ammonium bicarbonate(aq)) to afford the title compound (13 mg, 0.025 mmol, 98% purity) as a clear colourless glass. LCMS (Method 2): m/z 513 (M+H)$^+$ at 1.91 min. $^1$H NMR (400 MHz, DMSO-d$_6$) δ 10.60 (s, 1H), 8.32-8.29 (m, 1H), 8.15 (s, 1H), 7.42 (d, J=8.5 Hz, 2H), 7.35-7.30 (m, 3H), 7.20-7.15 (m, 2H), 7.06 (d, J=8.5 Hz, 2H), 4.22 (dd, J=8.7, 7.2 Hz, 2H), 3.50-3.40 (m, 3H), 2.54 (s, 1H), 2.33 (d, J=6.8 Hz, 2H), 2.15 (br s, 1H), 1.84-1.62 (m, 5H), 1.53-1.39 (m, 2H), 1.33 (s, 6H), 1.15-1.07 (m, 2H).

Example 65

N-(6-(4-(2-aminopropan-2-yl)phenyl)-5-phenylpyridazin-3-yl)-2-(trans-4-(2-oxooxazolidin-3-yl)cyclohexyl)acetamide

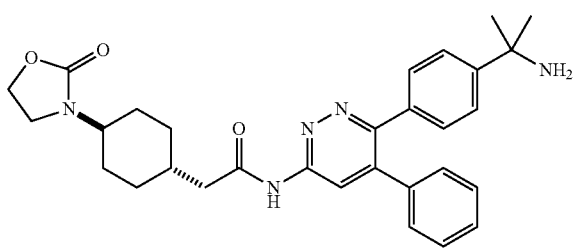 [SMILES: CC(C)(N)c1ccc(-c2nnc(NC(=O)C[C@H]3CC[C@H](N4CCOC4=O)CC3)cc2-c2ccccc2)cc1]

Step 1: tert-butyl (2-(4-(6-(2-(trans-4-(2-oxooxazolidin-3-yl)cyclohexyl)acetamido)-4-phenylpyridazin-3-yl)phenyl)propan-2-yl)carbamate: A suspension of the product from Example 42 Step 3 (59 mg) in DCM (5 ml) was treated with 1-chloro-N,N,2-trimethylprop-1-en-1-amine (36 µl, 0.272 mmol) and stirred at RT for 1 h. The mixture was treated with a solution of the product from Example 30 Step 1 (50 mg) in pyridine (2 ml, 24.7 mmol) and stirred at RT overnight. The reaction mixture was poured into 1 M HCl(aq) (50 ml) and extracted with DCM (3×100 ml). The combined extracts were washed with brine (100 ml), dried over MgSO$_4$, filtered and concentrated in vacuo. The residue was purified by column chromatography (12 g cartridge, 0-100% EtOAc/isohexane) to afford the title compound (44 mg, 65 µmol, 90% purity) as a white solid. $^1$H NMR (400 MHz, DMSO-d$_6$) δ 11.28 (s, 1H), 8.35 (s, 1H), 7.72-7.50 (m, 2H), 7.40-7.33 (m, 2H), 7.30-7.11 (m, 6H), 4.28-4.18 (m, 3H), 3.55-3.40 (m, 3H), 2.41 (d, J=6.7 Hz, 2H), 1.85-1.57 (m, 5H), 1.53-1.39 (m, 8H), 1.33 (s, 9H), 1.18-0.97 (m, 2H). The compound contained residual 4% w/w residual DCM and 6% w/w residual EtOAc. This material was used in subsequent reactions without further drying.

Step 2: N-(6-(4-(2-aminopropan-2-yl)phenyl)-5-phenylpyridazin-3-yl)-2-(trans-4-(2-oxooxazolidin-3-yl)cyclohexyl)acetamide: A stirred solution of the product from Step 1 above (40 mg, 59 µmol, 90% purity) in DCM (1 ml) was treated with TFA (0.5 ml, 6.49 mmol) and the resultant mixture stirred at RT for 1 h. The mixture was concentrated in vacuo and the residue was dissolved in DCM (100 ml) and then sequentially washed with saturated NaHCO$_3$(aq) (2×50 ml) and brine (50 ml). The organic phase was dried over MgSO$_4$, filtered and concentrated in vacuo. The residue was purified by column chromatography (12 g cartridge, 0-15% MeOH/DCM) to afford the title compound (22 mg, 43 µmol) as a white solid. LCMS (Method 1): m/z 514 (M+H)$^+$, 512 (M−H)$^−$ at 1.35 min. $^1$H NMR (400 MHz, DMSO-d$_6$) δ 11.27 (s, 1H), 8.35 (s, 1H), 7.51-7.44 (m, 2H), 7.42-7.35 (m, 3H), 7.29-7.23 (m, 4H), 4.30-4.18 (m, 2H), 3.55-3.41 (m, 3H), 2.40 (d, J=6.8 Hz, 2H), 2.01 (s, 2H), 1.87-1.62 (m, 5H), 1.57-1.41 (m, 2H), 1.35 (s, 6H), 1.22-1.06 (m, 2H).

Example 66

N-(6-(4-(1-aminocyclobutyl)phenyl)-5-phenylpyridazin-3-yl)-2-(trans-4-(2-oxooxazolidin-3-yl)cyclohexyl)acetamide

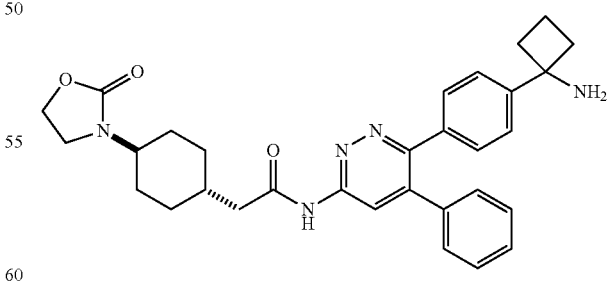

Step 1: tert-butyl (1-(4-(6-amino-4-phenylpyridazin-3-yl)phenyl)cyclobutyl)carbamate: 6-chloro-5-phenylpyridazin-3-amine (315 mg, 1.53 mmol, prepared according to US2008/0045536), the product from Intermediate 8 Step 1 (629 mg, 1.69 mmol) and tetrakis-(triphenylphosphine)palladium(0) (177 mg, 0.153 mmol) were combined in dioxane (5 ml) and treated with 2 M Na$_2$CO$_3$(aq) (1.7 ml, 3.40 mmol). The reaction mixture was degassed with nitrogen for 5 min and then heated at 90° C. overnight. After cooling, the mixture was partitioned between DCM (50 ml) and water (50 ml), the organic layer separated, dried over MgSO$_4$, filtered and concentrated in vacuo. The residue was purified by column chromatography (40 g cartridge, 0-5% MeOH/DCM) to afford the title compound (214 mg, 0.488 mmol, 95% purity) as a yellow foam. LCMS (Method 1): m/z 417 (M+H)$^+$ at 1.63 min.

Step 2: tert-butyl (1-(4-(6-(2-(trans-4-(2-oxooxazolidin-3-yl)cyclohexyl)acetamido)-4-phenylpyridazin-3-yl)phenyl)cyclobutyl)carbamate: A solution of the product from Example 42 Step 3 (57 mg) in DCM (5 ml) was treated with 1-chloro-N,N,2-trimethylprop-1-en-1-amine (35 µL, 0.265 mmol) and stirred at RT for 2 h. A solution of the product from Step 1 above (50 mg, 0.114 mmol, 95% purity) in pyridine (2 ml, 24.7 mmol) was added and the mixture was stirred at RT overnight, then partitioned between DCM (80 ml) and 1M HCl(aq) (50 ml). The organic layer was separated, passed through a phase separation cartridge and concentrated in vacuo. The residue, which contained predominantly tert-butyl (1-(4-(6-(2-(trans-4-(2-oxooxazolidin-3-yl)cyclohexyl)-N-(2-(trans-4-(2-oxooxazolidin-3-yl)cyclohexyl)acetyl)acetamido)-4-phenylpyridazin-3-yl)phenyl)cyclobutyl)carbamate, was purified by column chromatography (12 g cartridge, 0-100% EtOAc/isohexane). This material was dissolved in MeOH (3 ml), treated with K$_2$CO$_3$ (20 mg) added and stirred at RT for 30 min. The mixture was partitioned between DCM (30 ml) and water (30 ml), the organic layer separated, dried over MgSO$_4$, filtered and concentrated in vacuo. The residue was purified by column chromatography (4 g cartridge, 0-100% EtOAc/isohexane) to afford the title compound (48 mg, 74 µmol, 97% purity) as a white foam. LCMS (Method 1): m/z 626 (M+H)$^+$ at 2.47 min.

Step 3: N-(6-(4-(1-aminocyclobutyl)phenyl)-5-phenylpyridazin-3-yl)-2-(trans-4-(2-oxooxazolidin-3-yl)cyclohexyl)acetamide: The title compound was isolated as a white solid from the reaction of the product from Step 2 above (47 mg, 73 µmol, 97% purity) and TFA (0.5 ml, 6.49 mmol) in DCM (4 ml) using essentially the same procedure as in Example 65. LCMS (Method 1): m/z 526 (M+H)$^+$, 524 (M−H)$^−$, at 1.40 min. $^1$H NMR (400 MHz, DMSO-d$_6$) δ 11.28 (s, 1H), 8.35 (s, 1H), 7.40-7.26 (m, 9H), 4.30-4.17 (m, 2H), 3.51-3.41 (m, 3H), 2.42-2.32 (m, 4H), 2.19 (br s, 2H), 2.10-1.93 (m, 3H), 1.85-1.60 (m, 6H), 1.53-1.42 (m, 2H), 1.19-1.08 (m, 2H).

Example 67

Methyl (trans-4-(2-((5-(4-(trans-1-amino-3-hydroxy-3-methylcyclobutyl)phenyl)-4-phenylpyridin-2-yl)amino)-2-oxoethyl)cyclohexyl)(methyl)carbamate

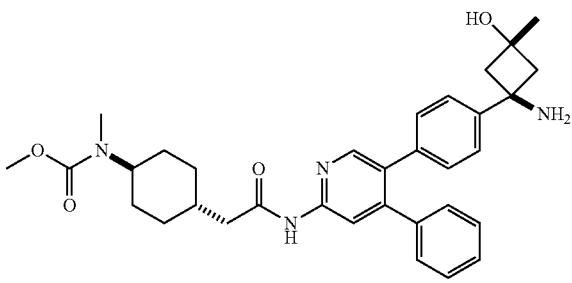 [SMILES: COC(=O)N(C)[C@H]1CC[C@H](CC(=O)Nc2cc(-c3ccccc3)c(-c3ccc([C@]4(N)C[C@](C)(O)C4)cc3)cn2)CC1]

Step 1: benzyl (5-(4-(trans-1-((tert-butoxycarbonyl)amino)-3-hydroxy-3-methylcyclobutyl)phenyl)-4-phenylpyridin-2-yl)carbamate: A solution of potassium phosphate tribasic (0.512 g, 2.61 mmol) in water (4 ml) was degassed with N$_2$. After 30 min, the solution was diluted with 2-methyltetrahydrofuran (20 ml) and treated with the product from Intermediate 20 Step 3 (0.5 g, 1.31 mmol), tert-butyl ((1r,3r)-3-hydroxy-3-methyl-1-(4-(4,4,5,5-tetramethyl-1,3,2-dioxaborolan-2-yl)phenyl)cyclobutyl)carbamate (0.724 g, 1.44 mmol, prepared according to Org. Process Res. Dev., 2012, 16, 1069), potassium phosphate tribasic (0.512 g, 2.61 mmol) and 1,1'-bis-(diisopropylphosphino)ferrocene (0.055 g, 0.130 mmol). The mixture was degassed with N$_2$ then heated at 50° C. for 18 h. The reaction mixture was cooled to RT, filtered through Celite®, washing with MeCN (2×50 ml), and concentrated in vacuo to afford a yellow solid. The residue was partitioned between DCM (50 ml) and water (50 ml) and the phases separated. The organic phase was dried over MgSO$_4$, filtered and concentrated in vacuo. The residue was purified by column chromatography (40 g cartridge, 0-100% EtOAc/isohexane) to afford the title compound (274 mg, 0.458 mmol, 97% purity) as a sticky brown oil. LCMS (Method 1): m/z 580 (M+H)+, at 2.71 min.

Step 2: tert-butyl (trans-1-(4-(6-amino-4-phenylpyridin-3-yl)phenyl)-3-hydroxy-3-methylcyclobutyl)carbamate: The product from Step 1 above (274 mg, 0.473 mmol) was combined with palladium (40 mg, 10% w/w on carbon, Type 39 paste) in THF (3 ml) and MeOH (4 ml). The mixture was stirred at RT under an atmosphere of H$_2$ (5 bar pressure) for 18 h. The mixture was filtered, the filtrate concentrated in vacuo and the residue purified by column chromatography (12 g cartridge, 0-10% MeOH/DCM) to afford the title compound (151 mg, 0.332 mmol, 98% purity) as a brown solid. LCMS (Method 1): m/z 446 (M+H)$^+$ at 1.41 min.

Step 3: Methyl (trans-4-(2-((5-(4-(trans-1-((tert-butoxycarbonyl)amino)-3-hydroxy-3-methylcyclobutyl)phenyl)-4-phenylpyridin-2-yl)amino)-2-oxoethyl)cyclohexyl)(methyl)carbamate: The title compound (42 mg, 51 µmol, 80% purity) was isolated as a white solid from the reaction of the product from Step 2 above (50 mg, 0.110 mmol, 98% purity), the product from Example 56 Step 3 (58 mg, 0.228 mmol, 90% purity), 1-chloro-N,N,2-trimethylprop-1-en-1-amine (35 µl, 0.265 mmol) in pyridine (2 ml) and DCM (4 ml) using essentially the same procedure as in Example 65 Step 1. LCMS (Method 1): m/z 657 (M+H)$^+$ at 2.44 min.

Step 4: Methyl (trans-4-(2-((5-(4-(trans-1-amino-3-hydroxy-3-methylcyclobutyl)phenyl)-4-phenylpyridin-2-yl)amino)-2-oxoethyl)cyclohexyl)(methyl)carbamate: A solution of the product from Step 3 above (41 mg, 50 µmol) in DCM (4 ml) was treated with TFA (0.5 ml, 6.49 mmol) and the resultant mixture stirred for 20 h. The mixture was concentrated in vacuo and the residue was partitioned between DCM (40 ml) and saturated NaHCO$_3$(aq) (20 ml). The organic phase was separated and dried over MgSO$_4$, then filtered and concentrated in vacuo. The residue was purified by column chromatography (12 g cartridge, 0-10% MeOH/DCM) to afford a gum. This material was further purified by preparative HPLC (Waters FractionLynx, Waters X-Bridge Prep-C18, 5 µm, 19×50 mm column, 35-65% MeCN in 10 mM ammonium bicarbonate) to afford the title compound (12 mg, 21 µmol, 99% purity) as a white solid. LCMS (Method 1): m/z 557 (M+H)$^+$, 555 (M−H)$^−$, at 1.44 min. $^1$H NMR (400 MHz, DMSO-d$_6$) δ 10.61 (s, 1H), 8.30 (s, 1H), 8.16 (s, 1H), 7.34-7.32 (m, 5H), 7.20-7.18 (m, 2H), 7.09 (d, J=8.4 Hz, 2H), 4.79 (s, 1H), 3.79 (br s, 1H), 3.58 (s, 3H), 2.70 (s, 3H), 2.36-2.32 (m, 4H), 2.33 (br s, 2H), 2.17-2.14 (m, 2H), 1.84-1.64 (m, 3H), 1.60-1.45 (m, 7H), 1.15-1.05 (m, 2H).

Example 68

N-(6-(4-(trans-1-amino-3-hydroxy-3-methylcyclobutyl)phenyl)-5-(2-fluorophenyl)-1,2,4-triazin-3-yl)-2-(trans-4-(2-oxooxazolidin-3-yl)cyclohexyl)acetamide

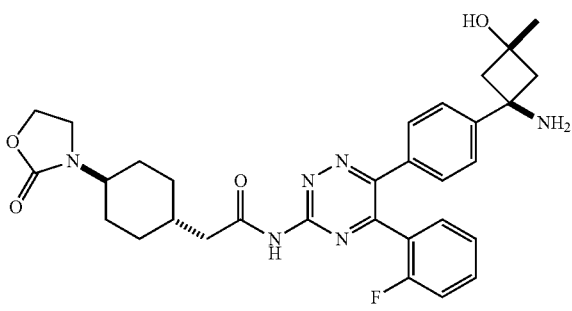 [SMILES: C[C@]1(O)C[C@@](N)(c2ccc(-c3nnc(NC(=O)C[C@H]4CC[C@H](N5CCOC5=O)CC4)nc3-c3ccccc3F)cc2)C1]

Step 1: 6-bromo-5-(2-fluorophenyl)-1,2,4-triazin-3-amine

A solution of 5-(2-fluorophenyl)-1,2,4-triazin-3-amine (3.96 g, 20.8 mmol, prepared according to WO 2010046780) was dissolved in DMF (10 ml) and cooled to −25° C. The mixture was treated with a solution of NBS (11.1 g, 62.5 mmol) in DMF (15 ml) and was allowed to warm to RT and stir overnight. The mixture was poured into saturated NaHCO$_3$(aq) (200 ml) and extracted with ether (3×200 ml). The combined organic phases were dried over MgSO$_4$, filtered and concentrated in vacuo. The residue was purified by column chromatography (80 g cartridge, 0-10% MeOH/DCM) to afford the title compound (1.5 g, 5.52 mmol, 99% purity) as pale yellow solid. LCMS (Method 1): m/z 269 (M+H)$^+$ at 1.66 min. 1H NMR (400 MHz, DMSO-d$_6$) δ 7.80-7.53 (m, 4H), 7.45-7.33 (m, 2H).

Step 2: N-(6-bromo-5-(2-fluorophenyl)-1,2,4-triazin-3-yl)-2-(trans-4-(2-oxooxazolidin-3-yl)cyclohexyl)-N-(2-(4-(2-oxooxazolidin-3-yl)cyclohexyl)acetyl)acetamide: The title compound (411 mg, 0.598 mmol) was isolated as a white solid from the reaction of the product from Step 1 above (200 mg, 0.736 mmol, 99% purity), the product from Example 42 Step 3 (422 mg), 1-chloro-N,N,2-trimethylprop-1-en-1-amine (0.251 ml, 1.90 mmol) in pyridine (5 ml) and DCM (5 ml) using essentially the same procedure as in Example 65 Step 1. $^1$H NMR (400 MHz, DMSO-d$_6$) δ 7.79-7.69 (m, 2H), 7.56-7.42 (m, 2H), 4.29-4.16 (m, 4H), 3.52-3.36 (m, 6H), 2.58 (d, J=6.2 Hz, 4H), 1.83-1.57 (m, 10H), 1.45 (qd, J=12.7, 3.2 Hz, 4H), 1.15-1.02 (m, 4H).

Step 3: N-(6-(4-(trans-1-amino-3-hydroxy-3-methylcyclobutyl)phenyl)-5-(2-fluorophenyl)-1,2,4-triazin-3-yl)-2-(trans-4-(2-oxooxazolidin-3-yl)cyclohexyl)acetamide: A stirred solution of tert-butyl (trans-3-hydroxy-3-methyl-1-(4-(4,4,5,5-tetramethyl-1,3,2-dioxaborolan-2-yl)phenyl)cyclobutyl)carbamate (103 mg, 0.256 mmol, prepared according to Org. Process Res. Dev., 2012, 16, 1069) and the product from Step 2 above (160 mg, 0.233 mmol) in dioxane (5 ml) was treated with a solution of Na$_2$CO$_3$ (74 mg, 0.698 mmol) in water (1 ml) and the resultant mixture was degassed with N$_2$ for 5 min and then SPhos Precatalyst 3G (9 mg, 0.012 mmol) was added. The resultant mixture was heated at 100° C. for 1 h. The mixture was poured into water (100 ml) and extracted with EtOAc (3×50 ml). The combined extracts were washed with brine (50 ml), dried over MgSO$_4$, filtered and concentrated in vacuo. The residue was dissolved in DCM (2 ml) and treated with TFA (1 ml). The resultant mixture was stirred at RT for 1 h and then concentrated in vacuo. The residue was dissolved in DCM (50 ml) and washed sequentially with NaHCO$_3$(aq) (2×50 ml) and brine (50 ml), then dried over MgSO$_4$, filtered and concentrated in vacuo. The residue was purified by column chromatography (12 g cartridge, 0-15% MeOH/DCM) to afford the title compound (35 mg, 59.8 μmol, 98% purity) as a pale yellow solid. LCMS (Method 1): m/z 575 (M+H)$^+$, 573 (M−H)$^−$, at 1.10 min. $^1$H NMR (400 MHz, DMSO-d$_6$) δ 11.26 (s, 1H), 7.72 (td, J=7.5, 1.8 Hz, 1H), 7.62-7.53 (m, 1H), 7.48-7.33 (m, 5H), 7.25-7.16 (m, 1H), 4.80 (s, 1H), 4.30-4.19 (m, 2H), 3.56-3.40 (m, 3H), 2.46 (d, J=6.6 Hz, 2H), 2.39-2.31 (m, 2H), 2.19-2.12 (m, 2H), 1.88-1.61 (m, 5H), 1.55-1.40 (m, 5H), 1.21-1.06 (m, 2H).

Example 69

N-(6-(4-(2-aminopropan-2-yl)phenyl)-5-phenyl-1,2,4-triazin-3-yl)-2-(trans-4-(2-oxooxazolidin-3-yl)cyclohexyl)acetamide

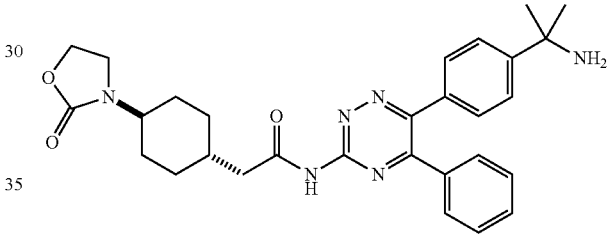

Step 1: N-(6-bromo-5-phenyl-1,2,4-triazin-3-yl)-2-(trans-4-(2-oxooxazolidin-3-yl)cyclohexyl)-N-(2-(trans-4-(2-oxooxazolidin-3-yl)cyclohexyl)acetyl)acetamide: A suspension of the product from Example 42 Step 3 (453 mg) in DCM (5 ml) was treated with 1-chloro-N,N,2-trimethylprop-1-en-1-amine (0.269 ml, 2.03 mmol) and stirred at RT for 2 h. The mixture was treated with a solution of 6-bromo-5-phenyl-1,2,4-triazin-3-amine (200 mg, 0.797 mmol, prepared according to J. Med. Chem., 2012, 55, 1898) in pyridine (5 ml, 61.8 mmol) and the resultant mixture was stirred at RT overnight. The reaction mixture was poured into 1M HCl(aq) (50 ml) and extracted with DCM (3×100 ml). The combined extracts were washed with brine (100 ml), dried over MgSO$_4$, filtered and concentrated in vacuo. The residue was purified by column chromatography (40 g cartridge, 0-100% EtOAc/isohexane) to afford the title compound (294 mg, 0.439 mmol) as a white solid. LCMS (Method 1): m/z 669 (M+H)$^+$ at 2.22 min.

Step 2: N-(6-(4-(2-aminopropan-2-yl)phenyl)-5-phenyl-1,2,4-triazin-3-yl)-2-(trans-4-(2-oxooxazolidin-3-yl)cyclohexyl)acetamide: A solution of Na$_2$CO$_3$ (85 mg, 0.806 mmol) in water (1 ml) was added to a stirred solution of the product from Intermediate 2 Step 2 (107 mg, 0.296 mmol) and the product from Step 1 above (180 mg, 0.269 mmol) in dioxane (5 ml). The resultant mixture was degassed for 5 min and then tetrakis-(triphenylphosphine)palladium(0) (31.1 mg, 0.027 mmol) was added and the resultant mixture heated at 90° C. overnight. The reaction mixture was poured into water (100 ml) and extracted with EtOAc (3×50 ml).

The combined extracts were washed with brine (50 ml), dried over MgSO$_4$, filtered and concentrated in vacuo. The residue was dissolved in DCM (2 ml) and then TFA (1 ml, 13.0 mmol) was added and the reaction mixture was stirred at RT for 1 h. The mixture was concentrated in vacuo. To remove residual TFA, the residue was thrice resuspended in toluene (20 ml) and concentrated in vacuo. The residue was purified by preparative HPLC (Varian PrepStar, Waters X-Bridge Prep-C18, 5 μm, 19×50 mm column, 20-40% MeCN in 10 mM ammonium bicarbonate(aq)) to afford the title compound (22 mg, 0.042 mmol, 99% purity) as a white solid. LCMS (Method 1): m/z 515 (M+H)$^+$, 513 (M−H)$^−$, at 1.21 min. $^1$H NMR (400 MHz, DMSO-d$_6$) δ 11.18 (s, 1H), 7.59-7.46 (m, 5H), 7.43-7.37 (m, 4H), 4.29-4.18 (m, 2H), 3.56-3.41 (m, 3H), 2.47 (d, J=6.6 Hz, 2H), 2.01 (s, 1H), 1.89-1.75 (m, 2H), 1.74-1.63 (m, 2H), 1.57-1.43 (m, 2H), 1.37 (s, 6H), 1.22-1.06 (m, 2H).

Example 70

N-(5-(4-(1-aminocyclobutyl)phenyl)-4-(thiophen-3-yl)pyridin-2-yl)-2-(trans-4-(2-oxooxazolidin-3-yl)cyclohexyl)acetamide

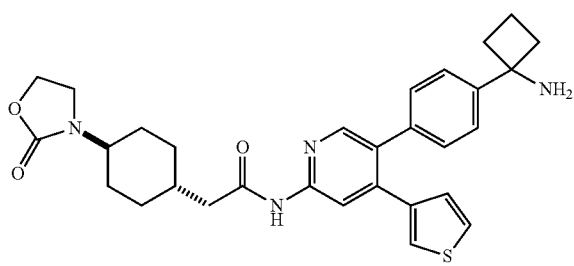 [SMILES: NC1(c2ccc(-c3cnc(NC(=O)C[C@H]4CC[C@H](N5CCOC5=O)CC4)cc3-c3ccsc3)cc2)CCC1]

Step 1: Benzyl (4-(thiophen-3-yl)pyridin-2-yl)carbamate: A solution of the product from Intermediate 20 Step 1 (1 g, 3.26 mmol), thiophen-3-ylboronic acid (0.625 g, 4.88 mmol), XPhos Precatalyst 2G (26 mg, 0.033 mmol) and 4 M K$_3$PO$_4$(aq) (1.83 ml, 7.33 mmol) in dioxane (20 ml) was degassed with N$_2$ for 10 min and the resultant solution heated at 60° C. for 1 h. The reaction mixture was cooled to RT and filtered through Celite®, washing with DCM (100 ml) and the filtrate was washed with water (50 ml). The organic phase was dried over MgSO$_4$, filtered and the solvent was removed in vacuo. The residue was recrystallised from DCM/isohexane. The resultant solid was filtered, rinsing with isohexane and dried in vacuo to afford the title compound (0.569 g, 1.80 mmol, 98% purity) as a white solid. $^1$H NMR (400 MHz, Chloroform-d) δ 9.15 (s, 1H), 8.31 (s, 1H), 8.23 (dd, J=5.3, 0.8 Hz, 1H), 7.72 (dd, J=2.9, 1.4 Hz, 1H), 7.56-7.31 (m, 7H), 7.13 (dd, J=5.3, 1.6 Hz, 1H), 5.29 (s, 2H).

Step 2: Benzyl (5-bromo-4-(thiophen-3-yl)pyridin-2-yl)carbamate: A solution of the product from Step 1 above (0.460 g, 1.45 mmol, 98% purity) in DCM (20 ml) was cooled to 0° C. and treated with NBS (0.396 g, 2.22 mmol). The resultant solution was stirred at RT in the dark for 24 h. Additional NBS (0.396 g, 2.22 mmol) was added and the resultant solution was stirred at RT in the dark for 3 days. The organic phase was washed with water (30 ml) and concentrated in vacuo. The residue was triturated with MeOH (20 ml). The resultant solid was filtered, rinsing with MeOH, and dried in vacuo to afford the title compound (0.306 g, 0.676 mmol, 86% purity) as an off-white solid. LCMS (Method 1): m/z 389 (M+H)$^+$ at 2.72 min.

Step 3: Benzyl (5-(4-(1-((tert-butoxycarbonyl)amino)cyclobutyl)phenyl)-4-(thiophen-3-yl)pyridin-2-yl)carbamate: A solution of 4 M K$_3$PO$_4$(aq) (385 μl, 1.54 mmol) was degassed with N$_2$ for 20 min. In a separate vial, a solution of the product from Step 2 above (300 mg, 0.663 mmol, 86% purity), the product from Intermediate 8 Step 1 (345 mg, 0.925 mmol), palladium(II) acetate (17.3 mg, 0.077 mmol) and DIPPF (32.2 mg, 0.077 mmol) in 2-methyltetrahydrofuran (6 ml) was degassed with N$_2$ for 20 min. The solutions were combined and degassing continued for 5 min. The resultant mixture was heated at 50° C. for 18 h. The reaction mixture was cooled to RT and filtered through Celite®, eluting with DCM (100 ml), and the filtrate was washed with water (50 ml). The organic phase was dried over MgSO$_4$, filtered and concentrated in vacuo. The residue was partially purified by column chromatography (12 g cartridge, 0-50% EtOAc/isohexane) to afford the title compound (0.428 g). This material was used directly in subsequent reactions without further purification.

Step 4: tert-Butyl (1-(4-(6-amino-4-(thiophen-3-yl)pyridin-3-yl)phenyl)cyclobutyl)carbamate: The product from Step 3 above (0.420 g) was dissolved in a mixture of MeOH (10 ml) and THF (10 ml). The reaction mixture was hydrogenated in a ThalesNano H-Cube® flow reactor (10% Pd/C, 30×4 mm, full hydrogen mode, 50° C., 1 ml/min flow rate, 8 passes) and then concentrated in vacuo. The residue was purified by column chromatography (40 g cartridge, 0-80% EtOAc/isohexane) to afford the title compound (0.106 g, 0.240 mmol, 96% purity) as a pale yellow solid. LCMS (Method 1): m/z 422 (M+H)$^+$ at 1.67 min.

Step 5: tert-butyl (1-(4-(6-(2-(trans-4-(2-oxooxazolidin-3-yl)cyclohexyl)acetamido)-4-(thiophen-3-yl)pyridin-3-yl)phenyl)cyclobutyl)carbamate: The title compound (38 mg, 0.057 mmol, 95% purity) was isolated as a white solid from the reaction of the product from Example 42 Step 3 (41.6 mg), 1-chloro-N,N,2-trimethylprop-1-en-1-amine (0.025 ml, 0.192 mmol), the product from Step 4 above (38.6 mg, 0.088 mmol, 96% purity) and pyridine (0.5 ml) in DCM (2 ml) using essentially the same procedure as in Example 65 Step 1. LCMS (Method 1): m/z 631 (M+H)$^+$ at 2.54 min.

Step 6: N-(5-(4-(1-aminocyclobutyl)phenyl)-4-(thiophen-3-yl)pyridin-2-yl)-2-(trans-4-(2-oxooxazolidin-3-yl)cyclohexyl)acetamide: A solution of the product from Step 5 above (38 mg, 0.057 mmol) in DCM (2 ml) was treated with TFA (0.5 ml) and the resultant mixture stirred at RT for 1 h. The reaction mixture was diluted with DCM (2 ml) and quenched with saturated NaHCO$_3$(aq) (4 ml). The phases were separated and the organic phase was concentrated in vacuo. The residue was diluted with MeOH and loaded onto a column of SCX. The column was washed with MeOH and the product was eluted with a 0.7 M solution of ammonia in MeOH. The solvent was removed in vacuo to afford the title compound (25.3 mg, 0.043 mmol, 90% purity) as a white solid. LCMS (Method 1): m/z 531 (M+H)$^+$ at 1.37 min. $^1$H NMR (400 MHz, Methanol-d$_4$) δ 8.24 (d, J=3.2 Hz, 2H), 7.47-7.38 (m, 2H), 7.32-7.25 (m, 2H), 7.25-7.17 (m, 2H), 6.80 (dd, J=4.3, 2.0 Hz, 1H), 4.38-4.27 (m, 2H), 3.68-3.53 (m, 3H), 2.66-2.52 (m, 2H), 2.38 (d, J=7.0 Hz, 2H), 2.33-2.23 (m, 2H), 2.16-2.04 (m, 1H), 1.99-1.88 (m, 2H), 1.85-1.75 (m, 3H), 1.58 (qd, J=12.7, 3.2 Hz, 2H), 1.39-1.16 (m, 4H).

Example 71

N-(trans-4-(2-((6-(4-(trans-1-amino-3-fluorocyclobutyl)phenyl)-5-phenylpyridazin-3-yl)amino)-2-oxoethyl)cyclohexyl)-N-methylcyclopropanecarboxamide

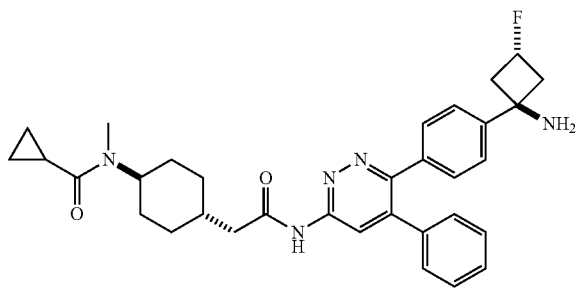 [SMILES: CN(C(=O)C1CC1)[C@H]1CC[C@H](CC(=O)Nc2cc(-c3ccccc3)c(-c3ccc([C@]4(N)C[C@H](F)C4)cc3)nn2)CC1]

A suspension of the product from Example 27 Step 2 (68.8 mg) in DCM (5 ml) was treated with 1-chloro-N,N,2-trimethylprop-1-en-1-amine (0.039 ml, 0.293 mmol) and stirred at RT for 2 h. The mixture was treated with a solution of the product from Example 45 Step 1 (50 mg, 0.104 mmol, 90% purity) in pyridine (5 ml, 61.8 mmol) and stirred at RT overnight. The reaction mixture was poured into 1M HCl (aq) (50 ml) and extracted with DCM (3×100 ml). The combined extracts were washed with brine (100 ml), dried over MgSO$_4$, filtered and concentrated in vacuo. The residue was purified by column chromatography (40 g cartridge, 0-100% EtOAc/isohexane). The resultant solid was dissolved DCM (2 ml) and treated with TFA (1 ml) and stirred at RT for 1 h. The mixture was concentrated in vacuo and the residue dissolved in DCM (50 ml) and sequentially washed with saturated NaHCO$_3$(aq) (2×50 ml) and brine (50 ml). The organic phase was dried over MgSO$_4$, filtered and concentrated in vacuo. The residue was purified by column chromatography (12 g cartridge, 0-15% MeOH/DCM) to afford the title compound (6 mg, 10.6 µmol, 98% purity) as a white solid. LCMS (Method 1): m/z 556 (M+H)$^+$, 554 (M−H)$^-$, at 1.53 min. $^1$H NMR (400 MHz, DMSO-d$^6$) (two rotamers in a 4:3 ratio) δ 11.32-11.18 (m, 1H), 8.40-8.31 (m, 1H), 7.45-7.24 (m, 9H), 5.35 (dp, J=57.4, 6.6 Hz, 1H), 4.29-4.17 (m, 1H, major), 4.06-3.95 (m, 1H, minor), 2.97 (s, 3H, major), 2.71 (s, 3H, minor), 2.62-2.24 (m, 6H, obscured by DMSO-d$_5$), 2.06-1.41 (m, 8H), 1.31-1.02 (m, 2H), 0.76-0.63 (m, 4H).

Example 72

N-(6-(4-(1-aminocyclopropyl)phenyl)-5-phenylpyridazin-3-yl)-2-(trans-4-(N-methylacetamido)cyclohexyl)acetamide

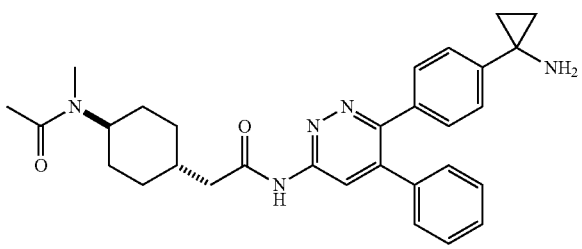 [SMILES: CC(=O)N(C)[C@H]1CC[C@H](CC(=O)Nc2cc(-c3ccccc3)c(-c3ccc(C4(N)CC4)cc3)nn2)CC1]

Step 1: tert-butyl (1-(4-(6-amino-4-phenylpyridazin-3-yl)phenyl)cyclopropyl)carbamate: 6-chloro-5-phenylpyridazin-3-amine (150 mg, 0.729 mmol), the product from Intermediate 10 Step 2 (262 mg, 0.729 mmol) and SPhos Precatalyst 3G (5.7 mg, 7.3 µmol) were combined in dioxane (5 ml) and treated with 2 M Na$_2$CO$_3$(aq) (0.821 ml, 1.641 mmol). The reaction mixture was degassed with N$_2$ for 2 min and then heated to 90° C. overnight. The mixture was cooled to RT, diluted with EtOAc (100 ml), and sequentially washed with water (100 ml) and brine (100 ml). The organic phase was dried over MgSO$_4$, filtered and concentrated in vacuo. The residue was purified by column chromatography (12 g cartridge, 0-90% EtOAc/isohexane) to afford the title compound (205 mg) as a tan solid. This material was used directly in subsequent reactions without analysis.

Step 2: N-(6-(4-(1-aminocyclopropyl)phenyl)-5-phenylpyridazin-3-yl)-2-(trans-4-(N-methylacetamido)cyclohexyl)acetamide: The title compound (22 mg, 0.044 mmol) was isolated as a white solid from the reaction of the product from Step 1 above (50 mg), the product from Example 1 Step 5 (45 mg), 1-chloro-N,N,2-trimethylprop-1-en-1-amine (33 µl, 0.248 mmol), and pyridine (2 ml) in DCM (5 ml), followed by TFA (1 ml) in DCM (2 ml) using essentially the same procedure as in Example 71. LCMS (Method 1): m/z 498 (M+H)$^+$, 496 (M−H)$^-$, at 1.33 min. $^1$H NMR (400 MHz, DMSO-d$_6$) (two rotamers in a 3:2 ratio) δ 11.26 (s, 1H, minor), 11.25 (s, 1H, major), 8.34 (s, 1H), 7.44-7.34 (m, 3H), 7.32-7.17 (m, 6H), 4.24-4.17 (m, 1H, major), 3.61-3.50 (m, 1H, minor), 2.79 (s, 3H, major), 2.67 (s, 3H, minor), 2.43-2.36 (m, 2H), 2.02 (s, 3H, minor), 1.96 (s, 3H, major), 1.86-1.70 (m, 3H), 1.68-1.42 (m, 4H), 1.28-1.04 (m, 2H), 1.02-0.87 (m, 4H).

Example 73

N-(6-(4-(1-amino-3,3-difluorocyclobutyl)phenyl)-5-phenylpyridazin-3-yl)-2-(trans-4-(N-methylacetamido)cyclohexyl)acetamide

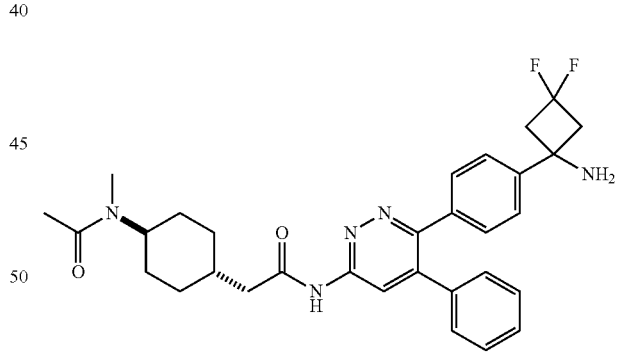

The title compound (22 mg, 0.044 mmol) was isolated as a white solid from the reaction of the product from Example 60 Step 1 (50 mg), the product from Example 1 Step 5 (59 mg), 1-chloro-N,N,2-trimethylprop-1-en-1-amine (37 µl, 0.282 mmol), and pyridine (5 ml) in DCM (5 ml), followed by TFA (1 ml) in DCM (2 ml) using essentially the same procedure as in Example 71. LCMS (Method 1): m/z 548 (M+H)$^+$, 546 (M−H)$^-$, at 1.42 min. $^1$H NMR (400 MHz, DMSO-d$_6$) (two rotamers in a 3:2 ratio) δ 11.29 (s, 1H, minor), 11.27 (s, 1H, major), 8.36 (s, 1H, minor), 8.36 (s, 1H, major), 7.45-7.35 (m, 5H), 7.35-7.30 (m, 2H), 7.30-7.23 (m, 2H), 4.30-4.16 (m, 1H, major), 3.63-3.49 (m, 1H, minor), 3.08-2.92 (m, 2H), 2.84-2.69 (m, 3H), 2.79 (s, 3H, major), 2.67 (s, 3H, minor), 2.47-2.37 (m, 4H), 2.02 (s, 3H, minor), 1.96 (s, 3H, major), 1.87-1.39 (m, 6H), 1.28-1.06 (m, 2H).

Example 74

N-(6-(4-(trans-1-amino-3-fluorocyclobutyl)phenyl)-5-phenylpyridazin-3-yl)-2-(trans-4-(2-oxopyrrolidin-1-yl)cyclohexyl)acetamide

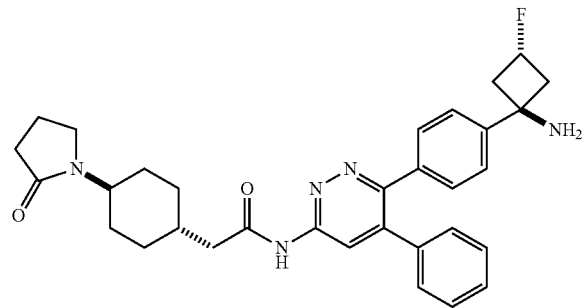 [SMILES: N[C@]1(c2ccc(-c3nnc(NC(=O)C[C@H]4CC[C@H](N5CCCC5=O)CC4)cc3-c3ccccc3)cc2)C[C@@H](F)C1]

A stirred solution of the product from Example 48 Step 3 (51.8 mg, 0.219 mmol) and HATU (131 mg, 0.345 mmol) in DMF (5 ml) was treated with DIPEA (0.095 ml, 0.575 mmol) and the resultant mixture was stirred at RT for 30 min. The product from Example 45 Step 1 (50 mg, 0.104 mmol, 90% purity) was added and the resultant mixture was stirred at 50° C. overnight. The mixture was poured into saturated NaHCO$_3$(aq) (100 ml) and then extracted with EtOAc (3×50 ml). The combined organic extracts were washed with brine (50 ml), dried over MgSO$_4$ and concentrated in vacuo. The residue was dissolved DCM (2 ml) and treated with TFA (1 ml) and stirred at RT for 1 h. The resultant mixture was concentrated in vacuo and the residue dissolved in DCM (50 ml) and sequentially washed with saturated NaHCO$_3$(aq) (2×50 ml) and brine (50 ml). The organic phase was dried over MgSO$_4$, filtered and concentrated in vacuo. The residue was purified by column chromatography (12 g cartridge, 0-15% MeOH/DCM) to afford the title compound (10 mg, 0.018 mmol, 98% purity) as a white solid. LCMS (Method 1): m/z 542 (M+H)$^+$, 540 (M−H)$^−$, at 1.43 min. $^1$H NMR (400 MHz, DMSO-d$_6$) δ 11.27 (s, 1H), 8.35 (s, 1H), 7.45-7.24 (m, 9H), 5.35 (dp, J=55.2, 8.5, 1H), 3.78-3.67 (m, 1H), 3.29 (t, J=7.0 Hz, 2H), 2.60-2.54 (m, 2H), 2.45-2.29 (m, 4H), 2.20 (t, J=7.5 Hz, 2H), 1.94-1.69 (m, 5H), 1.63-1.40 (m, 4H), 1.22-1.06 (m, 2H).

Example 75

N-(6-(4-(trans-1-amino-3-fluorocyclobutyl)phenyl)-5-(thiophen-3-yl)pyridazin-3-yl)-2-(trans-4-(N-methylacetamido)cyclohexyl)acetamide

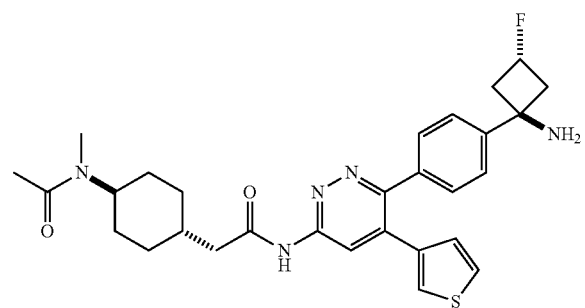 [SMILES: CC(=O)N(C)[C@H]1CC[C@H](CC(=O)Nc2cc(-c3ccsc3)c(-c3ccc([C@]4(N)C[C@H](F)C4)cc3)nn2)CC1]

Step 1: 4-(Thiophen-3-yl)-1,2-dihydropyridazine-3,6-dione: A solution of Na$_2$CO$_3$(s) (5.16 g, 48.7 mmol) in water (5 ml) was added to a stirred solution of thiophen-3-ylboronic acid (2.49 g, 19.5 mmol) and 4-bromo-1,2-dihydropyridazine-3,6-dione (3.1 g, 16.2 mmol) in dioxane (100 ml). The resultant mixture was degassed with N$_2$ for 5 min and then tetrakis-(triphenylphosphine)palladium(0) (1.88 g, 1.62 mmol) was added. The mixture was heated at 90° C. overnight. The reaction mixture was poured into water (200 ml) and washed with EtOAc (2×200 ml). The aqueous phase was acidified to pH 3 using 1M HCl(aq) and then extracted with EtOAc (5×150 ml). The combined extracts were washed with brine (200 ml), dried over MgSO$_4$ and concentrated in vacuo to afford the title compound (2.1 g, 10.7 mmol, 99% purity) as an off-white solid. $^1$H NMR (400 MHz, DMSO-d$_6$) δ 12.16 (s, 1H), 10.83 (s, 1H), 8.70 (s, 1H), 7.85-7.73 (m, 1H), 7.63 (dd, J=5.1, 3.0 Hz, 1H), 7.45 (s, 1H).

Step 2: 3,6-Dichloro-4-(thiophen-3-yl)pyridazine: The product from Step 1 above (2.1 g, 10.7 mmol, 99% purity) was heated at 105° C. in POCl$_3$ (100 ml, 10.8 mmol) for 4 h. The resultant solution was concentrated in vacuo and the residue dissolved in DCM (500 ml) and neutralised with ice-cooled saturated NaHCO$_3$(aq) (200 ml). The aqueous phase was extracted with DCM (2×250 ml), and the combined organic phases were washed with brine (200 ml), dried over MgSO$_4$ and concentrated in vacuo to afford the title compound (2.4 g, 10.1 mmol, 97% purity) as pale brown solid. $^1$H NMR (400 MHz, DMSO-d$_6$) δ 8.28 (dd, J=3.0, 1.4 Hz, 1H), 8.21 (s, 1H), 7.79 (dd, J=5.1, 2.9 Hz, 1H), 7.62 (dd, J=5.1, 1.4 Hz, 1H).

Step 3: 6-Chloro-5-(thiophen-3-yl)pyridazin-3-amine: A solution of the product from Step 2 above (2.4 g, 10.1 mmol, 97% purity) and 2,4-dimethoxybenzylamine (1.87 ml, 12.5 mmol) in dioxane (50 ml) was heated under reflux for 3 days. The reaction mixture was diluted with EtOAc (200 ml) and then sequentially washed with water (100 ml) and brine (100 ml). The organic phase was dried over MgSO$_4$, filtered and concentrated in vacuo. The residue was dissolved in DCM (50 ml) and treated with TFA (20 ml, 260 mmol). The resultant mixture was stirred at RT overnight. The reaction mixture was concentrated in vacuo and the residue was dissolved in DCM (200 ml) and washed with saturated NaHCO$_3$(aq) (2×200 ml). The organic phase was dried over MgSO$_4$, filtered and concentrated in vacuo. The residue was purified by column chromatography (40 g cartridge, 0-100% EtOAc/isohexane) to afford the title compound (736 mg, 3.37 mmol, 97% purity) as an off white solid. $^1$H NMR (400 MHz, DMSO-d$_6$) δ 7.97 (dd, J=2.9, 1.3 Hz, 1H), 7.72 (dd, J=5.0, 3.0 Hz, 1H), 7.40 (dd, J=5.0, 1.4 Hz, 1H), 6.90 (s, 1H), 6.66 (s, 2H).

Step 4: tert-butyl (trans-1-(4-(6-amino-4-(thiophen-3-yl)pyridazin-3-yl)phenyl)-3-fluorocyclobutyl)carbamate: A solution of Na$_2$CO$_3$(s) (242 mg, 2.287 mmol) in water (1 ml) was added into a stirred solution of the product from Step 3 above (220 mg, 1.01 mmol, 97% purity) and the product from Intermediate 13 Step 5 (407 mg) in dioxane (5 ml). The resultant mixture was degassed with N$_2$ for 5 min and then tetrakis-(triphenylphosphine)palladium(0) (120 mg, 0.104 mmol) was added and the mixture heated at 90° C. for 5 h. The reaction mixture was poured into water (100 ml) and extracted with EtOAc (3×150 ml). The combined extracts were washed with brine (100 ml), dried over MgSO$_4$, filtered and concentrated in vacuo. The residue was purified by column chromatography (12 g cartridge, 0-100% EtOAc/isohexane) to afford the title compound (195 mg, 0.421 mmol, 95% purity) as a yellow solid. $^1$H NMR (400 MHz, DMSO-d$_6$) (two rotamers in a 4:1 ratio) δ 7.64 (s, 1H), 7.53-7.44 (m, 2H), 7.29-7.18 (m, 4H), 6.81 (s, 1H), 6.78-6.69 (m, 1H), 6.49 (s, 2H), 5.22 (dt, J=56.1, 6.5 Hz, 1H), 3.08-2.85 (m, 2H), 2.48-2.39 (m, 2H), 1.34 (br s, 9H, major), 1.18 (br s, 9H, minor).

Step 5: N-(6-(4-(trans-1-amino-3-fluorocyclobutyl)phenyl)-5-(thiophen-3-yl)pyridazin-3-yl)-2-(trans-4-(N-methylacetamido)cyclohexyl)acetamide: The title compound (32 mg, 0.059 mmol, 99% purity) was isolated as a white solid from the reaction of the product from Step 4 above (70 mg, 0.151 mmol, 95% purity), the product from Example 1 Step 5 (85 mg), 1-chloro-N,N,2-trimethylprop-1-en-1-amine (33 μl, 0.248 mmol), and pyridine (5 ml) in DCM (5 ml), followed by TFA (1 ml) in DCM (2 ml) using essentially the same procedure as in Example 71. LCMS (Method 1): m/z 536 (M+H)$^+$, 534 (M−H)$^−$, at 1.38 min. $^1$H NMR (400 MHz, DMSO-d$_6$) (two rotamers in a 2:3 ratio) δ 11.24 (s, 1H, minor), 11.22 (s, 1H, major), 8.422 (s, 1H, minor), 8.417 (s, 1H, major), 7.66 (dd, J=3.0, 1.3 Hz, 1H), 7.58-7.54 (m, 1H), 7.40 (d, J=8.4 Hz, 2H), 7.35 (d, J=8.4 Hz, 2H), 6.80 (dd, J=5.0, 1.3 Hz, 1H), 5.37 (dp, J=56.7, 6.8 Hz, 1H), 4.29-4.17 (m, 1H, major), 3.62-3.49 (m, 1H, minor), 2.80 (s, 3H, major), 2.67 (s, 3H, minor), 2.63-2.53 (m, 2H), 2.48-2.35 (m, 4H), 2.03 (s, 3H, minor), 1.97 (s, 3H, major), 1.87-1.70 (m, 3H), 1.67-1.42 (m, 4H), 1.29-1.05 (m, 2H).

Example 76

N-(5'-(4-(1-aminocyclobutyl)phenyl)-[2,4'-bipyridin]-2'-yl)-2-(trans-4-(N-methylacetamido)cyclohexyl)acetamide

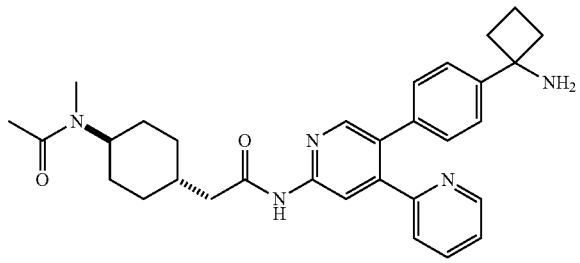 [SMILES: CC(=O)N(C)[C@H]1CC[C@H](CC(=O)Nc2cc(-c3ccccn3)c(-c3ccc(C4(N)CCC4)cc3)cn2)CC1]

Step 1: Benzyl [2,4'-bipyridin]-2'-ylcarbamate: A suspension of the product from Intermediate 20 Step 1 (8 g, 26.0 mmol), bis-(pinacolato)diboron (7.94 g, 31.3 mmol), palladium(II) acetate (0.292 g, 1.30 mmol), potassium acetate (7.67 g, 78.0 mmol) and XPhos (1.24 g, 2.60 mmol) in dioxane (100 ml) was degassed with N$_2$ for 10 min. The resultant solution was heated at 90° C. for 18 h. The reaction mixture was cooled to RT and filtered through Celite®, eluting with DCM (300 ml), and then dried over MgSO$_4$, filtered and concentrated in vacuo to afford a sticky orange solid. This material was combined with 2-bromopyridine (1.34 ml, 14.0 mmol), 4 M K$_3$PO$_4$(aq) (7.88 ml, 31.5 mmol) and SPhos Precatalyst 3G (85 mg, 0.105 mmol) in dioxane (70 ml). The mixture was degassed with N$_2$ for 10 min and the resultant solution was heated at 90° C. for 18 h. The reaction mixture was cooled to RT and filtered through a Celite®, eluting with DCM (200 ml). The solvent was removed in vacuo and the residue purified by column chromatography (40 g cartridge, 0-40% EtOAc/sohexane) to afford the title compound (2.27 g, 7.22 mmol, 97% purity) as a pale yellow solid. LCMS (Method 1): m/z 306 (M+H)$^+$ at 2.03 min.

Step 2: Benzyl (5'-bromo-[2,4'-bipyridin]-2'-yl)carbamate: A solution of the product from Step 1 above (2.27 g, 7.22 mmol, 97% purity) in DCM (40 ml) was treated with NBS (1.46 g, 8.18 mmol) and the resultant solution was stirred in the dark at RT for 18 h. Additional NBS (1.46 g, 8.18 mmol) was added and stirring continued for 30 h. Additional NBS (730 mg, 4.09 mmol) was added and stirring continued for 2 days. The reaction mixture was washed with water (100 ml). The organic phase was dried over MgSO$_4$, filtered and the solvent was removed in vacuo to afford an orange solid. This material was triturated with MeOH (50 ml), filtered and dried in vacuo to afford the title compound (1.97 g) as a white solid. This material was used directly in subsequent reactions without further purification.

Step 3: Benzyl (5'-(4-(1-((tert-butoxycarbonyl)amino)cyclobutyl)phenyl)-[2,4'-bipyridin]-2'-yl)carbamate: A solution of the product from Step 2 above (300 mg), 2 M Na$_2$CO$_3$(aq) (878 μl, 1.76 mmol), the product from Intermediate 8 Step 1 (350 mg, 0.937 mmol) and Pd(dppf)Cl$_2$ (28.6 mg, 0.039 mmol) in dioxane (10 ml) was degassed with N$_2$ for 20 min. The resultant solution was heated at 95° C. for 18 h. The reaction mixture was cooled to RT and filtered through Celite®, eluting with DCM (100 ml). The filtrate was concentrated in vacuo and the residue purified by column chromatography (12 g cartridge, 0-60% EtOAc/isohexane) to afford the title compound (61.1 mg, 0.103 mmol, 93% purity) as an orange oil. LCMS (Method 1): m/z 551 (M+H)$^+$ at 2.76 min.

Step 4: tert-butyl (1-(4-(6'-amino-[2,4'-bipyridin]-3'-yl)phenyl)cyclobutyl)carbamate: A solution of the product from Step 3 above (50 mg, 0.085 mmol, 93% purity) in a mixture of EtOH (2.5 ml) and THF (2.5 ml) was hydrogenated in a ThalesNano H-Cube® flow reactor (10% Pd/C, 30×4 mm cartridge, full hydrogen mode, 50° C., 1 ml/min flow rate). The solvent was removed in vacuo to afford the title compound (16.9 mg, 0.034 mmol, 85% purity) as a yellow solid. LCMS (Method 1): m/z 417 (M+H)$^+$ at 1.55 min. $^1$H NMR (400 MHz, Chloroform-d) δ 8.57 (ddd, J=4.9, 1.7, 0.9 Hz, 1H), 8.04 (s, 1H), 7.33 (td, J=7.7, 1.8 Hz, 1H), 7.22 (d, J=8.1 Hz, 2H), 7.10 (ddd, J=7.5, 4.9, 1.1 Hz, 1H), 7.01-6.96 (m, 2H), 6.83 (d, J=7.9 Hz, 1H), 6.79 (s, 1H), 5.06 (s, 1H), 2.55-2.34 (m, 3H), 2.37-2.08 (m, 3H), 2.08-1.93 (m, 1H), 1.86-1.69 (m, 1H), 1.32 (br s, 9H).

Step 5: tert-butyl (1-(4-(6'-(2-(trans-4-(N-methylacetamido)cyclohexyl)acetamido)-[2,4'-bipyridin]-3'-yl)phenyl)cyclobutyl)carbamate: The title compound was isolated as a white solid (14.7 mg, 0.023 mmol, 97% purity) from the reaction of the product from Example 1 Step 5 (17.3 mg), 1-chloro-N,N,2-trimethylprop-1-en-1-amine (0.025 ml, 0.192 mmol), the product from Step 4 above (16.9 mg, 0.034 mmol, 85% purity) and pyridine (0.5 ml) in DCM (2 ml) using essentially the same procedure as in Example 65 Step 1. LCMS (Method 1): m/z 612 (M+H)$^+$ at 2.22 min.

Step 6: N-(5'-(4-(1-aminocyclobutyl)phenyl)-[2,4'-bipyridin]-2'-yl)-2-(trans-4-(N-methylacetamido)cyclohexyl)acetamide: A solution of the product from Step 5 above (14 mg, 0.022 mmol, 97% purity) in DCM (2 ml) was treated with TFA (0.5 ml) and the resultant solution was stirred at RT for 1 h. The reaction mixture was diluted with DCM (2 ml) and quenched with saturated NaHCO$_3$(aq) (5 ml). The organic phase was concentrated in vacuo and the residue purified by column chromatography (4 g cartridge, 0-10% MeOH/DCM) to afford the title compound (7.2 mg, 0.014 mmol, 99% purity) as a white solid. LCMS (Method 1): m/z 512 (M+H)$^+$ at 1.31 min. $^1$H NMR (400 MHz, Methanol-d$_4$) (two rotamers in a 4:3 ratio) δ 8.58-8.54 (m, 1H), 8.40 (s, 1H), 8.38 (s, 1H), 7.70 (td, J=7.8, 1.7 Hz, 1H), 7.44-7.34 (m, 3H), 7.23-7.13 (m, 3H), 4.44-4.31 (m, 1H, major), 3.74-3.61 (m, 1H, minor), 2.93 (s, 3H, major), 2.82 (s, 3H, minor), 2.65-2.48 (m, 2H), 2.46-2.37 (m, 2H), 2.37-2.25 (m, 2H), 2.19-2.05 (m, 1H), 2.15 (s, 3H, minor), 2.10 (s, 3H, major), 2.04-1.51 (m, 9H), 1.36-1.19 (m, 2H).

Example 77

Methyl (trans-4-(2-((6-(4-(trans-1-amino-3-fluorocyclobutyl)phenyl)-5-phenylpyridin-3-yl)amino)-2-oxoethyl)cyclohexyl)(methyl)carbamate

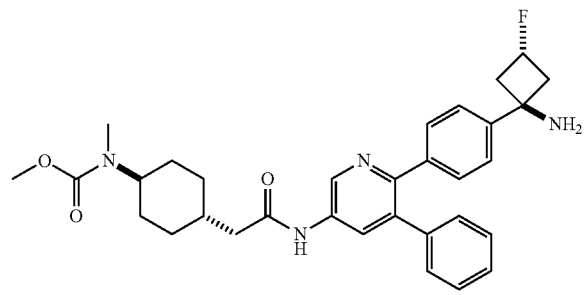 [SMILES: COC(=O)N(C)[C@H]1CC[C@H](CC(=O)Nc2cnc(-c3ccc([C@]4(N)C[C@H](F)C4)cc3)c(-c3ccccc3)c2)CC1]

Step 1: Methyl (trans-4-(2-((6-(4-(trans-1-((tert-butoxycarbonyl)amino)-3-fluorocyclobutyl)phenyl)-5-phenylpyridin-3-yl)amino)-2-oxoethyl)cyclohexyl)(methyl)carbamate: The title compound was isolated as a white solid (30.1 mg, 0.042 mmol, 90% purity) from the reaction of the product from Example 56 Step 3 (29.6 mg, 0.123 mmol, 95% purity), 1-chloro-N,N,2-trimethylprop-1-en-1-amine (0.018 ml, 0.136 mmol), Intermediate 13 (28 mg) and pyridine (0.5 ml) in DCM (2 ml) using essentially the same procedure as in Example 65 Step 1. $^1$H NMR (400 MHz, Methanol-$d_4$) δ 8.81 (d, J=2.4 Hz, 1H), 8.17 (d, J=2.5 Hz, 1H), 7.31-7.26 (m, 6H), 7.23-7.18 (m, 2H), 5.20 (dq, J=56.3, 6.9 Hz, 1H), 4.03-3.81 (m, 1H), 3.70 (s, 3H), 3.04-2.89 (m, 2H), 2.81 (s, 3H), 2.62-2.45 (m, 2H), 2.36 (d, J=7.0 Hz, 2H), 2.00-1.77 (m, 3H), 1.77-1.51 (m, 4H), 1.49-1.11 (m, 12H).

Step 2: Methyl (trans-4-(2-((6-(4-(trans-1-amino-3-fluorocyclobutyl)phenyl)-5-phenylpyridin-3-yl)amino)-2-oxoethyl)cyclohexyl)(methyl)carbamate: The product from Step 1 above (28.7 mg, 0.041 mmol, 90% purity) was dissolved in DCM (2 ml) and treated with TFA (500 μl, 6.49 mmol). The resultant solution was stirred at RT for 1 h. The reaction mixture was diluted with DCM (2 ml) and quenched with saturated NaHCO$_3$(aq) (5 ml). The organic phase was separated and concentrated in vacuo. The residue was purified by column chromatography (4 g cartridge, 0-10% MeOH/DCM), followed by preparative HPLC (Waters FractionLynx, Waters X-Bridge Prep-C18, 5 μm, 19×50 mm column, 25-50 MeCN in 10 mM ammonium bicarbonate) to afford the title compound (7.4 mg, 0.013 mmol, 97% purity) as a white solid. LCMS (Method 1): m/z 545 (M+H)$^+$ at 1.67 min. $^1$H NMR (400 MHz, Methanol-$d_4$) δ 8.82 (d, J=2.4 Hz, 1H), 8.17 (d, J=2.4 Hz, 1H), 7.32-7.25 (m, 7H), 7.24-7.19 (m, 2H), 5.36 (dp, J=56.0, 6.4 Hz, 1H), 4.00-3.85 (m, 1H), 3.70 (s, 3H), 2.81 (s, 3H), 2.75-2.64 (m, 3H), 2.63-2.50 (m, 3H), 2.36 (d, J=7.0 Hz, 2H), 2.00-1.55 (m, 8H), 1.33-1.17 (m, 2H).

Example 78

N-(6-(4-(trans-1-amino-3-fluorocyclobutyl)phenyl)-5-phenylpyridin-3-yl)-2-(trans-4-(2-oxooxazolidin-3-yl)cyclohexyl)acetamide

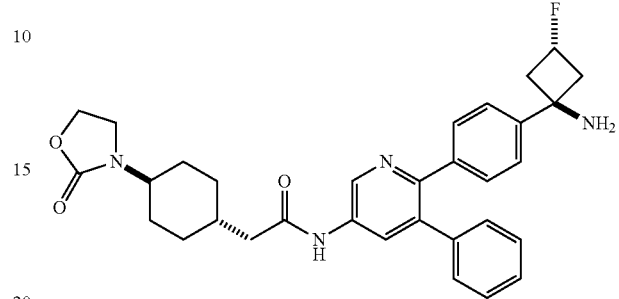

Step 1: tert-butyl (trans-3-fluoro-1-(4-(5-(2-(trans-4-(2-oxooxazolidin-3-yl)cyclohexyl)acetamido)-3-phenylpyridin-2-yl)phenyl)cyclobutyl)carbamate: The title compound was isolated as a white solid (25.2 mg, 0.031 mmol, 80% purity) from the reaction of the product from Example 42 Step 3 (29.4 mg, 0.123 mmol, 95% purity), 1-chloro-N,N,2-trimethylprop-1-en-1-amine (0.018 ml, 0.136 mmol), Intermediate 13 (28 mg) and pyridine (0.5 ml) in DCM (2 ml) using essentially the same procedure as in Example 65 Step 1. LCMS (Method 1): m/z 643 (M+H)$^+$ at 2.32 min.

Step 2: N-(6-(4-(trans-1-amino-3-fluorocyclobutyl)phenyl)-5-phenylpyridin-3-yl)-2-(trans-4-(2-oxooxazolidin-3-yl)cyclohexyl)acetamide: The title compound was isolated as a white solid (8.2 mg, 0.014 mmol) from the reaction of the product from Step 1 above (24.5 mg, 0.030 mmol, 80% purity) with TFA (0.5 ml) in DCM (2 ml) using essentially the same procedure as in Example 77 Step 2. LCMS (Method 1): m/z 543 (M+H)$^+$ at 1.50 min. $^1$H NMR (400 MHz, Methanol-$d_4$) δ 8.83 (d, J=2.4 Hz, 1H), 8.16 (d, J=2.4 Hz, 1H), 7.32-7.26 (m, 7H), 7.24-7.18 (m, 2H), 5.36 (dp, J=56.1, 6.6 Hz, 1H), 4.39-4.32 (m, 2H), 3.69-3.57 (m, 3H), 2.73-2.64 (m, 2H), 2.63-2.49 (m, 2H), 2.38 (d, J=7.0 Hz, 2H), 2.05-1.75 (m, 5H), 1.61 (qd, J=13.1, 3.9 Hz, 2H), 1.35-1.16 (m, 2H).

Example 79

N-(6-(4-(trans-1-amino-3-fluorocyclobutyl)phenyl)-5-(thiophen-3-yl)pyridazin-3-yl)-2-(trans-4-(2-oxooxazolidin-3-yl)cyclohexyl)acetamide

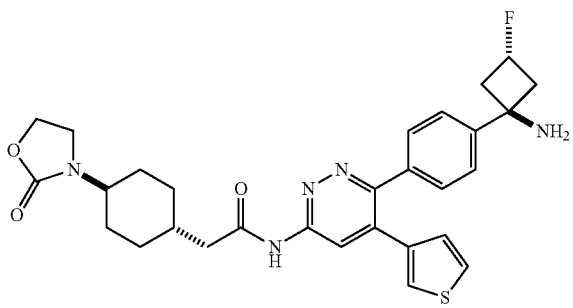 [SMILES: N[C@]1(c2ccc(-c3nnc(NC(=O)C[C@H]4CC[C@H](N5CCOC5=O)CC4)cc3-c3ccsc3)cc2)C[C@@H](F)C1]

The title compound (28 mg, 0.050 mmol, 99% purity) was isolated as a white solid from the reaction of the product from Example 75 Step 4 (50 mg, 0.107 mmol, 95% purity), the product from Example 42 Step 3 (64.5 mg, 0.270 mmol, 95% purity), 1-chloro-N,N,2-trimethylprop-1-en-1-amine (41 µl, 0.306 mmol), and pyridine (2 ml) in DCM (5 ml), followed by TFA (1 ml) in DCM (2 ml) using essentially the same procedure as in Example 71. LCMS (Method 1): m/z 550 (M+H)$^+$, 548 (M−H)$^-$, at 1.40 min. $^1$H NMR (400 MHz, DMSO-$d_6$) δ 11.23 (s, 1H), 8.42 (s, 1H), 7.66 (dd, J=2.9, 1.3 Hz, 1H), 7.56 (dd, J=5.0, 2.9 Hz, 1H), 7.45-7.31 (m, 4H), 6.80 (dd, J=5.0, 1.3 Hz, 1H), 5.37 (dp, J=56.8, 6.6 Hz, 1H), 4.29-4.19 (m, 2H), 3.53-3.42 (m, 3H), 2.65-2.36 (m, 6H), 1.88-1.62 (m, 5H), 1.48 (qd, J=12.6, 3.3 Hz, 2H), 1.26-1.05 (m, 2H).

Example 80

N-(6-(4-(2-aminopropan-2-yl)phenyl)-5-(thiophen-3-yl)pyridazin-3-yl)-2-(trans-4-(2-oxooxazolidin-3-yl)cyclohexyl)acetamide

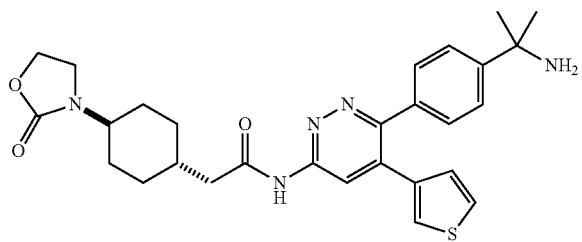 [SMILES: CC(C)(N)c1ccc(-c2nnc(NC(=O)C[C@H]3CC[C@H](N4CCOC4=O)CC3)cc2-c2ccsc2)cc1]

Step 1: tert-butyl (2-(4-(6-amino-4-(thiophen-3-yl)pyridazin-3-yl)phenyl)propan-2-yl)carbamate: The title compound (70 mg, 0.157 mmol, 92% purity) was isolated as a yellow solid from the reaction of the product from Example 75 Step 3 (160 mg, 0.733 mmol, 97% purity), the product from Intermediate 2 Step 2 (273 mg, 0.756 mmol), tetrakis-(triphenylphosphine)palladium(0) (87 mg, 0.076 mmol), Na$_2$CO$_3$(s) (176 mg, 1.66 mmol) in water (1 ml) and dioxane (5 ml) using essentially the same procedure as in Example 75 Step 4. $^1$H NMR (400 MHz, DMSO-$d_6$) δ 7.51-7.40 (m, 2H), 7.31-7.10 (m, 5H), 6.81 (s, 1H), 6.78-6.71 (m, 1H), 6.47 (s, 2H), 1.49 (s, 6H), 1.34 (s, 9H).

Step 2: N-(6-(4-(2-aminopropan-2-yl)phenyl)-5-(thiophen-3-yl)pyridazin-3-yl)-2-(trans-4-(2-oxooxazolidin-3-yl)cyclohexyl)acetamide: The title compound (7 mg, 0.013 mmol, 99% purity) was isolated as a white solid from the reaction of the product from Step 1 above (50 mg, 0.112 mmol, 92% purity), the product from Example 42 Step 3 (69.2 mg, 0.289 mmol, 95% purity), 1-chloro-N,N,2-trimethylprop-1-en-1-amine (44 µl, 0.329 mmol), and pyridine (2 ml) in DCM (5 ml), followed by TFA (1 ml) in DCM (2 ml) using essentially the same procedure as in Example 71. LCMS (Method 1): m/z 520 (M+H)$^+$, 518 (M−H)$^-$, at 1.36 min. $^1$H NMR (400 MHz, DMSO-$d_6$) δ 11.22 (s, 1H), 8.41 (s, 1H), 7.65 (dd, J=3.0, 1.3 Hz, 1H), 7.60-7.48 (m, 3H), 7.37-7.26 (m, 2H), 6.80 (dd, J=5.0, 1.3 Hz, 1H), 4.32-4.19 (m, 2H), 3.57-3.42 (m, 3H), 2.40 (d, J=6.8 Hz, 2H), 1.93-1.62 (m, 5H), 1.55-1.41 (m, 1H), 1.39 (s, 6H), 1.31-1.06 (m, 3H).

Example 81

Methyl (trans-4-(2-((6-(4-(1-aminocyclobutyl)phenyl)-5-(thiophen-3-yl)pyridazin-3-yl)amino)-2-oxoethyl)cyclohexyl)(methyl)carbamate

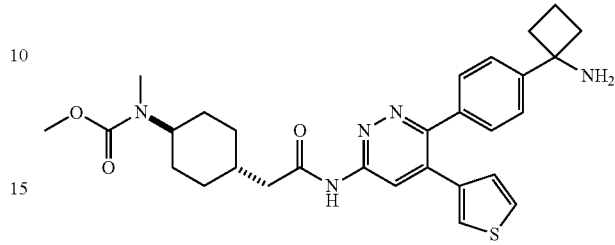

Step 1: tert-butyl (1-(4-(6-amino-4-(thiophen-3-yl)pyridazin-3-yl)phenyl)cyclobutyl)carbamate: The title compound (33 mg, 0.078 mmol) was isolated as a yellow solid from the reaction of the product from Example 75 Step 3 (140 mg, 0.593 mmol, 97% purity), the product from Intermediate 8 Step 1 (247 mg, 0.661 mmol), tetrakis-(triphenylphosphine)palladium(0) (76 mg, 0.066 mmol), Na$_2$CO$_3$(s) (154 mg, 1.46 mmol) in water (1 ml) and dioxane (5 ml) using essentially the same procedure as in Example 75 Step 4. $^1$H NMR (400 MHz, DMSO-$d_6$) (two rotamers in a 2:1 ratio) δ 7.60-7.54 (br s, 1H), 7.47-7.43 (m, 2H), 7.33-7.29 (m, 2H), 7.24-7.18 (m, 2H), 6.81 (s, 1H), 6.76-6.72 (m, 1H), 6.47 (s, 2H), 2.43-2.30 (m, 4H), 1.87-1.69 (m, 2H) 1.34 (s, 9H, major), 1.21 (s, 9H, minor).

Step 2: Methyl (trans-4-(2-((6-(4-(1-aminocyclobutyl)phenyl)-5-(thiophen-3-yl)pyridazin-3-yl)amino)-2-oxoethyl)cyclohexyl)(methyl)carbamate: The title compound (26 mg, 0.049 mmol) was isolated as a white solid from the reaction of the product from Step 1 above (33 mg, 0.078 mmol), the product from Example 56 Step 3 (67.8 mg, 0.281 mmol, 95% purity), 1-chloro-N,N,2-trimethylprop-1-en-1-amine (42 µl, 0.319 mmol), and pyridine (2 ml) in DCM (5 ml), followed by TFA (1 ml) in DCM (2 ml) using essentially the same procedure as in Example 71. LCMS (Method 1): m/z 534 (M+H)$^+$, 532 (M−H)$^-$, at 1.55 min. $^1$H NMR (400 MHz, DMSO-$d_6$) δ 11.22 (s, 1H), 8.42 (s, 1H), 7.67-7.63 (m, 1H), 7.55 (dd, J=5.0, 3.0 Hz, 1H), 7.50-7.42 (m, 2H), 7.41-7.29 (m, 2H), 6.80 (dd, J=5.0, 1.4 Hz, 1H), 3.92-3.70 (m, 1H), 3.58 (s, 3H), 2.71 (s, 3H), 2.46-2.32 (m, 4H), 2.18-1.96 (m, 3H), 1.88-1.43 (m, 8H), 1.23-1.05 (m, 2H).

Example 82

N-(trans-4-(2-((5-(4-(trans-1-amino-3-hydroxy-3-methylcyclobutyl)phenyl)-4-phenylpyridin-2-yl)amino)-2-oxoethyl)cyclohexyl)-N-methylpropionamide

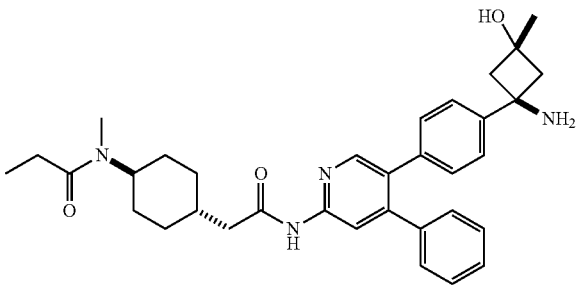 [SMILES: CCC(=O)N(C)[C@H]1CC[C@H](CC(=O)Nc2cc(-c3ccccc3)c(-c3ccc([C@]4(N)C[C@](C)(O)C4)cc3)cn2)CC1]

Step 1: Ethyl 2-(trans-4-(N-methylpropionamido)cyclohexyl)acetate: A suspension of the product from Example 1 Step 3 (1 g, 4.77 mmol) in DCM (15 ml) was treated with DIPEA (1.03 ml, 6.20 mmol), followed by propionyl chloride (0.479 ml, 5.48 mmol). The resultant mixture stirred at RT overnight. The reaction mixture was washed with saturated NH$_4$Cl(aq) (20 ml), the phases separated and the aqueous phase extracted with DCM (20 ml). The organic phases were combined and washed sequentially with 1 M HCl(aq) (10 ml), saturated NaHCO$_3$(aq) (10 ml) and brine (10 ml). The organic phase was dried over MgSO$_4$, filtered and concentrated to afford the title compound (1.05 g, 4.03 mmol, 98% purity) as an orange gum. $^1$H NMR (two rotamers in an 11:9 ratio) (400 MHz, DMSO-d$_6$) δ 4.30-4.16 (m, 1H, major), 4.05 (q, J=7.1 Hz, 2H), 3.63-3.44 (m, 1H, minor), 2.77 (s, 3H, major), 2.67 (s, 3H, minor), 2.37-2.11 (m, 4H), 1.83-1.37 (m, 6H), 1.27-0.73 (m, 9H).

Step 2: 2-(trans-4-(N-methylpropionamido)cyclohexyl)acetic acid: The product from Step 1 above (1.05 g, 4.03 mmol, 98% purity) was dissolved in a mixture of THF (10 ml), MeOH (5 ml), and 1 M LiOH(aq) (9.53 ml, 9.53 mmol) and the resultant mixture stirred at RT overnight. The reaction mixture was concentrated to approx 10 ml then washed with DCM (10 ml). The aqueous phase was acidified with conc. HCl and extracted with DCM (3×15 ml). The organic phases were combined, dried over MgSO$_4$, filtered and concentrated in vacuo to afford a gum. This material was dissolved in hot isohexane (ca. 20 ml) and the resultant solution allowed to cool. The resultant precipitate was collected by filtration to afford the title compound (652 mg, 2.81 mmol, 98% purity) as a colourless solid. $^1$H NMR (400 MHz, DMSO-d$_6$) δ 11.95 (s, 1H), 4.29-4.14 (m, 1H, major), 3.62-3.47 (m, 1H, minor), 2.78 (s, 3H, major), 2.68 (s, 3H, minor), 2.36-2.22 (m, 2H), 2.11 (d, J=7.0 Hz, 2H), 1.82-1.40 (m, 8H), 1.21-0.92 (m, 4H).

Step 3: N-(trans-4-(2-((5-bromo-4-phenylpyridin-2-yl)amino)-2-oxoethyl)cyclohexyl)-N-methylpropionamide: A solution of the product from Step 2 above (201 mg, 0.865 mmol, 98% purity) in DCM (5 ml) was treated with 1-chloro-N,N,2-trimethylprop-1-en-1-amine (215 μl, 1.61 mmol) and stirred for 1 h. Pyridine (294 μl, 3.45 mmol) was added followed by 5-bromo-4-phenylpyridin-2-amine (200 mg, 0.803 mmol). The reaction mixture was stirred at RT overnight. The reaction was quenched by addition of saturated NH$_4$Cl(aq) (3 ml) and passed through a phase separation cartridge. The organic phase was concentrated in vacuo and the residue purified by column chromatography (12 g cartridge, 0-100% EtOAc/isohexane) to afford the title compound (231 mg, 0.494 mmol, 98% purity). LCMS (Method 1): m/z 458 (M+H)$^+$ at 2.37 min. $^1$H NMR (two rotamers in a 7:5 ratio) (400 MHz, DMSO-d$_6$) δ 10.73 (s, 1H, minor), 10.72 (s, 1H, major), 8.57 (s, 1H), 8.18 (s, 1H), 7.61-7.36 (m, 5H), 4.30-4.17 (m, 1H, major), 3.62-3.53 (m, 1H, minor), 2.77 (s, 3H, major), 2.67 (s, 3H, minor), 2.41-2.19 (m, 4H), 1.77 (d, J=13.2 Hz, 3H), 1.64-1.38 (m, 4H), 1.25-1.01 (m, 2H), 0.97 (m, 3H).

Step 4: tert-butyl (trans-3-hydroxy-3-methyl-1-(4-(6-(2-(trans-4-(N-methylpropionamido)cyclohexyl)acetamido)-4-phenylpyridin-3-yl)phenyl)cyclobutyl)carbamate: The title compound (23 mg, 0.035 mmol, 99% purity) was isolated as a colourless solid from the reaction of the product from Step 3 above (50 mg, 0.107 mmol), tert-butyl (trans-3-hydroxy-3-methyl-1-(4-(4,4,5,5-tetramethyl-1,3,2-dioxaborolan-2-yl)phenyl)cyclobutyl)carbamate (53 mg, 0.131 mmol, prepared according to *Org. Process Res. Dev.*, 2012, 16, 1069), tetrakis-(triphenylphosphine)palladium(0) (12.6 mg, 10.9 μmol) and 2 M Na$_2$CO$_3$(aq) (136 μl, 0.273 mmol) in dioxane (2 ml) using essentially the same procedure as in Intermediate 1 Step 2. LCMS (Method 1): m/z 655 (M+H)$^+$ at 2.26 min.

Step 5: N-(trans-4-(2-((5-(4-(trans-1-amino-3-hydroxy-3-methylcyclobutyl)phenyl)-4-phenylpyridin-2-yl)amino)-2-oxoethyl)cyclohexyl)-N-methylpropionamide: The product from Step 4 above (23 mg, 0.035 mmol, 99% purity) was dissolved in DCM (3 ml) and treated with TFA (126 μl, 1.64 mmol). The resultant mixture was stirred for 1 h. The reaction mixture was loaded onto a column of SCX. The column was washed with MeOH and the product was eluted with a 0.7 M solution of ammonia in MeOH. The solvent was removed in vacuo to afford the title compound (17 mg, 0.030 mmol, 95% purity) as a colourless solid. LCMS (Method 1): m/z 555 (M+H)$^+$, 553 (M−H)$^−$, at 1.36 min. $^1$H NMR (two rotamers in a 2:1 ratio) (Methanol-d$_4$, 400 MHz) δ 8.30 (s, 1H), 8.19 (s, 1H), 7.42-7.34 (m, 2H), 7.34-7.09 (m, 7H), 4.46-4.30 (m, 1H, major), 3.81-3.61 (m, 1H, minor), 2.91 (s, 3H, major), 2.81 (s, 3H, minor), 2.76-2.59 (m, 2H), 2.52-2.33 (m, 6H), 2.07-1.50 (m, 10H), 1.38-1.18 (m, 2H), 1.12 (t, J=7.5 Hz, 3H, minor), 1.10 (t, J=7.5 Hz, 3H, minor).

Example 83

N-(trans-4-(2-((6-(4-(trans-1-amino-3-hydroxy-3-methylcyclobutyl)phenyl)-5-phenylpyridazin-3-yl)amino)-2-oxoethyl)cyclohexyl)-N-methylpropionamide

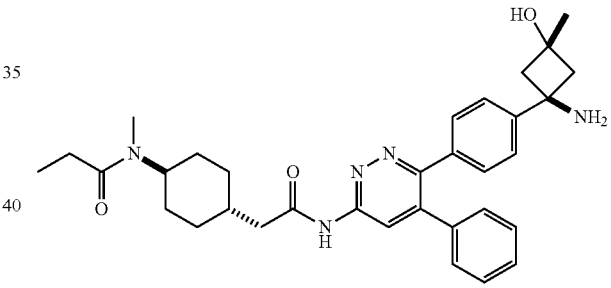

Step 1: tert-butyl (trans-3-hydroxy-3-methyl-1-(4-(6-(2-(trans-4-(N-methylpropionamido)cyclohexyl)acetamido)-4-phenylpyridazin-3-yl)phenyl)cyclobutyl)carbamate: The title compound (8 mg, 0.012 mmol, 95% purity) was isolated as a pale orange solid from the reaction of the product from Example 82 Step 2 (24 mg, 1.01 mmol, 98% purity), the product from Example 57 Step 1 (42 mg, 0.089 mmol, 95% purity), 1-chloro-N,N,2-trimethylprop-1-en-1-amine (25 μl, 0.188 mmol) and pyridine (35 μl, 0.404 mmol) in DCM (5 ml) using essentially the same procedure as in Example 82 Step 3. HPLC (Method 1): R$_T$ 2.23 min.

Step 2: N-(trans-4-(2-((6-(4-(trans-1-amino-3-hydroxy-3-methylcyclobutyl)phenyl)-5-phenylpyridazin-3-yl)amino)-2-oxoethyl)cyclohexyl)-N-methylpropionamide: The title compound (3 mg, 5.5 μmol, 95% purity) was isolated as a colourless solid from the reaction of the product from Step 1 above (8 mg, 0.012 mmol, 95% purity) and TFA (7 μl, 0.094 mmol) in DCM (1 ml) using essentially the same procedure as in Example 82 Step 5. LCMS (Method 1): m/z 556 (M+H)$^+$, 554 (M−H)$^−$, at 1.39 min. $^1$H NMR (400 MHz, Methanol-d$_4$) δ 8.54-8.46 (m, 1H), 7.45-7.30 (m, 7H), 7.28-7.22 (m, 2H), 4.45-4.31 (m, 1H, major), 3.76-3.63 (m, 1H, minor), 2.90 (s, 3H, major), 2.80 (s, 3H, minor), 2.66 (d, 2H), 2.50-2.30 (m, 6H), 2.01-1.50 (m, 9H), 1.40-1.19 (m, 3H), 1.12 (t, J=7.4 Hz, 3H, minor), 1.11 (t, J=7.4 Hz, 3H, major).

Example 84

Methyl (trans-4-(2-((6-(4-(trans-1-amino-3-hydroxy-3-methylcyclobutyl)phenyl)-5-(thiophen-3-yl)pyridazin-3-yl)amino)-2-oxoethyl)cyclohexyl)(methyl)carbamate

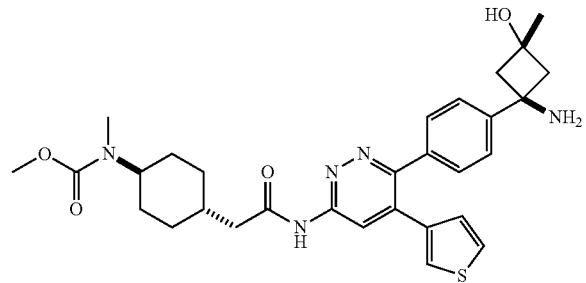

Step 1: tert-butyl ((1 r,3r)-1-(4-(6-amino-4-(thiophen-3-yl)pyridazin-3-yl)phenyl)-3-hydroxy-3-methylcyclobutyl)carbamate: The title compound (63 mg, 0.136 mmol, 98% purity) was isolated as a colourless solid from the reaction of the product from Example 75 Step 3 (100 mg, 0.458 mmol, 97% purity), tert-butyl (trans-3-hydroxy-3-methyl-1-(4-(4,4,5,5-tetramethyl-1,3,2-dioxaborolan-2-yl)phenyl)cyclobutyl)carbamate (191 mg, 0.472 mmol, prepared according to Org. Process Res. Dev., 2012, 16, 1069), tetrakis-(triphenylphosphine)palladium(0) (54.6 mg, 47 µmol) and 2 M Na$_2$CO$_3$(aq) (591 µl, 1.18 mmol) in dioxane using essentially the same procedure as in Intermediate 1 Step 2. HPLC (Method 1): R$_T$ 1.42 min.

Step 2: Methyl (trans-4-(2-((6-(4-(trans-1-((tert-butoxycarbonyl)amino)-3-hydroxy-3-methylcyclobutyl)phenyl)-5-(thiophen-3-yl)pyridazin-3-yl)amino)-2-oxoethyl)cyclohexyl)(methyl)carbamate: A solution of the product from Example 56 Step 3 (35.1 mg, 0.138 mmol, 90% purity), HATU (58.2 mg, 0.153 mmol) and DIPEA (53.5 µl, 0.306 mmol) in DMF (1 ml) was stirred at RT for 30 min, then a solution of the product from Step 1 above (63 mg, 0.136 mmol, 98% purity) in DMF (1 ml) was added. The resultant mixture was heated at 50° C. for 4 days. EtOAc (10 ml) was added and the organic phase was washed sequentially with water (10 ml), saturated NaHCO$_3$(aq) (10 ml) and brine (10 ml). The organic phase was dried over MgSO$_4$, filtered and concentrated in vacuo. The residue was purified by column chromatography (12 g cartridge, 0-7% (0.7 M NH$_3$ in MeOH)/DCM) to afford the title compound (11 mg, 0.015 mmol, 90% purity) as a colourless solid. LCMS (Method 1): m/z 664 (M+H)$^+$ at 2.30 min.

Step 3: Methyl (trans-4-(2-((6-(4-(trans-1-amino-3-hydroxy-3-methylcyclobutyl)phenyl)-5-(thiophen-3-yl)pyridazin-3-yl)amino)-2-oxoethyl)cyclohexyl)(methyl)carbamate: The title compound (7 mg, 12 µmol, 97% purity) was isolated as a colourless solid from the reaction of the product from Step 1 above (11 mg, 0.015 mmol, 90% purity) and TFA (119 µl, 1.54 mmol) in DCM (3 ml) using essentially the same procedure as in Example 82 Step 5. LCMS (Method 1): m/z 564 (M+H)$^+$, 562 (M−H)$^-$ at 1.39 min. $^1$H NMR (400 MHz, DMSO-d$_6$) δ 11.22 (s, 1H), 8.41 (s, 1H), 7.66 (dd, J=2.9, 1.3 Hz, 1H), 7.56 (dd, J=5.0, 2.9 Hz, 1H), 7.46-7.41 (m, 2H), 7.35-7.29 (m, 2H), 6.80 (dd, J=5.0, 1.3 Hz, 1H), 4.82 (s, 1H), 3.89-3.69 (m, 2H), 3.58 (s, 3H), 2.71 (s, 3H), 2.43-2.35 (m, 4H), 2.20-1.90 (m, 3H), 1.88-1.70 (m, 3H), 1.64-1.44 (m, 7H), 1.20-1.04 (m, 2H).

Example 85

N-(trans-4-(2-((5-(4-(trans-1-amino-3-hydroxy-3-methylcyclobutyl)phenyl)-4-phenylpyridin-2-yl)amino)-2-oxoethyl)cyclohexyl)-N-methylisobutyramide Step 1: 2-(trans-4-(N-methylisobutyramido)cyclohexyl)acetic acid: A suspension of the product from Example 1 Step 3 (1 g, 4.77 mmol) in DCM (15 ml) was treated with DIPEA (1.03 ml, 6.20 mmol), followed by isobutyryl chloride (0.574 ml, 5.48 mmol). The resultant mixture was stirred at RT overnight. The reaction mixture was washed with saturated NH$_4$Cl(aq) (20 ml) and the aqueous phase extracted with DCM (20 ml). The organic phases were combined and washed sequentially with 1M HCl(aq) (10 ml), saturated NaHCO$_3$(aq) (10 ml) and brine (10 ml). The organic phase was then dried over MgSO$_4$, filtered and concentrated to afford the crude ester (1.00 g) as an orange gum. This material was dissolved in a mixture of THF (10 ml), MeOH (5 ml), and 1 M LiOH(aq) (9.53 ml, 9.53 mmol) and stirred at RT overnight. The reaction mixture was concentrated to approx. 10 ml and then washed with DCM (10 ml). The aqueous phase was acidified with conc. HCl (aq) (ca. 2 ml) and extracted with DCM (3×15 ml). The organic phases were combined, dried over MgSO$_4$, filtered and concentrated to afford the title compound (667 mg) as a pale yellow oil, which solidified upon standing. This material was used directly in subsequent reactions without purification.

Step 2: N-(trans-4-(2-((5-bromo-4-phenylpyridin-2-yl)amino)-2-oxoethyl)cyclohexyl)-N-methylisobutyramide: The title compound (250 mg, 0.519 mmol, 98% purity) was isolated as a colourless solid from the reaction of 5-bromo-4-phenylpyridin-2-amine (200 mg, 0.803 mmol), 1-chloro-N,N,2-trimethylprop-1-en-1-amine (215 µl, 1.61 mmol), the product from Step 2 above (237 mg, 0.883 mmol, 90% purity) and pyridine (294 µl, 3.45 mmol) in DCM (5 ml) using essentially the same procedure as in Example 65 Step 1. LCMS (Method 1): m/z 472 (M+H)$^+$ at 2.49 min.

Step 3: tert-butyl (trans-3-hydroxy-3-methyl-1-(4-(6-(2-(trans-4-(N-methylisobutyramido)cyclohexyl)acetamido)-4-phenylpyridin-3-yl)phenyl)cyclobutyl)carbamate: The title compound (18 mg, 0.026 mmol, 95% purity) was isolated as a colourless solid from the reaction of the product from Step 2 above (50 mg, 0.095 mmol, 90% purity), tert-butyl (trans-3-hydroxy-3-methyl-1-(4-(4,4,5,5-tetramethyl-1,3,2-dioxaborolan-2-yl)phenyl)cyclobutyl)carbamate (51.2 mg, 0.127 mmol, prepared according to *Org. Process Res. Dev.*, 2012, 16, 1069), tetrakis-(triphenylphosphine)palladium(0) (12.2 mg, 10.6 µmol) and 2 M Na₂CO₃(aq) (132 µl, 0.265 mmol) in dioxane (2 ml) using essentially the same procedure as in Intermediate 1 Step 2. LCMS (Method 1): m/z 669 (M+H)⁺ at 2.36 min.

Step 4: N-(trans-4-(2-((5-(4-(trans-1-amino-3-hydroxy-3-methylcyclobutyl)phenyl)-4-phenylpyridin-2-yl)amino)-2-oxoethyl)cyclohexyl)-N-methylisobutyramide: The title compound (11 mg, 18 µmol, 95% purity) was isolated as a colourless solid from the reaction of the product from Step 3 above (18 mg, 0.026 mmol, 95% purity) and TFA (126 µl, 1.64 mmol) in DCM (3 ml) using essentially the same procedure as in Example 82 Step 5. LCMS (Method 1): m/z 569 (M+H)⁺, 567 (M−H)⁻, at 1.44 min. ¹H NMR (400 MHz, Methanol-d₄) δ 8.31 (d, J=2.0 Hz, 1H), 8.19 (d, J=2.1 Hz, 1H), 7.37 (d, J=8.0 Hz, 2H), 7.34-7.08 (m, 7H), 4.46-4.22 (m, 1H, major), 3.89-3.60 (m, 1H, minor), 3.03-2.84 (m, 1H), 2.95 (3H, s, major), 2.80 (s, 3H, minor), 2.74-2.59 (m, 2H), 2.49-2.32 (m, 4H), 2.06-1.49 (m, 10H), 1.40-1.19 (m, 2H), 1.13-1.08 (m, 6H).

Example 86

Methyl (trans-4-(2-((5'-(4-(1-aminocyclobutyl)phenyl)-[2,4'-bipyridin]-2'-yl)amino)-2-oxoethyl)cyclohexyl)(methyl)carbamate

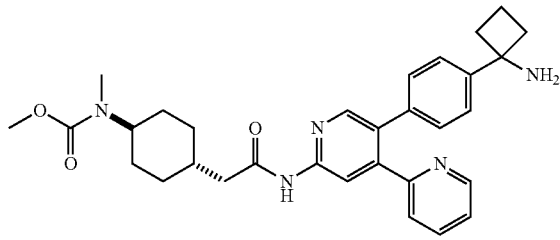 [SMILES: COC(=O)N(C)[C@H]1CC[C@H](CC(=O)Nc2cc(-c3ccccn3)c(-c3ccc(C4(N)CCC4)cc3)cn2)CC1]

Step 1: Methyl (trans-4-(2-((5'-bromo-[2,4'-bipyridin]-2'-yl)amino)-2-oxoethyl)cyclohexyl)(methyl)carbamate: The title compound (174 mg, 0.358 mmol, 95% purity) was isolated from the reaction of 5'-bromo-[2,4'-bipyridin]-2'-amine (100 mg, 0.400 mmol), the product from Example 56 Step 3 (120 mg, 0.523 mmol), 1-chloro-N,N,2-trimethylprop-1-en-1-amine (139 µl, 1.04 mmol) and pyridine (147 µl, 1.72 mmol) in DCM (5 ml) using essentially the same procedure as in Example 65 Step 1. LCMS (Method 1): m/z 461 (M+H)⁺ at 2.04 min.

Step 2: Methyl (trans-4-(2-((5'-(4-(1-((tert-butoxycarbonyl)amino)cyclobutyl)phenyl)-[2,4'-bipyridin]-2'-yl)amino)-2-oxoethyl)cyclohexyl)(methyl)carbamate: A solution of the product from Intermediate 8 Step 1 (48.5 mg, 0.130 mmol) and the product from Step 1 above (50 mg, 0.103 mmol, 95% purity) in dioxane (2 ml) was purged with N₂ for 5 min, then Pd(dppf)Cl₂ DCM complex (8.85 mg, 10.8 µmol) was added and the reaction mixture heated at 90° C. overnight. The reaction mixture was allowed to cool and was then concentrated and purified by column chromatography (12 g cartridge, 0-7% (0.7 M NH₃ in MeOH)/DCM) to afford the title compound (15 mg, 0.023 mmol, 98% purity) as a colourless gum. LCMS (Method 1): m/z 628 (M+H)⁺ at 2.48 min.

Step 3: Methyl (trans-4-(2-((5'-(4-(1-aminocyclobutyl)phenyl)-[2,4'-bipyridin]-2'-yl)amino)-2-oxoethyl)cyclohexyl)(methyl)carbamate: The title compound (10.9 mg, 20 µmol, 95% purity) was isolated as a colourless gum from the reaction of the product from Step 2 above (15 mg, 0.023 mmol, 98% purity) and TFA (83 µl, 1.08 mmol) in DCM (2 ml) using essentially the same procedure as in Example 82 Step 5. LCMS (Method 1): m/z 528 (M+H)⁺ at 1.40 min. ¹H NMR (400 MHz, Methanol-d₄) δ 8.57 (ddd, J=5.0, 1.8, 1.0 Hz, 1H), 8.44-8.31 (m, 2H), 7.71 (td, J=7.8, 1.8 Hz, 1H), 7.45-7.33 (m, 3H), 7.27-7.13 (m, 3H), 4.00-3.83 (m, 1H), 3.70 (s, 3H), 3.37 (s, 1H), 2.80 (s, 3H), 2.73-2.55 (m, 2H), 2.49-2.33 (m, 4H), 2.24-2.07 (m, 1H), 2.04-1.77 (m, 4H), 1.77-1.55 (m, 4H), 1.34-1.07 (m, 2H).

Example 87

N-(trans-4-(2-((6-(4-(1-aminocyclopropyl)phenyl)-5-phenylpyridazin-3-yl)amino)-2-oxoethyl)cyclohexyl)-N-methylcyclopropanecarboxamide

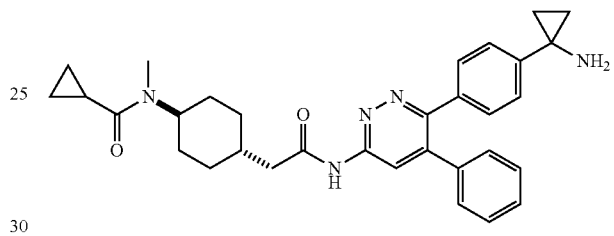

Step 1: 2-(trans-4-(N-methylcyclopropanecarboxamido)cyclohexyl)acetic acid: A suspension of the product from Example 1 Step 3 (1.1 g, 5.24 mmol) in DCM (15 ml) was treated with DIPEA (1.13 ml, 6.82 mmol), followed by cyclopropanecarbonyl chloride (0.548 ml, 6.03 mmol) and the reaction mixture was stirred at RT for 3 days. The reaction mixture was washed with saturated NH₄Cl(aq) (20 ml) and the aqueous phase extracted with DCM (20 ml). The organic phases were combined and washed sequentially with 1 M HCl(aq) (10 ml), saturated NaHCO₃(aq) (10 ml) and brine (10 ml). The organic phase was then dried over MgSO₄, filtered and concentrated to afford an orange gum. The residue was dissolved in a mixture of THF (10 ml), MeOH (5 ml), and treated with 1 M LiOH(aq) (10.5 ml, 10.5 mmol) and the mixture stirred at RT for 3 h. The reaction mixture was concentrated to approx. 10 ml and then washed with DCM (10 ml). The aqueous phase was acidified with conc. HCl (ca. 2 ml) and extracted with DCM (3×15 ml). The organic phases were combined, dried over MgSO₄, filtered and concentrated. The residue was then triturated with hot hexane (ca. 20 ml) to afford the title compound (1.19 g, 4.87 mmol, 98% purity) as a colourless solid. ¹H NMR (two rotamers in a 5:4 ratio) (400 MHz, DMSO-d₆) δ 12.03 (s, 1H), 4.25-4.16 (m, 1H, major), 4.07-3.89 (m, 1H, minor), 2.96 (s, 3H, major), 2.70 (s, 3H, minor), 2.15-1.99 (m, 2H), 1.99-1.41 (m, 7H), 1.26-0.56 (m, 7H).

Step 2: N-(trans-4-(2-((6-(4-(1-aminocyclopropyl)phenyl)-5-phenylpyridazin-3-yl)amino)-2-oxoethyl)cyclohexyl)-N-methylcyclopropanecarboxamide: A solution of the product of Step 1 above (38.1 mg, 0.156 mmol, 98% purity) in DCM (5 ml) was treated with 1-chloro-N,N,2-trimethylprop-1-en-1-amine (0.022 ml, 0.167 mmol) and the resultant solution was stirred at RT for 30 min. A solution of the product from Example 72 Step 1 (32 mg, 0.080 mmol) in pyridine (0.5 ml, 0.080 mmol) was added and the solution stirred at RT overnight. An additional portion of acid chloride intermediate was prepared in a separate vial as described above, then added to the reaction mixture. After an additional 4 h, 1 M HCl(aq) (5 ml) was added and the mixture stirred for 10 min. The organic phase was passed through a phase separation cartridge and the solvent removed in vacuo. The residue was dissolved in DCM (5 ml) and treated with TFA (0.5 ml, 0.119 mmol) and stirred at RT for 2 h. Saturated NaHCO₃(aq) (5 ml) was added and the mixture stirred for 10 min. The phases were separated and the aqueous phase was extracted with EtOAc (2×10 ml). The combined organic phases were dried over MgSO₄, filtered and the solvent removed in vacuo. The residue was loaded onto a column of SCX in MeOH. The column was washed with MeOH (20 ml) and then the product was eluted with 0.7 M ammonia in MeOH (20 ml). The resultant mixture was concentrated in vacuo. The residue was further purified by column chromatography (12 g cartridge, 0-10% (0.7 M Ammonia/MeOH)/DCM) to afford the title compound (11.4 mg, 0.022 mmol, 99% purity) as a white solid. LCMS (Method 1): m/z 524 (M+H)⁺ at 1.53 min. ¹H NMR (400 MHz, DMSO-d₆) (two rotamers in a 4:3 ratio) δ 11.27 (s, 1H, minor), 11.25 (s, 1H, major), 8.34 (s, 1H), 7.42-7.32 (m, 3H), 7.30-7.16 (m, 6H), 4.29-4.14 (m, 1H, major), 4.07-3.92 (m, 1H, minor), 2.96 (s, 3H, major), 2.70 (s, 3H, minor), 2.45-2.34 (m, 2H), 2.01-1.40 (m, 9H), 1.30-1.02 (m, 3H), 1.03-0.96 (m, 2H), 0.95-0.88 (m, 2H), 0.74-0.63 (m, 4H).

Example 88

N-(trans-4-(2-((6-(4-(2-aminopropan-2-yl)phenyl)-5-(thiophen-3-yl)pyridazin-3-yl)amino)-2-oxoethyl)cyclohexyl)-N-methylpropionamide

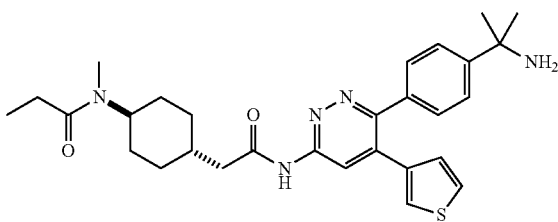 [SMILES: CCC(=O)N(C)[C@H]1CC[C@H](CC(=O)Nc2cc(-c3ccsc3)c(-c3ccc(C(C)(C)N)cc3)nn2)CC1]

A suspension of the product from Example 82 Step 2 (65 mg, 0.286 mmol) in DCM (5 ml) was treated with 1-chloro-N,N,2-trimethylprop-1-en-1-amine (40 μL, 0.302 mmol) and stirred at RT for 2 h. The mixture was treated with a solution of the product from Example 80 Step 1 (45 mg, 0.110 mmol) in pyridine (2 ml, 24.7 mmol) and stirred at RT overnight. In a separate vessel, a suspension of the product from Example 82 Step 2 (65 mg, 0.286 mmol) in DCM (5 ml) was treated with 1-chloro-N,N,2-trimethylprop-1-en-1-amine (40 μL, 0.302 mmol) and stirred at RT for 2 h and then added to the original mixture, which was stirred for 3 days. The mixture was concentrated in vacuo and the residue partitioned between water (5 ml) and DCM (5 ml). The phases were separated and the organic phase concentrated in vacuo. The residue was purified by column chromatography (40 g cartridge, 0-100% EtOAc/isohexane) to afford a colourless gum. This material was dissolved in acetone (1 ml), treated with methanesulfonic acid (25 μL, 0.385 mmol) and stirred at RT overnight. The mixture was diluted with EtOAc and the resultant white precipitate was collected by filtration. The resultant gum was dissolved in water (5 ml) then treated with saturated NaHCO₃(aq) (5 ml) and the resultant mixture extracted with DCM (2×5 ml). The organic phases were combined and concentrated in vacuo. The residue was purified by preparative HPLC (Waters Fraction-Lynx, Waters X-Bridge Prep-C18, 5 μm, 19×50 mm column, 20-50% MeCN in 10 mM ammonium bicarbonate(aq)) to afford the title compound (12 mg, 0.023 mmol, 99% purity) as a white solid. LCMS (Method 1): m/z 520 (M+H)+, 518 (M−H)⁻, at 1.44 min. ¹H NMR (400 MHz, DMSO-d6) (two rotamers in a 10:7 ratio) δ 11.23 (s, 1H), 8.41 (s, 1H), 7.65 (dd, J=3.0, 1.3 Hz, 1H), 7.60-7.54 (m, 1H), 7.53 (d, J=8.3 Hz, 2H), 7.36-7.24 (m, 2H), 6.79 (dd, J=5.0, 1.3 Hz, 1H), 4.39-4.12 (m, 1H, major), 3.73-3.51 (m, 1H, minor), 2.78 (s, 3H, major), 2.68 (s, 3H, minor), 2.40 (d, J=6.5 Hz, 2H), 2.34 (q, J=7.5 Hz, 2H, minor), 2.26 (q, J=7.4 Hz, 2H, major), 2.02-1.41 (m, 8H), 1.37 (s, 6H), 1.30-1.04 (m, 1H), 1.03-0.92 (m, 3H).

Example 89

Methyl (trans-4-(2-((5-(4-(trans-1-amino-3-hydroxy-3-methylcyclobutyl)phenyl)-4-(thiophen-3-yl)pyridin-2-yl)amino)-2-oxoethyl)cyclohexyl)(methyl)carbamate

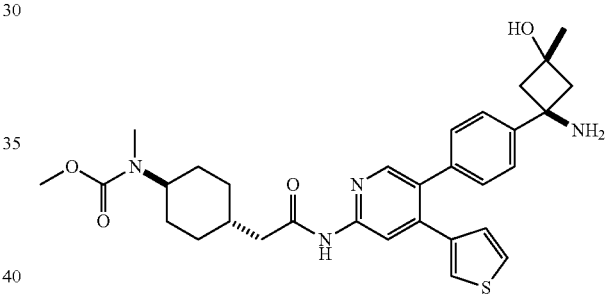

Step 1: tert-butyl (trans-1-(4-(6-amino-4-(thiophen-3-yl)pyridin-3-yl)phenyl)-3-hydroxy-3-methylcyclobutyl)carbamate: The title compound (201 mg) was isolated as a pale yellow foam from the reaction of 5-bromo-4-(thiophen-3-yl)pyridin-2-amine (228 mg, 0.893 mmol), tert-butyl (trans-3-hydroxy-3-methyl-1-(4-(4,4,5,5-tetramethyl-1,3,2-dioxaborolan-2-yl)phenyl)cyclobutyl)carbamate (300 mg, 0.744 mmol, prepared according to Org. Process Res. Dev., 2012, 16, 1069), tetrakis-(triphenylphosphine)palladium(0) (86 mg, 74 μmol) and 2 M Na₂CO₃(aq) (930 μl, 1.86 mmol) in dioxane (15 ml) using essentially the same procedure as in Intermediate 1 Step 2, except the reaction mixture was heated at 100° C. for 16 h, then concentrated on to silica (ca. 5 g) and partially purified by column chromatography (24 g cartridge, 20-100% EtOAc/isohexane). This material was used directly in subsequent reactions without further purification.

Step 2: Methyl (trans-4-(2-((5-(4-(trans-1-((tert-butoxycarbonyl)amino)-3-hydroxy-3-methylcyclobutyl)phenyl)-4-(thiophen-3-yl)pyridin-2-yl)amino)-2-oxoethyl)cyclohexyl)(methyl)carbamate: The title compound (6 mg, 9.05 μmol, 95% purity) was isolated as a yellow gum from the reaction of the product from Step 1 above (40 mg, 0.089 mmol), the product from Example 56 Step 3 (22.3 mg, 0.097 mmol), 1-chloro-N,N,2-trimethylprop-1-en-1-amine (23.4 μl, 0.177 mmol) and pyridine (28.7 μl, 0.354 mmol) in DCM (4 ml) using essentially the same procedure as in Example 82 Step 3, except following column chromatography using 0-100% EtOAc/isohexane the product was eluted with 0-3% (0.7 M NH₃/MeOH)/DCM. LCMS (Method 1): m/z 663 (M+H)⁺ at 2.40 min.

Step 3: Methyl (trans-4-(2-((5-(4-(trans-1-amino-3-hydroxy-3-methylcyclobutyl)phenyl)-4-(thiophen-3-yl)pyridin-2-yl)amino)-2-oxoethyl)cyclohexyl)(methyl)carbamate: The product from Step 2 above (6 mg, 9.05 μmol, 95% purity) in DCM (3 ml) was treated with TFA (68.2 μl, 0.886 mmol) and the reaction mixture stirred at RT for 3 days. The reaction mixture was loaded onto a column of SCX. The column was washed with MeOH and the product was eluted with a 0.7 M solution of ammonia in MeOH. The solvent was removed in vacuo to afford the title compound (4.0 mg, 6.61 μmol, 93% purity) as a colourless solid. LCMS (Method 1): m/z 563 (M+H)⁺ at 1.41 min. ¹H NMR (400 MHz, Methanol-d₄) δ 8.27 (s, 1H), 8.25 (s, 1H), 7.50-7.44 (m, 2H), 7.33-7.28 (m, 2H), 7.26-7.22 (m, 2H), 6.84 (dd, J=4.4, 2.0 Hz, 1H), 4.08-3.82 (m, 1H), 3.70 (s, 3H), 2.81 (s, 3H), 2.79-2.72 (m, 2H), 2.54-2.46 (m, 2H), 2.39 (d, J=7.0 Hz, 2H), 2.00-1.81 (m, 3H), 1.77-1.58 (m, 4H), 1.56 (s, 3H), 1.34-1.17 (m, 2H).

Example 90

N-(trans-4-(2-((6-(4-(1-aminocyclopropyl)-3-fluorophenyl)-5-phenylpyridin-3-yl)amino)-2-oxoethyl)cyclohexyl)-N-methylpropionamide

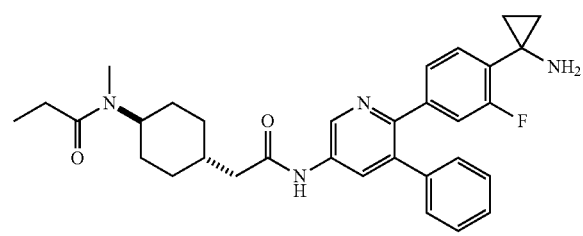 [SMILES: CCC(=O)N(C)[C@H]1CC[C@H](CC(=O)Nc2cnc(-c3ccc(C4(N)CC4)c(F)c3)c(-c3ccccc3)c2)CC1]

The title compound (30.6 mg, 0.057 mmol, 99% purity) was isolated as a white solid from the reaction of the product from Example 62 Step 6 (50 mg, 0.119 mmol), the product from Example 82 Step 2 (54.2 mg, 0.238 mmol), 1-chloro-N,N,2-trimethylprop-1-en-1-amine (33 μl, 0.250 mmol) and pyridine (0.5 ml, 0.119 mmol) in DCM (5 ml), followed by treatment with TFA (0.5 ml) in DCM (5 ml) using essentially the same procedure as in Example 71. LCMS (Method 1): m/z 529 (M+H)⁺ at 1.47 min. ¹H NMR (400 MHz, DMSO-d₆) (two rotamers in a 7:5 ratio) δ 10.32 (s, 1H), 8.81 (d, J=2.4 Hz, 1H), 8.12 (d, J=2.4 Hz, 1H), 7.41-7.31 (m, 3H), 7.29-7.18 (m, 3H), 7.06-6.95 (m, 2H), 4.32-4.20 (m, 1H), 3.65-3.52 (m, 1H), 2.78 (s, 3H, major), 2.68 (s, 3H, minor), 2.39-2.19 (m, 4H), 1.87-1.40 (m, 8H), 1.30-1.03 (m, 2H), 1.03-0.92 (m, 3H), 0.89-0.78 (m, 4H).

Example 91

N-(trans-4-(2-((6-(4-(trans-1-amino-3-hydroxy-3-methylcyclobutyl)phenyl)-5-(thiophen-3-yl)pyridazin-3-yl)amino)-2-oxoethyl)cyclohexyl)-N-methylpropionamide

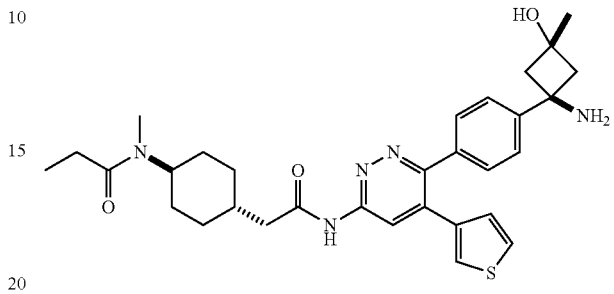

Step 1: tert-butyl (trans-1-(4-(6-amino-4-(thiophen-3-yl)pyridazin-3-yl)phenyl)-3-hydroxy-3-methylcyclobutyl)carbamate: The title compound (89 mg, 0.195 mmol, 99% purity) was isolated as a colourless gum from the reaction of Example 75 Step 3 (250 mg, 1.16 mmol, 98% purity), tert-butyl (trans-3-hydroxy-3-methyl-1-(4-(4,4,5,5-tetramethyl-1,3,2-dioxaborolan-2-yl)phenyl)cyclobutyl)carbamate (500 mg, 1.18 mmol, 95% purity, prepared according to Org. Process Res. Dev., 2012, 16, 1069), tetrakis-(triphenylphosphine)palladium(0) (100 mg, 87 μmol) and 2 M Na₂CO₃(aq) (1.75 ml, 3.5 mmol) in dioxane (10 ml) using essentially the same procedure as in Example 75 Step 4, except the product was purified by column chromatography on the Companion (24 g cartridge, 50-100% acetone/isohexane). LCMS (Method 1): m/z 453 (M+H)⁺, at 1.56 min.

Step 2: tert-butyl (trans-3-hydroxy-3-methyl-1-(4-(6-(2-(trans-4-(N-methylpropionamido)cyclohexyl)acetamido)-4-(thiophen-3-yl)pyridazin-3-yl)phenyl)cyclobutyl)carbamate: A solution of the product from Example 82 Step 2 (45 mg, 0.194 mmol), and DMF (2 μl, 0.026 mmol) in DCM (1 ml) was treated with oxalyl chloride (17 μl, 0.194 mmol) then stirred at RT for 1 h. The resultant mixture was added dropwise to a solution of the product from Step 1 above (50 mg, 0.110 mmol, 98% purity) in pyridine (1 ml) and the resultant mixture stirred for 1 h. In a separate vessel, a solution of the product from Example 82 Step 2 (45 mg, 0.194 mmol), and DMF (2 μl, 0.026 mmol) in DCM (1 ml) was treated with oxalyl chloride (17 μl, 0.194 mmol), then stirred at RT for 1 h and added to the original vessel. The resultant mixture was stirred for 3 days. The mixture was diluted with DCM (10 ml), then washed with water (10 ml). The organic phase was concentrated in vacuo then purified by column chromatography (12 g cartridge, 25-100% (10% MeOH/EtOAc)/DCM) to afford the title compound (24 mg) as an off-white solid. This material was used in subsequent reactions without analysis.

Step 3: N-(trans-4-(2-((6-(4-(trans-1-amino-3-hydroxy-3-methylcyclobutyl)phenyl)-5-(thiophen-3-yl)pyridazin-3-yl)amino)-2-oxoethyl)cyclohexyl)-N-methylpropionamide: A solution of the product from Step 2 above (24 mg) in DCM (1 ml) was treated with TFA (0.5 ml, 6.49 mmol) then stirred at RT for 1 h. The mixture was concentrated in vacuo then partitioned between saturated NaHCO₃(aq) (5 ml) and DCM (5 ml). The organic phase was concentrated in vacuo then purified by preparative HPLC (Gilson 215, Waters X-Bridge Prep-C18, 5 μm, 19×50 mm column, 15-60% MeCN in 10 mM ammonium bicarbonate(aq)) to afford the title compound (11 mg, 0.019 mmol, 99% purity) as a white solid. LCMS (Method 1): m/z 562 (M+H)$^+$, 560 (M−H)$^−$, at 1.32 min. $^1$H NMR (400 MHz, DMSO-d$_6$) (two rotamers in a 3:2 ratio) δ 11.22 (s, 1H), 8.40 (s, 1H), 7.65 (dd, J=3.0, 1.3 Hz, 1H), 7.55 (dd, J=5.0, 2.9 Hz, 1H), 7.47-7.39 (m, 2H), 7.31 (d, J=8.4 Hz, 2H), 6.79 (dd, J=5.0, 1.3 Hz, 1H), 4.81 (s, 1H), 4.34-4.17 (m, 1H, major), 3.65-3.50 (m, 1H, minor), 2.78 (s, 3H, major), 2.67 (s, 3H, minor), 2.44-2.35 (m, 4H), 2.33 (q, J=7.4 Hz, 2H, major), 2.26 (q, J=7.4 Hz, 2H, minor), 2.21-2.14 (m, 2H), 1.96 (br s, 2H), 1.89-1.68 (m, 3H), 1.67-1.37 (m, 4H), 1.52 (s, 3H), 1.30-1.01 (m, 2H), 0.98 (t, J=7.2 Hz, 3H, minor), 0.94 (d, J=7.3 Hz, 3H, major).

Example 92

N-(6-(4-(1-aminocyclopropyl)-3-fluorophenyl)-5-(thiophen-3-yl)pyridazin-3-yl)-2-(trans-4-(N-methylacetamido)cyclohexyl)acetamide

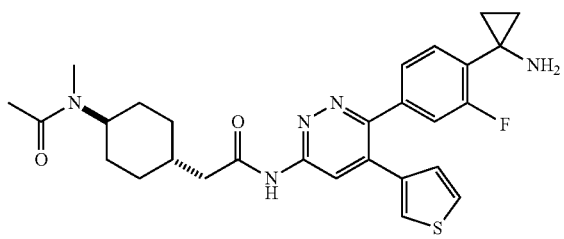 [SMILES: CC(=O)N(C)[C@H]1CC[C@H](CC(=O)Nc2cc(-c3ccsc3)c(-c3ccc(C4(N)CC4)c(F)c3)nn2)CC1]

Step 1: tert-butyl (1-(4-(6-amino-4-(thiophen-3-yl)pyridazin-3-yl)-2-fluorophenyl)cyclopropyl)carbamate: The title compound (149 mg, 0.342 mmol, 98% purity) was isolated as a tan solid from the reaction of Example 75 Step 3 (250 mg, 1.16 mmol, 98% purity), the product from Example 62 Step 3 (500 mg, 1.26 mmol, 95% purity), tetrakis-(triphenylphosphine)palladium(0) (100 mg, 87 μmol) and 2 M Na$_2$CO$_3$(aq) (1.75 ml, 3.5 mmol) in dioxane (10 ml) using essentially the same procedure as in Example 75 Step 4, except the product was purified by column chromatography on the Companion (24 g cartridge, 15-75% acetone/isohexane). LCMS (Method 1): m/z 427 (M+H)$^+$ at 1.83 min.

Step 2: tert-butyl (1-(2-fluoro-4-(6-(2-(trans-4-(N-methylacetamido)cyclohexyl)acetamido)-4-(thiophen-3-yl)pyridazin-3-yl)phenyl)cyclopropyl)carbamate: The title compound (60 mg) was isolated as an off-white solid from the reaction of the product from Step 1 above (50 mg, 0.115 mmol, 98% purity), the product from Example 1 Step 5 (2×40 mg, 2×0.188 mmol), oxalyl chloride (2×17 μl, 2×0.194 mmol) and DMF (2×2 μl, 2×0.026 mmol) in DCM (2×1 ml) and pyridine (1 ml) using essentially the same procedure as in Example 91 Step 2. This material was used in subsequent reactions without analysis.

Step 3: N-(6-(4-(1-aminocyclopropyl)-3-fluorophenyl)-5-(thiophen-3-yl)pyridazin-3-yl)-2-((1 r,4r)-4-(N-methylacetamido)cyclohexyl)acetamide: The title compound (30 mg, 0.057 mmol, 99% purity) was isolated as a white solid from the reaction of the product from Step 2 above (60 mg) with TFA (0.5 ml) in DCM (1 ml) using essentially the same procedure as in Example 91 Step 3. LCMS (Method 1): m/z 522 (M+H)$^+$ at 1.36 min. $^1$H NMR (400 MHz, DMSO-d$_6$) (two rotamers in a 3:2 ratio) δ 11.27 (s, 1H), 8.41 (d, J=1.8 Hz, 1H), 7.67 (dd, J=3.0, 1.3 Hz, 1H), 7.62-7.52 (m, 1H), 7.39 (t, J=8.0 Hz, 1H), 7.13 (dd, J=11.9, 1.7 Hz, 1H), 7.09 (dd, J=7.9, 1.7 Hz, 1H), 6.83 (dd, J=5.0, 1.3 Hz, 1H), 4.30-4.14 (m, 1H, major), 3.61-3.48 (m, 1H, minor), 2.78 (s, 3H, major), 2.66 (s, 3H, minor), 2.46-2.21 (m, 4H), 2.01 (s, 3H, minor), 1.95 (s, 3H, major), 1.88-1.68 (m, 3H), 1.68-1.36 (m, 4H), 1.28-1.00 (m, 2H), 0.85 (s, 4H).

Example 93

N-(5-(4-(trans-1-amino-3-hydroxy-3-methylcyclobutyl)phenyl)-4-(thiophen-3-yl)pyridin-2-yl)-2-(trans-4-(N-methylacetamido)cyclohexyl)acetamide

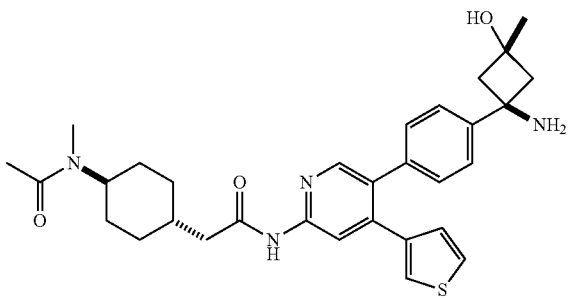 [SMILES: CC(=O)N(C)[C@H]1CC[C@H](CC(=O)Nc2cc(-c3ccsc3)c(-c3ccc([C@]4(N)C[C@](C)(O)C4)cc3)cn2)CC1]

A suspension of the product from Example 1 Step 5 (26.0 mg, 0.122 mmol) in DCM (2 ml) was treated with 1-chloro-N,N,2-trimethylprop-1-en-1-amine (29.3 μl, 0.221 mmol) and stirred for 1 h, then pyridine (35.8 μl, 0.443 mmol) was added. The resultant mixture was stirred for 5 min, then the product from Example 89 Step 1 (50 mg, 0.111 mmol) in DCM (2 ml) was added. The resultant mixture was stirred overnight. The mixture was then quenched by addition of saturated NH$_4$Cl(aq) (3 ml) and the phases separated. The aqueous phase was extracted with DCM (2×3 ml) and the organic phases were combined, dried over MgSO$_4$, filtered and concentrated in vacuo. The residue was partially purified by column chromatography (12 g cartridge, 0-6% (0.7 M NH$_3$/MeOH)/DCM) to afford a colourless foam (10 mg). This material was treated with TFA (171 μl, 2.21 mmol) in DCM (3 ml) and the resultant mixture was stirred at RT for 2 h, then the reaction mixture was loaded onto a column of SCX (ca. 0.1 g). The column was washed with MeOH and the product was eluted with a 0.7 M solution of ammonia in MeOH. The solvent was removed in vacuo and the crude product was purified by column chromatography on the Companion (12 g cartridge, 0-9% (0.7 M NH$_3$/MeOH)/DCM) to afford the title compound (1.0 mg, 1.65 μmol, 90% purity) as a colourless solid. LCMS (Method 1): m/z 547 (M+H)$^+$, 545 (M−H)$^−$, at 1.22 min. $^1$H NMR (400 MHz, Methanol-d$_4$) (two rotamers in an 11:9 ratio) δ 8.15-8.13 (m, 1H), 8.12-8.10 (m, 1H), 7.33-7.29 (m, 2H), 7.20-7.15 (m, 2H), 7.10-7.03 (m, 2H), 6.72-6.67 (m, 1H), 4.30-4.19 (m, 1H, major), 3.62-3.51 (m, 1H, minor), 2.80 (s, 3H, major), 2.69 (s, 3H, minor), 2.64-2.55 (m, 2H), 2.34-2.23 (m, 4H), 2.02 (s, 3H, minor), 1.97 (s, 3H, major), 1.89-1.69 (m, 3H), 1.69-1.56 (m, 2H), 1.56-1.43 (m, 2H), 1.44 (s, 3H), 1.24-1.07 (m, 2H).

Example 94

N-(5-(4-(trans-1-amino-3-hydroxy-3-methylcyclobutyl)phenyl)-4-(2-fluorophenyl)pyridin-2-yl)-2-(trans-4-(N-methylacetamido)cyclohexyl)acetamide

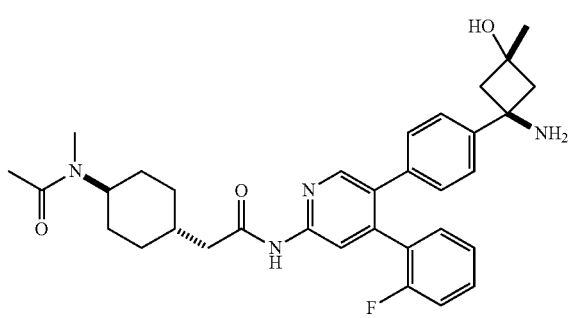 [SMILES: CC(=O)N(C)[C@H]1CC[C@H](CC(=O)Nc2cc(-c3ccccc3F)c(-c3ccc([C@]4(N)C[C@](C)(O)C4)cc3)cn2)CC1]

Step 1: tert-butyl (trans-1-(4-(6-amino-4-(2-fluorophenyl)pyridin-3-yl)phenyl)-3-hydroxy-3-methylcyclobutyl)carbamate: The title compound (172 mg, 0.334 mmol, 90% purity) was isolated as a brown foam from the reaction of 5-bromo-4-(2-fluorophenyl)pyridin-2-amine (318 mg, 1.19 mmol), tert-butyl (trans-3-hydroxy-3-methyl-1-(4-(4,4,5,5-tetramethyl-1,3,2-dioxaborolan-2-yl)phenyl)cyclobutyl)carbamate (400 mg, 0.992 mmol, prepared according to *Org. Process Res. Dev.*, 2012, 16, 1069), tetrakis-(triphenylphosphine)palladium(0) (115 mg, 99 μmol) and 2 M $Na_2CO_3$(aq) (1.24 ml, 2.48 mmol) in dioxane (12 ml) using essentially the same procedure as in Intermediate 1 Step 2, except the reaction mixture was heated at 100° C. for 16 h, then concentrated on to silica (ca. 2 g) and purified by column chromatography (24 g cartridge, 0-8% (0.7 M $NH_3$/MeOH)/DCM). LCMS (Method 1): m/z 464 (M+H)$^+$ at 1.45 min.

Step 2: N-(5-(4-(trans-1-amino-3-hydroxy-3-methylcyclobutyl)phenyl)-4-(2-fluorophenyl)pyridin-2-yl)-2-(trans-4-(N-methylacetamido)cyclohexyl)acetamide: A suspension of the product from Example 1 Step 5 (27.8 mg, 0.131 mmol) in DCM (2 ml) was treated with 1-chloro-N,N,2-trimethylprop-1-en-1-amine (31.4 μl, 0.237 mmol) and stirred for 1 h, then pyridine (38.4 μl, 0.475 mmol) was added. The resultant mixture was stirred for 5 min, then the product from Step 1 above (55 mg, 0.107 mmol) in DCM (2 ml) was added. The resultant mixture was stirred for 3 days. The mixture was then quenched by addition of MeOH (3 ml) and stirred for 5 min, then concentrated in vacuo. The residue was partially purified by column chromatography (12 g cartridge, 0-7% (0.7 M $NH_3$/MeOH)/DCM) to afford a colourless foam (60 mg). This material was treated with TFA (183 μl, 2.37 mmol) in DCM (3 ml) and the resultant mixture was stirred at RT for 2 h, then the reaction mixture was loaded onto a column of SCX (ca. 0.25 g). The column was washed with MeOH and the product was eluted with a 0.7 M solution of ammonia in MeOH. The solvent was removed in vacuo and the crude product was purified by preparative HPLC (Gilson 215, Waters X-Bridge Prep-C18, 5 μm, 19×50 mm column, 20-30% MeCN in 10 mM ammonium bicarbonate(aq)) to afford the title compound (11 mg, 19 μmol, 98% purity) as a colourless solid. LCMS (Method 1): m/z 559 (M+H)$^+$, 557 (M−H)$^−$, at 1.29 min. $^1$H NMR (400 MHz, DMSO-$d_6$) (two rotamers in a 3:2 ratio) δ 10.69 (s, 1H, minor), 10.67 (s, 1H, major), 8.14 (s, 1H), 7.47-7.38 (m, 1H), 7.38-7.29 (m, 3H), 7.24 (td, J=7.5, 1.0 Hz, 1H), 7.20-7.12 (m, 1H), 7.12-7.02 (m, 2H), 4.78 (s, 1H), 4.29-4.14 (m, 1H, major), 3.60-3.40 (m, 1H, minor), 2.79 (s, 3H, major), 2.66 (s, 3H, minor), 2.37-2.24 (m, 4H), 2.20-2.07 (m, 2H), 2.02 (s, 3H, minor), 1.98-1.85 (m, 2H), 1.96 (s, 3H, major) 1.84-1.68 (m, 3H), 1.68-1.38 (m, 7H), 1.27-0.96 (m, 2H).

Example 95

N-(trans-4-(2-((5-(4-(trans-1-amino-3-hydroxy-3-methylcyclobutyl)phenyl)-4-(2-fluorophenyl)pyridin-2-yl)amino)-2-oxoethyl)cyclohexyl)-N-methylpropionamide

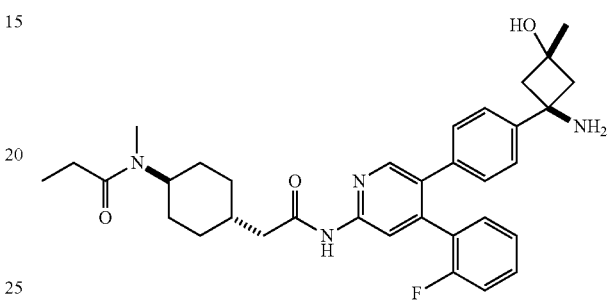

The title compound (5 mg, 8.56 μmol, 98% purity) was isolated as a colourless solid from the reaction of the product from Example 94 Step 1 (55 mg, 0.107 mmol, 90% purity), the product from Example 82 Step 2 (29.7 mg, 0.131 mmol), 1-chloro-N,N,2-trimethylprop-1-en-1-amine (31.4 μl, 0.237 mmol) and pyridine (38.4 μl, 0.475 mmol) in DCM (4 ml), followed by treatment with TFA (183 μl) in DCM (3 ml) using essentially the same procedure as in Example 94 Step 2. LCMS (Method 1): m/z 573 (M+H)$^+$, 571 (M−H)$^−$, at 1.39 min. $^1$H NMR (400 MHz, DMSO-$d_6$) (two rotamers in an 11:9 ratio) δ 10.69 (s, 1H, minor), 10.67 (s, 1H, major), 8.36 (s, 1H), 8.14 (s, 1H), 7.46-7.38 (m, 1H), 7.37-7.29 (m, 3H), 7.24 (td, J=7.5, 1.1 Hz, 1H), 7.16 (dd, J=10.1, 8.3 Hz, 1H), 7.12-7.05 (m, 2H), 4.78 (s, 1H), 4.30-4.19 (m, 1H, major), 3.63-3.52 (m, 1H, minor), 2.78 (s, 3H, major), 2.67 (s, 3H, minor), 2.39-2.18 (m, 6H), 2.17-2.03 (m, 2H), 2.02-1.84 (m, 2H), 1.84-1.65 (m, 3H), 1.64-1.40 (m, 6H), 1.28-1.03 (m, 3H), 1.02-0.92 (m, 3H).

Example 96

Methyl (trans-4-(2-((5-(4-(trans-1-amino-3-hydroxy-3-methylcyclobutyl)phenyl)-4-(2-fluorophenyl)pyridin-2-yl)amino)-2-oxoethyl)cyclohexyl)(methyl)carbamate

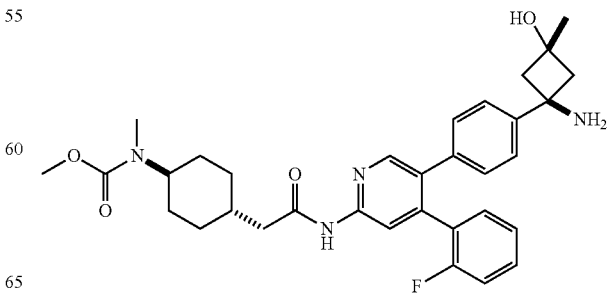

The title compound (16 mg, 26 µmol, 94% purity) was isolated as a colourless foam from the reaction of the product from Example 94 Step 1 (55 mg, 0.107 mmol, 90% purity), the product from Example 56 Step 3 (29.9 mg, 0.131 mmol), 1-chloro-N,N,2-trimethylprop-1-en-1-amine (31.4 µl, 0.237 mmol) and pyridine (38.4 µl, 0.475 mmol) in DCM (4 ml), followed by treatment with TFA (183 µl) in DCM (3 ml) using essentially the same procedure as in Example 94 Step 2. LCMS (Method 1): m/z 575 (M+H)$^+$ at 1.49 min. $^1$H NMR (400 MHz, DMSO-d$_6$) δ 10.67 (s, 1H), 8.36 (s, 1H), 8.14 (s, 1H), 7.45-7.38 (m, 1H), 7.37-7.29 (m, 3H), 7.24 (td, J=7.5, 1.1 Hz, 1H), 7.20-7.13 (m, 1H), 7.11-7.05 (m, 2H), 4.78 (s, 1H), 3.89-3.67 (m, 1H), 3.58 (s, 3H), 2.70 (s, 3H), 2.36-2.27 (m, 4H), 2.18-2.09 (m, 2H), 2.10-1.89 (m, 2H), 1.82-1.65 (m, 3H), 1.62-1.42 (m, 7H), 1.27-1.01 (m, 2H).

Example 97

Ethyl (4-(2-((6-(4-(trans-1-amino-3-hydroxy-3-methylcyclobutyl)phenyl)-5-phenylpyridin-3-yl)amino)-2-oxoethyl)cyclohexyl)(methyl)carbamate

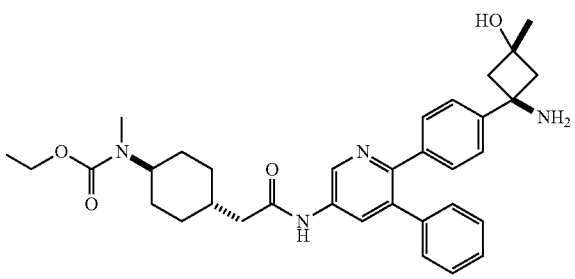 [SMILES: CCOC(=O)N(C)[C@H]1CC[C@H](CC(=O)Nc2cnc(-c3ccc([C@]4(N)C[C@](C)(O)C4)cc3)c(-c3ccccc3)c2)CC1]

Step 1: 2-(trans-4-((ethoxycarbonyl)(methyl)amino)cyclohexyl)acetic acid: A solution of the product from Example 1 Step 3 (0.63 g, 3.16 mmol) and DIPEA (1.66 ml, 9.48 mmol) in THF (20 ml) was cooled in an ice bath and treated dropwise with ethyl chloroformate (0.348 ml, 3.64 mmol). The resultant solution was stirred at RT overnight. Saturated NaHCO$_3$(aq) (20 ml) was added, the phases separated and the aqueous phase extracted with EtOAc (2×20 ml). The organic phases were combined and concentrated in vacuo. The residue was dissolved in THF (20 ml) and a solution of LiOH (0.151 g, 6.32 mmol) in water (5 ml) was added. The reaction mixture was stirred at RT overnight. The reaction mixture was concentrated in vacuo and the residue acidified with 1 M HCl(aq). The aqueous phase was extracted using EtOAc (3×20 ml) and the combined organic phases were dried over MgSO$_4$, filtered and concentrated in vacuo to afford the title compound (0.654 g, 2.69 mmol) as a pale yellow solid. $^1$H NMR (400 MHz, DMSO-d$_6$) δ 12.04 (br s, 1H), 4.02 (q, J=7.1 Hz, 2H), 3.77 (br s, 1H), 2.70 (s, 3H), 2.10 (d, J=7.0 Hz, 2H), 1.83-1.70 (m, 2H), 1.68-1.39 (m, 5H), 1.17 (t, J=7.1 Hz, 3H), 1.04 (qd, J=12.5, 4.3 Hz, 2H).

Step 2: Ethyl (4-(2-((6-(4-(trans-1-amino-3-hydroxy-3-methylcyclobutyl)phenyl)-5-phenylpyridin-3-yl)amino)-2-oxoethyl)cyclohexyl)(methyl)carbamate: A solution of the product from Step 1 above (26.2 mg, 0.108 mmol), Intermediate 1 (40 mg, 0.090 mmol) and DIPEA (31.4 µl, 0.180 mmol) in DMF (3 ml) was treated with HATU (41.0 mg, 0.108 mmol) and the resultant solution was heated at 50° C. for 3 days. Saturated NaHCO$_3$(aq) (5 ml) was added, the phases separated and the aqueous phase extracted with DCM (3×20 ml). The extracts were combined and concentrated in vacuo. The residue was purified by column chromatography (12 g cartridge, 0-10% (0.7 M Ammonia/MeOH)/DCM) to afford a pale yellow solid. This material was dissolved in DCM (5 ml), treated with TFA (0.5 ml) and stirred at RT for 4 h. Saturated NaHCO$_3$(aq) (5 ml) was added and the mixture stirred for 10 min. The organic phase was passed though a phase separation cartridge, washing with DCM (10 ml) and concentrated in vacuo. The residue was loaded onto a column of SCX in MeOH. The column was washed with MeOH (20 ml) and then the product was eluted with 0.7 M ammonia in MeOH (20 ml). The solvent was removed in vacuo to afford the title compound (22.9 mg, 0.040 mmol, 99% purity) as a pale yellow solid. LCMS (Method 1): m/z 571 (M+H)$^+$ at 1.49 min. $^1$H NMR (400 MHz, DMSO-d$_6$) δ 10.25 (s, 1H), 8.78 (d, J=2.4 Hz, 1H), 8.08 (d, J=2.4 Hz, 1H), 7.37-7.29 (m, 3H), 7.29-7.24 (m, 2H), 7.24-7.15 (m, 4H), 4.77 (s, 1H), 4.00 (q, J=7.1 Hz, 2H), 3.81 (br s, 1H), 2.69 (s, 3H), 2.36-2.29 (m, 2H), 2.25 (d, J=6.8 Hz, 2H), 2.20-2.11 (m, 2H), 1.86-1.65 (m, 3H), 1.64-1.49 (m, 6H), 1.48 (s, 3H), 1.16 (t, J=7.1 Hz, 3H), 1.12-1.03 (m, 2H).

Example 98

N-(4-(2-((6-(4-(trans-1-amino-3-hydroxy-3-methylcyclobutyl)phenyl)-5-phenylpyridin-3-yl)amino)-2-oxoethyl)cyclohexyl)-N-methylpropionamide

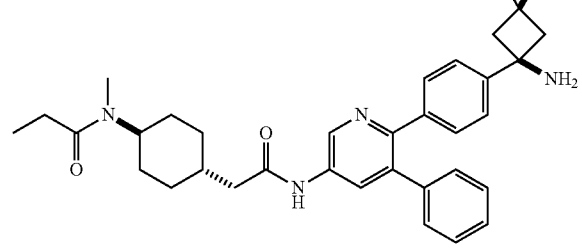

The title compound (22.1 mg, 0.039 mmol, 99% purity) was isolated as a pale yellow solid from the reaction of Intermediate 1 (40 mg, 0.090 mmol), the product from Example 82 Step 2 (24.5 mg, 0.108 mmol), HATU (41.0 mg, 0.108 mmol) and DIPEA (31.4 µl, 0.180 mmol), followed by treatment with TFA (0.5 ml) in DCM (5 ml) using essentially the same procedure as in Example 97 Step 2. LCMS (Method 1): m/z 555 (M+H)$^+$ at 1.30 min. $^1$H NMR (400 MHz, DMSO-d$_6$) (two rotamers in a 4:3 ratio) δ 10.33 (s, 1H), 8.85 (d, J=2.4 Hz, 1H), 8.16 (d, J=2.4 Hz, 1H), 7.45-7.37 (m, 3H), 7.37-7.31 (m, 2H), 7.30-7.22 (m, 4H), 4.85 (s, 1H), 4.39-4.26 (m, 1H), 3.77-3.60 (m, 1H), 2.84 (s, 3H, major), 2.74 (s, 3H, minor), 2.44-2.37 (m, 3H), 2.39-2.26 (m, 3H), 2.27-2.16 (m, 2H), 1.89-1.80 (m, 4H), 1.65-1.56 (m, 4H), 1.55 (s, 3H), 1.32-1.11 (m, 2H), 1.03 (q, J=7.2 Hz, 3H).

Example 99

N-(4-(2-((6-(4-(trans-1-amino-3-hydroxy-3-methyl-cyclobutyl)phenyl)-5-phenylpyridin-3-yl)amino)-2-oxoethyl)cyclohexyl)-N-methylisobutyramide

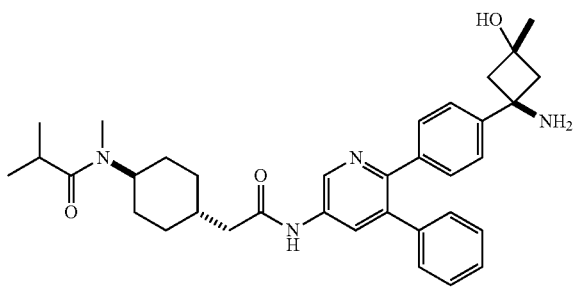 [SMILES: CC(C)C(=O)N(C)[C@H]1CC[C@H](CC(=O)Nc2cnc(-c3ccc([C@]4(N)C[C@](C)(O)C4)cc3)c(-c3ccccc3)c2)CC1]

The title compound (19.9 mg, 0.031 mmol, 90% purity) was isolated as a pale yellow solid from the reaction of Intermediate 1 (40 mg, 0.090 mmol), the product from Example 85 Step 1 (26.0 mg, 0.108 mmol), HATU (41.0 mg, 0.108 mmol) and DIPEA (31.4 µl, 0.180 mmol), followed by treatment with TFA (0.5 ml) in DCM (5 ml) using essentially the same procedure as in Example 97 Step 2. LCMS (Method 1): m/z 569 (M+H)$^+$ at 1.39 min. $^1$H NMR (400 MHz, DMSO-$d_6$) (two rotamers in a 7:5 ratio) δ 10.27 (s, 1H), 8.80 (d, J=2.3 Hz, 1H), 8.10 (d, J=2.5 Hz, 1H), 7.40-7.31 (m, 3H), 7.31-7.25 (m, 2H), 7.25-7.13 (m, 4H), 4.78 (s, 1H), 4.38-4.08 (m, 1H), 3.76-3.60 (m, 1H), 2.84 (s, 3H, major), 2.82-2.74 (m, 1H), 2.68 (s, 3H, minor), 2.37-2.23 (m, 2H), 2.19-2.09 (m, 3H), 1.90-1.60 (m, 4H), 1.50 (s, 3H), 1.60-1.38 (m, 4H), 1.30-1.04 (m, 3H), 0.99 (d, J=6.6 Hz, 3H), 0.97 (d, J=6.7 Hz, 3H).

Example 100

N-(6-(4-(trans-1-amino-3-hydroxy-3-methylcyclobutyl)phenyl)-5-phenylpyridazin-3-yl)-2-(trans-4-(N-isopropylacetamido)cyclohexyl)acetamide

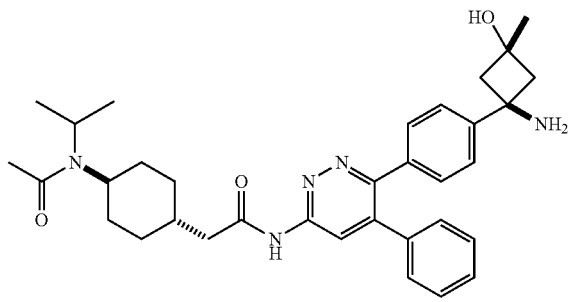 [SMILES: CC(=O)N(C(C)C)[C@H]1CC[C@H](CC(=O)Nc2cc(-c3ccccc3)c(-c3ccc([C@]4(N)C[C@](C)(O)C4)cc3)nn2)CC1]

Step 1: tert-butyl (trans-3-hydroxy-1-(4-(6-(2-(trans-4-(N-isopropylacetamido)cyclohexyl)acetamido)-4-phenylpyridazin-3-yl)phenyl)-3-methylcyclobutyl)carbamate: HATU (42.1 mg, 0.111 mmol) and DIPEA (39.4 µl, 0.222 mmol) were added to a solution of the product from Example 49 Step 3 (24.3 mg, 0.101 mmol) in DMF (1.5 ml) and the mixture was stirred for 30 min before the product from Example 57 Step 1 (45 mg, 0.101 mmol) was added. The mixture was heated to 50° C. and stirred for 20 h. After cooling to RT, a solution of HATU (42.1 mg, 0.111 mmol) and the product from Example 49 Step 3 (24.3 mg, 0.101 mmol) in DMF (1 ml) was added. After stirring for 1 h, the mixture was heated to 50° C. and stirred for a further 2 days. The resultant solution was poured into water (25 ml) and extracted with EtOAc (3×25 ml). The combined organic phases were sequentially washed with saturated NaHCO$_3$ (aq) (50 ml), 1 M HCl(aq) (50 ml), water (50 ml) and brine (50 ml), then dried over MgSO$_4$, filtered and concentrated in vacuo to afford a brown oil. This material was pre-absorbed onto silica and purified by column chromatography (12 g cartridge, 0-6% (0.7 M NH$_3$/MeOH/DCM) to furnish the title compound (26 mg, 0.036 mmol, 92% purity) as a beige solid. LCMS (Method 1): m/z 670 (M+H)$^+$ at 2.29 min.

Step 2: N-(6-(4-(trans-1-amino-3-hydroxy-3-methylcyclobutyl)phenyl)-5-phenylpyridazin-3-yl)-2-(trans-4-(N-isopropylacetamido)cyclohexyl)acetamide: A solution of the product from Step 1 above (26 mg, 0.036 mmol, 92% purity) in DCM (2 ml) was treated with TFA (0.060 ml, 0.776 mmol) and the mixture was stirred at RT for 90 min. Additional TFA (0.060 ml, 0.776 mmol) was added and the solution was stirred for a further 18 h. The mixture was concentrated in vacuo and loaded onto a column of SCX in MeOH. The column was washed with MeOH and then the product was eluted with 0.7 M ammonia in MeOH. The solvent was removed in vacuo to afford a pale yellow solid (27 mg). Purification by preparative HPLC (Waters FractionLynx, Waters X-Bridge Prep-C18, 5 µm, 19×50 mm column, 35-65% MeCN in 10 mM ammonium bicarbonate (aq)) afforded the title compound (7.0 mg, 0.012 mmol, 99% purity) as a colourless solid. LCMS (Method 2): m/z 570 (M+H)$^+$ at 1.45 min. $^1$H NMR (400 MHz, DMSO-$d_6$) (two rotamers in a 3:2 ratio) δ 11.26 (s, 1H, major), 11.25 (s, 1H, minor), 8.35 (s, 1H), 7.44-7.33 (m, 5H), 7.33-7.23 (m, 4H), 4.80 (s, 1H), 3.92 (m, 1H, minor), 3.44 (m, 1H, major), 2.43-2.31 (m, 5H), 2.20-2.11 (m, 2H), 1.97 (s, 3H), 1.78 (m, 3H), 1.67-1.54 (m, 2H), 1.51 (s, 3H), 1.44-1.35 (m, 1H), 1.26 (d, J=6.7 Hz, 3H), 1.18-1.04 (m, 6H).

Example 101

Methyl (trans-4-(2-((6-(4-(trans-1-amino-3-hydroxy-3-methylcyclobutyl)phenyl)-5-phenylpyridazin-3-yl)amino)-2-oxoethyl)cyclohexyl)(isopropyl)carbamate

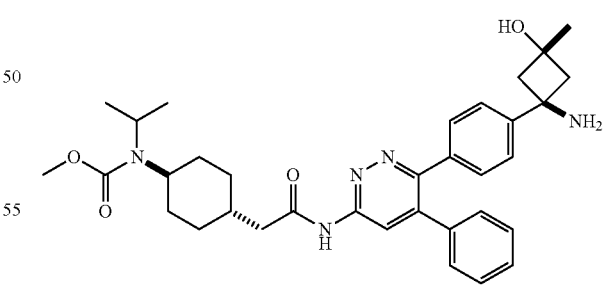

Step 1: Ethyl 2-(trans-4-(isopropyl(methoxycarbonyl)amino)cyclohexyl)acetate: A solution of the product from Example 49 Step 1 (209 mg, 0.919 mmol) and DIPEA (482 µl, 2.76 mmol) in THF (5 ml) was cooled to 0° C. and treated dropwise with methyl chloroformate (142 µl, 1.84 mmol), the mixture was allowed to warm to RT and stir for 18 h. The mixture was poured into saturated Na$_2$CO$_3$(aq) (25 ml) and extracted with EtOAc (2×25 ml). The combined organic phases were washed with 1 M HCl(aq) (25 ml), water (25 ml) and brine (25 ml), then dried over MgSO₄, filtered and concentrated in vacuo to furnish the title compound (260 mg) as a colourless oil. This material was used directly in subsequent reactions without purification.

Step 2: 2-(trans-4-(isopropyl(methoxycarbonyl)amino) cyclohexyl)acetic acid: A solution of the product from Step 1 above (260 mg) in a mixture of THF (1 ml), water (1 ml) and MeOH (0.2 ml) was treated with LiOH (43.6 mg, 1.82 mmol) and the mixture was stirred at RT for 3 h. The mixture was diluted with water (20 ml), then acidified to pH 1 using 1 M HCl(aq). The resultant mixture was extracted with EtOAc (3×20 ml). The combined organic phases were sequentially washed with water (20 ml) and brine (20 ml), then dried over MgSO₄, filtered and concentrated in vacuo to furnish the title compound (232 mg, 0.857 mmol, 95% purity) as a white solid. ¹H NMR (400 MHz, Chloroform-d) δ 3.61 (s, 3H), 2.17 (d, J=7.0 Hz, 2H), 1.85-1.49 (m, 8H), 1.13 (d, J=6.8 Hz, 6H), 1.10-0.94 (m, 3H).

Step 3: Methyl (trans-4-(2-((6-(4-(trans-1-((tert-butoxycarbonyl)amino)-3-hydroxy-3-methylcyclobutyl)phenyl)-5-phenylpyridazin-3-yl)amino)-2-oxoethyl)cyclohexyl)(isopropyl)carbamate: The title compound (29 mg, 0.038 mmol, 91% purity) was isolated as a beige solid from the reaction of the product from Example 57 Step 1 (45 mg, 0.101 mmol), the product from Step 1 above (2×25.9 mg, 2×0.096 mmol, 95% purity), HATU (2×42.1 mg, 2×0.111 mmol) and DIPEA (39.4 µl, 0.222 mmol) in DMF (2.5 ml) using essentially the same procedure as in Example 100 Step 1. LCMS (Method 1): m/z 686 (M+H)⁺ at 2.55 min.

Step 4: Methyl (trans-4-(2-((6-(4-(trans-1-amino-3-hydroxy-3-methylcyclobutyl)phenyl)-5-phenylpyridazin-3-yl)amino)-2-oxoethyl)cyclohexyl)(isopropyl)carbamate: The title compound (5.9 mg, 9.97 µmol, 99% purity) was isolated as a colourless solid from the reaction of the product from Step 3 above (29 mg, 0.038 mmol, 91% purity) with TFA (2×0.060 ml, 2×0.776 mmol) in DCM (2 ml) using essentially the same procedure as in Example 100 Step 2. LCMS (Method 2): m/z 586 (M+H)⁺ at 2.15 min. ¹H NMR (400 MHz, DMSO-d₆) δ 11.26 (s, 1H), 8.34 (s, 1H), 7.44-7.34 (m, 5H), 7.33-7.23 (m, 4H), 4.80 (s, 1H), 3.95-3.77 (m, 1H), 3.56 (s, 3H), 3.51-3.39 (m, 1H), 2.42-2.32 (m, 4H), 2.21-2.13 (m, 2H), 1.91-1.67 (m, 5H), 1.61-1.45 (m, 2H), 1.50 (s, 3H), 1.20-1.05 (m, 8H).

Example 102

N-(5-(4-(trans-1-amino-3-hydroxy-3-methylcyclobutyl)phenyl)-4-phenylpyridin-2-yl)-2-(trans-4-(N-isopropylacetamido)cyclohexyl)acetamide

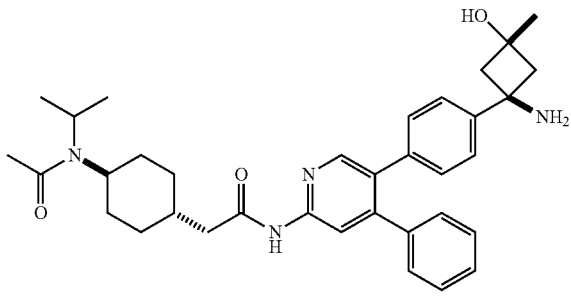

Step 1: tert-butyl (trans-3-hydroxy-1-(4-(6-(2-(trans-4-(N-isopropylacetamido)cyclohexyl)acetamido)-4-phenylpyridin-3-yl)phenyl)-3-methylcyclobutyl)carbamate: HATU (42.2 mg, 0.111 mmol) and DIPEA (39.4 µl, 0.222 mmol) were added to a solution of Example 49 Step 3 (26.8 mg, 0.111 mmol) in DMF (2 ml) and the mixture was stirred for 30 min before the product from Example 67 Step 2 (45 mg, 0.101 mmol) was added. The mixture was heated to 50° C. and stirred for 20 h. After cooling to RT the solution was poured into water (25 ml) and extracted with EtOAc (3×25 ml). The combined organic phases were sequentially washed with saturated NaHCO₃(aq) (50 ml), 1 M HCl(aq) (50 ml), water (50 ml) and brine (50 ml), then dried over MgSO₄, filtered and concentrated in vacuo to afford a brown oil. This material was pre-absorbed onto silica and partially purified by column chromatography (12 g cartridge, 0-6% (0.7 M NH₃/MeOH)/DCM) to furnish the title compound (39 mg, 0.037 mmol, 64% purity) as a white solid. LCMS (Method 1): m/z 669 (M+H)⁺ at 2.36 min. This material was used in subsequent reactions without further purification.

Step 2: N-(5-(4-(trans-1-amino-3-hydroxy-3-methylcyclobutyl)phenyl)-4-phenylpyridin-2-yl)-2-(trans-4-(N-isopropylacetamido)cyclohexyl)acetamide: The title compound (4.9 mg, 8.44 µmol, 98% purity) was isolated as a colourless solid from the reaction of the product from Step 1 above (39 mg, 0.037 mmol, 64% purity) with TFA (2×0.090 ml, 2×1.17 mmol) in DCM (0.5 ml) using essentially the same procedure as in Example 100 Step 2. LCMS (Method 2): m/z 569 (M+H)⁺ at 1.47 min. ¹H NMR (400 MHz, DMSO-d₆) (two rotamers in a 5:4 ratio) δ 10.62 (s, 1H, major), 10.61 (s, 1H, minor), 8.30 (s, 1H), 8.16 (s, 1H), 7.38-7.29 (m, 5H), 7.23-7.15 (m, 2H), 7.12-7.05 (m, 2H), 4.78 (s, 1H), 4.03-3.83 (m, 1H, minor), 3.52-3.37 (m, 1H), 3.13-2.90 (m, 1H, major), 2.38-2.27 (m, 5H), 2.19-2.11 (m, 2H), 1.97 (s, 3H), 1.82-1.54 (m, 5H), 1.50 (s, 3H), 1.44-1.35 (m, 1H), 1.26 (d, J=6.7 Hz, 3H), 1.21-1.01 (m, 2H), 1.13 (d, J=6.6 Hz, 3H).

Example 103

Methyl (trans-4-(2-((5-(4-(trans-1-amino-3-hydroxy-3-methylcyclobutyl)phenyl)-4-phenylpyridin-2-yl)amino)-2-oxoethyl)cyclohexyl)carbamate

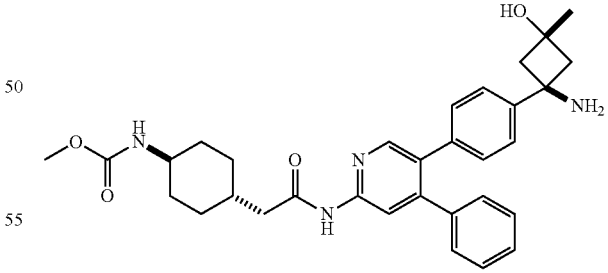

Step 1: 2-(trans-4-((methoxycarbonyl)amino)cyclohexyl) acetic acid: A mixture of the product from Example 56 Step 1 (500 mg, 2.06 mmol) in a mixture of THF (20 ml) and MeOH (5 ml) was treated with 2 M LiOH(aq) (2.06 ml, 4.11 mmol) and the resultant mixture stirred at RT for 48 h. The reaction mixture was concentrated in vacuo, and residue diluted with water (10 ml) then acidified with 1 M HCl(aq). The mixture was extracted with EtOAc (3×50 ml), dried over MgSO₄, filtered and concentrated in vacuo to afford the title compound (0.332 g, 1.47 mmol, 95% purity) as a white solid. $^1$H NMR (400 MHz, DMSO-$d_6$) δ 12.02 (s, 1H), 7.02 (d, J=8.0 Hz, 1H), 3.50 (s, 3H), 3.27-3.10 (m, 1H), 2.09 (d, J=7.0 Hz, 2H), 1.84-1.63 (m, 4H), 1.62-1.43 (m, 1H), 1.22-1.07 (m, 2H), 1.07-0.87 (m, 2H).

Step 2: Methyl (trans-4-(2-((5-(4-(trans-1-amino-3-hydroxy-3-methylcyclobutyl)phenyl)-4-phenylpyridin-2-yl)amino)-2-oxoethyl)cyclohexyl)carbamate: A solution of the product from Step 1 above (31.0 mg, 0.144 mmol) in DCM (5 ml) was treated with 1-chloro-N,N,2-trimethylprop-1-en-1-amine (0.021 ml, 0.156 mmol) and the resultant solution was stirred at RT for 30 min. A solution of the product from Example 67 Step 2 (53.5 mg, 0.120 mmol) in pyridine (0.5 ml, 0.080 mmol) was added and the solution stirred overnight at RT during which time a white precipitate had formed. DMF (2 ml) was added and stirring continued for 1 h. The resultant mixture was treated with 1 M HCl(aq) (10 ml) and stirred for 10 min. The phases were separated and the aqueous phase extracted with EtOAc (2×10 ml). The combined organic phases were dried over MgSO$_4$, filtered and the solvent removed in vacuo. The residue was purified by column chromatography (12 g cartridge, 0-100% EtOAc/isohexane) to afford a yellow solid. This material was dissolved in DCM (5 ml) and treated with TFA (0.5 ml). The resultant solution was stirred at RT for 3 h. Saturated NaHCO$_3$(aq) (10 ml) was added and the mixture stirred for 10 min. The phases were separated and the aqueous phase extracted with EtOAc (2×10 ml). The combined organic phases were dried over MgSO$_4$, filtered and the solvent removed in vacuo. The residue was purified by column chromatography (12 g cartridge, 0-10% (0.7 M NH$_3$/MeOH)/DCM) to afford the title compound (16.3 mg, 0.029 mmol, 98% purity) as a white solid. LCMS (Method 1): m/z 543 (M+H)$^+$ at 1.32 min. $^1$H NMR (400 MHz, DMSO-$d_6$) δ 10.60 (s, 1H), 8.29 (d, J=0.6 Hz, 1H), 8.15 (s, 1H), 7.37-7.29 (m, 5H), 7.20-7.13 (m, 2H), 7.09-7.03 (m, 2H), 7.02 (d, J=8.0 Hz, 1H), 4.78 (s, 1H), 3.49 (s, 3H), 3.25-3.16 (m, 1H), 2.36-2.27 (m, 5H), 2.19-2.10 (m, 2H), 1.81-1.60 (m, 5H), 1.49 (s, 3H), 1.25-0.96 (m, 5H).

Example 104

N-(trans-4-(2-((6-(4-(trans-1-amino-3-hydroxy-3-methylcyclobutyl)phenyl)-5-phenylpyridazin-3-yl)amino)-2-oxoethyl)cyclohexyl)-N-isopropylpropionamide

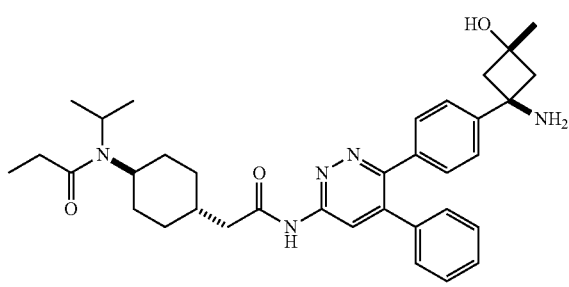

Step 1: Ethyl 2-(trans-4-(N-isopropylpropionamido)cyclohexyl)acetate: The title compound (379 mg) was isolated as an orange oil from the reaction of the product from Example 49 Step 1 (292 mg, 1.28 mmol), propionyl chloride (123 μl, 1.41 mmol) and DIPEA (673 μl, 3.85 mmol) in THF (5 ml) using essentially the same procedure as in Example 101 Step 1.

Step 2: 2-(trans-4-(N-isopropylpropionamido)cyclohexyl)acetic acid: The title compound (288 mg) was isolated as a waxy yellow solid from the reaction of the product from Step 1 above (375 mg) and LiOH (63.4 mg, 2.65 mmol) in a mixture of THF (2 ml), water (1.5 ml) and MeOH (0.2 ml) using essentially the same procedure as in Example 101 Step 2. This material was used directly in subsequent reactions without purification.

Step 3: tert-butyl (trans-3-hydroxy-1-(4-(6-(2-(trans-4-(N-isopropylpropionamido)cyclohexyl)acetamido)-4-phenylpyridazin-3-yl)phenyl)-3-methylcyclobutyl)carbamate: The title compound (25 mg, 0.034 mmol, 94% purity) was isolated as a beige solid from the reaction of the product from Example 57 Step 1 (40 mg, 0.090 mmol), the product from Step 2 above (22.9 mg), HATU (37.5 mg, 0.099 mmol) and DIPEA (35 μl, 0.197 mmol) in DMF (1.5 ml) using essentially the same procedure as in Example 102 Step 1. LCMS (Method 1): m/z 684 (M+H)$^+$ at 2.42 min.

Step 4: N-(trans-4-(2-((6-(4-(trans-1-amino-3-hydroxy-3-methylcyclobutyl)phenyl)-5-phenylpyridazin-3-yl)amino)-2-oxoethyl)cyclohexyl)-N-isopropylpropionamide: A solution of the product from Step 1 above (25 mg, 0.034 mmol, 94% purity) in DCM (0.5 ml) was treated with TFA (0.070 ml, 0.914 mmol) and the mixture was stirred at RT for 16 h. The mixture was concentrated in vacuo and loaded onto a column of SCX in MeOH. The column was washed with MeOH and then the product was eluted with 0.7 M ammonia in MeOH. The solvent was removed in vacuo to afford a pale yellow solid (20 mg). Purification by preparative HPLC (Waters FractionLynx, Waters X-Bridge Prep-C18, 5 μm, 19×50 mm column, 20-50% MeCN in 10 mM ammonium bicarbonate(aq)) afforded the title compound (6.0 mg, 10.1 μmol, 98% purity) as a colourless solid. LCMS (Method 2): m/z 584 (M+H)$^+$ at 2.01 min. $^1$H NMR (400 MHz, Methanol-$d_4$) (two rotamers in a 10:9 ratio) δ 8.52 (s, 1H), 7.52-7.44 (m, 2H), 7.44-7.31 (m, 5H), 7.31-7.25 (m, 2H), 4.22-4.02 (m, 1H, major), 3.71-3.51 (m, 1H, minor), 2.73 (d, J=13.0 Hz, 2H), 2.62-2.41 (m, 5H), 2.39 (q, J=7.5 Hz, 2H), 2.03-1.84 (m, 3H), 1.84-1.66 (m, 2H), 1.62-1.54 (m, 1H), 1.55 (s, 3H), 1.44-1.15 (m, 3H), 1.38 (d, J=6.7 Hz, 3H), 1.24 (d, J=6.6 Hz, 3H), 1.110 (t, J=7.4 Hz, 3H, major), 1.106 (t, J=7.4 Hz, 3H, minor).

Example 105

N-(trans-4-(2-((6-(4-(trans-1-amino-3-hydroxy-3-methylcyclobutyl)phenyl)-5-phenylpyridazin-3-yl)amino)-2-oxoethyl)cyclohexyl)-N-isopropylcyclopropanecarboxamide

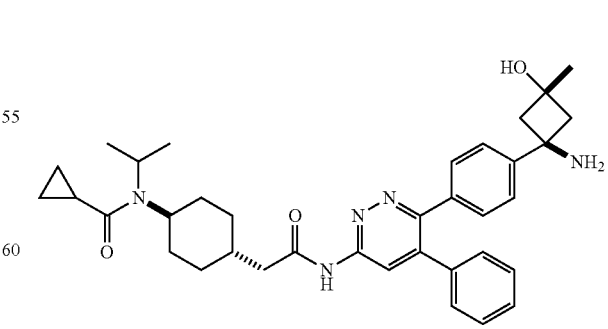

Step 1: Ethyl 2-(trans-4-(N-isopropylcyclopropanecarboxamido)cyclohexyl)acetate: The title compound (453 mg) was isolated as an orange oil from the reaction of the product from Example 49 Step 1 (338 mg, 1.49 mmol), cyclopropanecarbonyl chloride (148 µl, 1.64 mmol) and DIPEA (779 µl, 4.46 mmol) in THF (5 ml) using essentially the same procedure as in Example 101 Step 1.

Step 2: 2-(trans-4-(N-isopropylcyclopropanecarboxamido)cyclohexyl)acetic acid: The title compound (373 mg) was isolated as a colourless oil from the reaction of the product from Step 1 above (453 mg) and LiOH (73.4 mg, 3.07 mmol) in a mixture of THF (2 ml), water (1.5 ml) and MeOH (0.2 ml) using essentially the same procedure as in Example 101 Step 2. This material was used directly in subsequent reactions without purification.

Step 3: tert-butyl (trans-3-hydroxy-1-(4-(6-(2-(trans-4-(N-isopropylcyclopropanecarboxamido)cyclohexyl)acetamido)-4-phenylpyridazin-3-yl)phenyl)-3-methylcyclobutyl)carbamate: The title compound (23 mg, 0.030 mmol, 91% purity) was isolated as a beige solid from the reaction of the product from Example 57 Step 1 (40 mg, 0.090 mmol), the product from Step 2 above (24.0 mg), HATU (37.5 mg, 0.099 mmol) and DIPEA (35 µl, 0.197 mmol) in DMF (1.5 ml) using essentially the same procedure as in Example 102 Step 1. LCMS (Method 1): m/z 696 (M+H)$^+$ at 2.51 min.

Step 4: N-(trans-4-(2-((6-(4-(trans-1-amino-3-hydroxy-3-methylcyclobutyl)phenyl)-5-phenylpyridazin-3-yl)amino)-2-oxoethyl)cyclohexyl)-N-isopropylcyclopropanecarboxamide: The title compound (9.3 mg, 15 µmol, 98% purity) was isolated as a colourless solid from the reaction of the product from Step 3 above (23 mg, 0.030 mmol, 91% purity) with TFA (0.064 ml, 0.826 mmol) in DCM (0.5 ml) using essentially the same procedure as in Example 104 Step 4. LCMS (Method 2): m/z 596 (M+H)$^+$ at 2.06 min. $^1$H NMR (400 MHz, Methanol-d$_4$) (two rotamers in an 5:4 ratio) δ 8.52 (s, 1H), 7.50-7.43 (m, 2H), 7.43-7.32 (m, 5H), 7.31-7.25 (m, 2H), 4.40 (br s, 1H, major), 3.99 (br s, 1H, minor), 2.73 (d, J=13.4 Hz, 2H), 2.52-2.43 (m, 4H), 2.27 (br s, 1H), 2.04-1.80 (m, 6H), 1.66-1.50 (m, 1H), 1.55 (s, 3H), 1.42-1.11 (m, 9H), 0.92-0.71 (m, 4H).

Example 106

N-(6-(4-(trans-1-amino-3-hydroxy-3-methylcyclobutyl)phenyl)-5-phenylpyridazin-3-yl)-2-(trans-4-(N-ethylacetamido)cyclohexyl)acetamide

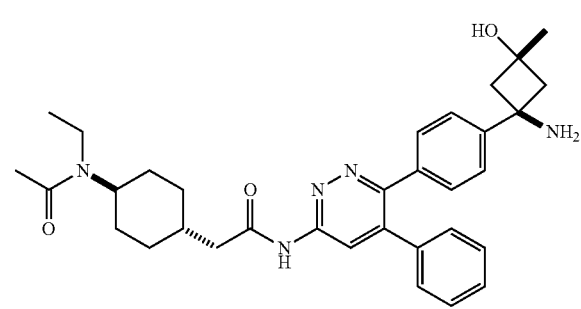

Step 1: Ethyl 2-(trans-4-(ethylamino)cyclohexyl)acetate: A solution of ethyl 2-(trans-4-aminocyclohexyl)acetate hydrochloride (222 mg, 1.00 mmol) in EtOH (3 ml) was treated with MgSO$_4$ (169 mg, 1.40 mmol), followed by acetaldehyde (0.040 ml, 1.20 mmol). The resultant mixture was stirred at RT for 60 min, then cooled to 0° C. and NaBH$_4$ (113 mg, 3.00 mmol) was added. The mixture was allowed to warm to RT and stir for 20 h. Additional acetaldehyde (0.040 ml, 1.20 mmol) was added and the mixture stirred at RT for a further 4 h. The mixture was poured into saturated Na$_2$CO$_3$(aq) (50 ml) and extracted with EtOAc (2×25 ml). The combined organic phases were sequentially washed with water (25 ml), brine (25 ml), dried over MgSO$_4$, filtered and concentrated in vacuo to afford the title compound as a colourless oil (209 mg). This material was used directly in subsequent reactions without purification.

Step 2: Ethyl 2-(trans-4-(N-ethylacetamido)cyclohexyl)acetate: The title compound (122 mg, 0.454 mmol, 95% purity) was isolated as a yellow oil from the reaction of the product from Step 1 above (209 mg), acetic anhydride (189 µl, 2.00 mmol) and DIPEA (175 µl, 1.00 mmol) in THF (5 ml) using essentially the same procedure as in Example 101 Step 1. $^1$H NMR (400 MHz, Chloroform-d) (two rotamers in a 4:3 ratio) δ 4.37 (tt, J=12.2, 3.8 Hz, 1H, major), 4.15 (q, J=7.1 Hz, 2H, minor), 4.13 (q, J=7.1 Hz, 2H, major), 3.50 (tt, J=11.8, 3.8 Hz, 1H, minor), 3.29 (q, J=7.1 Hz, 2H, minor), 3.25 (q, J=7.1 Hz, 2H, major), 2.22 (d, J=6.9 Hz, 2H, minor), 2.20 (d, J=7.0 Hz, 2H, major), 2.12 (s, 3H), 1.96-1.68 (m, 5H), 1.60 (qd, J=12.8, 3.5 Hz, 2H, minor), 1.48 (qd, J=12.5, 3.5 Hz, 2H, major), 1.31-1.08 (m, 8H).

Step 3: 2-(trans-4-(N-ethylacetamido)cyclohexyl)acetic acid: The title compound (68 mg) was isolated as a yellow solid from the reaction of the product from Step 2 above (122 mg, 0.454 mmol, 95% purity) and LiOH (23 mg, 0.960 mmol) in a mixture of THF (1 ml), water (1 ml) and MeOH (0.2 ml) using essentially the same procedure as in Example 101 Step 2. This material was used directly in subsequent reactions without purification.

Step 4: tert-butyl (trans-1-(4-(6-(2-(trans-4-(N-ethylacetamido)cyclohexyl)acetamido)-4-phenylpyridazin-3-yl)phenyl)-3-hydroxy-3-methylcyclobutyl)carbamate: The title compound (22 mg, 0.032 mmol, 94% purity) was isolated as a white solid from the reaction of the product from Example 57 Step 1 (40 mg, 0.090 mmol), the product from Step 3 above (20.4 mg), HATU (37.5 mg, 0.099 mmol) and DIPEA (35 µl, 0.197 mmol) in DMF (1.5 ml) using essentially the same procedure as in Example 102 Step 1. LCMS (Method 1): m/z 656 (M+H)$^+$ at 2.18 min.

Step 5: N-(6-(4-(trans-1-amino-3-hydroxy-3-methylcyclobutyl)phenyl)-5-phenylpyridazin-3-yl)-2-(trans-4-(N-ethylacetamido)cyclohexyl)acetamide: The title compound (16 mg, 28 µmol, 98% purity) was isolated as a cream solid from the reaction of the product from Step 4 above (22 mg, 0.032 mmol, 94% purity) with TFA (0.060 ml, 0.779 mmol) in DCM (0.6 ml) using essentially the same procedure as in Example 104 Step 4. LCMS (Method 2): m/z 556 (M+H)$^+$ at 1.77 min. $^1$H NMR (400 MHz, Methanol-d$_4$) two rotamers in a 1:1 ratio) δ 8.402 (s, 1H, rotamer), 8.399 (s, 1H, rotamer) 7.33 (d, J=8.3 Hz, 2H), 7.34-7.18 (m, 5H), 7.19-7.12 (m, 2H), 4.15 (tt, J=11.7, 4.2 Hz, 1H, rotamer), 3.56 (tt, J=11.8, 3.9 Hz, 1H, rotamer), 3.31-3.21 (m, 2H), 2.58 (d, J=13.2 Hz, 2H), 2.39-2.28 (m, 4H), 2.02 (s, 3H, rotamer), 2.01 (s, 3H, rotamer), 1.94-1.65 (m, 4H), 1.65-1.47 (m, 3H), 1.43 (s, 3H), 1.25-1.14 (m, 2H), 1.11 (t, J=7.1 Hz, 3H, rotamer), 1.01 (t, J=7.0 Hz, 3H, rotamer).

Example 107

N-(trans-4-(2-((5-(4-(trans-1-amino-3-hydroxy-3-methylcyclobutyl)phenyl)-4-phenylpyridin-2-yl)amino)-2-oxoethyl)cyclohexyl)-2-methoxy-N-methylacetamide

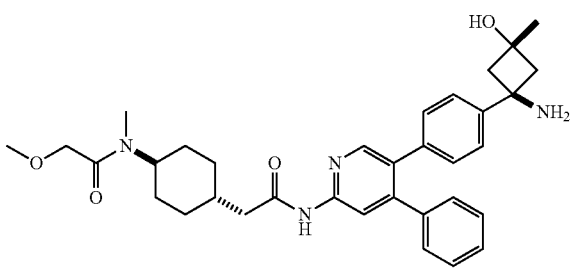

Step 1: 2-(trans-4-(2-methoxy-N-methylacetamido)cyclohexyl)acetic acid: A suspension of the product from Example 1 Step 3 (300 mg, 1.51 mmol) in DCM (5 ml) was treated with DIPEA (294 µl, 1.66 mmol), followed by 2-methoxyacetyl chloride (144 µl, 1.58 mmol) and the resultant mixture was stirred at RT for 16 h. The reaction mixture was washed with saturated NH$_4$Cl(aq) (5 ml) and the aqueous phase extracted with DCM (5 ml). The organic phases were combined and washed sequentially with 1 M HCl(aq) (10 ml), saturated NaHCO$_3$(aq) (10 ml) and brine (10 ml). The organic phase was then dried over MgSO$_4$, filtered and concentrated to afford an orange gum (348 mg). This material was dissolved in a mixture of THF (5 ml), MeOH (1 ml), and 1 M LiOH(aq) (3.01 ml, 3.01 mmol) and the resultant mixture stirred at RT for 2 h. The reaction mixture was concentrated to ca. 5 ml then diluted with water (5 ml) and washed with EtOAc (10 ml). The aqueous phase was then acidified with 1 M HCl and extracted with EtOAc (3×15 ml). The extracts were combined, dried over MgSO$_4$, filtered and concentrated to afford the title compound (152 mg) as a gum. This material was used in subsequent reactions without purification.

Step 2: N-(trans-4-(2-((5-(4-(trans-1-amino-3-hydroxy-3-methylcyclobutyl)phenyl)-4-phenylpyridin-2-yl)amino)-2-oxoethyl)cyclohexyl)-2-methoxy-N-methylacetamide: A suspension of the product from Step 1 above (30 mg) in DCM (2 ml) was treated with 1-chloro-N,N,2-trimethylprop-1-en-1-amine (29.7 µl, 0.224 mmol) and the resultant mixture stirred for 1 h. Pyridine (36.3 µl, 0.449 mmol) was added, and after a further 5 min, the product from Example 67 Step 2 (50 mg, 0.112 mmol) in DCM (2 ml) was added and the mixture stirred overnight. The reaction mixture was quenched by addition of saturated NH$_4$Cl(aq) (3 ml). The phases were separated and the aqueous phase extracted with DCM (2×3 ml). The organic phases were combined and concentrated. The residue was purified by column chromatography (12 g cartridge, 0-100% EtOAc/isohexane, then 0-10% (0.7 M NH$_3$/MeOH)/DCM) to afford a yellow gum (24 mg). This material was dissolved in DCM (3 ml) and TFA (173 µl, 2.24 mmol) was added. The reaction mixture was stirred at RT overnight. The mixture was loaded onto a column of SCX (ca. 100 mg). The column was washed with MeOH and then the product was eluted with 0.7 M ammonia in MeOH. The solvent was removed in vacuo and the residue partially purified by column chromatography (4 g cartridge, 0-10% (0.7 M NH$_3$/MeOH/DCM). Further purification by preparative HPLC (Waters FractionLynx, Waters X-Bridge Prep-C18, 5 µm, 19×50 mm column, 20-50% MeCN in 10 mM ammonium bicarbonate) afforded the title compound (1.2 mg, 2.06 µmol, 98% purity) as a colourless solid. LCMS (Method 1): m/z 571 (M+H)$^+$ at 1.27 min. $^1$H NMR (400 MHz, Methanol-d$_4$) (two rotamers in a 4:3 ratio) δ 8.18 (s, 1H), 8.07 (s, 1H), 7.28-7.23 (m, 2H), 7.21-7.13 (m, 3H), 7.12-7.06 (m, 2H), 7.06-7.00 (m, 2H), 4.32-4.17 (m, 2H), 4.08 (s, 2H, minor), 4.03 (s, 2H, major), 3.30-3.29 (m, 3H), 2.75 (s, 3H, major), 2.73 (s, 3H, minor), 2.62-2.50 (m, 2H), 2.35-2.24 (m, 4H), 1.90-1.47 (m, 6H), 1.43 (s, 3H), 1.23-1.07 (m, 2H).

Example 108

N-(5-(4-(trans-1-amino-3-hydroxy-3-methylcyclobutyl)phenyl)-4-phenylpyridin-2-yl)-2-(trans-4-(N-ethylacetamido)cyclohexyl)acetamide

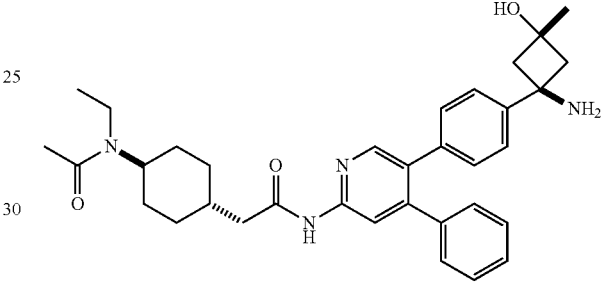

Step 1: tert-butyl (trans-1-(4-(6-(2-(trans-4-(N-ethylacetamido)cyclohexyl)acetamido)-4-phenylpyridin-3-yl)phenyl)-3-hydroxy-3-methylcyclobutyl)carbamate: A solution of the product from Example 106 Step 3 (25 mg) in DCM (5 ml) was treated with 1-chloro-N,N,2-trimethylprop-1-en-1-amine (19 µl, 0.142 mmol) and the resultant solution was stirred at RT for 30 min. A solution of the product from Example 67 Step 2 (40 mg, 0.090 mmol) in pyridine (0.5 ml) was added and the resultant solution was stirred overnight at RT. The mixture was poured into 1M HCl(aq) (20 ml), stirred for 10 min, then extracted with DCM (2×20 ml). The combined organic phases were sequentially washed with 1 M HCl(aq) (20 ml), 1 M NaOH(aq) (20 ml), water (20 ml) and brine (20 ml), then dried over MgSO$_4$, filtered and concentrated in vacuo to afford a colourless oil. Purification by column chromatography (12 g cartridge, 0-6% (0.7M NH$_3$/MeOH)/DCM) to furnish the title compound (45 mg, 0.062 mmol, 90% purity) as a colourless solid. LCMS (Method 1): m/z 655 (M+H)$^+$ at 2.24 min.

Step 2: N-(5-(4-(trans-1-amino-3-hydroxy-3-methylcyclobutyl)phenyl)-4-phenylpyridin-2-yl)-2-(trans-4-(N-ethylacetamido)cyclohexyl)acetamide: The title compound (8.3 mg, 15 µmol, 98% purity) was isolated as a colourless solid from the reaction of the product from Step 1 above (45 mg, 0.062 mmol, 90% purity) with TFA (0.060 ml, 0.779 mmol) in DCM (0.6 ml) using essentially the same procedure as in Example 104 Step 4. LCMS (Method 2): m/z 555 (M+H)$^+$ at 1.86 min. $^1$H NMR (400 MHz, Methanol-d$_4$) (two rotamers in a 1:1 ratio) δ 8.30 (s, 1H), 8.18 (s, 1H), 7.42-7.34 (m, 2H), 7.32-7.25 (m, 3H), 7.25-7.19 (m, 2H), 7.18-7.11 (m, 2H), 4.27 (tt, J=11.7, 4.0 Hz, 1H, rotamer), 3.68 (tt, J=11.9, 3.8 Hz, 1H, rotamer), 3.42-3.30 (m, 2H), 2.77-2.64 (m, 2H), 2.44-2.35 (m, 4H), 2.13 (d, J=6.2 Hz, 3H), 2.02-1.78 (m, 4H), 1.77-1.58 (m, 3H), 1.55 (s, 3H), 1.34-1.19 (m, 2H), 1.23 (t, J=7.0 Hz, 3H, rotamer), 1.13 (t, J=7.0 Hz, 3H, rotamer).

Example 109

N-(trans-4-(2-((5-(4-(trans-1-amino-3-hydroxy-3-methylcyclobutyl)phenyl)-4-phenylpyridin-2-yl)amino)-2-oxoethyl)cyclohexyl)-2,2-difluoro-N-methylacetamide

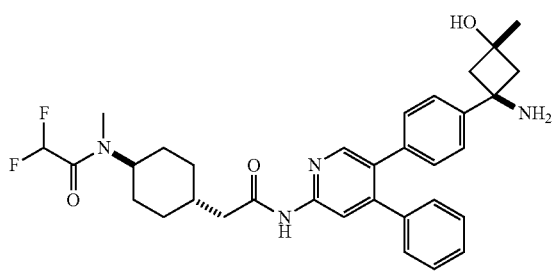

Step 1: Benzyl (trans-4-(2-((5-(4-(trans-1-((tert-butoxycarbonyl)amino)-3-hydroxy-3-methylcyclobutyl)phenyl)-4-phenylpyridin-2-yl)amino)-2-oxoethyl)cyclohexyl)(methyl)carbamate: A solution of the product from Example 4 Step 1 (329 mg, 1.08 mmol) in DCM (10 ml) was treated with 1-chloro-N,N,2-trimethylprop-1-en-1-amine (154 µl, 1.17 mmol) and the resultant solution was stirred at RT for 30 min. A solution of the product from Example 67 Step 2 (400 mg, 0.898 mmol) in a mixture of pyridine (1 ml) and DCM (2 ml) was added and the solution stirred overnight at RT. 1 M HCl(aq) (10 ml) was added and the mixture stirred for 10 min. The organic phase was filtered through a phase separation cartridge, washing with DCM (20 ml), and the solvent removed in vacuo. The residue was purified by column chromatography (40 g cartridge, 0-100% EtOAc/isohexane) to afford the title compound (483 mg, 0.633 mmol, 96% purity) as a white solid. LCMS (Method 1): m/z 733 (M+H)$^+$ at 2.74 min.

Step 2: tert-butyl (trans-3-hydroxy-3-methyl-1-(4-(6-(2-(trans-4-(methylamino)cyclohexyl)acetamido)-4-phenylpyridin-3-yl)phenyl)cyclobutyl)carbamate: The product from Step 1 above (480 mg, 0.629 mmol) was dissolved in EtOH (20 ml) and hydrogenated in a ThalesNano H-Cube® flow reactor (10% Pd/C, 30×4 mm, full hydrogen mode, 50° C., 1 ml/min flow rate, 4 passes). The solvent was removed in vacuo and the residue was purified by column chromatography (24 g cartridge, 0-100% EtOAc/isohexane, then 0-40% MeOH/DCM) to afford the title compound (0.287 g) as a white solid. This material was used directly in subsequent reactions without analysis.

Step 3: N-(trans-4-(2-((5-(4-(trans-1-amino-3-hydroxy-3-methylcyclobutyl)phenyl)-4-phenylpyridin-2-yl)amino)-2-oxoethyl)cyclohexyl)-2,2-difluoro-N-methylacetamide: A solution of the product from Step 2 above (50 mg) in THF (5 ml) cooled in an ice bath and DIPEA (32.1 µl, 0.184 mmol) was added. The mixture was treated dropwise with 2,2-difluoroacetic anhydride (11.4 µl, 0.092 mmol) and the resultant solution stirred at RT for 18 h. Saturated NaHCO$_3$ (aq) (20 ml) was added, the layers separated and the aqueous layer extracted with EtOAc (2×10 ml). The solvent was removed in vacuo and the residue purified by column chromatography (12 g cartridge, 0-10% (0.7 M NH$_3$/MeOH)/DCM) to afford a pale yellow solid. This material was dissolved in DCM (5 ml) and treated with TFA (0.5 ml). The resultant solution was stirred at RT for 2 h. The reaction mixture was was loaded onto a column of SCX in MeOH. The column was washed with MeOH (20 ml) and then the product was eluted with 0.7 M ammonia in MeOH (20 ml). The resultant mixture was concentrated in vacuo to afford the title compound (22.4 mg, 0.038 mmol, 99% purity) as a white solid. LCMS (Method 1): m/z 577 (M+H)$^+$ at 1.40 min. $^1$H NMR (400 MHz, DMSO-d$_6$) (two rotamers in an 11:10 ratio) δ 10.63 (s, 1H, minor), 10.62 (s, 1H, major), 8.31 (s, 1H), 8.17 (s, 1H), 7.37-7.31 (m, 5H), 7.27-7.16 (m, 2H), 7.12-7.05 (m, 2H), 6.81 (t, J=52.8 Hz, 1H, minor), 6.67 (t, J=52.9 Hz, 1H, major), 4.78 (s, 1H), 4.21-4.04 (m, 1H, major), 3.73-3.55 (m, 1H, minor), 2.89 (s, 3H, major), 2.78 (s, 3H, minor), 2.39-2.28 (m, 4H), 2.25-1.98 (m, 4H), 1.86-1.52 (m, 7H), 1.50 (s, 3H), 1.25-1.04 (m, 2H).

Example 110

N-(trans-4-(2-((5-(4-(trans-1-amino-3-hydroxy-3-methylcyclobutyl)phenyl)-4-(thiophen-3-yl)pyridin-2-yl)amino)-2-oxoethyl)cyclohexyl)-N-methylpropionamide

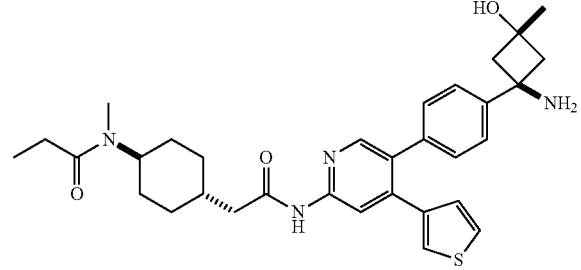

Step 1: tert-butyl (trans-3-hydroxy-3-methyl-1-(4-(6-(2-(trans-4-(N-methylpropionamido)cyclohexyl)acetamido)-4-(thiophen-3-yl)pyridin-3-yl)phenyl)cyclobutyl)carbamate: A solution of the produce from Example 82 Step 2 (25.2 mg, 0.111 mmol) in DCM (2 ml) was treated with 1-chloro-N,N,2-trimethylprop-1-en-1-amine (29.6 µl, 0.221 mmol) and stirred for 1 h. Pyridine (35.8 µl, 0.443 mmol) was added, followed by the product from Example 89 Step 1 (50 mg). The reaction mixture was stirred overnight at RT. The reaction was quenched by addition of saturated NH$_4$Cl(aq) (3 ml) and the organic phase filtered through a phase separation cartridge. The organic phase was concentrated and the residue purified by column chromatography (12 g cartridge, 0-100% EtOAc/isohexane) to afford the title compound (48 mg, 0.071 mmol, 98% purity) as a pale yellow gum. LCMS (Method 1): m/z 661 (M+H)$^+$ at 2.22 min.

Step 2: N-((1r,4r)-4-(2-((5-(4-((1r,3r)-1-amino-3-hydroxy-3-methylcyclobutyl)phenyl)-4-(thiophen-3-yl)pyridin-2-yl)amino)-2-oxoethyl)cyclohexyl)-N-methylpropionamide: The product from Step 1 above (48 mg, 0.071 mmol, 98% purity) in DCM (3 ml) was treated with TFA (128 µl, 1.66 mmol) and the reaction mixture was stirred at RT overnight. The reaction mixture was loaded onto a column of SCX (ca. 100 mg). The column was washed with MeOH and the product was eluted with a 0.7 M solution of ammonia in MeOH, then concentrated in vacuo. The residue was partially purified by column chromatography (4 g cartridge, 0-10% (0.7 M NH$_3$/MeOH)/DCM). Further purification by preparative HPLC (Waters FractionLynx, Waters X-Bridge Prep-C18, 5 μm, 19×50 mm column, 20-50% MeCN in 10 mM ammonium bicarbonate(aq)) afforded the title compound (1.2 mg, 2.06 μmol, 95% purity) as a colourless solid. LCMS (Method 1): m/z 561 (M+H)$^+$ at 1.36 min. $^1$H NMR (400 MHz, DMSO-d$_6$) (two rotamers in a 3:2 ratio) δ 10.59 (s, 1H, minor), 10.58 (s, 1H, major), 8.25 (s, 1H), 8.24 (s, 1H), 7.52-7.45 (m, 2H), 7.43-7.36 (m, 2H), 7.18-7.10 (m, 2H), 6.74 (dd, J=4.6, 1.7 Hz, 1H), 4.81 (s, 1H), 4.32-4.19 (m, 1H, major), 3.66-3.51 (m, 1H, minor), 2.78 (s, 3H, major), 2.68 (s, 3H, minor), 2.42-2.14 (m, 8H), 1.84-1.75 (m, 3H), 1.64-1.57 (m, 2H), 1.54-1.42 (m, 5H), 1.26-1.03 (m, 2H), 1.03-0.92 (m, 3H).

Example 111

N-(5-(4-(trans-1-amino-3-hydroxy-3-methylcyclobutyl)-3-fluorophenyl)-4-phenylpyridin-2-yl)-2-(trans-4-(N-methylacetamido)cyclohexyl)acetamide

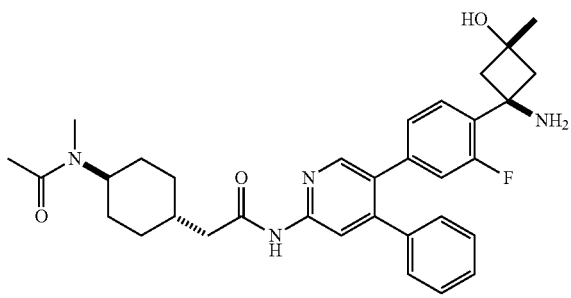

Step 1: cis-1-(4-chloro-2-fluorophenyl)-3-hydroxycyclobutanecarboxylic acid: A solution of 2-(4-chloro-2-fluorophenyl)acetic acid (25 g, 133 mmol) in THF (150 ml) was treated with isopropylmagnesium chloride (2 M in THF) (148 ml, 297 mmol) over ca. 30 min, whilst maintaining a temperature of <40° C. (water bath). The reaction mixture was heated at 35° C. for 60 min. The resultant pale brown suspension was then treated dropwise with epichlorohydrin (18.7 ml, 239 mmol) maintaining the temperature between 45-55° C. The reaction mixture was cooled to 30° C. and treated dropwise with isopropylmagnesium chloride (2 M in THF) (135 ml, 269 mmol) over ca. 15 min. The reaction mixture was allowed to stir at 30° C. overnight. The reaction mixture was cooled in an ice bath and quenched with 6 M HCl(aq) (120 ml, 720 mmol). The mixture was allowed to warm to RT and stir for 10 min. Toluene (100 ml) was then added and the phases separated. The organic phase was washed with brine (100 ml), dried over MgSO$_4$, filtered and concentrated to ca. 50 ml. Toluene (50 ml) was added and the mixture concentrated to dryness. The residue was suspended in toluene (100 ml) and cooled to 0° C. for ca. 45 min, then filtered, washing with ice cold toluene (2×10 ml) to afford the title compound (17.5 g, 57.2 mmol, 80% purity) as a colourless free-flowing solid. LCMS (Method 1): m/z 245 (M+H)$^+$ at 1.57 min.

Step 2: trans-methyl 1-(4-chloro-2-fluorophenyl)-3-hydroxycyclobutanecarboxylate: The product from Step 1 above (17.5 g, 57.2 mmol, 80% purity) was dissolved MeOH (100 ml) and treated with conc. H$_2$SO$_4$(aq) (1.14 ml, 21.5 mmol). The reaction mixture heated at 60° C. overnight. The mixture was cooled to 10° C. and quenched with 8% w/v K$_2$HPO$_4$(aq) (178 ml, 82 mmol), maintaining the temperature below 15° C. The mixture was concentrated to ca. 450 ml, then extracted with Et$_2$O (2×150 ml). The organic phases were combined, dried over MgSO$_4$, filtered and concentrated to afford the title compound (17.5 g, 57.5 mmol, 85% purity) as a colourless flocculent solid. $^1$H NMR (400 MHz, DMSO-d$_6$) δ 7.59 (t, J=8.6 Hz, 1H), 7.41 (dd, J=10.8, 2.2 Hz, 1H), 7.32-7.27 (m, 1H), 5.38 (d, J=6.3 Hz, 1H), 4.05-3.84 (m, 1H), 3.57 (s, 3H), 2.78-2.68 (m, 2H), 2.62-2.51 (m, 2H).

Step 3: Methyl 1-(4-chloro-2-fluorophenyl)-3-oxocyclobutanecarboxylate: A solution of the product from Step 2 above (17.5 g, 57.5 mmol, 85% purity) in DCM (180 ml) was cooled to 5° C. and treated with a solution of KBr (1.77 g, 14.9 mmol) in water (20 ml) maintaining temperature below 5° C. After the addition was complete, the mixture was stirred for 15 min whereupon TEMPO (0.846 g, 5.41 mmol) was added and the resultant mixture stirred for 5 min. In a separate vessel, a solution of KHCO$_3$ (101 g, 852 mmol) in water (330 ml) was combined with sodium hypochlorite (aq) (65.6 ml, 149 mmol, 14% w/w free chlorine content) and the resultant mixture added dropwise to the original mixture over ca. 90 min, whilst maintaining temperature below 5° C. Once addition was complete, the mixture was allowed to warm to 10° C. The mixture was then cooled to 0° C. and a solution of sodium thiosulfate (8.34 g, 52.8 mmol) in water (70 ml) was added, maintaining the temperature below 10° C. The reaction mixture was then allowed to warm to RT and the phases separated. The aqueous phase was extracted with DCM (2×200 ml) and the organic phases were combined, washed with water (400 ml), dried over MgSO$_4$, filtered and concentrated. The resulting red oil was twice dissolved in THF (100 ml) and concentrated to afford the title compound (17.1 g, 59.8 mmol, 90% purity) as a deep red oil, which crystallised on standing. $^1$H NMR (400 MHz, DMSO-d$_6$) δ 7.53 (d, J=8.5 Hz, 1H), 7.51-7.47 (m, 1H), 7.34 (ddd, J=8.3, 2.1, 0.7 Hz, 1H), 3.74-3.70 (m, 4H), 3.65 (s, 3H).

Step 4: Methyl 1-(4-chloro-2-fluorophenyl)-3-hydroxy-3-methylcyclobutanecarboxylate: A solution of the product from Step 3 above (17.1 g, 59.8 mmol, 90% purity) in THF (100 ml) was cooled to −70° C. and methylmagnesium bromide (3 M in Et$_2$O) (22.9 ml, 68.8 mmol) was added dropwise over 1 h, maintaining temperature below −60° C. The mixture was stirred at −70° C. for 4 h, then allowed to warm to −20° C. whereupon the reaction was quenched addition of MeOH (2.66 ml, 65.8 mmol), maintaining the temperature below 5° C. 1 M HCl(aq) (71.7 ml, 71.7 mmol) was added, maintaining the temperature below 10° C. Once the addition was complete, the mixture was stirred at RT for 15 min, then Et$_2$O (200 ml) was added and the phases separated. The organic phase was washed with brine (200 ml), dried over MgSO$_4$, filtered and concentrated to afford the title compound (17.5 g). This material was used directly in subsequent reactions without purification.

Step 5: trans-methyl 1-(4-chloro-2-fluorophenyl)-3-hydroxy-3-methylcyclobutanecarboxylate: A solution of the product from Step 4 above (2 g) in THF (20 ml) was treated with 0.2 M LiOH(aq) (18.3 ml, 3.67 mmol) and the reaction mixture was stirred at RT overnight. The reaction mixture was concentrated to ca. 20 ml and extracted with Et$_2$O (2×15 ml). The organic phases were combined, dried over MgSO$_4$, filtered and concentrated to afford the title compound (370 mg) as a red oil. This material was used directly in subsequent reactions without purification.

Step 6: trans-1-(4-chloro-2-fluorophenyl)-3-hydroxy-3-methylcyclobutanecarboxylic acid: A solution of the product from Step 5 above (370 mg) in EtOH (12 ml) was treated with water (6 ml) and sodium hydroxide (326 mg, 8.14 mmol). The mixture was stirred at RT overnight. The mixture was concentrated to ca. 6 ml and diluted with water (10 ml), then washed with Et₂O (20 ml). The aqueous phase was acidified with 1 M HCl (9.50 ml, 9.50 mmol), then extracted with EtOAc (3×20 ml). The combined organic extracts were dried over MgSO₄, filtered and concentrated to afford the title compound (281 mg, 1.03 mmol, 95% purity) as a sticky amber gum. ¹H NMR (400 MHz, DMSO-d₆) δ 12.51 (s, 1H), 7.39-7.26 (m, 3H), 5.03 (s, 1H), 2.91-2.77 (m, 2H), 2.50-2.42 (m, 2H), 1.29 (s, 3H).

Step 7: trans-3-amino-3-(4-chloro-2-fluorophenyl)-1-methylcyclobutanol: A solution of the product from Step 6 above (280 mg, 1.03 mmol, 95% purity) in THF (12 ml) was treated with Et₃N (362 μl, 2.60 mmol) and diphenyl phosphorazidate (233 μl, 1.08 mmol). The resultant mixture was heated at 35° C. for 1 h. In a separate vessel, 1 M HCl(aq) (5.41 ml, 5.41 mmol) was heated to 65° C. The original reaction mixture was added to the warm HCl solution dropwise over ca. 15 min. The resultant mixture was heated at 65° C. for 2 h, then allowed to cool to RT overnight. The reaction mixture was partially concentrated in vacuo, then EtOAc (30 ml) was added and the phases separated. The organic phase was extracted with 1M HCl (2×20 ml). The aqueous phases were combined and basified with 2 M NaOH(aq) (30 ml), then extracted with EtOAc (3×25 ml). The organic phases were combined, dried over MgSO₄, filtered and concentrated to afford the title compound (125 mg) as a pale yellow oil which was used in next step without further purification.

Step 8: tert-butyl (trans-1-(4-chloro-2-fluorophenyl)-3-hydroxy-3-methylcyclobutyl)carbamate: A solution of the product from Step 7 above (125 mg) in THF (4 ml) was treated with Boc₂O (143 mg, 0.653 mmol) and the resultant mixture was stirred at RT for 3 days. The solvent was evaporated in vacuo and the resultant gum was dissolved in EtOAc (10 ml) and sequentially washed with water (5 ml) and brine (5 ml). The organic phase was dried over MgSO₄, filtered and concentrated. The residue was purified by column chromatography (12 g cartridge, 0-60% EtOAc/isohexane) to afford the title compound (148 mg, 0.426 mmol, 95% purity) as a colourless solid. ¹H NMR (400 MHz, DMSO-d₆) δ 7.66 (s, 1H), 7.44-7.17 (m, 3H), 4.90 (s, 1H), 2.71-2.57 (m, 2H), 2.48-2.36 (m, 2H), 1.35 (s, 3H), 1.33-1.15 (m, 9H).

Step 9: tert-butyl (trans-1-(2-fluoro-4-(4,4,5,5-tetramethyl-1,3,2-dioxaborolan-2-yl)phenyl)-3-hydroxy-3-methylcyclobutyl)carbamate: The title compound (194 mg, 0.368 mmol, 80% purity) was isolated as a thick oil from the reaction of the product from Step 8 above (148 mg, 0.426 mmol, 95% purity), bis-(pinacolato)diboron (120 mg, 0.471 mmol), palladium(II) acetate (5 mg, 0.022 mmol), XPhos (21 mg, 0.045 mmol) and potassium acetate (132 mg, 1.35 mmol) in MeCN (3 ml) using essentially the same procedure as in Intermediate 2 Step 2, except the mixture was filtered through Celite®, washing with MeCN, and then concentrated and partially purified by column chromatography (12 g cartridge, 0-60% EtOAc/isohexane). LCMS (Method 1): m/z 444 (M+Na)⁺ at 2.41 min. This material was used in subsequent reactions without further purification.

Step 10: tert-butyl (trans-1-(2-fluoro-4-(6-(2-(trans-4-(N-methylacetamido)cyclohexyl)acetamido)-4-phenylpyridin-3-yl)phenyl)-3-hydroxy-3-methylcyclobutyl)carbamate: A suspension of the product from Example 1 Step 5 (25.3 mg, 0.119 mmol) in DCM (2 ml) was treated with 1-chloro-N,N,2-trimethylprop-1-en-1-amine (28.8 μl, 0.216 mmol) and stirred for 1 h. Pyridine (34.9 μl, 0.431 mmol) was added and the resultant mixture stirred for 5 min. The product from Step 9 above (50 mg, 0.086 mmol) in DCM (2 ml) was added and the mixture stirred overnight. EtOAc (15 ml) was added and the resultant mixture was sequentially washed with saturated NaHCO₃(aq) (5 ml) and brine (5 ml). The organic phase was dried over MgSO₄, filtered and concentrated. The residue was purified by column chromatography (12 g cartridge, 0-6% (0.7 M NH₃/MeOH)/DCM) to afford the title compound (15 mg, 0.022 mmol, 95% purity) as a colourless solid. LCMS (Method 1): m/z 659 (M+H)⁺ at 2.21 min.

Step 11: N-(5-(4-(trans-1-amino-3-hydroxy-3-methylcyclobutyl)-3-fluorophenyl)-4-phenylpyridin-2-yl)-2-(trans-4-(N-methylacetamido)cyclohexyl)acetamide: The product from Step 10 above (15 mg, 0.022 mmol, 95% purity) was dissolved in DCM (3 ml) and treated with TFA (166 μl, 2.16 mmol) and the reaction mixture was stirred at RT overnight. The reaction mixture was loaded onto a column of SCX (ca. 100 mg). The column was washed with MeOH and the product was eluted with a 0.7 M solution of ammonia in MeOH, then concentrated in vacuo. The residue was purified by column chromatography (4 g cartridge, 0-10% (0.7 M NH₃/MeOH)/DCM) to afford the title compound (10 mg, 0.017 mmol, 95% purity) as a colourless solid. LCMS (Method 1): m/z 559 (M+H)+, 557 (M−H)⁻, at 1.35 min. ¹H NMR (400 MHz, DMSO-d₆) (two rotamers in an 11:9 ratio) δ 10.67 (s, 1H, minor), 10.65 (s, 1H, major), 8.34-8.32 (m, 1H), 8.19-8.15 (m, 1H), 7.39-7.35 (m, 3H), 7.23-7.19 (m, 2H), 7.12 (t, J=8.2 Hz, 1H), 6.93-6.87 (m, 2H), 4.74 (s, 1H), 4.28-4.17 (m, 1H, major), 3.60-3.48 (m, 1H, minor), 2.79 (s, 3H, major), 2.66 (s, 3H, minor), 2.38 (d, J=12.2 Hz, 2H), 2.35-2.29 (m, 3H), 2.22-2.16 (m, 2H), 2.02 (s, 3H, minor), 1.96 (s, 3H, minor), 1.96-1.84 (m, 1H), 1.83-1.67 (m, 3H), 1.67-1.41 (m, 6H), 1.28-1.02 (m, 3H).

Example 112

N-(trans-4-(2-((5-(4-(trans-1-amino-3-hydroxy-3-methylcyclobutyl)-3-fluorophenyl)-4-phenylpyridin-2-yl)amino)-2-oxoethyl)cyclohexyl)-N-methylpropionamide

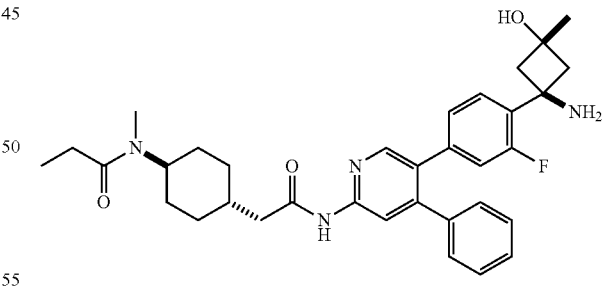

Step 1: tert-butyl (trans-1-(2-fluoro-4-(6-(2-(trans-4-(N-methylpropionamido)cyclohexyl)acetamido)-4-phenylpyridin-3-yl)phenyl)-3-hydroxy-3-methylcyclobutyl)carbamate: The title compound (15 mg, 0.021 mmol, 95% purity) was isolated as a colourless solid from the reaction of the product from Example 111 Step 9 (50 mg, 0.086 mmol, 80% purity), the product from Example 82 Step 2 (27 mg, 0.119 mmol), 1-chloro-N,N,2-trimethylprop-1-en-1-amine (28.8 μl, 0.216 mmol) and pyridine (34.9 μl, 0.431 mmol) in DCM (4 ml) using essentially the same procedure as in Example 111 Step 10. LCMS (Method 1): m/z 673 (M+H)⁺ at 2.33 min.

Step 2: N-(trans-4-(2-((5-(4-(trans-1-amino-3-hydroxy-3-methylcyclobutyl)-3-fluorophenyl)-4-phenylpyridin-2-yl)amino)-2-oxoethyl)cyclohexyl)-N-methylpropionamide:
The title compound (9 mg, 0.015 mmol, 95% purity) was isolated as a colourless solid from the reaction of the product from Step 1 above (15 mg, 0.021 mmol, 95% purity) with TFA (166 μl, 2.16 mmol) in DCM (3 ml) using essentially the same procedure as in Example 111 Step 11. LCMS (Method 1): m/z 573 (M+H)+, 571 (M−H)−, at 1.44 min. $^1$H NMR (400 MHz, DMSO-d$_6$) δ 10.67 (s, 1H, minor), 10.65 (s, 1H, major), 8.33 (s, 1H), 8.17 (s, 1H), 7.41-7.35 (m, 3H), 7.24-7.18 (m, 2H), 7.12 (t, J=8.2 Hz, 1H), 6.93-6.86 (m, 2H), 4.74 (s, 1H), 4.31-4.18 (m, 1H, major), 3.64-3.54 (m, 1H, minor), 2.78 (s, 3H, major), 2.68 (s, 3H, minor), 2.42-2.30 (m, 4H), 2.26 (q, J=7.3 Hz, 2H), 2.22-2.13 (m, 2H), 1.94-1.67 (m, 4H), 1.64-1.54 (m, 1H), 1.54-1.39 (m, 2H), 1.49 (s, 3H), 1.27-1.05 (m, 2H), 0.98 (t, J=7.3 Hz, 3H, major), 0.97 (t, J=7.3 Hz, 3H, major).

Example 113

N-(trans-4-(2-((6-(4-(trans-1-amino-3-hydroxy-3-methylcyclobutyl)phen)-5-phenylpyridazin-3-yl)amino)-2-oxoethyl)cyclohexyl)-N-ethylpropionamide

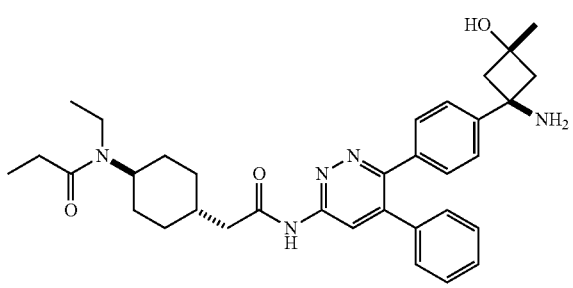

Step 1: Ethyl 2-(trans-4-(N-ethylpropionamido)cyclohexyl)acetate: The title compound (84 mg, 0.296 mmol, 95% purity) was isolated as a yellow oil from the reaction of the product from Example 106 Step 1 (200 mg), propionyl chloride (90 μl, 1.03 mmol) and DIPEA (491 μl, 2.81 mmol) in THF (5 ml) using essentially the same procedure as in Example 101 Step 1. LCMS (Method 1): m/z 270 (M+H)$^+$ at 2.02 min.

Step 2: 2-(trans-4-(N-ethylpropionamido)cyclohexyl)acetic acid: A solution of the product from Step 1 above (84 mg, 0.296 mmol, 95% purity) in THF (2 ml), water (1.5 ml) and MeOH (0.2 ml) was treated with LiOH (14.9 mg, 0.624 mmol) and the resultant mixture was stirred at RT for 18 h. The mixture was diluted with 0.5 M NaOH (20 ml) and washed with EtOAc (20 ml). The aqueous phase was acidified to pH 1 using 1 M HCl(aq) and extracted with EtOAc (2×20 ml). The combined extracts were washed with water (20 ml), brine (20 ml), dried over MgSO$_4$, filtered and concentrated under reduced pressure. To remove residual acetic acid formed during the EtOAc washes, five times the residue was suspended in toluene (5 ml) and concentrated in vacuo to afford the title compound (67 mg) as a colourless solid. This material was used directly in subsequent reactions without purification.

Step 3: tert-butyl (trans-1-(4-(6-(2-(trans-4-(N-ethylpropionamido)cyclohexyl)acetamido)-4-phenylpyridazin-3-yl)phenyl)-3-hydroxy-3-methylcyclobutyl)carbamate: The title compound (24 mg, 0.034 mmol, 95% purity) was isolated as a pale pink solid from the reaction of the product from Example 57 Step 1 (38 mg, 0.085 mmol), the product from Step 2 above (24 mg), HATU (42 mg, 0.110 mmol) and DIPEA (38.2 μl, 0.215 mmol) in DMF (1.5 ml) using essentially the same procedure as in Example 102 Step 1. LCMS (Method 1): m/z 670 (M+H)$^+$ at 2.30 min.

Step 4: N-(trans-4-(2-((6-(4-(trans-1-amino-3-hydroxy-3-methylcyclobutyl)phenyl)-5-phenylpyridazin-3-yl)amino)-2-oxoethyl)cyclohexyl)-N-ethylpropionamide: A solution of the product from Step 3 above (24 mg, 0.034 mmol, 95% purity) in DCM (1 ml) was treated with TFA (100 μl, 1.30 mmol) and the resultant mixture stirred at RT for 16 h. The reaction mixture was loaded onto a column of SCX. The column was washed with MeOH and the product was eluted with a 0.7 M solution of ammonia in MeOH, then concentrated in vacuo to afford a white solid (17.3 mg). Purification by preparative HPLC (Gilson 215, Waters X-Bridge Prep-C18, 5 μm, 19×50 mm column, 20-50% MeCN in ammonium bicarbonate(aq)) afforded a colourless solid (14.5 mg). This material was loaded onto a column of SCX in MeOH. The column was washed with MeOH and the product was eluted with a 0.7 M solution of ammonia in MeOH, then concentrated in vacuo to afford the title compound (5.5 mg, 9.56 μmol, 99% purity) as a colourless solid. LCMS (Method 2): m/z 570 (M+H)$^+$ at 1.91 min. $^1$H NMR (400 MHz, Methanol-d$_4$) (two rotamers in a 1:1 ratio) δ 8.52 (m, 1H), 7.50-7.42 (m, 2H), 7.40-7.32 (m, 5H), 7.29-7.26 (m, 2H), 4.38-4.15 (m, 1H, rotamer), 3.82-3.62 (m, 1H, rotamer), 2.72 (d, J=13.3 Hz, 2H), 2.51-2.36 (m, 6H), 2.02-1.90 (m, 4H), 1.85-1.61 (m, 4H), 1.55 (s, 3H), 1.46-1.18 (m, 4H), 1.18-1.09 (m, 5H).

Example 114

N-(trans-4-(2-((6-(4-(trans-1-amino-3-hydroxy-3-methylcyclobutyl)phenyl)-5-phenylpyridazin-3-yl)amino)-2-oxoethyl)cyclohexyl)-N-ethylcyclopropanecarboxamide

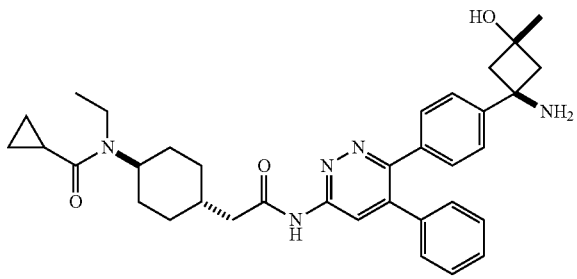

Step 1: Ethyl 2-(trans-4-(N-ethylcyclopropanecarboxamido)cyclohexyl)acetate: The title compound (96 mg, 0.324 mmol, 95% purity) was isolated as a beige solid from the reaction of the product from Example 106 Step 1 (200 mg), cyclopropanecarbonyl chloride (170 μl, 1.88 mmol) and DIPEA (491 μl, 2.81 mmol) in THF (5 ml) using essentially the same procedure as in Example 101 Step 1. LCMS (Method 1): m/z 254 (M+H)$^+$ at 1.60 min.

Step 2: 2-(trans-4-(N-ethylcyclopropanecarboxamido)cyclohexyl)acetic acid: The title compound (79 mg) was isolated as a colourless gum from the reaction of the product from Step 1 above (96 mg, 0.324 mmol, 95% purity) with LiOH (16.3 mg, 0.682 mmol) in a mixture of THF (2 ml), water (1.5 ml) and MeOH (0.2 ml) using essentially the same procedure as in Example 113 Step 2.

Step 3: tert-butyl (trans-1-(4-(6-(2-(trans-4-(N-ethylcyclopropanecarboxamido)cyclohexyl)acetamido)-4-phenylpyridazin-3-yl)phenyl)-3-hydroxy-3-methylcyclobutyl)carbamate: The title compound (18.7 mg, 0.017 mmol, 62% purity) was isolated as a colourless solid from the reaction of the product from Example 57 Step 1 (40 mg, 0.090 mmol), the product from Step 2 above (27.3 mg), HATU (41 mg, 0.108 mmol) and DIPEA (39 µl, 0.220 mmol) in DMF (1.5 ml) using essentially the same procedure as in Example 102 Step 1. LCMS (Method 1): m/z 682 (M+H)$^+$ at 2.37 min.

Step 4: N-(trans-4-(2-((6-(4-(trans-1-amino-3-hydroxy-3-methylcyclobutyl)phenyl)-5-phenylpyridazin-3-yl)amino)-2-oxoethyl)cyclohexyl)-N-ethylcyclopropanecarboxamide: The title compound (8.1 mg, 0.014 mmol, 99% purity) was isolated as a colourless solid from the reaction of the product from Step 3 above (18.7 mg, 0.017 mmol, 62% purity) with TFA (100 µl, 1.30 mmol) in DCM (1 ml) using essentially the same procedure as in Example 113 Step 4. LCMS (Method 2): m/z 582 (M+H)$^+$ at 1.98 min. $^1$H NMR (400 MHz, Methanol-$d_4$) (two rotamers in a 2:1 ratio) δ 8.51 (m, 1H), 7.49-7.42 (m, 2H), 7.42-7.30 (m, 5H), 7.29-7.23 (m, 2H), 4.30 (m, 1H, major), 4.17-4.05 (m, 1H, minor), 3.53 (q, J=7.1 Hz, 1H), 2.73 (d, J=13.2 Hz, 2H), 2.53-2.40 (m, 4H), 2.02-1.84 (m, 5H), 1.78-1.56 (m, 3H), 1.53 (s, 3H), 1.40-1.17 (m, 5H), 1.10 (t, J=7.0 Hz, 1H), 0.94-0.76 (m, 4H).

Example 115

N-(trans-4-(2-((5-(4-(trans-1-amino-3-hydroxy-3-methylcyclobutyl)phenyl)-4-phenylpyridin-2-yl)amino)-2-oxoethyl)cyclohexyl)-N-ethylpropionamide

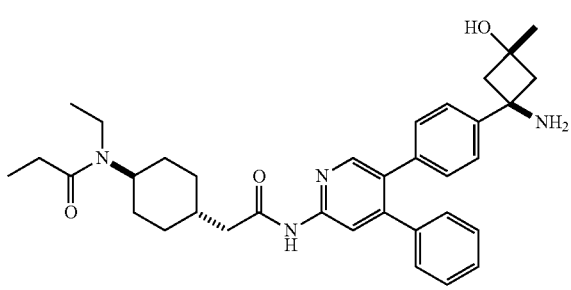

Step 1: tert-butyl (trans-1-(4-(6-(2-(trans-4-(N-ethylpropionamido)cyclohexyl)acetamido)-4-phenylpyridin-3-yl)phenyl)-3-hydroxy-3-methylcyclobutyl)carbamate: A solution of the product from Example 113 Step 2 (26.0 mg) in DCM (5 ml) was treated with 1-chloro-N,N,2-trimethylprop-1-en-1-amine (18 µl, 0.135 mmol) and the resultant solution was stirred at RT for 30 min. A solution of the product from Example 67 Step 2 (40 mg, 0.090 mmol) in pyridine (0.5 ml) was added and the resultant solution stirred for 18 h at RT. The mixture was diluted with DCM (10 ml), then 1 M HCl(aq) (10 ml) was added and the mixture was stirred for 15 min. The phases were separated and the organic phase concentrated under reduced pressure to afford a colourless oil. Purification by column chromatography (12 g cartridge, 0-6% (0.7 M NH$_3$/MeOH)/DCM) furnished the title compound (55 mg, 0.049 mmol, 60% purity) as a white solid. LCMS (Method 1): m/z 669 (M+H)$^+$ (ES$^+$) at 2.37 min.

Step 2: N-(trans-4-(2-((5-(4-(trans-1-amino-3-hydroxy-3-methylcyclobutyl)phenyl)-4-phenylpyridin-2-yl)amino)-2-oxoethyl)cyclohexyl)-N-ethylpropionamide: The title compound (15.8 mg, 0.028 mmol, 99% purity) was isolated as a colourless solid from the reaction of the product from Step 3 above (55 mg, 0.049 mmol, 60% purity) with TFA (200 µl, 2.60 mmol) in DCM (1 ml) using essentially the same procedure as in Example 113 Step 4. LCMS (Method 1): m/z 569 (M+H)$^+$ at 1.99 min. $^1$H NMR (400 MHz, Methanol-$d_4$) (two rotamers in a 1:1 ratio) δ 8.29 (s, 1H), 8.17 (s, 1H), 7.41-7.34 (m, 2H), 7.33-7.23 (m, 3H), 7.27-7.07 (m, 4H), 4.25 (m, 1H, rotamer), 3.69 (m, 1H, rotamer), 2.75-2.65 (m, 2H), 2.48-2.34 (m, 6H), 1.99-1.82 (m, 4H), 1.81-1.58 (m, 4H), 1.53 (s, 3H), 1.39-1.16 (m, 4H), 1.16-1.07 (m, 5H).

Example 116

Methyl (trans-4-(2-((5-(4-(trans-1-amino-3-hydroxy-3-methylcyclobutyl)phenyl)-4-phenylpyridin-2-yl)amino)-2-oxoethyl)cyclohexyl) (ethyl)carbamate

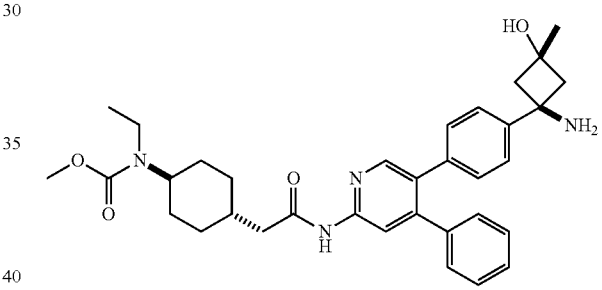

Step 1: Ethyl 2-(trans-4-(ethyl(methoxycarbonyl)amino)cyclohexyl)acetate: The title compound (112 mg, 0.392 mmol, 95% purity) was isolated as a waxy colourless solid from the reaction of the product from Example 106 Step 1 (224 mg), methyl chloroformate (177 µl, 2.29 mmol) and DIPEA (599 µl, 3.43 mmol) in THF (5 ml) using essentially the same procedure as in Example 101 Step 1, except the compound was purified by column chromatography (12 g cartridge, 0-50% EtOAc/isohexane). LCMS (Method 1): m/z 272 (M+H)$^+$ at 2.27 min.

Step 2: 2-(trans-4-(ethyl(methoxycarbonyl)amino)cyclohexyl)acetic acid: a solution of the product from Step 1 above (112 mg, 0.392 mmol, 95% purity) in THF (2 ml), water (1.5 ml) and MeOH (0.2 ml) was treated with LiOH (20 mg, 0.835 mmol) and the mixture was stirred at RT for 18 h. The mixture was diluted with 0.5 M NaOH(aq) (20 ml) and washed with DCM (20 ml). The aqueous phase was acidified to pH 1 using 1 M HCl(aq) and extracted with EtOAc (2×20 ml). The combined extracts were sequentially washed with water (20 ml) and brine (20 mL), dried over MgSO$_4$, filtered and concentrated under reduced pressure to furnish the title compound (97 mg, 0.379 mmol, 95% purity) as a colourless gum. $^1$H NMR (400 MHz, DMSO-$d_6$) δ

12.04 (s, 1H), 3.70 (br s, 1H), 3.58 (s, 3H), 3.13 (m, 2H), 2.10 (d, J=7.0 Hz, 2H), 1.75 (m, 2H), 1.64-1.44 (m, 5H), 1.11-0.95 (m, 5H).

Step 3: Methyl (trans-4-(2-((5-(4-(1-((tert-butoxycarbonyl)amino)-3-hydroxy-3-methylcyclobutyl)phenyl)-4-phenylpyridin-2-yl)amino)-2-oxoethyl)cyclohexyl)(ethyl)carbamate: The title compound (42 mg, 0.060 mmol, 96% purity) was isolated as a colourless solid from the reaction of the product from Example 67 Step 2 (40 mg, 0.090 mmol), the product from Step 2 above (21.8 mg, 0.086 mmol), 1-chloro-N,N,2-trimethylprop-1-en-1-amine (18 µl, 0.135 mmol) and pyridine (0.5 ml) in DCM (5 ml) using essentially the same procedure as in Example 115 Step 1. LCMS (Method 1): m/z 671 (M+H)$^+$ at 2.54 min.

Step 4: Methyl (trans-4-(2-((5-(4-(trans-1-amino-3-hydroxy-3-methylcyclobutyl)phenyl)-4-phenylpyridin-2-yl)amino)-2-oxoethyl)cyclohexyl)(ethyl)carbamate: A solution of the product from Step 3 above (42 mg, 0.060 mmol, 96% purity) in DCM (1 ml) was treated with TFA (200 µl, 2.60 mmol) and the resultant mixture stirred at RT for 18 h. The reaction mixture was concentrated in vacuo and loaded onto a column of SCX in MeOH. The column was washed with MeOH and the product was eluted with a 0.7 M solution of ammonia in MeOH, then concentrated in vacuo to afford a colourless solid (31 mg). Purification by preparative HPLC (Waters FractionLynx, Waters X-Bridge Prep-C18, 5 µm, 19×50 mm column, 35-65% MeCN in ammonium bicarbonate(aq)) afforded the title compound (7.7 mg, 13 µmol, 99% purity) as a colourless solid. LCMS (Method 2): m/z 571 (M+H)$^+$ at 2.18 min. $^1$H NMR (400 MHz, Methanol-d$_4$) δ 8.30 (s, 1H), 8.18 (s, 1H), 7.42-7.34 (m, 2H), 7.33-7.26 (m, 3H), 7.25-7.19 (m, 2H), 7.18-7.12 (m, 2H), 3.87 (m, 1H), 3.70 (s, 3H), 3.24 (m, 2H), 2.77-2.64 (m, 2H), 2.45-2.35 (m, 4H), 1.91 (m, 3H), 1.79-1.58 (m, 4H), 1.55 (s, 3H), 1.23 (m, 2H), 1.13 (t, J=7.0 Hz, 3H).

Example 117

N-(5-(4-(trans-1-amino-3-hydroxy-3-methylcyclobutyl)phenyl)-4-phenylpyridin-2-yl)-2-(trans-4-(N-(2,2,2-trifluoroethyl)acetamido)cyclohexyl)acetamide

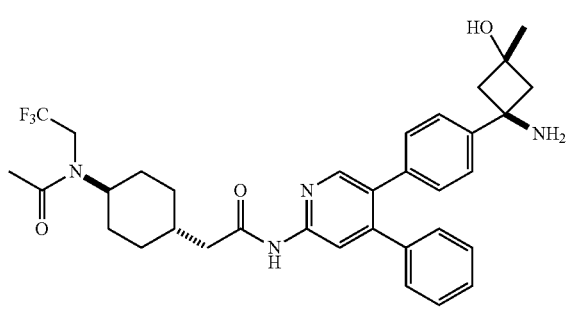 [SMILES: CC(=O)N(CC(F)(F)F)[C@H]1CC[C@H](CC(=O)Nc2cc(-c3ccccc3)c(-c3ccc([C@]4(N)C[C@](C)(O)C4)cc3)cn2)CC1]

Step 1: Ethyl 2-(trans-4-((2,2,2-trifluoroethyl)amino)cyclohexyl)acetate: A solution of ethyl 2-(trans-4-aminocyclohexyl)acetate hydrochloride (1.11 g, 5.01 mmol) and DIPEA (2.19 ml, 12.5 mmol) in THF (10 ml) was treated with 2,2,2-trifluoroethyl trifluoromethanesulfonate (1.08 ml, 7.51 mmol) and the resultant mixture stirred at 50° C. for 3 days. Additional 2,2,2-trifluoroethyl trifluoromethanesulfonate (1.08 ml, 7.51 mmol) was added and the mixture was stirred at 50° C. for a further 5 days. The reaction mixture was cooled to RT and concentrated in vacuo. The residue was partitioned between water (10 ml) and DCM (10 ml). The organic phase was passed through a phase separation cartridge and concentrated in vacuo to afford the title compound as pale brown gum (2.1 g). This material was used in subsequent reactions without purification.

Step 2: Ethyl 2-(trans-4-(N-(2,2,2-trifluoroethyl)acetamido)cyclohexyl)acetate: A solution of the product from Step 1 above (730 mg) and DIPEA (1.43 ml, 8.19 mmol) in THF (10 ml) was cooled to 0° C. and treated dropwise with acetic anhydride (515 µl, 5.46 mmol). The resultant mixture was allowed to warm to RT and stir for 20 h. Additional DIPEA (1.43 ml, 8.19 mmol) and acetic anhydride (515 µl, 5.46 mmol) were added and the mixture heated to 40° C. for a further 20 h. The mixture was cooled to RT, then poured into saturated Na$_2$CO$_3$(aq) (25 ml) and extracted with EtOAc (2×25 ml). The combined organic phases were sequentially washed with 1 M HCl(aq) (25 ml), water (25 ml) and brine (25 ml), then dried over MgSO$_4$, filtered and concentrated under reduced pressure to furnish the title compound (580 mg) as a pale brown oil. This material was used in subsequent reactions without purification.

Step 3: 2-(trans-4-(N-(2,2,2-trifluoroethyl)acetamido)cyclohexyl)acetic acid: The title compound (520 mg, 1.76 mmol, 95% purity) was isolated as a colourless oil from the reaction of the product from Step 2 above (580 mg) with LiOH (90 mg, 3.75 mmol) in a mixture of THF (4 ml), water (3 ml) and MeOH (0.2 ml) using essentially the same procedure as in Example 113 Step 2. LCMS (Method 1): m/z 282 (M+H)$^+$ at 1.57 min.

Step 4: tert-butyl (3-hydroxy-3-methyl-1-(4-(4-phenyl-6-(2-(trans-4-(N-(2,2,2-trifluoroethyl)acetamido)cyclohexyl)acetamido)pyridin-3-yl)phenyl)cyclobutyl)carbamate: The title compound (45 mg, 0.062 mmol, 98% purity) was isolated as a colourless solid from the reaction of the product from Example 67 Step 2 (40 mg, 0.090 mmol), the product from Step 3 above (25.3 mg, 0.086 mmol), 1-chloro-N,N,2-trimethylprop-1-en-1-amine (18 µl, 0.135 mmol) and pyridine (0.5 ml) in DCM (5 ml) using essentially the same procedure as in Example 115 Step 1. LCMS (Method 1): m/z 709 (M+H)$^+$ at 2.41 min.

Step 5: N-(5-(4-(trans-1-amino-3-hydroxy-3-methylcyclobutyl)phenyl)-4-phenylpyridin-2-yl)-2-(trans-4-(N-(2,2,2-trifluoroethyl)acetamido)cyclohexyl)acetamide: The title compound (16.7 mg, 0.027 mmol, 99% purity) was isolated as a white solid from the reaction of the product from Step 4 above (45 mg, 0.062 mmol, 98% purity) with TFA (200 µl, 2.60 mmol) in DCM (1 ml) using essentially the same procedure as in Example 116 Step 4. LCMS (Method 2): m/z 609 (M+H)$^+$ at 2.06 min. $^1$H NMR (400 MHz, Methanol-d$_4$) (two rotamers in a 2:1 ratio) δ 8.30 (s, 1H), 8.19 (s, 1H), 7.42-7.34 (m, 2H), 7.32-7.26 (m, 3H), 7.30-7.18 (m, 2H), 7.19-7.11 (m, 2H), 4.22-4.04 (m, 2H), 4.00-3.87 (m, 1H, minor), 3.86-3.70 (m, 1H, major), 2.72-2.64 (m, 2H), 2.44-2.35 (m, 4H), 2.24 (s, 3H, major), 2.16 (s, 3H, minor), 2.01-1.59 (m, 7H), 1.55 (s, 3H), 1.29 (m, 2H).

Example 118

Methyl (trans-4-(2-((6-(4-(trans-1-amino-3-hydroxy-3-methylcyclobutyl)phenyl)-5-phenylpyridin-3-yl)amino)-2-oxoethyl)cyclohexyl) (ethyl)carbamate

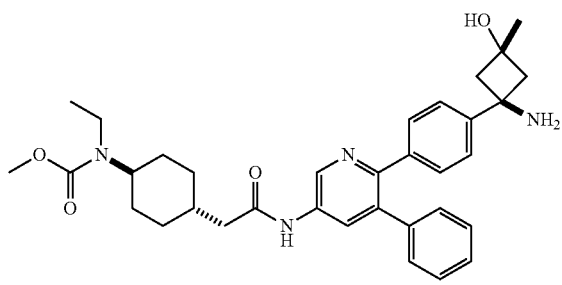 [SMILES: CCN(C(=O)OC)[C@H]1CC[C@H](CC(=O)Nc2cnc(-c3ccc([C@]4(N)C[C@](C)(O)C4)cc3)c(-c3ccccc3)c2)CC1]

Step 1: Methyl (trans-4-(2-((6-(4-(trans-1-((tert-butoxycarbonyl)amino)-3-hydroxy-3-methylcyclobutyl)phenyl)-5-phenylpyridin-3-yl)amino)-2-oxoethyl)cyclohexyl)(ethyl)carbamate: The title compound (42 mg, 0.061 mmol, 98% purity) was isolated as a pale yellow solid from the reaction of Intermediate 1 (40 mg, 0.090 mmol), the product from Example 116 Step 2 (21 mg, 0.082 mmol, 95% purity), HATU (38.8 mg, 0.102 mmol) and DIPEA (41 μl, 0.236 mmol) in DMF (2 ml) using essentially the same procedure as in Example 102 Step 1. LCMS (Method 1): m/z 671 (M+H)$^+$ at 2.20 min.

Step 2: Methyl (trans-4-(2-((6-(4-(trans-1-amino-3-hydroxy-3-methylcyclobutyl)phenyl)-5-phenylpyridin-3-yl)amino)-2-oxoethyl)cyclohexyl)(ethyl)carbamate: The title compound (17.7 mg, 0.031 mmol, 99% purity) was isolated as a pale yellow solid from the reaction of the product from Step 1 above (42 mg, 0.061 mmol, 98% purity) with TFA (200 μl, 2.60 mmol) in DCM (1 ml) using essentially the same procedure as in Example 116 Step 4. LCMS (Method 2): m/z 571 (M+H)$^+$ at 2.05 min. $^1$H NMR (400 MHz, Methanol-d$_4$) δ 8.82 (d, J=2.4 Hz, 1H), 8.16 (d, J=2.4 Hz, 1H), 7.40-7.32 (m, 2H), 7.31-7.27 (m, 5H), 7.28-7.16 (m, 2H), 3.86 (br s, 1H), 3.70 (s, 3H), 3.31-3.17 (m, 2H), 2.71-2.63 (m, 2H), 2.45-2.32 (m, 4H), 1.97-1.83 (m, 3H), 1.79-1.72 (m, 2H), 1.65 (qd, J=12.6, 3.4 Hz, 2H), 1.55 (s, 3H), 1.29-1.18 (m, 2H), 1.14 (t, J=7.0 Hz, 3H).

Example 119

N-(6-(4-(trans-1-amino-3-hydroxy-3-methylcyclobutyl)phenyl)-5-phenylpyridin-3-yl)-2-(trans-4-(N-ethylacetamido)cyclohexyl)acetamide

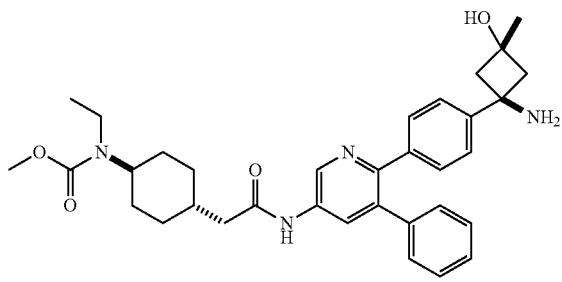 [SMILES: CCN(C(=O)OC)[C@H]1CC[C@H](CC(=O)Nc2cnc(-c3ccc([C@]4(N)C[C@](C)(O)C4)cc3)c(-c3ccccc3)c2)CC1]

Step 1: tert-butyl (trans-1-(4-(5-(2-(trans-4-(N-ethylacetamido)cyclohexyl)acetamido)-3-phenylpyridin-2-yl)phenyl)-3-hydroxy-3-methylcyclobutyl)carbamate: The title compound (30 mg, 37 μmol, 82% purity) was isolated as a yellow solid from the reaction of Intermediate 1 (24 mg, 0.054 mmol), the product from Example 113 Step 2 (13 mg), HATU (26.6 mg, 0.070 mmol) and DIPEA (28 μl, 0.162 mmol) in DMF (2 ml) using essentially the same procedure as in Example 102 Step 1. LCMS (Method 1): m/z 669 (M+H)$^+$ at 2.10 min.

Step 2: N-(6-(4-(trans-1-amino-3-hydroxy-3-methylcyclobutyl)phenyl)-5-phenylpyridin-3-yl)-2-(trans-4-(N-ethylacetamido)cyclohexyl)acetamide: The title compound (10.6 mg, 0.019 mmol, 99% purity) was isolated as a white solid from the reaction of the product from Step 1 above (30 mg, 37 μmol, 82% purity) with TFA (200 μl, 2.60 mmol) in DCM (1 ml) using essentially the same procedure as in Example 116 Step 4. LCMS (Method 2): m/z 569 (M+H)$^+$ at 1.83 min. $^1$H NMR (400 MHz, Methanol-d$_4$) (two rotamers in a 1:1 ratio) δ 8.82 (d, J=2.2 Hz, 1H, rotamer), 8.81 (d, J=2.2 Hz, 1H, rotamer), 8.16 (t, J=2.3 Hz, 1H, rotamer), 8.15 (t, J=2.3 Hz, 1H, rotamer), 7.42-7.33 (m, 2H), 7.31-7.27 (m, 5H), 7.25-7.17 (m, 2H), 4.34-4.22 (m, 1H, rotamer), 3.78-3.64 (m, 1H, rotamer), 3.36-3.34 (m, 2H), 2.71-2.61 (m, 2H), 2.49-2.31 (m, 6H), 2.05-1.60 (m, 7H), 1.55 (s, 3H), 1.42-1.11 (m, 8H).

Example 120

N-(6-(4-(trans-1-amino-3-hydroxy-3-methylcyclobutyl)phenyl)-5-phenylpyridin-3-yl)-2-(trans-4-(N-isopropylacetamido)cyclohexyl)acetamide

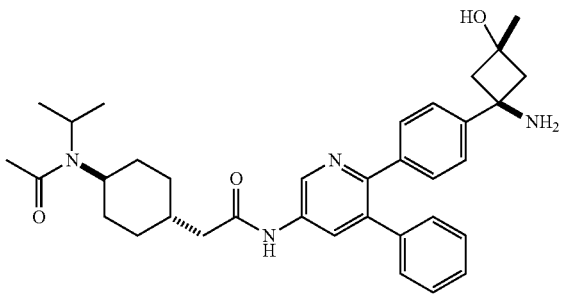 [SMILES: CC(=O)N(C(C)C)[C@H]1CC[C@H](CC(=O)Nc2cnc(-c3ccc([C@]4(N)C[C@](C)(O)C4)cc3)c(-c3ccccc3)c2)CC1]

Step 1: tert-butyl (trans-3-hydroxy-1-(4-(5-(2-(trans-4-(N-isopropylacetamido)cyclohexyl)acetamido)-3-phenylpyridin-2-yl)phenyl)-3-methylcyclobutyl)carbamate: The title compound (26.3 mg, 0.038 mmol, 97% purity) was isolated as a yellow solid from the reaction of Intermediate 1 (40 mg, 0.090 mmol), the product from Example 49 Step 3 (26 mg, 0.108 mmol), HATU (44.4 mg, 0.117 mmol) and DIPEA (47 μl, 0.269 mmol) in DMF (2 ml) using essentially the same procedure as in Example 102 Step 1. LCMS (Method 1): m/z 669 (M+H)$^+$ at 2.13 min.

Step 2: N-(6-(4-(trans-1-amino-3-hydroxy-3-methylcyclobutyl)phenyl)-5-phenylpyridin-3-yl)-2-(trans-4-(N-isopropylacetamido)cyclohexyl)acetamide: A solution of the product from Step 1 above (26.3 mg, 0.038 mmol, 97% purity) in DCM (1 ml) was treated with TFA (200 μl, 2.60 mmol) and the resultant mixture was stirred at RT for 16 h. The mixture was concentrated in vacuo and the residue loaded onto a column of SCX. The column was washed with MeOH (3×5 ml) and the product was eluted with a 0.7 M solution of ammonia in MeOH (3×5 ml), then concentrated in vacuo to afford a white solid (20 mg). Further purification by column chromatography (12 g RediSep® Rf Reversed phase C-18 cartridge, 20-65% MeCN in 0.1% ammonium bicarbonate(aq)) to furnish a yellow solid. Further purification using SCX as described above furnished the title compound (14.6 mg, 0.024 mmol, 94% purity) as a pale yellow solid. LCMS (Method 2): m/z 569 (M+H)$^+$ at 1.84 min. $^1$H NMR (400 MHz, Methanol-d$_4$) (two rotamers in a 1:1 ratio) δ 8.82 (d, J=2.5 Hz, 1H, rotamer), 8.81 (d, J=2.5 Hz, 1H, rotamer), 8.17 (d, J=2.5 Hz, 1H), 7.39-7.34 (m, 2H), 7.34-7.22 (m, 5H), 7.25-7.17 (m, 2H), 4.07 (p, J=6.7 Hz, 1H, rotamer), 3.59 (s, 1H, rotamer), 2.72-2.66 (m, 2H), 2.56-2.46 (m, 1H), 2.46-2.32 (m, 4H), 2.10 (s, 3H), 2.01-1.66 (m, 6H), 1.59 (br s, 1H), 1.55 (s, 3H), 1.38 (d, J=6.8 Hz, 3H), 1.34-1.17 (m, 5H).

Example 121

Methyl (trans-4-(2-((6-(4-(trans-1-amino-3-hydroxy-3-methylcyclobutyl)phenyl)-5-phenylpyridin-3-yl)amino)-2-oxoethyl)cyclohexyl) (isopropyl)carbamate

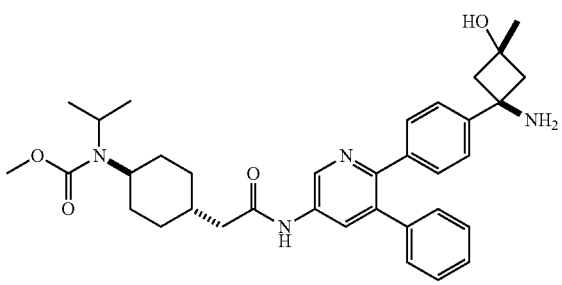 [SMILES: COC(=O)N(C(C)C)[C@H]1CC[C@H](CC(=O)Nc2cnc(-c3ccc([C@]4(N)C[C@](C)(O)C4)cc3)c(-c3ccccc3)c2)CC1]

Step 1: Methyl (trans-4-(2-((6-(4-(trans-1-((tert-butoxycarbonyl)amino)-3-hydroxy-3-methylcyclobutyl)phenyl)-5-phenylpyridin-3-yl)amino)-2-oxoethyl)cyclohexyl)(isopropyl)carbamate: The title compound (47.1 mg, 0.069 mmol) was isolated as a pale yellow solid from the reaction of Intermediate 1 (40 mg, 0.090 mmol), the product from Example 101 Step 2 (27.7 mg, 0.103 mmol, 95% purity), HATU (44.4 mg, 0.117 mmol) and DIPEA (47 μl, 0.269 mmol) in DMF (2 ml) using essentially the same procedure as in Example 102 Step 1. LCMS (Method 1): m/z 685 (M+H)$^+$ at 2.32 min.

Step 2: Methyl (trans-4-(2-((6-(4-(trans-1-amino-3-hydroxy-3-methylcyclobutyl)phenyl)-5-phenylpyridin-3-yl)amino)-2-oxoethyl)cyclohexyl)(isopropyl)carbamate: The title compound (28.8 mg, 0.047 mmol, 96% purity) was isolated as a yellow solid from the reaction of the product from Step 1 above (47.1 mg, 0.069 mmol) with TFA (200 μl, 2.60 mmol) in DCM (1 ml) using essentially the same procedure as in Example 120 Step 2, except, after column chromatography, no further purification was carried out. LCMS (Method 2): m/z 585 (M+H)$^+$ at 2.09 min. $^1$H NMR (400 MHz, Methanol-d$_4$) δ 8.82 (d, J=2.5 Hz, 1H), 8.16 (d, J=2.4 Hz, 1H), 7.39-7.34 (m, 2H), 7.32-7.23 (m, 5H), 7.26-7.17 (m, 2H), 3.91 (br s, 1H), 3.68 (s, 3H), 3.59 (br s, 1H), 2.72-2.61 (m, 2H), 2.44-2.32 (m, 4H), 1.99-1.81 (m, 5H), 1.72-1.63 (m, 2H), 1.55 (s, 3H), 1.31-1.16 (m, 8H).

Example 122

N-(trans-4-(2-((6-(4-(trans-1-amino-3-hydroxy-3-methylcyclobutyl)phenyl)-5-phenylpyridin-3-yl)amino)-2-oxoethyl)cyclohexyl)-N-isopropylpropionamide

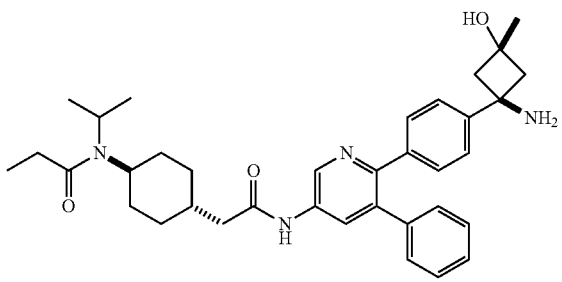 [SMILES: CCC(=O)N(C(C)C)[C@H]1CC[C@H](CC(=O)Nc2cnc(-c3ccc([C@]4(N)C[C@](C)(O)C4)cc3)c(-c3ccccc3)c2)CC1]

Step 1: tert-butyl (trans-3-hydroxy-1-(4-(5-(2-(trans-4-(N-isopropylpropionamido)cyclohexyl)acetamido)-3-phenylpyridin-2-yl)phenyl)-3-methylcyclobutyl)carbamate: The title compound (44.7 mg, 0.062 mmol, 95% purity) was isolated as a pale yellow solid from the reaction of Intermediate 1 (40 mg, 0.090 mmol), the product from Example 104 Step 2 (27.5 mg), HATU (44.4 mg, 0.117 mmol) and DIPEA (47 μl, 0.269 mmol) in DMF (2 ml) using essentially the same procedure as in Example 102 Step 1. LCMS (Method 1): m/z 683 (M+H)$^+$ at 2.25 min.

Step 2: N-(trans-4-(2-((6-(4-(trans-1-amino-3-hydroxy-3-methylcyclobutyl)phenyl)-5-phenylpyridin-3-yl)amino)-2-oxoethyl)cyclohexyl)-N-isopropylpropionamide: The title compound (25.7 mg, 0.041 mmol, 94% purity) was isolated as a pale yellow solid from the reaction of the product from Step 1 above (44.7 mg, 0.062 mmol, 95% purity) with TFA (200 μl, 2.60 mmol) in DCM (1 ml) using essentially the same procedure as in Example 120 Step 2, except, after column chromatography, no further purification was carried out. LCMS (Method 3): m/z 583 (M+H)$^+$ (ES$^+$) at 4.95 min. $^1$H NMR (400 MHz, Methanol-d$_4$) (two rotamers in a 1:1 ratio) δ 8.82 (d, J=2.4 Hz, 1H, rotamer), 8.81 (d, J=2.4 Hz, 1H, rotamer), 8.17 (d, J=2.4 Hz, 1H), 7.40-7.33 (m, 2H), 7.33-7.22 (m, 5H), 7.26-7.16 (m, 2H), 4.21-4.03 (m, 1H, rotamer), 3.69-3.58 (m, 1H), 3.22-3.06 (m, 1H, rotamer), 2.71-2.63 (m, 2H), 2.61-2.44 (m, 1H), 2.45-2.31 (m, 4H), 2.00-1.69 (m, 5H), 1.76-1.51 (m, 4H), 1.38 (d, J=6.7 Hz, 3H), 1.33-1.17 (m, 5H), 1.11 (t, J=7.4 Hz, 3H).

Example 123

N-(trans-4-(2-((6-(4-(trans-1-amino-3-fluorocyclobutyl)phenyl)-5-phenylpyridazin-3-yl)amino)-2-oxoethyl)cyclohexyl)-N-methylpropionamide

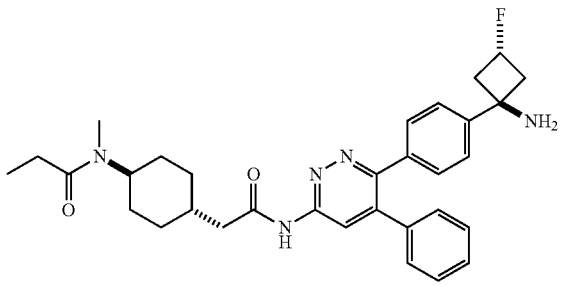 [SMILES: CCC(=O)N(C)[C@H]1CC[C@H](CC(=O)Nc2cc(-c3ccccc3)c(-c3ccc([C@]4(N)C[C@H](F)C4)cc3)nn2)CC1]

A stirred solution of the product from Example 82 Step 2 (50.2 mg, 0.221 mmol) and HATU (252 mg, 0.663 mmol) in DMF (5 ml) was treated with DIPEA (0.183 ml, 1.11 mmol) and the reaction was stirred at RT for 30 min. The product from Example 45 Step 1 (96 mg, 0.221 mmol) was added and the resultant mixture was stirred at 50° C. overnight. The reaction mixture was allowed to cool and saturated NaHCO$_3$ (aq) (10 ml) was added. EtOAc (5 ml) was added and the phases separated. The aqueous phase was extracted with EtOAc (10 ml) and the combined organic phases were washed with brine (10 ml), dried over MgSO$_4$, filtered and the solvent removed in vacuo. The residue was purified by column chromatography (12 g cartridge, 0-10% (0.7 M NH$_3$/MeOH)/DCM) to afford a yellow solid. This material was dissolved in DCM (5 ml), treated with TFA (0.5 ml) and the resultant solution was stirred at RT for 4 h. NaHCO$_3$(aq) solution (10 ml) was added and the mixture was stirred for 10 min. The organic phase was passed through a phase separation cartridge and concentrated in vacuo. The residue was purified by column chromatography (12 g cartridge, 0-10% (0.7 M NH$_3$/MeOH)/DCM) to afford the title compound (15.2 mg, 0.027 mmol, 98% purity) as a white solid. LCMS (Method 1): m/z 544 (M+H)$^+$ at 1.60 min. $^1$H NMR (400 MHz, DMSO-d$_6$) (two rotamers in a 6:5 ratio) δ 11.25 (s, 1H, minor), 11.24 (s, 1H, major), 8.32 (s, 1H), 7.40-7.30 (m, 3H), 7.31-7.19 (m, 6H), 5.73 (s, 1H), 5.31 (dp, J=56.8, 6.6 Hz, 1H), 4.37-4.10 (m, 1H, major), 3.65-3.47 (m, 1H, minor), 2.75 (s, 3H, major), 2.64 (s, 3H, minor), 2.55-2.48 (m, 1H, obscured by DMSO-d$_5$), 2.41-2.05 (m, 8H), 1.85-1.66 (m, 3H), 1.63-1.32 (m, 4H), 1.23-1.00 (m, 2H), 0.94 (q, J=7.2 Hz, 3H).

Example 124

N-(6-(4-(trans-1-amino-3-hydroxy-3-methylcyclobutyl)-3-fluorophenyl)-5-phenylpyridin-3-yl)-2-(trans-4-(N-methylacetamido)cyclohexyl)acetamide

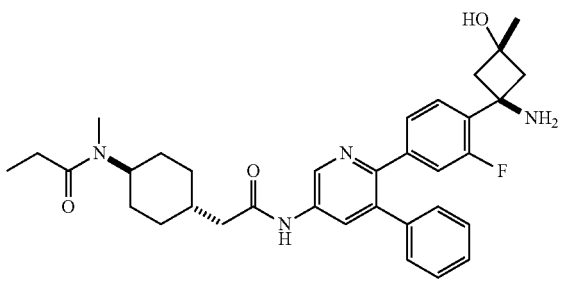 [SMILES: CCC(=O)N(C)[C@H]1CC[C@H](CC(=O)Nc2cnc(-c3ccc([C@]4(N)C[C@](C)(O)C4)c(F)c3)c(-c3ccccc3)c2)CC1]

Step 1: tert-butyl (trans-1-(4-(3-chloro-5-nitropyridin-2-yl)-2-fluorophenyl)-3-hydroxy-3-methylcyclobutyl)carbamate: A suspension of 2,3-dichloro-5-nitropyridine (300 mg, 1.56 mmol), the product from Example 111 Step 9 (688 mg, 1.31 mmol, 80% purity), tetrakis-(triphenylphosphine)palladium(0) (180 mg, 0.155 mmol) and 2 M Na$_2$CO$_3$(aq) (1.94 ml, 3.89 mmol) in dioxane (10 ml) was degassed with N$_2$ for 5 min and the resultant mixture was heated at 80° C. overnight. The reaction mixture was cooled to room temperature and concentrated on to silica, then purified by column chromatography (40 g cartridge, 0-50% EtOAc/isohexane) to afford the title compound (538 mg, 1.13 mmol, 95% purity) as a yellow oil. LCMS (Method 1): m/z 474 (M+Na)$^+$ at 2.25 min.

Step 2: tert-butyl (trans-1-(2-fluoro-4-(5-nitro-3-phenylpyridin-2-yl)phenyl)-3-hydroxy-3-methylcyclobutyl)carbamate: A solution of the product from Step 1 above (538 mg, 1.13 mmol, 95% purity), phenylboronic acid (0.172 g, 1.41 mmol), 2 M Na$_2$CO$_3$(aq) (1.32 ml, 2.64 mmol) and tetrakis-(triphenylphosphine)palladium(0) (0.136 g, 0.117 mmol) in dioxane (10 ml) was degassed with N$_2$ for 5 min and the resultant mixture was heated to 90° C. overnight. The reaction mixture was cooled to RT and concentrated on to silica, then purified by column chromatography (40 g cartridge, 0-50% EtOAc/isohexane) to afford the title compound (120 mg, 0.243 mmol) as a pale yellow solid. LCMS (Method 1): m/z 494 (M+H)$^+$ at 2.46 min. $^1$H NMR (400 MHz, DMSO-d$_6$) δ 9.45 (d, J=2.5 Hz, 1H), 8.52 (d, J=2.5 Hz, 1H), 7.58 (s, 1H), 7.47-7.15 (m, 6H), 7.06 (dd, J=26.5, 9.6 Hz, 2H), 4.90 (s, 1H), 2.79-2.19 (m, 4H), 1.46-1.09 (m, 12H).

Step 3: tert-butyl (trans-1-(4-(5-amino-3-phenylpyridin-2-yl)-2-fluorophenyl)-3-hydroxy-3-methylcyclobutyl)carbamate: The product from Step 2 above (120 mg, 0.243 mmol) was dissolved in a mixture of IPA (10 ml) and water (5 ml) and treated with iron powder (136 mg, 2.43 mmol) and NH$_4$Cl(s) (15.6 mg, 0.292 mmol). The resultant mixture was heated under reflux for 2 h. The reaction mixture was allowed to cool and was filtered through Celite®, washing with MeOH (50 ml). The filtrate was concentrated in vacuo and the residue dissolved in DCM (50 ml) and sequentially washed with water (50 ml) and brine (50 ml). The organic phase was dried over MgSO$_4$, filtered and the solvent was removed in vacuo to afford the title compound (103 mg, 0.220 mmol, 99% purity) as a white solid. LCMS (Method 1): m/z 464 (M+H)$^+$ at 1.55 min. $^1$H NMR (400 MHz, DMSO-d$_6$) δ 8.12 (d, J=2.6 Hz, 1H), 7.56 (s, 1H), 7.43-7.35 (m, 2H), 7.32-7.08 (m, 4H), 6.98 (d, J=2.6 Hz, 2H), 6.92-6.83 (m, 1H), 5.67 (s, 2H), 4.96 (s, 1H), 2.74-2.44 (m, 4H), 1.55-1.18 (m, 12H).

Step 4: N-(6-(4-(trans-1-amino-3-hydroxy-3-methylcyclobutyl)-3-fluorophenyl)-5-phenylpyridin-3-yl)-2-(trans-4-(N-methylacetamido)cyclohexyl)acetamide: A solution of the product from Example 1 Step 5 (27.6 mg, 0.129 mmol) and the product from Step 3 above (50 mg, 0.108 mmol, 99% purity) in DMF (5 ml) was treated with DIPEA (37.7 μl, 0.216 mmol) followed by HATU (49.2 mg, 0.129 mmol). The resultant mixture was heated at 50° C. for 3 days. The reaction mixture was allowed to cool and saturated NaHCO$_3$ (aq) (10 ml) was added. EtOAc (5 ml) was added and the phases separated. The aqueous phase was extracted with EtOAc (10 ml) and the combined organic phases were washed with brine (10 ml), dried over MgSO$_4$, filtered and the solvent removed in vacuo. The residue was purified by column chromatography (12 g cartridge, 0-10% (0.7 M NH$_3$/MeOH)/DCM). The resultant yellow solid was dissolved in DCM (5 ml) and treated with TFA (0.5 ml) and the solution was stirred at RT for 3 h. NaHCO$_3$(aq) (10 ml) was added and the mixture was stirred for 10 min. The organic phase was filtered through a phase separation cartridge and the concentrated in vacuo. The residue was purified by column chromatography (12 g cartridge, 0-10% (0.7 M NH$_3$/MeOH)/DCM) to afford the title compound (11 mg, 0.019 mmol, 96% purity) as a white solid. LCMS (Method 1): m/z 559 (M+H)$^+$ at 1.35 min. $^1$H NMR (400 MHz, Methanol-d$_4$) (two rotamers in a 6:5 ratio) δ 8.87 (d, J=2.4

Hz, 1H, major), 8.86 (d, J=2.4 Hz, 1H, major), 8.18 (t, J=2.2 Hz, 1H), 7.43-7.31 (m, 4H), 7.24 (dd, J=6.6, 3.0 Hz, 2H), 7.20-7.11 (m, 2H), 4.43-4.28 (m, 1H, major), 3.78-3.60 (m, 1H, minor), 2.93 (s, 3H, major), 2.85 (d, J=13.7 Hz, 2H), 2.82 (s, 3H, minor), 2.64 (d, J=13.7 Hz, 2H), 2.38 (t, J=6.5 Hz, 2H), 2.15 (s, 3H, minor), 2.10 (s, 3H, major), 2.02-1.54 (m, 7H), 1.52 (s, 3H), 1.39-1.16 (m, 2H).

Example 125

N-(6-(4-(trans-1-amino-3-fluorocyclobutyl)phenyl)-5-(thiophen-3-yl)pyridazin-3-yl)-2-(trans-4-(N-ethylacetamido)cyclohexyl)acetamide

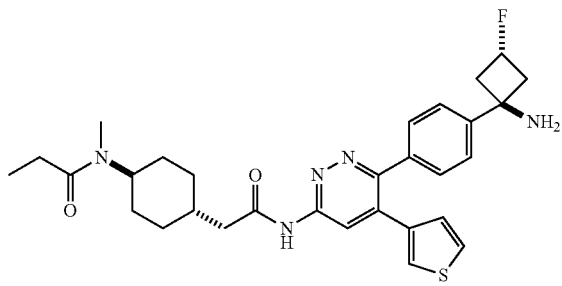 [SMILES: CCC(=O)N(C)[C@H]1CC[C@H](CC(=O)Nc2cc(-c3ccsc3)c(-c3ccc([C@]4(N)C[C@H](F)C4)cc3)nn2)CC1]

A solution of the product from Example 75 Step 4 (50 mg, 0.113 mmol) and the product from Example 82 Step 2 (31 mg, 0.136 mmol) in DMF (5 ml) was treated with DIPEA (39.6 µl, 0.227 mmol) followed by HATU (51.8 mg, 0.136 mmol). The resultant mixture was heated at 50° C. overnight. The reaction temperature was increased to 80° C. and the mixture stirred for a further 24 h. The reaction mixture was allowed to cool and saturated NaHCO$_3$(aq) (10 ml) was added. EtOAc (5 ml) was added and the phases separated. The aqueous phase was extracted with EtOAc (10 ml) and the combined organic phases were washed with brine (10 ml), dried over MgSO$_4$, filtered and the solvent removed in vacuo. The residue was purified by column chromatography (12 g cartridge, 0-10% (0.7 M NH$_3$/MeOH)/DCM) to afford a yellow solid, which was dissolved in DCM (5 ml) and treated with TFA (0.5 ml). The resultant solution was stirred at RT for 2 h. The reaction mixture was loaded directly onto a column of SCX in MeOH. The column was washed with MeOH (20 ml) and then the product was eluted with 0.7 M ammonia in MeOH (20 ml). The resultant mixture was concentrated in vacuo to afford the title compound (25.2 mg, 0.045 mmol, 99% purity) as an off-white solid. LCMS (Method 1): m/z 550 (M+H)$^+$ at 1.51 min. $^1$H NMR (400 MHz, DMSO-d$_6$) (two rotamers in a 3:2 ratio) δ 11.34 (s, 1H, minor), 11.33 (s, 1H, major), 8.52 (d, J=1.0 Hz, 1H), 7.75 (dd, J=2.9, 1.3 Hz, 1H), 7.65 (dd, J=5.0, 2.9 Hz, 1H), 7.50 (d, J=8.4 Hz, 2H), 7.47-7.43 (m, 2H), 6.90 (dd, J=5.0, 1.3 Hz, 1H), 5.47 (dp, J=56.8, 6.6 Hz, 1H), 4.43-4.28 (m, 1H, major), 3.77-3.62 (m, 1H, minor), 2.88 (s, 3H, major), 2.77 (s, 3H, minor), 2.74-2.64 (m, 2H), 2.58-2.31 (m, 6H), 2.02-1.79 (m, 3H), 1.75-1.49 (m, 4H), 1.40-1.13 (m, 2H), 1.07 (t, J=7.2 Hz, 3H, minor), 1.06 (t, J=7.2 Hz, 3H, major)

Example 126

N-(trans-4-(2-((6-(4-(trans-1-amino-3-hydroxy-3-methylcyclobutyl)-3-fluorophenyl)-5-phenylpyridazin-3-yl)amino)-2-oxoethyl)cyclohexyl)-N-methylpropionamide

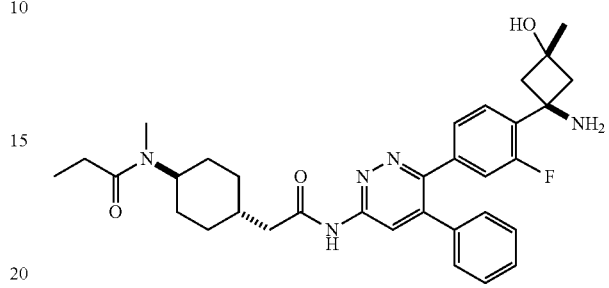

Step 1: tert-butyl (trans-1-(4-(6-amino-4-phenylpyridazin-3-yl)-2-fluorophenyl)-3-hydroxy-3-methylcyclobutyl)carbamate: A vessel containing a solution of 6-chloro-5-phenylpyridazin-3-amine (189 mg, 0.918 mmol) and the product from Example 111 Step 9 (350 mg, 0.600 mmol, 85% purity) in a mixture of 2 M Na$_2$CO$_3$(aq) (883 µl, 1.765 mmol) and dioxane (5 ml) was purged with N$_2$ for 5 min, then tetrakis-(triphenylphosphine)palladium(0) (82 mg, 0.071 mmol) was added and the resultant mixture heated at 100° C. for 3 days. The mixture was cooled, filtered through Celite® washing with EtOAc (20 ml). EtOAc (50 ml) was added and the organic phase was sequentially washed with water (20 ml) and brine (20 ml). The organic phase was dried over MgSO$_4$, filtered and concentrated on to silica (ca. 2 g) and purified by column chromatography (24 g cartridge, 0-10% (0.7 M NH$_3$/MeOH)/DCM) to afford the title compound (88 mg, 0.170 mmol, 90% purity) as a brown foam. LCMS (Method 1): m/z 465 (M+H)$^+$ at 1.51 min. $^1$H NMR (400 MHz, DMSO-d$_6$) δ 7.52 (s, 1H), 7.40-7.25 (m, 3H), 7.25-7.08 (m, 3H), 7.01-6.80 (m, 2H), 6.73 (s, 1H), 6.60 (s, 2H), 4.89 (s, 1H), 2.69-2.57 (m, 2H), 2.47-2.35 (m, 2H), 1.44-1.08 (m, 12H).

Step 2: N-(trans-4-(2-((6-(4-(trans-1-amino-3-hydroxy-3-methylcyclobutyl)-3-fluorophenyl)-5-phenylpyridazin-3-yl)amino)-2-oxoethyl)cyclohexyl)-N-methylpropionamide:
The title compound (15.5 mg, 0.026 mmol, 97% purity) was isolated as a white solid from the reaction of reaction of the product from Step 1 above (40 mg, 0.086 mmol), the product from Example 82 Step 2 (23.5 mg, 0.103 mmol), HATU (39.3 mg, 0.103 mmol) and DIPEA (30 µl, 0.172 mmol) in DMF (5 ml) using essentially the same procedure as in Example 125. LCMS (Method 1): m/z 574 (M+H)$^+$ at 1.38 min. $^1$H NMR (400 MHz, Methanol-d$_4$) (two rotamers in a 3:2 ratio) δ 8.56 (s, 1H), 7.52 (t, J=8.1 Hz, 1H), 7.46-7.35 (m, 3H), 7.35-7.23 (m, 4H), 4.48-4.31 (m, 1H, major), 3.82-3.66 (m, 1H, minor), 2.97-2.90 (m, 1H), 2.92 (s, 3H), 2.81-2.68 (m, 2H), 2.51-2.44 (m, 3H), 2.40 (q, J=7.5 Hz, 2H), 2.03-1.84 (m, 3H), 1.81-1.55 (m, 4H), 1.51 (s, 3H), 1.48-1.21 (m, 2H), 1.14 (t, J=7.3 Hz, 3H, minor), 1.12 (t, J=7.3 Hz, 3H, major).

Example 127

N-(6-(4-(trans-1-amino-3-hydroxy-3-methylcyclobutyl)-3-fluorophenyl)-5-phenylpyridazin-3-yl)-2-(trans-4-(N-methylacetamido)cyclohexyl)acetamide

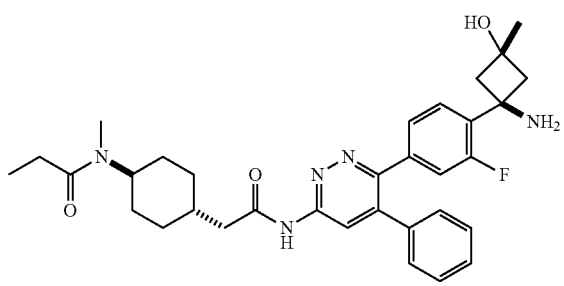 [SMILES: CCC(=O)N(C)[C@H]1CC[C@H](CC(=O)Nc2cc(-c3ccccc3)c(-c3ccc([C@]4(N)C[C@](C)(O)C4)c(F)c3)nn2)CC1]

The title compound (15.5 mg, 0.026 mmol, 97% purity) was isolated as a white solid from the reaction of reaction of the product from Example 126 Step 1 (40 mg, 0.086 mmol), the product from Example 1 Step 5 (22 mg, 0.103 mmol), HATU (39.3 mg, 0.103 mmol) and DIPEA (30 µl, 0.172 mmol) in DMF (5 ml) using essentially the same procedure as in Example 125. LCMS (Method 1): m/z 560 (M+H)$^+$ at 1.29 min. $^1$H NMR (400 MHz, Methanol-d$_4$) (two rotamers in a 7:5 ratio) δ 8.53 (s, 1H, minor), 8.53 (s, 1H, major), 7.48-7.35 (m, 3H), 7.34-7.23 (m, 3H), 7.19-7.10 (m, 2H), 4.45-4.28 (m, 1H, major), 3.78-3.65 (m, 1H, minor), 2.93 (s, 3H, major), 2.82 (s, 3H, minor), 2.70 (d, J=12.9 Hz, 2H), 2.56-2.39 (m, 4H), 2.15 (s, 3H, minor), 2.10 (s, 3H, major), 2.06-1.58 (m, 7H), 1.56 (s, 3H), 1.38-1.19 (m, 2H).

Example 128

N-(5-(4-(trans-1-amino-3-hydroxy-3-methylcyclobutyl)phenyl)-4-phenylpyridin-2-yl)-2-(trans-4-((2-methoxyethyl)(methyl)amino)cyclohexyl)acetamide

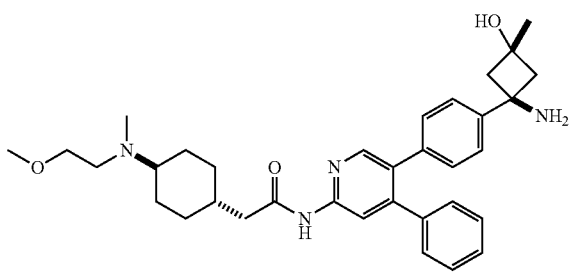 [SMILES: COCCN(C)[C@H]1CC[C@H](CC(=O)Nc2cc(-c3ccccc3)c(-c3ccc([C@]4(N)C[C@](C)(O)C4)cc3)cn2)CC1]

A suspension of the product from Example 109 Step 2 (50 mg), NaI(s) (12.5 mg, 0.084 mmol) and K$_2$CO$_3$ (23.1 mg, 0.167 mmol) in MeCN (10 ml) was treated with 1-bromo-2-methoxyethane (8.64 µl, 0.092 mmol) and the mixture was heated under reflux overnight. Additional 1-bromo-2-methoxyethane (8.64 µl, 0.092 mmol) was added and heating continued for 6 h and then the mixture stirred at RT for 3 days. Water (20 ml) was added and the phases separated. The aqueous phase was extracted with EtOAc (2×10 ml), dried over MgSO$_4$, filtered and concentrated in vacuo. The residue was purified by column chromatography (12 g cartridge, 0-100% EtOAc/isohexane, then 0-20% (0.7 M NH$_3$/MeOH)/DCM) to afford a colourless solid. This material was dissolved in DCM (5 ml) and treated with TFA (0.5 ml). The resultant solution was stirred at RT for 2 h. The reaction mixture was loaded directly onto a column of SCX in MeOH. The column was washed with MeOH and then the product was eluted with 0.7 M ammonia in MeOH. The resultant mixture was concentrated in vacuo to afford the title compound (11 mg, 0.020 mmol, 99% purity) as a white solid. LCMS (Method 1): m/z 557 (M+H)$^+$ at 0.97 min. $^1$H NMR (400 MHz, DMSO-d$_6$) δ 10.68 (s, 1H), 8.34 (s, 1H), 8.18 (s, 1H), 7.52-7.41 (m, 2H), 7.35 (dd, J=5.1, 2.0 Hz, 3H), 7.29-7.14 (m, 4H), 5.00 (s, 1H), 3.69-3.57 (m, 2H), 3.31 (s, 3H), 3.29-2.97 (m, 3H), 2.71-2.63 (m, 4H), 2.60 (s, 3H), 2.37-2.30 (m, 2H), 2.06-1.62 (m, 5H), 1.54-1.44 (m, 2H), 1.42 (s, 3H), 1.19-0.96 (m, 2H).

Example 129

Methyl (trans-4-(2-((6-(4-(trans-1-amino-3-hydroxy-3-methylcyclobutyl)phenyl)-5-phenylpyridazin-3-yl)amino)-2-oxoethyl)cyclohexyl) (ethyl)carbamate

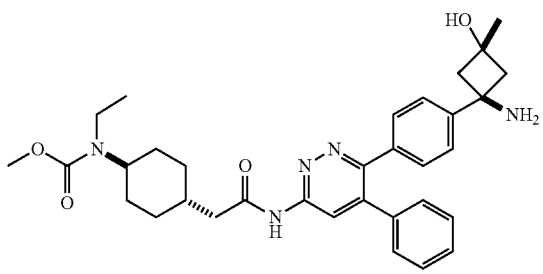 [SMILES: CCN(C(=O)OC)[C@H]1CC[C@H](CC(=O)Nc2cc(-c3ccccc3)c(-c3ccc([C@]4(N)C[C@](C)(O)C4)cc3)nn2)CC1]

Step 1: Methyl (trans-4-(2-((6-(4-(trans-1-((tert-butoxycarbonyl)amino)-3-hydroxy-3-methylcyclobutyl)phenyl)-5-phenylpyridazin-3-yl)amino)-2-oxoethyl)cyclohexyl)(ethyl)carbamate: The title compound (37.6 mg) was isolated as a brown oil from the reaction of the product from Example 57 Step 1 (25 mg, 0.053 mmol, 95% purity), the product from Example 116 Step 2 (15 mg, 58.9 mmol, 95% purity), HATU (27.7 mg, 0.168 mmol) and DIPEA (29 µl, 0.168 mmol) in DMF (2 ml) using essentially the same procedure as in Example 102 Step 1, except after work-up, the crude product was used in subsequent reactions without purification by column chromatography.

Step 2: N-(trans-4-(2-((6-(4-(trans-1-amino-3-hydroxy-3-methylcyclobutyl)phenyl)-5-phenylpyridin-3-yl)amino)-2-oxoethyl)cyclohexyl)-N-isopropylpropionamide: The title compound (7.3 mg, 0.013 mmol, 98% purity) was isolated as a colourless solid from the reaction of the product from Step 1 above (37.6 mg) with TFA (200 µl, 2.60 mmol) in DCM (1 ml) using essentially the same procedure as in Example 120 Step 2, except, after column chromatography, no further purification was carried out. LCMS (Method 2): m/z 572 (M+H)$^+$ (ES$^+$) at 2.01 min. $^1$H NMR (400 MHz, Methanol-d$_4$) δ 8.52 (s, 1H), 7.48-7.42 (m, 2H), 7.40-7.32 (m, 5H), 7.36-7.20 (m, 2H), 3.88 (br s, 1H), 3.70 (s, 3H), 3.29-3.19 (m, 2H), 2.69 (d, J=13.3 Hz, 2H), 2.49-2.38 (m, 4H), 2.00-1.59 (m, 7H), 1.56 (s, 3H), 1.32-1.18 (m, 2H), 1.14 (t, J=7.0 Hz, 3H).

The following examples were prepared by methods analogous to the examples described above, substituting appropriate starting materials and intermediates where necessary:

| Example | Structure | Name/Method/Analytical Data |
|---|---|---|
| A1 | 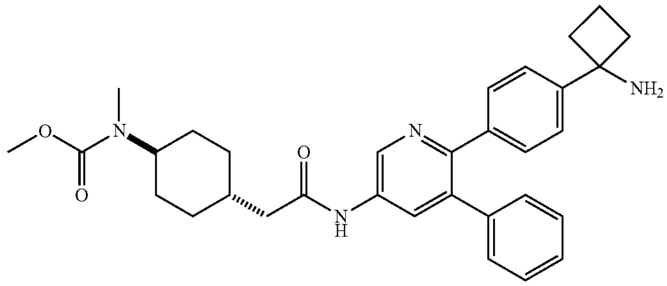 [SMILES: COC(=O)N(C)[C@H]1CC[C@H](CC(=O)Nc2cnc(-c3ccc(C4(N)CCC4)cc3)c(-c3ccccc3)c2)CC1] | Methyl (trans-4-(2-((6-(4-(1-aminocyclobutyl)phenyl)-5-phenylpyridin-3-yl)amino)-2-oxoethyl)cyclohexyl)(methyl)carbamate<br>Prepared by a method analogous to Example 34.<br>LCMS (Method 1): m/z 527 (M + H)+, 525 (M − H)−, at 1.57 min. |
| A2 | 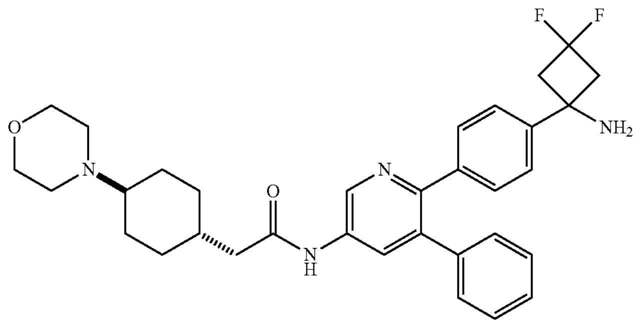 [SMILES: NC1(c2ccc(-c3ncc(NC(=O)C[C@H]4CC[C@H](N5CCOCC5)CC4)cc3-c3ccccc3)cc2)CC(F)(F)C1] | N-(6-(4-(1-amino-3,3-difluorocyclobutyl)phenyl)-5-phenylpyridin-3-yl)-2-(trans-4-morpholinocyclohexyl)acetamide<br>Prepared by a method analogous to Example 38.<br>LCMS (Method 1): m/z 561 (M + H)+, 559 (M − H)−, at 1.06 min. |
| A3 | 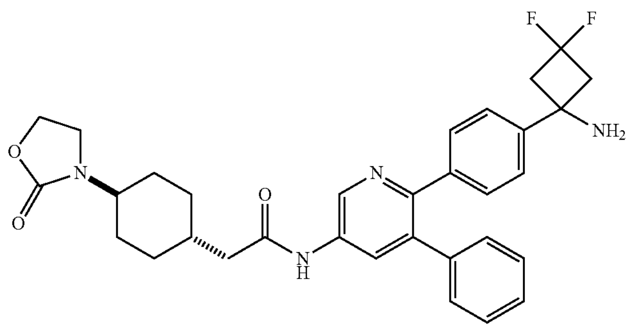 [SMILES: NC1(c2ccc(-c3ncc(NC(=O)C[C@H]4CC[C@H](N5CCOC5=O)CC4)cc3-c3ccccc3)cc2)CC(F)(F)C1] | N-(6-(4-(1-amino-3,3-difluorocyclobutyl)phenyl)-5-phenylpyridin-3-yl)-2-(trans-4-(2-oxooxazolidin-3-yl)cyclohexyl)acetamide<br>Prepared by a method analogous to Example 42.<br>LCMS (Method 1): m/z 561 (M + H)+, 559 (M − H)−, at 1.43 min. |
| A4 | 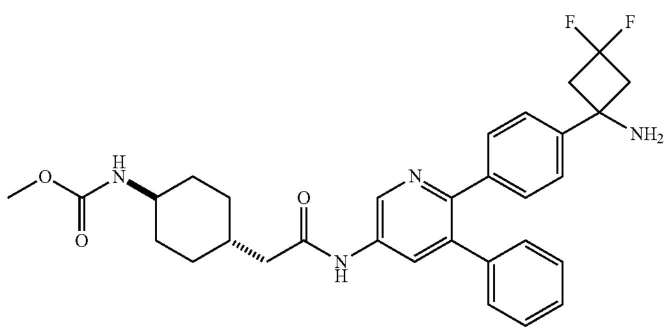 | Methyl (trans-4-(2-((6-(4-(1-amino-3,3-difluorocyclobutyl)phenyl)-5-phenylpyridin-3-yl)amino)-2-oxoethyl)cyclohexyl)carbamate<br>Prepared by a method analogous to Example 44.<br>LCMS (Method 1): m/z 563 (M + H)+, 561 (M − H)−, at 1.61 min. |
| A5 | 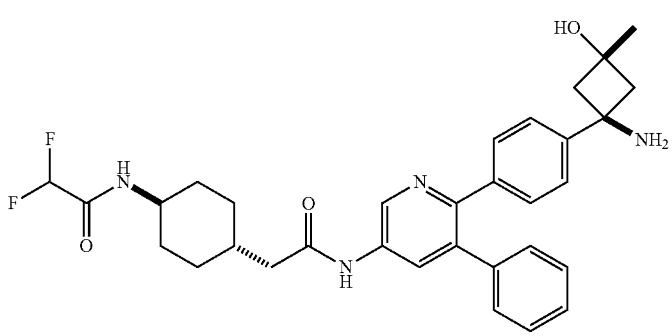 [SMILES: C[C@]1(O)C[C@@](N)(c2ccc(-c3ncc(NC(=O)C[C@H]4CC[C@H](NC(=O)C(F)F)CC4)cc3-c3ccccc3)cc2)C1] | N-(trans-4-(2-((6-(4-(trans-1-amino-3-hydroxy-3-methylcyclobutyl)phenyl)-5-phenylpyridin-3-yl)amino)-2-oxoethyl)cyclohexyl)-2,2-difluoroacetamide<br>Prepared by a method analogous to Example 2.<br>LCMS (Method 1): m/z 563 (M + H)+, 546 (M + H − NH$_3$)+, at 1.20 min. |

| Example | Structure | Name/Method/Analytical Data |
|---|---|---|
| A6 | 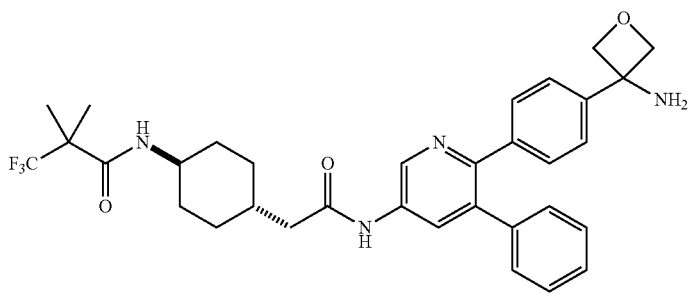 [SMILES: CC(C)(C(=O)N[C@H]1CC[C@H](CC(=O)Nc2cnc(-c3ccc(C4(N)COC4)cc3)c(-c3ccccc3)c2)CC1)C(F)(F)F] | N-(trans-4-(2-((6-(4-(3-aminooxetan-3-yl)phenyl)-5-phenylpyridin-3-yl)amino)-2-oxoethyl)cyclohexyl)-3,3,3-trifluoro-2,2-dimethylpropanamide<br>Prepared by a method analogous to Example 21.<br>LCMS (Method 1): m/z 595 (M + H)$^+$, at 1.57 min. |
| A7 | 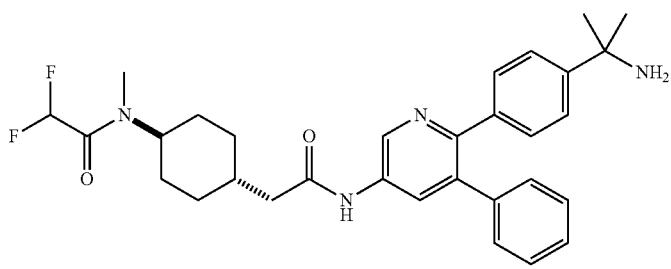 [SMILES: CN(C(=O)C(F)F)[C@H]1CC[C@H](CC(=O)Nc2cnc(-c3ccc(C(C)(C)N)cc3)c(-c3ccccc3)c2)CC1] | N-(trans-4-(2-((6-(4-(2-aminopropan-2-yl)phenyl)-5-phenylpyridin-3-yl)amino)-2-oxoethyl)cyclohexyl)-2,2-difluoro-N-methylacetamide<br>Prepared by a method analogous to Example 4.<br>LCMS (Method 1): m/z 259 (M + 2H − NH$_3$)$^{2+}$, 518 (M + H − NH$_3$)$^+$, 535 (M + H)$^+$ at 1.44 min. |
| A8 | 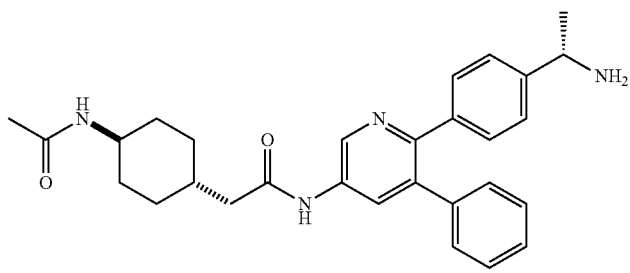 [SMILES: CC(=O)N[C@H]1CC[C@H](CC(=O)Nc2cnc(-c3ccc([C@H](C)N)cc3)c(-c3ccccc3)c2)CC1] | 2-(trans-4-acetamidocyclohexyl)-N-(6-(4-((S)-1-aminoethyl)phenyl)-5-phenylpyridin-3-yl)acetamide<br>Prepared by a method analogous to Example 2.<br>LCMS (Method 1): m/z 227 (M + 2H − NH$_3$)$^{2+}$, 236 (M + 2H)$^{2+}$, 454 (M + H − NH$_3$)$^+$, 471 (M + H)$^+$ at 1.22 min. |
| A9 | 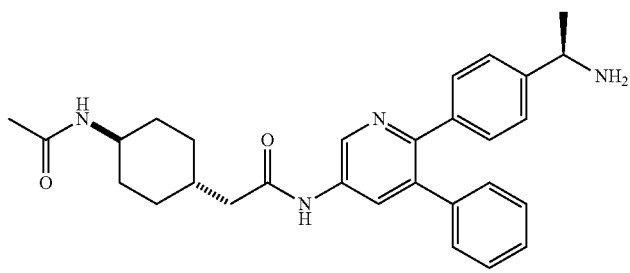 [SMILES: CC(=O)N[C@H]1CC[C@H](CC(=O)Nc2cnc(-c3ccc([C@@H](C)N)cc3)c(-c3ccccc3)c2)CC1] | 2-(trans-4-acetamidocyclohexyl)-N-(6-(4-((R)-1-aminoethyl)phenyl)-5-phenylpyridin-3-yl)acetamide<br>Prepared by a method analogous to Example 2.<br>LCMS (Method 1): m/z 227 (M + 2H − NH$_3$)$^{2+}$, 236 (M + 2H)$^{2+}$, 454 (M + H − NH$_3$)$^+$, 471 (M + H)$^+$ at 1.23 min. |
| A10 | 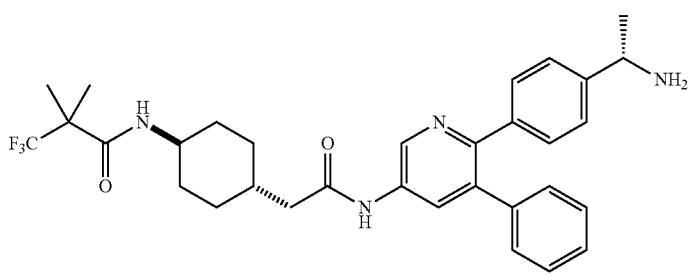 [SMILES: C[C@H](N)c1ccc(-c2ncc(NC(=O)C[C@H]3CC[C@H](NC(=O)C(C)(C)C(F)(F)F)CC3)cc2-c2ccccc2)cc1] | N-(trans-4-(2-((6-(4-((S)-1-aminoethyl)phenyl)-5-phenylpyridin-3-yl)amino)-2-oxoethyl)cyclohexyl)-3,3,3-trifluoro-2,2-dimethylpropanamide<br>Prepared by a method analogous to Example 20.<br>LCMS (Method 1): m/z 275 (M + 2H − NH$_3$)$^{2+}$, 284 (M + 2H)$^{2+}$, 550 (M + H − NH$_3$)$^+$, 567 (M + H)$^+$ at 1.61 min. |

| Example | Structure | Name/Method/Analytical Data |
|---|---|---|
| A11 | 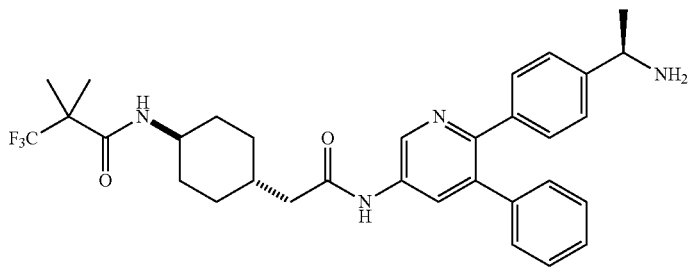 [SMILES: C[C@@H](N)c1ccc(-c2ncc(NC(=O)C[C@H]3CC[C@H](NC(=O)C(C)(C)C(F)(F)F)CC3)cc2-c2ccccc2)cc1] | N-(trans-4-(2-((6-(4-((R)-1-aminoethyl)phenyl)-5-phenylpyridin-3-yl)amino)-2-oxoethyl)cyclohexyl)-3,3,3-trifluoro-2,2-dimethylpropanamide<br>Prepared by a method analogous to Example 20.<br>LCMS (Method 2): m/z 275 (M + 2H − $NH_3$)$^{2+}$, 284 (M + 2H)$^{2+}$, 550 (M + H − $NH_3$)$^+$, 567 (M + H)$^+$ at 2.11 min. |
| A12 | 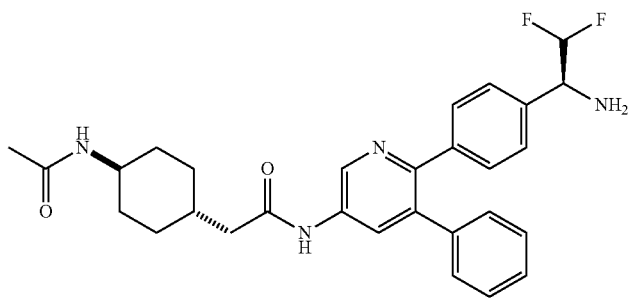 [SMILES: CC(=O)N[C@H]1CC[C@H](CC(=O)Nc2cnc(-c3ccc([C@H](N)C(F)F)cc3)c(-c3ccccc3)c2)CC1] | 2-(trans-4-acetamidocyclohexyl)-N-(6-(4-((S)-1-amino-2,2-difluoroethyl)phenyl)-5-phenylpyridin-3-yl)acetamide<br>Prepared by a method analogous to Example 2.<br>LCMS (Method 2): m/z 254 (M + 2H)$^{2+}$, 507 (M + H)$^+$, at 1.80 min. |
| A13 | 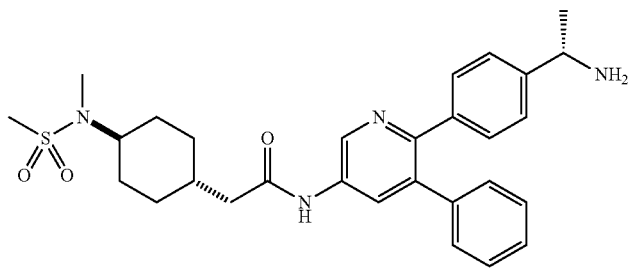 [SMILES: C[C@H](N)c1ccc(-c2ncc(NC(=O)C[C@H]3CC[C@H](N(C)S(C)(=O)=O)CC3)cc2-c2ccccc2)cc1] | N-(6-(4-((S)-1-aminoethyl)phenyl)-5-phenylpyridin-3-yl)-2-(trans-4-(N-methylmethylsulfonamido)cyclohexyl)acetamide<br>Prepared by a method analogous to Example 17.<br>LCMS (Method 2): m/z 521 (M + H)$^+$, at 1.80 min. |
| A14 | 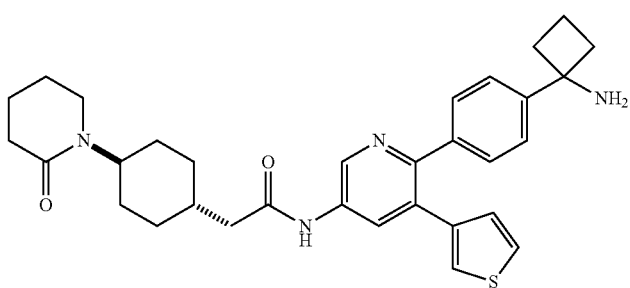 [SMILES: NC1(c2ccc(-c3ncc(NC(=O)C[C@H]4CC[C@H](N5CCCCC5=O)CC4)cc3-c3ccsc3)cc2)CCC1] | N-(6-(4-(1-aminocyclobutyl)phenyl)-5-(thiophen-3-yl)pyridin-3-yl)-2-(trans-4-(2-oxopiperidin-1-yl)cyclohexyl)acetamide<br>Prepared by a method analogous to Example 28.<br>LCMS (Method 2): m/z 263 (M + 2H − $NH_3$)$^{2+}$, 272 (M + 2H)$^{2+}$, 543 (M + H)$^+$, at 1.97 min. |
| A15 | 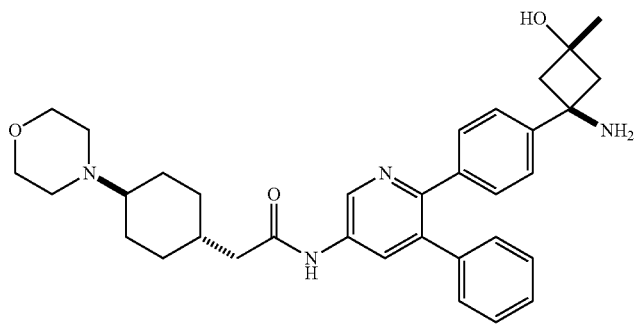 [SMILES: C[C@]1(O)C[C@@](N)(c2ccc(-c3ncc(NC(=O)C[C@H]4CC[C@H](N5CCOCC5)CC4)cc3-c3ccccc3)cc2)C1] | N-(6-(4-(trans-1-amino-3-hydroxy-3-methylcyclobutyl)phenyl)-5-phenylpyridin-3-yl)-2-(trans-4-morpholinocyclohexyl)acetamide<br>Prepared by a method analogous to Example 38.<br>LCMS (Method 2): m/z 555 (M + H)$^+$, at 1.64 min. |

-continued

| Example | Structure | Name/Method/Analytical Data |
|---|---|---|
| A16 | 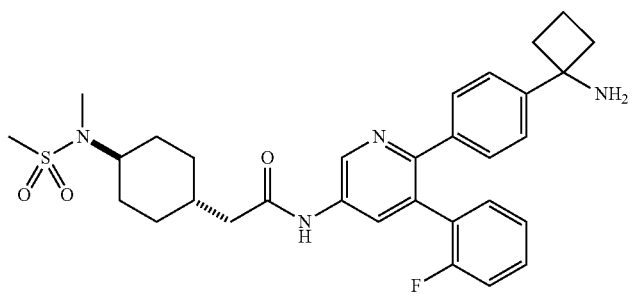 [SMILES: CN([C@H]1CC[C@H](CC(=O)Nc2cnc(-c3ccc(C4(N)CCC4)cc3)c(-c3ccccc3F)c2)CC1)S(C)(=O)=O] | N-(6-(4-(1-aminocyclobutyl)phenyl)-5-(2-fluorophenyl)pyridin-3-yl)-2-(trans-4-(N-methylmethylsulfonamido)cyclohexyl)acetamide<br>Prepared by a method analogous to Example 17.<br>LCMS (Method 1): m/z 565 (M + H)$^+$, 563 (M − H)$^-$, at 1.51 min. |
| A17 | 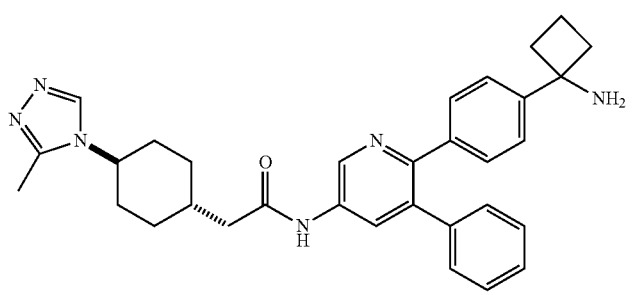 [SMILES: Cc1nncn1[C@H]1CC[C@H](CC(=O)Nc2cnc(-c3ccc(C4(N)CCC4)cc3)c(-c3ccccc3)c2)CC1] | N-(6-(4-(1-aminocyclobutyl)phenyl)-5-phenylpyridin-3-yl)-2-(trans-4-(3-methyl-1,2,4-triazol-4-yl)cyclohexyl)acetamide<br>Prepared by a method analogous to Example 23.<br>LCMS (Method 1): m/z 521 (M + H)$^+$, 519 (M − H)$^-$, at 1.20 min. |
| A18 | 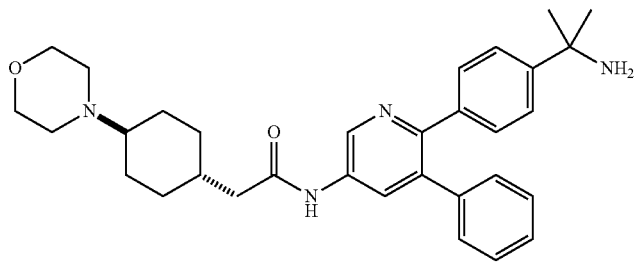 [SMILES: CC(C)(N)c1ccc(-c2ncc(NC(=O)C[C@H]3CC[C@H](N4CCOCC4)CC3)cc2-c2ccccc2)cc1] | N-(6-(4-(2-aminopropan-2-yl)phenyl)-5-phenylpyridin-3-yl)-2-(trans-4-morpholinocyclohexyl)acetamide<br>Prepared by a method analogous to Example 38.<br>LCMS (Method 1): m/z 513.4 (M + H)$^+$, 511 (M − H)$^-$, at 0.976 min. |
| A19 | 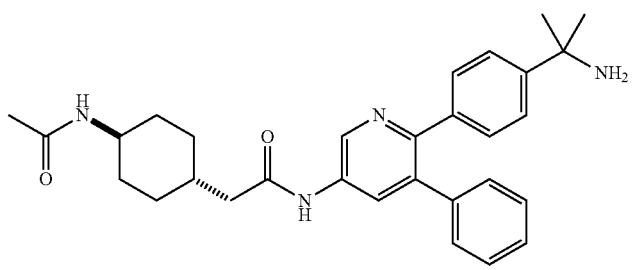 [SMILES: CC(=O)N[C@H]1CC[C@H](CC(=O)Nc2cnc(-c3ccc(C(C)(C)N)cc3)c(-c3ccccc3)c2)CC1] | 2-(trans-4-acetamidocyclohexyl)-N-(6-(4-(2-aminopropan-2-yl)phenyl)-5-phenylpyridin-3-yl)acetamide<br>Prepared by a method analogous to Example 18.<br>LCMS (Method 1): m/z 485 (M + H)$^+$, 483 (M − H)$^-$, at 1.25 min. |
| A20 | 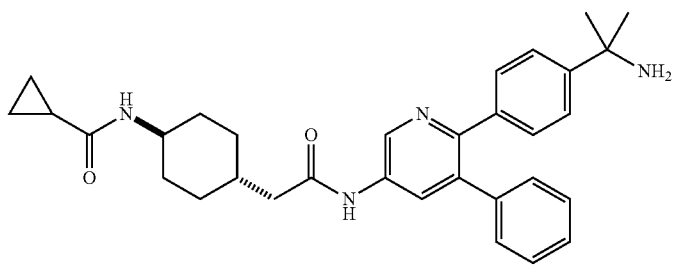 [SMILES: CC(C)(N)c1ccc(-c2ncc(NC(=O)C[C@H]3CC[C@H](NC(=O)C4CC4)CC3)cc2-c2ccccc2)cc1] | N-(trans-4-(2-((6-(4-(2-aminopropan-2-yl)phenyl)-5-phenylpyridin-3-yl)amino)-2-oxoethyl)cyclohexyl)cyclopropanecarboxamide<br>Prepared by a method analogous to Example 26.<br>LCMS (Method 1): m/z 511 (M + H)$^+$, at 1.51 min. |

| Example | Structure | Name/Method/Analytical Data |
|---|---|---|
| A21 | 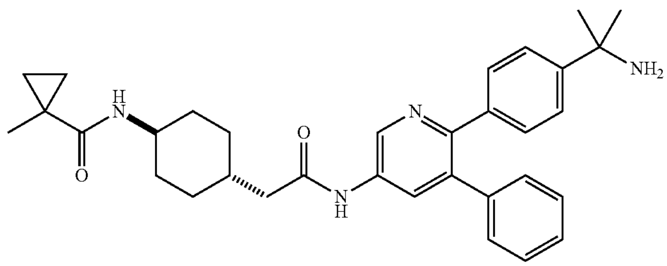 [SMILES: CC1(C(=O)N[C@H]2CC[C@H](CC(=O)Nc3cnc(-c4ccc(C(C)(C)N)cc4)c(-c4ccccc4)c3)CC2)CC1] | N-(trans-4-(2-((6-(4-(2-aminopropan-2-yl)phenyl)-5-phenylpyridin-3-yl)amino)-2-oxoethyl)cyclohexyl)-1-methylcyclopropane-1-carboxamide<br>Prepared by a method analogous to Example 27.<br>LCMS (Method 1): m/z 525 (M + H)+, at 1.48 min. |
| A22 | 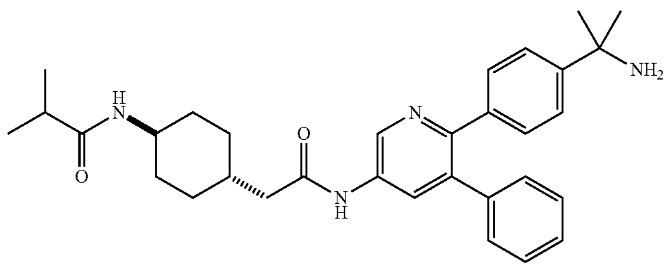 [SMILES: CC(C)C(=O)N[C@H]1CC[C@H](CC(=O)Nc2cnc(-c3ccc(C(C)(C)N)cc3)c(-c3ccccc3)c2)CC1] | N-(trans-4-(2-((6-(4-(2-aminopropan-2-yl)phenyl)-5-phenylpyridin-3-yl)amino)-2-oxoethyl)cyclohexyl)isobutyramide<br>Prepared by a method analogous to Example 4.<br>LCMS (Method 2): m/z 513 (M + H)+, at 1.85 min. |
| A23 | 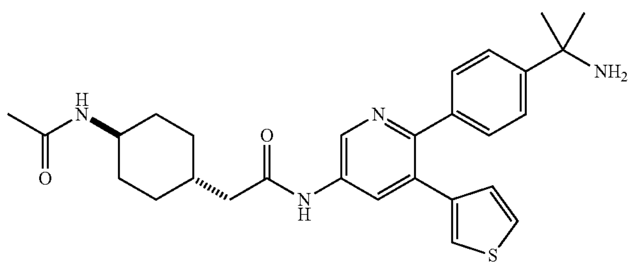 | 2-(trans-4-acetamidocyclohexyl)-N-(6-(4-(2-aminopropan-2-yl)phenyl)-5-(thiophen-3-yl)pyridin-3-yl)acetamide<br>Prepared by a method analogous to Example 2.<br>LCMS (Method 2) m/z 491(M + H)+, at 1.61 min. |
| A24 | 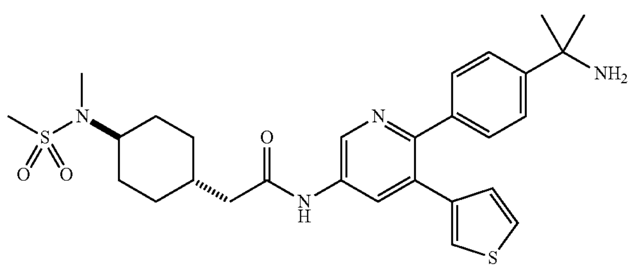 [SMILES: CN([C@H]1CC[C@H](CC(=O)Nc2cnc(-c3ccc(C(C)(C)N)cc3)c(-c3ccsc3)c2)CC1)S(C)(=O)=O] | N-(6-(4-(2-aminopropan-2-yl)phenyl)-5-(thiophen-3-yl)pyridin-3-yl)-2-(trans-4-(N-methylmethylsulfonamido)cyclohexyl)acetamide<br>Prepared by a method analogous to Example 17.<br>LCMS (Method 2): m/z 541 (M + H)+, at 1.88 min. |
| A25 | 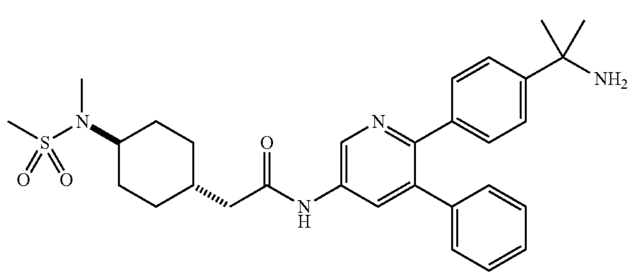 [SMILES: CN([C@H]1CC[C@H](CC(=O)Nc2cnc(-c3ccc(C(C)(C)N)cc3)c(-c3ccccc3)c2)CC1)S(C)(=O)=O] | N-(6-(4-(2-aminopropan-2-yl)phenyl)-5-phenylpyridin-3-yl)-2-(trans-4-(N-methylmethylsulfonamido)cyclohexyl)acetamide<br>Prepared by a method analogous to Example 17.<br>LCMS (Method 2): m/z 535 (M + H)+, at 1.91 min. |

| Example | Name/Method/Analytical Data |
|---|---|
| A26 | N-(6-(4-(2-aminopropan-2-yl)phenyl)-5-(2-fluorophenyl)pyridin-3-yl)-2-(trans-4-(N-methylmethylsulfonamido)cyclohexyl)acetamide<br>Prepared by a method analogous to Example 17.<br>LCMS (Method 2): m/z 553 (M + H)$^+$, at 1.90 min. |
| A27 | N-(6-(4-(1-aminocyclobutyl)phenyl)-5-phenylpyridin-3-yl)-2-(trans-4-(2-oxooxazolidin-3-yl)cyclohexyl)acetamide<br>Prepared by a method analogous to Example 45.<br>LCMS (Method 2): m/z 525 (M + H)$^+$, at 1.95 min. |
| A28 | Methyl (trans-4-(2-((6-(4-(2-aminopropan-2-yl)-3-fluorophenyl)-5-phenylpyridin-3-yl)amino)-2-oxoethyl)cyclohexyl)(methyl)carbamate<br>Prepared by a method analogous to Example 44.<br>LCMS (Method 1): m/z 533 (M + H)$^+$, at 1.60 min. |
| A29 | N-(trans-4-(2-((6-(4-(2-aminopropan-2-yl)phenyl)-5-phenylpyridin-3-yl)amino)-2-oxoethyl)cyclohexyl)-N-methylcyclopropanecarboxamide<br>Prepared by a method analogous to Example 47.<br>LCMS (Method 1): m/z 525 (M + H)$^+$, 523 (M − H)$^-$, at 1.46 min. |
| A30 | N-(trans-4-(2-((6-(4-(2-aminopropan-2-yl)phenyl)-5-phenylpyridin-3-yl)amino)-2-oxoethyl)cyclohexyl)-N,3,3-trimethylbutanamide<br>Prepared by a method analogous to Example 47.<br>LCMS (Method 1): m/z 269 (M + 2H − NH$_3$)$^{2+}$, 278 (M + 2H)$^{2+}$, 538 (M + H − NH$_3$)$^+$, 555 (M + H)$^+$, at 1.60 min. |

| Example | Structure | Name/Method/Analytical Data |
|---|---|---|
| A31 | 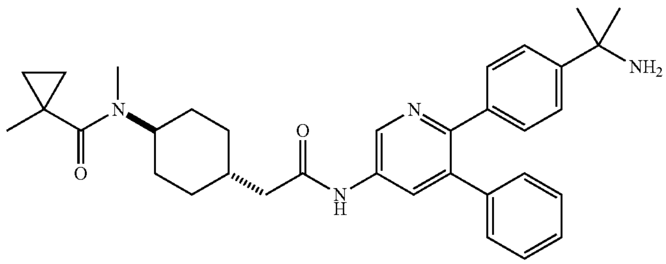 [SMILES: CN(C(=O)C1(C)CC1)[C@H]1CC[C@H](CC(=O)Nc2cnc(-c3ccc(C(C)(C)N)cc3)c(-c3ccccc3)c2)CC1] | N-(trans-4-(2-((6-(4-(2-aminopropan-2-yl)phenyl)-5-phenylpyridin-3-yl)amino)-2-oxoethyl)cyclohexyl)-N,1-dimethylcyclopropane-1-carboxamide<br>Prepared by a method analogous to Example 47.<br>LCMS (Method 1): m/z 261 (M + 2H − NH$_3$)$^{2+}$, 270 (M + 2H)$^{2+}$, 522 (M + H − NH$_3$)$^+$, 539 (M + H)$^+$, at 1.45 min. |
| A32 | 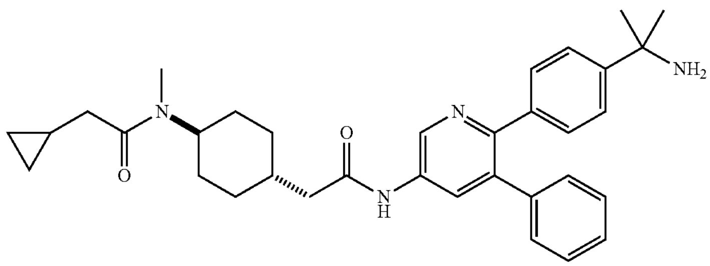 [SMILES: CN(C(=O)CC1CC1)[C@H]1CC[C@H](CC(=O)Nc2cnc(-c3ccc(C(C)(C)N)cc3)c(-c3ccccc3)c2)CC1] | N-(trans-4-(2-((6-(4-(2-aminopropan-2-yl)phenyl)-5-phenylpyridin-3-yl)amino)-2-oxoethyl)cyclohexyl)-2-cyclopropyl-N-methylacetamide<br>Prepared by a method analogous to Example 47.<br>LCMS (Method 1): m/z 261 (M + 2H − NH$_3$)$^{2+}$, 270 (M + 2H)$^{2+}$, 522 (M + H − NH$_3$)$^+$, 539 (M + H)$^+$, at 1.51 min. |
| A33 | 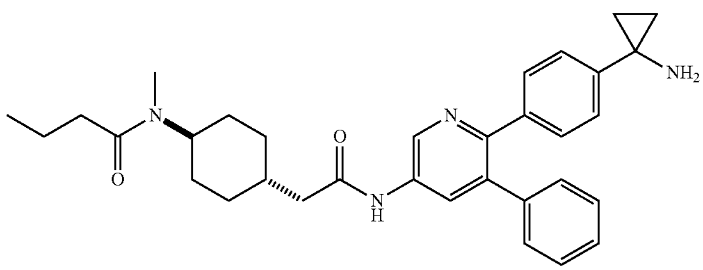 [SMILES: CCCC(=O)N(C)[C@H]1CC[C@H](CC(=O)Nc2cnc(-c3ccc(C4(N)CC4)cc3)c(-c3ccccc3)c2)CC1] | N-(trans-4-(2-((6-(4-(1-aminocyclopropyl)phenyl)-5-phenylpyridin-3-yl)amino)-2-oxoethyl)cyclohexyl)-N-methylbutyramide<br>Prepared by a method analogous to Example 20.<br>LCMS (Method 2): m/z 263 (M + 2H)$^{2+}$, 525 (M + H)$^+$, at 2.10 min. |
| A34 | 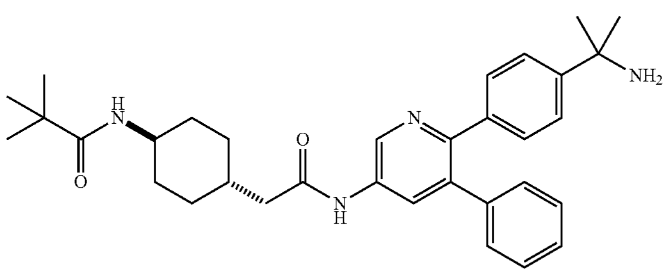 [SMILES: CC(C)(C)C(=O)N[C@H]1CC[C@H](CC(=O)Nc2cnc(-c3ccc(C(C)(C)N)cc3)c(-c3ccccc3)c2)CC1] | N-(trans-4-(2-((6-(4-(2-aminopropan-2-yl)phenyl)-5-phenylpyridin-3-yl)amino)-2-oxoethyl)cyclohexyl)pivalamide<br>Prepared by a method analogous to Example 2.<br>LCMS (Method 1): m/z 527 (M + H)$^+$, 525 (M − H)$^−$, at 1.49 min. |
| A35 | 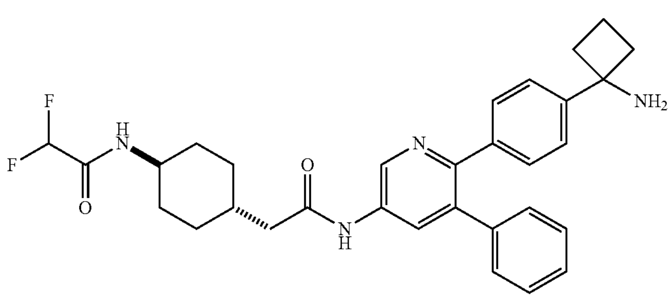 [SMILES: NC1(c2ccc(-c3ncc(NC(=O)C[C@H]4CC[C@H](NC(=O)C(F)F)CC4)cc3-c3ccccc3)cc2)CCC1] | N-(trans-4-(2-((6-(4-(1-aminocyclobutyl)phenyl)-5-phenylpyridin-3-yl)amino)-2-oxoethyl)cyclohexyl)-2,2-difluoroacetamide<br>Prepared by a method analogous to Example 2.<br>LCMS (Method 1): m/z 533 (M + H)$^+$, at 1.41 min. |

| Example | Structure | Name/Method/Analytical Data |
|---|---|---|
| A36 | 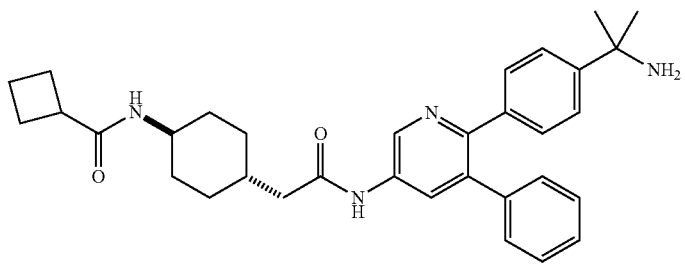 [SMILES: CC(C)(N)c1ccc(-c2ncc(NC(=O)C[C@H]3CC[C@H](NC(=O)C4CCC4)CC3)cc2-c2ccccc2)cc1] | N-(trans-4-(2-((6-(4-(2-aminopropan-2-yl)phenyl)-5-phenylpyridin-3-yl)amino)-2-oxoethyl)cyclohexyl)cyclobutanecarboxamide<br>Prepared by a method analogous to Example 26.<br>LCMS (Method 2): m/z 525 (M + H)$^+$, at 1.43 min. |
| A37 | 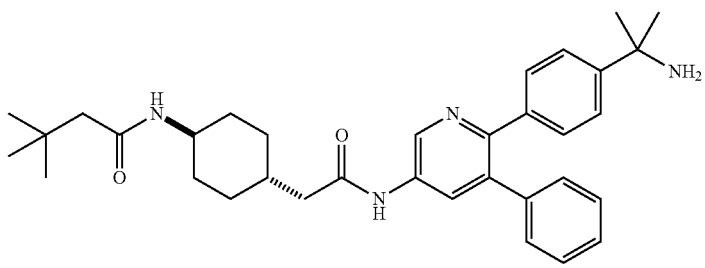 | N-(trans-4-(2-((6-(4-(2-aminopropan-2-yl)phenyl)-5-phenylpyridin-3-yl)amino)-2-oxoethyl)cyclohexyl)-3,3-dimethylbutanamide<br>Prepared by a method analogous to Example 29.<br>LCMS (Method 2): m/z 541 (M + H)$^+$, at 2.05 min. |
| A38 | 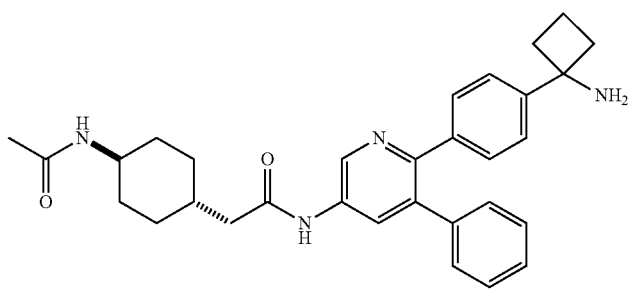 [SMILES: CC(=O)N[C@H]1CC[C@H](CC(=O)Nc2cnc(-c3ccc(C4(N)CCC4)cc3)c(-c3ccccc3)c2)CC1] | 2-(trans-4-acetamidocyclohexyl)-N-(6-(4-(1-aminocyclobutyl)phenyl)-5-phenylpyridin-3-yl)acetamide<br>Prepared by a method analogous to Example 10.<br>LCMS (Method 1): m/z 497 (M + H)$^+$, at 1.34 min. |
| A39 | 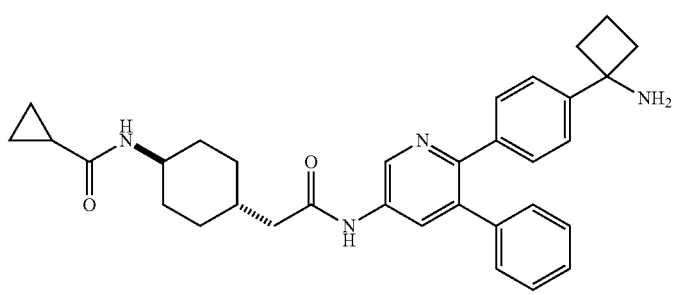 [SMILES: NC1(c2ccc(-c3ncc(NC(=O)C[C@H]4CC[C@H](NC(=O)C5CC5)CC4)cc3-c3ccccc3)cc2)CCC1] | N-(trans-4-(2-((6-(4-(1-aminocyclobutyl)phenyl)-5-phenylpyridin-3-yl)amino)-2-oxoethyl)cyclohexyl)cyclopropane-carboxamide<br>Prepared by a method analogous to Example 29.<br>LCMS (Method 1): m/z 523 (M + H)$^+$, 521 (M − H)$^−$, at 1.49 min. |
| A40 | 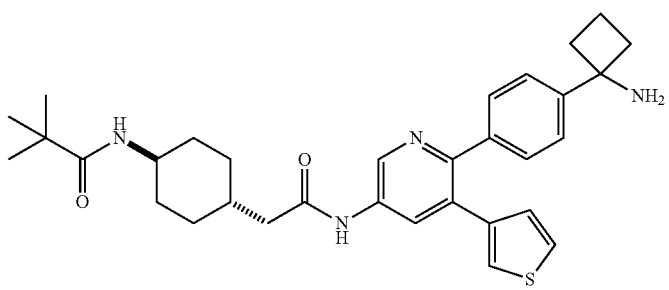 [SMILES: CC(C)(C)C(=O)N[C@H]1CC[C@H](CC(=O)Nc2cnc(-c3ccc(C4(N)CCC4)cc3)c(-c3ccsc3)c2)CC1] | N-(trans-4-(2-((6-(4-(1-aminocyclobutyl)phenyl)-5-(thiophen-3-yl)pyridin-3-yl)amino)-2-oxoethyl)cyclohexyl)pivalamide<br>Prepared by a method analogous to Example 2.<br>LCMS (Method 1): m/z 545 (M + H)$^+$, 543 (M − H)$^−$, at 1.61 min. |

| Example | Structure | Name/Method/Analytical Data |
|---|---|---|
| A41 | 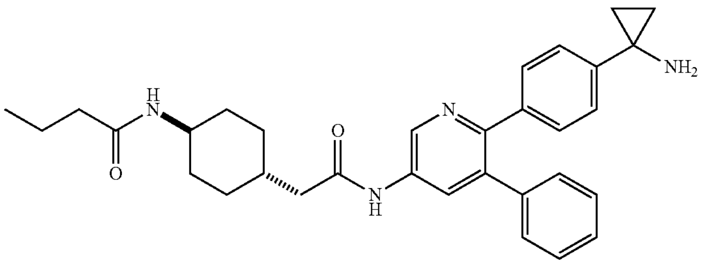 | N-(trans-4-(2-((6-(4-(1-aminocyclopropyl)phenyl)-5-phenylpyridin-3-yl)amino)-2-oxoethyl)cyclohexyl)butyramide<br>Prepared by a method analogous to Example 20.<br>LCMS (Method 1): m/z 256 (M + 2H)$^{2+}$, 247.5 (M + 2H − NH$_3$)$^{2+}$, at 1.46 min. |
| A42 | 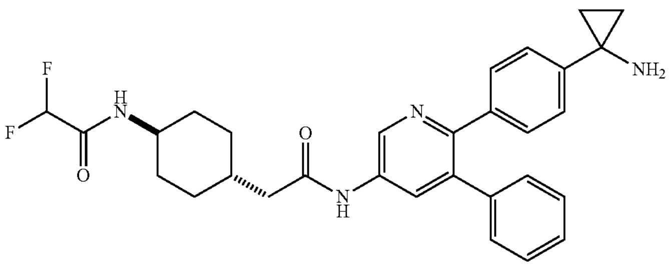 [SMILES: NC1(c2ccc(-c3ncc(NC(=O)C[C@H]4CC[C@H](NC(=O)C(F)F)CC4)cc3-c3ccccc3)cc2)CC1] | N-(trans-4-(2-((6-(4-(1-aminocyclopropyl)phenyl)-5-phenylpyridin-3-yl)amino)-2-oxoethyl)cyclohexyl)-2,2-difluoroacetamide<br>Prepared by a method analogous to Example 2.<br>LCMS (Method 1): m/z 519 (M + H)$^+$, 517 (M − H)$^-$, at 1.43 min. |
| A43 | 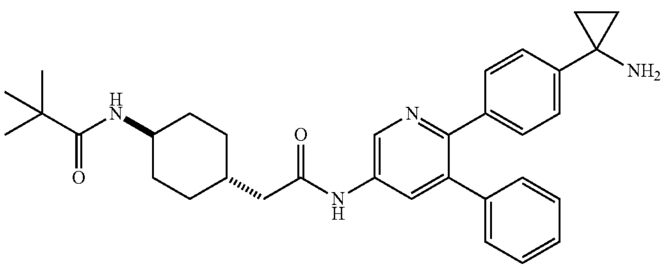 [SMILES: CC(C)(C)C(=O)N[C@H]1CC[C@H](CC(=O)Nc2cnc(-c3ccc(C4(N)CC4)cc3)c(-c3ccccc3)c2)CC1] | N-(trans-4-(2-((6-(4-(1-aminocyclopropyl)phenyl)-5-phenylpyridin-3-yl)amino)-2-oxoethyl)cyclohexyl)pivalamide<br>Prepared by a method analogous to Example 2.<br>LCMS (Method 1): m/z 525 (M + H)$^+$, at 1.59 min. |
| A44 | 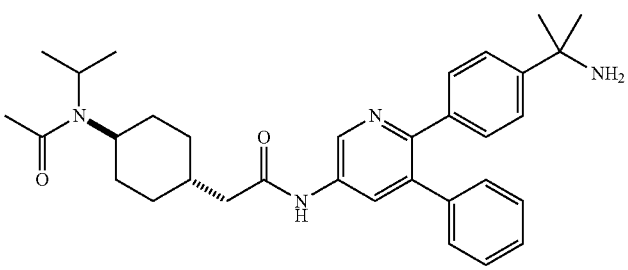 [SMILES: CC(=O)N(C(C)C)[C@H]1CC[C@H](CC(=O)Nc2cnc(-c3ccc(C(C)(C)N)cc3)c(-c3ccccc3)c2)CC1] | N-(6-(4-(2-aminopropan-2-yl)phenyl)-5-phenylpyridin-3-yl)-2-(trans-4-(N-isopropylacetamido)cyclohexyl)acetamide<br>Prepared by a method analogous to Example 49.<br>LCMS (Method 2): m/z 527 (M + H)$^+$, at 2.01 min. |
| A45 | 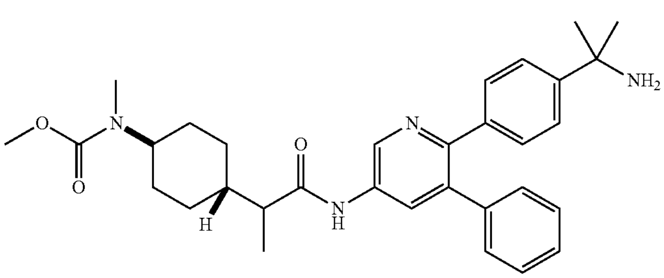 [SMILES: COC(=O)N(C)[C@H]1CC[C@H](C(C)C(=O)Nc2cnc(-c3ccc(C(C)(C)N)cc3)c(-c3ccccc3)c2)CC1] | Methyl (trans-4-(1-((6-(4-(2-aminopropan-2-yl)phenyl)-5-phenylpyridin-3-yl)amino)-1-oxopropan-2-yl)cyclohexyl)(methyl)carbamate<br>Prepared by a method analogous to Example 54.<br>LCMS (Method 2): m/z 529 (M + H)$^+$, 2.14 min. |

| Example | Structure | Name/Method/Analytical Data |
|---|---|---|
| A46 | 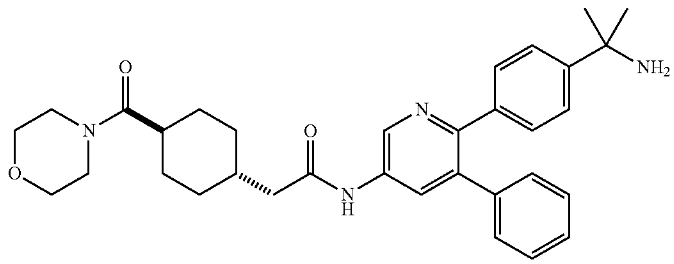 [SMILES: CC(C)(N)c1ccc(-c2ncc(NC(=O)C[C@H]3CC[C@H](C(=O)N4CCOCC4)CC3)cc2-c2ccccc2)cc1] | N-(6-(4-(2-aminopropan-2-yl)phenyl)-5-phenylpyridin-3-yl)-2-(trans-4-(morpholine-4-carbonyl)cyclohexyl)acetamide<br>Prepared by a method analogous to Example 55.<br>LCMS (Method 1): m/z 541 (M + H)+, at 1.31 min. |
| A47 | 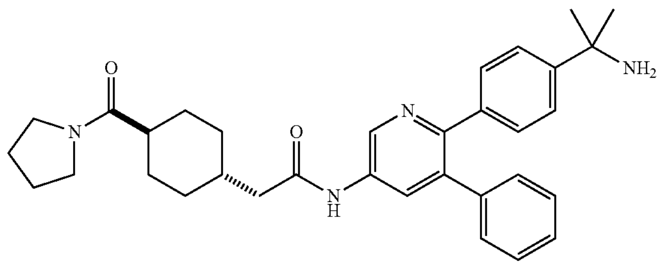 [SMILES: CC(C)(N)c1ccc(-c2ncc(NC(=O)C[C@H]3CC[C@H](C(=O)N4CCCC4)CC3)cc2-c2ccccc2)cc1] | N-(6-(4-(2-aminopropan-2-yl)phenyl)-5-phenylpyridin-3-yl)-2-(trans-4-(pyrrolidine-1-carbonyl)cyclohexyl)acetamide<br>Prepared by a method analogous to Example 55.<br>LCMS (Method 1): m/z 525 (M + H)+ at 1.45 min. |
| A48 | 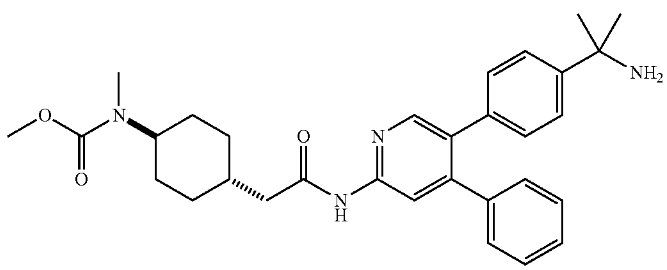 [SMILES: COC(=O)N(C)[C@H]1CC[C@H](CC(=O)Nc2cc(-c3ccccc3)c(-c3ccc(C(C)(C)N)cc3)cn2)CC1] | Methyl (trans-4-(2-((5-(4-(2-aminopropan-2-yl)phenyl)-4-phenylpyridin-2-yl)amino)-2-oxoethyl)cyclohexyl)(methyl)carbamate<br>Prepared by a method analogous to Example 63.<br>LCMS (Method 1): m/z 515 (M + H)+ at 1.62 min. |
| A49 | 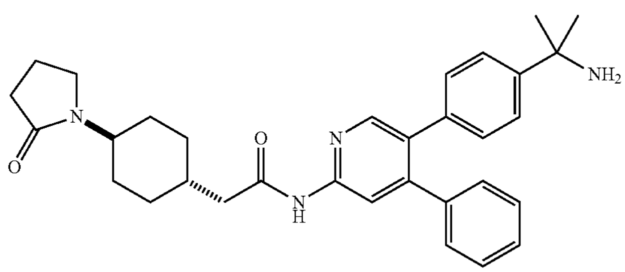 [SMILES: CC(C)(N)c1ccc(-c2cnc(NC(=O)C[C@H]3CC[C@H](N4CCCC4=O)CC3)cc2-c2ccccc2)cc1] | N-(5-(4-(2-aminopropan-2-yl)phenyl)-4-phenylpyridin-2-yl)-2-(trans-4-(2-oxopyrrolidin-1-yl)cyclohexyl)acetamide<br>Prepared by a method analogous to Example 63.<br>LCMS (Method 2): m/z 511 (M + H)+ at 1.98 min. |
| A50 | 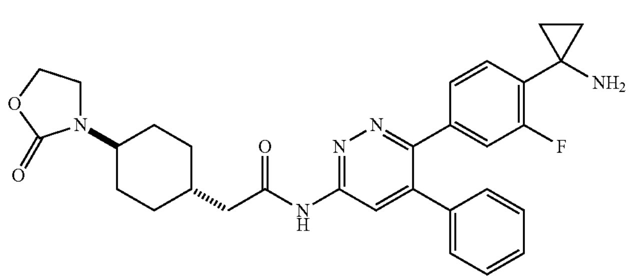 [SMILES: NC1(c2ccc(-c3nnc(NC(=O)C[C@H]4CC[C@H](N5CCOC5=O)CC4)cc3-c3ccccc3)cc2F)CC1] | N-(6-(4-(1-aminocyclopropyl)-3-fluorophenyl)-5-phenylpyridazin-3-yl)-2-(trans-4-(2-oxooxazolidin-3-yl)cyclohexyl)acetamide<br>Prepared by a method analogous to Example 30.<br>LCMS (Method 1): m/z 530 (M + H)+, 528 (M − H)−, at 1.34 min. |

| Example | Structure | Name/Method/Analytical Data |
|---|---|---|
| A51 | 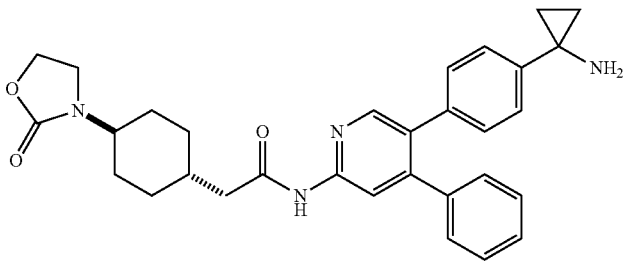 [SMILES: NC1(c2ccc(-c3cnc(NC(=O)C[C@H]4CC[C@H](N5CCOC5=O)CC4)cc3-c3ccccc3)cc2)CC1] | N-(5-(4-(1-aminocyclopropyl)phenyl)-4-phenylpyridin-2-yl)-2-(trans-4-(2-oxooxazolidin-3-yl)cyclohexyl)acetamide<br>Prepared by a method analogous to Example 65.<br>LCMS (Method 1): m/z 511 (M + H)$^+$ at 1.45 min. |
| A52 | 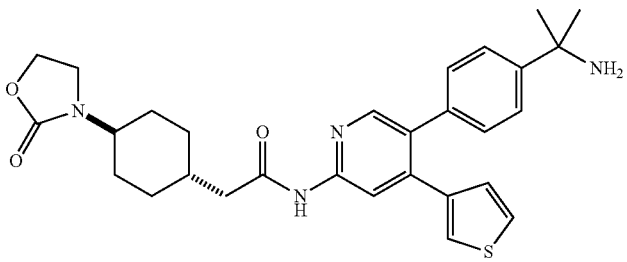 [SMILES: CC(C)(N)c1ccc(-c2cnc(NC(=O)C[C@H]3CC[C@H](N4CCOC4=O)CC3)cc2-c2ccsc2)cc1] | N-(5-(4-(2-aminopropan-2-yl)phenyl)-4-(thiophen-3-yl)pyridin-2-yl)-2-(trans-4-(2-oxooxazolidin-3-yl)cyclohexyl)acetamide<br>Prepared by a method analogous to Example 64.<br>LCMS (Method 2): m/z 519 (M + H)+ (ES+) at 1.89 min. |
| A53 | 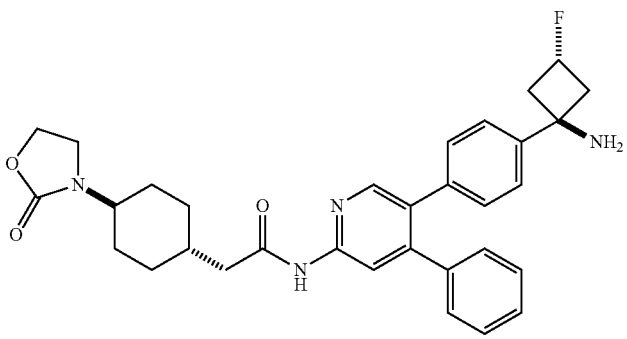 [SMILES: N[C@]1(c2ccc(-c3cnc(NC(=O)C[C@H]4CC[C@H](N5CCOC5=O)CC4)cc3-c3ccccc3)cc2)C[C@@H](F)C1] | N-(5-(4-(trans-1-amino-3-fluorocyclobutyl)phenyl)-4-phenylpyridin-2-yl)-2-(trans-4-(2-oxooxazolidin-3-yl)cyclohexyl)acetamide<br>Prepared by a method analogous to Example 65.<br>LCMS (Method 1): m/z 543 (M + H)$^+$ at 1.44 min. |
| A54 | 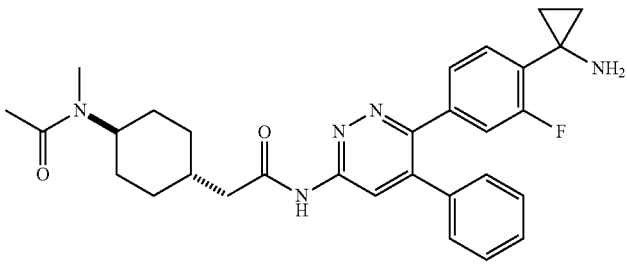 [SMILES: CC(=O)N(C)[C@H]1CC[C@H](CC(=O)Nc2cc(-c3ccccc3)c(-c3ccc(C4(N)CC4)c(F)c3)nn2)CC1] | N-(6-(4-(1-aminocyclopropyl)-3-fluorophenyl)-5-phenylpyridazin-3-yl)-2-(trans-4-(N-methylacetamido)cyclohexyl)acetamide<br>Prepared by a method analogous to Example 30.<br>LCMS (Method 1): m/z 516 (M + H)$^+$, 514 (M − H)$^−$, at 1.39 min. |
| A55 | 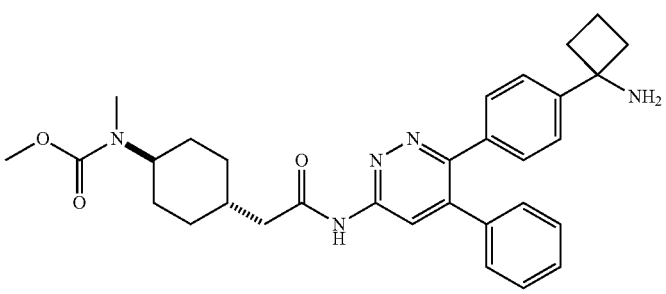 [SMILES: COC(=O)N(C)[C@H]1CC[C@H](CC(=O)Nc2cc(-c3ccccc3)c(-c3ccc(C4(N)CCC4)cc3)nn2)CC1] | Methyl (trans-4-(2-((6-(4-(1-aminocyclobutyl)phenyl)-5-phenylpyridazin-3-yl)amino)-2-oxoethyl)cyclohexyl)(methyl)carbamate<br>Prepared by a method analogous to Example 66.<br>LCMS (Method 1): m/z 528 (M + H)$^+$, 526 (M − H)$^−$, at 1.58 min. |

| Example | Structure | Name/Method/Analytical Data |
|---|---|---|
| A56 | 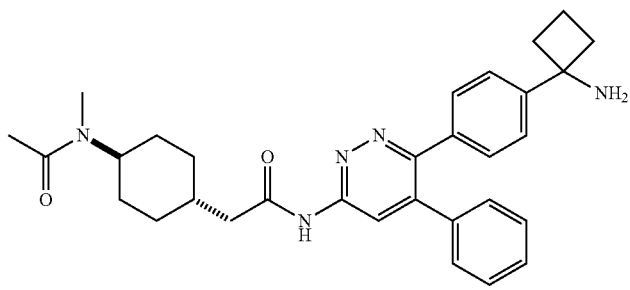 [SMILES: CC(=O)N(C)[C@H]1CC[C@H](CC(=O)Nc2cc(-c3ccccc3)c(-c3ccc(C4(N)CCC4)cc3)nn2)CC1] | N-(6-(4-(1-aminocyclobutyl)phenyl)-5-phenylpyridazin-3-yl)-2-(trans-4-(N-methylacetamido)cyclohexyl)acetamide<br>Prepared by a method analogous to Example 65.<br>LCMS (Method 1): m/z 512 (M + H)$^+$, 510 (M − H)$^−$, at 1.40 min. |
| A57 | 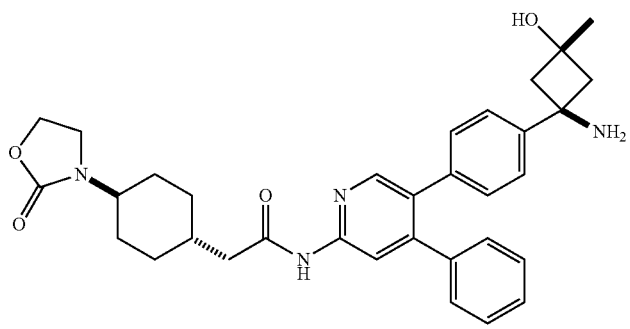 [SMILES: C[C@]1(O)C[C@@](N)(c2ccc(-c3cnc(NC(=O)C[C@H]4CC[C@H](N5CCOC5=O)CC4)cc3-c3ccccc3)cc2)C1] | N-(5-(4-(trans-1-amino-3-hydroxy-3-methylcyclobutyl)phenyl)-4-phenylpyridin-2-yl)-2-(trans-4-(2-oxooxazolidin-3-yl)cyclohexyl)acetamide<br>Prepared by a method analogous to Example 65.<br>LCMS (Method 1): m/z 555 (M + H)$^+$ at 1.31 min. |
| A58 | 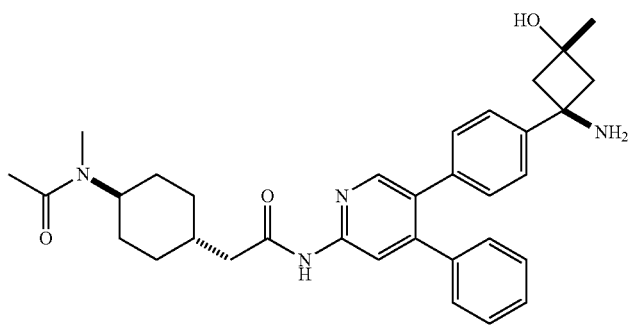 [SMILES: CC(=O)N(C)[C@H]1CC[C@H](CC(=O)Nc2cc(-c3ccccc3)c(-c3ccc([C@]4(N)C[C@](C)(O)C4)cc3)cn2)CC1] | N-(5-(4-(trans-1-amino-3-hydroxy-3-methylcyclobutyl)phenyl)-4-phenylpyridin-2-yl)-2-(trans-4-(N-methylacetamido)cyclohexyl)acetamide<br>Prepared by a method analogous to Example 66.<br>LCMS (Method 1): m/z 541 (M + H)$^+$ at 1.31 min. |
| A59 | 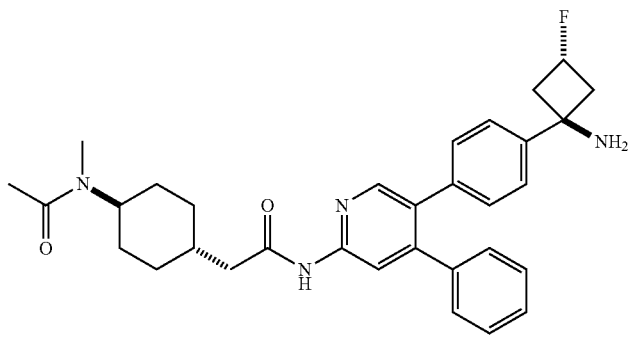 [SMILES: CC(=O)N(C)[C@H]1CC[C@H](CC(=O)Nc2cc(-c3ccccc3)c(-c3ccc([C@]4(N)C[C@H](F)C4)cc3)cn2)CC1] | N-(5-(4-((1r,3r)-1-amino-3-fluorocyclobutyl)phenyl)-4-phenylpyridin-2-yl)-2-(trans-4-(N-methylacetamido)cyclohexyl)acetamide<br>Prepared by a method analogous to Example 65.<br>LCMS (Method): m/z 529 (M + H)$^+$ at 1.51 min. |

| Example | Structure | Name/Method/Analytical Data |
|---|---|---|
| A60 | 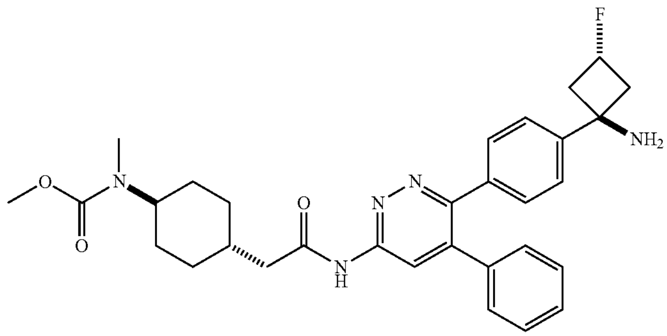 [SMILES: COC(=O)N(C)[C@H]1CC[C@H](CC(=O)Nc2cc(-c3ccccc3)c(-c3ccc([C@]4(N)C[C@H](F)C4)cc3)nn2)CC1] | Methyl (trans-4-(2-((6-(4-(trans-1-amino-3-fluorocyclobutyl)phenyl)-5-phenylpyridazin-3-yl)amino)-2-oxoethyl)cyclohexyl)(methyl)carbamate<br>Prepared by a method analogous to Example 65.<br>LCMS (Method 1): m/z 546 (M + H)+, 544 (M − H)−, at 1.60 min. |
| A61 | 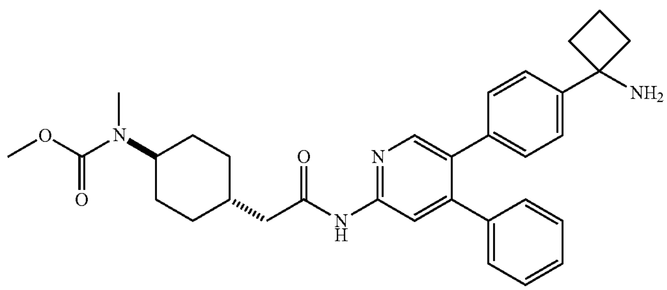 [SMILES: COC(=O)N(C)[C@H]1CC[C@H](CC(=O)Nc2cc(-c3ccccc3)c(-c3ccc(C4(N)CCC4)cc3)cn2)CC1] | Methyl (trans-4-(2-((5-(4-(1-aminocyclobutyl)phenyl)-4-phenylpyridin-2-yl)amino)-2-oxoethyl)cyclohexyl)(methyl)carbamate<br>Prepared by a method analogous to Example 63.<br>LCMS (Method 1): m/z 527 (M + H)+ at 2.36 min. |
| A62 | 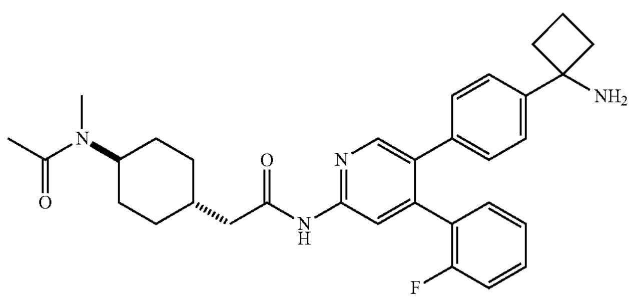 [SMILES: CC(=O)N(C)[C@H]1CC[C@H](CC(=O)Nc2cc(-c3ccccc3F)c(-c3ccc(C4(N)CCC4)cc3)cn2)CC1] | N-(5-(4-(1-aminocyclobutyl)phenyl)-4-(2-fluorophenyl)pyridin-2-yl)-2-(trans-4-(N-methylacetamido)cyclohexyl)acetamide<br>Prepared by a method analogous to Example 63.<br>LCMS (Method 1): m/z 529 (M + H)+ at 1.41 min. |
| A63 | 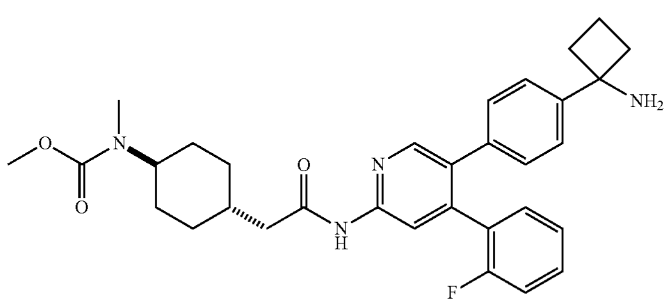 | Methyl (trans-4-(2-((5-(4-(1-aminocyclobutyl)phenyl)-4-(2-fluorophenyl)pyridin-2-yl)amino)-2-oxoethyl)cyclohexyl)(methyl)carbamate<br>Prepared by a method analogous to Example 63.<br>LCMS (Method 1): m/z 545 (M + H)+ at 1.59 min. |
| A64 | 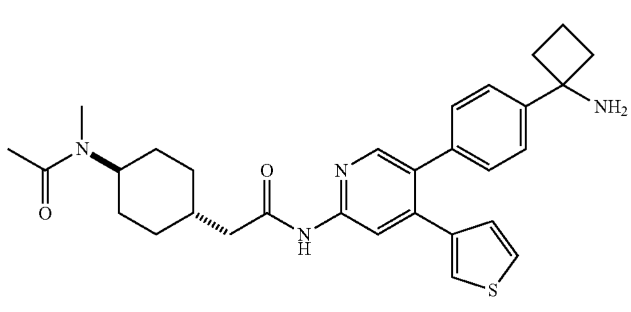 [SMILES: CC(=O)N(C)[C@H]1CC[C@H](CC(=O)Nc2cc(-c3ccsc3)c(-c3ccc(C4(N)CCC4)cc3)cn2)CC1] | N-(5-(4-(1-aminocyclobutyl)phenyl)-4-(thiophen-3-yl)pyridin-2-yl)-2-(trans-4-(N-methylacetamido)cyclohexyl)acetamide<br>Prepared by a method analogous to Example 63.<br>LCMS (Method 1): m/z 517 (M + H)+ at 1.39 min. |

-continued

| Example | Structure | Name/Method/Analytical Data |
|---|---|---|
| A65 | 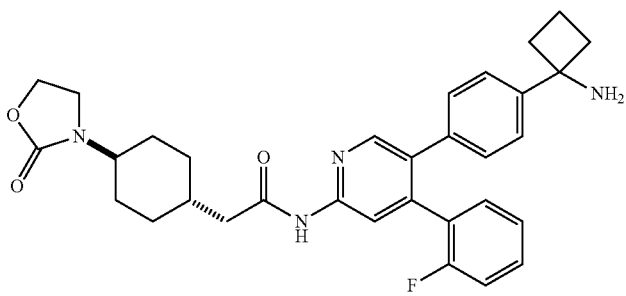 [SMILES: NC1(c2ccc(-c3cnc(NC(=O)C[C@H]4CC[C@H](N5CCOC5=O)CC4)cc3-c3ccccc3F)cc2)CCC1] | N-(5-(4-(1-aminocyclobutyl)phenyl)-4-(2-fluorophenyl)pyridin-2-yl)-2-(trans-4-(2-oxooxazolidin-3-yl)cyclohexyl)acetamide Prepared by a method analogous to Example 63. LCMS (Method 1): m/z 543 (M + H)$^+$ at 1.42 min. |
| A66 | 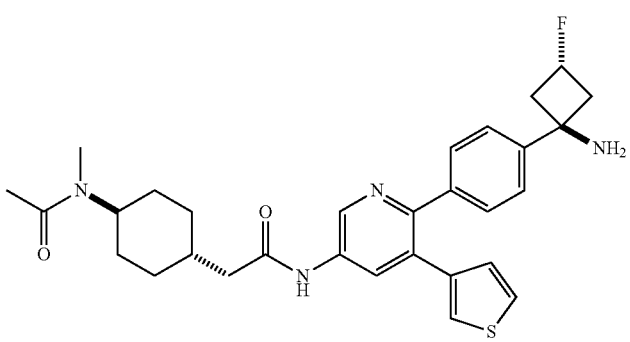 | Methyl (trans-4-(2-((6-(4-(trans-1-amino-3-fluorocyclobutyl)phenyl)-5-(thiophen-3-yl)pyridin-3-yl)amino)-2-oxoethyl)cyclohexyl)(methyl)carbamate Prepared by a method analogous to Example 70. LCMS (Method 1): m/z 551 (M + H)$^+$ at 2.01 min. |
| A67 | 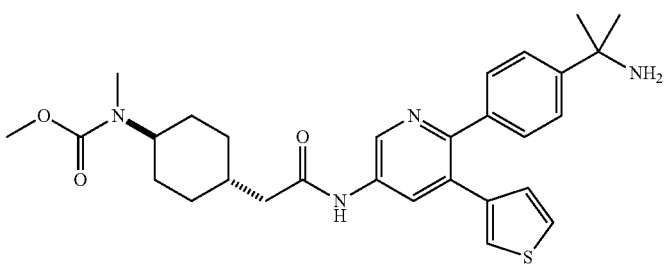 [SMILES: COC(=O)N(C)[C@H]1CC[C@H](CC(=O)Nc2cnc(-c3ccc(C(C)(C)N)cc3)c(-c3ccsc3)c2)CC1] | Methyl (trans-4-(2-((6-(4-(2-aminopropan-2-yl)phenyl)-5-(thiophen-3-yl)pyridin-3-yl)amino)-2-oxoethyl)cyclohexyl)(methyl)carbamate Prepared by a method analogous to Example 70. LCMS (Method 1): m/z 521 (M + H)$^+$ at 1.96 min. |
| A68 | 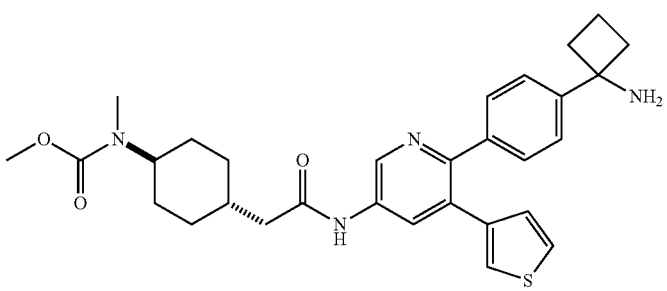 [SMILES: COC(=O)N(C)[C@H]1CC[C@H](CC(=O)Nc2cnc(-c3ccc(C4(N)CCC4)cc3)c(-c3ccsc3)c2)CC1] | Methyl (trans-4-(2-((6-(4-(1-aminocyclobutyl)phenyl)-5-(thiophen-3-yl)pyridin-3-yl)amino)-2-oxoethyl)cyclohexyl)(methyl)carbamate Prepared by a method analogous to Example 70. LCMS (Method 2): m/z 533 (M + H)$^+$ at 2.08 min. |
| A69 | 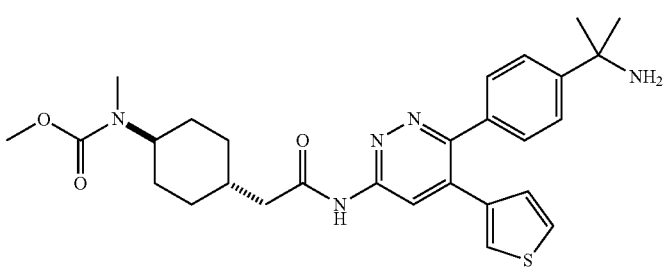 [SMILES: COC(=O)N(C)[C@H]1CC[C@H](CC(=O)Nc2cc(-c3ccsc3)c(-c3ccc(C(C)(C)N)cc3)nn2)CC1] | Methyl (trans-4-(2-((6-(4-(2-aminopropan-2-yl)phenyl)-5-(thiophen-3-yl)pyridazin-3-yl)amino)-2-oxoethyl)cyclohexyl)(methyl)carbamate Prepared by a method analogous to Example 65. LCMS (Method 1): m/z 522 (M + H)$^+$, 520 (M − H)$^-$, at 1.50 min. |

| Example | Structure | Name/Method/Analytical Data |
|---|---|---|
| A70 | 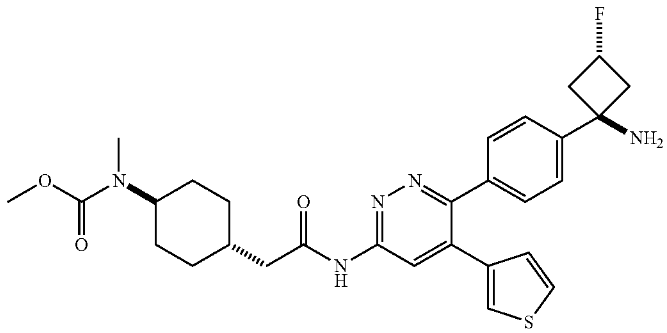 [SMILES: COC(=O)N(C)[C@H]1CC[C@H](CC(=O)Nc2cc(-c3ccsc3)c(-c3ccc([C@]4(N)C[C@H](F)C4)cc3)nn2)CC1] | Methyl (trans-4-(2-((6-(4-(trans-1-amino-3-fluorocyclobutyl)phenyl)-5-(thiophen-3-yl)pyridazin-3-yl)amino)-2-oxoethyl)cyclohexyl)(methyl)carbamate<br>Prepared by a method analogous to Example 65.<br>LCMS (Method 1): m/z 552 (M + H)⁺, 550 (M − H)⁻, at 1.57 min. |
| A71 | 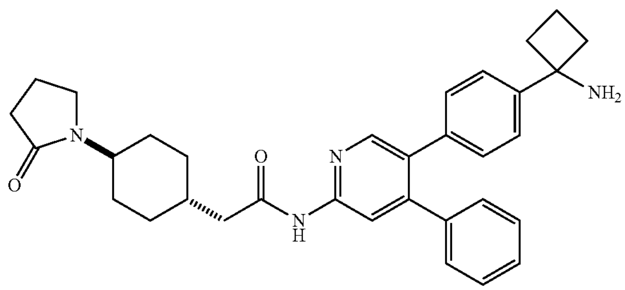 [SMILES: NC1(c2ccc(-c3cnc(NC(=O)C[C@H]4CC[C@H](N5CCCC5=O)CC4)cc3-c3ccccc3)cc2)CCC1] | N-(5-(4-(1-aminocyclobutyl)phenyl)-4-phenylpyridin-2-yl)-2-(trans-4-(2-oxopyrrolidin-1-yl)cyclohexyl)acetamide<br>Prepared by a method analogous to Example 65.<br>LCMS (Method 2): m/z 523 (M + H)⁺, at 2.09 min. |
| A72 | 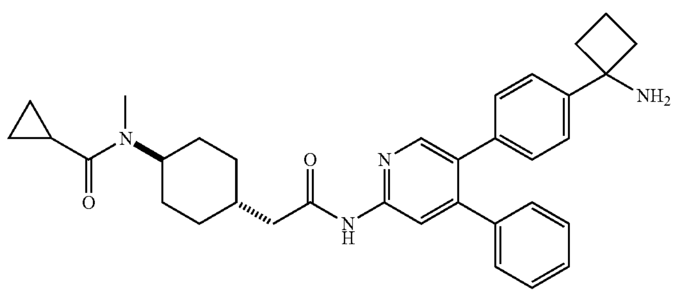 [SMILES: CN(C(=O)C1CC1)[C@H]1CC[C@H](CC(=O)Nc2cc(-c3ccccc3)c(-c3ccc(C4(N)CCC4)cc3)cn2)CC1] | N-(trans-4-(2-((5-(4-(1-aminocyclobutyl)phenyl)-4-phenylpyridin-2-yl)amino)-2-oxoethyl)cyclohexyl)-N-methylcyclopropanecarboxamide<br>Prepared by a method analogous to Example 65.<br>LCMS (Method 2): m/z 537 (M + H)⁺ at 2.25 min. |
| A73 | 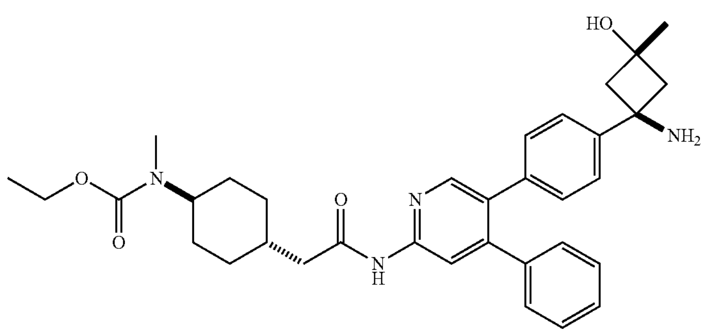 [SMILES: CCOC(=O)N(C)[C@H]1CC[C@H](CC(=O)Nc2cc(-c3ccccc3)c(-c3ccc([C@]4(N)C[C@](C)(O)C4)cc3)cn2)CC1] | Ethyl (trans-4-(2-((5-(4-(trans-1-amino-3-hydroxy-3-methylcyclobutyl)phenyl)-4-phenylpyridin-2-yl)amino)-2-oxoethyl)cyclohexyl)(methyl)carbamate<br>Prepared by a method analogous to Example 85.<br>LCMS (Method 1): m/z 571 (M + H)⁺ at 1.55 min. |
| A74 | 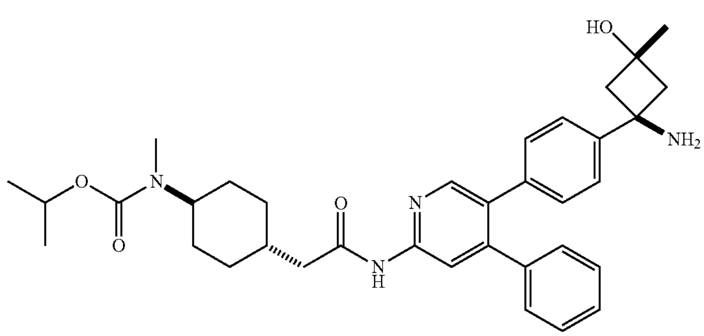 [SMILES: CC(C)OC(=O)N(C)[C@H]1CC[C@H](CC(=O)Nc2cc(-c3ccccc3)c(-c3ccc([C@]4(N)C[C@](C)(O)C4)cc3)cn2)CC1] | Isopropyl (trans-4-(2-((5-(4-(trans-1-amino-3-hydroxy-3-methylcyclobutyl)phenyl)-4-phenylpyridin-2-yl)amino)-2-oxoethyl)cyclohexyl)(methyl)carbamate<br>Prepared by a method analogous to Example 85.<br>LCMS (Method 1): m/z 585 (M + H)⁺ at 1.65 min. |

-continued

| Example | Structure | Name/Method/Analytical Data |
|---|---|---|
| A75 | 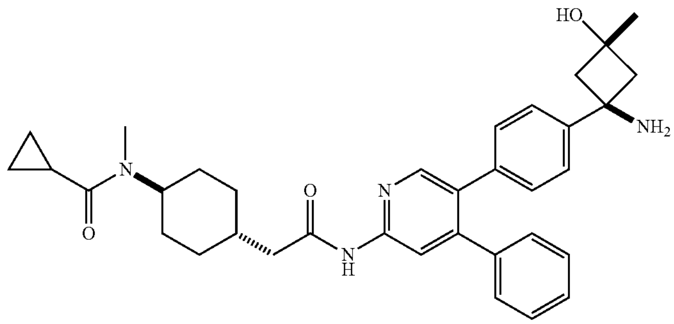 [SMILES: CN(C(=O)C1CC1)[C@H]1CC[C@H](CC(=O)Nc2cc(-c3ccccc3)c(-c3ccc([C@]4(N)C[C@](C)(O)C4)cc3)cn2)CC1] | N-(trans-4-(2-((5-(4-(trans-1-amino-3-hydroxy-3-methylcyclobutyl)phenyl)-4-phenylpyridin-2-yl)amino)-2-oxoethyl)cyclohexyl)-N-methylcyclopropanecarboxamide<br>Prepared by a method analogous to Example 85.<br>LCMS (Method 1): m/z 567 (M + H)+ at 1.40 min. |
| A76 | 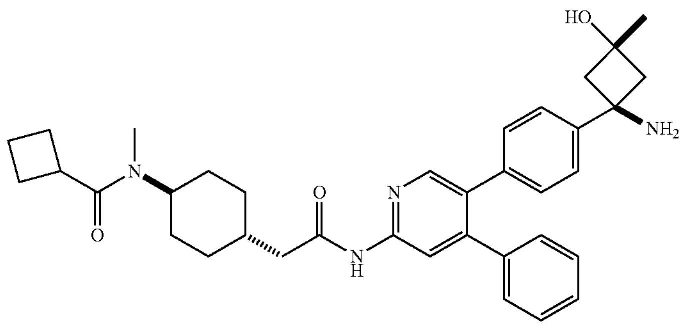 [SMILES: CN(C(=O)C1CCC1)[C@H]1CC[C@H](CC(=O)Nc2cc(-c3ccccc3)c(-c3ccc([C@]4(N)C[C@](C)(O)C4)cc3)cn2)CC1] | N-(trans-4-(2-((5-(4-(trans-1-amino-3-hydroxy-3-methylcyclobutyl)phenyl)-4-phenylpyridin-2-yl)amino)-2-oxoethyl)cyclohexyl)-N-methylcyclobutanecarboxamide<br>Prepared by a method analogous to Example 85.<br>LCMS (Method 1): m/z 581 (M + H)+ at 1.50 min. |
| A77 | 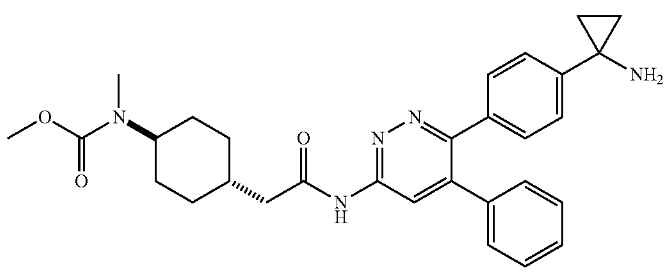 [SMILES: COC(=O)N(C)[C@H]1CC[C@H](CC(=O)Nc2cc(-c3ccccc3)c(-c3ccc(C4(N)CC4)cc3)nn2)CC1] | Methyl (trans-4-(2-((6-(4-(1-aminocyclopropyl)phenyl)-5-phenylpyridazin-3-yl)amino)-2-oxoethyl)cyclohexyl)(methyl)carbamate<br>Prepared by a method analogous to Example 65.<br>LCMS (Method 1): m/z 514 (M + H)+ at 1.57 min. |
| A78 | 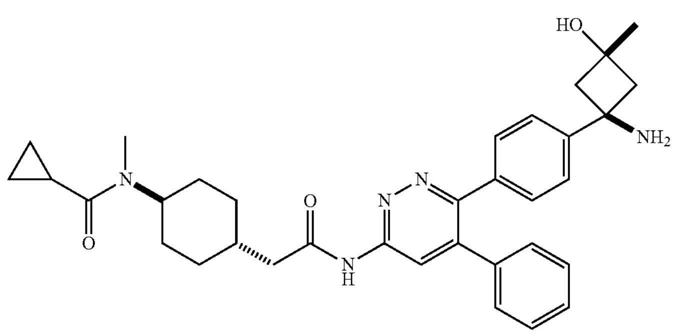 [SMILES: CN(C(=O)C1CC1)[C@H]1CC[C@H](CC(=O)Nc2cc(-c3ccccc3)c(-c3ccc([C@]4(N)C[C@](C)(O)C4)cc3)nn2)CC1] | N-(trans-4-(2-((6-(4-(trans-1-amino-3-hydroxy-3-methylcyclobutyl)phenyl)-5-phenylpyridazin-3-yl)amino)-2-oxoethyl)cyclohexyl)-N-methylcyclopropanecarboxamide<br>Prepared by a method analogous to Example 30.<br>LCMS (Method 1): m/z 568 (M + H)+, 566 (M − H)−, at 1.39 min. |
| A79 | 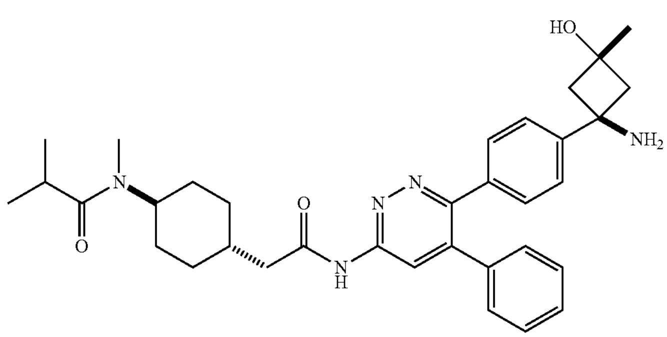 [SMILES: CC(C)C(=O)N(C)[C@H]1CC[C@H](CC(=O)Nc2cc(-c3ccccc3)c(-c3ccc([C@]4(N)C[C@](C)(O)C4)cc3)nn2)CC1] | N-(trans-4-(2-((6-(4-(trans-1-amino-3-hydroxy-3-methylcyclobutyl)phenyl)-5-phenylpyridazin-3-yl)amino)-2-oxoethyl)cyclohexyl)-N-methylisobutyramide<br>Prepared by a method analogous to Example 30.<br>LCMS (Method 1): m/z 570 (M + H)+, 568 (M − H)−, at 1.44 min. |

| Example | Structure | Name/Method/Analytical Data |
|---|---|---|
| A80 | 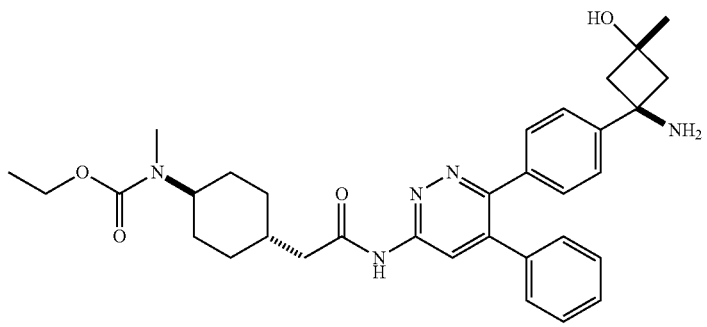 [SMILES: CCOC(=O)N(C)[C@H]1CC[C@H](CC(=O)Nc2cc(-c3ccccc3)c(-c3ccc([C@]4(N)C[C@](C)(O)C4)cc3)nn2)CC1] | Ethyl (trans-4-(2-((6-(4-(trans-1-amino-3-hydroxy-3-methylcyclobutyl)phenyl)-5-phenylpyridazin-3-yl)amino)-2-oxoethyl)cyclohexyl)(methyl)carbamate<br>Prepared by a method analogous to Example 30.<br>LCMS (Method 1): m/z 572 (M + H)⁺, 570 (M − H)⁻, at 1.54 min. |
| A81 | 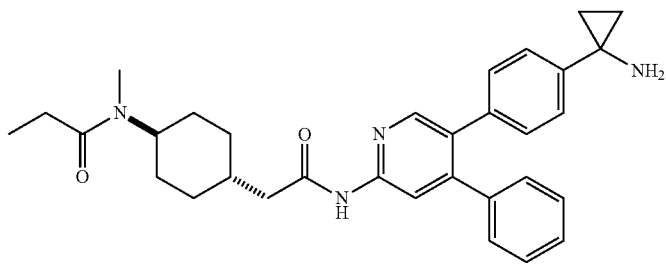 [SMILES: CCC(=O)N(C)[C@H]1CC[C@H](CC(=O)Nc2cc(-c3ccccc3)c(-c3ccc(C4(N)CC4)cc3)cn2)CC1] | N-(trans-4-(2-((5-(4-(1-aminocyclopropyl)phenyl)-4-phenylpyridin-2-yl)amino)-2-oxoethyl)cyclohexyl)-N-methylpropionamide<br>Prepared by a method analogous to Example 85.<br>LCMS (Method 1): m/z 511 (M + H)⁺, 509 (M − H)⁻, at 1.48 min. |
| A82 | 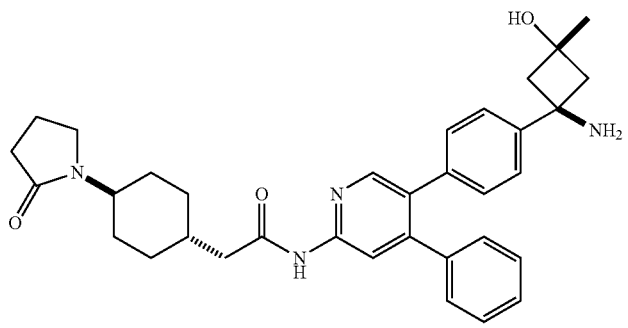 [SMILES: C[C@]1(O)C[C@@](N)(c2ccc(-c3cnc(NC(=O)C[C@H]4CC[C@H](N5CCCC5=O)CC4)cc3-c3ccccc3)cc2)C1] | N-(5-(4-(trans-1-amino-3-hydroxy-3-methylcyclobutyl)phenyl)-4-phenylpyridin-2-yl)-2-(trans-4-(2-oxopyrrolidin-1-yl)cyclohexyl)acetamide<br>Prepared by a method analogous to Example 85.<br>LCMS (Method 1): m/z 553 (M + H)⁺, 551 (M − H)⁻, at 1.29 min. |
| A83 | 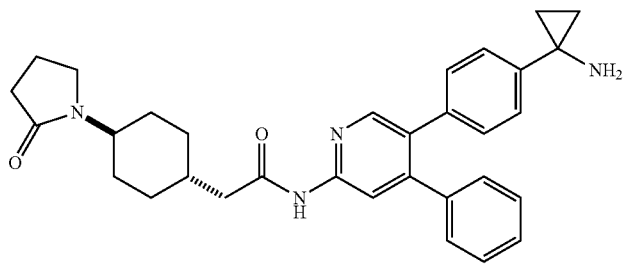 [SMILES: NC1(c2ccc(-c3cnc(NC(=O)C[C@H]4CC[C@H](N5CCCC5=O)CC4)cc3-c3ccccc3)cc2)CC1] | N-(5-(4-(1-aminocyclopropyl)phenyl)-4-phenylpyridin-2-yl)-2-(trans-4-(2-oxopyrrolidin-1-yl)cyclohexyl)acetamide<br>Prepared by a method analogous to Example 76.<br>LCMS (Method 1): m/z 509 (M + H)⁺, 507 (M − H)⁻, at 1.42 min. |
| A84 | 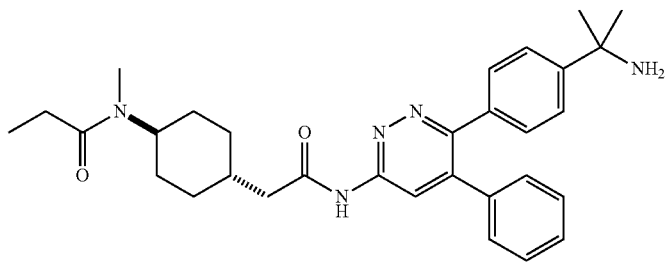 | N-(trans-4-(2-((6-(4-(2-aminopropan-2-yl)phenyl)-5-phenylpyridazin-3-yl)amino)-2-oxoethyl)cyclohexyl)-N-methylpropionamide<br>Prepared by a method analogous to Example 30.<br>LCMS (Method 1): m/z 514 (M + H)⁺, 512 (M − H)⁻, at 1.46 min. |

| Example | Structure | Name/Method/Analytical Data |
|---|---|---|
| A85 | 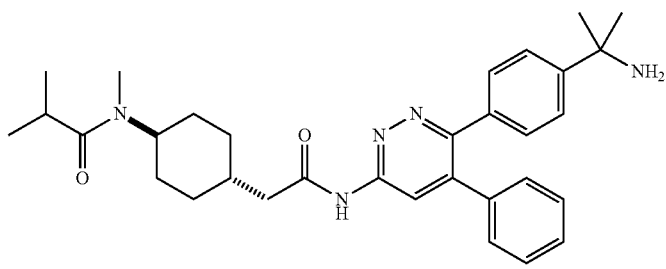 [SMILES: CC(C)C(=O)N(C)[C@H]1CC[C@H](CC(=O)Nc2cc(-c3ccccc3)c(-c3ccc(C(C)(C)N)cc3)nn2)CC1] | N-(trans-4-(2-((6-(4-(2-aminopropan-2-yl)phenyl)-5-phenylpyridazin-3-yl)amino)-2-oxoethyl)cyclohexyl)-N-methylisobutyramide<br>Prepared by a method analogous to Example 30.<br>LCMS (Method 1): m/z 528 (M + H)$^+$, 526 (M − H)$^−$, at 1.54 min. |
| A86 | 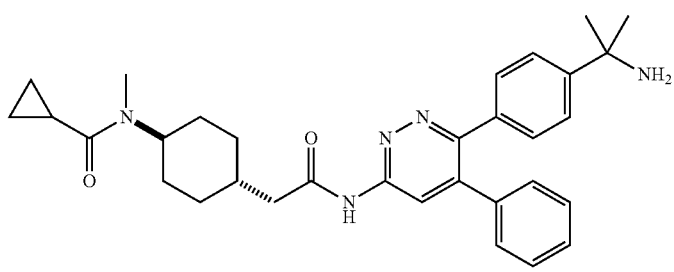 [SMILES: CN(C(=O)C1CC1)[C@H]1CC[C@H](CC(=O)Nc2cc(-c3ccccc3)c(-c3ccc(C(C)(C)N)cc3)nn2)CC1] | N-(trans-4-(2-((6-(4-(2-aminopropan-2-yl)phenyl)-5-phenylpyridazin-3-yl)amino)-2-oxoethyl)cyclohexyl)-N-methylcyclopropanecarboxamide<br>Prepared by a method analogous to Example 30.<br>LCMS (Method 1): m/z 526 (M + H)$^+$, 524 (M − H)$^−$, at 1.50 min. |
| A87 | 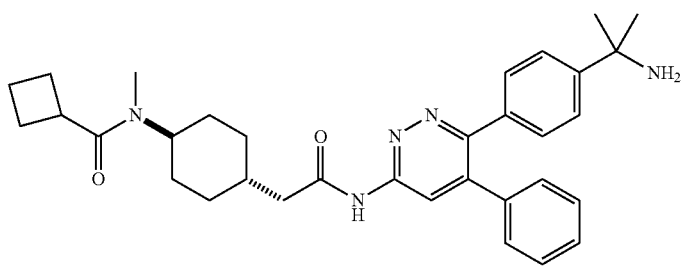 [SMILES: CN(C(=O)C1CCC1)[C@H]1CC[C@H](CC(=O)Nc2cc(-c3ccccc3)c(-c3ccc(C(C)(C)N)cc3)nn2)CC1] | N-(trans-4-(2-((6-(4-(2-aminopropan-2-yl)phenyl)-5-phenylpyridazin-3-yl)amino)-2-oxoethyl)cyclohexyl)-N-methylcyclobutanecarboxamide<br>Prepared by a method analogous to Example 30.<br>LCMS (Method 1): m/z 540 (M + H)$^+$, 538 (M − H)$^−$, at 1.59 min. |
| A88 | 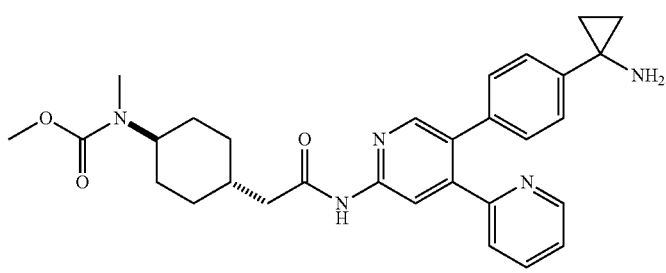 [SMILES: COC(=O)N(C)[C@H]1CC[C@H](CC(=O)Nc2cc(-c3ccccn3)c(-c3ccc(C4(N)CC4)cc3)cn2)CC1] | Methyl ((1r,4r)-4-(2-((5'-(4-(1-aminocyclopropyl)phenyl)-[2,4'-bipyridin]-2'-yl)amino)-2-oxoethyl)cyclohexyl)(methyl)carbamate<br>Prepared by a method analogous to Example 86.<br>LCMS (Method 1): m/z 514 (M + H)$^+$, 512 (M − H)$^−$, at 1.34 min. |
| A89 | 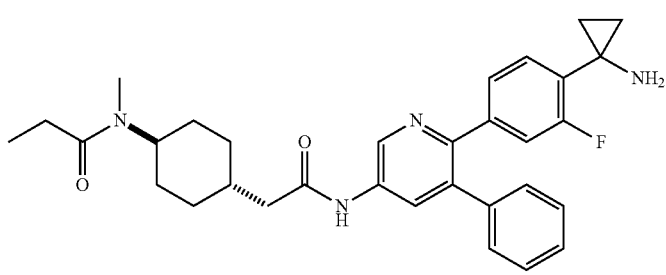 [SMILES: CCC(=O)N(C)[C@H]1CC[C@H](CC(=O)Nc2cnc(-c3ccc(C4(N)CC4)c(F)c3)c(-c3ccccc3)c2)CC1] | N-(trans-4-(2-((6-(4-(1-aminocyclopropyl)-3-fluorophenyl)-5-phenylpyridin-3-yl)amino)-2-oxoethyl)cyclohexyl)-N-methylpropionamide<br>Prepared by a method analogous to Example 65.<br>LCMS (Method 1): m/z 529 (M + H)$^+$ at 1.47 min. |

| Example | Structure | Name/Method/Analytical Data |
|---|---|---|
| A90 | 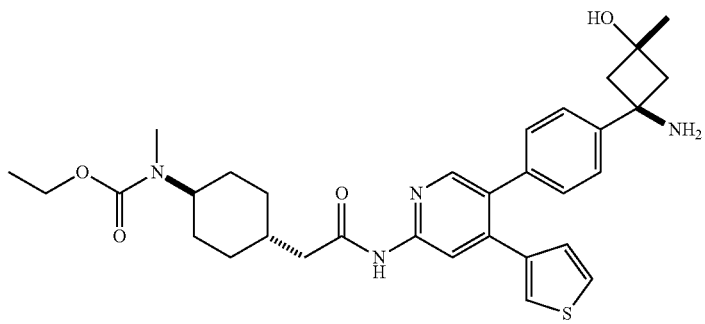 [SMILES: CCOC(=O)N(C)[C@H]1CC[C@H](CC(=O)Nc2cc(-c3ccsc3)c(-c3ccc([C@]4(N)C[C@](C)(O)C4)cc3)cn2)CC1] | Ethyl (trans-4-(2-((5-(4-(trans-1-amino-3-hydroxy-3-methylcyclobutyl)phenyl)-4-(thiophen-3-yl)pyridin-2-yl)amino)-2-oxoethyl)cyclohexyl)(methyl)carbamate<br>Prepared by a method analogous to Example 85.<br>LCMS (Method 1): m/z 577 (M + H)$^+$, 575 (M − H)$^-$, at 1.51 min. |
| A91 | 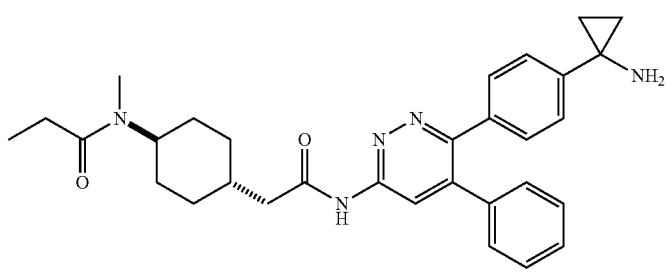 [SMILES: CCC(=O)N(C)[C@H]1CC[C@H](CC(=O)Nc2cc(-c3ccccc3)c(-c3ccc(C4(N)CC4)cc3)nn2)CC1] | N-(trans-4-(2-((6-(4-(1-aminocyclopropyl)phenyl)-5-phenylpyridazin-3-yl)amino)-2-oxoethyl)cyclohexyl)-N-methylpropionamide<br>Prepared by a method analogous to Example 65.<br>LCMS (Method 1): m/z 512 (M + H)$^+$ at 1.49 min. |
| A92 | 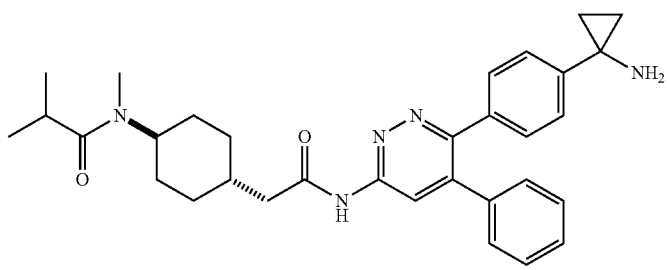 [SMILES: CC(C)C(=O)N(C)[C@H]1CC[C@H](CC(=O)Nc2cc(-c3ccccc3)c(-c3ccc(C4(N)CC4)cc3)nn2)CC1] | N-(trans-4-(2-((6-(4-(1-aminocyclopropyl)phenyl)-5-phenylpyridazin-3-yl)amino)-2-oxoethyl)cyclohexyl)-N-methylisobutyramide<br>Prepared by a method analogous to Example 65.<br>LCMS (Method 1): m/z 526 (M + H)$^+$ at 1.54 min. |
| A93 | 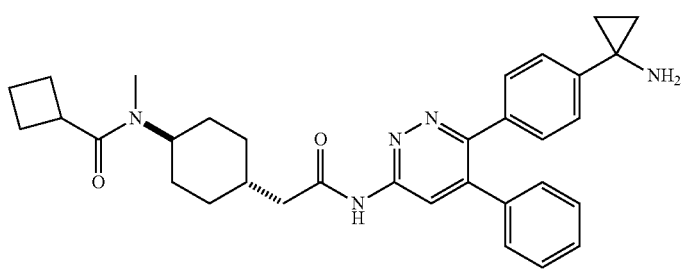 [SMILES: CN(C(=O)C1CCC1)[C@H]1CC[C@H](CC(=O)Nc2cc(-c3ccccc3)c(-c3ccc(C4(N)CC4)cc3)nn2)CC1] | N-(trans-4-(2-((6-(4-(1-aminocyclopropyl)phenyl)-5-phenylpyridazin-3-yl)amino)-2-oxoethyl)cyclohexyl)-N-methylcyclobutanecarboxamide<br>Prepared by a method analogous to Example 65.<br>LCMS (Method 1): m/z 538 (M + H)$^+$ at 1.59 min. |
| A94 | 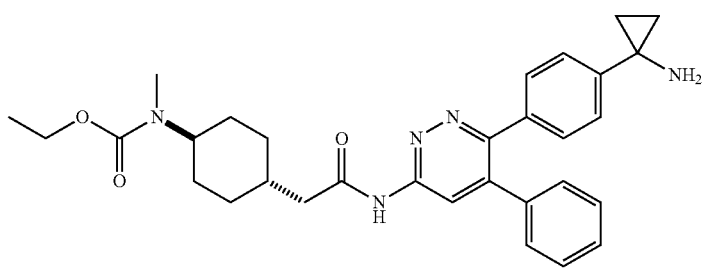 [SMILES: CCOC(=O)N(C)[C@H]1CC[C@H](CC(=O)Nc2cc(-c3ccccc3)c(-c3ccc(C4(N)CC4)cc3)nn2)CC1] | Ethyl (trans-4-(2-((6-(4-(1-aminocyclopropyl)phenyl)-5-phenylpyridazin-3-yl)amino)-2-oxoethyl)cyclohexyl)(methyl)carbamate<br>Prepared by a method analogous to Example 65.<br>LCMS (Method 1): m/z 528 (M + H)$^+$ at 1.64 min. |

| Example | Structure | Name/Method/Analytical Data |
|---|---|---|
| A95 | 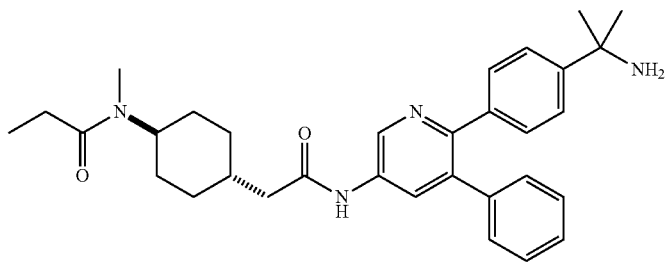 [SMILES: CCC(=O)N(C)[C@H]1CC[C@H](CC(=O)Nc2cnc(-c3ccc(C(C)(C)N)cc3)c(-c3ccccc3)c2)CC1] | N-(trans-4-(2-((6-(4-(2-aminopropan-2-yl)phenyl)-5-phenylpyridin-3-yl)amino)-2-oxoethyl)cyclohexyl)-N-methylpropionamide<br>Prepared by a method analogous to Example 5.<br>LCMS (Method 1): m/z 513 (M + H)$^+$ at 1.43 min. |
| A96 | 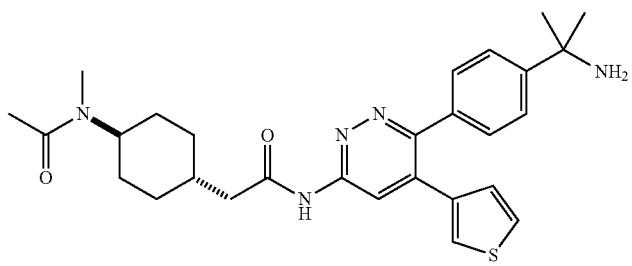 [SMILES: CC(=O)N(C)[C@H]1CC[C@H](CC(=O)Nc2cc(-c3ccsc3)c(-c3ccc(C(C)(C)N)cc3)nn2)CC1] | N-(6-(4-(2-aminopropan-2-yl)phenyl)-5-(thiophen-3-yl)pyridazin-3-yl)-2-(trans-4-(N-methylacetamido)cyclohexyl)acetamide<br>Prepared by a method analogous to Example 80.<br>LCMS (Method 1): m/z 506 (M + H)$^+$, 504 (M − H)$^−$, at 1.34 min. |
| A97 | 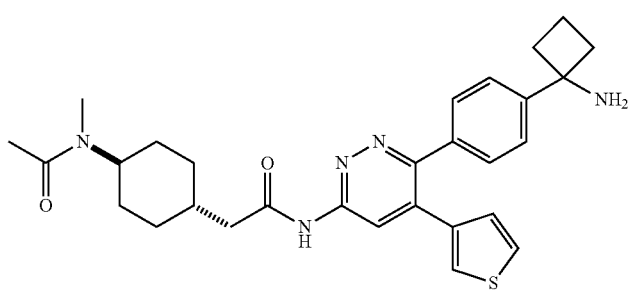 [SMILES: CC(=O)N(C)[C@H]1CC[C@H](CC(=O)Nc2cc(-c3ccsc3)c(-c3ccc(C4(N)CCC4)cc3)nn2)CC1] | N-(6-(4-(1-aminocyclobutyl)phenyl)-5-(thiophen-3-yl)pyridazin-3-yl)-2-(trans-4-(N-methylacetamido)cyclohexyl)acetamide<br>Prepared by a method analogous to Example 80.<br>LCMS (Method 1): m/z 518 (M + H)$^+$, 516 (M − H)$^−$, at 1.40 min. |
| A98 | 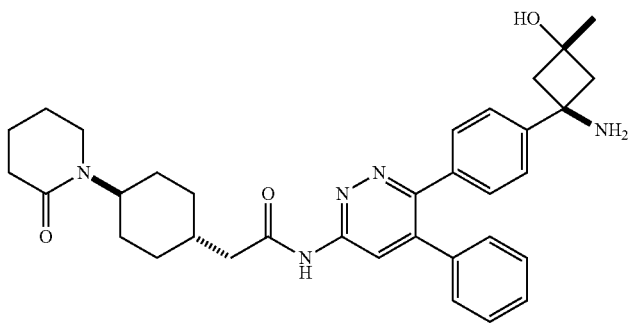 [SMILES: C[C@]1(O)C[C@@](N)(c2ccc(-c3nnc(NC(=O)C[C@H]4CC[C@H](N5CCCCC5=O)CC4)cc3-c3ccccc3)cc2)C1] | N-(6-(4-(trans-1-amino-3-hydroxy-3-methylcyclobutyl)phenyl)-5-phenylpyridazin-3-yl)-2-(trans-4-(2-oxopiperidin-1-yl)cyclohexyl)acetamide<br>Prepared by a method analogous to Example 80.<br>LCMS (Method 1): m/z 568 (M + H)$^+$, 566 (M − H)$^−$, at 1.38 min. |
| A99 | 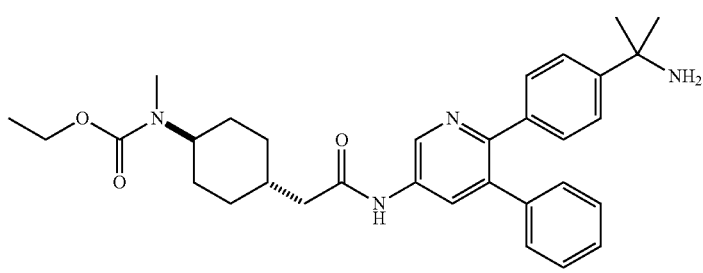 [SMILES: CCOC(=O)N(C)[C@H]1CC[C@H](CC(=O)Nc2cnc(-c3ccc(C(C)(C)N)cc3)c(-c3ccccc3)c2)CC1] | Ethyl (trans-4-(2-((6-(4-(2-aminopropan-2-yl)phenyl)-5-phenylpyridin-3-yl)amino)-2-oxoethyl)cyclohexyl)(methyl)carbamate<br>Prepared by a method analogous to Example 56.<br>LCMS (Method 1): m/z 529 (M + H)$^+$ at 1.62 min. |

| Example | Structure | Name/Method/Analytical Data |
|---|---|---|
| A100 | 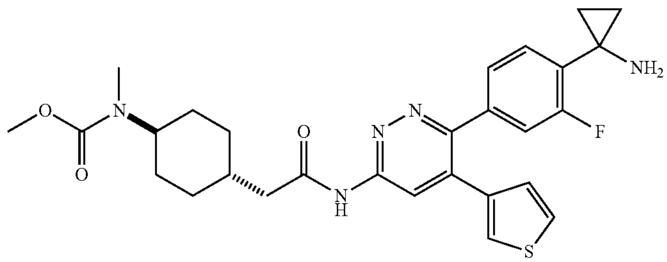 [SMILES: COC(=O)N(C)[C@H]1CC[C@H](CC(=O)Nc2cc(-c3ccsc3)c(-c3ccc(C4(N)CC4)c(F)c3)nn2)CC1] | Methyl (trans-4-(2-((6-(4-(1-aminocyclopropyl)-3-fluorophenyl)-5-(thiophen-3-yl)pyridazin-3-yl)amino)-2-oxoethyl)cyclohexyl)(methyl)carbamate<br>Prepared by a method analogous to Example 91.<br>LCMS (Method 1): m/z 538 (M + H)+, 536 (M − H)−, at 1.54 min. |
| A101 | 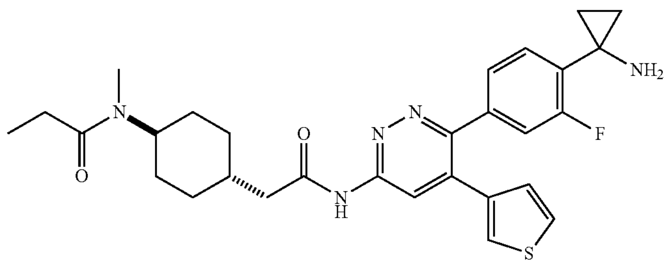 [SMILES: CCC(=O)N(C)[C@H]1CC[C@H](CC(=O)Nc2cc(-c3ccsc3)c(-c3ccc(C4(N)CC4)c(F)c3)nn2)CC1] | N-(trans-4-(2-((6-(4-(1-aminocyclopropyl)-3-fluorophenyl)-5-(thiophen-3-yl)pyridazin-3-yl)amino)-2-oxoethyl)cyclohexyl)-N-methylpropionamide<br>Prepared by a method analogous to Example 91.<br>LCMS (Method 1): m/z 536 (M + H)+, 534 (M − H)−, at 1.45 min. |
| A102 | 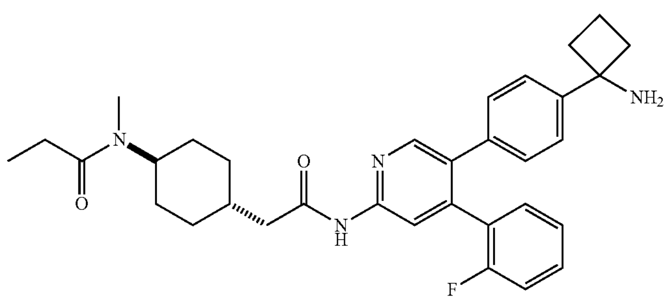 [SMILES: CCC(=O)N(C)[C@H]1CC[C@H](CC(=O)Nc2cc(-c3ccccc3F)c(-c3ccc(C4(N)CCC4)cc3)cn2)CC1] | N-(trans-4-(2-((5-(4-(1-aminocyclobutyl)phenyl)-4-(2-fluorophenyl)pyridin-2-yl)amino)-2-oxoethyl)cyclohexyl)-N-methylpropionamide<br>Prepared by a method analogous to Example 65.<br>LCMS (Method 1): m/z 543 (M + H)+ at 1.56 min. |
| A103 | 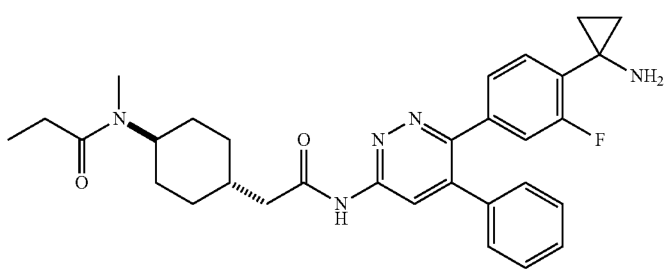 [SMILES: CCC(=O)N(C)[C@H]1CC[C@H](CC(=O)Nc2cc(-c3ccccc3)c(-c3ccc(C4(N)CC4)c(F)c3)nn2)CC1] | N-(trans-4-(2-((6-(4-(1-aminocyclopropyl)-3-fluorophenyl)-5-phenylpyridazin-3-yl)amino)-2-oxoethyl)cyclohexyl)-N-methylpropionamide<br>Prepared by a method analogous to Example 30.<br>LCMS (Method 1): m/z 530 (M + H)+, 528 (M − H)−, at 1.47 min. |
| A104 | 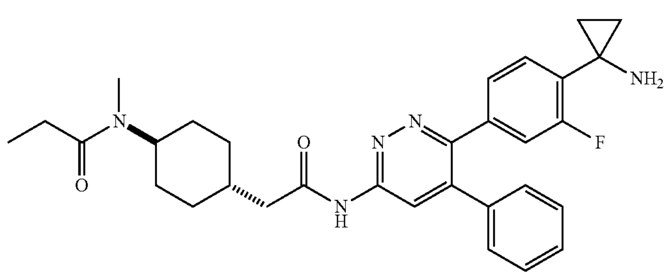 [SMILES: CCC(=O)N(C)[C@H]1CC[C@H](CC(=O)Nc2cc(-c3ccccc3)c(-c3ccc(C4(N)CC4)c(F)c3)nn2)CC1] | Methyl (trans-4-(2-((6-(4-(1-aminocyclopropyl)-3-fluorophenyl)-5-phenylpyridazin-3-yl)amino)-2-oxoethyl)cyclohexyl)(methyl)carbamate<br>Prepared by a method analogous to Example 30.<br>LCMS (Method 1): m/z 532 (M + H)+, 530 (M − H)−, at 1.55 min. |

| Example | Structure | Name/Method/Analytical Data |
|---|---|---|
| A105 | 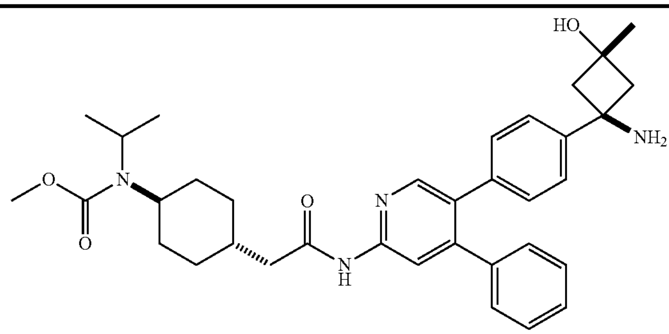 | Methyl (trans-4-(2-((5-(4-(trans-1-amino-3-hydroxy-3-methylcyclobutyl)phenyl)-4-phenylpyridin-2-yl)amino)-2-oxoethyl)cyclohexyl)(isopropyl)carbamate<br>Prepared by a method analogous to Example 49.<br>LCMS (Method 2): m/z 585 (M + H)$^+$ at 2.26 min. |
| A106 | 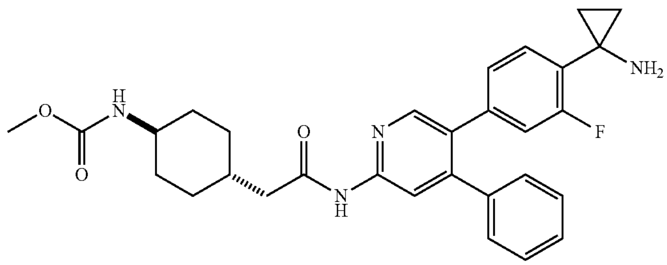 [SMILES: COC(=O)N[C@H]1CC[C@H](CC(=O)Nc2cc(-c3ccccc3)c(-c3ccc(C4(N)CC4)c(F)c3)cn2)CC1] | Methyl (trans-4-(2-((5-(4-(1-aminocyclopropyl)-3-fluorophenyl)-4-phenylpyridin-2-yl)amino)-2-oxoethyl)cyclohexyl)carbamate<br>Prepared by a method analogous to Example 30.<br>LCMS (Method 1): m/z 517 (M + H)$^+$ at 1.49 min. |
| A107 | 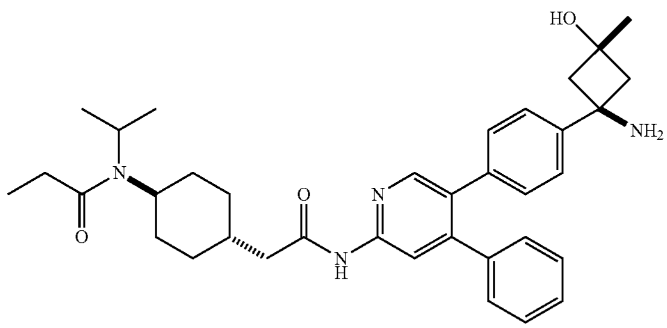 [SMILES: CCC(=O)N(C(C)C)[C@H]1CC[C@H](CC(=O)Nc2cc(-c3ccccc3)c(-c3ccc([C@]4(N)C[C@](C)(O)C4)cc3)cn2)CC1] | N-(trans-4-(2-((5-(4-(trans-1-amino-3-hydroxy-3-methylcyclobutyl)phenyl)-4-phenylpyridin-2-yl)amino)-2-oxoethyl)cyclohexyl)-N-isopropylpropionamide<br>Prepared by a method analogous to Example 102.<br>LCMS (Method 2): m/z 583 (M + H)$^+$ at 2.11 min. |
| A108 | 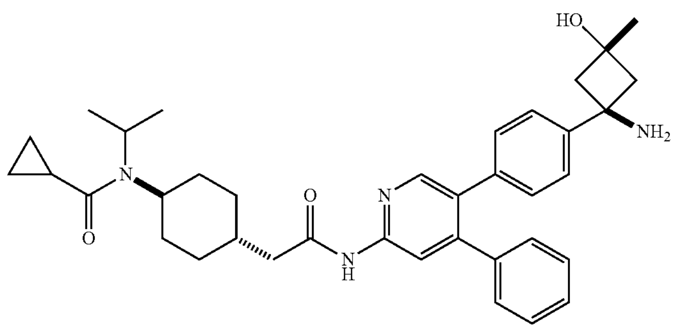 [SMILES: CC(C)N(C(=O)C1CC1)[C@H]1CC[C@H](CC(=O)Nc2cc(-c3ccccc3)c(-c3ccc([C@]4(N)C[C@](C)(O)C4)cc3)cn2)CC1] | N-(trans-4-(2-((5-(4-(trans-1-amino-3-hydroxy-3-methylcyclobutyl)phenyl)-4-phenylpyridin-2-yl)amino)-2-oxoethyl)cyclohexyl)-N-isopropylcyclopropanecarboxamide<br>Prepared by a method analogous to Example 102.<br>LCMS (Method 2): m/z 595 (M + H)$^+$ at 2.17 min. |

The following example compounds may be prepared by methods analogous to those described above:

B1  N-(6-(4-(2-aminobutan-2-yl)-3-fluorophenyl)-5-phenylpyridin-3-yl)-2-(trans-4-(N-methylacetamido)cyclohexyl)acetamide;

B2  methyl (trans-4-(2-((6-(4-(2-aminobutan-2-yl)-3-fluorophenyl)-5-phenylpyridin-3-yl)amino)-2-oxoethyl)cyclohexyl)(methyl)carbamate;

B3  N-(6-(4-(2-aminopropan-2-yl)-3-methoxyphenyl)-5-phenylpyridin-3-yl)-2-(trans-4-(N-methylacetamido)cyclohexyl)acetamide;

B4  methyl (trans-4-(2-((6-(4-(2-aminopropan-2-yl)-3-methoxyphenyl)-5-phenylpyridin-3-yl)amino)-2-oxoethyl)cyclohexyl)(methyl)carbamate;

B5  2-(trans-4-acetamidocyclohexyl)-N-(5-(4-(trans-1-amino-3-hydroxy-3-methylcyclobutyl)phenyl)-4-phenylpyridin-2-yl)acetamide;

B6  N-(trans-4-(2-((5-(4-(2-aminopropan-2-yl)phenyl)-4-phenylpyridin-2-yl)amino)-2-oxoethyl)cyclohexyl)-N-methylisobutyramide;

B7  N-(5-(4-(1-amino-3,3-difluorocyclobutyl)phenyl)-4-phenylpyridin-2-yl)-2-(trans-4-(N-methylacetamido)cyclohexyl)acetamide;

B8 N-(5-(4-(2-aminopropan-2-yl)phenyl)-4-(thiophen-3-yl)pyridin-2-yl)-2-(trans-4-(N-methylacetamido)cyclohexyl)acetamide;

B9 N-(5-(4-(2-aminopropan-2-yl)phenyl)-4-(2-fluorophenyl)pyridin-2-yl)-2-(trans-4-(N-methylacetamido)cyclohexyl)acetamide;

B10 N-(5-(4-(1-aminocyclopropyl)phenyl)-4-phenylpyridin-2-yl)-2-(trans-4-(N-methylacetamido)cyclohexyl)acetamide;

B11 2-(trans-4-acetamidocyclohexyl)-N-(5-(4-(3-aminooxetan-3-yl)phenyl)-4-phenylpyridin-2-yl)acetamide;

B12 2-(trans-4-acetamidocyclohexyl)-N-(5-(4-(trans-1-amino-3-fluorocyclobutyl)phenyl)-4-phenylpyridin-2-yl)acetamide;

B13 N-(5-(4-(1-aminocyclobutyl)phenyl)-4-(thiophen-3-yl)pyridin-2-yl)-2-(trans-4-(N-methylmethylsulfonamido)cyclohexyl)acetamide;

B14 N-(5-(4-(3-aminooxetan-3-yl)phenyl)-4-phenylpyridin-2-yl)-2-((2R,6S)-2,6-dimethyltetrahydro-2H-pyran-4-yl)acetamide;

B15 N-(trans-4-(2-((5-(4-(2-aminopropan-2-yl)phenyl)-4-(thiophen-3-yl)pyridin-2-yl)amino)-2-oxoethyl)cyclohexyl)cyclopropanecarboxamide;

B16 N-(trans-4-(2-((5-(4-(2-aminopropan-2-yl)phenyl)-4-(thiophen-3-yl)pyridin-2-yl)amino)-2-oxoethyl)cyclohexyl)-N-methylcyclopropanecarboxamide;

B17 N-(5-(4-(2-aminopropan-2-yl)phenyl)-4-phenylpyridin-2-yl)-2-(trans-4-(2-oxopiperidin-1-yl)cyclohexyl)acetamide;

B18 N-(5-(4-(2-aminopropan-2-yl)phenyl)-4-phenylpyridin-2-yl)-2-(trans-4-(2-cyclopropylacetamido)cyclohexyl)acetamide;

B19 N-(5-(4-(trans-1-amino-3-fluorocyclobutyl)phenyl)-4-phenylpyridin-2-yl)-2-(trans-4-(N-methylacetamido)cyclohexyl)acetamide;

B20 2-(trans-4-acetamidocyclohexyl)-N-(5-(4-(1-aminocyclobutyl)phenyl)-4-phenylpyridin-2-yl)acetamide;

B21 N-(trans-4-(2-((5-(4-(1-aminocyclobutyl)phenyl)-4-phenylpyridin-2-yl)amino)-2-oxoethyl)cyclohexyl)cyclopropanecarboxamide;

B22 N-(trans-4-(2-((5-(4-(2-aminopropan-2-yl)phenyl)-4-phenylpyridin-2-yl)amino)-2-oxoethyl)cyclohexyl)pivalamide;

B23 N-(trans-4-(2-((5-(4-(1-amino-3-hydroxy-3-methylcyclobutyl)phenyl)-4-phenylpyridin-2-yl)amino)-2-oxoethyl)cyclohexyl)-2,2-difluoroacetamide;

B24 N-(5-(4-(3-aminooxetan-3-yl)phenyl)-4-phenylpyridin-2-yl)-2-(trans-4-(cyclopropanesulfonamido)cyclohexyl)acetamide;

B25 2-(trans-4-acetamidocyclohexyl)-N-(5-(4-(2-aminopropan-2-yl)phenyl)-4-phenylpyridin-2-yl)acetamide;

B26 N-(trans-4-(2-((5-(4-(1-aminocyclobutyl)phenyl)-4-(thiophen-3-yl)pyridin-2-yl)amino)-2-oxoethyl)cyclohexyl)pivalamide;

B27 N-(trans-4-(2-((5-(4-(2-aminopropan-2-yl)phenyl)-4-phenylpyridin-2-yl)amino)-2-oxoethyl)cyclohexyl)cyclopropanecarboxamide;

B28 N-(trans-4-(2-((5-(4-(1-aminocyclobutyl)phenyl)-4-phenylpyridin-2-yl)amino)-2-oxoethyl)cyclohexyl)cyclopropanecarboxamide;

B29 N-(trans-4-(2-((5-(4-(2-aminopropan-2-yl)phenyl)-4-phenylpyridin-2-yl)amino)-2-oxoethyl)cyclohexyl)isobutyramide;

B30 N-(trans-4-(2-((5-(4-(2-aminopropan-2-yl)phenyl)-4-phenylpyridin-2-yl)amino)-2-oxoethyl)cyclohexyl)-N-methylcyclobutanecarboxamide;

B31 N-(trans-4-(2-((5-(4-(2-aminopropan-2-yl)phenyl)-4-phenylpyridin-2-yl)amino)-2-oxoethyl)cyclohexyl)-2,2-difluoro-N-methylacetamide;

B32 N-(trans-4-(2-((5-(4-(2-aminopropan-2-yl)phenyl)-4-phenylpyridin-2-yl)amino)-2-oxoethyl)cyclohexyl)-N,3,3-trimethylbutanamide;

B33 N-(trans-4-(2-((5-(4-(2-aminopropan-2-yl)phenyl)-4-phenylpyridin-2-yl)amino)-2-oxoethyl)cyclohexyl)-2-cyclopropyl-N-methylacetamide;

B34 N-(trans-4-(2-((5-(4-(1-aminocyclopropyl)phenyl)-4-phenylpyridin-2-yl)amino)-2-oxoethyl)cyclohexyl)-2,2-difluoro acetamide;

B35 N-(trans-4-(2-((5-(4-(1-aminocyclopropyl)phenyl)-4-phenylpyridin-2-yl)amino)-2-oxoethyl)cyclohexyl)pivalamide;

B36 2-(trans-4-acetamidocyclohexyl)-N-(5-(4-(2-aminopropan-2-yl)phenyl)-4-(thiophen-3-yl)pyridin-2-yl)acetamide;

B37 N-(trans-4-(2-((5-(4-(2-aminopropan-2-yl)phenyl)-4-phenylpyridin-2-yl)amino)-2-oxoethyl)cyclohexyl)-N-methylcyclopropanecarboxamide;

B38 N-(5-(4-(1-aminocyclobutyl)phenyl)-4-(thiophen-3-yl)pyridin-2-yl)-2-(trans-4-(2-oxopiperidin-1-yl)cyclohexyl) acetamide;

B39 N-(5-(4-(1-amino-3,3-difluorocyclobutyl)phenyl)-4-phenylpyridin-2-yl)-2-(trans-4-(2-oxooxazolidin-3-yl)cyclohexyl)acetamide;

B40 N-(5-(4-(1-aminocyclobutyl)phenyl)-4-(thiophen-3-yl)pyridin-2-yl)-2-(trans-4-(2-oxopyrrolidin-1-yl)cyclohexyl)acetamide;

B41 methyl (trans-4-(2-((5-(4-(1-amino-3,3-difluorocyclobutyl)phenyl)-4-phenylpyridin-2-yl)amino)-2-oxoethyl)cyclohexyl)(methyl)carbamate;

B42 N-(5-(4-(1-aminocyclobutyl)phenyl)-4-phenylpyridin-2-yl)-2-(trans-4-(2-oxooxazolidin-3-yl)cyclohexyl)acetamide;

B43 trans-4-(2-((5-(4-(2-aminopropan-2-yl)phenyl)-4-phenylpyridin-2-yl)amino)-2-oxoethyl)-N,N-dimethylcyclohexane-1-carboxamide;

B44 trans-4-(2-((5-(4-(trans-1-amino-3-hydroxy-3-methylcyclobutyl)phenyl)-4-phenylpyridin-2-yl)amino)-2-oxoethyl)-N,N-dimethylcyclohexane-1-carboxamide;

B45 N-(5-(4-(2-aminopropan-2-yl)phenyl)-4-phenylpyridin-2-yl)-2-(trans-4-(morpholine-4-carbonyl)cyclohexyl) acetamide;

B46 N-(5-(4-(trans-1-amino-3-hydroxy-3-methylcyclobutyl)phenyl)-4-phenylpyridin-2-yl)-2-(trans-4-(morpholine-4-carbonyl)cyclohexyl)acetamide;

B47 2-(trans-4-acetamidocyclohexyl)-N-(6-(4-(trans-1-amino-3-hydroxy-3-methylcyclobutyl)phenyl)-5-phenylpyridazin-3-yl)acetamide;

B48 N-(6-(4-(trans-1-amino-3-hydroxy-3-methylcyclobutyl)phenyl)-5-phenylpyridazin-3-yl)-2-(trans-4-(2-oxopyrrolidin-1-yl)cyclohexyl)acetamide;

B49 2-(trans-4-acetamidocyclohexyl)-N-(6-(4-(3-aminooxetan-3-yl)phenyl)-5-phenylpyridazin-3-yl)acetamide;

B50 2-(trans-4-acetamidocyclohexyl)-N-(6-(4-(trans-1-amino-3-fluorocyclobutyl)phenyl)-5-phenylpyridazin-3-yl)acetamide;

B51 N-(6-(4-(3-aminooxetan-3-yl)phenyl)-5-phenylpyridazin-3-yl)-2-((2R,6S)-2,6-dimethyltetrahydro-2H-pyran-4-yl)acetamide;

B52 N-(6-(4-(2-aminopropan-2-yl)phenyl)-5-phenylpyridazin-3-yl)-2-(trans-4-(2-oxopyrrolidin-1-yl)cyclohexyl)acetamide;

B53 2-(trans-4-acetamidocyclohexyl)-N-(6-(4-(1-amino-3,3-difluorocyclobutyl)phenyl)-5-phenylpyridazin-3-yl)acetamide
B54 N-(6-(4-(2-aminopropan-2-yl)phenyl)-5-phenylpyridazin-3-yl)-2-(trans-4-(2-oxopiperidin-1-yl)cyclohexyl)acetamide;
B55 N-(6-(4-(2-aminopropan-2-yl)phenyl)-5-phenylpyridazin-3-yl)-2-(trans-4-(2-cyclopropylacetamido)cyclohexyl)acetamide;
B56 2-(trans-4-acetamidocyclohexyl)-N-(6-(4-(1-aminocyclobutyl)phenyl)-5-phenylpyridazin-3-yl)acetamide;
B57 N-(trans-4-(2-((6-(4-(1-aminocyclobutyl)phenyl)-5-phenylpyridazin-3-yl)amino)-2-oxoethyl)cyclohexyl)cyclopropanecarboxamide;
B58 N-(trans-4-(2-((6-(4-(1-aminocyclobutyl)phenyl)-5-phenylpyridazin-3-yl)amino)-2-oxoethyl)cyclohexyl)-2,2-difluoro acetamide
B59 N-(trans-4-(2-((6-(4-(2-aminopropan-2-yl)phenyl)-5-phenylpyridazin-3-yl)amino)-2-oxoethyl)cyclohexyl) pivalamide;
B60 N-(trans-4-(2-((6-(4-(1-amino-3-hydroxy-3-methylcyclobutyl)phenyl)-5-phenylpyridazin-3-yl)amino)-2-oxoethyl)cyclohexyl)-2,2-difluoroacetamide;
B61 N-(6-(4-(3-aminooxetan-3-yl)phenyl)-5-phenylpyridazin-3-yl)-2-(trans-4-(cyclopropanesulfonamido)cyclohexyl)acetamide;
B62 2-(trans-4-acetamidocyclohexyl)-N-(6-(4-(2-aminopropan-2-yl)phenyl)-5-phenylpyridazin-3-yl)acetamide;
B63 N-(trans-4-(2-((6-(4-(2-aminopropan-2-yl)phenyl)-5-phenylpyridazin-3-yl)amino)-2-oxoethyl)cyclohexyl)cyclopropanecarboxamide;
B64 N-(trans-4-(2-((6-(4-(2-aminopropan-2-yl)phenyl)-5-phenylpyridazin-3-yl)amino)-2-oxoethyl)cyclohexyl) isobutyramide;
B65 N-(trans-4-(2-((6-(4-(2-aminopropan-2-yl)phenyl)-5-phenylpyridazin-3-yl)amino)-2-oxoethyl)cyclohexyl)-2,2-difluoro-N-methylacetamide;
B66 N-(trans-4-(2-((6-(4-(2-aminopropan-2-yl)phenyl)-5-phenylpyridazin-3-yl)amino)-2-oxoethyl)cyclohexyl)-N,3,3-trimethylbutanamide;
B67 N-(trans-4-(2-((6-(4-(2-aminopropan-2-yl)phenyl)-5-phenylpyridazin-3-yl)amino)-2-oxoethyl)cyclohexyl)-2-cyclopropyl-N-methylacetamide;
B68 N-(trans-4-(2-((6-(4-(1-aminocyclopropyl)phenyl)-5-phenylpyridazin-3-yl)amino)-2-oxoethyl)cyclohexyl)-2,2-difluoroacetamide;
B69 N-(trans-4-(2-((6-(4-(1-aminocyclopropyl)phenyl)-5-phenylpyridazin-3-yl)amino)-2-oxoethyl)cyclohexyl) pivalamide;
B70 trans-4-(2-((6-(4-(2-aminopropan-2-yl)phenyl)-5-phenylpyridazin-3-yl)amino)-2-oxoethyl)-N,N-dimethylcyclohexane-1-carboxamide;
B71 trans-4-(2-((6-(4-(trans-1-amino-3-hydroxy-3-methylcyclobutyl)phenyl)-5-phenylpyridazin-3-yl)amino)-2-oxoethyl)-N,N-dimethylcyclohexane-1-carboxamide;
B72 N-(6-(4-(2-aminopropan-2-yl)phenyl)-5-phenylpyridazin-3-yl)-2-(trans-4-(morpholine-4-carbonyl)cyclohexyl)acetamide;
B73 N-(6-(4-(trans-1-amino-3-hydroxy-3-methylcyclobutyl)phenyl)-5-phenylpyridazin-3-yl)-2-(trans-4-(morpholine-4-carbonyl)cyclohexyl)acetamide.

Biological Investigations

The following assays can be used to illustrate the commercial utilities of the compounds according to the present invention.

Examples were tested in selected biological assays one or more times. When tested more than once, data are reported as the geometric mean value.

Examples were synthesised one or more times. When synthesised more than once, data from the biological assays represent the geometric mean value calculated using data sets obtained from testing of one or more synthetic batch.

Biological Assay 1: Akt Activation Assay

The following describes an Akt activation assay in which PDK1 is used to phosphorylate inactive Akt enzymes, which then phosphorylate the GSK3α-derived Ultra Ulight™-labelled crosstide substrate. Addition of a Europium-labelled antibody specific to the phosphopeptide allows energy transfer from the Europium donor to the Ultra Ulight™ acceptor if close enough in proximity.

Materials and Solutions:

All reagents are from Sigma-Aldrich unless specified otherwise.

Inactive, full length and detagged Akt1, Akt2 and Akt3 proteins were obtained from SignalChem and Proteros. Full length active His6-tagged PDK1 was obtained from Merck Millipore (14-452).

LANCE® Ultra Ulight™-Crosstide (Perkin Elmer, TRF0106-M)

LANCE® Ultra Europium-anti-phospho-Crosstide (GSK-3α Ser21) (Perkin Elmer, TRF0202-M)

LANCE® Detection Buffer, 10× (Perkin Elmer, CR97-100)

PtdIns(3,4,5)$P_3$ (P4240)

1:1 DOPS/DOPC lipid blend (Avanti polar lipids, 790595)

ATP (A7699) made up to 10 mM with MilliQ water

HEPES buffer pH 7.0-7.6 (H0887)

0.5 M EGTA solution (Bioquote 40520008-1)

1 M MgCl$_2$ solution (M1028)

DTT (43815) made up to 0.1 M in MilliQ water

Tween-20 (P1379)

0.5 M EDTA (E7889)

1× assay buffer (AB): 50 mM HEPES pH 7.5, 1 mM EGTA, 10 mM MgCl$_2$, 0.01% Tween. Immediately before use, DTT to a concentration of 2 mM was added.

To prepare lipid vesicles: 1 mg/ml PtdIns(3,4,5)$P_3$ solution (in 10 mM HEPES 7.5) was added to 16.7 mg/ml DOPS/DOPC mixture (in 10 mM HEPES pH 7.5) in a ratio of 1:8.3. MilliQ water was added to the solution to generate concentrations of 400 µM DOPS, 400 µM DOPC and 40 µM PtdIns(3,4,5)$P_3$. The mixture was subjected to 5× freeze/thaw cycles and aliquots stored at −20° C.

Assay Procedure:

5 µL enzyme in 1×AB was incubated with 2.5 µL test compound. To start the reaction 2.5 µL reaction mix was added which consisted of PDK1, lipid preparations, crosstide and ATP in 1×AB. Final assay concentrations were as follows: 1% DMSO, 5 nM SignalChem Akt1/15 nM SignalChem Akt2/3 nM Signalchem Akt3/5 nM Proteros Akt1/5 nM proteros Akt2/5 nM Proteros Akt3, 5 nM PDK1, 5.5 µM DOPS, 5.5 µM DOPC, 0.55 µM PtdIns(3,4,5)$P_3$, 100 µM ATP, 100 nM LANCE® Ultra Ulight™-Crosstide. After 30 min, the reaction was stopped using 5 µL 40 µM EDTA in 1× Detection buffer for 5 min. For detection, 5 µL 8 nM LANCE® Ultra Europium-anti-phospho-Crosstide antibody in 1× Detection buffer was added to each well and incubated for 1 h. Plates read with the EnVision® Multilabel Plate Reader, excitation at 320 nm and emission at 665 nm and 615 nm. Compound IC$_{50}$ was determined using a 4-parameter equation.

Biological Assay 2: Phospho-Akt (p-Akt) Cellular SureFire Assays

The following describes SureFire assays to detect cellular p-Akt1, p-Akt2 and p-Akt3 levels in WM115 cells (Akt2/3) and LNCaP cells (Akt1). In the case of Akt2 and Akt3, Streptavidin-coated donor beads capture a biotinylated anti-mouse antibody that in turn recognises a mouse total Akt antibody which is specific to each isoform. The protein A-conjugated acceptor beads capture an antibody that recognises the phosphoprotein. Similarly in the Akt1 kit, the donor and acceptor beads are used to capture each antibody pair consisting of an antibody that specifically recognises Akt1 as well as an antibody that recognises the phosphoprotein. In each case, close proximity of the beads allows energy transfer from donor to acceptor.

Materials and Solutions:

All reagents are from Sigma-Aldrich unless specified otherwise.

AlphaScreen® SureFire™ Phospho-Akt1 (pThr308) Kit from Perkin Elmer (TGRA2S10K)

Custom kit from TGR/Perkin Elmer for Akt2/3 containing anti-(pThr308)Akt antibody and biotinylated anti-mouse capture antibody.

Total Akt2 antibody (NEB UK, 5239)

Total Akt3 antibody (R&D Systems MAB 1463)

Protein A general IgG detection kit (Perkin Elmer, 6760617C)

Insulin solution (I9278)

WM115 cells (ECACC, 91061232) cultured in MEM culture media (M2279) supplemented with 2 mM L-glutamine (G7513), 1% non-essential amino acids (M7145), 1% sodium pyruvate (S8636) and 10% FBS (F0804)

LNCaP cells (ECACC, 89110211) cultured in RPMI-1640 culture media (Fisher, 10665193) supplemented with 2 mM L-glutamine, 1% sodium pyruvate and 10% FBS All buffers mentioned below are included with the kits above unless specified otherwise.

Assay Procedure:

Cell treatment: $1 \times 10^5$ WM115 cells or $5 \times 10^4$ LNCaP cells were seeded into each well of a 96 well poly-D-Lysine coated tissue culture plate and incubated overnight at 37° C.+5% $CO_2$. Media was removed from cells and replaced with assay buffer consisting of the full culture media described above but with 0.1% FBS instead of 10% FBS. Only WM115 cells were stimulated at 37° C.+5% $CO_2$ for 10 min with 5 µL insulin at a final concentration of 100 nM. Cells were incubated with 5 µL of test compound at a final DMSO concentration of 0.3% for 15 min at 37° C.+5% $CO_2$. Cell lysis was carried out according to kit instructions.

Assay format (performed in subdued lighting): 4 µL cell lysate and 5 µL reaction buffer were incubated together in the dark at room temperature for 2 h. Reaction buffer was supplemented with a 1/5 dilution of activation buffer, a 1/50 dilution of acceptor beads and in the case of the custom kits, antibodies were added at dilutions of 1/20,000 for Akt2 and 1/2,000 for Akt3.

2 µL dilution buffer, supplemented with a 1/20 dilution of donor beads was added to each well and incubated for a further 2 h. Plates were read with the EnVision® Multilabel Plate Reader and using the AlphaScreen settings. Compound $IC_{50}$ was determined using a 4-parameter equation.

Table 1 shows the inhibition activity of representative compounds of the invention against Akt1, Akt2 and Akt3 in the above activation and cellular SureFire assays.

TABLE 1

| Example | Biological Assay 1 $IC_{50}$ (nM) | | | Biological Assay 2 $IC_{50}$ (nM) | | |
|---|---|---|---|---|---|---|
| | Akt1 | Akt2 | Akt3 | Akt1 LNCaP | Akt2 WM115 | Akt3 WM115 |
| 1 | 780 | 110 | 15 | 2700 | 1800 | 30 |
| 2 | 980 | 94 | 20 | 8700 | 4400 | 150 |
| 3 | >30000 | >30000 | 72 | >26000 | 10000 | 170 |
| 4 | >30000 | 7300 | 73 | >30000 | 7400 | 190 |
| 5 | 3900 | 800 | 110 | 14000 | 3000 | 61 |
| 6 | >30000 | >24000 | 720 | >30000 | >21000 | 340 |
| 7 | >30000 | 9200 | 350 | >30000 | 10000 | 300 |
| 8 | 12000 | 710 | 51 | | | |
| 9 | >30000 | 2500 | 150 | >30000 | 3500 | 110 |
| 10 | 6200 | 260 | 30 | 6700 | 970 | 39 |
| 11 | >30000 | >20000 | 630 | | | |
| 12 | 17000 | 1000 | 84 | 16000 | 2300 | 220 |
| 13 | 13000 | 480 | 220 | | | |
| 14 | >30000 | 1300 | 600 | | | |
| 15 | 7700 | 580 | 180 | >22000 | 1100 | 21 |
| 16 | 7800 | 380 | 24 | 11000 | 710 | 45 |
| 17 | >26000 | 1200 | 48 | 7100 | 1900 | 140 |
| 18 | >30000 | 6900 | 1300 | >30000 | 14000 | 1100 |
| 19 | >30000 | >26000 | 6400 | | | |
| 20 | >30000 | >15000 | 6800 | | | |
| 21 | >55000 | 1100 | 210 | | | |
| 22 | >30000 | 2600 | 210 | | | |
| 23 | >30000 | 11000 | 430 | | | |
| 24 | >30000 | 10000 | 300 | >18000 | 6700 | 170 |
| 25 | 8300 | 270 | 170 | | | |
| 26 | >30000 | 12000 | 1600 | >16000 | 9000 | 380 |
| 27 | >30000 | 12000 | 680 | >30000 | 10000 | 380 |
| 28 | >30000 | 7000 | 440 | >30000 | 13000 | 260 |
| 29 | >33000 | 2200 | 53 | >13000 | 8400 | 170 |
| 30 | >30000 | 12000 | 470 | >30000 | 6800 | 72 |
| 31 | >30000 | >15000 | 1700 | >30000 | >30000 | 440 |
| 32 | 2000 | 470 | 34 | 6900 | 1400 | 36 |
| 33 | 13000 | 540 | 92 | 9800 | 2500 | 100 |
| 34 | >29000 | 6500 | 380 | >15000 | 5200 | 150 |
| 35 | >30000 | 25000 | 17000 | >30000 | 17000 | 1500 |
| 36 | >30000 | >30000 | 100 | >30000 | 3800 | 230 |
| 37 | >30000 | 590 | 56 | | | |
| 38 | 9000 | 1900 | 560 | 7000 | 3000 | 92 |
| 39 | 19000 | 3100 | 2300 | >14000 | 4200 | 180 |
| 40 | 9800 | 440 | 360 | 15000 | 2900 | 220 |
| 41 | 14000 | 240 | 170 | >30000 | 1500 | 130 |
| 42 | >30000 | 4500 | 960 | >30000 | 7900 | 210 |
| 43 | >30000 | >30000 | 1100 | >30000 | >30000 | 1700 |
| 44 | 1200 | 110 | 22 | 1100 | 350 | 6 |
| 45 | >17000 | 380 | 67 | >30000 | >3600 | 38 |
| 46 | 11000 | 440 | 100 | 13000 | 2600 | 46 |
| 47 | >30000 | 6100 | 75 | >30000 | 5300 | 240 |
| 48 | 17000 | 910 | 240 | >27000 | 2700 | 110 |
| 49 | 6900 | 530 | 280 | 17000 | 2900 | 140 |
| 50 | 5800 | 670 | 370 | >30000 | 6800 | 580 |
| 51 | 8900 | 1500 | 190 | >30000 | 9100 | 670 |
| 52 | 6100 | 520 | 92 | >10000 | 5000 | 180 |
| 53 | >30000 | >30000 | 4100 | >30000 | 18000 | 680 |
| 54 | 19000 | 970 | 280 | >21000 | 6400 | 240 |
| 55 | >30000 | 3300 | 1600 | >30000 | 3800 | 160 |
| 56 | >30000 | 10000 | 100 | >30000 | >30000 | 330 |
| 57 | 1600 | 190 | 7 | 5300 | 600 | 8 |
| 58 | 1300 | 98 | 3 | 4000 | 750 | 8 |
| 59 | 1400 | 50 | 4 | 1600 | 380 | 24 |
| 60 | >30000 | 710 | 50 | >30000 | 8800 | 290 |
| 61 | >22800 | 200 | 17 | >30000 | >10510 | 66 |
| 62 | >30000 | 2300 | 170 | >30000 | 13000 | 360 |
| 63 | >30000 | >30000 | 300 | >30000 | >28000 | 360 |
| 64 | >30000 | 2800 | 180 | >30000 | 6600 | 210 |
| 65 | >30000 | 4100 | 61 | >30000 | 6500 | 190 |
| 66 | 7200 | 150 | 5 | 9800 | 940 | 48 |
| 67 | >6500 | 180 | 8 | >9300 | 1500 | 37 |
| 68 | 6400 | 860 | 99 | >30000 | 13000 | 410 |
| 69 | >30000 | >30000 | 1800 | >30000 | >30000 | 480 |
| 70 | >30000 | 830 | 42 | >30000 | 910 | 39 |
| 71 | 10000 | 350 | 16 | 9100 | 1300 | 44 |
| 72 | >22000 | 460 | 10 | >7500 | 1400 | 35 |
| 73 | >30000 | 540 | 22 | >17000 | 12000 | 66 |
| 74 | >30000 | 190 | 4 | >30000 | 1700 | 40 |

TABLE 1-continued

| Example | Biological Assay 1 IC$_{50}$ (nM) | | | Biological Assay 2 IC$_{50}$ (nM) | | |
|---|---|---|---|---|---|---|
| | Akt1 | Akt2 | Akt3 | Akt1 LNCaP | Akt2 WM115 | Akt3 WM115 |
| 75 | >16000 | 580 | 18 | >30000 | 3200 | 46 |
| 76 | >30000 | >30000 | 1000 | >30000 | >30000 | 140 |
| 77 | 7900 | 1100 | 62 | >30000 | 5100 | 100 |
| 78 | 5900 | 230 | 14 | 2000 | 810 | 30 |
| 79 | >30000 | 590 | 26 | >30000 | >30000 | 59 |
| 80 | >30000 | 8900 | 130 | >30000 | 18000 | 150 |
| 81 | 14000 | 1300 | 59 | >27000 | 4300 | 120 |
| 82 | >19000 | 130 | 6 | 2400 | 380 | 10 |
| 83 | 2100 | 86 | 4 | 820 | 250 | 7 |
| 84 | 2600 | 140 | 5 | >19000 | 830 | 8 |
| 85 | 21000 | 77 | 13 | 4700 | 600 | 20 |
| 86 | >30000 | 14000 | 480 | >30000 | 12000 | 430 |
| 87 | >30000 | 510 | 29 | >30000 | 3300 | 130 |
| 88 | >30000 | 8600 | 64 | >30000 | 16000 | 240 |
| 89 | | | | 13000 | 3000 | 57 |
| 90 | >30000 | 2500 | 120 | >30000 | 6500 | 170 |
| 91 | 7000 | 160 | 5 | 3800 | 900 | 13 |
| 92 | >30000 | 14000 | 170 | >30000 | >30000 | 230 |
| 93 | 3900 | 320 | 10 | 2200 | 520 | 9 |
| 94 | 20000 | 120 | 11 | 14000 | 550 | 13 |
| 95 | >22000 | 120 | 10 | 18000 | 660 | 17 |
| 96 | 18000 | 140 | 18 | 20000 | 1300 | 51 |
| 97 | 2900 | 48 | 5 | 880 | 600 | 6 |
| 98 | 3500 | 53 | 5 | 880 | 470 | 7 |
| 99 | 2400 | 44 | 6 | 670 | 390 | 12 |
| 100 | 2400 | 170 | 8 | 790 | 1000 | 26 |
| 101 | 8900 | 120 | 7 | 5900 | 2600 | 48 |
| 102 | 4100 | 140 | 16 | 1800 | 1700 | 57 |
| 103 | 18000 | 78 | 11 | 2600 | 390 | 15 |
| 104 | 3200 | 120 | 10 | 1900 | 1300 | 27 |
| 105 | 4600 | 210 | 8 | 5300 | 1400 | 26 |
| 106 | >13000 | 210 | 8 | 4000 | 1500 | 25 |
| 107 | >30000 | 94 | 9 | 7300 | 390 | 9 |
| 108 | 19000 | 220 | 10 | 14000 | 670 | 16 |
| 109 | >30000 | 220 | 12 | 13000 | 780 | 13 |
| 110 | 15000 | 380 | 17 | 8800 | 1200 | 16 |
| 111 | >27000 | 1400 | 68 | 15000 | 3200 | 29 |
| 112 | >30000 | 1300 | 55 | 27000 | 3400 | 31 |
| 113 | >14000 | 130 | 8 | 4100 | 510 | 7 |
| 114 | >23000 | 110 | 7 | 3300 | 440 | 5 |
| 115 | >30000 | 330 | 24 | 13000 | 1000 | 15 |
| 116 | >30000 | 220 | 21 | 19000 | 1400 | 72 |
| 117 | >24000 | 290 | 42 | 12000 | 980 | 33 |
| 118 | 8500 | 110 | 5 | 1600 | 230 | 6 |
| 119 | 5900 | 70 | 5 | 2300 | 410 | 22 |
| 120 | 8600 | 65 | 7 | 1300 | 350 | 15 |
| 121 | 13000 | 160 | 7 | 1800 | 390 | 11 |
| 122 | 6100 | 87 | 8 | 1400 | 390 | 13 |
| 123 | >25000 | 230 | 12 | 21000 | 1700 | 38 |
| 124 | >21000 | 880 | 36 | 10000 | 2400 | 27 |
| 125 | >30000 | 1500 | 26 | >30000 | 3000 | 22 |
| 126 | >30000 | 3000 | 31 | >30000 | 3300 | 32 |
| 127 | >25000 | 2900 | 31 | >30000 | 2900 | 42 |
| 128 | >18000 | 370 | 110 | 5500 | 810 | 93 |
| 129 | 11000 | 190 | 7 | 2000 | 620 | 7 |
| A1 | 4000 | 420 | 110 | >16000 | 2800 | 130 |
| A2 | 5500 | 2600 | 1400 | 7700 | 6000 | 560 |
| A3 | >5100 | 530 | 150 | 17000 | 2600 | 100 |
| A4 | 11000 | 2400 | 630 | >30000 | 7600 | 440 |
| A5 | 760 | 43 | 10 | | | |
| A6 | >30000 | 1400 | 130 | | | |
| A7 | >30000 | 5800 | 70 | >30000 | 7100 | 230 |
| A8 | >30000 | 6900 | 530 | | | |
| A9 | 17000 | 400 | 80 | | | |
| A10 | >30000 | 18000 | 4600 | | | |
| A11 | 16000 | 1500 | 880 | | | |
| A12 | >30000 | 16000 | 4500 | >20000 | 24000 | 590 |
| A13 | >30000 | 8100 | 830 | | | |
| A14 | >30000 | 1800 | 170 | >30000 | 3200 | 80 |
| A15 | 260 | 350 | 290 | 760 | 810 | 48 |
| A16 | 9800 | 260 | 210 | | | |
| A17 | 1500 | 420 | 62 | 5700 | 12000 | 1000 |
| A18 | >30000 | 25000 | 6300 | >27000 | 7900 | 270 |
| A19 | >45000 | >50000 | 110 | >30000 | >30000 | 1800 |
| A20 | >36000 | 2300 | 55 | >30000 | 5400 | 200 |
| A21 | >37000 | 4100 | 55 | | | |
| A22 | >30000 | 3500 | 68 | | | |
| A23 | >30000 | 22000 | 1900 | | | |
| A24 | >30000 | 9600 | 2000 | >30000 | 8900 | 510 |
| A25 | >30000 | 5100 | 560 | >15000 | 5400 | 260 |
| A26 | >30000 | 3300 | 740 | >30000 | 7000 | 390 |
| A27 | 4100 | 180 | 19 | 10000 | 790 | 51 |
| A28 | >30000 | >30000 | 5900 | >30000 | >20000 | 1500 |
| A29 | >30000 | 5700 | 490 | >28000 | 5800 | 150 |
| A30 | >30000 | 16000 | 290 | | | |
| A31 | >30000 | 11000 | 1400 | | | |
| A32 | >30000 | 9700 | 630 | | | |
| A33 | 13000 | 380 | 98 | >16000 | 2500 | 140 |
| A34 | >30000 | 15000 | 160 | | | |
| A35 | 9400 | 370 | 20 | | | |
| A36 | >30000 | 6800 | 160 | | | |
| A37 | >30000 | 3500 | 61 | >30000 | 8700 | 340 |
| A38 | 10000 | 190 | 18 | >5700 | 1600 | 120 |
| A39 | 3100 | 140 | 15 | | | |
| A40 | >27000 | 810 | 25 | | | |
| A41 | 11000 | 370 | 75 | 3600 | 840 | 59 |
| A42 | 6900 | 810 | 280 | | | |
| A43 | >22000 | 520 | 300 | | | |
| A44 | >30000 | 13000 | 1800 | >30000 | 11000 | 440 |
| A45 | >30000 | 24000 | 2600 | >30000 | 12000 | 480 |
| A46 | >30000 | 2400 | 1000 | >30000 | 6300 | 190 |
| A47 | >30000 | 2100 | 370 | >30000 | 11000 | 440 |
| A48 | | | | >30000 | >30000 | 1700 |
| A49 | >30000 | 3600 | 120 | >30000 | 4400 | 200 |
| A50 | >30000 | 2200 | 140 | >30000 | >3794 | 270 |
| A51 | >30000 | 340 | 42 | >30000 | 2000 | 150 |
| A52 | >30000 | 11000 | 640 | >30000 | 2600 | 240 |
| A53 | >30000 | 480 | 39 | >30000 | 5400 | 410 |
| A54 | >30000 | 6300 | 160 | >30000 | >13000 | 520 |
| A55 | >16000 | 380 | 16 | >30000 | 5000 | 310 |
| A56 | 11000 | 270 | 7 | 10000 | 1300 | 43 |
| A57 | 17000 | 130 | 8 | 5800 | 360 | 17 |
| A58 | 15000 | 190 | 8 | 7900 | 480 | 11 |
| A59 | >30000 | 740 | 28 | 9700 | 8000 | 250 |
| A60 | 18000 | 630 | 22 | >30000 | 15000 | 670 |
| A61 | >30000 | 1300 | 77 | >30000 | >27000 | 910 |
| A62 | >30000 | 1100 | 57 | 7100 | 1200 | 81 |
| A63 | >30000 | 5700 | 120 | >30000 | 6100 | 470 |
| A64 | >30000 | 1400 | 30 | >30000 | 1400 | 85 |
| A65 | >30000 | 270 | 17 | >30000 | 570 | 37 |
| A66 | 14000 | 1100 | 44 | 16000 | 10000 | 420 |
| A67 | >30000 | 8900 | 200 | >30000 | >30000 | 830 |
| A68 | 13000 | 850 | 40 | >30000 | 7400 | 250 |
| A69 | >30000 | 12000 | 220 | >30000 | >30000 | 710 |
| A70 | >30000 | 1100 | 36 | >30000 | >28000 | 960 |
| A71 | 7500 | 110 | 15 | 3400 | 1500 | 130 |
| A72 | 13000 | 290 | 24 | 8800 | 3500 | 220 |
| A73 | 8800 | 130 | 7 | 2900 | 1200 | 77 |
| A74 | 16000 | 210 | 22 | 11000 | 3000 | 160 |
| A75 | 12000 | 140 | 6 | 1400 | 320 | 13 |
| A76 | 18000 | 190 | 13 | 4300 | 1200 | 59 |
| A77 | >25000 | 590 | 22 | >30000 | 20000 | 240 |
| A78 | 1900 | 71 | 4 | 1400 | 370 | 8 |
| A79 | 3900 | 63 | 4 | 1900 | 370 | 10 |
| A80 | 2400 | 74 | 4 | 2400 | 710 | 10 |
| A81 | >30000 | 1200 | 69 | >30000 | 9100 | 390 |
| A82 | 3100 | 91 | 7 | 1800 | 460 | 14 |
| A83 | >30000 | 500 | 33 | >20000 | 3400 | 220 |
| A84 | >30000 | 4000 | 51 | >30000 | 7100 | 150 |
| A85 | >30000 | 3400 | 74 | >20000 | 8800 | 270 |
| A86 | >30000 | 3900 | 45 | >21000 | 8300 | 170 |
| A87 | >30000 | 5500 | 99 | >23000 | 12000 | 400 |
| A88 | >30000 | >27000 | 1400 | >30000 | >30000 | 1600 |
| A89 | >30000 | 4000 | 80 | >30000 | 8300 | 130 |
| A90 | 10000 | 300 | 15 | 14000 | 4700 | 180 |
| A91 | >30000 | 490 | 24 | >30000 | 2000 | 90 |
| A92 | >13000 | 1200 | 29 | >30000 | 2200 | 140 |
| A93 | >19000 | 1400 | 37 | >30000 | 2600 | 200 |

TABLE 1-continued

| Example | Biological Assay 1 IC$_{50}$ (nM) | | | Biological Assay 2 IC$_{50}$ (nM) | | |
|---|---|---|---|---|---|---|
| | Akt1 | Akt2 | Akt3 | Akt1 LNCaP | Akt2 WM115 | Akt3 WM115 |
| A94 | >23000 | 2200 | 57 | >30000 | 6000 | 370 |
| A95 | >30000 | 3300 | 54 | >30000 | 3100 | 110 |
| A96 | >30000 | 10000 | 92 | >30000 | 15000 | 180 |
| A97 | 16000 | 430 | 9 | 19000 | 3200 | 41 |
| A98 | 2600 | 53 | 4 | 1900 | 320 | 5 |
| A99 | >27000 | 3000 | 130 | >30000 | 7800 | 440 |
| A100 | >30000 | >30000 | 520 | >30000 | >30000 | 1400 |
| A101 | >30000 | 11000 | 140 | >30000 | >30000 | 350 |
| A102 | >19000 | 100 | 14 | 15000 | 2300 | 160 |
| A103 | >30000 | 2300 | 110 | >30000 | >30000 | 730 |
| A104 | >30000 | 5600 | 200 | >30000 | >30000 | 1000 |
| A105 | >15000 | 220 | 20 | 9000 | 5100 | 300 |
| A106 | 19000 | 11000 | 750 | >30000 | 23000 | 1700 |
| A107 | 8100 | 230 | 23 | 7100 | 2200 | 76 |
| A108 | 19000 | 360 | 23 | >10000 | 2700 | 110 |

In Vitro Data

A: EX34 and EX33 Prevent 3D Tumour Cell Growth in the TNBC Cell Line MDA-MB-231

In order to evaluate the role of Akt3 in tumour cell growth and invasion, the effect of two compounds of the invention, the compound of Example 34 (denoted hereafter as EX34) and the compound of Example 33 (denoted hereafter as EX33), on 3D growth in matrigel was assessed.

The TNBC cell line MDA-MB-231 was seeded in matrigel and the cell cultures were treated with increasing concentrations of EX34 or EX33 for 9 days. Treatment was initiated one day after tumour cell seeding. DMSO was used as control. The average tumour sphere size was then evaluated for each treatment. Representative pictures are shown in FIG. 1 for each of the indicated treatment conditions.

Figure 2:
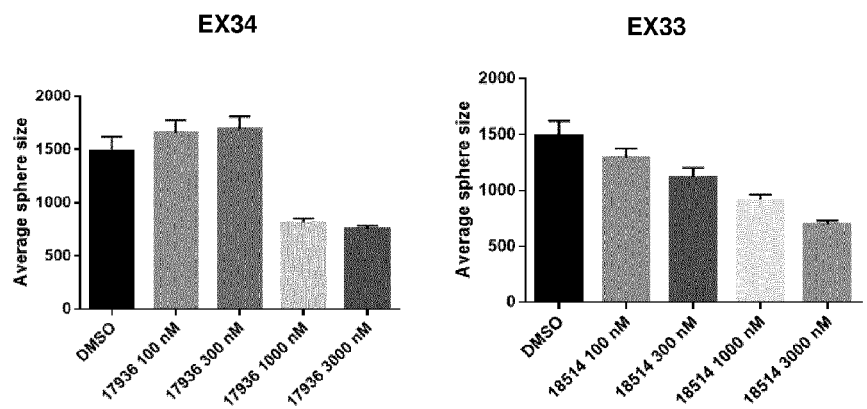

Images of the 3D cultures were batch analysed with AMIDA software to quantify the 3D tumour sphere size. Average size±SEM is shown in FIG. 2.

Conclusion:

Treatment with EX34 and EX33 resulted in a dose-dependent inhibition of 3D tumour cell growth.

B: EX34 and EX33 Prevent Invasive 3D Tumour Cell Growth in the Aggressive TNBC Cell Line MDA-MB-231-D3H2LN/GPF-Luc The TNBC aggressive cell line MDA-MB-231-D3H2LN/GPF-Luc was seeded in matrigel on cover slides to obtain invasive 3D tumour cell colonies. Cell cultures were treated for 72 hours with DMSO (control), 2 µM EX34 or 2 µM EX33, and colonies were evaluated by fluorescence microscopy for 3D invasive growth. The results are shown in FIG. 3.

Conclusion:

Treatment with EX34 and EX33 inhibited tumour cell growth.

C: EX34 Prevents Nuclear Localization of Akt3 in the TNBC Cell Line MDA-MB-231

The cellular program of epithelial to mesenchymal transition (EMT) is utilized by tumour cells to develop drug resistance and to metastasize. Nuclear translocation of Akt3 is considered crucial for Akt3's ability to phosphorylate SNAIL and induce EMT.

MDA-MB-231 cells were treated for 36 hours with Vehicle (DMSO) or 2 µM EX34. Cells were stained to visualize the nucleus and Akt3. Results are shown in FIG. 4. After treatment with EX33, Akt3 stains cytoplasmic. Mean intensity of Akt3 in the nucleus was evaluated after treatment with DMSO (control) or EX33 using TissueQuest Software (see FIG. 5).

Conclusion:

Treatment with EX34 prevents nuclear localization of Akt3.

D: Highly Invasive Areas in Breast Cancer Biopsies Correlates with Nuclear Localization of Akt3

The localization of Akt3, whether it was nuclear or cytoplasmic, was analyzed in Formalin fixed-paraffin embedded (FFPE) biopsies from patients with breast cancer.

Figure 6:
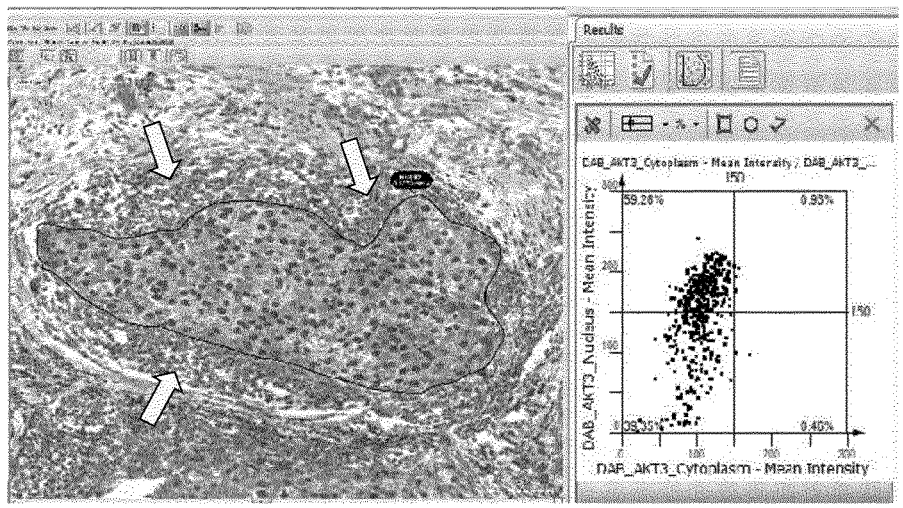
FIG. 6 shows formalin fixed-paraffin embedded (FFPE) biopsies from patients with breast cancer that were stained for Akt3 with IHC. The localization of Akt3, whether cytoplasmic or nuclear, was determined using TissueQuest Software and was correlated to level of invasiveness of the specific area. Top panel: Staining for Akt3 in a highly invasive area shows predominantly nuclear Akt3 localization. Lower panel: Staining for Akt3 in a less invasive area shows predominantly cytoplasmic Akt3 localization.
Figure 6:
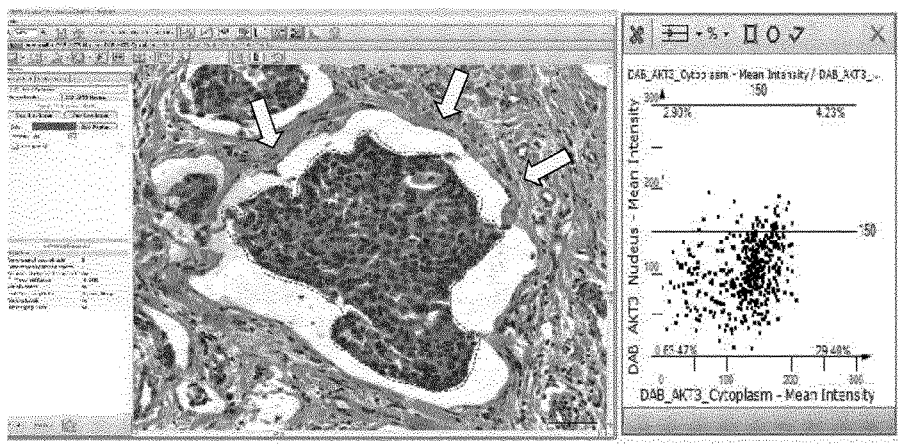

FFPE biopsies from patients with breast cancer were stained for Akt3 with immunohistochemisty (IHC). The localization of Akt3, whether cytoplasmic or nuclear, was determined using TissueQuest Software and was correlated to level of invasiveness of the specific area. The results are shown in FIG. 6. Top panel: Staining for Akt3 in a highly invasive area shows predominantly nuclear Akt3 localization. Lower panel: Staining for Akt3 in a less invasive area shows predominantly cytoplasmic Akt3 localization.

Conclusion:

Nuclear Akt3 expression correlates to highly invasive areas in biopsies from patients with breast cancer.

E: EX33 and EX34 Prevent EMT Induction in the Non Small Cell Lung Cancer (NSCLC) Cell Line H2086

Figure 7:
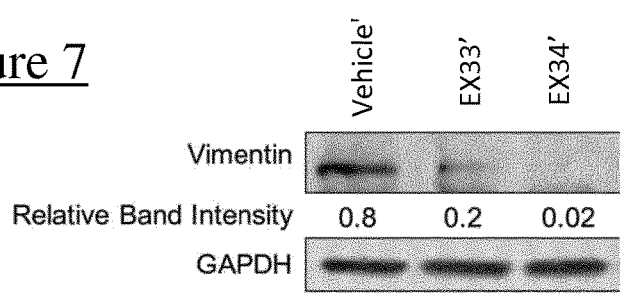
FIG. 7 demonstrates the ability of EX33 and EX34 to prevent EMT in the Non Small Cell Lung Cancer (NSCLC) cell line H2086. EMT induction was evaluated by quantification of the EMT marker Vimentin. NSCLC H2086 cells were treated with 20 ng/ml TGF-β under hypoxic conditions (1% O$_2$) for 5 days. The effect on Vimentin was evaluated by immune blotting for cells treated with Vehicle (DMSO), 1 μM EX33 or 1 μM EX34, and the results are shown in FIG. 7. Glyceraldehyde-3-phosphate dehydrogenase (GAPDH) was used as loading control. The band intensity of Vimentin has been related to the intensity of the GAPDH band.

NSCLC H2086 cells were treated with 20 ng/ml TGF-β under hypoxic conditions (1% $O_2$) for 5 days to induce EMT. The ability of EX33 and EX34 to prevent EMT was evaluated by quantification of the EMT marker Vimentin. The effect on Vimentin was evaluated by immune blotting for cells treated with Vehicle (DMSO), 1 µM EX33 or 1 µM EX34. GAPDH was used as loading control. Results are shown in FIG. 7. The band intensity of Vimentin has been related to the intensity of the GAPDH band.

Conclusion:

EX33 and EX34 prevent EMT induction.

F: EX34 Restores Sensitivity to Paclitaxel in the Paclitaxel-resistant NSCLC Cell Line H2073

The NSCLC cell line H2073 was established from a patient that was resistant to treatment with paclitaxel. Illumina array data from the Hamon Center Lung Cancer Panel (Dallas, Tex.; US) shows that Akt3 is increased in this cell line compared to the cell line isolated from the same person prior to development of paclitaxel resistance.

Figure 8:
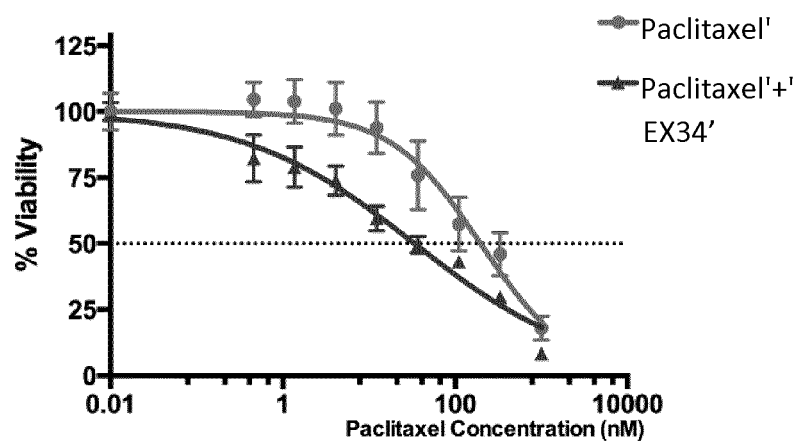
FIG. 8 shows the effect on cell viability for H2073 cells treated for 72 hours with paclitaxel in the absence or presence of EX34. Cell viability was evaluated using resazurin reduction. Average±SEM are shown, n=3.

H2073 cells were treated with increasing dosages of paclitaxel in the absence or presence of EX34 for 72 hours, and cell viability was evaluated using resazurin reduction. Results are shown in FIG. 8. Average±SEM are shown, n=3.

Conclusion:

EX34 sensitizes the paclitaxel resistant cell line H2073 to paclitaxel.

G: EX33 Reduces Production of Alpha-smooth Muscle Actin in Activated Hepatic Stellate Cells Liver fibrosis is characterized by accumulation of extracellular matrix components such as alpha-smooth muscle actin (α-sma) mainly derived from activated hepatic stellate cells (HSCs).

Figure 9:
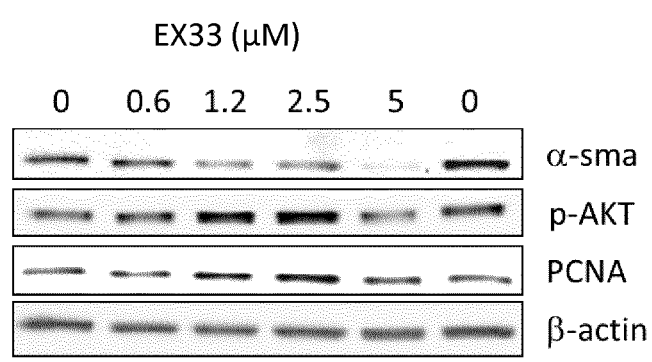
FIG. 9 shows the effect of different dosages of EX33 on α-sma protein levels. LX2 cells were treated for 72 hours with the indicated dosages of EX33 (μM). Cell lysates were analyzed by immune blotting for alpha-smooth muscle actin (α-SMA), PCNA and total p-Akt. Actin was used as a loading control.
Figure 10:
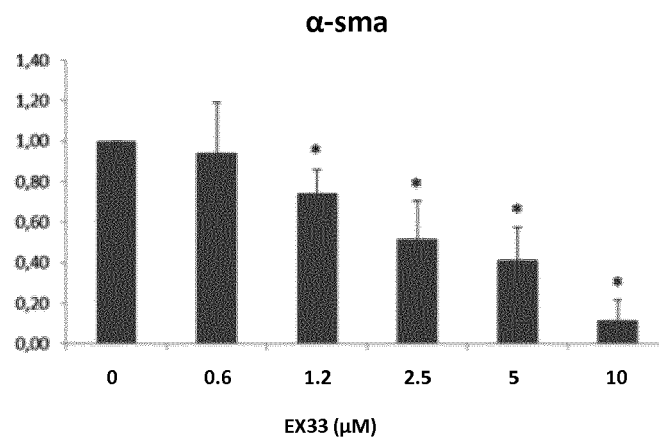

The role of AKT3 in liver fibrosis was analyzed by studying the efficacy of EX33 to block HSC activation. The human activated hepatic stellate cell line LX2 was treated with different dosages of EX33 and the effects on α-sma protein and mRNA levels were analysed by immune blotting (see FIG. 9) and RT-PCR (see FIG. 10) respectively.

Conclusion:

Inhibiting Akt with EX33 decreases the levels of α-sma mRNA and protein in activated hepatic stellate cells.

In Vivo Data

A: Treatment with EX33 Selectively Inhibits Akt3 Phosphorylation in MCF10DCIS Xenograft Tumours Genetic down-regulation of Akt3 has been shown to significantly inhibit growth of the MCF10DCIS TNBC cell line in mouse xenograft models (Chin et al., Cancer Res. 2014). We used this model to test whether EX33 selectively reduced the level of Akt3 phosphorylation in xenograft tumours.

Figure 11:
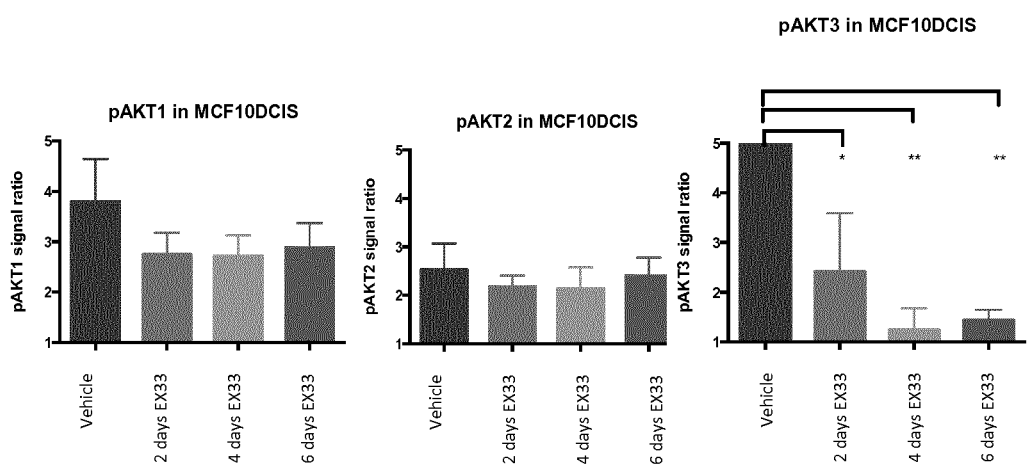
FIG. 11 shows the level of Akt3 phosphorylation in xenograft tumours following treatment with EX33. Mice carrying MCF10DCIS xenograft tumours were treated with Vehicle or EX33 at 25 mg/kg once a day for 2, 4 or 6 days. Tumours were harvested and analyzed by SureFire assay for levels of pAkt1, pAkt2 and pAkt3. Average±SEM are shown, n=4.

Nude mice were injected subcutaneously with MCF10DCIS cells. When the average tumour size reached 440 mm$^3$, EX33 was administered at 25 mg/kg for 2, 4 or 6 days. EX33 was given by oral gavage once a day. Tumours were harvested and analyzed by SureFire assay for levels of pAkt1, pAkt2 and pAkt3. Results are shown in FIG. 11. Average±SEM are shown, n=4.

Conclusion:

EX33 selectively reduced the level of Akt3 phosphorylation after in vivo administration to mice carrying MCF10DCIS xenograft tumours.

B: EX34 and EX33 Prevent Tumour Initiation in a HMLER-Akt3 Tumour Seeding Model

HMLER cells are not very tumourigenic. However, after enforced expression of Akt3, these cells are able to initiate tumours. Hence, the HMLER-Akt3 cells can be utilized to study the affect of inhibiting Akt3 on tumour initiation.

Mice implanted with 10$^5$ or 10$^6$ HMLER-Akt3 cells were treated with vehicle, EX34 or EX33 at 100 mg/kg once a day. Treatment was initiated on the day of tumour cell implantation. A total of 10 tumours were implanted for each treatment condition. Tumour incidence was evaluated after 2 weeks and tumour size cut of was set at 20 mm$^3$. Significance determined by unpaired Student two-tailed t test.

Conclusion:

Treatment with EX33 and EX34 prevented tumour initiation in a HMLER-Akt3 tumour seeding model.

TABLE

Tumour incidence in a HMLER-Akt3 tumour seeding xenograft model in NSG mice.

| Treatment | Tumour incidence | |
|---|---|---|
| | 10$^5$ | 10$^6$ |
| VEHICLE | 7/10 | 10/10 |
| EX34 | 3/10$^{ns}$ | 0/10$^{0.0002}$ |
| EX33 | 0/10$^{<0.0001}$ | 0/10$^{<0.0001}$ |

The table shows the number of tumours that were formed after 2 weeks of treatment and that exceeded 20 mm$^3$. The numbers are given as tumours formed/total number of implantations. Significance was determined by unpaired two-tailed Student t-test. Ns: not significant.

C: EX33 Prevents Primary Tumour Growth in a TNBC MDA-MB-468 Subcutaneous Xenograft Model The MDA-MB-468 model has previously been reported in the literature to be dependent upon Akt3 for xenograft tumour growth (Chin et al., Cancer Res 2014).

NSG mice were injected subcutaneously with MDA-MB-468 cells, and the effect on tumour growth of EX33 was evaluated. EX33 was administered at 50 mg/kg, and was given by oral gavage twice a day in a 5-days on and 2-days off cycle. Tumour growth was monitored by caliper measurements twice a week.

Figure 12:
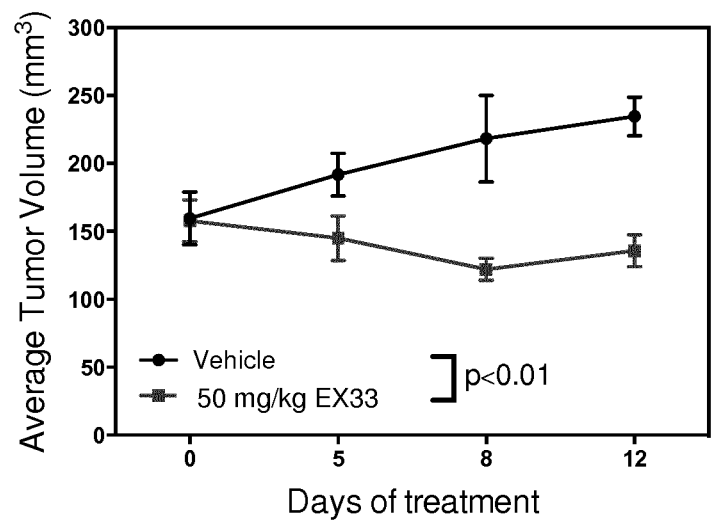
FIG. 12 shows the effect of EX33 on primary tumour growth in a triple-negative breast cancer (TNBC) MDA-MB-468 subcutaneous xenograft model. Tumour volumes of mice treated with vehicle or EX33 (50 mg/kg b.i.d.) were measured by caliper twice a week, over the course of 19 days. Data is given as Mean±SEM, n=6-10. Statistical analysis was performed by an unpaired two-tailed Student t test.

FIG. 12 shows the tumour volumes of mice treated with vehicle or EX33 (50 mg/kg b.i.d.) over the course of 19 days. Data are given as Mean±SEM, n=6-10. Statistical analysis was performed by unpaired two-tailed Student t test.

Conclusion:

Treatment with EX33 reduced tumour growth compared to vehicle treated mice.

D: EX33 Prevents Primary Tumour Growth in a MBBR3A Human Melanoma Cancer Cell Line in a Sub-cutaneous Xenograft Model in Nude Mice Akt3 is overexpressed in 16% of all melanomas, and has been related to treatment resistance.

Nude mice were injected subcutaneously with MBBR3A cells, and the effect on tumour growth of EX33 was evaluated. EX33 was administered at 50 mg/kg EX33 given by oral gavage twice a day in a 5-days on and 2-days off cycle. Tumour growth was monitored by caliper measurements twice a week.

Figure 13:
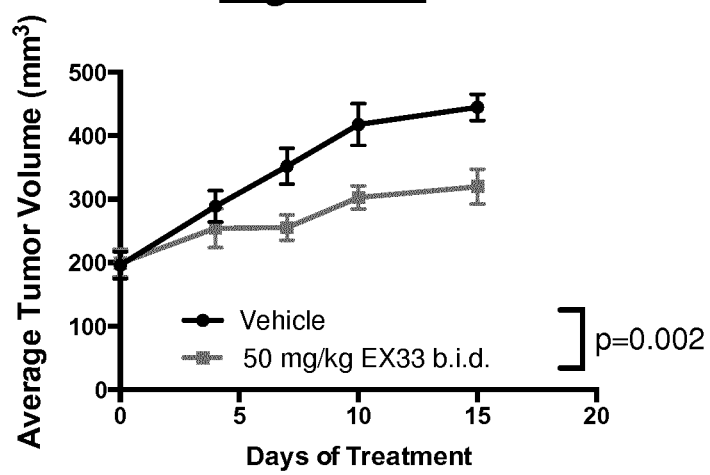
FIG. 13 shows the effect of EX33 on primary tumour growth in a MBBR3A human melanoma cancer cell line in a sub-cutaneous xenograft model in Nude mice. Tumour volumes of mice treated with vehicle or EX33 (50 mg/kg b.i.d.) were measured by caliper twice a week, over the course of 15 days. Data is given as Mean±SEM, n=10-12. Statistical analysis was performed by an unpaired two-tailed Student t test.

FIG. 13 shows the tumour volumes of mice treated with vehicle or EX33 (50 mg/kg b.i.d.) over the course of 15 days. Data are given as Mean±SEM, n=10-12. Statistical analysis was performed by unpaired two-tailed Student t test.

Conclusion:

Treatment with EX33 reduced tumour growth compared to vehicle treated mice.

E: EX67 Reduces Lung Metastasis after Tail Vein Injection of the TNBC Cell Line MDA-MB-231

The cellular program of epithelial to mesenchymal transition (EMT) is utilized by tumor cells to metastasize. The effect of EX67 on lung metastases was evaluated in a TNBC model.

Figure 14:
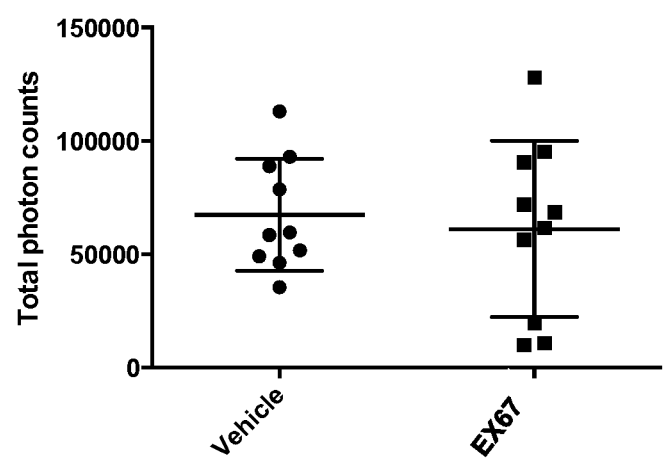
FIG. 14 shows the effect of the compound of Example 67 (denoted hereafter as EX67) on lung metastases in a TNBC model. Mice injected with MDA-MB-231D3H2LN/GFP-Luc mammary carcinoma cells and treated with vehicle or EX67 (25 mg/kg b.i.d.) over the course of 14 days were injected with D-luciferin (150 mg/kg) IP 10 minutes before being imaged. Whole-body imaging was performed on an Optix MX2 Small Animal Molecular Imager to measure the total photon count for each animal±SEM. n=10 for vehicle and n=10 for EX67 group.

NSG mice were injected in the tail vein with 500 000 MDA-MB-231D3H2LN/GFP-Luc mammary carcinoma cells. Mice were treated with Vehicle or 25 mg/kg EX67 twice a day. Metastases to the lung were evaluated by in vivo imaging after 3 weeks. Lung metastases were also evaluated macroscopically at the day of culling (see FIG. 14).

After 14 days, lung metastases were detected in 10/10 mice treated with Vehicle and 7/10 mice treated with EX67.

Conclusion:

Treatment with EX67 prevented metastases compared to vehicle-treated mice in a sub-set of animals.

The invention claimed is:

1. A compound of formula (I):

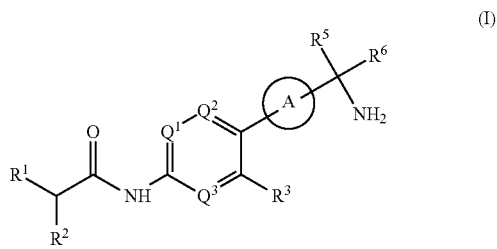

wherein
one of $Q^1$ and $Q^2$ represents a nitrogen atom and the other represents CH, or both $Q^1$ and $Q^2$ represent nitrogen atoms, and $Q^3$ represents CH;
A represents an optionally substituted five- or six-membered aromatic ring;

$R^1$ represents an aliphatic carbocyclic or heterocyclic ring, optionally substituted by $-(C=O)_xNR^aR^b$, $-OR^c$, $-SO_2R^g$ or optionally substituted alkyl, in which
x is 0 or 1;
$R^a$ and $R^b$ independently represent (a) H, (b) optionally substituted alkyl, (c) optionally substituted cycloalkyl, (d) optionally substituted heterocycloalkyl, (e) $-(C=O)R^d$, or (f) $-SO_2R^e$, wherein $R^d$ and $R^e$ independently represent (i) optionally substituted alkyl, (ii) optionally substituted alkoxy, or (iii) optionally substituted cycloalkyl; or $R^a$ and $R^b$ together with the nitrogen atom to which they are attached form an optionally substituted aromatic or aliphatic heterocyclic ring;
$R^c$ represents optionally substituted alkyl;
and
$R^g$ represents optionally substituted cycloalkyl;
$R^2$ represents H, optionally substituted alkyl or halo;
$R^3$ represents an optionally substituted aryl or heteroaryl ring;
$R^5$ and $R^6$ independently represent H or optionally substituted alkyl; or $R^5$ and $R^6$ together with the carbon atom to which they are attached form an optionally substituted cycloalkyl ring, optionally containing a heteroatom;
and the corresponding N-oxides; and pharmaceutically acceptable salts and solvates of such compounds and their N-oxides and prodrugs.

2. A compound according to claim 1, which is of formula (Ic):

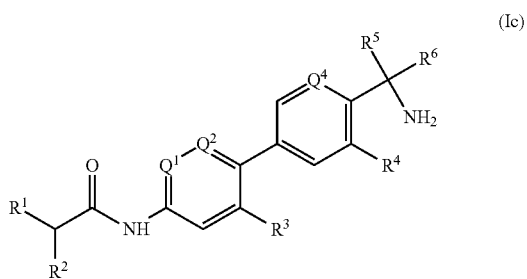

wherein
one of $Q^1$ and $Q^2$ represents a nitrogen atom and the other represents CH, or both $Q^1$ and $Q^2$ represent nitrogen atoms;
$Q^4$ represents CH or a nitrogen atom;
$R^1$ represents a six-membered aliphatic carbocyclic or heterocyclic ring, optionally substituted by $-(C=O)_xNR^aR^b$, $-OR^c$, $-SO_2R^g$ or $C_{1-6}$ alkyl, in which
x is 0 or 1;
$R^a$ and $R^b$ independently represent (a) H, (b) $C_{1-6}$ alkyl optionally substituted by $C_{1-6}$ alkoxy, (c) $C_{3-6}$ cycloalkyl optionally substituted by $C_{1-6}$ alkyl, (d) a 3- to 6-membered heterocycloalkyl ring optionally substituted by $C_{1-6}$ alkyl, (ie) $-(C=O)R^d$, or (f) $-SO_2R^e$, wherein $R^d$ and $R^e$ independently represent (i) $C_{1-6}$ alkyl optionally substituted by cycloalkyl or halo, (ii) $C_{1-6}$ alkoxy, or (iii) $C_{3-6}$ cycloalkyl optionally substituted by $C_{1-6}$ alkyl; or $R^a$ and $R^b$ together with the nitrogen atom to which they are attached form a 5- or 6-membered aromatic or aliphatic heterocyclic ring optionally substituted by oxo or $C_{1-6}$ alkyl;
$R^c$ represents $C_{1-6}$ alkyl;
and
$R^g$ represents $C_{3-6}$ cycloalkyl;
$R^2$ represents H, $C_{1-6}$ alkyl or halo;
$R^3$ represents a 5- or 6-membered aryl or heteroaryl ring, optionally substituted by $C_{1-6}$ alkyl or halo;
$R^4$ represents H, halo or $-OR^f$, where $R^f$ is $C_{1-6}$ alkyl;
$R^5$ and $R^6$ independently represent H or $C_{1-6}$ alkyl optionally substituted by halo; or $R^5$ and $R^6$ together with the carbon atom to which they are attached form a 3- or 4-membered cycloalkyl ring, optionally containing a heteroatom and optionally substituted by $-OH$, $C_{1-6}$ alkyl or halo;
and the corresponding N-oxides; and pharmaceutically acceptable salts and solvates of such compounds and their N-oxides and prodrugs.

3. A compound according to claim 2, wherein $R^1$ represents a six-membered aliphatic carbocyclic ring, optionally substituted by $-(C=O)_xNR^aR^b$.

4. A compound according to claim 3, wherein x is 0.

5. A compound according to claim 4, wherein $R^a$ and/or $R^b$ represent:
(a) $C_{1-6}$ alkyl optionally substituted by $-OCH_3$; or
(b) cyclopropyl or cyclobutyl, any of which is optionally substituted by $C_{1-6}$ alkyl; or
(c) a 4-membered heterocycloalkyl ring, optionally substituted by $C_{1-6}$ alkyl; or
(d) $-(C=O)R^d$; or
(e) $-SO_2R^e$.

6. A compound according to claim 2, wherein $R^a$ and $R^b$, together with the nitrogen atom to which they are attached, form a 5- or 6-membered aromatic or aliphatic heterocyclic ring selected from triazinyl, oxazolidinyl, pyrrolidinyl, piperidinyl and morpholinyl, any of which may be optionally substituted by oxo or $C_{1-6}$ alkyl.

7. A compound according to claim 2, wherein one of $R^a$ and $R^b$ represents H or $C_{1-6}$ alkyl optionally substituted by $C_{1-6}$ alkoxy, while the other of $R^a$ and $R^b$ represents (i) $C_{1-6}$ alkyl optionally substituted by $C_{1-6}$ alkoxy, (ii) $C_{3-6}$ cycloalkyl optionally substituted by $C_{1-6}$ alkyl, (iii) a 3- to 6-membered heterocycloalkyl ring optionally substituted by $C_{1-6}$ alkyl, (v) $-(C=O)R^d$, or (vi) $-SO_2R^e$.

8. A compound according to claim 7, wherein $R^d$ and/or $R^e$ represent:
(a) $-CH_3$, $-CHF_2$, $-C(CH_3)_2CF_3$, $-C(CH_3)_3$, $-CH_2C(CH_3)_3$, $-CH(CH_3)_2$, $-CH_2CH_3$ or $-CH_2CH_2CH_3$; or $C_{1-6}$ alkyl optionally substituted by cycloalkyl, halo or alkoxy
(b) $C_{1-6}$ alkyl optionally substituted by cyclopropyl or cyclobutyl; or
(c) $-OCH_3$ or $-OCH_2CH_3$; or
(d) $C_{3-6}$ cycloalkyl optionally substituted by $C_{1-6}$ alkyl.

9. A compound according to claim 2, wherein $R^c$ represents methyl.

10. A compound according to claim 2, wherein $R^g$ represents cyclopropyl.

11. A compound according to claim 2, wherein $R^2$ is selected from H, methyl, and F.

12. A compound according to claim 2, wherein $R^3$ is selected from phenyl optionally substituted by $C_{1-6}$ alkyl or halo; thienyl optionally substituted by $C_{1-6}$ alkyl or halo; and pyridyl optionally substituted by $C_{1-6}$ alkyl or halo.

13. A compound according to claim 2, wherein $R^4$ is selected from H and halo.

14. A compound according to claim 2, wherein $R^5$ and/or $R^6$ represent methyl optionally substituted by F.

15. A compound according to claim 2, wherein $R^5$ and $R^6$, together with the carbon atom to which they are attached, form a cyclopropyl or cyclobutyl ring, optionally substituted by —OH, $C_{1-6}$ alkyl and/or F.

16. A compound according to claim 15, wherein $R^5$ and $R^6$, together with the carbon atom to which they are attached, form 2,2-difloro-cyclobutyl or 2-methyl-2-hydroxy-cyclobutyl.

17. A compound according to claim 15, wherein $R^5$ and $R^6$, together with the carbon atom to which they are attached, form a 3- or 4-membered cycloalkyl ring, containing a heteroatom selected from N, O and S, and optionally substituted by —OH, $C_{1-6}$ alkyl and/or halo.

18. A compound according to claim 17, wherein $R^5$ and $R^6$, together with the carbon atom to which they are attached, form an oxetanyl ring, optionally substituted by —OH, $C_{1-6}$ alkyl and/or halo.

19. A compound according to claim 1, which is of formula (Id):

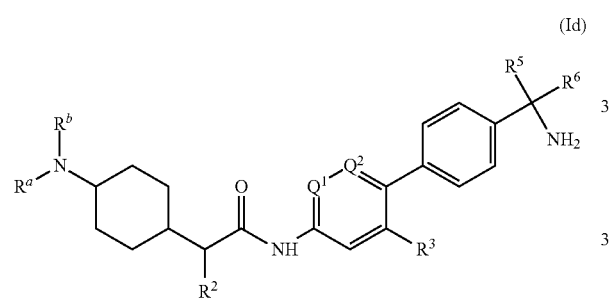

(Id)

wherein
one of $Q^1$ and $Q^2$ represents a nitrogen atom and the other represents CH, or both $Q^1$ and $Q^2$ represent nitrogen atoms;
$R^a$ and $R^b$ independently represent (a) H, (b) optionally substituted alkyl, (c) optionally substituted cycloalkyl, (d) optionally substituted heterocycloalkyl, (e) —(C=O)$R^d$, or (f) —SO$_2$$R^e$, wherein $R^d$ and $R^e$ independently represent (i) optionally substituted alkyl, (ii) alkoxy, or (iii) optionally substituted cycloalkyl; or $R^a$ and $R^b$ together with the nitrogen atom to which they are attached form an optionally substituted aromatic or aliphatic heterocyclic ring;
$R^2$ is H, optionally substituted alkyl or halo;
$R^3$ is an optionally substituted aryl or heteroaryl ring;
$R^5$ and $R^6$ independently represent H or optionally substituted alkyl; or $R^5$ and $R^6$ together with the carbon atom to which they are attached form an optionally substituted cycloalkyl ring, optionally containing a heteroatom;
and the corresponding N-oxides; and pharmaceutically acceptable salts and solvates of such compounds and their N-oxides and prodrugs.

20. A compound according to claim 1, which is of formula (Ie):

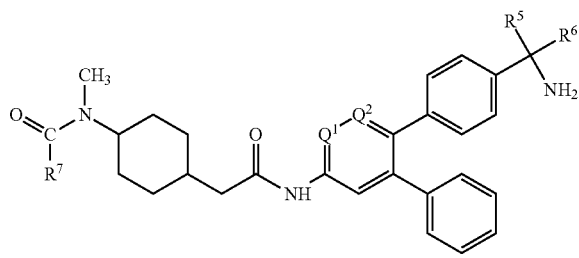

(Ie)

wherein
one of $Q^1$ and $Q^2$ represents a nitrogen atom and the other represents CH, or both $Q^1$ and $Q^2$ represent nitrogen atoms;
$R^5$ and $R^6$ independently represent H or optionally substituted alkyl; or $R^5$ and $R^6$ together with the carbon atom to which they are attached form an optionally substituted cycloalkyl ring, optionally containing a heteroatom;
$R^7$ represents alkyl, alkoxy or cycloalkyl;
and the corresponding N-oxides; and pharmaceutically acceptable salts and solvates of such compounds and their N-oxides and prodrugs.

21. A compound according to claim 1, which is selected from the group consisting of:

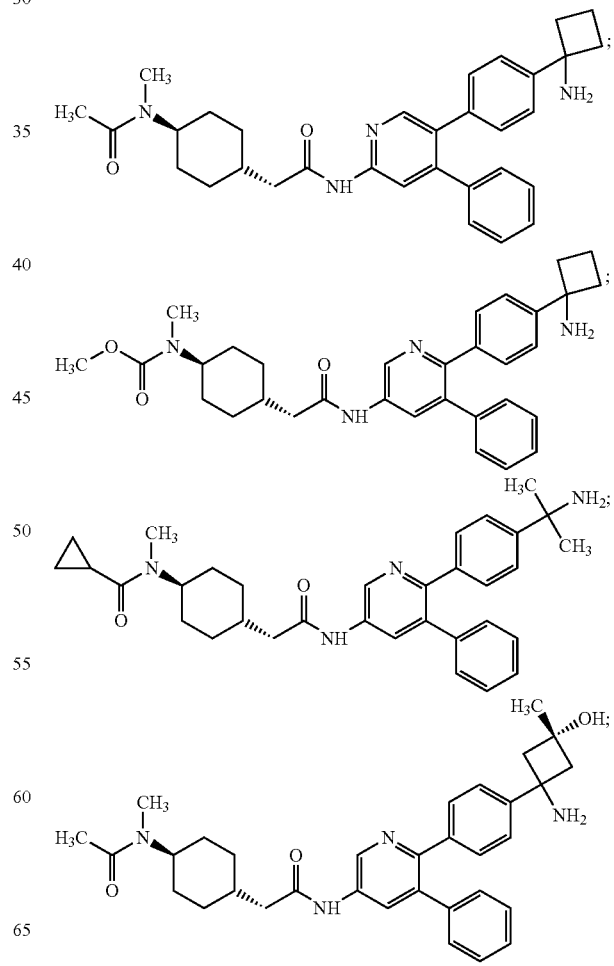

281
-continued
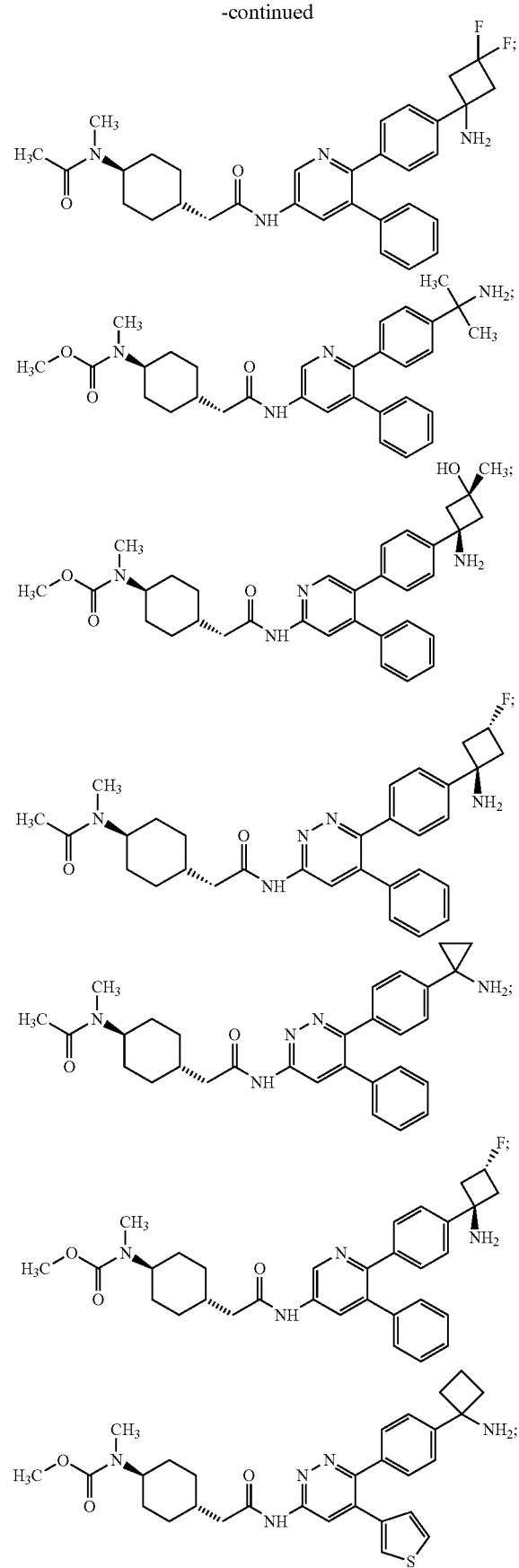
282
-continued
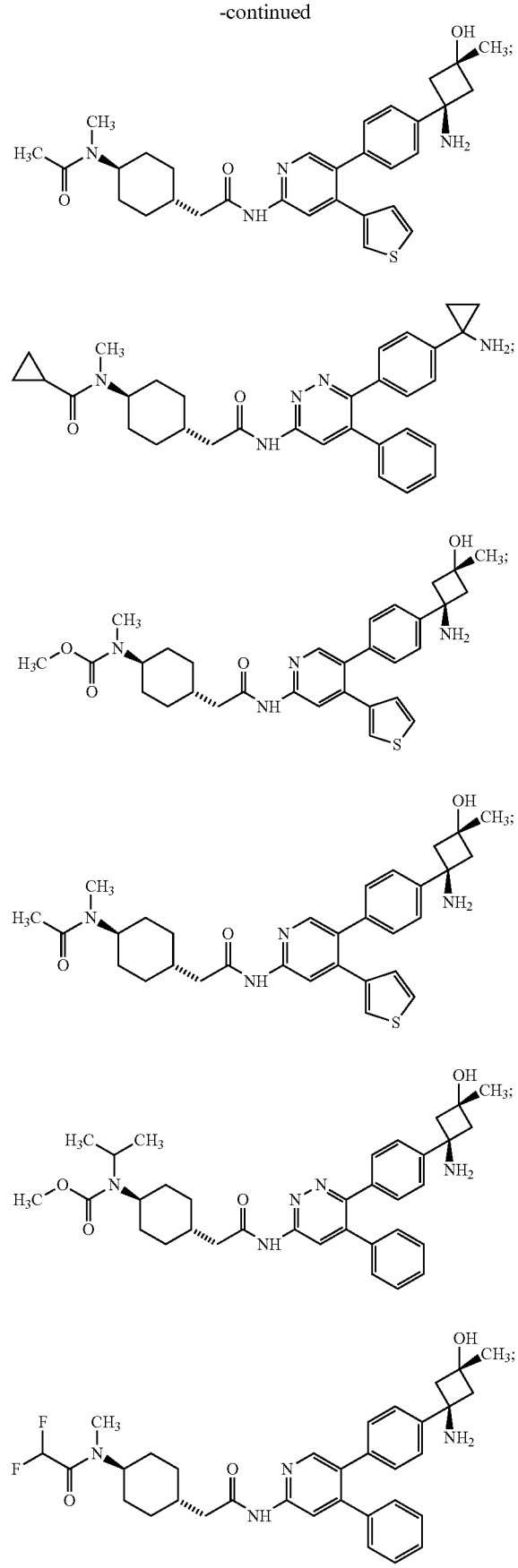

-continued

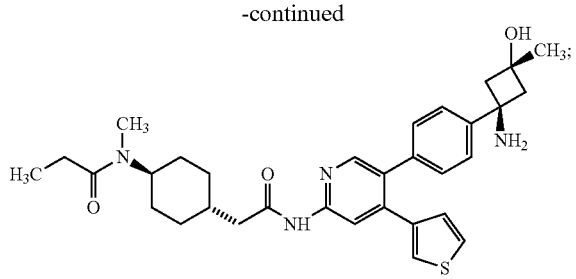

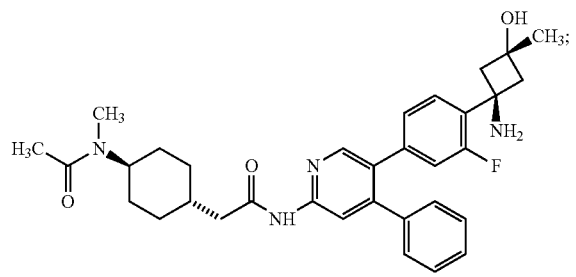

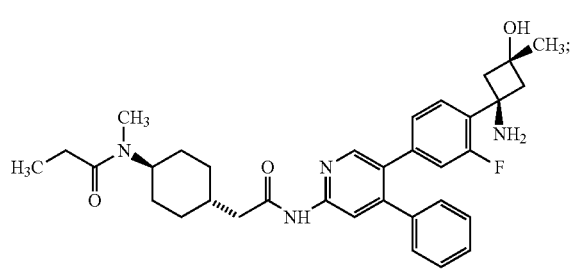

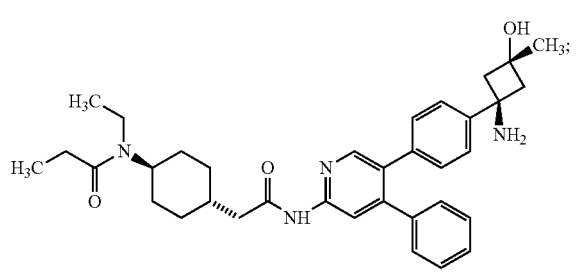

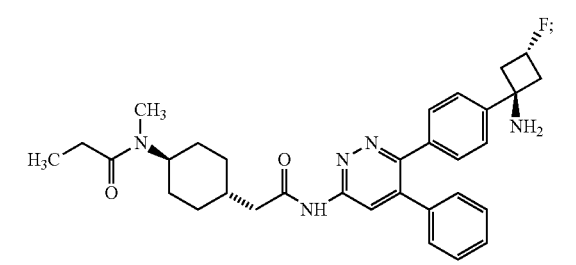

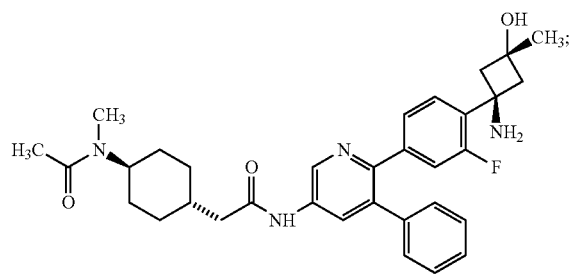

-continued

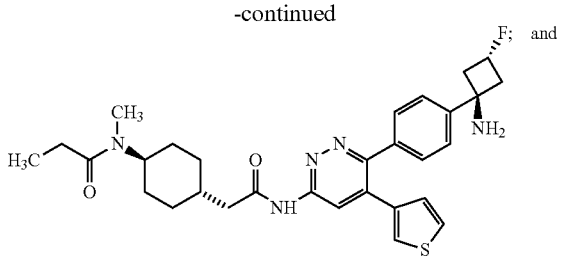

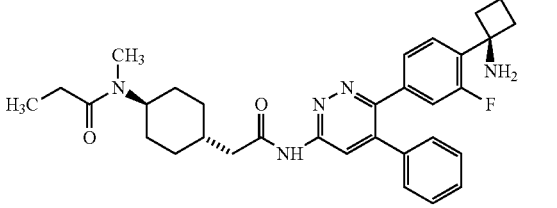

and the corresponding N-oxides; and pharmaceutically acceptable salts and solvates of such compounds and their N-oxides and prodrugs.

22. A compound according to claim 1, which is selected from the group consisting of:

N-(6-(4-(trans-1-amino-3-hydroxy-3-methylcyclobutyl)phenyl)-5-phenylpyridin-3-yl)-2-(trans-4-(N-methylacetamido)cyclohexyl)acetamide;

2-(trans-4-acetamidocyclohexyl)-N-(6-(4-(trans-1-amino-3-hydroxy-3-methylcyclobutyl)phenyl)-5-phenylpyridin-3-yl)acetamide;

N-(6-(4-(2-aminopropan-2-yl)phenyl)-5-phenylpyridin-3-yl)-2-(trans-4-(N-methylacetamido)cyclohexyl)acetamide;

N-(trans-4-(2-((6-(4-(2-aminopropan-2-yl)phenyl)-5-phenylpyridin-3-yl)amino)-2-oxoethyl)cyclohexyl)-N-methylisobutyramide;

N-(6-(4-(1-amino-3,3-difluorocyclobutyl)phenyl)-5-phenylpyridin-3-yl)-2-(trans-4-(N-methylacetamido)cyclohexyl)acetamide;

N-(6-(4-(2-aminopropan-2-yl)phenyl)-5-(thiophen-3-yl)pyridin-3-yl)-2-(trans-4-(N-methylacetamido)cyclohexyl)acetamide;

N-(6-(4-((S)-1-aminoethyl)phenyl)-5-phenylpyridin-3-yl)-2-(trans-4-(N-methylacetamido)cyclohexyl)acetamide;

N-(6-(4-((R)-1-aminoethyl)phenyl)-5-phenylpyridin-3-yl)-2-(trans-4-(N-methylacetamido)cyclohexyl)acetamide;

N-(6-(4-(2-aminopropan-2-yl)phenyl)-5-(2-fluorophenyl)pyridin-3-yl)-2-(trans-4-(N-methylacetamido)cyclohexyl)acetamide;

N-(6-(4-(1-aminocyclobutyl)phenyl)-5-phenylpyridin-3-yl)-2-(trans-4-(N-methylacetamido)cyclohexyl)acetamide;

N-(6-(4-((S)-1-amino-2,2-difluoroethyl)phenyl)-5-phenylpyridin-3-yl)-2-(trans-4-(N-methylacetamido)cyclohexyl)acetamide;

N-(6-(4-(1-aminocyclopropyl)phenyl)-5-phenylpyridin-3-yl)-2-(trans-4-(N-methylacetamido)cyclohexyl)acetamide;

2-(trans-4-acetamidocyclohexyl)-N-(6-(4-(trans-1-amino-3-hydroxycyclobutyl)phenyl)-5-phenylpyridin-3-yl)acetamide;

2-(trans-4-acetamidocyclohexyl)-N-(6-(4-(3-aminooxetan-3-yl)phenyl)-5-phenylpyridin-3-yl)acetamide;

2-(trans-4-acetamidocyclohexyl)-N-(6-(4-(trans-1-amino-3-fluorocyclobutyl)phenyl)-5-phenylpyridin-3-yl)acetamide;

N-(6-(4-(1-aminocyclobutyl)phenyl)-5-(2-fluorophenyl)pyridin-3-yl)-2-(trans-4-(N-methylacetamido)cyclohexyl)acetamide;

N-(6-(4-(1-aminocyclobutyl)phenyl)-5-(thiophen-3-yl)pyridin-3-yl)-2-(trans-4-(N-methylmethylsulfonamido)cyclohexyl)acetamide;

2-(trans-4-acetamidocyclohexyl)-N-(6-(4-(1-aminocyclobutyl)phenyl)-5-(2-methylthiophen-3-yl)pyridin-3-yl)acetamide;

N-(6-(4-(1-aminocyclobutyl)phenyl)-5-(4-methylthiophen-3-yl)pyridin-3-yl)-2-(trans-4-(N-methylmethylsulfonamido)cyclohexyl)acetamide;

N-(trans-4-(2-((2-(4-(1-aminocyclobutyl)phenyl)-[3,3'-bipyridin]-5-yl)amino)-2-oxoethyl)cyclohexyl)-3,3,3-trifluoro-2,2-dimethylpropanamide;

N-(6-(4-(3-aminooxetan-3-yl)phenyl)-5-phenylpyridin-3-yl)-2-(4-methoxycyclohexyl)acetamide;

N-(6-(4-(3-aminooxetan-3-yl)phenyl)-5-phenylpyridin-3-yl)-2-((2R,6S)-2,6-dimethyltetrahydro-2H-pyran-4-yl)acetamide;

N-(6-(4-(2-aminopropan-2-yl)phenyl)-5-phenylpyridin-3-yl)-2-(trans-4-(3-methyl-4H-1,2,4-triazol-4-yl)cyclohexyl)acetamide;

N-(6-(4-(2-aminopropan-2-yl)phenyl)-5-phenylpyridin-3-yl)-2-(trans-4-(2-oxopyrrolidin-1-yl)cyclohexyl)acetamide;

2-(trans-4-acetamidocyclohexyl)-N-(6-(4-(1-amino-3,3-difluorocyclobutyl)phenyl)-5-phenylpyridin-3-yl)acetamide;

N-(trans-4-(2-((6-(4-(2-aminopropan-2-yl)phenyl)-5-(thiophen-3-yl)pyridin-3-yl)amino)-2-oxoethyl)cyclohexyl)cyclopropanecarboxamide;

N-(trans-4-(2-((6-(4-(2-aminopropan-2-yl)phenyl)-5-(thiophen-3-yl)pyridin-3-yl)amino)-2-oxoethyl)cyclohexyl)-N-methylcyclopropanecarboxamide;

N-(6-(4-(2-aminopropan-2-yl)phenyl)-5-phenylpyridin-3-yl)-2-(trans-4-(2-oxopiperidin-1-yl)cyclohexyl)acetamide;

N-(6-(4-(2-aminopropan-2-yl)phenyl)-5-phenylpyridin-3-yl)-2-(trans-4-(2-cyclopropylacetamido)cyclohexyl)acetamide;

N-(6-(4-(2-aminopropan-2-yl)phenyl)-5-phenylpyridazin-3-yl)-2-(trans-4-(N-methylacetamido)cyclohexyl)acetamide;

N-(6-(4-(2-aminopropan-2-yl)-3-fluorophenyl)-5-phenylpyridin-3-yl)-2-(trans-4-(N-methylacetamido)cyclohexyl)acetamide;

N-(6-(4-(trans-1-amino-3-fluorocyclobutyl)phenyl)-5-phenylpyridin-3-yl)-2-(trans-4-(N-methylacetamido)cyclohexyl)acetamide;

N-(5-(4-(1-aminocyclobutyl)phenyl)-4-phenylpyridin-2-yl)-2-(trans-4-(N-methylacetamido)cyclohexyl)acetamide;

methyl(trans-4-(2-((6-(4-(2-aminopropan-2-yl)phenyl)-5-phenylpyridin-3-yl)amino)-2-oxoethyl)cyclohexyl)(methyl)carbamate;

N-(6-(4-(2-aminopropan-2-yl)phenyl)-5-phenylpyridin-3-yl)-2-(trans-4-(methyl(3-methyloxetan-3-yl)amino)cyclohexyl)acetamide;

N-(6-(4-(3-aminooxetan-3-yl)phenyl)-5-phenylpyridin-3-yl)-2-(4,4-dimethoxycyclohexyl)acetamide;

N-(6-(4-(3-aminooxetan-3-yl)phenyl)-5-phenylpyridin-3-yl)-2-(trans-4-(cyclopropanesulfonamido)cyclohexyl)acetamide;

N-(6-(4-(1-aminocyclobutyl)phenyl)-5-(thiophen-3-yl)pyridin-3-yl)-2-(trans-4-morpholinocyclohexyl)acetamide;

N-(6-(4-(1-aminocyclobutyl)phenyl)-5-(thiophen-3-yl)pyridin-3-yl)-2-(trans-4-((2-methoxyethyl)(methyl)amino)cyclohexyl)acetamide;

N-(6-(4-(1-aminocyclobutyl)phenyl)-5-phenylpyridin-3-yl)-2-(1-(cyclopropylsulfonyl)piperidin-4-yl)-2-fluoroacetamide;

2-(trans-4-acetamidocyclohexyl)-N-(6-(4-(1-aminocyclobutyl)phenyl)-5-phenylpyridin-3-yl)propanamide;

N-(6-(4-(2-aminopropan-2-yl)phenyl)-5-phenylpyridin-3-yl)-2-(trans-4-(2-oxooxazolidin-3-yl)cyclohexyl)acetamide;

N-(6'-(2-aminopropan-2-yl)-3-phenyl-[2,3'-bipyridin]-5-yl)-2-(trans-4-(N-methylacetamido)cyclohexyl)acetamide;

methyl(trans-4-(2-((6-(4-(trans-1-amino-3-hydroxy-3-methylcyclobutyl)phenyl)-5-phenylpyridin-3-yl)amino)-2-oxoethyl)cyclohexyl)(methyl)carbamate;

N-(6-(4-(trans-1-amino-3-fluorocyclobutyl)phenyl)-5-phenylpyridazin-3-yl)-2-(trans-4-(2-oxooxazolidin-3-yl)cyclohexyl)acetamide;

N-(6-(4-(trans-1-amino-3-fluorocyclobutyl)phenyl)-5-phenylpyridazin-3-yl)-2-(trans-4-(N-methylacetamido)cyclohexyl)acetamide;

N-(trans-4-(2-((6-(4-(2-aminopropan-2-yl)phenyl)-5-phenylpyridin-3-yl)amino)-2-oxoethyl)cyclohexyl)-N-methylcyclobutanecarboxamide;

N-(6-(4-(1-aminocyclobutyl)phenyl)-5-(thiophen-3-yl)pyridin-3-yl)-2-(trans-4-(2-oxopyrrolidin-1-yl)cyclohexyl)acetamide;

N-(6-(4-(1-aminocyclobutyl)phenyl)-5-phenylpyridin-3-yl)-2-(trans-4-(N-isopropylacetamido)cyclohexyl)acetamide;

(S)—N-(6-(4-(1-aminocyclobutyl)phenyl)-5-phenylpyridin-3-yl)-2-(1-(cyclopropylsulfonyl)piperidin-4-yl)-2-fluoroacetamide;

methyl(trans-4-(2-((6-(4-(1-aminocyclobutyl)phenyl)-5-phenylpyridin-3-yl)amino)-2-oxoethyl)cyclohexyl)(isopropyl)carbamate;

methyl(trans-4-(2-((6-(4-(1-aminocyclobutyl)phenyl)-5-phenylpyridin-3-yl)amino)-1-fluoro-2-oxoethyl)cyclohexyl)(methyl)carbamate;

N-(trans-4-(2-((6-(4-(2-aminopropan-2-yl)-3-fluorophenyl)-5-phenylpyridin-3-yl)amino)-2-oxoethyl)cyclohexyl)-N-methylcyclopropanecarboxamide;

methyl(trans-4-(1-((6-(4-(1-aminocyclobutyl)phenyl)-5-phenylpyridin-3-yl)amino)-1-oxopropan-2-yl)cyclohexyl)(methyl)carbamate;

trans-4-(2-((6-(4-(2-aminopropan-2-yl)phenyl)-5-phenylpyridin-3-yl)amino)-2-oxoethyl)-N,N-dimethylcyclohexane-1-carboxamide;

methyl(trans-4-(2-((6-(4-(2-aminopropan-2-yl)phenyl)-5-phenylpyridazin-3-yl)amino)-2-oxoethyl)cyclohexyl)(methyl)carbamate;

N-(6-(4-(trans-1-amino-3-hydroxy-3-methylcyclobutyl)phenyl)-5-phenylpyridazin-3-yl)-2-(trans-4-(N-methylacetamido)cyclohexyl)acetamide;

N-(6-(4-(trans-1-amino-3-hydroxy-3-methylcyclobutyl)phenyl)-5-phenylpyridazin-3-yl)-2-(trans-4-(2-oxooxazolidin-3-yl)cyclohexyl)acetamide;

methyl(trans-4-(2-((6-(4-(trans-1-amino-3-hydroxy-3-methylcyclobutyl)phenyl)-5-phenylpyridazin-3-yl)amino)-2-oxoethyl)cyclohexyl)(methyl)carbamate;

methyl(trans-4-(2-((6-(4-(1-amino-3,3-difluorocyclobutyl)phenyl)-5-phenylpyridazin-3-yl)amino)-2-oxoethyl)cyclohexyl)(methyl)carbamate;

N-(6-(4-(1-amino-3,3-difluorocyclobutyl)phenyl)-5-phenylpyridazin-3-yl)-2-(trans-4-(2-oxooxazolidin-3-yl)cyclohexyl)acetamide;

methyl(trans-4-(2-((6-(4-(1-aminocyclopropyl)-3-fluorophenyl)-5-phenylpyridin-3-yl)amino)-2-oxoethyl)cyclohexyl(methyl)carbamate;

N-(5-(4-(2-aminopropan-2-yl)phenyl)-4-phenylpyridin-2-yl)-2-(trans-4-(N-methylacetamido)cyclohexyl)acetamide;

N-(5-(4-(2-aminopropan-2-yl)phenyl)-4-phenylpyridin-2-yl)-2-(trans-4-(2-oxooxazolidin-3-yl)cyclohexyl)acetamide;

N-(6-(4-(2-aminopropan-2-yl)phenyl)-5-phenylpyridazin-3-yl)-2-(trans-4-(2-oxooxazolidin-3-yl)cyclohexyl)acetamide;

N-(6-(4-(1-aminocyclobutyl)phenyl)-5-phenylpyridazin-3-yl)-2-(trans-4-(2-oxooxazolidin-3-yl)cyclohexyl)acetamide;

methyl(trans-4-(2-((5-(4-(trans-1-amino-3-hydroxy-3-methylcyclobutyl)phenyl)-4-phenylpyridin-2-yl)amino)-2-oxoethyl)cyclohexyl)(methyl)carbamate;

N-(6-(4-(trans-1-amino-3-hydroxy-3-methylcyclobutyl)phenyl)-5-(2-fluorophenyl)-1,2,4-triazin-3-yl)-2-(trans-4-(2-oxooxazolidin-3-yl)cyclohexyl)acetamide;

N-(6-(4-(2-aminopropan-2-yl)phenyl)-5-phenyl-1,2,4-triazin-3-yl)-2-(trans-4-(2-oxooxazolidin-3-yl)cyclohexyl)acetamide;

N-(5-(4-(1-aminocyclobutyl)phenyl)-4-(thiophen-3-yl)pyridin-2-yl)-2-(trans-4-(2-oxooxazolidin-3-yl)cyclohexyl)acetamide;

N-(trans-4-(2-((6-(4-(trans-1-amino-3-fluorocyclobutyl)phenyl)-5-phenylpyridazin-3-yl)amino)-2-oxoethyl)cyclohexyl)-N-methylcyclopropanecarboxamide;

N-(6-(4-(1-aminocyclopropyl)phenyl)-5-phenylpyridazin-3-yl)-2-(trans-4-(N-methylacetamido)cyclohexyl)acetamide;

N-(6-(4-(1-amino-3,3-difluorocyclobutyl)phenyl)-5-phenylpyridazin-3-yl)-2-(trans-4-(N-methylacetamido)cyclohexyl)acetamide;

N-(6-(4-(trans-1-amino-3-fluorocyclobutyl)phenyl)-5-phenylpyridazin-3-yl)-2-(trans-4-(2-oxopyrrolidin-1-yl)cyclohexyl)acetamide;

N-(6-(4-(trans-1-amino-3-fluorocyclobutyl)phenyl)-5-(thiophen-3-yl)pyridazin-3-yl)-2-(trans-4-(N-methylacetamido)cyclohexyl)acetamide;

N-(5'-(4-(1-aminocyclobutyl)phenyl)[2,4'-bipyridin]-2'-yl)-2-(trans-4-(N-methylacetamido)cyclohexyl)acetamide;

Methyl(trans-4-(2-((6-(4-(trans-1-amino-3-fluorocyclobutyl)phenyl)-5-phenylpyridin-3-yl)amino)-2-oxoethyl)cyclohexyl)(methyl)carbamate;

N-(6-(4-(trans-1-amino-3-fluorocyclobutyl)phenyl)-5-phenylpyridin-3-yl)-2-(trans-4-(2-oxooxazolidin-3-yl)cyclohexyl)acetamide;

N-(6-(4-(trans-1-amino-3-fluorocyclobutyl)phenyl)-5-(thiophen-3-yl)pyridazin-3-yl)-2-(trans-4-(2-oxooxazolidin-3-yl)cyclohexyl)acetamide;

N-(6-(4-(2-aminopropan-2-yl)phenyl)-5-(thiophen-3-yl)pyridazin-3-yl)-2-(trans-4-(2-oxooxazolidin-3-yl)cyclohexyl)acetamide;

methyl(trans-4-(2-((6-(4-(1-aminocyclobutyl)phenyl)-5-(thiophen-3-yl)pyridazin-3-yl)amino)-2-oxoethyl)cyclohexyl)(methyl)carbamate;

N-(trans-4-(2-((5-(4-(trans-1-amino-3-hydroxy-3-methylcyclobutyl)phenyl)-4-phenylpyridin-2-yl)amino)-2-oxoethyl)cyclohexyl)-N-methylpropionamide;

N-(trans-4-(2-((6-(4-(trans-1-amino-3-hydroxy-3-methylcyclobutyl)phenyl)-5-phenylpyridazin-3-yl)amino)-2-oxoethyl)cyclohexyl)-N-methylpropionamide;

methyl(trans-4-(2-((6-(4-(trans-1-amino-3-hydroxy-3-methylcyclobutyl)phenyl)-5-(thiophen-3-yl)pyridazin-3-yl)amino)-2-oxoethyl)cyclohexyl)(methyl)carbamate;

N-(trans-4-(2-((5-(4-(trans-1-amino-3-hydroxy-3-methylcyclobutyl)phenyl)-4-phenylpyridin-2-yl)amino)-2-oxoethyl)cyclohexyl)-N-methylisobutyramide;

methyl (trans-4-(2-((5'-(4-(1-aminocyclobutyl)phenyl)-[2,4'-bipyridin]-2'-yl)amino)-2-oxoethyl)cyclohexyl)(methyl)carbamate;

N-(trans-4-(2-((6-(4-(1-aminocyclopropyl)phenyl)-5-phenylpyridazin-3-yl)amino)-2-oxoethyl)cyclohexyl)-N-methylcyclopropanecarboxamide;

N-(trans-4-(2-((6-(4-(2-aminopropan-2-yl)phenyl)-5-(thiophen-3-yl)pyridazin-3-yl)amino)-2-oxoethyl)cyclohexyl)-N-methylpropionamide;

methyl(trans-4-(2-((5-(4-(trans-1-amino-3-hydroxy-3-methylcyclobutyl)phenyl)-4-(thiophen-3-yl)pyridin-2-yl)amino)-2-oxoethyl)cyclohexyl)(methyl)carbamate;

N-(trans-4-(2-((6-(4-(1-aminocyclopropyl)-3-fluorophenyl)-5-phenylpyridin-3-yl)amino)-2-oxoethyl)cyclohexyl)-N-methylpropionamide;

N-(trans-4-(2-((6-(4-(trans- 1-amino-3-hydroxy-3-methylcyclobutyl)phenyl)-5-(thiophen-3-yl)pyridazin-3-yl)amino)-2-oxoethyl)cyclohexyl)-N-methylpropionamide;

N-(6-(4-(1-aminocyclopropyl)-3-fluorophenyl)-5-(thiophen-3-yl)pyridazin-3-yl)-2-(trans-4-(N-methylacetamido)cyclohexyl)acetamide;

N-(5-(4-(trans-1-amino-3-hydroxy-3-methylcyclobutyl)phenyl)-4-(thiophen-3-yl)pyridin-2-yl)-2-(trans-4-(N-methylacetamido)cyclohexyl)acetamide;

N-(5-(4-(trans-1-amino-3-hydroxy-3-methylcyclobutyl)phenyl)-4-(2-fluorophenyl)pyridin-2-yl)-2-(trans-4-(N-methylacetamido)cyclohexyl)acetamide;

N-(trans-4-(2-((5-(4-(trans-1-amino-3-hydroxy-3-methylcyclobutyl)phenyl)-4-(2-fluorophenyl)pyridin-2-yl)amino)-2-oxoethyl)cyclohexyl)-N-methylpropionamide;

methyl(trans-4-(2-((5-(4-(trans-1-amino-3-hydroxy-3-methylcyclobutyl)phenyl)-4-(2-fluorophenyl)pyridin-2-yl)amino)-2-oxoethyl)cyclohexyl)(methyl)carbamate;

ethyl(trans-4-(2-((6-(4-(trans-1-amino-3-hydroxy-3-methylcyclobutyl)phenyl)-5-phenylpyridin-3-yl)amino)-2-oxoethyl)cyclohexyl)(methyl)carbamate;

N-(trans-4-(2-((6-(4-(trans-1-amino-3-hydroxy-3-methylcyclobutyl)phenyl)-5-phenylpyridin-3-yl)amino)-2-oxoethyl)cyclohexyl)-N-methylpropionamide;

N-(trans-4-(2-((6-(4-(trans-1-amino-3-hydroxy-3-methylcyclobutyl)phenyl)-5-phenylpyridin-3-yl)amino)-2-oxoethyl)cyclohexyl)-N-methylisobutyramide;

N-(6-(4-(trans-1-amino-3-hydroxy-3-methylcyclobutyl)phenyl)-5-phenylpyridazin-3-yl)-2-(trans-4-(N-isopropylacetamido)cyclohexyl)acetamide;

methyl(trans-4-(2-((6-(4-(trans-1-amino-3-hydroxy-3-methylcyclobutyl)phenyl)-5-phenylpyridin-3-yl)amino)-2-oxoethyl)cyclohexyl)(isopropyl)carbamate;

N-(5-(4-(trans-1-amino-3-hydroxy-3-methylcyclobutyl)phenyl)-4-phenylpyridin-2-yl)-2-(trans-4-(N-isopropylacetamido)cyclohexyl)acetamide;

methyl(trans-4-(2-((5-(4-(trans-1-amino-3-hydroxy-3-methylcyclobutyl)phenyl)-4-phenylpyridin-2-yl)amino)-2-oxoethyl)cyclohexyl)carbamate;
N-(trans-4-(2-((6-(4-(trans-1-amino-3-hydroxy-3-methylcyclobutyl)phenyl)-5-phenylpyridazin-3-yl)amino)-2-oxoethyl)cyclohexyl)-N-isopropylpropionamide;
N-(trans-4-(2-((6-(4-(trans-1-amino-3-hydroxy-3-methylcyclobutyl)phenyl)-5-phenylpyridazin-3-yl)amino)-2-oxoethyl)cyclohexyl)-N-isopropylcyclopropanecarboxamide;
N-(6-(4-(trans-1-amino-3-hydroxy-3-methylcyclobutyl)phenyl)-5-phenylpyridazin-3-yl)-2-(trans-4-(N-ethylacetamido)cyclohexyl)acetamide;
N-(trans-4-(2-((5-(4-(trans-1-amino-3-hydroxy-3-methylcyclobutyl)phenyl)-4-phenylpyridin-2-yl)amino)-2-oxoethyl)cyclohexyl)-2-methoxy-N-methylacetamide;
N-(5-(4-(trans-1-amino-3-hydroxy-3-methylcyclobutyl)phenyl)-4-phenylpyridin-2-yl)-2-(trans-4-(N-ethylacetamido)cyclohexyl)acetamide;
N-(trans-4-(2-((5-(4-(trans-1-amino-3-hydroxy-3-methylcyclobutyl)phenyl)-4-phenylpyridin-2-yl)amino)-2-oxoethyl)cyclohexyl)-2,2-difluoro-N-methylacetamide;
N-(trans-4-(2-((5-(4-(trans-1-amino-3-hydroxy-3-methylcyclobutyl)phenyl)-4-(thiophen-3-yl)pyridin-2-yl)amino)-2-oxoethyl)cyclohexyl)-N-methylpropionamide;
N-(5-(4-(trans- 1-amino-3-hydroxy-3-methylcyclobutyl)-3-fluorophenyl)-4-phenylpyridin-2-yl)-2-(trans-4-(N-methylacetamido)cyclohexyl)acetamide;
N-(trans-4-(2-((5-(4-(trans-1-amino-3-hydroxy-3-methylcyclobutyl)-3-fluorophenyl)-4-phenylpyridin-2-yl)amino)-2-oxoethyl)cyclohexyl)-N-methylpropionamide;
N-(trans-4-(2-((6-(4-(trans-1-amino-3-hydroxy-3-methylcyclobutyl)phenyl)-5-phenylpyridazin-3-yl)amino)-2-oxoethyl)cyclohexyl)-N-ethylpropionamide;
N-(trans-4-(2-((6-(4-(trans-1-amino-3-hydroxy-3-methylcyclobutyl)phenyl)-5-phenylpyridazin-3-yl)amino)-2-oxoethyl)cyclohexyl)-N-ethylcyclopropanecarboxamide;
N-(trans-4-(2-((5-(4-(trans-1-amino-3-hydroxy-3-methylcyclobutyl)phenyl)-4-phenylpyridin-2-yl)amino)-2-oxoethyl)cyclohexyl)-N-ethylpropionamide;
methyl(trans-4-(2-((5-(4-(trans-1-amino-3-hydroxy-3-methylcyclobutyl)phenyl)-4-phenylpyridin-2-yl)amino)-2-oxoethyl)cyclohexyl)(ethyl)carbamate;
N-(5-(4-(trans-1-amino-3-hydroxy-3-methylcyclobutyl)phenyl)-4-phenylpyridin-2-yl)-2-(trans-4-(N-(2,2,2-trifluoroethyl)acetamido)cyclohexyl)acetamide;
methyl(trans-4-(2-((6-(4-(trans-1-amino-3-hydroxy-3-methylcyclobutyl)phenyl)-5-phenylpyridin-3-yl)amino)-2-oxoethyl)cyclohexyl)(ethyl)carbamate;
N-(trans-4-(2-((6-(4-(trans-1-amino-3-hydroxy-3-methylcyclobutyl)phenyl)-5-phenylpyridin-3-yl)amino)-2-oxoethyl)cyclohexyl)-N-ethylpropionamide;
N-(6-(4-(trans-1-amino-3-hydroxy-3-methylcyclobutyl)phenyl)-5-phenylpyridin-3-yl)-2-(trans-4-(N-isopropylacetamido)cyclohexyl)acetamide;
methyl(trans-4-(2-((6-(4-(trans-1-amino-3-hydroxy-3-methylcyclobutyl)phenyl)-5-phenylpyridin-3-yl)amino)-2-oxoethyl)cyclohexyl)(isopropyl)carbamate;
N-(trans-4-(2-((6-(4-(trans-1-amino-3-hydroxy-3-methylcyclobutyl)phenyl)-5-phenylpyridin-3-yl)amino)-2-oxoethyl)cyclohexyl)-N-isopropylpropionamide;
N-(trans-4-(2-((6-(4-(trans-1-amino-3-fluorocyclobutyl)phenyl)-5-phenylpyridazin-3-yl)amino)-2-oxoethyl)cyclohexyl)-N-methylpropionamide;
N-(6-(4-(trans-1-amino-3-hydroxy-3-methylcyclobutyl)-3-fluorophenyl)-5-phenylpyridin-3-yl)-2-(trans-4-(N-methylacetamido)cyclohexyl)acetamide;
N-(trans-4-(2-((6-(4-(trans-1-amino-3-fluorocyclobutyl)phenyl)-5-(thiophen-3-yl)pyridazin-3-yl)amino)-2-oxoethyl)cyclohexyl)-N-methylpropionamide;
N-(trans-4-(2-((6-(4-(trans-1-amino-3-hydroxy-3-methylcyclobutyl)-3-fluorophenyl)-5-phenylpyridazin-3-yl)amino)-2-oxoethyl)cyclohexyl)-N-methylpropionamide;
N-(6-(4-(trans-1-amino-3-hydroxy-3-methylcyclobutyl)-3-fluorophenyl)-5-phenylpyridazin-3-yl)-2-(trans-4-(N-methylacetamido)cyclohexyl)acetamide;
N-(5-(4-(trans-1-amino-3-hydroxy-3-methylcyclobutyl)phenyl)-4-phenylpyridin-2-yl)-2-(trans-4-((2-methoxyethyl)(methyl)amino)cyclohexyl)acetamide; and
methyl(trans-4-(2-((6-(4-(trans-1-amino-3-hydroxy-3-methylcyclobutyl)phenyl)-5-phenylpyridazin-3-yl)amino)-2-oxoethyl)cyclohexyl)(ethyl)carbamate.

23. A compound according to claim 1, which is selected from the group consisting of:
methyl(trans-4-(2-((6-(4-(1-aminocyclobutyl)phenyl)-5-phenylpyridin-3-yl)amino)-2-oxoethyl)cyclohexyl)(methyl)carbamate;
N-(6-(4-(1-amino-3,3-difluorocyclobutyl)phenyl)-5-phenylpyridin-3-yl)-2-(trans-4-morpholinocyclohexyl)acetamide;
N-(6-(4-(1-amino-3,3-difluorocyclobutyl)phenyl)-5-phenylpyridin-3-yl)-2-(trans-4-(2-oxooxazolidin-3-yl)cyclohexyl)acetamide;
methyl(trans-4-(2-((6-(4-(1-amino-3,3-difluorocyclobutyl)phenyl)-5-phenylpyridin-3-yl)amino)-2-oxoethyl)cyclohexyl)(methyl)carbamate;
N-(trans-4-(2-((6-(4-(1-amino-3-hydroxy-3-methylcyclobutyl)phenyl)-5-phenylpyridin-3-yl)amino)-2-oxoethyl)cyclohexyl)-2,2-difluoroacetamide;
N-(trans-4-(2-((6-(4-(3-aminooxetan-3-yl)phenyl)-5-phenylpyridin-3-yl)amino)-2-oxoethyl)cyclohexyl)-3,3,3-trifluoro-2,2-dimethylpropanamide;
N-(trans-4-(2-((6-(4-(2-aminopropan-2-yl)phenyl)-5-phenylpyridin-3-yl)amino)-2-oxoethyl)cyclohexyl)-2,2-difluoro-N-methylacetamide;
2-(trans-4-acetamidocyclohexyl)-N-(6-(4-((S)-1-aminoethyl)phenyl)-5-phenylpyridin-3-yl)acetamide;
2-(trans-4-acetamidocyclohexyl)-N-(6-(4-((R)-1-aminoethyl)phenyl)-5-phenylpyridin-3-yl) acetamide;
N-(trans-4-(2-((6-(4-((S)-1-aminoethyl)phenyl)-5-phenylpyridin-3-yl)amino)-2-oxoethyl)cyclohexyl)-3,3,3-trifluoro-2,2-dimethylpropanamide;
N-(trans-4-(2-((6-(4-((R)-1-aminoethyl)phenyl)-5-phenylpyridin-3-yl)amino)-2-oxoethyl)cyclohexyl)-3,3,3-trifluoro-2,2-dimethylpropanamide;
2-(trans-4-acetamidocyclohexyl)-N-(6-(4-((S)-1-amino-2,2-difluoroethyl)phenyl)-5-phenylpyridin-3-yl)acetamide;
N-(6-(4-((S)-1-aminoethyl)phenyl)-5-phenylpyridin-3-yl)-2-(trans-4-(N-methylmethylsulfonamido)cyclohexyl)acetamide;
N-(6-(4-(1-aminocyclobutyl)phenyl)-5-(thiophen-3-yl)pyridin-3-yl)-2-(trans-4-(2-oxopiperidin-1-yl)cyclohexyl)acetamide;

N-(6-(4-(trans-1-amino-3-hydroxy-3-methylcyclobutyl)phenyl)-5-phenylpyridin-3-yl)-2-(trans-4-morpholinocyclohexyl)acetamide;

N-(6-(4-(1-aminocyclobutyl)phenyl)-5-(2-fluorophenyl)pyridin-3-yl)-2-(trans-4-(N-methylmethylsulfonamido)cyclohexyl)acetamide;

N-(6-(4-(1-aminocyclobutyl)phenyl)-5-phenylpyridin-3-yl)-2-(trans-4-(3-methyl-4H-1,2,4-triazol-4-yl)cyclohexyl)acetamide;

N-(6-(4-(2-aminopropan-2-yl)phenyl)-5-phenylpyridin-3-yl)-2-(trans-4-morpholinocyclohexyl)acetamide;

2-(trans-4-acetamidocyclohexyl)-N-(6-(4-(2-aminopropan-2-yl)phenyl)-5-phenylpyridin-3-yl)acetamide;

N-(trans-4-(2-((6-(4-(2-aminopropan-2-yl)phenyl)-5-phenylpyridin-3-yl)amino)-2-oxoethyl)cyclohexyl)cyclopropanecarboxamide;

N-(trans-4-(2-((6-(4-(2-aminopropan-2-yl)phenyl)-5-phenylpyridin-3-yl)amino)-2-oxoethyl)cyclohexyl)-1-methylcyclopropane-1-carboxamide;

N-(trans-4-(2-((6-(4-(2-aminopropan-2-yl)phenyl)-5-phenylpyridin-3-yl)amino)-2-oxoethyl)cyclohexyl)isobutyramide;

2-(trans-4-acetamidocyclohexyl)-N-(6-(4-(2-aminopropan-2-yl)phenyl)-5-(thiophen-3-yl)pyridin-3-yl)acetamide;

N-(6-(4-(2-aminopropan-2-yl)phenyl)-5-(thiophen-3-yl)pyridin-3-yl)-2-(trans-4-(N-methylmethylsulfonamido)cyclohexyl)acetamide;

N-(6-(4-(2-aminopropan-2-yl)phenyl)-5-phenylpyridin-3-yl)-2-(trans-4-(N-methylmethylsulfonamido)cyclohexyl)acetamide;

N-(6-(4-(2-aminopropan-2-yl)phenyl)-5-(2-fluorophenyl)pyridin-3-yl)-2-(trans-4-(N-methylmethylsulfonamido)cyclohexyl)acetamide;

N-(6-(4-(1-aminocyclobutyl)phenyl)-5-phenylpyridin-3-yl)-2-(trans-4-(2-oxooxazolidin-3-yl)cyclohexyl)acetamide;

methyl(trans-4-(2-((6-(4-(2-aminopropan-2-yl)-3-fluorophenyl)-5-phenylpyridin-3-yl)amino)-2-oxoethyl)cyclohexyl)(methyl)carbamate;

N-(trans-4-(2-((6-(4-(2-aminopropan-2-yl)phenyl)-5-phenylpyridin-3-yl)amino)-2-oxoethyl)cyclohexyl)-N-methylcyclopropanecarboxamide;

N-(trans-4-(2-((6-(4-(2-aminopropan-2-yl)phenyl)-5-phenylpyridin-3-yl)amino)-2-oxoethyl)cyclohexyl)-N,3,3-trimethylbutanamide;

N-(trans-4-(2-((6-(4-(2-aminopropan-2-yl)phenyl)-5-phenylpyridin-3-yl)amino)-2-oxoethyl)cyclohexyl)-N,1-dimethylcyclopropane-1-carboxamide;

N-(trans-4-(2-((6-(4-(2-aminopropan-2-yl)phenyl)-5-phenylpyridin-3-yl)amino)-2-oxoethyl)cyclohexyl)-2-cyclopropyl-N-methylacetamide;

N-(trans-4-(2-((6-(4-(1-aminocyclopropyl)phenyl)-5-phenylpyridin-3-yl)amino)-2-oxoethyl)cyclohexyl)-N-methylbutyramide;

N-(trans-4-(2-((6-(4-(2-aminopropan-2-yl)phenyl)-5-phenylpyridin-3-yl)amino)-2-oxoethyl)cyclohexyl)pivalamide;

N-(trans-4-(2-((6-(4-(1-aminocyclobutyl)phenyl)-5-phenylpyridin-3-yl)amino)-2-oxoethyl)cyclohexyl)-2,2-difluoroacetamide;

N-(trans-4-(2-((6-(4-(2-aminopropan-2-yl)phenyl)-5-phenylpyridin-3-yl)amino)-2-oxoethyl)cyclohexyl)cyclobutanecarboxamide;

N-(trans-4-(2-((6-(4-(2-aminopropan-2-yl)phenyl)-5-phenylpyridin-3-yl)amino)-2-oxoethyl)cyclohexyl)-3,3-dimethylbutanamide;

2-(trans-4-acetamidocyclohexyl)-N-(6-(4-(1-aminocyclobutyl)phenyl)-5-phenylpyridin-3-yl)acetamide;

N-(trans-4-(2-((6-(4-(1-aminocyclobutyl)phenyl)-5-phenylpyridin-3-yl)amino)-2-oxoethyl)cyclohexyl)cyclopropanecarboxamide;

N-(trans-4-(2-((6-(4-(1-aminocyclobutyl)phenyl)-5-(thiophen-3-yl)pyridin-3-yl)amino)-2-oxoethyl)cyclohexyl)pivalamide;

N-(trans-4-(2-((6-(4-(1-aminocyclopropyl)phenyl)-5-phenylpyridin-3-yl)amino)-2-oxoethyl)cyclohexyl)butyramide;

N-(trans-4-(2-((6-(4-(1-aminocyclopropyl)phenyl)-5-phenylpyridin-3-yl)amino)-2-oxoethyl)cyclohexyl)-2,2-difluoroacetamide;

N-(trans-4-(2-((6-(4-(1-aminocyclopropyl)phenyl)-5-phenylpyridin-3-yl)amino)-2-oxoethyl)cyclohexyl)pivalamide;

N-(6-(4-(2-aminopropan-2-yl)phenyl)-5-phenylpyridin-3-yl)-2-(trans-4-(N-isopropylacetamido)cyclohexyl)acetamide;

methyl(trans-4-(1-((6-(4-(2-aminopropan-2-yl)phenyl)-5-phenylpyridin-3-yl)amino)-1-oxopropan-2-yl)cyclohexyl)(methyl)carbamate;

N-(6-(4-(2-aminopropan-2-yl)phenyl)-5-phenylpyridin-3-yl)-2-(trans-4-(morpholine-4-carbonyl)cyclohexyl)acetamide;

N-(6-(4-(2-aminopropan-2-yl)phenyl)-5-phenylpyridin-3-yl)-2-(trans-4-(pyrrolidine-1-carbonyl)cyclohexyl)acetamide;

methyl(trans-4-(2-((5-(4-(2-aminopropan-2-yl)phenyl)-4-phenylpyridin-2-yl)amino)-2-oxoethyl)cyclohexyl)(methyl)carbamate;

N-(5-(4-(2-aminopropan-2-yl)phenyl)-4-phenylpyridin-2-yl)-2-(trans-4-(2-oxopyrrolidin-1-yl)cyclohexyl)acetamide;

N-(6-(4-(1-aminocyclopropyl)-3-fluorophenyl)-5-phenylpyridazin-3-yl)-2-(trans-4-(2-oxooxazolidin-3-yl)cyclohexyl)acetamide;

N-(5-(4-(1-aminocyclopropyl)phenyl)-4-phenylpyridin-2-yl)-2-(trans-4-(2-oxooxazolidin-3-yl)cyclohexyl)acetamide;

N-(5-(4-(2-aminopropan-2-yl)phenyl)-4-(thiophen-3-yl)pyridine-2-yl)-2-(trans-4-(2-oxooxazolidin-3-yl)cyclohexyl)acetamide;

N-(5-(4-(trans-1-amino-3-fluorocyclobutyl)phenyl)-4-phenylpyridin-2-yl)-2-(trans-4-(2-oxooxazolidin-3-yl)cyclohexyl)acetamide;

N-(6-(4-(1-aminocyclopropyl)-3-fluorophenyl)-5-phenylpyridazin-3-yl)-2-(trans-4-(N-methylacetamido)cyclohexyl)acetamide;

methyl(trans-4-(2-((6-(4-(1-aminocyclobutyl)phenyl)-5-phenylpyridazin-3-yl)amino)-2-oxoethyl)cyclohexyl)(methyl)carbamate;

N-(6-(4-(1-aminocyclobutyl)phenyl)-5-phenylpyridazin-3-yl)-2-(trans-4-(N-methylacetamido)cyclohexyl)acetamide;

N-(5-(4-(trans-1-amino-3-hydroxy-3-methylcyclobutyl)phenyl)-4-phenylpyridin-2-yl)-2-(trans-4-(2-oxooxazolidin-3-yl)cyclohexyl)acetamide;

N-(5-(4-(trans-1-amino-3-hydroxy-3-methylcyclobutyl)phenyl)-4-phenylpyridin-2-yl)-2-(trans-4-(N-methylacetamido)cyclohexyl)acetamide;

N-(5-(4-((1r,3r)-1-amino-3-fluorocyclobutyl)phenyl)-4-phenylpyridin-2-yl)-2-(trans-4-(N-methylacetamido)cyclohexyl)acetamide;

methyl(trans-4-(2-((6-(4-(trans-1-amino-3-fluorocyclobutylphenyl)-5-phenylpyridazin-3-yl)amino)-2-oxoethyl)cyclohexyl)(methyl)carbamate;
methyl(trans-4-(2-((5-(4-(1-aminocyclobutyl)phenyl)-4-phenylpyridin-2-yl)amino)-2-oxoethyl)cyclohexyl)(methyl)carbamate;
N-(5-(4-(1-aminocyclobutyl)phenyl)-4-(2-fluorophenyl)pyridin-2-yl)-2-(trans-4-(N-methylacetamido)cyclohexyl)acetamide;
methyl(trans-4-(2-((5-(4-(1-aminocyclobutyl)phenyl)-4-(2-fluorophenyl)pyridin-2-yl)amino)-2-oxoethyl)cyclohexyl)(methyl)carbamate;
N-(5-(4-(1-aminocyclobutyl)phenyl)-4-(thiophen-3-yl)pyridin-2-yl)-2-(trans-4-(N-methylacetamido)cyclohexyl)acetamide;
N-(5-(4-(1-aminocyclobutyl)phenyl)-4-(2-fluorophenyl)pyridin-2-yl)-2-(trans-4-(2-oxooxazolidin-3-yl)cyclohexyl)acetamide; methyl(trans-4-(2-((6-(4-(trans-1-amino-3-fluorocyclobutyl)phenyl)-5-(thiophen-3-yl)pyridin-3-yl)amino)-2-oxoethyl)cyclohexyl)(methyl)carbamate;
methyl(trans-4-(2-((6-(4-(2-aminopropan-2-yl)phenyl)-5-(thiophen-3-yl)pyridin-3-yl)amino)-2-oxoethyl)cyclohexyl)(methyl)carbamate;
methyl(trans-4-(2-((6-(4-(1-aminocyclobutyl)phenyl)-5-(thiophen-3-yl)pyridin-3-yl)amino)-2-oxoethyl)cyclohexyl)(methyl)carbamate;
methyl(trans-4-(2-((6-(4-(2-aminopropan-2-yl)phenyl)-5-(thiophen-3-yl)pyridazin-3-yl)amino)-2-oxoethyl)cyclohexyl)(methyl)carbamate;
methyl(trans-4-(2-((6-(4-(trans-1-amino-3-fluorocyclobutyl)phenyl)-5-(thiophen-3-yl)pyridazin-3-yl)amino)-2-oxoethyl)cyclohexyl)(methyl)carbamate;
N-(5-(4-(1-aminocyclobutyl)phenyl)-4-phenylpyridin-2-yl)-2-(trans-4-(2-oxopyrrolidin-1-yl)cyclohexyl)acetamide;
N-(trans-4-(2-((5-(4-(1-aminocyclobutyl)phenyl)-4-phenylpyridin-2-yl)amino)-2-oxoethyl)cyclohexyl)-N-methylcyclopropanecarboxamide;
ethyl(trans-4-(2-((5-(4-(trans-1-amino-3-hydroxy-3-methylcyclobutyl)phenyl)-4-phenylpyridin-2-yl)amino)-2-oxoethyl)cyclohexyl)(methyl)carbamate;
isopropyl(trans-4-(2-((5-(4-(trans-1-amino-3-hydroxy-3-methylcyclobutyl)phenyl)-4-phenylpyridin-2-yl)amino)-2-oxoethyl)cyclohexyl)(methyl)carbamate;
N-(trans-4-(2-((5-(4-(trans-1-amino-3-hydroxy-3-methylcyclobutyl)phenyl)-4-phenylpyridin-2-yl)amino)-2-oxoethyl)cyclohexyl)-N-methylcyclopropanecarboxamide;
N-(trans-4-(2-((5-(4-(trans-1-amino-3-hydroxy-3-methylcyclobutyl)phenyl)-4-phenylpyridin-2-yl)amino)-2-oxoethyl)cyclohexyl)-N-methylcyclobutanecarboxamide;
methyl(trans-4-(2-((6-(4-(1-aminocyclopropyl)phenyl)-5-phenylpyridazin-3-yl)amino)-2-oxoethyl)cyclohexyl)(methyl)carbamate;
N-(trans-4-(2-((6-(4-(trans-1-amino-3-hydroxy-3-methylcyclobutyl)phenyl)-5-phenylpyridazin-3-yl)amino)-2-oxoethyl)cyclohexyl)-N-methylcyclopropanecarboxamide;
N-(trans-4-(2-((6-(4-(trans-1-amino-3-hydroxy-3-methylcyclobutyl)phenyl)-5-phenylpyridazin-3-yl)amino)-2-oxoethyl)cyclohexyl)-N-methylisobutyramide;
ethyl(trans-4-(2-((6-(4-(trans-1-amino-3-hydroxy-3-methylcyclobutyl)phenyl)-5-phenylpyridazin-3-yl)amino)-2-oxoethyl)cyclohexyl)(methyl)carbamate;
N-(trans-4-(2-((5-(4-(1-aminocyclopropyl)phenyl)-4-phenylpyridin-2-yl)amino)-2-oxoethyl)cyclohexyl)-N-methylpropionamide;
N-(5-(4-(trans-1-amino-3-hydroxy-3-methylcyclobutyl)phenyl)-4-phenylpyridin-2-yl)-2-(trans-4-(2-oxopyrrolidin-1-yl)cyclohexyl)acetamide;
N-(5-(4-(1-aminocyclopropyl)phenyl)-4-phenylpyridin-2-yl)-2-(trans-4-(2-oxopyrrolidin-1-yl)cyclohexyl)acetamide;
N-(trans-4-(2-((6-(4-(2-aminopropan-2-yl)phenyl)-5-phenylpyridazin-3-yl)amino)-2-oxoethyl)cyclohexyl)-N-methylpropionamide;
N-(trans-4-(2-((6-(4-(2-aminopropan-2-yl)phenyl)-5-phenylpyridazin-3-yl)amino)-2-oxoethyl)cyclohexyl)-N-methylisobutyramide;
N-(trans-4-(2-((6-(4-(2-aminopropan-2-yl)phenyl)-5-phenylpyridazin-3-yl)amino)-2-oxoethyl)cyclohexyl)-N-methylcyclopropanecarboxamide;
N-(trans-4-(2-((6-(4-(2-aminopropan-2-yl)phenyl)-5-phenylpyridazin-3-yl)amino)-2-oxoethyl)cyclohexyl)-N-methylcyclobutanecarboxamide;
methyl(trans-4-(2-((5'-(4-(1-aminocyclopropyl)phenyl)-[2,4'-bipyridin]-2'-yl)amino)-2-oxoethyl)cyclohexyl)(methyl)carbamate;
N-(6-(4-(1-aminocyclopropyl)-3-fluorophenyl)-5-phenylpyridin-3-yl)-2-(trans-4-(N-methylacetamido)cyclohexyl)acetamide;
ethyl(trans-4-(2-((5-(4-(trans-1-amino-3-hydroxy-3-methylcyclobutyl)phenyl)-4-(thiophen-3-yl)pyridin-2-yl)amino)-2-oxoethyl)cyclohexyl)(methyl)carbamate;
N-(trans-4-(2-((6-(4-(1-aminocyclopropyl)phenyl)-5-phenylpyridazin-3-yl)amino)-2-oxoethyl)cyclohexyl)-N-methylpropionamide;
N-(trans-4-(2-((6-(4-(1-aminocyclopropyl)phenyl)-5-phenylpyridazin-3-yl)amino)-2-oxoethyl)cyclohexyl)-N-methylisobutyramide;
N-(trans-4-(2-((6-(4-(1-aminocyclopropyl)phenyl)-5-phenylpyridazin-3-yl)amino)-2-oxoethyl)cyclohexyl)-N-methylcyclobutanecarboxamide;
ethyl(trans-4-(2-((6-(4-(1-aminocyclopropyl)phenyl)-5-phenylpyridazin-3-yl)amino)-2-oxoethyl)cyclohexyl)(methyl)carbamate;
N-(trans-4-(2-((6-(4-(2-aminopropan-2-yl)phenyl)-5-phenylpyridin-3-yl)amino)-2-oxoethyl)cyclohexyl)-N-methylpropionamide;
N-(6-(4-(2-aminopropan-2-yl)phenyl)-5-(thiophen-3-yl)pyridazin-3-yl)-2-(trans-4-(N-methylacetamido)cyclohexyl)acetamide;
N-(6-(4-(1-aminocyclobutyl)phenyl)-5-(thiophen-3-yl)pyridazin-3-yl)-2-(trans-4-(N-methylacetamido)cyclohexyl)acetamide;
N-(6-(4-(trans-1-amino-3-hydroxy-3-methylcyclobutyl)phenyl)-5-phenylpyridazin-3-yl)-2-(trans-4-(2-oxopiperidin-1-yl)cyclohexyl)acetamide;
ethyl(trans-4-(2-((6-(4-(2-aminopropan-2-yl)phenyl)-5-phenylpyridin-3-yl)amino)-2-oxoethyl)cyclohexyl)(methyl)carbamate;
methyl(trans-4-(2-((6-(4-(1-aminocyclopropyl)-3-fluorophenyl)-5-(thiophen-3-yl)pyridazin-3-yl)amino)-2-oxoethyl)cyclohexyl)(methyl)carbamate;
N-(trans-4-(2-((6-(4-(1-aminocyclopropyl)-3-fluorophenyl)-5-(thiophen-3-yl)pyridazin-3-yl)amino)-2-oxoethyl)cyclohexyl)-N-methylpropionamide;
N-(trans-4-(2-((5-(4-(1-aminocyclobutyl)phenyl)-4-(2-fluorophenyl)pyridin-2-yl)amino)-2-oxoethyl)cyclohexyl)-N-methylpropionamide;

N-(trans-4-(2-((6-(4-(1-aminocyclopropyl)-3-fluorophenyl)-5-phenylpyridazin-3-yl)amino)-2-oxoethyl)cyclohexyl)-N-methylpropionamide;

methyl(trans-4-(2-((6-(4-(1-aminocyclopropyl)-3-fluorophenyl)-5-phenylpyridazin-3-yl)amino)-2-oxoethyl)cyclohexyl)(methyl)carbamate;

methyl(trans-4-(2-((5-(4-(trans-1-amino-3-hydroxy-3-methylcyclobutyl)phenyl)-4-phenylpyridin-2-yl)amino)-2-oxoethyl)cyclohexyl)(isopropyl)carbamate;

methyl(trans-4-(2-((5-(4-(1-aminocyclopropyl)-3-fluorophenyl)-4-phenylpyridin-2-yl)amino)-2-oxoethyl)cyclohexyl)carbamate;

N-(trans-4-(2-((5-(4-(trans-1-amino-3-hydroxy-3-methylcyclobutyl)phenyl)-4-phenylpyridin-2-yl)amino)-2-oxoethyl)cyclohexyl)-N-isopropylpropionamide; and N-(trans-4-(2-((5-(4-(trans-1-amino-3-hydroxy-3-methylcyclobutyl)phenyl)-4-phenylpyridin-2-yl)amino)-2-oxoethyl)cyclohexyl)-N-isopropylcyclopropanecarboxamide.

24. A method of treating cancer, comprising administering a therapeutically effective amount of a compound according to claim 1, to a subject with cancer.

25. The method according to claim 24, wherein the cancer is lung cancer, melanoma, breast cancer, ovarian cancer or carcinoma.

26. The method according to claim 24, wherein the method further comprises administering one or more chemotherapeutic agents.

27. A method of treating pheochromocytoma; inflammatory conditions, endometriosis, vascular disease/injury, psoriasis, visual impairment due to macular degeneration, diabetic retinopathy, retinopathy of prematurity, kidney disease, pulmonary disorders, osteoporosis, osteoarthritis, viral infections, fibrotic disease, cataracts, infant tauopathies, tuberous sclerosis complex, focal cortical dysplasia 2 or ganglioglioma comprising administering a therapeutically effective amount of a compound of claim 1 to a subject in need thereof.

28. A pharmaceutical composition comprising a compound according to claim 1 and one or more pharmaceutically acceptable excipients.

* * * * *

UNITED STATES PATENT AND TRADEMARK OFFICE
CERTIFICATE OF CORRECTION

PATENT NO. : 10,336,702 B2
APPLICATION NO. : 15/533048
DATED : July 2, 2019
INVENTOR(S) : Jason John Shiers et al.

Page 1 of 1

It is certified that error appears in the above-identified patent and that said Letters Patent is hereby corrected as shown below:

On the Title Page

Item (30):
"(30) Foreign Application Priority Data
May 22, 2015 (GB).................................. 1508787.7"

Should read:
--(30) Foreign Application Priority Data
November 11, 2015 (GB)......................... 1519919.3
May 22, 2015 (GB)................................. 1508787.7
December 23, 2014 (GB)......................... 1423087.4--

Signed and Sealed this
Tenth Day of September, 2019

Andrei Iancu
*Director of the United States Patent and Trademark Office*